US012595478B2

(12) United States Patent
Choudhary et al.

(10) Patent No.: US 12,595,478 B2
(45) Date of Patent: Apr. 7, 2026

(54) CRISPR-Cas SYSTEMS HAVING DESTABILIZATION DOMAIN

(71) Applicants: THE BROAD INSTITUTE, INC., Cambridge, MA (US); MASSACHUSETTS INSTITUTE OF TECHNOLOGY, Cambridge, MA (US); THE BRIGHAM AND WOMEN'S HOSPITAL, INC., Boston, MA (US)

(72) Inventors: Amit Choudhary, Boston, MA (US); Basudeb Maji, Cambridge, MA (US); Bernd Zetsche, Cambridge, MA (US); Feng Zhang, Cambridge, MA (US)

(73) Assignees: The Broad Institute, Inc., Cambridge, MA (US); Massachusetts Institute of Technology, Cambridge, MA (US); The Brigham and Women's Hospital, Inc., Boston, MA (US)

( * ) Notice: Subject to any disclaimer, the term of this patent is extended or adjusted under 35 U.S.C. 154(b) by 589 days.

(21) Appl. No.: 16/314,375

(22) PCT Filed: Jun. 29, 2017

(86) PCT No.: PCT/US2017/040115
§ 371 (c)(1),
(2) Date: Dec. 28, 2018

(87) PCT Pub. No.: WO2018/005873
PCT Pub. Date: Jan. 4, 2018

(65) Prior Publication Data

US 2021/0222164 A1 Jul. 22, 2021

Related U.S. Application Data

(60) Provisional application No. 62/356,028, filed on Jun. 29, 2016.

(51) Int. Cl.
*C12N 15/11* (2006.01)
*C12N 9/22* (2006.01)

(52) U.S. Cl.
CPC .............. *C12N 15/111* (2013.01); *C12N 9/22* (2013.01); *C12N 2310/20* (2017.05)

(58) Field of Classification Search
None
See application file for complete search history.

(56) References Cited

U.S. PATENT DOCUMENTS

| | | | | |
|---|---|---|---|---|
| 7,262,005 | B1 * | 8/2007 | Stack | A61P 43/00 536/23.4 |
| 8,697,359 | B1 | 4/2014 | Zhang et al. | |
| 8,771,945 | B1 | 7/2014 | Zhang et al. | |
| 8,795,965 | B2 | 8/2014 | Zhang et al. | |
| 8,865,406 | B2 | 10/2014 | Zhang et al. | |
| 8,871,445 | B2 | 10/2014 | Cong et al. | |
| 8,889,356 | B2 | 11/2014 | Zhang et al. | |
| 8,889,418 | B2 | 11/2014 | Zhang et al. | |
| 8,895,308 | B1 | 11/2014 | Zhang et al. | |
| 8,906,616 | B2 | 12/2014 | Zhang et al. | |
| 8,932,814 | B2 | 1/2015 | Cong et al. | |
| 8,945,839 | B2 | 2/2015 | Zhang et al. | |
| 8,993,233 | B2 | 3/2015 | Zhang et al. | |
| 8,999,641 | B2 | 4/2015 | Zhang et al. | |
| 10,550,372 | B2 * | 2/2020 | Konermann | C12N 15/907 |
| 2010/0267950 | A1 * | 10/2010 | Khire | C07D 211/60 544/130 |
| 2014/0068797 | A1 * | 3/2014 | Doudna | C12N 15/746 800/18 |
| 2014/0170753 | A1 | 6/2014 | Zhang et al. | |
| 2014/0179006 | A1 | 6/2014 | Zhang et al. | |
| 2014/0179770 | A1 | 6/2014 | Zhang et al. | |
| 2014/0186843 | A1 | 7/2014 | Zhang et al. | |
| 2014/0186919 | A1 | 7/2014 | Zhang et al. | |
| 2014/0186958 | A1 | 7/2014 | Zhang et al. | |
| 2014/0189896 | A1 | 7/2014 | Zhang et al. | |
| 2014/0227787 | A1 | 8/2014 | Zhang et al. | |
| 2014/0234972 | A1 | 8/2014 | Zhang et al. | |
| 2014/0242664 | A1 | 8/2014 | Zhang et al. | |
| 2014/0242699 | A1 | 8/2014 | Zhang et al. | |
| 2014/0242700 | A1 | 8/2014 | Zhang et al. | |
| 2014/0248702 | A1 | 9/2014 | Zhang et al. | |

(Continued)

FOREIGN PATENT DOCUMENTS

| | | | |
|---|---|---|---|
| EP | 2764103 | A2 | 8/2014 |
| EP | 2771468 | B1 | 9/2014 |

(Continued)

OTHER PUBLICATIONS

Addgene blog by Mary Gearing Comparing Cas9 to NgAgo: Can the Argonautes Best CRISPR?, pp. 1-6 retrieved on line Aug. 9, 2021 from https://blog.addgene.org (Year: 2019).*
Swarts et al. Nature vol. 507 pp. 258-261 and Supplementary Material, pp. 1-13 (Year: 2014).*
Chylinski et al. Nucleic Acids Research Vo. 42, pp. 6091-6105 (Year: 2014).*
Retraction note: Gao et al. 34,768-773, 2016 (Year: 2017).*
Polstein et al. Nature Chemical Biology vol. 11, Mar. 2015, pp. 198-201 (Year: 2015).*

(Continued)

*Primary Examiner* — Brian Whiteman
(74) *Attorney, Agent, or Firm* — F. Brent Nix, Esq.; Johnson, Marcou, Isaacs & Nix, LLC; Drew P. Harding

(57) ABSTRACT

The disclosure includes non-naturally occurring or engineered DNA- or RNA-guided nuclease systems, comprising guide-binding adaptors each associated with at least one destabilization domain (DD), along with compositions, systems and complexes involving such systems, nucleic acid molecules and vectors encoding the same, delivery systems involving the same, uses therefor.

31 Claims, 29 Drawing Sheets

Specification includes a Sequence Listing.

(56) References Cited

U.S. PATENT DOCUMENTS

| | | | | |
|---|---|---|---|---|
| 2014/0256046 | A1 | 9/2014 | Zhang et al. | |
| 2014/0273231 | A1 | 9/2014 | Zhang et al. | |
| 2014/0273232 | A1 | 9/2014 | Zhang et al. | |
| 2014/0273234 | A1 | 9/2014 | Zhang et al. | |
| 2014/0287938 | A1 | 9/2014 | Zhang et al. | |
| 2014/0310830 | A1 | 10/2014 | Zhang et al. | |
| 2014/0357530 | A1 | 12/2014 | Zhang et al. | |
| 2015/0132269 | A1* | 5/2015 | Orkin | C12N 15/113<br>424/93.21 |
| 2015/0184139 | A1 | 7/2015 | Zhang et al. | |
| 2016/0208243 | A1* | 7/2016 | Zhang | C12N 15/11 |
| 2017/0211142 | A1* | 7/2017 | Smargon | C12N 9/22 |
| 2017/0306307 | A1* | 10/2017 | Zhang | C12N 15/907 |
| 2017/0321198 | A1* | 11/2017 | Severinov | C12N 15/85 |
| 2019/0264186 | A1* | 8/2019 | Yamano | C12N 15/102 |
| 2019/0359971 | A1* | 11/2019 | Zhang | C12N 15/102 |
| 2021/0317429 | A1* | 10/2021 | Choudhary | C07D 239/49 |

FOREIGN PATENT DOCUMENTS

| | | | | |
|---|---|---|---|---|
| EP | 2784162 | A1 | 10/2014 | |
| WO | 2014018423 | A2 | 1/2014 | |
| WO | 2014093595 | A1 | 6/2014 | |
| WO | 2014093622 | A2 | 6/2014 | |
| WO | 2014093635 | A1 | 6/2014 | |
| WO | 2014093655 | A2 | 6/2014 | |
| WO | 2014093661 | A2 | 6/2014 | |
| WO | 2014093694 | A1 | 6/2014 | |
| WO | 2014093701 | A1 | 6/2014 | |
| WO | 2014093709 | A1 | 6/2014 | |
| WO | 2014093712 | A1 | 6/2014 | |
| WO | 2014093718 | A1 | 6/2014 | |
| WO | 2014204723 | A1 | 12/2014 | |
| WO | 2014204724 | A1 | 12/2014 | |
| WO | 2014204725 | A1 | 12/2014 | |
| WO | 2014204726 | A1 | 12/2014 | |
| WO | 2014204727 | A1 | 12/2014 | |
| WO | 2014204728 | A1 | 12/2014 | |
| WO | 2014204729 | A1 | 12/2014 | |
| WO | 2015048577 | A2 | 4/2015 | |
| WO | 2015065964 | A1 | 5/2015 | |
| WO | 2015070083 | A1 | 5/2015 | |
| WO | 2015089351 | A1 | 6/2015 | |
| WO | 2015089354 | A1 | 6/2015 | |
| WO | 2015089364 | A1 | 6/2015 | |
| WO | 2015089419 | A2 | 6/2015 | |
| WO | 2015089427 | A1 | 6/2015 | |
| WO | 2015089462 | A1 | 6/2015 | |
| WO | 2015089465 | A1 | 6/2015 | |
| WO | 2015089473 | A1 | 6/2015 | |
| WO | 2015089486 | A2 | 6/2015 | |
| WO | 2015134812 | A1 | 9/2015 | |
| WO | 2015138510 | A1 | 9/2015 | |
| WO | 2015148670 | A1 | 10/2015 | |
| WO | 2015153780 | A1 | 10/2015 | |
| WO | 2015161276 | A2 | 10/2015 | |
| WO | 2016028682 | A1 | 2/2016 | |
| WO | 2016049163 | A2 | 3/2016 | |
| WO | 2016049258 | A2 | 3/2016 | |
| WO | WO-2016040395 | A1 * | 3/2016 | A61K 48/0066 |
| WO | 2016106244 | A1 | 6/2016 | |
| WO | WO-2016205613 | A1 * | 12/2016 | A61P 11/00 |
| WO | 2018005873 | A1 | 1/2018 | |

OTHER PUBLICATIONS

Ballister et al. Nature Communications 5:5475, pp. 1-9 (Year: 2014).*

Khakhar, et al., "Cell-cell communication in yeast using auxin biosynthesis and auxin responsive CRISPR transcription factors", ACS Synthetic Biology, vol. 5, No. 4, Apr. 15, 2016, 279-286.

Khakhar, et al., "Supplementary Information: Cell-cell communication in yeast using auxin biosynthesis and auxin responsive CRISPR transcription factors", Apr. 15, 2016 (Apr. 15, 2016), XP055407618,retrieved from the Internet: URL: http://pubs.acs.org/doi/suppl/10.1021/+acssynbio.5b00064/suppl+file/sb5b00064+si+001.

Konermann, et al., "Genome-scale transcriptional activation by an engineered CRISPR-Cas9 complex", Nature, vol. 517, No. 7536, Dec. 10, 2014, 583-588.

Balboa, et al., "Conditionally stabilized dCas9 activator for controlling gene expression in human cell reprogramming and differentiation", Stem Cell Reports, vol. 5, Sep. 8, 2015, 448-459.

Geisinger, et al., "In vivo blunt-end cloning through CRISPR/CAS9-facilitated non-homologous end-joining", Nucleic Acids Research, Information Retrieval Ltd., Jan. 1, 2016, 1-15.

Geisinger, et al., "Supplementary data: In vivo blunt-end cloning through CRISPR/CAS9-facilitated non-homologous end-joining", May 5, 2016 (May 5, 2016), XP055407601,retrieved from the Internet: URL:https://academic.oup.com/nar/article-1 ookup/doi/10.1093/nar/gkv1542#supplementar y-data.

International Search Report and Written Opinion issued by the European Patent Office (EPO) on Feb. 10, 2017 for PCT Application No. PCT/US2017/040115.

Platt et al., "CRISPR-Cas9 Knockin Mice for Genome Editing and Cancer Modeling", Cell vol. 159, Issue 2, pp. 440-455, Oct. 9, 2014.

Miyazaki, J. et al., "Destabilizing Domains Derived from the Human Estrogen Receptor", Am Chem Soc., vol. 134, Issue No. 9, pp. 3942-3945, Mar. 7, 2012.

Chung H. et al., "Tunable and reversible drug control of protein production via a self-excising degron", Nature Chemical Biology, vol. 11 , Issue 9, pp. 713-720, Sep. 2015.

Banaszynski LA, et al., "A Rapid, Reversible, and Tunable Method to Regulate Protein Function in Living Cells Using Synthetic Small Molecules", Cell, vol. 126, pp. 995-1004, Sep. 8, 2006.

Banaszynski LA, et al., "Chemical control of protein stability and function in living animals", Nat Med., vol. 10, pp. 1123-1127, Oct. 2008.

Maynard-Smith LA et al., "A Directed Approach for Engineering Conditional Protein Stability Using Biologically Silent Small Molecules", The Journal of Biological Chemistry, vol. 282, No. 34, pp. 24866-24872, Aug. 24, 2007.

Rodriguez et al., "Targeted Chemical-Genetic Regulation of Protein Stability In Vivo", Chem Biol., vol. 19, Issue 3, pp. 391-398, Mar. 23, 2012.

Ibsen et al., "A Novel Doxorubicin Prodrug with Controllable Photolysis Activation for Cancer Chemotherapy", Pharm Res., vol. 27, pp. 1848-1860, Published online: Jul. 2, 2010.

Horbert et al., "Photoactivatable prodrugs of antimelanoma agent Vemurafenib", ACS Chem. Biol, vol. 10, pp. 2099-2107, 2015.

Zetsche et al., "A split-Cas9 architecture for inducible genome editing and transcription modulation," Nature Biotechnology, vol. 33, pp. 139-142, Feb. 2015.

Konermann et al., "Genome-scale transcriptional activation by an engineered CRISPR-Cas9 complex", Nature, vol. 517, pp. 583-588, Jan. 29, 2015.

Nishimasu et al., "Crystal Structure of Cas9 in Complex with Guide RNA and Target DNA," Cell, vol. 156, Issue 5, pp. 935-949, Feb. 27, 2014.

Shalem, O. et al., "Genome-Scale CRISPR-Cas9 Knockout Screening in Human Cells", Science, vol. 343, Issue 6166, pp. 84-87, Dec. 12, 2013.

Canver et al., "BCL11A enhancer dissection by Cas9-mediated in situ saturating mutagenesis", Nature | vol. 527 | pp. 192-197, Nov. 12, 2015.

Belhaj et al., "Plant genome editing made easy: targeted mutagenesis in model and crop plants using the CRISPR/Cas system," Plant Methods, vol. 9, Issue 39, pp. 1-10, Published: Oct. 13, 2013.

Brooks et al., "Efficient Gene Editing in Tomato in the First Generation Using the Clustered Regularly Interspaced Short Palindromic Repeats/CRISPR-Associated9 System1," Plant Physiology, vol. 166, pp. 1292-1297, Nov. 2014.

Shan et al., "Targeted genome modification of crop plants using a CRISPR-Cas system," Nature Biotechnology, vol. 31, Issue 8, pp. 686-688, Aug. 2013.

(56) References Cited

OTHER PUBLICATIONS

Feng et al., "Efficient genome editing in plants using a CRISPR/Cas system," Cell Research, vol. 23, Issue 10, pp. 1229-1232, Oct. 2013.
Xie et al., "RNA-guided genome editing in plants using a CRISPR-Cas system," Mol Plant., vol. 6, Issue 6, pp. 1975-1983, Nov. 2013.
Xu et al., "Gene targeting using the Agrobacterium tumefaciens-mediated CRISPR-Cas system in rice," Rice, vol. 7, Issue 5, 2014.
Zhou et al., "Exploiting SNPs for biallelic CRISPR mutations in the outcrossing woody perennial Populus reveals 4-coumarate: CoA ligase specificity and redundancy," New Phytologist Forum 299, vol. 208, pp. 298-301, 2015.
Caliando et al., Targeted DNA degradation using a CRISPR device stably carried in the host genome, Nature Communications, 6:6989 | DOI: 10.1038/ncomms7989 | Published May 19, 2015.
Sugano et al., "CRISPR/Cas9-mediated targeted mutagenesis in the liverwort *Marchantia polymorpha* L.", Plant Cell Physiol., vol. 55, Issue 3, pp. 475-481, Accepted: Jan. 13, 2014.
Kabadi et al., "Multiplex CRISPR/Cas9-based genome engineering from a single lentiviral vector", Nucleic Acids Research, 2014, vol. 42, No. 19, e147, Published Online: Aug. 13, 2014.
Xing et al., "A CRISPR/Cas9 toolkit for multiplex genome editing in plants", BMC Plant Biology, vol. 14, Issue 327, pp. 1-12, 2014.
Ma et al., :A Robust CRISPR/Cas9 System for Convenient, High-Efficiency Multiplex Genome Editing in Monocot and Dicot Plants, Mol. Plant., vol. 8, Issue 8, pp. 1274-1284, Aug. 2015.
Lowder et al., "A CRISPR/Cas9 Toolbox for Multiplexed Plant Genome Editing and Transcriptional Regulation", Plant Physiol., vol. 169, pp. 971-985, Oct. 2015.
Harrison et al., "A CRISPR view of development", Genes & Development, vol. 28, pp. 1859-1872, 2014.
Jiang et al., "RNA-guided editing of bacterial genomes using CRISPR-Cas systems," Nature Biotechnology, vol. 31, No. 3, pp. 233-239, Published Online: Jan. 29, 2013.
Bikard et al., "Exploiting CRISPR-Cas nucleases to produce sequence-specific antimicrobials," Nature Biotechnology vol. 32, No. 11, pp. 1146-1150, Published Online: Oct. 5, 2014.
Yousef et al., "Temperate and lytic bacteriophages programmed to sensitize and kill antibiotic-resistant bacteria," Proc. Natl. Acad. Sci. USA, vol. 112, No. 23, pp. 7267-7272, Published Online: May 18, 2015.
Zhang C. et al., "Efficient editing of malaria parasite genome using the CRISPR/Cas9 system", MBio, vol. 5, Issue 4, pp. 1-9, Jul./Aug. 2014.
Ghorbal et al., "Genome editing in the human malaria parasite Plasmodium falciparumusing the CRISPR-Cas9 system," Nature Biotechnology, vol. 32, No. 8, pp. 819-821, Aug. 2014.
Shen et al., "Efficient gene disruption in diverse strains of Toxoplasma gondii using CRISPR/CAS9," MBio, vol. 5, Issue 3, pp. 1-11, May/Jun. 2014.
Sidik et al., "Efficient Genome Engineering of Toxoplasma gondii Using CRISPR/Cas9," PLoS One, vol. 9, Issue 6, e100450, Jun. 27, 2014.
Vyas et al., "A Candida albicans CRISPR system permits genetic engineering of essential genes and gene families," Science Advances, vol. 1, e1500248, pp. 1-6, Apr. 3, 2015.
Xu et al., "Both TALENs and CRISPR/Cas9 directly target the HBB IVS2-654 (C>T) mutation in β-thalassemia-derived iPSCs", Sci Rep., vol. 5, No. 12065, pp. 1-12, Jul. 9, 2015.
Wagner et al., "Efficient CRISPR-Cas9-mediated genome editing in Plasmodium falciparum", Nature Methods, vol. 11, Issue 9, pp. 915-918, Sep. 2014.
Yin et al., "Genome editing with Cas9 in adult mice corrects a disease mutation and phenotype", Nat Biotechnol., vol. 32, Issue 6, pp. 551-553, Jun. 2014.
Wang et al., "CCR5 Gene Disruption via Lentiviral Vectors Expressing Cas9 and Single Guided RNA Renders Cells Resistant to HIV-1 Infection", Plos One, vol. 9, Issue 12, pp. 1-26, e115987, Dec. 26, 2014.
Fine et al., "Trans-spliced Cas9 allows cleavage of HBB and CCR5 genes in human cells using compact expression cassettes", Sci. Rep., vol. 5, No. 10777, pp. 1-9, Jul. 1, 2015.
Li et al., "Inhibition of HIV-1 infection of primary CD4+ T-cells by gene editing of CCR5 using adenovirus-delivered CRISPR/Cas9", J Gen Virol., vol. 96, No. 8, pp. 2381-2393, Aug. 2015.
Holt, et al., "Human hematopoietic stem/progenitor cells modified by zinc-finger nucleases targeted to CCR5 control HIV-1 in vivo", Nature biotechnology, vol. 28, No. 8, pp. 839-847, Aug. 2010.
Li, et al., "Genomic Editing of the HIV-1 Coreceptor CCR5 in Adult Hematopoietic Stem and Progenitor Cells Using Zinc Finger Nucleases", Molecular Therapy, vol. 21, No. 6, pp. 1259-1269, Jun. 2013.
Mandal et al., "Efficient ablation of genes in human hematopoietic stem and effector cells using CRISPR/Cas9", Cell Stem Cell, vol. 15, No. 5, pp. 643-652, Nov. 6, 2014.
Lin et al., "The CRISPR/Cas9 System Facilitates Clearance of the Intrahepatic HBV Templates In Vivo", Mol Ther Nucleic Acids., pp. 1-7, e186, Aug. 19, 2014.
Dong et al., "Targeting hepatitis B virus cccDNA by CRISPR/Cas9 nuclease efficiently inhibits viral replication", Antiviral Res., vol. 118, pp. 110-117, Available Online: Apr. 3, 2015.
Liu et al. "Inhibition of hepatitis B virus by the CRISPR/Cas9 system via targeting the conserved regions of the viral genome", vol. 96, Issue 8, pp. 2252-2561, Accepted: Apr. 21, 2015.
Wang et al., "Histological outcome for chronic hepatitis B patients treated with entecavir vs lamivudine-based therapy", World J Gastroenterol., vol. 21, Issue 32, pp. 9598-9606, Aug. 28, 2015.
Karimova et al., "CRISPR/Cas9 nickase-mediated disruption of hepatitis B virus open reading frame S and X", Sci Rep., vol. 5, No. 13734, Sep. 3, 2015.
Song et al., "Improved hematopoietic differentiation efficiency of gene-corrected beta-thalassemia induced pluripotent stem cells by CRISPR/Cas9 system", Stem Cells Dev., vol. 24, Issue 9, pp. 1053-1065, May 1, 2015.
Doudna et al., "The new frontier of genomeengineering with CRISPR-Cas9", Science, vol. 346, Issue 6213, pp. 1258096-1-1258096-9, 2014.
Hsu et al., "Development and Applications of CRISPR-Cas9 for Genome Engineering", Cell, vol. 157, pp. 1262-1278, Jun. 5, 2014.
Hilton, I.B. et al. Epigenome editing by a CRISPR-Cas9-based acetyltransferase activates genes from promoters and enhancers, Nat. Biotechnol., vol. 33, Issue 5, pp. 510-517, May 2015.
Dominguez et al., "Beyond editing: repurposing CRISPR-Cas9 for precision genome regulation and interrogation", Nat. Rev. Mol. Cell Biol., vol. 17, pp. 5-15, Jan. 2016.
Nunez et al., "Chemical and Biophysical Modulation of Cas9 for Tunable Genome Engineering", ACS Chem. Biol., vol. 11, Issue 3, pp. 681-688, Feb. 9, 2016.
Oakes, et al., "Profiling of engineering hotspots identifies an allosteric CrlsPr-Cas9 switch", Nat. Biotechnol. vol. 34, No. 6, pp. 646-651, Jun. 2016.
Perez-Pinera, P. et al., "RNA-guided gene activation by CRISPR-Cas9-based transcription factors", Nat. Methods, vol. 10, Issue 10, pp. 973-976, Oct. 2013.
Balboa, D. et al., "Conditionally stabilized dCas9 activator for controlling gene expression in human cell reprogramming and differentiation", Stem Cell Rep, vol. 5, pp. 448-459, Sep. 8, 2015.
Zalatan, J.G. et al., "Engineering complex synthetic transcriptional programs with CRISPR RNA scaffolds", Cell, vol. 160, pp. 339-350, Jan. 15, 2015.
Nishimasu, H. et al., "Crystal structure of *Staphylococcus aureus* Cas9", Cell, vol. 162, pp. 1113-1126 , Aug. 27, 2015.
Davis, K.M., "Small molecule-triggered Cas9 protein with improved genome-editing specificity", Nat. Chem. Biol., vol. 11, Issue 5, pp. 316-318, May 2015.
Tsai et al., "Defining and improving the genome-wide specificities of CRISPR-Cas9 nucleases", Nat. Rev. Genet., vol. 17, pp. 300-312, May 2016.
Zuris, J.A. et al., "Cationic lipid-mediated delivery of proteins enables efficient protein-based genome editing in vitro and in vivo", Nat. Biotechnol., vol. 33, Issue 1, pp. 73-80, Published Online: Oct. 30, 2014.

(56) References Cited

OTHER PUBLICATIONS

Fu, Y. et al., "High-frequency off-target mutagenesis induced by CRISPR-Cas nucleases in human cells", Nat. Biotechnol., vol. 31, pp. 822-826, Published Online: Jun. 23, 2013.
Slaymaker, I.M. et al., "Rationally engineered Cas9 nucleases with improved specificity", Science vol. 351, pp. 84-88, Dec. 1, 2015.
Kleinstiver, B.P. et al., "High-fidelity CRISPR-Cas9 nucleases with no detectable genome-wide off-target effects", Nature, vol. 529, pp. 490-495, Jan. 28, 2016.
Cong et al., "Multiplex genome engineering using CRISPR/Cas systems", Science, vol. 339, Issue 6121, pp. 819-823, Feb. 15, 2013.
Wang et al., One-step generation of mice carrying mutations in multiple genes by CRISPR/Cas-mediated genome engineering, Cell, vol. 153, Issue 4, pp. 910-918, May 9, 2013.
Konermann et al., "Optical control of mammalian endogenous transcription and epigenetic states", Nature, vol. 500, No. 7463, pp. 472-476, Aug. 22, 2013.
Ran et al., "Double nicking by RNA-guided CRISPR Cas9 for enhanced genome editing specificity", vol. 154, Issue 6, pp. 1380-1389, Sep. 12, 2013.
Hsu et al., "DNA targeting specificity of RNA-guided Cas9 nucleases", Nat Biotechnol., vol. 31, Issue 9, pp. 827-832, Sep. 2013.
Ran et al., "Genome engineering using the CRISPR-Cas9 system", Nat Protoc., vol. 8, Issue 11, pp. 2281-2308, Nov. 2013.
Wu et al., "Genome-wide binding of the CRISPR endonuclease Cas9 in mammalian cells", Nat Biotechnol., vol. 32, Issue 7, pp. 670-676, Jul. 2014.
Wang et al., "Genetic screens in human cells using the CRISPR/Cas9 system", Science, vol. 343, Issue 6166, pp. 80-84, Jan. 3, 2014.
Doench et al., "Rational design of highly active sgrNAs for CrlsPr-Cas9-mediated gene inactivation", Nature Biotechnology, vol. 32, Issue 12, pp. 1262-1267, Published Online: Sep. 3, 2014.
Swiech et al., "In vivo interrogation of gene function in the mammalian brain using CRISPR-Cas9", Nature Biotechnology, vol. 33, pp. 102-106, published Online: Oct. 19, 2014.
Zetsche et al., "Cpf1 is a Single RNA-Guided Endonuclease of a Class 2 CRISPR-Cas System", Cell, vol. 163, Issue 3, pp. 1-26, Oct. 22, 2015.
Shmakov et al., "Discovery and Functional Characterization of Diverse Class 2 CRISPR-Cas Systems", Molecular Cell, vol. 60, Issue 3, pp. 385-397, 2015.
Abudayyeh et al., "C2c2 is a single-component programmable RNA-guided RNA-targeting CRISPR effector", Science, vol. 353, Issue 6299, Aug. 5, 2016.
Maji et al., "Multidimensional chemical control of CRISPR-Cas9", Nat. Chem. Biol., vol. 13, Issue 1, pp. 1-11, Jan. 2017.

* cited by examiner

TMP

4OHT

CMP8

A

B

CRISPR-Cas SYSTEMS HAVING DESTABILIZATION DOMAIN

RELATED APPLICATIONS AND INCORPORATION BY REFERENCE

This application is the U.S. National Stage of International Application No PCT/US2017/040115, filed Jun. 29, 2017, which claims the benefit of U.S. Provisional Patent Application No. 62/356,028, filed Jun. 29, 2016. The entire contents of the above-identified priority applications are hereby fully incorporated herein by reference.

Each of these patents, patent publications, and applications, and all documents cited therein or during their prosecution ("appln cited documents") and all documents cited or referenced in the appln cited documents, together with any instructions, descriptions, product specifications, and product sheets for any products mentioned therein are incorporated by reference herein, and may be employed in the practice of the invention. Moreover, all documents cited or referenced herein ("herein cited documents"), and all documents cited or referenced in herein cited documents, together with any manufacturer's instructions, descriptions, product specifications, and product sheets for any products mentioned herein or in any document incorporated by reference herein, are hereby incorporated herein by reference, and may be employed in the practice of the invention. All referenced documents are incorporated by reference to the same extent as if each individual document was specifically and individually indicated to be incorporated by reference.

STATEMENT AS TO FEDERALLY SPONSORED RESEARCH

This invention was made with government support under grant nos. MH100706 and MH110049 awarded by the National Institutes of Health. The government has certain rights in the invention.

REFERENCE TO AN ELECTRONIC SEQUENCE LISTING

The contents of the electronic sequence listing ("BROD-2730US_ST25.txt"; Size is 112,770 bytes and it was created on Aug. 20, 2021) is herein incorporated by reference in its entirety.

FIELD OF THE INVENTION

The present invention generally relates to Clustered Regularly Interspaced Short Palindromic Repeats (CRISPR), CRISPR enzyme or effector (e.g. Cas9, Cpf1, C2c1, C2c2, C2c3, Group 29/30, Cas13) and variants thereof, CRISPR-Cas or CRISPR system or CRISPR-Cas complex, components thereof, nucleic acid molecules, e.g., vectors, involving the same and uses of all of the foregoing, amongst other aspects.

BACKGROUND OF THE INVENTION

Recent advances in genome sequencing techniques and analysis methods have significantly accelerated the ability to catalog and map genetic factors associated with a diverse range of biological functions and diseases. Precise genome targeting technologies are needed to enable systematic reverse engineering of causal genetic variations by allowing selective perturbation of individual genetic elements, as well as to advance synthetic biology, biotechnological, and medical applications. Although genome-editing techniques such as designer zinc fingers, transcription activator-like effectors (TALEs), or homing meganucleases are available for producing targeted genome perturbations, there remains a need for new genome engineering technologies that employ novel strategies and molecular mechanisms and are affordable, easy to set up, scalable, and amenable to targeting multiple positions within the eukaryotic genome. This would provide a major resource for new applications in genome engineering and biotechnology.

RNA-guided endonucleases, such as Cas9, are easily targeted to any desired DNA or RNA locus using guide RNAs (gRNA), ushering in a slew of transformative technologies. For example, Cas9 has enabled facile and efficient induction of genomic alterations in cells and multiple organisms, and Cas9-based gene drives permit super-Mendelian self-propagation of such modifications (3). Furthermore, catalytically inactive CRISPR effectors, such as Cas9 (dCas9) can be fused to a wide range of effectors, including fluorescent proteins for genome imaging (4), enzymes that modify DNA or histones for epigenome editing (5), and transcription regulating domains for controlling endogenous gene expression (6).

Despite such advances, a critical need still exists for methods to precisely and switchably regulate CRISPR effector activities across multiple dimensions, including dose, target, and time (7). Finely-tuned control of CRISPR effector proteins levels is important, as high concentrations result in elevated off-target DNA cleavage. Rapid disabling of activity after a desired genomic modification is also essential (8), but the genome editing toolkit currently lacks highly transportable and modular methodologies that can be applied with minimal optimization to diverse RNA-guided nucleases. In the context of gene regulation, such as by dead CRISPR effector-based transcriptional activators, dose control of transcript induction is critical to ensure that physiologically relevant levels of gene expression are induced. Similarly useful would be the abilities to rapidly reverse transcript induction and to control the expression of multiple genes with orthogonal inducers.

Citation or identification of any document in this application is not an admission that such document is available as prior art to the present invention.

SUMMARY OF THE INVENTION

There exists a pressing need for alternative and robust systems and techniques for sequence targeting with a wide array of applications. This invention addresses this need and provides related advantages. The CRISPR/Cas or the CRISPR-Cas system (both terms may be used interchangeably throughout this application) does not require the generation of customized proteins to target specific sequences but rather a single Cas enzyme can be programmed by a short RNA molecule to recognize a specific DNA target, in other words the Cas enzyme can be recruited to a specific DNA target using said short RNA molecule. It will be appreciated that reference herein to the Cas protein includes any type of CRISPR/Cas system effector protein, such as without limitation Cas9, Cpf1, C2c1, C2c2, C2c3, Cas13, group 29/30, as well as variants or modified effectors, as also described herein elsewhere (e.g. catalytically inactive variants, nickases, variants having modified activity, stability and/or specificity, variants having altered PAM recognition, split effectors, etc.). As an alternative to the CRISPR/Cas system, the present invention also envisages the use of argonaute systems, as for instance detailed in Gao et al. (2016) "DNA-guided genome editing using the Natronobacterium gregoryi Argonaute" Nat Biotechnol. 2016 May 2. doi: 10.1038/nbt.3547. [Epub ahead of print]. It will be understood that whenever reference is made herein to CRISPR/Cas proteins or systems, such is equally applicable to argonautes. As a corollary, reference to a guide, guide polynucleotide, guide RNA (gRNA) may include guide RNA or guide DNA in the context of argonautes.

Adding the CRISPR-Cas system to the repertoire of genome sequencing techniques and analysis methods may significantly simplify the methodology and accelerate the ability to catalog and map genetic factors associated with a diverse range of biological functions and diseases. To utilize the CRISPR-Cas system effectively for genome editing without deleterious effects, it is critical to understand aspects of engineering and optimization of these genome engineering tools, which are aspects of the claimed invention. In some embodiments, the terms 'CRISPR enzyme' and 'nucleic acid-targeting effector protein' may be used interchangeably. Indeed, these terms and 'effector protein' may also be used interchangeably, and as indicated above, also include argonautes. The terms 'CRISPR Cas' or 'CRISPR Cas system' and 'nucleic acid-targeting system' may be used interchangeably. The terms 'CRISPR complex' and 'nucleic acid-targeting complex' be used interchangeably. Where reference is made herein to a 'target locus,' for example a target locus of interest, then it will be appreciated that this may be used interchangeably with the phrase 'sequences associated with or at a target locus of interest.' Unless otherwise apparent, or explicitly defined, the term CRISPR-enzyme includes any variant or modified protein, such as including catalytically inactive CRISPR-enzymes, nickases, etc.

The present invention is in particular captured by the appended claims, which are incorporated herein by reference.

In an aspect, the invention relates to a fusion protein comprising one or more destabilization domains (DD), one or more adaptor proteins capable of binding to a guide, including but not limited to a guide RNA or guide DNA or a RNA- or DNA-guided nuclease complex or system, and optionally one or more functional domains.

In certain embodiments, the guide or the guide RNA or guide DNA of a RNA- or DNA-guided nuclease complex or system is a CRISPR/Cas complex or system.

In certain embodiments, the guide or the RNA or guide DNA of a RNA- or DNA-guided nuclease complex or system is an argonaute system.

It will be understood that whenever reference is made herein to "CRISPR/Cas system", such preferably includes the presence of the fusion protein of the invention as described herein.

It will be understood that "adaptor" (protein) as used herein preferably does not include in its scope "CRISPR enzyme", "Cas", "CRISPR effector", and the like, or any variant or modified version thereof as described herein. Hence, an "adaptor protein" is preferably not a CRISPR protein. An adaptor protein is preferably not Cas9, Cas13, Cpf1, C2c1, C2c2, C2c3, Cas13, or group 29/30. In certain embodiments, an adaptor protein is also not an argonaute.

In further aspects, the invention relates to polynucleic acid sequences encoding such fusion protein, as well as vectors or vector systems comprising such polynucleic acid sequences, and compositions, complexes, or systems comprising the fusion proteins, polynucleic acid sequences, or vectors (systems). Such compositions, complexes, or systems may further comprise one or more suitable guides, e.g., guide polynucleotides, guide RNAs or guide DNAs and/or one or more suitable RNA- or DNA-guided nuclease or modified variant thereof, as described herein elsewhere (e.g. catalytically inactive variants). The present inventors have surprisingly demonstrated that providing a destabilizing domain on a fusion protein, as described herein, capable of binding to a guide, provides better control of the CRISPR/Cas system than providing the DD (only) on the CRISPR enzyme. Lower off-target events were detected, as well as improved conditional or inducible activity was observed with the novel systems of the invention, i.e. making use of the fusion protein according to the invention as described herein for targeted polynucleic acid modifications.

The organization of the different constituents in the fusion protein is of no particular importance. By means of example, and without limitation, the fusion protein may comprise one or more N-terminal DD and one or more C-terminal adaptor proteins. The fusion protein may comprise one or more C-terminal DD and one or more N-terminal adaptor proteins. The fusion protein may comprise one or more C-terminal DD and one or more N-terminal DD flanking one or more adaptor proteins. The fusion protein may comprise one or more C-terminal adaptor proteins and one or more N-terminal adaptor proteins flanking one or more DD. In certain embodiments, the fusion protein comprises one or more (heterologous) functional domains. These functional domains may be N-terminal, C-terminal, or internal and flanked by an adaptor protein and/or DD. In certain embodiments, the fusion protein comprises one or more N-terminal DD, one or more C-terminal functional domain, both of which are flanking one or more internal adaptor protein.

In certain embodiments, adapter proteins mediate association of functional domains with a CRISPR protein or enzyme complex, for example by binding to an aptamer incorporated in to the guide sequence. Suitable adaptor proteins include, but are not limited to bacteriophage coat proteins such as MS2, PP7, Qβ, F2, GA, fr, JP501, M12, R17, BZ13, JP34, JP500, KU1, M11, MX1, TW18, VK, SP, FI, ID2, NL95, TW19, AP205, ϕCb5, ϕCb8r, ϕCb12r, ϕCb23r, 7s and PRR1, which advantageously can bind RNA aptamers. Suitable corresponding aptamers are known in the art. As further guidance, and without limitation, reference is made to Witherell et al. (Prog Nucleic Acid Res Mol Biol; 1991; 40:185-220); Stockley et al. (Nucleic Acid Res; 1995; 23(13):2512-8); Lim et al. (Nucleic Acid Research; 2002; 30(19):4138-4144).

By way of example specific, non-limiting embodiments, of the invention, preferred in some instances, may include

- DD-adaptor protein
- DD-adaptor protein-DD
- DD-DD-adaptor protein
- DD-DD-adaptor protein-DD
- Functional Domain-adaptor protein-DD
- DD-adaptor protein-Functional Domain
- DD-adaptor protein-Functional Domain-DD
- DD-Functional Domain-adaptor protein
- DD-adaptor protein-adaptor protein-DD
- DD-adaptor protein-adaptor protein-Functional Domain-DD
- DD-Functional Domain-adaptor protein-adaptor protein-Functional Domain-DD and so forth, including all re-arrangement possibilities. Further examples, preferred in some embodiments, include:
- ER50.MS2.p65.HSF1 (i.e. where ER50=DD: MS2=adaptor protein; and p65.HSF1=Functional Domain)

DHFR.PP7.VP64 (i.e where DHFR=DD; PP7=adaptor protein; and VP64=Functional Domain)

DHFR.MS2-Functional Domain (such as those described herein)

ER50.PP7—Functional Domain (such as those described herein).

In some embodiments, two or more fusion proteins may be used, each comprising a different adaptor protein, so as to bind to different (engineered) guides adapted for each particular adaptor protein. Each of these two or more fusion proteins may therefore bind to different guides which may in turn target two or more different nucleotide sequences of interest. If each of these two or more fusion proteins is fused to a functional domain, then the two or more different nucleotide sequences of interest may be treated orthogonally, for example up-regulating one or more and repressing another or others (through use of appropriate activator and repressor Functional Domains, respectively). Of course, the two or more different nucleotide sequences of interest may also all be activated or all be repressed by fusion of just activators or repressors to the DD-adaptor protein fusion protein.

Where an adaptor protein, such as MS2 or PP7, are mentioned below, it will be appreciated that this includes reference a fusion protein comprising said adaptor protein and at least one DD, and optionally comprising at least one Functional Domain, unless otherwise apparent.

In an aspect, the invention provides activatable ligands of destabilizing domains, i.e. DD ligands that can be activated or deactivated. In the "on" state, such ligands bind to and stabilize a DD. In the "off" state, the ligands are inhibited from binding to the DD. Preferably the DD-ligands are small molecules. Small molecule ligands and be advantageously provided in cell or organism at a high concentration by comparison to the DD and CRISPR system components. In an embodiment of the invention, a DD-ligand comprises a cleavable moiety, which blocks or inhibits binding of the DD ligand to its counterpart DD. When the cleavable moiety is removed, the DD-ligand is capable of binding to and stabilizing the DD. In an embodiment of the invention, the cleavable moiety of the activatable DD ligand is photocleavable or photolytic. In an embodiment of the invention, the DD-ligand is active and cleavable or otherwise degradable such that once cleaved, the cleavage products do not effectively bind to the DD or stabilize the DD. In an embodiment of the invention, the active or activated DD-ligand is photocleavable or photolytic. According to the invention, photocleavable or photolytic means subject to cleavage by EM radiation. In a non-limiting embodiment of the invention, the EM radiation is at a visible wavelength. In a non-limiting embodiment of the invention, the EM radiation is near infrared (IR). In a non-limiting embodiment, the EM radiation is at a wavelength that does not damage cells or tissues. In a non-limiting embodiment, the EM is locally upconverted, i.e., an upconverting mechanism such as an upconverting nanoparticle (UCNP) is employed to change the wavelength of the EM radiation in the vicinity of the activatable DD-ligand. See, Upconversion Nanoparticles in Theranostics, Theranostics Special Issue, Gang Han and Guanying Chen, eds.

In an aspect, the invention relates to a method of modifying a polynucleic acid target locus or introducing a polynucleic acid locus event, comprising delivering to or contacting with a polynucleic acid target locus or a host cell comprising said locus the fusion protein, polynucleic acid, vector, or composition according to the invention as described herein. As also described herein elsewhere, the modification or locus event may for instance be a polynucleic acid (DNA or RNA) single strand or double strand break. The modification or locus event may be modulation of transcription or translation (e.g. increased or decreased transcription or translation), epigenetic modulation (e.g. methylation), increase or decrease of polynucleic acid stability, location, etc.

In an aspect, the invention relates to a host cell comprising or capable of expressing the fusion protein of the invention as described herein, optionally further including gRNA or gDNA (including any variant as described herein) and/or effector protein (e.g. CRISPR protein or argonaute, including any variant as described herein). In a further aspect, the invention relates to the progeny of such host cell. In a further aspect, the invention relates to an organism, such as a prokaryotic or eukaryotic organisms comprising or capable of expressing the fusion protein of the invention as described herein, or comprising a host cell as described herein. It will be understood that also gRNA or gDNA (including any variant as described herein) and/or effector protein (e.g. CRISPR protein or argonaute, including any variant as described herein) may be comprised or expressed in such organism. The organism may be a transgenic organism. Which may be human or animal or non-human, or non-animal. The organism may also be a plant.

In an aspect, the invention relates to the use of the fusion protein of the invention as described herein for therapy, as also described herein elsewhere.

In certain embodiments, a guide (e.g., gRNA or gDNA) when used with the fusion protein of the invention may be a functionalized guide. Such guide may advantageously be bound by the fusion protein of the invention, in particular by the adaptor protein of the fusion protein. To this extent, in certain embodiments, the guide is modified and comprises adaptor binding domains, such as for instance aptamers, such as RNA or DNA aptamers, which may advantageously be provided in loop sections of the guide, as also described herein elsewhere.

In certain embodiments, the DD is a degron. A degron is a portion of a protein that is important in regulation of protein degradation rates. Known degrons include short amino acid sequences, structural motifs, and exposed amino acids (often Lysine or Arginine) located anywhere in the protein. In fact, some proteins can even contain multiple degrons. Degrons are present in a variety of organisms, from the N-degrons (see N-end Rule) first characterized in yeast to the PEST sequence of mouse ornithine decarboxylase. Degrons have been identified in prokaryotes as well as eukaryotes. While there are many types of different degrons, and a high degree of variability even within these groups, degrons are all similar for their involvement in regulating the rate of a protein's degradation. Much like protein degradation (see proteolysis) mechanisms are categorized by their dependence or lack thereof on Ubiquitin, a small protein involved in proteasomal protein degradation, degrons are also be referred to as "Ubiquitin-dependent" or "Ubiquitin-independent".

In certain embodiments, the invention provides a non-naturally occurring or engineered CRISPR enzyme or argonaute ("effector protein") associated with at least one destabilization domain (DD); and, for shorthand purposes, such a non-naturally occurring or engineered effector protein associated with at least one destabilization domain (DD) is herein termed a "DD-effector protein", e.g. "DD-CRISPR enzyme". In one aspect, the invention provides an engineered, non-naturally occurring DD-CRISPR-Cas system comprising a fusion protein comprising one or more destabilization domains, one or more adaptor proteins capable of binding to a RNA-guided or DNA-guided (endo)nuclease (such as CRISPR enzyme or argonaute) system guide RNA (gRNA) or guide DNA (gDNA), and optionally one or more functional domains, a CRISPR enzyme or argonaute, wherein the CRISPR enzyme is preferably a Cas9, Cpf1, C2c1, C2c2, C2c3, Cas13, or group 29/30 protein. "DD" before a term such as "DD-CRISPR-Cas complex" means a CRISPR-Cas complex comprising the Cas, gRNA or gDNA that targets a nucleic acid molecule such as a DNA or RNA molecule, and fusion protein of the invention, wherein at least the fusion protein comprises or is associated with a DD, optionally wherein a Cas protein also having at least one destabilization domain associated therewith. The nucleic acid molecule, e.g., DNA or RNA molecule can encode a gene product. In some embodiments the effector protein may cleave the DNA molecule encoding the gene product. In some embodiments expression of the gene product is altered. In certain preferred embodiments, the effector protein is catalytically (substantially) inactive, as defined herein elsewhere. The effector protein, the fusion protein, and the guide RNA do not naturally occur together. The invention comprehends the guide RNA comprising a guide sequence fused to a tracr sequence where applicable (i.e. where required for proper functioning of the CRISPR enzyme). The invention further comprehends coding for the fusion protein and/or effector protein being codon optimized for expression in a eukaryotic cell. In a preferred embodiment the eukaryotic cell is a mammalian cell and in a more preferred embodiment the mammalian cell is a human cell. Expression of the gene product may be decreased or increased. The CRISPR enzyme may form part of a CRISPR-Cas system, which further comprises the fusion protein of the invention and a guide RNA (gRNA) comprising a guide sequence capable of hybridizing to a target sequence in a polynucleic acid locus of interest in a cell. In some embodiments, the functional CRISPR-Cas system binds to the target sequence. In some embodiments, the functional CRISPR-Cas system may edit the target sequence, e.g., the target sequence may comprise a polynucleic acid locus, and in some embodiments there may be an alteration of gene expression. In some embodiments, the functional CRISPR-Cas system may comprise further functional domains. In some embodiments, the invention provides a method for altering or modifying expression of a gene product. The method may comprise introducing into a cell containing a target nucleic acid, e.g., DNA or RNA molecule, or containing and expressing a target nucleic acid, e.g., DNA or RNA molecule; for instance, the target nucleic acid may encode a gene product or provide for expression of a gene product (e.g., a regulatory sequence).

In some embodiments, the CRISPR enzyme is a Cas9, such as an Sp Cas9 (*Streptococcus pyogenes* Cas9). In some embodiments, the CRISPR enzyme is an Sa Cas9 (*Staphylococcus aureus* Cas9). In some embodiments, the CRISPR enzyme is a Cj Cas9 (*Campylobacter jejuni*). In some embodiments, the CRISPR enzyme is an St Cas9 (*Streptococcus thermophilus*) or Fn Cas9 (*Francisella novicida* Cas9), although other orthologs are envisaged. Sp and Sa Cas9s are particularly preferred, in some embodiments. In some embodiments, the CRISPR enzyme is Cpf1, such as AsCpf1 (Acidaminococcus sp. Cpf1) or LbCpf1 (Lachnospiraceae bacterium ND2006). In some embodiments, the CRISPR enzyme is Cas13 including but not limited to Cas13a (also known as C2c2) and Cas13b, non-limiting examples of which include LshC2c2 (Leptotrichia shahii C2c2), LwC2c2 (Leptotrichia *wadei*, e.g. strain F0279), and (LnC2c2 (*Listeria* newyorkensis, e.g. strain FSL M6-0635 C2c2).

In some embodiments, the CRISPR enzyme cleaves both strands of DNA to produce a double strand break (DSB). In some embodiments, the CRISPR enzyme is a nickase. In some embodiments, the CRISPR enzyme is a dual nickase. In some embodiments, the CRISPR enzyme cleaves RNA. In some embodiments, the CRISPR enzyme is a catalytically (substantially) inactive CRISPR enzyme, e.g. deadCas9, e.g., a Cas9 having substantially no nuclease activity, e.g., no more than 5% nuclease activity as compared with a wild-type Cas9 or Cas9 not having had mutations to it.

In some general embodiments, the CRISPR enzyme is associated with one or more functional domains. In some more specific embodiments, the CRISPR enzyme is a catalytically (substantially) inactive CRISPR enzyme, e.g. deadCas9 and/or is associated with one or more functional domains.

In some embodiments, the DD-CRISPR enzyme comprises a Rec2 or HD2 truncation. In some embodiments, the CRISPR enzyme is associated with a DD by way of a fusion protein. In some embodiments, the CRISPR enzyme is fused to the DD. In other words, the DD may be associated with the CRISPR enzyme by fusion with said CRISPR enzyme. In some embodiments, the enzyme may be considered to be a modified CRISPR enzyme, wherein the CRISPR enzyme is fused to at least one destabilization domain (DD).

In some embodiments, the DD may be associated to the fusion protein of the invention and optionally the CRISPR enzyme via a connector protein, for example using a system such as a marker system such as the streptavidin-biotin system. As such, provided is a fusion of a fusion protein or CRISPR enzyme with a connector protein specific for a high affinity ligand for that connector, whereas the DD is bound to said high affinity ligand. For example, streptavidin may be the connector fused to the fusion protein or CRISPR enzyme, while biotin may be bound to the DD. Upon co-localization, the streptavidin will bind to the biotin, thus connecting the fusion protein or optionally additionally the CRISPR enzyme to the DD. For simplicity, a fusion of the fusion protein or CRISPR enzyme and the DD is preferred in some embodiments. In some embodiments, the fusion may be to the N-terminal end of the fusion protein or CRISPR enzyme. In some embodiments, at least one DD is fused to the N-terminus of the fusion protein or CRISPR enzyme. In some embodiments, the fusion may be to the C-terminal end of the fusion protein or CRISPR enzyme. In some embodiments, at least one DD is fused to the C-terminus of the fusion protein or CRISPR enzyme. In some embodiments, one DD may be fused to the N-terminal end of the fusion protein or CRISPR enzyme with another DD fused to the C-terminal of the fusion protein or CRISPR enzyme. In some embodiments, the fusion protein or CRISPR enzyme is associated with at least two DDs and wherein a first DD is fused to the N-terminus of the fusion protein or CRISPR enzyme and a second DD is fused to the C-terminus of the fusion protein or CRISPR enzyme, the first and second DDs being the same or different. In some embodiments, the fusion may be to the N-terminal end of the DD. In some embodiments, the fusion may be to the C-terminal end of the DD. In some embodiments, the fusion may between the C-terminal end of the fusion protein or CRISPR enzyme and the N-terminal end of the DD. In some embodiments, the fusion may between the C-terminal end of the DD and N-terminal end of the fusion protein or CRISPR enzyme. Less background was observed with a DD comprising at least one N-terminal fusion than a DD comprising at least one C terminal fusion. Combining N- and C-terminal fusions had the least background but lowest overall activity. Advantageously a DD is provided through at least one N-terminal fusion or at least one N terminal fusion plus at least one C-terminal fusion. And of course, a DD can be provided by at least one C-terminal fusion.

In some embodiments, the DD is ER50. A corresponding stabilizing ligand (also called "small molecule") for this DD is, in some embodiments, 4-hydroxytamoxifen (4HT). As such, in some embodiments, one of the at least one DDs is ER50 and a stabilizing ligand therefor is 4HT or CMP8. In some embodiments, the DD is DHFR50. A corresponding stabilizing ligand for this DD is, in some embodiments, trimethoprim (TMP). As such, in some embodiments, one of the at least one DDs is DHFR50 and a stabilizing ligand therefor is TMP. In some embodiments, the DD is ER50. A corresponding stabilizing ligand for this DD is, in some embodiments, CMP8. CMP8 may therefore be an alternative stabilizing ligand to 4HT in the ER50 system. While it may be possible that CMP8 and 4HT can/should be used in a competitive matter, some cell types may be more susceptible to one or the other of these two ligands, and from this disclosure and the knowledge in the art the skilled person can use CMP8 and/or 4HT.

In some embodiments, one or two DDs may be fused to the N-terminal end of the fusion protein or CRISPR enzyme with one or two DDs fused to the C-terminal of the fusion protein or CRISPR enzyme. In some embodiments, the at least two DDs are associated with the fusion protein or CRISPR enzyme and the DDs are the same DD, i.e. the DDs are homologous. Thus, both (or two or more) of the DDs could be ER50 DDs. This is preferred in some embodiments. Alternatively, both (or two or more) of the DDs could be DHFR50 DDs. This is also preferred in some embodiments. In some embodiments, the at least two DDs are associated with the fusion protein or CRISPR enzyme and the DDs are different DDs, i.e. the DDs are heterologous. Thus, one of the DDS could be ER50 while one or more of the or any other DDs could be DHFR50. Having two or more DDs which are heterologous may be advantageous as it would provide a greater level of degradation control. A tandem fusion of more than one DD at the N or C-term may enhance degradation; and such a tandem fusion can be, for example ER50-ER50-adaptor protein (optionally further fused to a (heterologous) functional domain) or DHFR-DHFR-adaptor protein (optionally further fused to a (heterologous) functional domain) and optionally ER50-ER50-Cas9 or DHFR-DHFR-Cas9. High levels of degradation would occur in the absence of either stabilizing ligand, intermediate levels of degradation would occur in the absence of one stabilizing ligand and the presence of the other (or another) stabilizing ligand, while low levels of degradation would occur in the presence of both (or two of more) of the stabilizing ligands. Control may also be imparted by having an N-terminal ER50 DD and a C-terminal DHFR50 DD.

In some embodiments, the fusion of the fusion/adaptor protein or CRISPR enzyme with the DD comprises a linker between the DD and the CRISPR enzyme. In some embodiments, the linker is a GlySer linker. In some embodiments, the fusion protein and/or CRISPR enzyme further comprises at least one Nuclear Export Signal (NES). In some embodiments, the fusion protein and/or CRISPR enzyme comprises two or more NESs. In some embodiments, the fusion protein and/or CRISPR enzyme comprises at least one Nuclear Localization Signal (NLS). This may be in addition to an NES. In some embodiments, the fusion protein and/or CRISPR enzyme comprises or consists essentially of or consists of a localization (nuclear import or export) signal as, or as part of, the linker between the fusion protein and/or CRISPR enzyme and the DD. HA or Flag tags are also within the ambit of the invention as linkers. Applicants use NLS and/or NES as linker and also use Glycine Serine linkers as short as GS up to $(GGGGS)_3$ (SEQ ID NO: 1). More than one linker may be used and these may frame a DD on either side (i.e. both N' an C' terminal ends).

In an aspect, the present invention provides a polynucleotide encoding the fusion protein and/or CRISPR enzyme and associated DD. In some embodiments, the encoded fusion protein and/or CRISPR enzyme and associated DD are operably linked to a first regulatory element. In some embodiments, a DD is also encoded and is operably linked to a second regulatory element. Advantageously, the DD here is to "mop up" the stabilizing ligand and so it is advantageously the same DD (i.e. the same type of Domain) as that associated with the enzyme, e.g., as herein discussed (with it understood that the term "mop up" is meant as discussed herein and may also convey performing so as to contribute or conclude activity). In some embodiments, the first regulatory element is a promoter and may optionally include an enhancer. In some embodiments, the second regulatory element is a promoter and may optionally include an enhancer. In some embodiments, the first regulatory element is an early promoter. In some embodiments, the second regulatory element is a late promoter. In some embodiments, the second regulatory element is or comprises or consists essentially of an inducible control element, optionally the tet system, or a repressible control element, optionally the tetr system. An inducible promoter may be favorable e.g. rTTA to induce tet in the presence of doxycycline.

In an aspect, the present invention provides a stabilizing ligand for a DD (i.e. a DD ligand) which is capable of being activated or deactivated. In an embodiment of the invention, the DD ligand is activated or inactivated in vivo. In an embodiment of the invention, the DD ligand is activated or inactivated in situ. In an embodiment of the invention, the DD ligand is electromagnetically activated or inactivated, including but not limited to visible light and infrared. In an embodiment of the invention, the activatable DD ligand is selected taking into account its half life such that when activated, the DD ligand binds to a CRISPR system-associated DD, thereby promoting the activity of the CRISPR system, followed by reduced activity of the CRISPR system as the DD ligand is degraded. In one embodiment, In certain embodiments, a photocaging system based on o-nitrobenzyl is employed. In one embodiment a 6-nitroveratryl carbamate (NVOC)-based photocage is employed. In another embodiment, a boron-dipyrromethene (BODIPY)-based photocage is employed.

In an aspect, the present invention provides a means for delivering the CRISPR-Cas complex of the invention or polynucleotides discussed herein, e.g., particle(s) delivering component(s) of the complex, vector(s) comprising the polynucleotide(s) discussed herein (e.g., encoding the CRISPR enzyme, the DD; providing RNA of the CRISPR-Cas complex). In some embodiments, the vector may be a plasmid or a viral vector such as AAV, or lentivirus. Transient transfection with plasmids, e.g., into HEK cells may be advantageous, especially given the size limitations of AAV and that while SpCas9 fits into AAV, one may reach an upper limit with additional coding as to the association with the DD(s).

Also provided is a model that constitutively expresses the fusion protein and/or CRISPR enzyme (and optionally associated DD). The organism may be a transgenic and may have been transfected the present vectors or may be the offspring of an organism so transfected. In a further aspect, the present invention provides compositions comprising the fusion protein and/or CRISPR enzyme and associated DD or the polynucleotides or vectors described herein. Also provided are CRISPR-Cas systems comprising guide RNAs.

Also provided is a method of treating a subject, e.g., a subject in need thereof, comprising inducing gene editing by transforming the subject with the polynucleotide encoding the system or any of the present vectors and administering stabilizing ligand to the subject. A suitable repair template may also be provided, for example delivered by a vector comprising said repair template. Also provided is a method of treating a subject, e.g., a subject in need thereof, comprising inducing transcriptional activation or repression by transforming the subject with the polynucleotide encoding the present system or any of the present vectors, wherein said polynucleotide or vector encodes or comprises fusion protein of the invention and/or the catalytically inactive CRISPR enzyme and optionally one or more associated functional domains and/or gRNA; the method further comprising administering a stabilizing ligand to the subject. These methods may also include delivering and/or expressing excess DD to the subject. Where any treatment is occurring ex vivo, for example in a cell culture, then it will be appreciated that the term 'subject' may be replaced by the phrase "cell or cell culture."

Compositions comprising the present system for use in said method of treatment are also provided. A separate composition may comprise the stabilizing ligand. A kit of parts may be provided including such compositions. Use of the present system in the manufacture of a medicament for such methods of treatment are also provided. Use of the present system in screening is also provided by the present invention, e.g., gain of function screens. Cells which are artificially forced to overexpress a gene are be able to down regulate the gene over time (re-establishing equilibrium) e.g. by negative feedback loops. By the time the screen starts the unregulated gene might be reduced again. Using an inducible CRISPR protein activator allows one to induce transcription right before the screen and therefore minimizes the chance of false negative hits. Accordingly, by use of the instant invention in screening, e.g., gain of function screens, the chance of false negative results may be minimized.

In one aspect, the invention provides an engineered, non-naturally occurring CRISPR-Cas (or argonaute) system comprising a fusion protein of the invention, a Cas protein or argonaute, and a guide RNA (or guide DNA) that targets a DNA or RNA molecule encoding a gene product in a cell, whereby the guide RNA/DNA targets the DNA/RNA molecule encoding the gene product and the Cas or argonaute protein cleaves the DNA or RNA molecule encoding the gene product, whereby expression of the gene product is altered; and, wherein the Cas protein or argonaute and the guide RNA (or DNA) do not naturally occur together. The invention comprehends the guide RNA comprising a guide sequence fused to a tracr sequence, if appropriate or necessary). In an embodiment of the invention the Cas protein is a type II CRISPR-Cas protein and is a Cas9, Cpf1, C2c1, C2c2, C2c3, Cas13, or group 29/30 protein. The invention further comprehends coding for the Cas protein being codon optimized for expression in a eukaryotic cell. In a preferred embodiment the eukaryotic cell is a mammalian cell and in a more preferred embodiment the mammalian cell is a human cell. In a further embodiment of the invention, the expression of the gene product is decreased.

In another aspect, the invention provides an engineered, non-naturally occurring vector system comprising one or more vectors comprising (a) a first regulatory element operably linked to a CRISPR-Cas system guide RNA or an argonaute system guide DNA or guide RNA that targets a DNA or RNA molecule encoding a gene product; (b) a second regulatory element operably linked coding for a Cas protein or argonaute; and (c) a fusion protein of the invention as described herein. Components (a), (b), and (c) may be located on same or different vectors of the system. The guide targets the polynucleic acid molecule encoding the gene product in a cell and the effector protein may cleave or otherwise modify (e.g. transcriptional or translational modulation) the polynucleic acid molecule encoding the gene product (it may cleave one or both strands or have substantially no nuclease activity), whereby expression of the gene product is altered; and, wherein the effector protein and the guide do not naturally occur together. The invention comprehends the guide RNA comprising a guide sequence fused to a tracr sequence where appropriate. In an embodiment of the invention the effector protein is a type II CRISPR-Cas protein. The invention further comprehends coding for the effector protein being codon optimized for expression in a eukaryotic cell. In a preferred embodiment the eukaryotic cell is a mammalian cell and in a more preferred embodiment the mammalian cell is a human cell. In a further embodiment of the invention, the expression of the gene product is decreased.

In one aspect, the invention provides a vector system comprising one or more vectors. In some embodiments, the system comprises: (a) a first regulatory element operably linked to a tracr mate sequence and one or more insertion sites for inserting one or more guide sequences upstream of the tracr mate sequence, wherein when expressed, the guide sequence directs sequence-specific binding of a CRISPR complex to a target sequence in a eukaryotic cell, wherein the CRISPR complex comprises a CRISPR enzyme complexed with (1) the guide sequence that is hybridized to the target sequence, and (2) the tracr mate sequence that is hybridized to the tracr sequence (where applicable); (b) a second regulatory element operably linked to an enzyme-coding sequence encoding said CRISPR enzyme comprising at least one nuclear localization sequence and/or at least one NES; and (c) a fusion protein according to the invention; wherein components (a), (b), and (c) are located on the same or different vectors of the system. In some embodiments, component (a) further comprises the tracr sequence (whenever required) upstream or downstream of the tracr mate sequence under the control of the first regulatory element. In some embodiments, component (a) further comprises two or more guide sequences operably linked to the first regulatory element, wherein when expressed, each of the two or more guide sequences direct sequence specific binding of a CRISPR complex to a different target sequence in a eukaryotic cell. In some embodiments, the system comprises the tracr sequence under the control of a third regulatory element, such as a polymerase III promoter. In some embodiments, the tracr sequence exhibits at least 50%, 60%, 70%, 80%, 90%, 95%, or 99% of sequence complementarity along the length of the tracr mate sequence when optimally aligned. Determining optimal alignment is within the purview of one of skill in the art. For example, there are publically and commercially available alignment algorithms and programs such as, but not limited to, Clustal W, Smith-Waterman in matlab, Bowtie, Geneious, Biopython and SeqMan. In some embodiments, the CRISPR complex comprises one or more nuclear localization sequences and/or one or more NES of sufficient strength to drive accumulation of said CRISPR complex in a detectable amount in or out of the nucleus of a eukaryotic cell. Without wishing to be bound by theory, it is believed that a nuclear localization sequence and/or NES is not necessary for CRISPR complex activity in eukaryotes, but that including such sequences enhances activity of the system, especially as to targeting nucleic acid molecules in the nucleus and/or having molecules exit the nucleus. In some embodiments, the CRISPR enzyme is a type II CRISPR system enzyme and is a Cas9, Cpf1, C2c1, C2c2, C2c3, Cas13, or group 29/30 enzyme. In some embodiments, the Cas9 enzyme is derived from *S. pneumoniae, S. pyogenes, S. thermophiles, F. novicida* or *S. aureus* Cas9. The CRISPR protein may include further mutations or alterations or be a chimeric CRISPR protein. The enzyme may be a CRISPR protein homolog or ortholog. In some embodiments, the CRISPR enzyme is codon-optimized for expression in a eukaryotic cell. In some embodiments, the CRISPR enzyme directs cleavage of one or two strands at the location of the target sequence. In some embodiments, the CRISPR enzyme lacks DNA or RNA strand cleavage activity. In some embodiments, the first regulatory element is a polymerase III promoter. In some embodiments, the second regulatory element is a polymerase II promoter. In some embodiments, the guide sequence is at least 15, 16, 17, 18, 19, 20, 25 nucleotides, or between 10-30, or between 15-25, or between 15-20 nucleotides in length. In general, and throughout this specification, the term "vector" refers to a nucleic acid molecule capable of transporting another nucleic acid to which it has been linked. Vectors include, but are not limited to, nucleic acid molecules that are single-stranded, double-stranded, or partially double-stranded; nucleic acid molecules that comprise one or more free ends, no free ends (e.g., circular); nucleic acid molecules that comprise DNA, RNA, or both; and other varieties of polynucleotides known in the art. One type of vector is a "plasmid," which refers to a circular double stranded DNA loop into which additional DNA segments can be inserted, such as by standard molecular cloning techniques. Another type of vector is a viral vector, wherein virally-derived DNA or RNA sequences are present in the vector for packaging into a virus (e.g., retroviruses, replication defective retroviruses, adenoviruses, replication defective adenoviruses, and adeno-associated viruses). Viral vectors also include polynucleotides carried by a virus for transfection into a host cell. Certain vectors are capable of autonomous replication in a host cell into which they are introduced (e.g., bacterial vectors having a bacterial origin of replication and episomal mammalian vectors). Other vectors (e.g., non-episomal mammalian vectors) are integrated into the genome of a host cell upon introduction into the host cell, and thereby are replicated along with the host genome. Moreover, certain vectors are capable of directing the expression of genes to which they are operatively-linked. Such vectors are referred to herein as "expression vectors." Common expression vectors of utility in recombinant DNA techniques are often in the form of plasmids.

Recombinant expression vectors can comprise a nucleic acid of the invention in a form suitable for expression of the nucleic acid in a host cell, which means that the recombinant expression vectors include one or more regulatory elements, which may be selected on the basis of the host cells to be used for expression, that is operatively-linked to the nucleic acid sequence to be expressed. Within a recombinant expression vector, "operably linked" is intended to mean that the nucleotide sequence of interest is linked to the regulatory element(s) in a manner that allows for expression of the nucleotide sequence (e.g., in an in vitro transcription/translation system or in a host cell when the vector is introduced into the host cell).

The term "regulatory element" is intended to include promoters, enhancers, internal ribosomal entry sites (IRES), and other expression control elements (e.g., transcription termination signals, such as polyadenylation signals and poly-U sequences). Such regulatory elements are described, for example, in Goeddel, GENE EXPRESSION TECHNOLOGY: METHODS IN ENZYMOLOGY 185, Academic Press, San Diego, Calif. (1990). Regulatory elements include those that direct constitutive expression of a nucleotide sequence in many types of host cell and those that direct expression of the nucleotide sequence only in certain host cells (e.g., tissue-specific regulatory sequences). A tissue-specific promoter may direct expression primarily in a desired tissue of interest, such as muscle, neuron, bone, skin, blood, specific organs (e.g., liver, pancreas), or particular cell types (e.g., lymphocytes). Regulatory elements may also direct expression in a temporal-dependent manner, such as in a cell-cycle dependent or developmental stage-dependent manner, which may or may not also be tissue or cell-type specific. In some embodiments, a vector comprises one or more pol III promoter (e.g., 1, 2, 3, 4, 5, or more pol III promoters), one or more pol II promoters (e.g., 1, 2, 3, 4, 5, or more pol II promoters), one or more pol I promoters (e.g., 1, 2, 3, 4, 5, or more pol I promoters), or combinations thereof. Examples of pol III promoters include, but are not limited to, U6 and H1 promoters. Examples of pol II promoters include, but are not limited to, the retroviral Rous sarcoma virus (RSV) LTR promoter (optionally with the RSV enhancer), the cytomegalovirus (CMV) promoter (optionally with the CMV enhancer) [see, e.g., Boshart et al, Cell, 41:521-530 (1985)], the SV40 promoter, the dihydrofolate reductase promoter, the β-actin promoter, the phosphoglycerol kinase (PGK) promoter, and the EF1α promoter. Also encompassed by the term "regulatory element" are enhancer elements, such as WPRE; CMV enhancers; the R-U5' segment in LTR of HTLV-I (Mol. Cell. Biol., Vol. 8(1), p. 466-472, 1988); SV40 enhancer; and the intron sequence between exons 2 and 3 of rabbit β-globin (Proc. Natl. Acad. Sci. USA., Vol. 78(3), p. 1527-31, 1981). It will be appreciated by those skilled in the art that the design of the expression vector can depend on such factors as the choice of the host cell to be transformed, the level of expression desired, etc. A vector can be introduced into host cells to thereby produce transcripts, proteins, or peptides, including fusion proteins or peptides, encoded by nucleic acids as described herein (e.g., clustered regularly interspersed short palindromic repeats (CRISPR) transcripts, proteins, enzymes, mutant forms thereof, fusion proteins thereof, etc.).

Advantageous vectors include lentiviruses and adeno-associated viruses, and types of such vectors can also be selected for targeting particular types of cells.

In one aspect, the invention provides a vector comprising a regulatory element operably linked to a fusion protein of the invention and/or an enzyme-coding sequence encoding a CRISPR enzyme comprising one or more nuclear localization sequences and/or NES. In some embodiments, said regulatory element drives transcription of the fusion protein and/or CRISPR enzyme in a eukaryotic cell such that said fusion protein and/or CRISPR enzyme accumulates in a detectable amount in the nucleus of the eukaryotic cell and/or is exported from the nucleus. In some embodiments, the regulatory element is a polymerase II promoter. In some embodiments, the CRISPR enzyme is a type II CRISPR system enzyme and is a Cas9, Cpf1, C2c1, C2c2, C2c3, Cas13, or group 29/30 enzyme.

In one aspect, the invention provides a eukaryotic host cell comprising (a) a first regulatory element operably linked to a tracr mate sequence and one or more insertion sites for inserting one or more guide sequences upstream of the tracr mate sequence, wherein when expressed, the guide sequence directs sequence-specific binding of a CRISPR complex to a target sequence in a eukaryotic cell, wherein the CRISPR complex comprises a CRISPR enzyme complexed with (1) the guide sequence that is hybridized to the target sequence, and (2) the tracr mate sequence that is hybridized to the tracr sequence (where applicable); and/or (b) a second regulatory element operably linked to an enzyme-coding sequence encoding said CRISPR enzyme comprising at least one nuclear localization sequence and/or NES; and/or (c) a fusion protein according to the invention as described herein. In some embodiments, the host cell comprises components (a) and (b) and (c). In some embodiments, component (a), component (b), component (c), or any combination thereof are stably integrated into a genome of the host eukaryotic cell. In some embodiments, component (a) further comprises the tracr sequence upstream or downstream of the tracr mate sequence (if applicable) under the control of the first regulatory element. In some embodiments, component (a) further comprises two or more guide sequences operably linked to the first regulatory element, wherein when expressed, each of the two or more guide sequences direct sequence specific binding of a CRISPR complex to a different target sequence in a eukaryotic cell. In some embodiments, the eukaryotic host cell further comprises a regulatory element, such as a polymerase III promoter, operably linked to said tracr sequence. In some embodiments, the tracr sequence exhibits at least 50%, 60%, 70%, 80%, 90%, 95%, or 99% of sequence complementarity along the length of the tracr mate sequence when optimally aligned. In some embodiments, the first regulatory element is a polymerase III promoter. In some embodiments, the second regulatory element is a polymerase II promoter. In some embodiments, the guide sequence is at least 15, 16, 17, 18, 19, 20, 25 nucleotides, or between 10-30, or between 15-25, or between 15-20 nucleotides in length. In an aspect, the invention provides a non-human eukaryotic organism; preferably a multicellular eukaryotic organism, comprising a eukaryotic host cell according to any one of the described embodiments. In other aspects, the invention provides a eukaryotic organism; preferably a multicellular eukaryotic organism, comprising a eukaryotic host cell according to any one of the described embodiments. The organism in some embodiments of these aspects may be an animal; for example a mammal such as a mouse. Also, the organism may be an arthropod such as an insect, for instance, a fly (especially fruit flies including model organisms such as *Drosophila melanogaster* as well as agricultural pests such as olive fly) or a mosquito. Indeed, insect and arthropod models, disease vectors and pests are preferred, including moths, mosquitoes, boring insects, fruit flies etc. The organism may be a nematode such as *C. elegans*. The organism also may be a plant. Further, the organism may be a fungus.

With respect to use of the CRISPR-Cas system generally, mention is made of the documents, including patent applications, patents, and patent publications cited throughout this disclosure as embodiments of the invention can be used as in those documents. CRISPR-Cas system(s) (e.g., single or multiplexed) can be used in conjunction with recent advances in crop genomics. Such CRISPR-Cas system(s) can be used to perform efficient and cost effective plant gene or genome interrogation or editing or manipulation—for instance, for rapid investigation and/or selection and/or interrogations and/or comparison and/or manipulations and/or transformation of plant genes or genomes; e.g., to create, identify, develop, optimize, or confer trait(s) or characteristic(s) to plant(s) or to transform a plant genome. There can accordingly be improved production of plants, new plants with new combinations of traits or characteristics or new plants with enhanced traits. Such CRISPR-Cas system(s) can be used with regard to plants in Site-Directed Integration (SDI) or Gene Editing (GE) or any Near Reverse Breeding (NRB) or Reverse Breeding (RB) techniques. With respect to use of the CRISPR-Cas system in plants, mention is made of the University of Arizona website "CRISPR-PLANT" www.genome.arizona.edu/crispr/) (supported by Penn State and AGI). Embodiments of the invention can be used in genome editing in plants or where RNAi or similar genome editing techniques have been used previously; see, e.g., Nekrasov, "Plant genome editing made easy: targeted mutagenesis in model and crop plants using the CRISPR/Cas system," Plant Methods 2013, 9:39 (doi:10.1186/1746-4811-9-39); Brooks, "Efficient gene editing in tomato in the first generation using the CRISPR/Cas9 system," Plant Physiology September 2014 pp 114.247577; Shan, "Targeted genome modification of crop plants using a CRISPR-Cas system," Nature Biotechnology 31, 686-688 (2013); Feng, "Efficient genome editing in plants using a CRISPR/Cas system," Cell Research (2013) 23:1229-1232. doi: 10.1038/cr.2013.114; published online 20 Aug. 2013; Xie, "RNA-guided genome editing in plants using a CRISPR-Cas system," Mol Plant. 2013 November; 6(6):1975-83. doi: 10.1093/mp/sstl19. Epub 2013 Aug 17; Xu, "Gene targeting using the *Agrobacterium tumefaciens*-mediated CRISPR-Cas system in rice," Rice 2014, 7:5 (2014), Zhou et al., "Exploiting SNPs for biallelic CRISPR mutations in the outcrossing woody perennial *Populus* reveals 4-coumarate: CoA ligase specificity and Redundancy," New Phytologist (2015) (Forum) 1-4 (available online only at www.newphytologist.com); Caliando et al, "Targeted DNA degradation using a CRISPR device stably carried in the host genome, NATURE COMMUNICATIONS 6:6989, DOI: 10.1038/ncomms7989, www.nature.com/naturecommunications DOI: 10.1038/ncomms7989; U.S. Pat. No. 6,603,061-*Agrobacterium*-Mediated Plant Transformation Method; U.S. Pat. No. 7,868,149—Plant Genome Sequences and Uses Thereof and US 2009/0100536—Transgenic Plants with Enhanced Agronomic Traits, all the contents and disclosure of each of which are herein incorporated by reference in their entirety. In the practice of the invention, the contents and disclosure of Morrell et al "Crop genomics: advances and applications," Nat Rev Genet. 2011 Dec. 29; 13(2):85-96; each of which is incorporated by reference herein including as to how herein embodiments may be used as to plants. Accordingly, reference herein to animal cells may also apply, mutatis mutandis, to plant cells unless otherwise apparent.

In one aspect, the invention provides a kit comprising one or more of the components described herein. In some embodiments, the kit comprises a vector system and instructions for using the kit.

In one aspect, the invention provides a method of modifying a target polynucleotide in a eukaryotic cell. In some embodiments, the method comprises allowing a CRISPR or argonaute complex to bind to the target polynucleotide, e.g., to effect cleavage of said target polynucleotide, thereby modifying the target polynucleotide, or otherwise modifying the target locus, such as transcriptionally or translationally modulating gene expression, wherein the CRISPR or argonaute complex comprises a fusion protein of the invention, a CRISPR or argonaute enzyme complexed with a guide sequence hybridized to a target sequence within said target polynucleotide, wherein said guide sequence is linked to a tracr mate sequence (in case of CRISPR systems) which in turn hybridizes to a tracr sequence where required. In some embodiments, said cleavage comprises cleaving one or two strands at the location of the target sequence by said CRISPR enzyme. In some embodiments, said cleavage results in increased or decreased transcription or translation of a target gene. In some embodiments, the method further comprises repairing said cleaved target polynucleotide by homologous recombination with an (exogenous) template polynucleotide, wherein said repair results in a mutation comprising an insertion, deletion, or substitution of one or more nucleotides of said target polynucleotide. In some embodiments, said mutation results in one or more amino acid changes in a protein expressed from a gene comprising the target sequence. In some embodiments, the method further comprises delivering one or more vectors to said eukaryotic cell, wherein the one or more vectors drive expression of one or more of: the fusion protein of the invention, the CRISPR enzyme or argonaute, the guide sequence linked to the tracr mate sequence, and the tracr sequence. In some embodiments, said vectors are delivered to the eukaryotic cell in a subject. In some embodiments, said modifying takes place in said eukaryotic cell in a cell culture. In some embodiments, the method further comprises isolating said eukaryotic cell from a subject prior to said modifying. In some embodiments, the method further comprises returning said eukaryotic cell and/or cells derived therefrom to said subject.

In one aspect, the invention provides a method of modifying expression of a polynucleotide in a eukaryotic cell. In some embodiments, the method comprises allowing a CRISPR or argonaute complex to bind to the polynucleotide such that said binding results in increased or decreased expression of said polynucleotide; wherein the complex comprises a effector protein complexed with a guide sequence hybridized to a target sequence within said polynucleotide, wherein said guide sequence is linked to a tracr mate sequence which in turn hybridizes to a tracr sequence where applicable, and a fusion protein of the invention. In some embodiments, the method further comprises delivering one or more vectors to said eukaryotic cells, wherein the one or more vectors drive expression of one or more of: the fusion protein of the invention, the effector protein, the guide sequence linked to the tracr mate sequence, and the tracr sequence (if required).

In one aspect, the invention provides a method of generating a model eukaryotic cell comprising a mutated disease gene. In some embodiments, a disease gene is any gene associated an increase in the risk of having or developing a disease. In some embodiments, the method comprises (a) introducing one or more vectors into a eukaryotic cell, wherein the one or more vectors drive expression of one or more of: a fusion protein of the invention, a CRISPR or argonaute enzyme, a guide sequence linked to a tracr mate sequence, and a tracr sequence (if required); and (b) allowing a CRISPR or argonaute complex to bind to a target polynucleotide, e.g., to effect cleavage of the target polynucleotide within said disease gene, wherein the CRISPR or argonaute complex comprises the CRISPR or argonaute enzyme complexed with (1) the guide sequence that is hybridized to the target sequence within the target polynucleotide, and (2) the tracr mate sequence that is optionally hybridized to the tracr sequence, and (3) a fusion protein of the invention, thereby generating a model eukaryotic cell comprising a mutated disease gene. In some embodiments, said cleavage comprises cleaving one or two strands at the location of the target sequence by said CRISPR/argonaute enzyme. In some embodiments, said cleavage results in decreased transcription of a target gene. In some embodiments, the method further comprises repairing said cleaved target polynucleotide by homologous recombination with an (exogenous) template polynucleotide, wherein said repair results in a mutation comprising an insertion, deletion, or substitution of one or more nucleotides of said target polynucleotide. In some embodiments, said mutation results in one or more amino acid changes in a protein expression from a gene comprising the target sequence.

In one aspect, the invention provides a method for developing a biologically active agent that modulates a cell signaling event associated with a disease gene. In some embodiments, a disease gene is any gene associated an increase in the risk of having or developing a disease. In some embodiments, the method comprises (a) contacting a test compound with a model cell of any one of the described embodiments; and (b) detecting a change in a readout that is indicative of a reduction or an augmentation of a cell signaling event associated with said mutation in said disease gene, thereby developing said biologically active agent that modulates said cell signaling event associated with said disease gene.

In one aspect, the invention provides a recombinant polynucleotide comprising a guide sequence upstream of a tracr mate sequence, wherein the guide sequence when expressed directs sequence-specific binding of a CRISPR or argonaute complex to a corresponding target sequence present in a eukaryotic cell. In some embodiments, the target sequence is a viral sequence present in a eukaryotic cell. In some embodiments, the target sequence is a proto-oncogene or an oncogene.

In one aspect the invention provides for a method of selecting one or more cell(s) by introducing one or more mutations in a gene in the one or more cell (s), the method comprising: introducing one or more vectors into the cell (s), wherein the one or more vectors drive expression of one or more of: a CRISPR or argonaute enzyme, a guide sequence linked to a tracr mate sequence, a tracr sequence (if required), a fusion protein of the invention, and an editing template; wherein the editing template comprises the one or more mutations that abolish CRISPRor argonaute enzyme cleavage; allowing homologous recombination of the editing template with the target polynucleotide in the cell(s) to be selected; allowing a CRISPR or argonaute complex to bind to a target polynucleotide to effect cleavage of the target polynucleotide within said gene, wherein the CRISPR or argonaute complex comprises the CRISPR or argonaute enzyme complexed with (1) the guide sequence that is hybridized to the target sequence within the target polynucleotide, and (2) the tracr mate sequence that is hybridized to the tracr sequence (if required), and (3) a fusion protein of the invention; wherein binding of the complex to the target polynucleotide induces cell death, thereby allowing one or more cell(s) in which one or more mutations have been introduced to be selected. In another aspect of the invention the cell to be selected may be a eukaryotic cell. Aspects of the invention allow for selection of specific cells without requiring a selection marker or a two-step process that may include a counter-selection system. The cell(s) may be prokaryotic or eukaryotic cells.

With respect to mutations of the CRISPR enzyme, when the enzyme is not SpCas9, mutations may be made at any or all residues corresponding to positions 10, 762, 840, 854, 863 and/or 986 of SpCas9 (which may be ascertained for instance by standard sequence comparison tools). In particular, any or all of the following mutations are preferred in SpCas9: D10A, E762A, H840A, N854A, N863A and/or D986A; as well as conservative substitution for any of the replacement amino acids is also envisaged. In an aspect the invention provides as to any or each or all embodiments herein-discussed wherein the CRISPR enzyme comprises at least one or more, or at least two or more mutations, wherein the at least one or more mutation or the at least two or more mutations is as to D10, E762, H840, N854, N863, or D986 according to SpCas9 protein, e.g., D10A, E762A, H840A, N854A, N863A and/or D986A as to SpCas9, or N580 according to SaCas9, e.g., N580A as to SaCas9, or any corresponding mutation(s) in a Cas9 of an ortholog to Sp or Sa, or the CRISPR enzyme comprises at least one mutation wherein at least H840 or N863A as to Sp Cas9 or N580A as to Sa Cas9 is mutated; e.g., wherein the CRISPR enzyme comprises H840A, or D10A and H840A, or D10A and N863A, according to SpCas9 protein, or any corresponding mutation(s) in a Cas9 of an ortholog to Sp protein or Sa protein. By means of further guidance, if the CRISPR protein is Cpf1, a modified Cpf1 may comprise one or more mutations D917A, E1006, E1028, D1227, D1255A, N1257, according to FnCpf1 protein or a corresponding position in an ortholog. The amino acid mutations in may be selected from D908A, E993A, D1263A according to AsCpf1 protein or a corresponding position in an ortholog. The amino acid mutations may be selected from D832A, E925A, D947A or D1180A according to LbCpf1 protein or a corresponding position in an ortholog. In an aspect the invention provides a herein-discussed composition wherein the Cpf1 enzyme comprises two or more mutations selected from the group consisting of D917A, E1006A, E1028A, D1227A, D1255A, N1257A, D917A, E1006A, E1028A, D1227A, D1255A and N1257A according to FnCpf1 protein or any corresponding ortholog or D908A, E993A, D1263A according to AsCpf1 protein or a corresponding position in an ortholog or D832A, E925A, D947A or D1180A according to LbCpf1 protein or a corresponding position in an ortholog. In an aspect the invention provides a herein-discussed composition, wherein the CRISPR enzyme comprises D917, or E1006 and D917, or D917 and D1255, according to FnCpf1 protein or any corresponding ortholog or D908, E993, D1263 according to AsCpf1 protein or a corresponding position in an ortholog or D832, E925, D947 or D1 180A according to LbCpf1 protein or a corresponding position in an ortholog. By means of further guidance, if the CRISPR protein is C2c2, a modified C2c2 may comprise one or more mutations corresponding to R597, H602, R1278 and H1283 (referenced to Lsh C2c2 amino acids and C2c2 consensus numbering), such as mutations R597A, H602A, R1278A and H1283A, or the corresponding amino acid residues in Lsh C2c2 orthologues.

In a further aspect, the invention involves a computer-assisted method for identifying or designing potential compounds to fit within or bind to CRISPR-Cas system or a functional portion thereof or vice versa (a computer-assisted method for identifying or designing potential CRISPR-Cas systems or a functional portion thereof for binding to desired compounds) or a computer-assisted method for identifying or designing potential CRISPR-Cas systems (e.g., with regard to predicting areas of the CRISPR-Cas system to be able to be manipulated—for instance, based on crystal structure data or based on data of Cas orthologs, or with respect to where a functional group such as an activator or repressor can be attached to the CRISPR-Cas system, or as to Cas truncations or as to designing nickases), said method comprising: using a computer system, e.g., a programmed computer comprising a processor, a data storage system, an input device, and an output device, the steps of. (a) inputting into the programmed computer through said input device data comprising the three-dimensional co-ordinates of a subset of the atoms from or pertaining to the CRISPR-Cas crystal structure, e.g., in the CRISPR-Cas system binding domain or alternatively or additionally in domains that vary based on variance among Cas orthologs or as to Cas or as to nickases or as to functional groups, optionally with structural information from CRISPR-Cas system complex(es), thereby generating a data set; (b) comparing, using said processor, said data set to a computer database of structures stored in said computer data storage system, e.g., structures of compounds that bind or putatively bind or that are desired to bind to a CRISPR-Cas system or as to Cas orthologs (e.g., as Cas or as to domains or regions that vary amongst Cas orthologs) or as to the CRISPR-Cas crystal structure or as to nickases or as to functional groups; (c) selecting from said database, using computer methods, structure(s)—e.g., CRISPR-Cas structures that may bind to desired structures, desired structures that may bind to certain CRISPR-Cas structures, portions of the CRISPR-Cas system that may be manipulated, e.g., based on data from other portions of the CRISPR-Cas crystal structure and/or from Cas orthologs, truncated Cas, novel nickases or particular functional groups, or positions for attaching functional groups to or mutating CRISPR-Cas systems; (d) constructing, using computer methods, a model of the selected structure(s); and (e) outputting to said output device the selected structure(s); and optionally synthesizing one or more of the selected structure(s); and further optionally testing said synthesized selected structure(s) as or in a CRISPR-Cas system; or, said method comprising: providing the co-ordinates of at least two atoms of the CRISPR-Cas crystal structure, e.g., at least two atoms of the herein cited materials or co-ordinates of at least a sub-domain of the CRISPR-Cas crystal structure ("selected co-ordinates"), providing the structure of a candidate comprising a binding molecule or of portions of the CRISPR-Cas system that may be manipulated, e.g., based on data from other portions of the CRISPR-Cas crystal structure and/or from Cas orthologs, or the structure of functional groups, and fitting the structure of the candidate to the selected co-ordinates, to thereby obtain product data comprising CRISPR-Cas structures that may bind to desired structures, desired structures that may bind to certain CRISPR-Cas structures, portions of the CRISPR-Cas system that may be manipulated, truncated Cas, novel nickases, or particular functional groups, or positions for attaching functional groups or for mutating CRISPR-Cas systems, with output thereof, and optionally synthesizing compound(s) from said product data and further optionally comprising testing said synthesized compound(s) as or in a CRISPR-Cas system. The testing can comprise analyzing the CRISPR-Cas system resulting from said synthesized selected structure(s), e.g., with respect to binding, or performing a desired function. The output in the foregoing methods can comprise data transmission, e.g., transmission of information via telecommunication, telephone, video conference, mass communication, e.g., presentation such as a computer presentation (e.g. POWERPOINT), internet, email, documentary communication such as a computer program (e.g. WORD)

document and the like. Accordingly, the invention also comprehends computer readable media containing: atomic co-ordinate data according to the herein cited materials, said data defining the three dimensional structure of CRISPR-Cas or at least one sub-domain thereof, or structure factor data for CRISPR-Cas, said structure factor data being derivable from the herein cited materials. The computer readable media can also contain any data of the foregoing methods. The invention further comprehends methods a computer system for generating or performing rational design as in the foregoing methods containing either: atomic co-ordinate data according to herein cited materials, said data defining the three dimensional structure of CRISPR-Cas or at least one sub-domain thereof, or structure factor data for CRISPR-Cas, said structure factor data being derivable from the atomic co-ordinate data of herein cited materials. The invention further comprehends a method of doing business comprising providing to a user the computer system or the media or the three dimensional structure of CRISPR-Cas or at least one sub-domain thereof, or structure factor data for CRISPR-Cas, said structure set forth in and said structure factor data being derivable from the atomic co-ordinate data of herein cited materials, or the herein computer media or a herein data transmission.

A "binding site" or an "active site" comprises or consists essentially of or consists of a site (such as an atom, a functional group of an amino acid residue or a plurality of such atoms and/or groups) in a binding cavity or region, which may bind to a compound such as a nucleic acid molecule, which is/are involved in binding. By "fitting", is meant determining by automatic, or semi-automatic means, interactions between one or more atoms of a candidate molecule and at least one atom of a structure of the invention, and calculating the extent to which such interactions are stable. Interactions include attraction and repulsion, brought about by charge, steric considerations and the like. Various computer-based methods for fitting are described further By "root mean square (or rms) deviation", we mean the square root of the arithmetic mean of the squares of the deviations from the mean. By a "computer system", is meant the hardware means, software means and data storage means used to analyze atomic coordinate data. The minimum hardware means of the computer-based systems of the present invention typically comprises a central processing unit (CPU), input means, output means and data storage means. Desirably a display or monitor is provided to visualize structure data. The data storage means may be RAM or means for accessing computer readable media of the invention. Examples of such systems are computer and tablet devices running Unix, Windows or Apple operating systems. By "computer readable media", is meant any medium or media, which can be read and accessed directly or indirectly by a computer e.g., so that the media is suitable for use in the above-mentioned computer system. Such media include, but are not limited to: magnetic storage media such as floppy discs, hard disc storage medium and magnetic tape; optical storage media such as optical discs or CD-ROM; electrical storage media such as RAM and ROM; thumb drive devices; cloud storage devices and hybrids of these categories such as magnetic/optical storage media.

In particular embodiments of the invention, the conformational variations in the crystal structures of the CRISPR-Cas system or of components of the CRISPR-Cas provide important and critical information about the flexibility or movement of protein structure regions relative to nucleotide (RNA or DNA) structure regions that may be important for CRISPR-Cas system function. The structural information provided for Cas9 (e.g., *S. pyogenes* Cas9) in the herein cited materials may be used to further engineer and optimize the herein CRISPR-Cas system and this may be extrapolated to interrogate structure-function relationships in other CRISPR enzyme, e.g., CRISPR enzyme systems as well, e.g., other Type II CRISPR enzyme systems (for instance other Type II CRISPR enzyme systems). The invention comprehends optimized functional CRISPR-Cas enzyme systems. In particular the CRISPR enzyme comprises one or more mutations that converts it to a DNA binding protein to which functional domains exhibiting a function of interest may be recruited or appended or inserted or attached. In certain embodiments, the CRISPR enzyme comprises one or more mutations which include but are not limited to D10A, E762A, H840A, N854A, N863A or D986A (based on the amino acid position numbering of a *S. pyogenes* Cas9) and/or the one or more mutations is in a RuvC1 or HNH domain of the CRISPR enzyme and/or is a mutation as otherwise as discussed herein. In some embodiments, the CRISPR enzyme has one or more mutations in a catalytic domain, wherein when transcribed, the tracr mate sequence hybridizes to the tracr sequence and the guide sequence directs sequence-specific binding of a CRISPR complex to the target sequence, and wherein the enzyme further comprises a functional domain (e.g., for providing the destabilized domain or contributing thereto). The structural information provided in the herein cited materials allows for interrogation of gRNA interaction with the target DNA and the CRISPR enzyme (e.g., Cas9) permitting engineering or alteration of gRNA structure to optimize functionality of the entire CRISPR-Cas system. For example, loops of the gRNA may be extended, without colliding with the Cas protein by the insertion of adaptor proteins that can bind to RNA. These adaptor proteins can further recruit effector proteins or fusions which comprise one or more functional domains. The functional domain may comprise, consist essentially of or consist of a transcriptional activation domain, e.g. VP64. The functional domain may comprise, consist essentially of a transcription repression domain, e.g., KRAB. In some embodiments, the transcription repression domain is or comprises or consists essentially of SID, or concatemers of SID (e.g. SID4X). In some embodiments, the functional domain comprise, consist essentially of an epigenetic modifying domain, such that an epigenetic modifying enzyme is provided. In some embodiments, the functional domain comprise, consist essentially of an activation domain, which may be the P65 activation domain. In certain embodiments, the functional domain may comprise a translational activation domain or a translation repression domain (e.g. eIF, such as eIF1, eIF2, eIF3, eIF4, eIF5, eIF6 including any of their subunits).

Aspects of the invention encompass a non-naturally occurring or engineered composition that may comprise a guide RNA or guide DNA comprising a guide sequence capable of hybridizing to a target sequence in a genomic locus of interest in a cell and a CRISPR or argonaute enzyme and a fusion protein of the invention, one or both of which may comprise at least one or more nuclear localization sequences, wherein the CRISPR enzyme comprises one or two or more mutations, such that the enzyme has altered or diminished nuclease activity compared with the wild type enzyme, wherein at least one loop of the gRNA is modified by the insertion of distinct RNA sequence(s) that bind to one or more adaptor proteins, and wherein the adaptor protein further recruits one or more heterologous functional domains. In an embodiment of the invention the CRISPR enzyme comprises one or two or more mutations in a residue selected from the group comprising, consisting essentially of, or consisting of D10, E762, H840, N854, N863, or D986. In a further embodiment the CRISPR enzyme comprises one or two or more mutations selected from the group comprising D1OA, E762A, H840A, N854A, N863A or D986A. In another embodiment, the functional domain provided on the fusion protein of the invention and/or effector protein comprise, consist essentially of a transcriptional activation domain, e.g., VP64. In another embodiment, the functional domain comprise, consist essentially of a transcriptional repressor domain, e.g., KRAB domain, SID domain or a SID4X domain. In embodiments of the invention, the one or more heterologous functional domains have one or more activities selected from the group comprising, consisting essentially of, or consisting of methylase activity, demethylase activity, transcription activation activity, transcription repression activity, transcription release factor activity, histone modification activity, RNA cleavage activity and nucleic acid binding activity. In further embodiments of the invention the cell is a eukaryotic cell or a mammalian cell or a human cell. In further embodiments, the adaptor protein is selected from the group comprising, consisting essentially of, or consisting of MS2, PP7, Qβ, F2, GA, fr, JP501, M12, R17, BZ13, JP34, JP500, KU1, M11, MX1, TW18, VK, SP, FI, ID2, NL95, TW19, AP205, ϕCb5, ϕCb8r, ϕCb12r, ϕCb23r, 7s, PRR1. In another embodiment, the at least one loop of the gRNA is tetraloop and/or loop2. An aspect of the invention encompasses methods of modifying a genomic locus of interest to change gene expression in a cell by introducing into the cell any of the compositions described herein.

An aspect of the invention is that the above elements are comprised in a single composition or comprised in individual compositions. These compositions may advantageously be applied to a host to elicit a functional effect on the genomic level.

In general, the gRNA are modified in a manner that provides specific binding sites (e.g., aptamers) for adapter proteins optionally comprising one or more functional domains (e.g., via fusion protein) to bind to. The modified gRNA are modified such that once the gRNA forms a CRISPR complex (i.e. CRISPR enzyme binding to gRNA and target) the adapter proteins bind and, the functional domain on the adapter protein is positioned in a spatial orientation which is advantageous for the attributed function to be effective. For example, if the functional domain comprise, consist essentially of a transcription activator (e.g., VP64 or p65), the transcription activator is placed in a spatial orientation which allows it to affect the transcription of the target. Likewise, a transcription repressor will be advantageously positioned to affect the transcription of the target and a nuclease (e.g., Fok1) will be advantageously positioned to cleave or partially cleave the target. Alternatively a transcriptional repressor may be provided. Alternatively, a translational activator or repressor may be provided.

By means of example, and without limitation, the MS2-binding loop ggccAACATGAGGATCACC-CATGTCTGCAGggcc (SEQ ID NO: 2) may replace nucleotides +13 to +16 and nucleotides+53 to +56 of the standard gRNA backbone. The resulting structure is an gRNA scaffold in which the tetraloop and stemloop 2 sequences have been replaced by an MS2 binding loop. Without being bound by theory, the tetraloop and stemloop 2 were selected for replacement based on information obtained from the Cas9/RNA/DNA crystal structure. Specifically, the tetraloop and stemloop 2 were found to protrude from the Cas9 protein in such a way which suggested that adding an MS2 binding loop would not interfere with any Cas9 residues. Additionally, the proximity of the tetraloop and stemloop 2 sites to the DNA suggested that localization to these locations would result in a high degree of interaction between the DNA and any recruited protein, such as a transcriptional activator.

In some embodiments, the guide is modified such that nucleotides corresponding to +13 to +16 and/or nucleotides corresponding to +53 to +56 of the standard gRNA backbone are replaced by the distinct RNA.

Both insertions in the tetraloop and stem loop 2 are effective. In this particular example, the most efficient combination uses an insertion of aptamers (in this case MS2 loops, but we later show that other aptamers may be used as well) in both in the tetraloop and in loop 2 of the gRNA. We also show that this may be used in combination with a dCas9-vp64 and MS2-vp64 construct, in other words where the CRISPR enzyme is also modified. This new activator design was found to mediate much higher target gene upregulation compared to the previous design.

It is also envisaged that other activators may be used. For instance, it was shown that an improved effector, e.g. Cas9, activator architecture consists of a gRNA with MS2 loop insertions in the tetraloop and loop 2 in combination with either MS2-VP64 and dCas9-P65 or MS2-P65 and dCas9-VP64. In other words, 2 different activators can be used, one associated with the CRISPR enzyme (Cas9) and one with the guide via the aptamer. Applicants showed increased effectiveness of this design compared to the standard C-terminal fusion of VP64 to Cas9. Applicants further confirmed the hypothesis that a combination of two different activation domains could improve target gene activation (via synergy, e.g. by recruiting different epigenetic modulators, general transcription factors and co-activators). Applicants also determined that the alternative guide architecture optimized for CRISPR/Cas9 imaging in: Chen, Baohui, et al. "Dynamic Imaging of Genomic Loci in Living Human Cells by an Optimized CRISPR/Cas System." Cell 155.7 (2013): 1479-1491 did not exhibit any improvement over the standard architecture.

Of course, it is envisaged that the activators in these instances may be replaced with repressors.

Applicants also looked at the arrangement of the distinct RNA sequences (preferably aptamers) within the stem loop 2 and tetraloop of the modified guides of the present invention. GC tracts are preferred in some embodiments. The GC tract may be GC or GGGGC or CCCCG or CGCC or compliments thereof or a mixture of C and G from 2 nucleotides up to, for example 10, 15 or 20 nucleotides. In the particular instance, the MS2-binding loop sequence: ggccAACATGAGGATCACCCATGTCTGCAGggcc (SEQ ID NO: 2) replaced nucleotides+13 to +16 of the standard gRNA backbone, as above. Of interest here, the sequence CGCC replaced nucleotides+49 to +52 of the standard gRNA backbone. The sequence GGCG also replaced nucleotides+57 to +60 of the standard gRNA backbone. The tetraloop MS2-binding loop insertion was designed with the same rationale as described herein. Essentially, CGCC and GGCG sequences replace the stem portion of stemloop 2. The increased base-pairing strength of the CGCC-GGCG stem compared to the original ACTT-AAGT stem was hypothesized to provide additional stability to the stemloop 2 structure, thereby increasing gRNA performance or longevity.

Accordingly, in some embodiments, one or more GC tracts may replace stem portion of stemloop 2. In some embodiments, one or more GC tracts may replace stem portion of the tetraloop.

When reference is made to the stemloop 2 or tetraloop being modified (including replaced) by distinct RNA sequence(s) then this preferably encompasses modification (or replacement) of the 3 or 4 nucleotides of the guide that were found to protrude beyond the enzyme-gRNA-DNA complex. Suitable numbering will be apparent based on the secondary structure of the guide on its own, i.e. by looking for the loops corresponding to the stem loop 2 and the tetraloop (or by engineering them in), but exemplary number is around +13-16 and/or either side of +49-52 (with one or two nucleotides leeway either side possible, such as +48-52, or +49 to 53 for example).

A particularly preferred arrangement is to have the aptamer followed by a GGGS (SEQ ID NO: 3) linker, preferably $(GGGS)_3$ (SEQ ID NO: 4), together with an NLS, preferably that from SV40.

Applicants, generated a dCas9-based light-inducible MS2-effector, characterized by an MS2-CIB1 recruitment component bound to dCas9—gRNA, and a CRY2-VP64 transcriptional activator domain. Upon activation with blue light, CRY2-VP64 associate with MS2-CIB1, enabling the recruitment of the transcriptional machinery to the target locus.

Thus, in some embodiments, the adaptor protein may be fused to (or otherwise associated with) a first inducible element, whilst the functional domain may be fused (or otherwise associated) to a second and complimentary inducible element. The complementarity may be provided by heterodimeric binding partners. A preferred example of first and second complementary inducible elements is the CIB1 and CRY2 system. The CIB1 domain is a heterodimeric binding partner of the light-sensitive Cryptochrome 2 (CRY2).

Applicants replaced dCas9 Rec2 domain with a transcriptional effector domain; replace dCas9 HNH domain with a transcriptional effector domain; inserted a transcriptional effector domain at sites of flexible linkers within dCas9 (amino acid 553, 575, or 1153); and created catalytically inactive dCas9 by combination of D10A and N863A mutations, rather than D10A and H840A mutations. Any of these are preferred in certain distinct embodiments.

In some embodiments, Rec2 may be modified, preferably where amino acids 175-306 of dCas9 were replaced with one of the following inserts, with subdomains listed from N- to C-terminus:

VP64 activation domain

3X GGGGS linker (SEQ ID NO: 1), VP64 activation domain, 3X GGGGS linker (SEQ ID NO: 1)

p65 activation domain

3X GGGGS linker (SEQ ID NO: 1), p65 activation domain, 3X GGGGS linker (SEQ ID NO: 1)

In some embodiments, HNH may be modified. For example, in Applicants replaced AA775-901 (of the HNH domain). This may be with either an activator, such as vp64 or P65, or a repressor. The activator or repressor may be flanked by a $(GGGGS)_3$ (SEQ ID NO: 1) or a $(GGGGS)_6$ (SEQ ID NO: 5) linker on both sides of the inserted transcriptional effector domain.

Insertions of transcriptional domains into 3 loops of dCas9 are also envisaged. In addition to replacing an existing domain (e.g. HNH, Rec2) with a transcriptional effector domain, it may be useful, in some embodiments, to insert a transcriptional effector domain at different positions in the Cas9 protein. Applicants identified three favorable positions: G533, F575 and K1153. Applicants insert either vp64 or P65 flanked by a (GGGGS)i (SEQ ID NO: 6) or a $(GGGGS)_3$ (SEQ ID NO: 1) linker on both sides of the inserted transcriptional effector domain at these three locations. As such, in some embodiments, the Cas9 may be modified by insertion of one or more functional domains at any one or more of position corresponding to G533, F575 and K1153 according to SpCas9.

In some embodiments, novel dCas9 mutants are provided. Catalytically inactive dCas9 may be generated by combination of D10A and N863A mutations, rather than D10A and H840A mutations, as shown in Example 18. This numbering refers to Sp Cas9, so corresponding positions in orthologs are envisaged. We also provide N580A as a preferred alternative in Sa Cas9, especially in combination with D10. N863, especially N863A, referring to Sp Cas9, is also useful in a dead Cas9 and is preferred in some embodiments.

A combination of different activator domains had an improved effect. For example a construct with a p65-HSF1 fusion was found to be a more potent activator than the construct with p65 alone. Thus, fusions of two or more activators are preferred in some embodiments. Fusions of two or more repressors are also preferred in some embodiments. The activators or repressors may be in any combination of those known in the art and in particular those especially reference herein.

Of particular note was the use in this Example of an orthogonal system, a combined approach using one activator and one repressor. Different guides and different RNA/adaptor protein pairs allowed for activation at one locus and repression at another locus.

Applicants observed significant activation for each of a number purportedly difficult gene targets. Additionally, Applicants observed that the success rate of guide sequences typically increased with closer proximity to the transcriptional start site (TSS) of the target gene. In a preferred embodiment of the invention, for particular targets, within 200 bp of the TSS is deemed to be an advantageous window to select guide RNAs. This information may also be useful for selection of gRNA guide sequences.

Multiplexed activation has also been shown. One important possible advantage of the ability of Applicants' system to provide robust activation with a single guide would be the capacity to easily activate a panel of genes simultaneously (by co-delivery to multiple guides for these genes), which would be intractable if a large number of guides would be required for activation of each gene alone. In order to test the ability of Applicants' system (NLS-dCAS(D10,H840A)-NLS-VP64 in combination with MS2-NLS-P65-HSF1) to activate multiple genes simultaneously, Applicants co-transfected guides targeting 2, 4, 6, 8 or 10 genes at once. Activation of multiple genes was highly successful, as even for a combination of 10 genes each gene was activated significantly. In some embodiments, therefore, an adaptor protein may advantageously be linked or fused to fused or linked activators, as also discussed above, or repressors. This may then be delivered with multiple guides to different targets. This is therefore especially useful in a screening method where the activation or repression of one or more genes is to be interrogated.

Two 4nt stretches have been identified in the guides that are exposed "outside" of Cas9-guide-target DNA complex. One 4nt stretch falls in the tetraloop, the other 4nt stretch falls in the stem loop 2. These 4nt stretches can be replaced by aptamer sequence. The one or more aptamer(s) is a polynucleotide and may be DNA or RNA, but RNA is preferred. The aptamer has a corresponding RNA-binding protein that recognises a specific RNA sequence.

Thus, the MS2 system used here comprises an RNA sequence inserted into the guide (at one or both of the above locations) and a corresponding MS2 (RNA-binding) protein. The RNA-binding protein may then be fused to a functional domain such as an activator or a repressor. Instead of being fused directly to a functional domain, the RNA-binding protein could be fused to a further element such as an antibody that can then bind to and recognise a functional domain or a molecule fused to a functional domain, similar to the heteroduplex CIB1-Cry2 system described above. This may allow for greater temporal or spatial control.

In short, a specific RNA sequence may be inserted into the exposed guide loop(s) and a corresponding RNA-binding protein may be used, whether that is fused to a functional domain, or a further element which in turn recognises or binds specifically to a functional domain. The functional domain may be a transacting activator or a repressor.

This can be used in Screening Methods to assess G.O.F (Gain Of Function) and/or L.O.F. (Loss of Function).

In some embodiments, the tetraloop is or includes nucleotides G29 to A41 of the guide tested and comprises 5'-GCUAGAAUAGCA-3' (positions 29-41) (SEQ ID NO: 7). Guide nucleotides, such as C40, may preferably interact with Cas9 amino acid Arg340. In some embodiments, stem loop 2 may be or include nucleotides A68 to G81 of the guide used (5'-AACUUGAAAAAGUG-3') (SEQ ID NO: 8). Enzyme amino acids His1349 and Ser1351 may, in some embodiments, interact with guide nucleotides, such as A68. In some embodiments, Lys33 and Tyr1356 may interact with nucleotide G81.

In some embodiments, it is preferable to use complimentary GGCC inserts (GC tracts) flanking the MS insert (the 5'-GGCC-3' being complimentary to the same sequence at the 3' end (and in the opposite orientation i.e. 3'CCGG-5').

Although single MS2 addition (i.e. to one or other of the tetraloop or stem loop 2) shows an improvement in terms of Gain of Function (gene upregulation) compared to a standard guide, the double addition (MS2 on both loops) shows even stronger upregulation. The use of two or more functional domains with the guide is therefore preferred.

As mentioned herein, having one activator, such as VP64, bound to Cas9 and a separate similar activator, again VP64 in this example, bound to the guide via MS2 shows the greatest improvement in terms of Gain of Function (gene upregulation). Other activators or repressors may be exchanged here for the activator mentioned.

We also show in this Example an improvement in terms of Gain of Function (gene upregulation) compared to a prior art MS-guide RNA arrangement where the MS2 is attached at the 3' end of the guide. This art approach is as opposed to the present loops which are both internal and certainly not 3' terminal or are at least followed (in the 3' direction) by an additional loop (stem loop 3).

LincRNAs (a non-coding RNA produced from bi-directional promoters—the other direction being RNA corresponding to the gene of interest) may also be targeted via the guides and/or interrogated.

Applicants, without being bound by theory, believe that guide direction does not significantly affect activation activity, instead the primary factor influencing activation potency is that the gRNA site is located within the −200 to +1 bp proximal promoter region. This region is therefore a preferred target for the guide(s).

The adaptor protein (and hence its corresponding distinct RNA (preferably an aptamer) is preferably chosen from within bacteriophage coat proteins. Preferred examples include those already listed elsewhere herein.

An inducible structural design activation mediator transgenic model, in this case a mouse, may be established. A repression model may be similarity generated. Preferably, a mouse engineered with the Lox-Stop-polyA-Lox(LSL) cassette upstream to the coding region of the SpCas9—VP64 fusion protein is established. A second mouse may be engineered with the Lox-Stop-polyA-Lox(LSL) cassette upstream to the coding region of the SpCas9—VP64 fusion protein and upstream to the coding region of the MS2-P65-HSF1 fusion protein.

When looking at lincRNAs, guides may be designed to target the promoter region. Ideally, this should be within 1000 nucleotides upstream of the TTS of the target, in this case, lincRNAs of unknown function. Animals, such as mice, may then be screened for aberrant phenotypes.

Cells for which the gRNA has an activator may be monitored for Gain of Function, whilst cells for which the gRNA has a repressor may be monitored for Loss of Function. In this fashion, mammalian, including mouse and human cells, can be screened.

In an aspect, the vector systems used in the methods of the invention comprise one or more lentiviral vector(s). In a preferred embodiment, the one or more lentiviral vectors may comprise a codon optimized nuclear localization signal (NLS), a codon optimized P2A bicistronic linker sequence and an optimally placed U6 driven guide RNA cassette. In another aspect the vector system comprises two lentiviral vectors, wherein one lentiviral vector comprises the Cas9 enzyme and the other lentiviral vector comprises the guide RNA selected from the libraries of the invention. In an embodiment of the invention, each vector has a different selection marker, e.g. a different antibiotic resistance marker. The invention also comprehends kits comprising the libraries of the invention. In certain aspects, the kit comprises a single container comprising vectors comprising the library of the invention. In other aspects, the kit comprises a single container comprising plasmids comprising the library of the invention. The invention also comprehends kits comprising a panel comprising a selection of unique CRISPR-Cas system guide sequences from the library of the invention, wherein the selection is indicative of a particular physiological condition. In preferred embodiments, the targeting is of about 100 or more sequences, about 1000 or more sequences or about 20,000 or more sequences or the entire genome. In other embodiments a panel of target sequences is focused on a relevant or desirable pathway, such as an immune pathway or cell division.

Creation of a non-human animal or cell may be realistically provided. It has preferably been altered, or is a progeny of said altered animal or cell, to constitutively or conditionally express a Cas9 with one or more mutations to modify catalytic activity, as discussed herein. The model may be used for screening with appropriate guides and with different adaptors and activators or repressors as discussed herein for multiplexing to show up and/or down-regulation of target gene function. Thus, corresponding cell lines and transgenic mammalian models are provided. Further guidance on models and cell lines is provided herein.

The exposed or extraneous portion of the guide (when the guide-Cas9-DNA complex is formed) is preferably a 4 (four) nucleotide stretch. In some embodiments, the stretch may be in the tetraloop. In some embodiments, the stretch may be in the stem loop 2. In some embodiments, stretches in both the tetraloop and the stem loop 2 are envisaged.

This stretch may be modified, altered or entirely replaced. It is not generally preferred to reduce the number of nucleotides in the exposed stretch to less than 4 for stearic reasons as this could affect the secondary structure of the rest of the guide and thus affect formation of the Cas9-guide-DNA complex or the exposure of the stretch.

It may be modified or altered in that all four of the original 4 nucleotides in the stretch are retained and additions (or further nucleotides) are made between 1 and 2, 2 and 3, or 3 and 4. It is also envisaged that additions may be made immediately 5' to 1 or 3' immediately to 4. The stem may be flexible, but it is preferred that it is largely self-complementary throughout.

Unafold is a software tool that can be used to help predict RNA secondary structure in the guide and so assist the skilled person in determine what changes to the guide RNA may be acceptable within the framework discussed herein.

Ideally, the loop feature should be retained but protein binding section of the distinct RNA added to the guide will determine this. The non-loop ends abutting the edge of the enzyme should ideally be retained in the sense that they need to be present, but the primary sequence of the original guide can be changed, for example by insertion of one or more GC tract(s). Ideally, this should be done at the non-loop (non-protein-binding end) of the distinct RNA added, which may be extended. The secondary structure of the non-protein-binding region of the distinct RNA should preferably form a stem, as mentioned.

It is preferred to avoid bulges or loops in the exposed section (non-protein-binding section of the distinct RNA, i.e. that between the edge of the enzyme complex and the protein binding domain of the distinct RNA/Aptamer). Rather, it is preferred to retain a stem as secondary structure in the exposed section.

A stem may be formed in the RNA through use of complimentary sections of roughly the same length, with mismatches minimized. The maximum length of the stem (or number of nucleotides forming the stem in both the 5' to 3' and 3'*to* 5' strands) is preferably 100 nucleotides or so in total (i.e. 2 sections of approx. 50 nucleotides) to reduce stearic effects and reduce possible formation of additional secondary or tertiary structure in the nucleotides. However, 50-60 nucleotides may be a more preferable maximum, but given the general need to keep package size down, 10 to 20 or 30 is most preferable, whilst, 8, 10 or 12 is most preferred.

A preferred minimum length is 4 nucleotides either side of the protein-binding loop.

In some embodiments, the adaptor protein is an RNA-binding protein. The RNA-binding protein recognises corresponding distinct RNA sequences, which may be aptamers. For example, the MS2 RNA-binding protein recognises and binds specifically to the MS2 aptamer (or vice versa) .The skilled person will understand that modifications to the gRNA which allow for binding of the adapter+functional domain but not proper positioning of the adapter+functional domain (e.g., due to steric hindrance within the three dimensional structure of the CRISPR complex) are modifications which are not intended. The one or more modified gRNA may be modified at the tetra loop, the stem loop 1, stem loop 2, or stem loop 3, as described herein, preferably at either the tetra loop or stem loop 2, and most preferably at both the tetra loop and stem loop 2.

As explained herein the functional domains may be, for example, one or more domains from the group comprising, consisting essentially of, or consisting of methylase activity, demethylase activity, transcription activation activity, transcription repression activity, transcription release factor activity, histone modification activity, RNA cleavage activity, DNA cleavage activity, nucleic acid binding activity, and molecular switches (e.g., light inducible). In some cases it is advantageous that additionally at least one NLS and/or NES is provided. In some instances, it is advantageous to position the NLS and/or NES at the N terminus. When more than one functional domain is included, the functional domains may be the same or different.

The gRNA may be designed to include multiple binding recognition sites (e.g., aptamers) specific to the same or different adapter protein. The gRNA may be designed to bind to the promoter region −1000-+1 nucleic acids upstream of the transcription start site (i.e. TSS), preferably −200 nucleic acids. This positioning improves functional domains which affect gene activation (e.g., transcription activators) or gene inhibition (e.g., transcription repressors). The modified gRNA may be one or more modified gRNAs targeted to one or more target loci (e.g., at least 1 gRNA, at least 2 gRNA, at least 5 gRNA, at least 10 gRNA, at least 20 gRNA, at least 30 sg RNA, at least 50 gRNA) comprised in a composition.

Further, the CRISPR enzyme (or argonaute) with diminished nuclease activity is most effective when the nuclease activity is inactivated (e.g., nuclease inactivation of at least 70%, at least 80%, at least 90%, at least 95%, at least 97%, or 100% as compared with the wild type enzyme; or to put in another way, a CRISPR enzyme having advantageously about 0% of the nuclease activity of the non-mutated or wild type CRISPR enzyme, or no more than about 3% or about 5% or about 10% of the nuclease activity of the non-mutated or wild type CRISPR enzyme). This is possible by introducing mutations into the RuvC and HNH nuclease domains of the SpCas9 and orthologs thereof. For example utilizing mutations in a residue selected from the group comprising, consisting essentially of, or consisting of D10, E762, H840, N854, N863, or D986 and more preferably introducing one or more of the mutations selected from the group comprising, consisting essentially of, or consisting of D10A, E762A, H840A, N854A, N863A or D986A. A preferable pair of mutations is D10A with H840A, more preferable is D10A with N863A of SpCas9 and orthologs thereof. The inactivated CRISPR enzyme may have associated (e.g., via fusion protein) one or more functional domains, e.g., at least one destabilizing domain; or, for instance like those as described herein for the modified gRNA adaptor proteins, including for example, one or more domains from the group comprising, consisting essentially of, or consisting of methylase activity, demethylase activity, transcription activation activity, transcription repression activity, transcription release factor activity, histone modification activity, RNA cleavage activity, DNA cleavage activity, nucleic acid binding activity, and molecular switches (e.g., light inducible). Preferred domains are Fok1, VP64, P65, HSF1, MyoD1. In the event that Fok1 is provided, it is advantageous that multiple Fok1 functional domains are provided to allow for a functional dimer and that gRNAs are designed to provide proper spacing for functional use (Fok1) as specifically described in Tsai et al. Nature Biotechnology, Vol. 32, Number 6, June 2014). The adaptor protein may utilize known linkers to attach such functional domains. In some cases it is advantageous that additionally at least one NLS or NES is provided. In some instances, it is advantageous to position the NLS or NES at the N terminus. When more than one functional domain is included, the functional domains may be the same or different. In general, the positioning of the one or more functional domain on the inactivated fusion protein and/or CRISPR enzyme is one which allows for correct spatial orientation for the functional domain to affect the target with the attributed functional effect. For example, if the functional domain is a transcription activator (e.g., VP64 or p65), the transcription activator is placed in a spatial orientation which allows it to affect the transcription of the target. Likewise, a transcription repressor will be advantageously positioned to affect the transcription of the target, and a nuclease (e.g., Fok1) will be advantageously positioned to cleave or partially cleave the target. This may include positions other than the N-/C-terminus of the fusion protein and/or CRISPR enzyme. Positioning the functional domain in the Rec domain, the Rec2 domain, the HNH domain, or the PI domain of the SpCas9 protein or any ortholog corresponding to these domains is advantageous; and again, it is mentioned that the functional domain can be a DD. Positioning of the functional domains to the Rec domain or the Rec2 domain, of the SpCas9 protein or any ortholog corresponding to these domains, in some instances may be preferred. Positioning of the functional domains to the Rec domain at position 553, Rec domain at 575, the Rec2 domain at any position of 175-306 or replacement thereof, the HNH domain at any position of 715-901 or replacement thereof, or the PI domain at position 1153 of the SpCas9 protein or any ortholog corresponding to these domains, in some instances may be preferred. Fok1 functional domain may be attached at the N terminus. When more than one functional domain is included, the functional domains may be the same or different.

An adaptor protein may be any number of proteins that binds to an aptamer or recognition site introduced into the modified gRNA and which allows proper positioning of one or more functional domains, once the gRNA has been incorporated into the CRISPR complex, to affect the target with the attributed function. As explained in detail in this application such may be coat proteins, preferably bacteriophage coat proteins. The functional domains associated with such adaptor proteins (e.g., in the form of fusion protein) may include, for example, one or more domains from the group comprising, consisting essentially of, or consisting of methylase activity, demethylase activity, transcription activation activity, transcription repression activity, transcription release factor activity, histone modification activity, RNA cleavage activity, DNA cleavage activity, nucleic acid binding activity, and molecular switches (e.g., light inducible). Preferred domains are Fok1, VP64, P65, HSF1, MyoD1. In the event that the functional domain is a transcription activator or transcription repressor it is advantageous that additionally at least an NLS or NES is provided and preferably at the N terminus. When more than one functional domain is included, the functional domains may be the same or different. The adaptor protein may utilize known linkers to attach such functional domains. Such linkers may be used to associate the DD with the fusion protein and/or CRISPR enzyme or have the fusion protein and/or CRISPR enzyme comprise the DD.

In certain embodiments, the RNA aptamer sequence may for example be from 10 to 200 nucleotides in length. In some embodiments, the gRNA may include more than one RNA aptamer sequence.

Thus, gRNA (or gDNA), e.g., modified gRNA/gDNA, the inactivated CRISPR enzyme/argonaute (with or without functional domains), and the fusion protein of the invention with one or more functional domains, may each individually be comprised in a composition and administered to a host individually or collectively. Alternatively, these components may be provided in a single composition for administration to a host. Administration to a host may be performed via viral vectors known to the skilled person or described herein for delivery to a host (e.g., lentiviral vector, adenoviral vector, AAV vector). As explained herein, use of different selection markers (e.g., for lentiviral gRNA selection) and concentration of gRNA (e.g., dependent on whether multiple gRNAs are used) may be advantageous for eliciting an improved effect. On the basis of this concept, several variations are appropriate to elicit a genomic locus event, including DNA cleavage, gene activation, or gene deactivation. Using the provided compositions, the person skilled in the art can advantageously and specifically target single or multiple loci with the same or different functional domains to elicit one or more genomic locus events. The compositions may be applied in a wide variety of methods for screening in libraries in cells and functional modeling in vivo (e.g., gene activation of lincRNA and identification of function; gain-of-function modeling; loss-of-function modeling; the use the compositions of the invention to establish cell lines and transgenic animals for optimization and screening purposes).

The current invention comprehends the use of the compositions of the current invention to establish and utilize conditional or inducible fusion protein and/or CRISPR transgenic cell/animals; see, e.g., Platt et al., Cell (2014), 159(2): 440-455, or PCT patent publications cited herein, such as WO 2014/093622 (PCT/US2013/074667). For example, cells or animals such as non-human animals, e.g., vertebrates or mammals, such as rodents, e.g., mice, rats, or other laboratory or field animals, e.g., cats, dogs, sheep, etc., may be 'knock-in' whereby the animal conditionally or inducibly expresses the fusion protein and/or effector protein akin to Platt et al. The target cell or animal thus comprises fusion protein or CRISPR enzyme (e.g., Cas9, Cpf1, C2c1, C2c2, C2c3, Cas13, group 29/30) or alternatively an argonaute conditionally or inducibly (e.g., in the form of Cre dependent constructs) and the fusion protein (i.e. comprising DD and adapter protein) and optionally DD (without being fused to fusion protein or effector protein) conditionally or inducibly and, on expression of a vector introduced into the target cell, the vector expresses that which induces or gives rise to the condition of fusion protein or CRISPR enzyme expression and/or fusion protein or DD expression in the target cell. By applying the teaching and compositions of the current invention with the known method of creating a CRISPR complex, inducible genomic events are also an aspect of the current invention. One more example of this is the creation of a CRISPR knock-in/conditional transgenic animal (e.g., mouse comprising e.g., a Lox-Stop-polyA-Lox (LSL) cassette) and subsequent delivery of one or more compositions providing one or more modified gRNA (e.g., −200 nucleotides to TSS of a target gene of interest for gene activation purposes, e.g., modified gRNA with one or more aptamers recognized by coat proteins, e.g., MS2), one or more adapter proteins as described herein (MS2 binding protein linked to one or more VP64) and means for inducing the conditional animal (e.g., Cre recombinase for rendering fusion protein or effector protein expression inducible). Alternatively, the fusion protein or DD may be provided as a conditional or inducible element with a conditional or inducible CRISPR enzyme to provide an effective model for screening purposes, which advantageously only requires minimal design and administration of specific gRNAs for a broad number of applications.

In some embodiments, phenotypic alteration is preferably the result of genome modification when a genetic disease is targeted, especially in methods of therapy and preferably where a repair template is provided to correct or alter the phenotype.

In some embodiments diseases that may be targeted include those concerned with disease-causing splice defects.

In some embodiments, cellular targets include Hemopoietic Stem/Progenitor Cells (CD34+); Human T cells; and Eye (retinal cells)—for example photoreceptor precursor cells.

In some embodiments Gene targets include: Human Beta Globin—HBB (for treating Sickle Cell Anemia, including by stimulating gene-conversion (using closely related HBD gene as an endogenous template)); CD3 (T-Cells); and CEP920—retina (eye).

In some embodiments disease targets also include: cancer; Sickle Cell Anemia (based on a point mutation); HBV, HIV; Beta-Thalassemia; and ophthalmic or ocular disease—for example Leber Congenital Amaurosis (LCA)-causing Splice Defect.

In some embodiments delivery methods include: Cationic Lipid Mediated "direct" delivery of Enzyme-Guide complex (RiboNucleoProtein) and electroporation of plasmid DNA.

Methods, products and uses described herein may be used for non-therapeutic purposes. Furthermore, any of the methods described herein may be applied in vitro and ex vivo.

In an aspect, provided is a non-naturally occurring or engineered composition comprising:

I. one or more CRISPR-Cas system polynucleotide sequences comprising
   (a) a first guide sequence capable of hybridizing to a first target sequence in a polynucleotide locus,
   (b) a second guide sequence capable of hybridizing to a second target sequence in a polynucleotide locus,
   (c) a tracr mate sequence, and
   (d) optionally a tracrRNA sequence, and II. a Type II CRISPR enzyme or a second polynucleotide sequence encoding it, wherein the Type II CRISPR enzyme is optionallya modified enzyme comprising one or more DD as described herein, III. a fusion protein according to the invention as described herein;

wherein when transcribed, the first and the second tracr mate sequences hybridize to the first and second tracrRNA sequences respectively and the first and the second guide sequences direct sequence-specific binding of a first and a second CRISPR complex to the first and second target sequences respectively, wherein the first CRISPR complex comprises the CRISPR enzyme complexed with (1) the first guide sequence that is hybridizable to the first target sequence, and (2) the first tracr mate sequence that is hybridized to the first tracrRNA sequence, wherein the second CRISPR complex comprises the CRISPR enzyme complexed with (1) the second guide sequence that is hybridizable to the second target sequence, (2) the second tracr mate sequence that is hybridized to the second tracrRNA sequence, and (3) the fusion protein of the invention, and wherein the first guide sequence directs modification of one strand of the DNA or RNA duplex near the first target sequence and the second guide sequence directs cleavage of the other strand near the second target sequence inducing a double strand break or other modification, such as transcriptional or translational modulation, thereby modifying the organism or the non-human or non-animal organism.

In another embodiment, the fusion protein according to the invention as described herein and/or effector protein, such as CRISPR/Cas system effector protein (including Cas9, Cpf1, C2c1, C2c2, C2c3, Cas13, group 29/30) or argonaute is delivered into the cell as a protein. In another and particularly preferred embodiment, the fusion protein of the invention and/or effector protein is delivered into the cell as a protein or as a nucleotide sequence encoding it. Delivery to the cell as a protein may include delivery of a Ribonucleoprotein (RNP) complex, where the effector and fusion protein is complexed with the guide.

In some embodiments, the ortholog is *Staphylococcus aureus* so that the Cas9 is that from or derived from *Staphylococcus aureus* (referred to as SaCas9). In some embodiments, the *Staphylococcus aureus* is *Staphylococcus aureus* subspecies *aureus*. Guidance is provided below in respect of guide length (the spacer or guide sequence). In some embodiments, for Sp, optimal guide length can vary as low as a 17-nucleotides or what is known in the art as a tru-guide or tru-gRNAs (see, e.g., Fu et al., "Improving CRISPR-Cas nuclease specificity using truncated guide RNAs," Nature Biotechnology 32, 279-284 (2014) doi: 10.1038/nbt.2808 Received 17 Nov. 2013 Accepted 6 Jan. 2014 Published online 26 Jan. 2014 Corrected online 29 Jan. 2014) In some embodiments, for Sa, the optimal guide length may be 19, 20 or 21 or 22 or 23 or 24 nucleotides in length (Ran et al. (2015), mentioned below).

In an aspect, host cells and cell lines modified by or comprising the compositions, systems or modified enzymes of present invention are provided, including stem cells, and progeny thereof.

In an aspect, methods of cellular therapy are provided, where, for example, a single cell or a population of cells is sampled or cultured, wherein that cell or cells is or has been modified ex vivo as described herein, and is then re-introduced (sampled cells) or introduced (cultured cells) into the organism. Stem cells, whether embryonic or induce pluripotent or totipotent stem cells, are also particularly preferred in this regard. But, of course, in vivo embodiments are also envisaged.

Inventive methods can further comprise delivery of templates, such as repair templates, which may be dsODN or ssODN, see below. Delivery of templates may be via the cotemporaneous or separate from delivery of any or all the CRISPR enzyme, guide, tracr mate or tracrRNA (when required) and via the same delivery mechanism or different. In some embodiments, it is preferred that the template is delivered together with the guide, tracr mate and/or tracrRNA and, preferably, also the CRISPR enzyme. An example may be an AAV vector where the CRISPR enzyme is SaCas9 (with the N580 mutation).

Inventive methods can further comprise: (a) delivering to the cell a double-stranded oligodeoxynucleotide (dsODN) comprising overhangs complimentary to the overhangs created by said double strand break, wherein said dsODN is integrated into the locus of interest; or -(b) delivering to the cell a single-stranded oligodeoxynucleotide (ssODN), wherein said ssODN acts as a template for homology directed repair of said double strand break. Inventive methods can be for the prevention or treatment of disease in an individual, optionally wherein said disease is caused by a defect in said locus of interest. Inventive methods can be conducted in vivo in the individual or ex vivo on a cell taken from the individual, optionally wherein said cell is returned to the individual.

The tracr sequence may be referred to as the tracrRNA. In some embodiments, it may be at least 30, at least 40 or at least 50 nucleotides in length.

The invention also comprehends products obtained from using CRISPR enzyme or Cas enzyme or Cas9 enzyme or CRISPR-Cas system or CRISPR-Cas9 system of the invention.

The present invention is in particular captured by the following numbered statements:

1. A fusion protein comprising one or more destabilization domains, one or more adaptor proteins capable of binding to a CRISPR/Cas or argonaute system guide, and optionally one or more functional domains.
2. A polynucleic acid encoding one or more fusion proteins according to statement 1.
3. A vector comprising one or more polynucleic acid according to statement 2.
4. The vector according to statement 3, wherein said vector is an expression vector capable or expressing said fusion protein.
5. The vector according to statement 4, wherein said expression is conditional and/or inducible.
6. The vector according to statement 4 or 5, wherein said vector comprises one or more polynucleic acid encoding the fusion protein according to statement 1 and regulatory element(s) operable in a host cell operably linked to said polynucleic acid.
7. A composition comprising one or more fusion proteins, polynucleic acids, or vectors according to any one of the preceding statements.
8. The composition according to statement 7, comprising one or more CRISPR/Cas system guide RNAs (gRNA) capable of being bound by said adaptor protein, one or more argonaute system guide DNAs (gDNA) or guide RNAs (gRNA) capable of being bound by said adaptor protein or a polynucleic acid encoding said gRNA or gDNA, or a vector comprising said polynucleic acid.
9. The composition according to statement 7 or 8, comprising one or more CRISPR/Cas system effector proteins or argonaute effector proteins, a polynucleic acid encoding said effector proteins, or a vector comprising said polynucleic acid.
10. The composition according to any one of statements 8 to 9, wherein said effector protein is or comprises Cas9 (optionally SpCas9 or SaCas9), Cpf1, C2c1, C2c2, C2c3, Cas13, group 29/30, argonaute (optionally NgAgo), or a variant thereof.
11. The composition according to any one of statements 8 to 10, wherein said effector protein comprises one or more functional domains.
12. The composition according to any one of statements 8 to 11, wherein said effector protein comprises one or more nuclear localization signals or one or more nuclear export signals.
13. The composition according to any one of statements 8 to 12, wherein said effector protein has a modified activity.
14. The composition according to any one of statements 8 to 13, wherein said effector protein comprises one or more mutations, preferably in the catalytic domain.
15. The composition according to any one of statements 8 to 14, wherein said effector protein is catalytically inactive.
16. The composition according to any one of statements 8 to 15, wherein said effector protein comprises at least one mutation, such that the effector protein has no more than 5% of the nuclease activity of the effector protein not having the at least one mutation.
17. The composition according to any one of statements 8 to 16, wherein said effector protein is a nickase, optionally a nickase comprising or corresponding to N863A in SpCas9.
18. The composition according to any one of statements 8 to 17, wherein said effector protein is codon optimized, preferably codon optimized for expression in a eukaryotic cell.
19. The composition according to any one of statements 8 to 18, wherein said effector protein is a chimeric effector protein.
20. The composition according to any one of statements 8 to 19, wherein said effector protein is a split effector protein.
21. The composition according to any one of statements 8 to 20, comprising a stabilizing ligand of the destabilization domain.
22. The composition according to statement 21, wherein said stabilizing ligand is conditionally or inducibly activatable.
23. The composition according to statement 22, wherein the stabilizing ligand is activated by photolytic cleavage of a precursor.
24. The composition according to statement 21 or 22, wherein said stabilizing ligand stabilizes said fusion protein.
25. The composition according to statement 22, wherein the activated stabilizing ligand is TMP or 4HT.
26. The composition according to statement 22, wherein the activatable stabilizing ligand is photocaged TMP, optionally TMP-NVOC

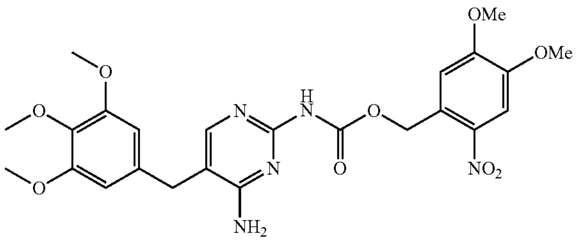 [SMILES: COc1cc(COC(=O)Nc2ncc(Cc3cc(OC)c(OC)c(OC)c3)c(N)n2)c([N+](=O)[O-])cc1OC]

27. The composition according to statement 22, wherein the activatable stabilizing ligand is:

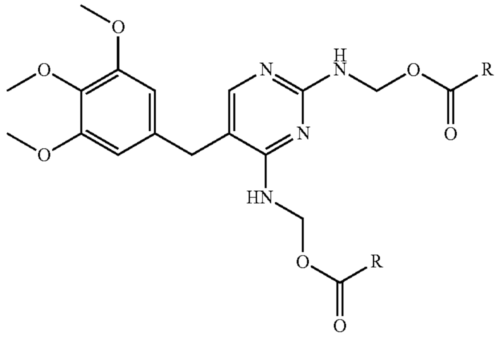

DM1_138D: R = 1
DM1_147D: R = 2
DM1_148D: R = 3
DM1_150D: R = 4

-continued

1: 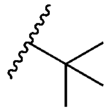 2: 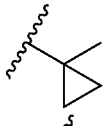 3: 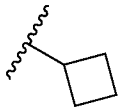

4: 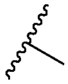

28. The composition according to any one of statements 8 to 26, wherein said effector protein comprises one or more mutations affecting PAM recognition, specificity, stability, and/or activity, optionally comprising or corresponding to D1135V/G1218R/R1335E/T1337R in SpCas9, or corresponding to D10A, E762A, H840A, N854A, N863A and/or D986A in SpCas9, or the corresponding positions in a homologue or orthologue.
29. A method of modifying a polynucleic acid target locus or introducing a polynucleic acid locus event, comprising delivering to or contacting with a polynucleic acid target locus or a host cell comprising said locus the fusion protein, polynucleic acid, vector, or composition according to any one of the preceding statements.
30. The method according to statement 29, comprising delivering to or introducing in a host cell a polynucleic acid target locus the fusion protein, polynucleic acid, vector, or composition according to any one of the preceding statements.
31. The method according to statement 29 or 30, which is a method of treating or inhibiting a condition caused by a defect in a target sequence in a polynucleic acid locus of interest in a subject or a non-human subject in need thereof.
32. The method according to any one of statements 29 to 31, wherein said host cell is a non-human and/or non-animal host cell.
33. The method according to any one of statements 29 to 32, wherein said method is an in vivo, ex vivo, or in vitro method.
34. The method according to any one of statements 29 to 33, wherein method results in gene activation, gene inhibition, or cleavage at the locus.
35. The method according to any one of statements 29 to 34, wherein said fusion protein, polynucleic acid, vector, or composition is delivered with a viral delivery system, preferably a lentiviral, adenoviral, or AAV system.
36. The method according to any one of statements 29 to 35, wherein a CRISPR/Cas system effector protein forms a complex with the gRNA and optionally tracr RNA, and upon binding of said complex to a target locus of interest, the effector protein induces a modification of the target locus of interest; or wherein an argonaute system effector protein forms a complex with the gDNA or gRNA, and upon binding of said complex to a target locus of interest, the effector protein induces a modification of the target locus of interest.
37. The method according to any one of statements 29 to 36, comprising adding, inducing, or (conditionally) activating a stabilizing ligand of the destabilization domain, such as a stabilizing ligand according to any one of statements 21 to 27.
38. The fusion protein, polynucleic acid, vector, or composition according to any one of the preceding statements for use in therapy.
39. Use of the fusion protein, polynucleic acid, vector, or composition according to any one of the preceding statements for the manufacture of a medicament.
40. A host cell or progeny thereof comprising or capable of expressing the fusion protein, polynucleic acid, vector, or composition according to any one of the preceding statements.
41. The host cell according to statement 40, wherein the cell is a eukaryotic cell.
42. The host cell according to statement 41, wherein the eukaryotic cell is a mammalian cell, optionally a mouse cell.
43. The host cell according to statement 42, wherein the mammalian cell is a human cell.
44. The host cell according to statement 40, wherein the eukaryotic cell is a plant cell.
45. The host cell according to any one of statements 40 to 44, wherein said cell is a cell line.
46. A non-human eukaryote comprising or transformed with one or more polynucleic acid, vector, composition, or host cell, or comprising or capable of expressing one or more fusion protein according to any one of the preceding statements or the composition or complex according to any one of statements 76 to 78, optionally, wherein said eukaryote is an animal or a plant.
47. A kit comprising the fusion protein, polynucleic acid, vector, composition, method, host cell, or eukaryote according to any one of the preceding statements, optionally further comprising one or more stabilizing ligand of the destabilization domain, such as a stabilizing ligand according to any one of statements 21 to 27.
48. The fusion protein, polynucleic acid, vector, composition, method, host cell, eukaryote, or kit according to any one of the preceding statements, wherein said gRNA or gDNA is a functionalized gRNA or gDNA.
49. The fusion protein, polynucleic acid, vector, composition, method, host cell, eukaryote, or kit according to any one of the preceding statements, wherein at least one loop of the gRNA or gDNA is modified by the insertion of one or more aptamer that bind to said adaptor protein.
50. The fusion protein, polynucleic acid, vector, composition, method, host cell, eukaryote, or kit according to statement 49, wherein said aptamer is an RNA or DNA sequence.
51. The fusion protein, polynucleic acid, vector, composition, method, host cell, eukaryote, or kit according to statement 49 or 50, wherein said gRNA or gDNA comprises two or more aptamer sequences.
52. The fusion protein, polynucleic acid, vector, composition, method, host cell, eukaryote, or kit according to any one of statements 49 to 51, wherein said gRNA or gDNA comprises two or more different aptamer sequences.
53. The fusion protein, polynucleic acid, vector, composition, method, host cell, eukaryote, or kit according to any one of statements 49 to 52, wherein said gRNA comprises two or more different aptamer sequences binding to different adaptor proteins.
54. The fusion protein, polynucleic acid, vector, composition, method, host cell, eukaryote, or kit according to any one of the preceding statements, wherein said at least one loop of the gRNA or gDNA is a tetraloop and/or stem loop2.
55. The fusion protein, polynucleic acid, vector, composition, method, host cell, eukaryote, or kit according to any one of the preceding statements, wherein the gRNA or gDNA is modified by insertion of one or more distinct RNA or DNA sequence capable of binding said adaptor protein.

56. The fusion protein, polynucleic acid, vector, composition, method, host cell, eukaryote, or kit according to any one of the preceding statements, wherein the gRNA or gDNA is modified to have at least one non-coding functional loop.

57. The fusion protein, polynucleic acid, vector, composition, method, host cell, eukaryote, or kit according to any one of the preceding statements, wherein said gRNA or gDNA comprises a guide sequence capable of hybridizing to a target sequence in a polynucleic acid locus of interest in a cell.

58. The fusion protein, polynucleic acid, vector, composition, method, host cell, eukaryote, or kit according to any one of the preceding statements, wherein said gRNA/gDNA is an escorted gRNA/gDNA, a protected gRNA/gDNA, or a dead gRNA/gDNA.

59. The fusion protein, polynucleic acid, vector, composition, method, host cell, eukaryote, or kit according to any of the preceding statements, wherein said polynucleic acid locus is single or double stranded DNA, single or double stranded RNA, or DNA/RNA hybrid.

60. The fusion protein, polynucleic acid, vector, composition, method, host cell, eukaryote, or kit according to any one of the preceding statements, wherein said gRNA or gDNA comprises a direct repeat sequence capable of being bound by a CRISPR/Cas system effector protein or an argonaute.

61. The fusion protein, polynucleic acid, vector, composition, method, host cell, eukaryote, or kit according to any one of the preceding statements, wherein said gRNA comprises a tracr RNA sequence fused to a guide sequence.

62. The fusion protein, polynucleic acid, vector, composition, method, host cell, eukaryote, or kit according to any one of the preceding statements, wherein said gRNA is a single guide RNA (gRNA).

63. The fusion protein, polynucleic acid, vector, composition, method, host cell, eukaryote, or kit according to any one of the preceding statements, wherein a CRISPR/Cas effector protein forms a complex with the gRNA and upon binding of the said complex to the locus of interest the effector protein induces a modification of the sequences associated with or at the target locus of interest; or wherein an argonaute forms a complex with the gDNA or gRNA and upon binding of the said complex to the locus of interest the effector protein induces a modification of the sequences associated with or at the target locus of interest.

64. The fusion protein, polynucleic acid, vector, composition, method, host cell, eukaryote, or kit according to any one of the preceding statements, wherein said adaptor protein is an aptamer ligand.

65. The fusion protein, polynucleic acid, vector, composition, method, host cell, eukaryote, or kit according to any one of the preceding statements, wherein said functional domain is a heterologous functional domain.

66. The fusion protein, polynucleic acid, vector, composition, method, host cell, eukaryote, or kit according to any one of the preceding statements, wherein said functional domain is selected from transcription or translation activator, transcription or translation repressor, (DNA or RNA), argonaute, methyltransferase, methylase, demethylase, DNA hydroxylmethylase, histone acetylase, histone deacetylases, transcription or translation release factor domain, histone modification domain, nuclease, single-strand RNA cleavage domain, double-strand RNA cleavage domain, single-strand DNA cleavage domain, double-strand DNA cleavage domain, nucleic acid binding domain, a protein acetyltransferase, a protein deacetylase, a protein methyltransferase, a protein deaminase, a protein kinase, a protein phosphatase, transposase, integrase, recombinase, resolvase, invertase, protease, repressor, activator, nuclear-localization signal, nuclear export signal, transcription-regulatory protein (or transcription complex recruiting) domain, cellular uptake activity associated domain, nucleic acid binding domain, antibody presentation domain, histone modifying enzymes, recruiter of histone modifying enzymes; inhibitor of histone modifying enzymes, histone methyltransferase, histone demethylase, histone kinase, histone phosphatase, histone ribosylase, histone deribosylase, histone ubiquitinase, histone deubiquitinase, histone biotinase, histone tail protease, HDACs, histone methyltransferases (HMTs), histone acetyltransferase (HAT) inhibitors, HDAC and HMT recruiting proteins, HDAC effector Domains, HDAC recruiter effector domains, histone methyltransferase (HMT) effector domains, histone methyltransferase (HMT) recruiter effector domains, histone acetyltransferase inhibitor effector domains, or domains having molecular switch activity or chemical inducibility or light inducibility.

67. The fusion protein, polynucleic acid, vector, composition, method, host cell, eukaryote, or kit according to any one of the preceding statements, wherein said functional domain is a transcriptional activation domain comprising VP64, p65, MyoD1, HSF1, RTA or SET7/9.

68. The fusion protein, polynucleic acid, vector, composition, method, host cell, eukaryote, or kit according to any one of the preceding statements, wherein said functional domain is a transcriptional repressor domain comprising a KRAB domain, a NuE domain, NcoR domain, SID domain or a SID4X domain.

69. The fusion protein, polynucleic acid, vector, composition, method, host cell, eukaryote, or kit according to any one of the preceding statements, wherein said adaptor protein comprises MS2, PP7, Qβ, F2, GA, fr, JP501, M12, R17, BZ13, JP34, JP500, KU1, M11, MX1, TW18, VK, SP, FI, ID2, NL95, TW19, AP205, ϕCb5, ϕCb8r, ϕCb12r, ϕCb23r, 7s, or PRR1.

70. The fusion protein, polynucleic acid, vector, composition, method, host cell, eukaryote, or kit according to any one of the preceding statements, wherein the destabilization domain and/or the functional domain is attached so that upon binding to the gRNA or gDNA and target the respective domain is in a spatial orientation allowing for the respective domain to function in its attributed function; or, optionally, wherein the one or more respective domain is attached via a linker, optionally a GlySer linker.

71. The fusion protein, polynucleic acid, vector, composition, method, host cell, eukaryote, or kit according to any one of the preceding statements, wherein said destabilization domain is N-terminally and/or C-terminally present in said fusion protein.

72. The fusion protein, polynucleic acid, vector, composition, method, host cell, eukaryote, or kit according to any one of the preceding statements, comprising two destabilizing domains.

73. The fusion protein, polynucleic acid, vector, composition, method, host cell, or eukaryote according to any one of the preceding statements, comprising two different destabilizing domains.
74. The fusion protein, polynucleic acid, vector, composition, method, host cell, eukaryote, or kit according to any one of the preceding statements, wherein said destabilizing domain is a degron.
75. The fusion protein, polynucleic acid, vector, composition, method, host cell, eukaryote, or kit according to any one of the preceding statements, wherein said destabilizing domain comprises ER50 or DHFR50.
76. A complex comprising one or more fusion proteins, gRNAs, and/or CRISPR/Cas effector proteins according to any one of the preceding statements; or comprising one or more fusion proteins, gDNAs or gRNAs, and/or argonaute effector proteins according to any one of the preceding statements.
77. The composition or complex according to any one of the preceding statements, further comprising a polynucleotide template for homologous recombination.
78. The composition or complex according to statement 77, wherein said template comprises at least 250 nucleotides, preferably at least 500 nucleotides, more preferably at least 1000 nucleotides, at least 2000 nucleotides, at least 3000 nucleotides, at least 4000 nucleotides, at least 5000 nucleotides, at least 6000 nucleotides, at least 7000 nucleotides, at least 8000 nucleotides, at least 9000 nucleotides, or at least 10000 nucleotides
79. The fusion protein, polynucleic acid, vector, host cell, composition, or complex according to any one of the preceding statements for use in treating pathogenic diseases, preferably viral diseases.
80. The fusion protein, polynucleic acid, vector, host cell, composition, or complex according to statement 79, wherein said viral disease is HBV.
81. The fusion protein, polynucleic acid, vector, host cell, composition, or complex according to any one of the preceding statements for use in delivery to the eye or to eye cells.
82. The fusion protein, polynucleic acid, vector, host cell, composition, or complex according to any one of the preceding statements for preventing, alleviating, or treating eye diseases or disorders.
83. The fusion protein, polynucleic acid, vector, host cell, composition, or complex according to statement 82, wherein said eye disease or disorder is selected from glaucoma (e.g. primary open angle glaucoma), macular degeneration (e.g. advanced neovascular age related macular degeneration), retinitis pigmentosa, retinopathies, or leber congenital amaurosis.
84. The fusion protein, polynucleic acid, vector, host cell, composition, or complex according to any one of the preceding statements for use in delivery to blood or hematopoietic stem cells.
85. The fusion protein, polynucleic acid, vector, host cell, composition, or complex according to any one of the preceding statements for use in preventing, alleviating, or treating blood diseases or disorders.
86. The fusion protein, polynucleic acid, vector, host cell, composition, or complex according to any one of the preceding statements for use in preventing, alleviating, or treating hemoglobinopathies, Immunodeficiency disorders, Hematologic conditions, a Leukodystrophy, genetic lysosomal storage disease, Hemophilia B, sickle cell anemia, SCID, SCID-X1, ADA-SCID, Hereditary tyrosinemia, 0-thalassemia, X-linked CGD, Wiskott-Aldrich syndrome, Fanconi anemia, adrenoleukodystrophy (ALD), metachromatic leukodystrophy (MLD), HIV/AIDS, Krabbe Disease, Polycythemia vera (PCV), myeloproliferative neoplasm, Familial essential thrombocythaemia (ET) or Alpha-mannosidosis.
87. The composition or complex according to statement 77 or 78, operable in plants or wherein the host cell is a plant cell.
88. A plant transformed by the composition or complex according to any one of statements 77 to 79 or progeny thereof.
89. A composition comprising an activatable stabilizing ligand of a deactivation domain, and A) a fusion protein comprising one or more destabilization domains, one or more adaptor proteins capable of binding to a CRISPR/Cas or argonaute system guide, and optionally one or more functional domains, or (B) a fusion protein comprising a CRISPR/Cas effector protein or argonaute effector protein associated with or fused to one or more destabilization domains, and optionally one or more functional domains.
90. The composition of paragraph 89, wherein the stabilizing ligand is activated by photolytic cleavage of a precursor.
91. The composition of any one of paragraphs 89 to 90, wherein said activated stabilizing ligand is TMP or 4HT.
92. The composition according to any one of paragraphs 89 to 90, wherein the activatable stabilizing ligand is photocaged TMP, optionally TMP-NVOC

UV

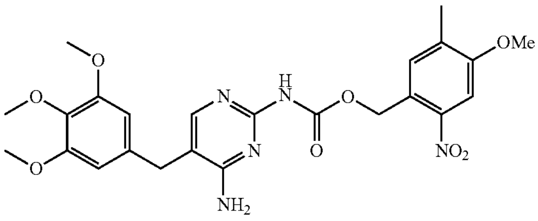

93. The composition according to any one of paragraphs 89 to 90, wherein the activatable stabilizing ligand is

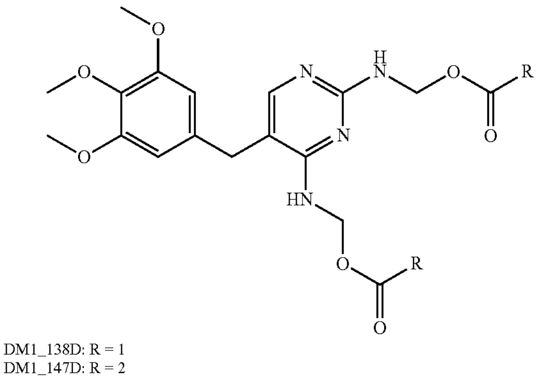

DM1_138D: R = 1
DM1_147D: R = 2
DM1_148D: R = 3
DM1_150D: R = 4

-continued

1: 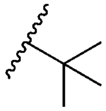 2: 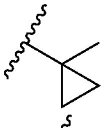 3: 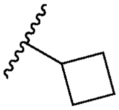

4: 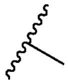

94. The composition of any one of paragraphs 89 to 93, wherein the effector protein is or comprises Cas9 (optionally SpCas9 or SaCas9), Cpf1, C2c1, C2c2, C2c3, Cas13, group 29/30, argonaute (optionally NgAgo), or a variant thereof.
95. The composition of any one of paragraphs 89 to 94, wherein the effector protein comprises one or more nuclear localization signals or one or more nuclear export signals.
96. The composition of any one of paragraphs 89 to 95, wherein the effector protein has a modified activity.
97. The composition of any one of paragraphs 89 to 96, wherein said effector protein comprises one or more mutations, preferably in the catalytic domain.
98. The composition according to any one of paragraphs 89 to 97, wherein said effector protein is catalytically inactive.
99. The composition according to any one of paragraphs 89 to 98, wherein said effector protein comprises at least one mutation, such that the effector protein has no more than 5% of the nuclease activity of the effector protein not having the at least one mutation.
100. The composition according to any one of paragraphs 89 to 99, wherein said effector protein is a nickase, optionally a nickase comprising or corresponding to N863A in SpCas9.
101. The composition according to any one of paragraphs 89 to 100, wherein said effector protein is codon optimized, preferably codon optimized for expression in a eukaryotic cell.
102. The composition according to any one of paragraphs 89 to 101, wherein said fusion protein comprising one or more destabilization domains, one or more adaptor proteins capable of binding to a CRISPR/Cas or argonaute system guide is codon optimized, preferably codon optimized for expression in a eukaryotic cell.
103. The composition according to any one of paragraphs 89 to 102, wherein said effector protein is a chimeric effector protein.
104. The composition according to any one of paragraphs 89 to 103, wherein said effector protein is a split effector protein.
105. A method of modifying a polynucleic acid target locus or introducing a polynucleic acid locus event, comprising delivering to or contacting with a polynucleic acid target locus or a host cell comprising said locus the activatable stabilizing ligand of a deactivation domain and fusion protein of any one of paragraphs 89 to 104.
106. The method according to paragraph 105, comprising delivering to or introducing in a host cell comprising a polynucleic acid target locus the activatable stabilizing ligand of a deactivation domain and fusion protein of any one of paragraphs 89 to 104.
107. The method according to paragraph 105 or 106, which is a method of treating or inhibiting a condition caused by a defect in a target sequence in a polynucleic acid locus of interest in a subject or a non-human subject in need thereof.
108. The method according to any one of paragraphs 105 to 107, wherein said host cell is a non-human and/or non-animal host cell.
109. The method according to any one of paragraphs 105 to 108, wherein said method is an in vivo, ex vivo, or in vitro method.
110. The method according to any one of paragraphs 105 to 109, wherein method results in gene activation, gene inhibition, or cleavage at the locus.
111. The method according to any one of paragraphs 105 to 110, wherein said fusion protein, polynucleic acid, vector, or composition is delivered with a viral delivery system, preferably a lentiviral, adenoviral, or AAV system.
112. The activatable stabilizing ligand composition of any one of paragraphs 89 to 104 for use in therapy.
113. Use of the activatable stabilizing ligand composition of any one of paragraphs 89 to 104 for the manufacture of a medicament.
114. A host cell or progeny thereof comprising or capable of expressing the activatable stabilizing ligand composition of any one of paragraphs 89 to 104.
115. The host cell according to paragraph 114, wherein the cell is a eukaryotic cell.
116. The host cell according to paragraph 115, wherein the eukaryotic cell is a mammalian cell, optionally a mouse cell.
117. The host cell according to paragraph 116, wherein the mammalian cell is a human cell.
118. The host cell according to paragraph 114, wherein the eukaryotic cell is a plant cell.
119. The host cell according to any one of paragraphs 114 to 118, wherein said cell is a cell line.
120. A non-human eukaryote comprising or transformed with the activatable stabilizing ligand and one or more polynucleic acids, vector, composition, or host cell, or comprising the activatable stabilizing ligand and capable of expressing one or more fusion proteins according to any one of paragraphs 89 to 112, optionally, wherein said eukaryote is an animal or a plant.
121. A kit comprising the activatable stabilizing ligand of a deactivation domain and fusion protein of any one of paragraphs 89 to 112.

Accordingly, it is an object of the invention not to encompass within the invention any previously known product, process of making the product, or method of using the product such that Applicants reserve the right and hereby disclose a disclaimer of any previously known product, process, or method. It is further noted that the invention does not intend to encompass within the scope of the invention any product, process, or making of the product or method of using the product, which does not meet the written description and enablement requirements of the USPTO (35 U.S.C. § 112, first paragraph) or the EPO (Article 83 of the EPC), such that Applicants reserve the right and hereby disclose a disclaimer of any previously described product, process of making the product, or method of using the product. It may be advantageous in the practice of the invention to be in compliance with Art. 53(c) EPC and Rule 28(b) and (c) EPC. Nothing herein is to be construed as a promise.

It is noted that in this disclosure and particularly in the claims and/or paragraphs, terms such as "comprises", "comprised", "comprising" and the like can have the meaning attributed to it in U.S. Patent law; e.g., they can mean "includes", "included", "including", and the like; and that terms such as "consisting essentially of" and "consists essentially of" have the meaning ascribed to them in U.S. Patent law, e.g., they allow for elements not explicitly recited, but exclude elements that are found in the prior art or that affect a basic or novel characteristic of the invention.

These and other embodiments are disclosed or are obvious from and encompassed by, the following Detailed Description.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

and SAM-dependent expression of ASCL1 mRNA was measured. Increased ASCL1 expression is observed in the presence of stabilibing ligand. Positive control: pSAM88. Negative control: GFP.

FIG. 13A-13D. Multidimensional 'chemical' control of endogenous transcript levels. (a) Top, small-molecule-mediated transcription induction via a destabilized domain-fused transcription activation domain (DHFR.PP7.VP64), dSpCas9, and an sgRNA. Bottom, HEK293T cells transfected with dSpCas9 and an RFP control, PP7.VP64, or TMP-regulated DHFR.PP7.VP64 targeted to ILIRNwere treated with 10 μM TMP for 18 h before qPCR analysis. (b) Rapid turn-off of transcription. Cells were transfected and treated with 100 nM TMP to upregulate endogenous ILIRN or NANOG. After 18 h of TMP treatment, cells were provided with fresh media containing or lacking TMP before harvesting and analysis by qPCR. (c) Independent, small-molecule-mediated control of transcript expression for two genes in cells expressing dSpCas9 and two orthogonal destabilized domain-regulated transcription activation domains. DHFR.PP7.VP64 was targeted to ILIRN, and ER50.MS2.p65.HSF1 was targeted to ASCL1. Transfected cells were treated as indicated (TMP, 100 nM; 40HT, 10 nM) for 18 h before qPCR analysis. (d) Highly dose-responsive endogenous gene upregulation in cells transfected with dSpCas9, appropriate sgRNAs, and either DHFR.PP7.VP64 (left) or ER50.MS2.p65.HSF1 (right) targeted to ILIRN or ASCL1, respectively. Transfected cells were treated with increasing concentrations of TMP or 40HT for 18 h before qPCR analysis. Error bars represent s.e.m. from biological replicates (n=3; a,c) or ±s.d. across technical replicates (n=4; b,d).

FIG. 14A-14D. Destabilized Domain (DD) ligand prodrug. (A) Inactive trimethoprim (TMP) derivatives and their hydrolysis by pig liver esterase (PLE). (B) TMP's binding pocket in *S. aureus* DHFR (pdb:2W9H). (C) Stepwise hydrolysis of DM1_147D by PLE monitored by LCMS. (D) eGFP-disruption in U20S.eGFP-PEST cells transfected with either SpCas9 or DHFR.SpCas9.DHFR and Pig Liver Esterase (PLE, pCAG-PLEIRES-mCherry) along with gRNA following treatment with the stabilizing small molecules TMP or TMP-derivatives (500 nM) for 48 h. Representative images of conditional control of SpCas9 mediated EGFP knockout by TMP or TMP-derivatives in the presence of increasing amount of PLE plasmid in U20S.EGFP-PEST cells. Error bars represent standard deviation of n=5.

Figure 15A:
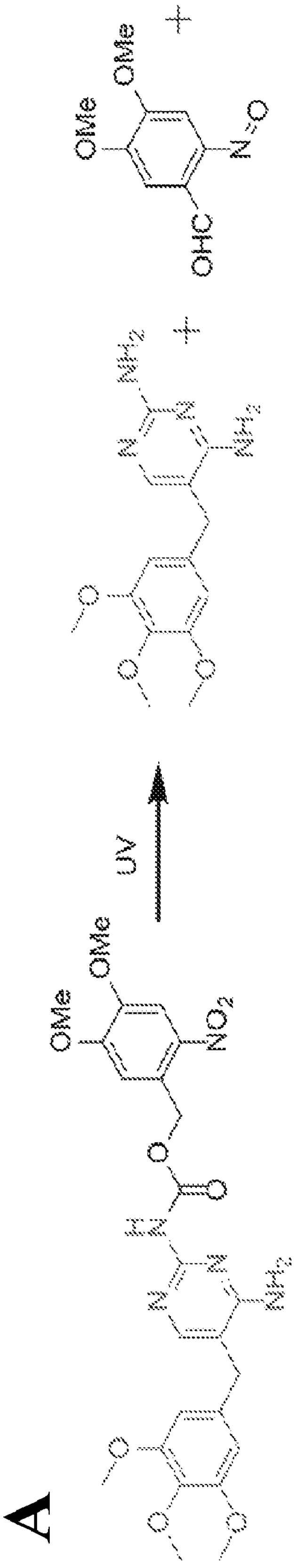
Figure 15B:
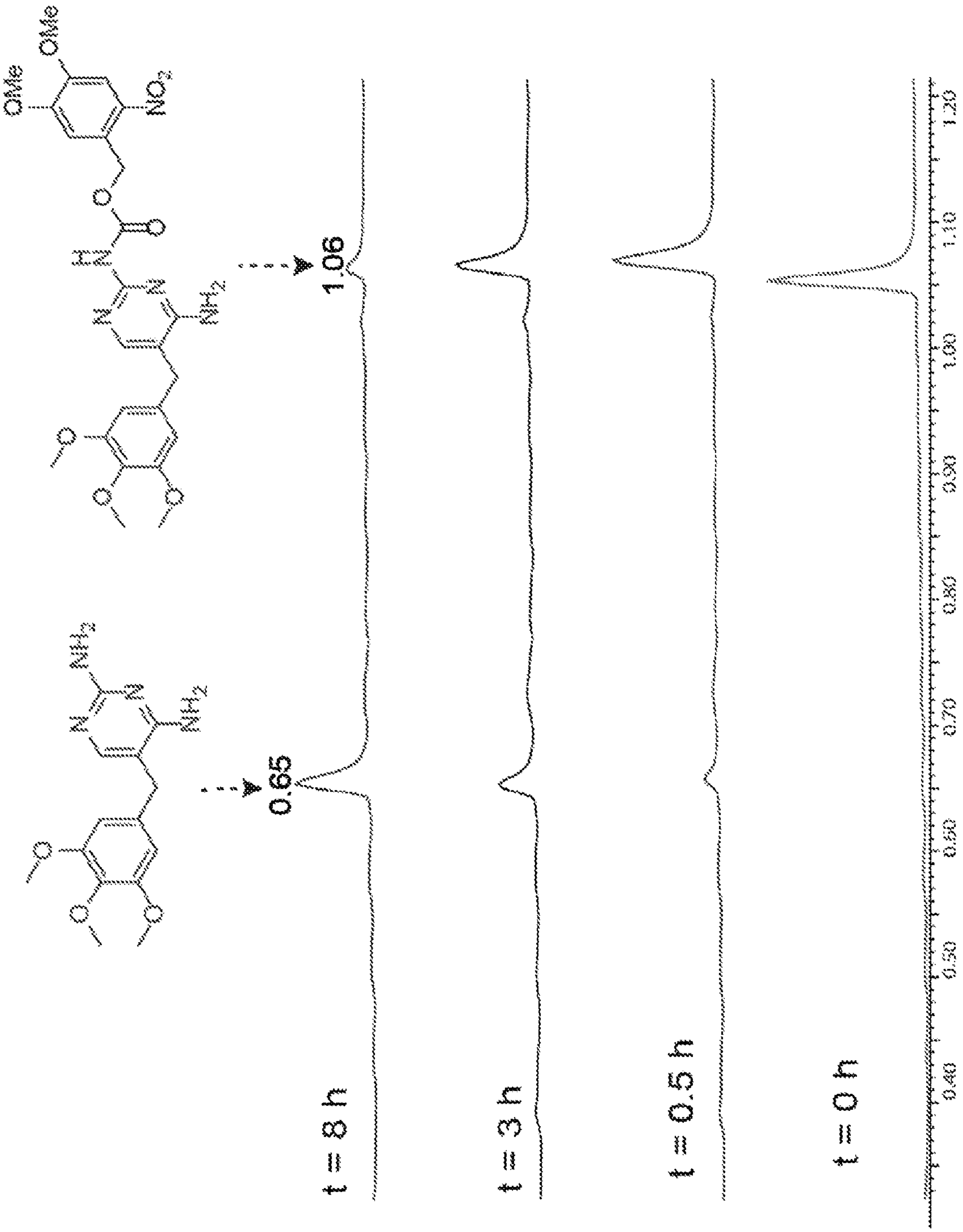
Figures 16A, 16B, 16C:
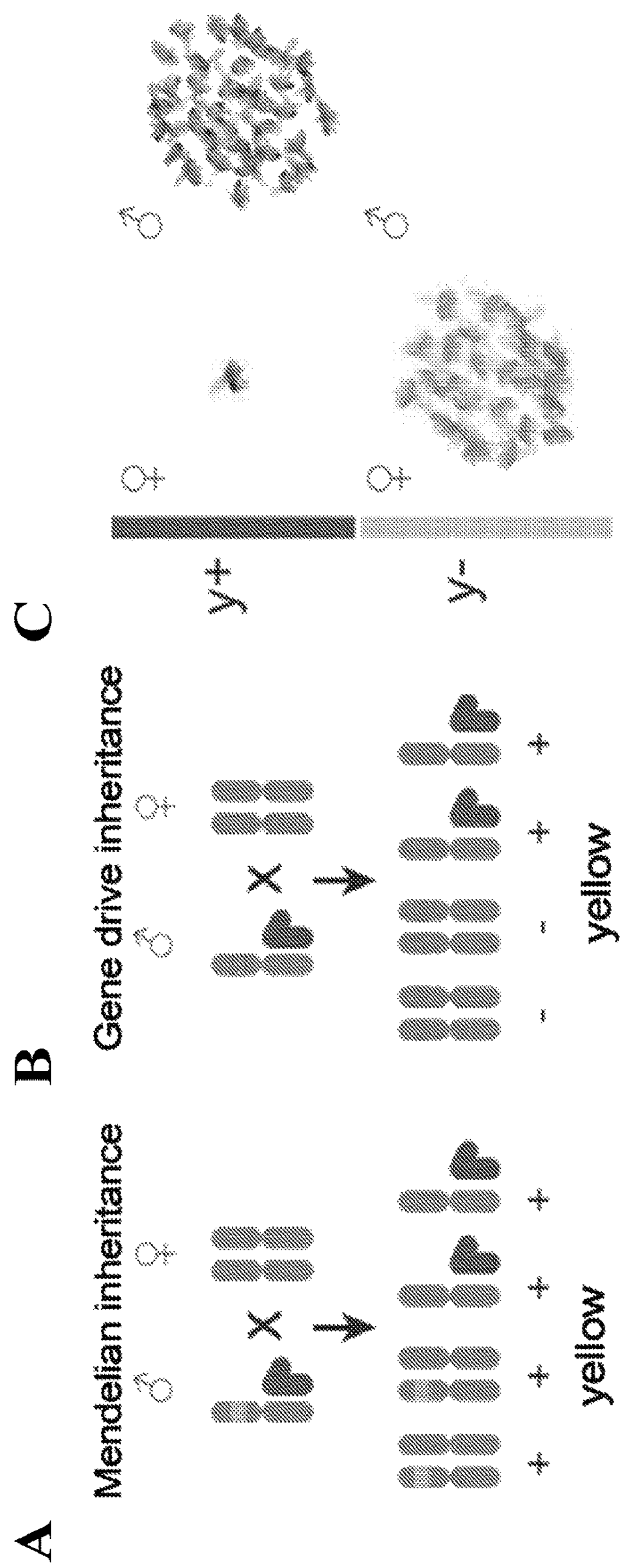
Figure 16D:
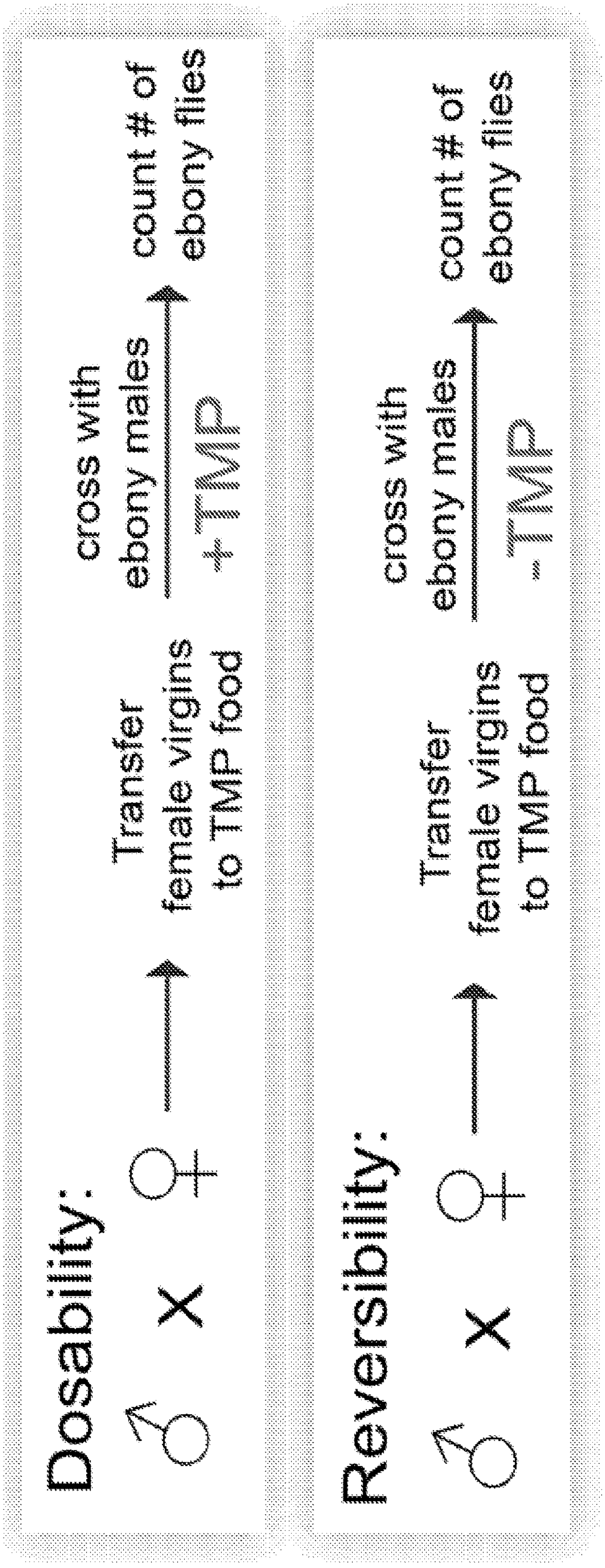
Figures 16E, 16F:
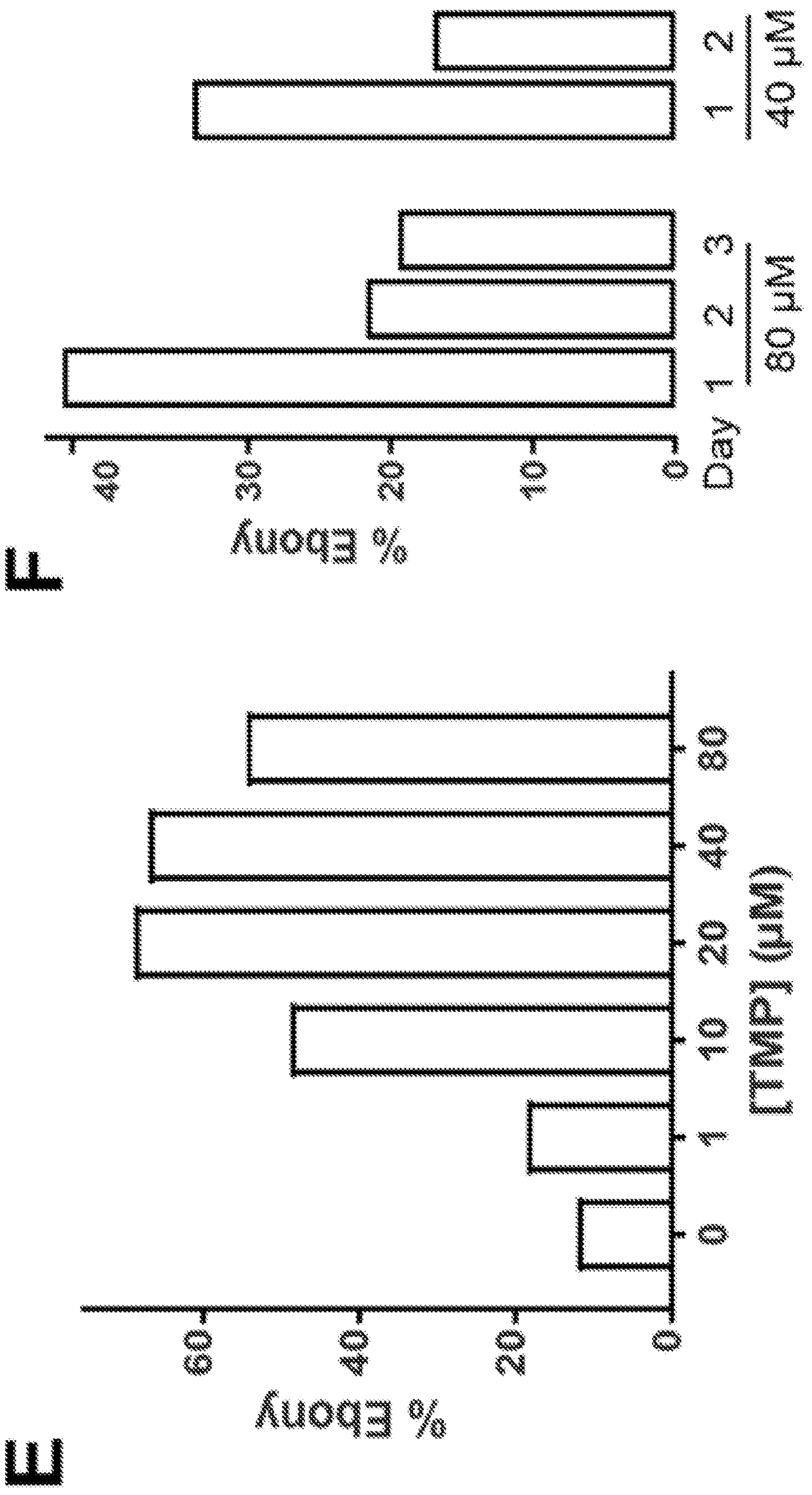
Figure 16G:
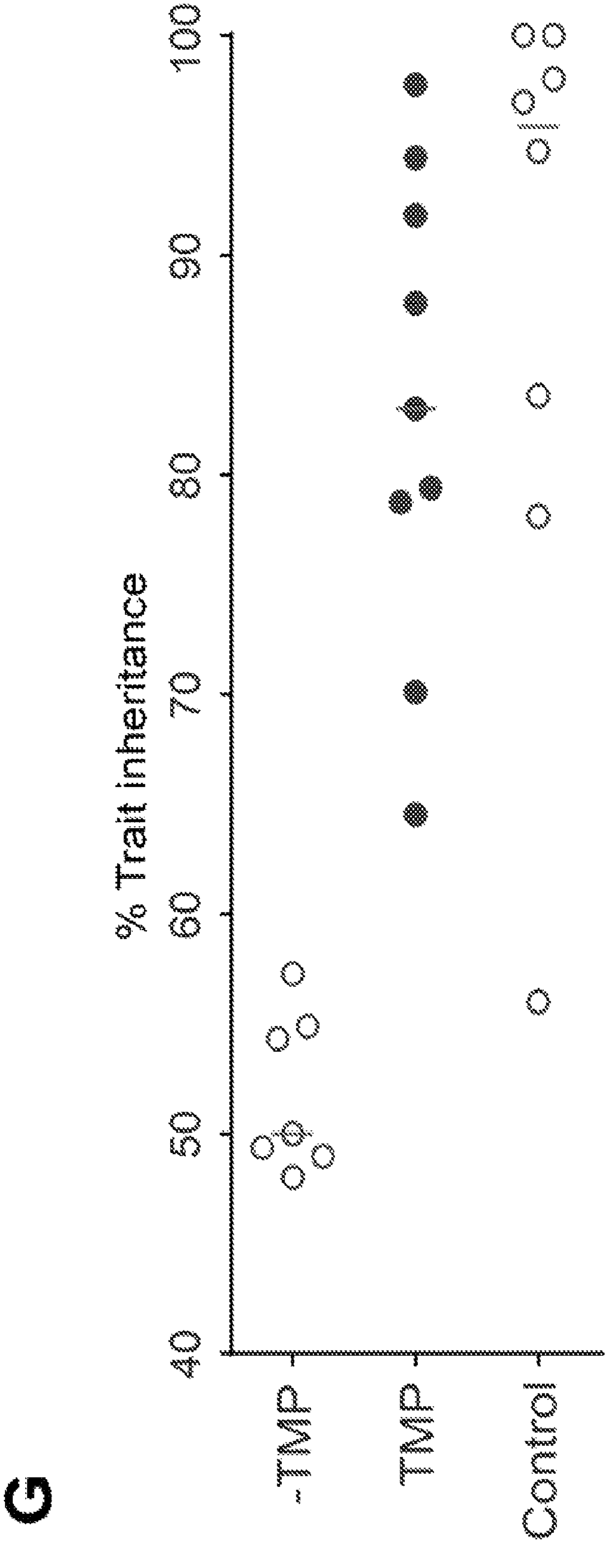

FIG. 15A-15B. Photoactivatable TMP derivative. (A) Structure of inactive photocaged TMP derivative. The bulky 6-nitroveratryl carbamate (NVOC) group attached to trimethoprim prevents photocaged TMP-NVOC from binding to DHFR. Upon exposure to light, the NVOC group is released, and TMP binds to and stabilizes the DHFR-DD. (B) HPLC analysis showing time course of conversion of photocaged TMP-NVOC to TMP upon exposure to light.

FIG. 16A-16G. Small-molecule-based gene drive control in *Drosophila*. (A) Mendelian inheritance of the yellow locus where all the females have the dark pigmentation. (B) & (C) Gene drive inheritance where all the females have the light pigmentation. (D) Demonstration of dose-dependent SpCas9 activation by Trimethoprim (TMP) and deactivation of SpCas9 upon removal of TMP. The female fly carries DHFR-SpCas9-DHFR driven by the pNOS promoter in the germline, while the male fly carries the gRNA targeting the ebony loci. (E) Dose-dependent SpCas9-mediated knockout of the ebony gene. (F) TMP removal from the fly food lowers % ebony knockout within 24 hrs post TMP removal. (G) A TMP-controlled gene drive in *Drosophila* for green body color. In the presence of TMP, SpCas9 is activated and 84% inheritance of the green-body color is observed (wt Cas9 ~92% green body color, while DMSO control is ~50% in accord with Mendelian inheritance.

The figures herein are for illustrative purposes only and are not necessarily drawn to scale.

DETAILED DESCRIPTION OF THE INVENTION

In general, the CRISPR-Cas or CRISPR system is as used in the foregoing documents, such as WO 2014/093622 (PCT/US2013/074667) and refers collectively to transcripts and other elements involved in the expression of or directing the activity of CRISPR-associated ("Cas") genes, including sequences encoding a Cas gene, in particular a Cas9, Cpf1, C2c1, C2c2, C2c3, Cas13, Group 29/30 gene, a tracr (trans-activating CRISPR, if or where applicable, e.g. in the case of CRISPR-Cas9) sequence (e.g., tracrRNA or an active partial tracrRNA), a tracr-mate sequence (encompassing a "direct repeat" and a tracrRNA-processed partial direct repeat in the context of an endogenous CRISPR system), a guide sequence (also referred to as a "spacer" in the context of an endogenous CRISPR system), or "RNA(s)" as that term is herein used (e.g., RNA(s) to guide Cas, e.g., CRISPR RNA and transactivating (tracr) RNA or a single guide RNA (sgRNA) (chimeric RNA)) or other sequences and transcripts from a CRISPR locus. In general, a CRISPR system is characterized by elements that promote the formation of a CRISPR complex at the site of a target sequence (also referred to as a protospacer in the context of an endogenous CRISPR system). In the context of formation of a CRISPR complex, "target sequence" refers to a sequence to which a guide sequence is designed to have complementarity, where hybridization between a target sequence and a guide sequence promotes the formation of a CRISPR complex. A target sequence may comprise any polynucleotide, such as DNA or RNA polynucleotides. In some embodiments, a target sequence is located in the nucleus or cytoplasm of a cell, and may include nucleic acids in or from mitochondrial, organelles, vesicles, liposomes or particles present within the cell. In some embodiments, especially for non-nuclear uses, NLSs are not preferred. In some embodiments, a CRISPR system comprises one or more nuclear exports signals (NESs). In some embodiments, a CRISPR system comprises one or more NLSs and one or more NESs. In some embodiments, direct repeats may be identified in silico by searching for repetitive motifs that fulfill any or all of the following criteria: 1. found in a 2Kb window of genomic sequence flanking the type II CRISPR locus; 2. span from 20 to 50 bp; and 3. interspaced by 20 to 50 bp. In some embodiments, 2 of these criteria may be used, for instance 1 and 2, 2 and 3, or 1 and 3. In some embodiments, all 3 criteria may be used.

As used herein, the terms "guide", "crRNA" or "guide RNA" or "single guide RNA" or "sgRNA" refer to any polynucleotide sequence having sufficient complementarity with a target nucleic acid sequence to hybridize with the target nucleic acid sequence and direct sequence-specific binding of a nucleic acid-targeting complex to the target nucleic acid sequence. The portion of the guide that is complementary to the target sequence may be refered to as the "targeting sequence." In some embodiments, the degree of complementarity, when optimally aligned using a suitable alignment algorithm, is about or more than about 50%, 60%, 75%, 80%, 85%, 90%, 95%, 97.5%, 99%, or more. Optimal alignment may be determined with the use of any suitable algorithm for aligning sequences, non-limiting example of which include the Smith-Waterman algorithm, the Needleman-Wunsch algorithm, algorithms based on the Burrows-Wheeler Transform (e.g., the Burrows Wheeler Aligner), Clustal W, Clustal X, BLAT, Novoalign (Novocraft Technologies; available at www.novocraft.com), ELAND (Illumina, San Diego, CA), SOAP (available at soap.genomics.org.cn), and Maq (available at maq.sourceforge.net). The ability of a guide sequence (within a nucleic acid-targeting guide) to direct sequence-specific binding of a nucleic acid-targeting complex to a target nucleic acid sequence may be assessed by any suitable assay. For example, the components of a nucleic acid-targeting CRISPR system sufficient to form a nucleic acid-targeting complex, including the guide sequence to be tested, may be provided to a host cell having the corresponding target nucleic acid sequence, such as by transfection with vectors encoding the components of the nucleic acid-targeting complex, followed by an assessment of preferential targeting (e.g., cleavage) within the target nucleic acid sequence, such as by Surveyor assay as described herein. Similarly, cleavage of a target nucleic acid sequence may be evaluated in a test tube by providing the target nucleic acid sequence, components of a nucleic acid-targeting complex, including the guide sequence to be tested and a control guide sequence different from the test guide sequence, and comparing binding or rate of cleavage at the target sequence between the test and control guide sequence reactions. Other assays are possible, and will occur to those skilled in the art. A guide sequence, and hence a nucleic acid-targeting guide may be selected to target any target nucleic acid sequence.

In some embodiments, a guide sequence is about or more than about 5, 10, 11, 12, 13, 14, 15, 16, 17, 18, 19, 20, 21, 22, 23, 24, 25, 26, 27, 28, 29, 30, 35, 40, 45, 50, 75, or more nucleotides in length. In some embodiments, a guide sequence is less than about 75, 50, 45, 40, 35, 30, 25, 20, 15, 12, or fewer nucleotides in length. Preferably the guide sequence is 10-30 nucleotides long. The skilled person will understand that guide sequence length may change depending on the type of Cas protein. The ability of a guide sequence to direct sequence-specific binding of a CRISPR complex to a target sequence may be assessed by any suitable assay. For example, the components of a CRISPR system sufficient to form a CRISPR complex, including the guide sequence to be tested, may be provided to a host cell having the corresponding target sequence, such as by transfection with vectors encoding the components of the CRISPR sequence, followed by an assessment of preferential cleavage within the target sequence, such as by Surveyor assay as described herein. Similarly, cleavage of a target polynucleotide sequence may be evaluated in a test tube by providing the target sequence, components of a CRISPR complex, including the guide sequence to be tested and a control guide sequence different from the test guide sequence, and comparing binding or rate of cleavage at the target sequence between the test and control guide sequence reactions. Other assays are possible, and will occur to those skilled in the art.

In some embodiments, the targeting sequence may be DNA. In some embodiments, the targeting sequence may be any RNA sequence. In some embodiments, the targeting sequence may comprise both DNA and RNA, for example one or more DNA nucleotides with the rest being RNA, or one or more RNA nucleotides with the rest being DNA.

In some embodiments, the target sequence may be a sequence within a RNA molecule selected from the group consisting of messenger RNA (mRNA), pre-mRNA, ribosomal RNA (rRNA), transfer RNA (tRNA), micro-RNA (miRNA), small interfering RNA (siRNA), small nuclear RNA (snRNA), small nucleolar RNA (snoRNA), double stranded RNA (dsRNA), non-coding RNA (ncRNA), long non-coding RNA (lncRNA), and small cytoplasmatic RNA (scRNA). In some preferred embodiments, the target sequence may be a sequence within a RNA molecule selected from the group consisting of mRNA, pre-mRNA, and rRNA. In some preferred embodiments, the target sequence may be a sequence within a RNA molecule selected from the group consisting of ncRNA, and lncRNA. In some more preferred embodiments, the target sequence may be a sequence within an mRNA molecule or a pre-mRNA molecule.

In a classic CRISPR-Cas system, the degree of complementarity between a guide sequence and its corresponding target sequence can be about or more than about 50%, 60%, 75%, 80%, 85%, 90%, 95%, 97.5%, 99%, or 100%; a guide or RNA or gRNA can be about or more than about 5, 10, 11, 12, 13, 14, 15, 16, 17, 18, 19, 20, 21, 22, 23, 24, 25, 26, 27, 28, 29, 30, 35, 40, 45, 50, 75, or more nucleotides in length; or guide or RNA or gRNA can be less than about 75, 50, 45, 40, 35, 30, 25, 20, 15, 12, or fewer nucleotides in length; and advantageously tracr RNA is 30 or 50 nucleotides in length. However, an aspect of the invention is to reduce off-target interactions, e.g., reduce the guide interacting with a target sequence having low complementarity. Indeed, in the examples, it is shown that the invention involves mutations that result in the CRISPR-Cas system being able to distinguish between target and off-target sequences that have greater than 80% to about 95% complementarity, e.g., 83%-84% or 88-89% or 94-95% complementarity (for instance, distinguishing between a target having 18 nucleotides from an off-target of 18 nucleotides having 1, 2 or 3 mismatches). Accordingly, in the context of the present invention the degree of complementarity between a guide sequence and its corresponding target sequence is greater than 94.5% or 95% or 95.5% or 96% or 96.5% or 97% or 97.5% or 98% or 98.5% or 99% or 99.5% or 99.9%, or 100%. Off target is less than 100% or 99.9% or 99.5% or 99% or 99% or 98.5% or 98% or 97.5% or 97% or 96.5% or 96% or 95.5% or 95% or 94.5% or 94% or 93% or 92% or 91% or 90% or 89% or 88% or 87% or 86% or 85% or 84% or 83% or 82% or 81% or 80% complementarity between the sequence and the guide, with it advantageous that off target is 100% or 99.9% or 99.5% or 99% or 99% or 98.5% or 98% or 97.5% or 97% or 96.5% or 96% or 95.5% or 95% or 94.5% complementarity between the sequence and the guide.

In some embodiments, a nucleic acid-targeting guide is selected to reduce the degree secondary structure within the nucleic acid-targeting guide. In some embodiments, about or less than about 75%, 50%, 40%, 30%, 25%, 20%, 15%, 10%, 5%, 1%, or fewer of the nucleotides of the nucleic acid-targeting guide participate in self-complementary base pairing when optimally folded. Optimal folding may be determined by any suitable polynucleotide folding algorithm. Some programs are based on calculating the minimal Gibbs free energy. An example of one such algorithm is mFold, as described by Zuker and Stiegler (Nucleic Acids Res. 9 (1981), 133-148). Another example folding algorithm is the online webserver RNAfold, developed at Institute for Theoretical Chemistry at the University of Vienna, using the centroid structure prediction algorithm (see e.g., A. R. Gruber et al., 2008, Cell 106(1): 23-24; and PA Carr and GM Church, 2009, Nature Biotechnology 27(12): 1151-62).

In certain embodiments, a guide RNA or crRNA may comprise, consist essentially of, or consist of a direct repeat (DR) sequence and a guide sequence or spacer sequence. In certain embodiments, the guide RNA or crRNA may comprise, consist essentially of, or consist of a direct repeat sequence fused or linked to a guide sequence or spacer sequence. In certain embodiments, the direct repeat sequence may be located upstream (i.e., 5') from the guide sequence or spacer sequence. In other embodiments, the direct repeat sequence may be located downstream (i.e., 3') from the guide sequence or spacer sequence.

In certain embodiments, the crRNA comprises a stem loop, preferably a single stem loop. In certain embodiments, the direct repeat sequence forms a stem loop, preferably a single stem loop.

In particularly preferred embodiments according to the invention, a protected guide RNA (capable of guiding Cas to a target locus) may comprise (1) a guide sequence (including its protector sequence) capable of hybridizing to a genomic target locus in the eukaryotic cell; (2) a tracr sequence; and (3) a tracr mate sequence. All (1) to (3) may reside in a single RNA, i.e. an gRNA (arranged in a 5' to 3' orientation), or the tracr RNA (if applicable) may be a different RNA than the RNA containing the guide and tracr sequence. The tracr hybridizes to the tracr mate sequence and directs the CRISPR/Cas complex to the target sequence.

The methods according to the invention as described herein comprehend inducing one or more mutations or modifications in a eukaryotic cell (in vitro, i.e. in an isolated eukaryotic cell) as herein discussed comprising delivering to cell a vector as herein discussed. The mutation(s) can include the introduction, deletion, or substitution of one or more nucleotides at each target sequence of cell(s) via the guide(s) RNA(s) or gRNA(s). The mutations can include the introduction, deletion, or substitution of 1-75 nucleotides at each target sequence of said cell(s) via the guide(s) RNA(s) or gRNA(s). The mutations can include the introduction, deletion, or substitution of 1, 5, 10, 11, 12, 13, 14, 15, 16, 17, 18, 19, 20, 21, 22, 23, 24, 25, 26, 27, 28, 29, 30, 35, 40, 45, 50, or 75 nucleotides at each target sequence of said cell(s) via the guide(s) RNA(s) or gRNA(s). The mutations can include the introduction, deletion, or substitution of 5, 10, 11, 12, 13, 14, 15, 16, 17, 18, 19, 20, 21, 22, 23, 24, 25, 26, 27, 28, 29, 30, 35, 40, 45, 50, or 75 nucleotides at each target sequence of said cell(s) via the guide(s) RNA(s) or gRNA(s). The mutations include the introduction, deletion, or substitution of 10, 11, 12, 13, 14, 15, 16, 17, 18, 19, 20, 21, 22, 23, 24, 25, 26, 27, 28, 29, 30, 35, 40, 45, 50, or 75 nucleotides at each target sequence of said cell(s) via the guide(s) RNA(s) or gRNA(s). The mutations can include the introduction, deletion, or substitution of 20, 21, 22, 23, 24, 25, 26, 27, 28, 29, 30, 35, 40, 45, 50, or 75 nucleotides at each target sequence of said cell(s) via the guide(s) RNA(s) or gRNA(s). The mutations can include the introduction, deletion, or substitution of 40, 45, 50, 75, 100, 200, 300, 400 or 500 nucleotides at each target sequence of said cell(s) via the guide(s) RNA(s) or gRNA(s).

Aptamers and Ligands

Aptamers are biomolecules that can be designed or selected to bind tightly to other ligands, for example using a technique called systematic evolution of ligands by exponential enrichment (SELEX; Tuerk C, Gold L: "Systematic evolution of ligands by exponential enrichment: RNA ligands to bacteriophage T4 DNA polymerase." Science 1990, 249:505-510). Nucleic acid aptamers can for example be selected from pools of random-sequence oligonucleotides, with high binding affinities and specificities for a wide range of biomedically relevant targets, suggesting a wide range of therapeutic utilities for aptamers (Keefe, Anthony D., Supriya Pai, and Andrew Ellington. "Aptamers as therapeutics." Nature Reviews Drug Discovery 9.7 (2010): 537-550). These characteristics also suggest a wide range of uses for aptamers as drug delivery vehicles (Levy-Nissenbaum, Etgar, et al. "Nanotechnology and aptamers: applications in drug delivery." Trends in biotechnology 26.8 (2008): 442-449; and, Hicke BJ, Stephens AW. "Escort aptamers: a delivery service for diagnosis and therapy." J Clin Invest 2000, 106:923-928.). Aptamers may also be constructed that function as molecular switches, responding to a que by changing properties, such as RNA aptamers that bind fluorophores to mimic the activity of green fluorescent protein (Paige, Jeremy S., Karen Y. Wu, and Samie R. Jaffrey. "RNA mimics of green fluorescent protein." Science 333.6042 (2011): 642-646). It has also been suggested that aptamers may be used as components of targeted siRNA therapeutic delivery systems, for example targeting cell surface proteins (Zhou, Jiehua, and John J. Rossi. "Aptamer-targeted cell-specific RNA interference." Silence 1.1 (2010): 4).

Reference is also made to Magalhaes ("A general RNA motif for cellular transfection."), the contents of which are hereby incorporated by reference. This paper described the use of aptamers such as Otter and C1, as well as their minimal versions: OtterMin and C1Min. In some embodiments, one or more, preferably two, of Otter and/or C1 are used in the present invention as the escort RNA aptamer sequence. In some embodiments, OtterMin may replace Otter. In some embodiments, C1Min may replace C1. In some embodiments, 2× Otter, 2× C1, 2× C1Min, or 2× OtterMin may be used. Combinations of two of any of the four are also preferred in some embodiments. In some embodiments, it is preferred to have one of Otter or Otter-Min, and one of C1 or C1Min. Where a certain aptamer is used as an escort RNA aptamer sequence, then it will be appreciated that the corresponding RNA (escort RNA aptamer sequence) will be required. Modified Systems The present invention provides compositions and methods by which gRNA-mediated gene editing activity can be adapted. The invention provides gRNA secondary structures that improve cutting efficiency by increasing gRNA and/or increasing the amount of RNA delivered into the cell. The gRNA includes light labile or inducible nucleotides.

To increase the effectiveness of gRNA, for example gRNA delivered with viral or non-viral technologies, Applicants added secondary structures into the gRNA that enhance its stability and improve gene editing. Separately, to overcome the lack of effective delivery, Applicants modified gRNAs with cell penetrating RNA aptamers; the aptamers bind to cell surface receptors and promote the entry of gRNAs into cells. Notably, the cell-penetrating aptamers can be designed to target specific cell receptors, in order to mediate cell-specific delivery. Applicants also have created guides that are inducible.

Light responsiveness of an inducible system may be achieved via the activation and binding of cryptochrome-2 and CIB1. Blue light stimulation induces an activating conformational change in cryptochrome-2, resulting in recruitment of its binding partner CIB1. This binding is fast and reversible, achieving saturation in <15 sec following pulsed stimulation and returning to baseline <15 min after the end of stimulation. These rapid binding kinetics result in a system temporally bound only by the speed of transcription/translation and transcript/protein degradation, rather than uptake and clearance of inducing agents. Cryptochrome-2 activation is also highly sensitive, allowing for the use of low light intensity stimulation and mitigating the risks of phototoxicity. Further, in a context such as the intact mammalian brain, variable light intensity may be used to control the size of a stimulated region, allowing for greater precision than vector delivery alone may offer.

The invention contemplates energy sources such as electromagnetic radiation, sound energy or thermal energy to induce the guide. Advantageously, the electromagnetic radiation is a component of visible light. In a preferred embodiment, the light is a blue light with a wavelength of about 450 to about 495 nm. In an especially preferred embodiment, the wavelength is about 488 nm. In another preferred embodiment, the light stimulation is via pulses. The light power may range from about 0-9 mW/cm2. In a preferred embodiment, a stimulation paradigm of as low as 0.25 sec every 15 sec should result in maximal activation.

Cells involved in the practice the present invention may be a prokaryotic cell or a eukaryotic cell, advantageously an animal cell, more advantageously a mammalian cell.

The chemical or energy sensitive guide may undergo a conformational change upon induction by the binding of a chemical source or by the energy allowing it act as a guide and have the CRISPR-Cas system or complex function. The invention can involve applying the chemical source or energy so as to have the guide function and the CRISPR-Cas system or complex function; and optionally further determining that the expression of the genomic locus is altered.

There are several different designs of this chemical inducible system: 1. ABI-PYL based system inducible by Abscisic Acid (ABA) (see, e.g., stke.sciencemag.org/cgi/content/abstract/sigtrans;4/164/rs2), 2. FKBP-FRB based system inducible by rapamycin (or related chemicals based on rapamycin) (see, e.g., www.nature.com/nmeth/journal/v2/n6/full/nmeth763.html), 3. GID1-GAI based system inducible by Gibberellin (GA) (see, e.g., www.nature.com/nchembio/journal/v8/n5/full/nchembio.922.html).

Another system contemplated by the present invention is a chemical inducible system based on change in sub-cellular localization. Applicants also developed a system in which the polypeptide include a DNA binding domain comprising at least five or more Transcription activator-like effector (TALE) monomers and at least one or more half-monomers specifically ordered to target the genomic locus of interest linked to at least one or more effector domains are further linker to a chemical or energy sensitive protein. This protein will lead to a change in the sub-cellular localization of the entire polypeptide (i.e. transportation of the entire polypeptide from cytoplasm into the nucleus of the cells) upon the binding of a chemical or energy transfer to the chemical or energy sensitive protein. This transportation of the entire polypeptide from one sub-cellular compartments or organelles, in which its activity is sequestered due to lack of substrate for the effector domain, into another one in which the substrate is present would allow the entire polypeptide to come in contact with its desired substrate (i.e. genomic DNA in the mammalian nucleus) and result in activation or repression of target gene expression.

This type of system could also be used to induce the cleavage of a genomic locus of interest in a cell when the effector domain is a nuclease.

A chemical inducible system can be an estrogen receptor (ER) based system inducible by 4-hydroxytamoxifen (40HT) (see, e.g., www.pnas.org/content/104/3/1027.abstract). A mutated ligand-binding domain of the estrogen receptor called ERT2 translocates into the nucleus of cells upon binding of 4-hydroxytamoxifen. In further embodiments of the invention any naturally occurring or engineered derivative of any nuclear receptor, thyroid hormone receptor, retinoic acid receptor, estrogen receptor, estrogen-related receptor, glucocorticoid receptor, progesterone receptor, androgen receptor may be used in inducible systems analogous to the ER based inducible system.

Another inducible system is based on the design using Transient receptor potential (TRP) ion channel based system inducible by energy, heat or radio-wave (see, e.g., www.sciencemag.org/content/336/6081/604). These TRP family proteins respond to different stimuli, including light and heat. When this protein is activated by light or heat, the ion channel will open and allow the entering of ions such as calcium into the plasma membrane. This inflex of ions will bind to intracellular ion interacting partners linked to a polypeptide including the guide and the other components of the CRISPR-Cas complex or system, and the binding will induce the change of sub-cellular localization of the polypeptide, leading to the entire polypeptide entering the nucleus of cells. Once inside the nucleus, the guide protein and the other components of the CRISPR-Cas complex will be active and modulating target gene expression in cells.

This type of system could also be used to induce the cleavage of a genomic locus of interest in a cell; and, in this regard, it is noted that the CRISPR enzyme, i.e., Cas9, is a nuclease. The light could be generated with a laser or other forms of energy sources. The heat could be generated by raise of temperature results from an energy source, or from nano-particles that release heat after absorbing energy from an energy source delivered in the form of radio-wave.

While light activation may be an advantageous embodiment, sometimes it may be disadvantageous especially for in vivo applications in which the light may not penetrate the skin or other organs. In this instance, other methods of energy activation are contemplated, in particular, electric field energy and/or ultrasound which have a similar effect.

Electric field energy is preferably administered substantially as described in the art, using one or more electric pulses of from about 1 Volt/cm to about 10 kVolts/cm under in vivo conditions. Instead of or in addition to the pulses, the electric field may be delivered in a continuous manner. The electric pulse may be applied for between 1 μs and 500 milliseconds, preferably between 1 μs and 100 milliseconds. The electric field may be applied continuously or in a pulsed manner for 5 about minutes.

As used herein, 'electric field energy' is the electrical energy to which a cell is exposed. Preferably the electric field has a strength of from about 1 Volt/cm to about 10 kVolts/cm or more under in vivo conditions (see WO97/49450).

As used herein, the term "electric field" includes one or more pulses at variable capacitance and voltage and including exponential and/or square wave and/or modulated wave and/or modulated square wave forms. References to electric fields and electricity should be taken to include reference the presence of an electric potential difference in the environment of a cell. Such an environment may be set up by way of static electricity, alternating current (AC), direct current (DC), etc, as known in the art. The electric field may be uniform, non-uniform or otherwise, and may vary in strength and/or direction in a time dependent manner.

Single or multiple applications of electric field, as well as single or multiple applications of ultrasound are also possible, in any order and in any combination. The ultrasound and/or the electric field may be delivered as single or multiple continuous applications, or as pulses (pulsatile delivery).

Electroporation has been used in both in vitro and in vivo procedures to introduce foreign material into living cells. With in vitro applications, a sample of live cells is first mixed with the agent of interest and placed between electrodes such as parallel plates. Then, the electrodes apply an electrical field to the cell/implant mixture. Examples of systems that perform in vitro electroporation include the Electro Cell Manipulator ECM600 product, and the Electro Square Porator T820, both made by the BTX Division of Genetronics, Inc (see U.S. Pat. No. 5,869,326).

The known electroporation techniques (both in vitro and in vivo) function by applying a brief high voltage pulse to electrodes positioned around the treatment region. The electric field generated between the electrodes causes the cell membranes to temporarily become porous, whereupon molecules of the agent of interest enter the cells. In known electroporation applications, this electric field comprises a single square wave pulse on the order of 1000 V/cm, of about 100.mu.s duration. Such a pulse may be generated, for example, in known applications of the Electro Square Porator T820.

Preferably, the electric field has a strength of from about 1 V/cm to about 10 kV/cm under in vitro conditions. Thus, the electric field may have a strength of 1 V/cm, 2 V/cm, 3 V/cm, 4 V/cm, 5 V/cm, 6 V/cm, 7 V/cm, 8 V/cm, 9 V/cm, 10 V/cm, 20 V/cm, 50 V/cm, 100 V/cm, 200 V/cm, 300 V/cm, 400 V/cm, 500 V/cm, 600 V/cm, 700 V/cm, 800 V/cm, 900 V/cm, 1 kV/cm, 2 kV/cm, 5 kV/cm, 10 kV/cm, 20 kV/cm, 50 kV/cm or more. More preferably from about 0.5 kV/cm to about 4.0 kV/cm under in vitro conditions. Preferably the electric field has a strength of from about 1 V/cm to about 10 kV/cm under in vivo conditions. However, the electric field strengths may be lowered where the number of pulses delivered to the target site are increased. Thus, pulsatile delivery of electric fields at lower field strengths is envisaged.

Preferably the application of the electric field is in the form of multiple pulses such as double pulses of the same strength and capacitance or sequential pulses of varying strength and/or capacitance. As used herein, the term "pulse" includes one or more electric pulses at variable capacitance and voltage and including exponential and/or square wave and/or modulated wave/square wave forms.

Preferably the electric pulse is delivered as a waveform selected from an exponential wave form, a square wave form, a modulated wave form and a modulated square wave form.

A preferred embodiment employs direct current at low voltage. Thus, Applicants disclose the use of an electric field which is applied to the cell, tissue or tissue mass at a field strength of between 1V/cm and 20V/cm, for a period of 100 milliseconds or more, preferably 15 minutes or more.

Ultrasound is advantageously administered at a power level of from about 0.05 W/cm2 to about 100 W/cm2. Diagnostic or therapeutic ultrasound may be used, or combinations thereof.

As used herein, the term "ultrasound" refers to a form of energy which consists of mechanical vibrations the frequencies of which are so high they are above the range of human hearing. Lower frequency limit of the ultrasonic spectrum may generally be taken as about 20 kHz. Most diagnostic applications of ultrasound employ frequencies in the range 1 and 15 MHz' (From Ultrasonics in Clinical Diagnosis, P. N. T. Wells, ed., 2nd. Edition, Publ. Churchill Livingstone [Edinburgh, London & NY, 1977]).

Ultrasound has been used in both diagnostic and therapeutic applications. When used as a diagnostic tool ("diagnostic ultrasound"), ultrasound is typically used in an energy density range of up to about 100 mW/cm2 (FDA recommendation), although energy densities of up to 750 mW/cm2 have been used. In physiotherapy, ultrasound is typically used as an energy source in a range up to about 3 to 4 W/cm2 (WHO recommendation). In other therapeutic applications, higher intensities of ultrasound may be employed, for example, HIFU at 100 W/cm up to 1 kW/cm2 (or even higher) for short periods of time. The term "ultrasound" as used in this specification is intended to encompass diagnostic, therapeutic and focused ultrasound.

Focused ultrasound (FUS) allows thermal energy to be delivered without an invasive probe (see Morocz et al 1998 Journal of Magnetic Resonance Imaging Vol. 8, No. 1, pp. 136-142. Another form of focused ultrasound is high intensity focused ultrasound (HIFU) which is reviewed by Moussatov et al in Ultrasonics (1998) Vol. 36, No. 8, pp.893-900 and Tran Huu Hue et al in Acustica (1997) Vol. 83, No. 6, pp.1103-1106.

Preferably, a combination of diagnostic ultrasound and a therapeutic ultrasound is employed. This combination is not intended to be limiting, however, and the skilled reader will appreciate that any variety of combinations of ultrasound may be used. Additionally, the energy density, frequency of ultrasound, and period of exposure may be varied.

Preferably the exposure to an ultrasound energy source is at a power density of from about 0.05 to about 100 Wcm−2. Even more preferably, the exposure to an ultrasound energy source is at a power density of from about 1 to about 15 Wcm−2.

Preferably the exposure to an ultrasound energy source is at a frequency of from about 0.015 to about 10.0 MHz. More preferably the exposure to an ultrasound energy source is at a frequency of from about 0.02 to about 5.0 MHz or about 6.0 MHz. Most preferably, the ultrasound is applied at a frequency of 3 MHz.

Preferably the exposure is for periods of from about 10 milliseconds to about 60 minutes. Preferably the exposure is for periods of from about 1 second to about 5 minutes. More preferably, the ultrasound is applied for about 2 minutes. Depending on the particular target cell to be disrupted, however, the exposure may be for a longer duration, for example, for 15 minutes.

Advantageously, the target tissue is exposed to an ultrasound energy source at an acoustic power density of from about 0.05 Wcm−2 to about 10 Wcm−2 with a frequency ranging from about 0.015 to about 10 MHz (see WO 98/52609). However, alternatives are also possible, for example, exposure to an ultrasound energy source at an acoustic power density of above 100 Wcm−2, but for reduced periods of time, for example, 1000 Wcm−2 for periods in the millisecond range or less.

Preferably the application of the ultrasound is in the form of multiple pulses; thus, both continuous wave and pulsed wave (pulsatile delivery of ultrasound) may be employed in any combination. For example, continuous wave ultrasound may be applied, followed by pulsed wave ultrasound, or vice versa. This may be repeated any number of times, in any order and combination. The pulsed wave ultrasound may be applied against a background of continuous wave ultrasound, and any number of pulses may be used in any number of groups.

Preferably, the ultrasound may comprise pulsed wave ultrasound. In a highly preferred embodiment, the ultrasound is applied at a power density of 0.7 Wcm−2 or 1.25 Wcm−2 as a continuous wave. Higher power densities may be employed if pulsed wave ultrasound is used.

Use of ultrasound is advantageous as, like light, it may be focused accurately on a target. Moreover, ultrasound is advantageous as it may be focused more deeply into tissues unlike light. It is therefore better suited to whole-tissue penetration (such as but not limited to a lobe of the liver) or whole organ (such as but not limited to the entire liver or an entire muscle, such as the heart) therapy. Another important advantage is that ultrasound is a non-invasive stimulus which is used in a wide variety of diagnostic and therapeutic applications. By way of example, ultrasound is well known in medical imaging techniques and, additionally, in orthopedic therapy. Furthermore, instruments suitable for the application of ultrasound to a subject vertebrate are widely available and their use is well known in the art.

The rapid transcriptional response and endogenous targeting of the instant invention make for an ideal system for the study of transcriptional dynamics. For example, the instant invention may be used to study the dynamics of variant production upon induced expression of a target gene. On the other end of the transcription cycle, mRNA degradation studies are often performed in response to a strong extracellular stimulus, causing expression level changes in a plethora of genes. The instant invention may be utilized to reversibly induce transcription of an endogenous target, after which point stimulation may be stopped and the degradation kinetics of the unique target may be tracked.

The temporal precision of the instant invention may provide the power to time genetic regulation in concert with experimental interventions. For example, targets with suspected involvement in long-term potentiation (LTP) may be modulated in organotypic or dissociated neuronal cultures, but only during stimulus to induce LTP, so as to avoid interfering with the normal development of the cells. Similarly, in cellular models exhibiting disease phenotypes, targets suspected to be involved in the effectiveness of a particular therapy may be modulated only during treatment. Conversely, genetic targets may be modulated only during a pathological stimulus. Any number of experiments in which timing of genetic cues to external experimental stimuli is of relevance may potentially benefit from the utility of the instant invention.

The in vivo context offers equally rich opportunities for the instant invention to control gene expression. Photoinducibility provides the potential for spatial precision. Taking advantage of the development of optrode technology, a stimulating fiber optic lead may be placed in a precise brain region. Stimulation region size may then be tuned by light intensity. This may be done in conjunction with the delivery of the CRISPR-Cas system or complex of the invention, or, in the case of transgenic Cas9 animals, guide RNA of the invention may be delivered and the optrode technology can allow for the modulation of gene expression in precise brain regions. A transparent Cas9 expressing organism, such as an immobilized Cas9 expressing zebrafish, can have guide RNA of the invention administered to it and then there can be extremely precise laser induced local gene expression changes.

A culture medium for culturing host cells includes a medium commonly used for tissue culture, such as M199-earle base, Eagle MEM (E-MEM), Dulbecco MEM (DMEM), SC-UCM102, UP-SFM (GIBCO BRL), EX-CELL302 (Nichirei), EX-CELL293-S(Nichirei), TFBM-01 (Nichirei), ASF104, among others. Suitable culture media for specific cell types may be found at the American Type Culture Collection (ATCC) or the European Collection of Cell Cultures (ECACC). Culture media may be supplemented with amino acids such as L-glutamine, salts, anti-fungal or anti-bacterial agents such as Fungizone®, penicillin-streptomycin, animal serum, and the like. The cell culture medium may optionally be serum-free.

The invention may also offer valuable temporal precision in vivo. The invention may be used to alter gene expression during a particular stage of development. The invention may be used to time a genetic cue to a particular experimental window. For example, genes implicated in learning may be overexpressed or repressed only during the learning stimulus in a precise region of the intact rodent or primate brain. Further, the invention may be used to induce gene expression changes only during particular stages of disease development. For example, an oncogene may be overexpressed only once a tumor reaches a particular size or metastatic stage. Conversely, proteins suspected in the development of Alzheimer's may be knocked down only at defined time points in the animal's life and within a particular brain region. Although these examples do not exhaustively list the potential applications of the invention, they highlight some of the areas in which the invention may be a powerful technology.

In certain embodiments, the gRNA (or gDNA) as used herein is an escorted gRNA (or gDNA). By "escorted" is meant that the CRISPR-Cas system or complex or guide is delivered to a selected time or place within a cell, so that activity of the CRISPR-Cas system or complex or guide is spatially or temporally controlled. For example, the activity and destination of the CRISPR-Cas system or complex or guide may be controlled by an escort RNA aptamer sequence that has binding affinity for an aptamer ligand, such as a cell surface protein or other localized cellular component. Alternatively, the escort aptamer (escort RNA aptamer sequence) may for example be responsive to, i.e. activated or inactivated by, an aptamer effector on or in the cell. The aptamer effector may be a transient effector, such as an external energy source that is applied to the cell at a particular time. In some embodiments, the external energy source is light energy.

It will be appreciated that the terms "escort RNA aptamer sequence" and "escort aptamer" are used interchangeably herein. In some embodiments, the escort RNA aptamer sequence comprises an aptamer sequence and is fused to the guide at one or more of the tetraloop and/or stem loop 2. Preferably, the escort RNA aptamer sequence is completely, RNA although it may comprise DNA or other nucleotides: preferably it is predominantly, i.e. at least 50%, RNA. Examples of aptamers comprised within the escort RNA aptamer sequence include Otter and C1, as well as their minimal versions: OtterMin and C1Min.

The invention involves gRNA of CRISPR-Cas systems or complexes and hence such complexes or systems having an gRNA with a functional structure designed to improve gRNA structure, architecture, stability, genetic expression, or any combination thereof. Such a structure can include an aptamer. Accordingly, the invention provides an gRNA modified, e.g., by one or more aptamer(s) designed to improve gRNA delivery, including delivery across the cellular membrane, to intracellular compartments, or into the nucleus. Such a structure can include, either in addition to the one or more aptamer(s) or without such one or more aptamer(s), moiety(ies) so as to render the guide deliverable, inducible or responsive to (for example activatable or inactivatable by) a selected effector. The invention accordingly comprehends an gRNA that responds to normal or pathological physiological conditions, including without limitation pH, hypoxia, O2 concentration, temperature, protein concentration, enzymatic concentration, lipid structure, light exposure, mechanical disruption (e.g. ultrasound waves), magnetic fields, electric fields, or electromagnetic radiation.

In some embodiments, the escort RNA aptamer sequence has binding affinity for an aptamer ligand on or in the cell. In some embodiments, the aptamer ligand is on the cell, for example so that it is at least partially available on the extra-cellular face or side of the cell membrane. For example, the aptamer ligand may be a cell-surface protein. The aptamer ligand may therefore be one part of a fusion protein, one other part of the fusion protein having a membrane anchor or membrane-spanning domain. In some embodiments, the aptamer ligand is in the cell. For example, the aptamer ligand may be internalised within a cell, i.e. within (beyond) the cell membrane, for example in the cytoplasm, within an organelle (including mitochondria), within an endosome, or in the nucleus (if the cell has one, i.e. it is a eukaryotic cell).

In some embodiments, the escort RNA aptamer sequence is responsive to a localized aptamer effector on or in the cell. In some embodiments, the aptamer effector is localized on the cell, for example so that it is at least partially available on the extra-cellular face or side of the cell membrane. The aptamer effector may therefore be one part of a fusion protein, one other part of the fusion protein having a membrane anchor or membrane-spanning domain. In some embodiments, the aptamer effector is in the cell. For example, the aptamer effector may be internalised within a cell, i.e. within (beyond) the cell membrane, for example in the cytoplasm, within an organelle (including mitochondria), within an endosome, or in the nucleus (if the cell has one, i.e. it is a eukaryotic cell).

In some embodiments, the (escort) RNA aptamer sequence is 'responsive to' the aptamer effector such that the escort RNA aptamer sequence is activated and, optionally, the guide itself is activated so that target recognition and hybridization and optionally, recruitment of the CRISPR protein is increased. Optionally, this results in greater nicking or cleavage in the case of nickases and nucleases. In other embodiments, the escort RNA aptamer sequence is 'responsive to' the aptamer effector such that the escort RNA aptamer sequence is de-activated and, optionally, the guide itself is de-activated so that target recognition and hybridization and optionally, recruitment of the CRISPR protein is decreased. Optionally, this results in reduced nicking or cleavage in the case of nickases and nucleases.

In some embodiments, the (escort) aptamer (escort RNA aptamer sequence) may for example change conformation in response to an interaction with the aptamer ligand or effector in the cell. In some embodiments, it may have specific binding affinity for the aptamer ligand.

The aptamer ligand may be localized in a location or compartment of the cell, for example on or in a membrane of the cell. In some embodiments, binding of the escort aptamer (escort RNA aptamer sequence) to the aptamer ligand may accordingly direct the e gRNA to a location of interest in the cell, such as the interior of the cell by way of binding to an aptamer ligand that is a cell surface ligand. In this way, a variety of spatially restricted locations within the cell may be targeted, such as the cell nucleus or mitochondria.

Once intended alterations have been introduced, such as by editing intended copies of a gene in the genome of a cell, continued CRISPR-Cas expression in that cell is no longer necessary. Indeed, sustained expression would be undesirable in certain cases in case of off-target effects at unintended genomic sites, etc. Thus time-limited expression would be useful. Inducible expression offers one approach, but in addition Applicants have engineered a Self-Inactivating CRISPR-Cas system that relies on the use of a non-coding guide target sequence within the CRISPR vector itself.

In some embodiments, the targeting sequence in the gRNA is a CRISPR protein or argonaute gene sequence. In such instances, an additional guide RNA may be provided with a guide sequence directed to a different target sequence.

In some embodiments, the target sequence in the e gRNA and in an additional guide RNA is a CRISPR protein or argonaute gene sequence.

Thus, using these self-inactivating systems and after expression begins, the CRISPR system will lead to its own destruction, but before destruction is complete it will have time to edit the genomic copies of the target gene (which, with a normal point mutation in a diploid cell, requires at most two edits). Simply, the self-inactivating CRISPR-Cas system includes additional RNA (i.e., guide RNA) that targets the coding sequence for the CRISPR enzyme itself or that targets one or more non-coding guide target sequences complementary to unique sequences present in one or more of the following: (a) within the promoter driving expression of the non-coding RNA elements, (b) within the promoter driving expression of the Cas9 gene, (c) within 100 bp of the ATG translational start codon in the Cas9 coding sequence, (d) within the inverted terminal repeat (iTR) of a viral delivery vector, e.g., in an AAV genome.

In some embodiments, the e gRNA may include an RNA aptamer linking sequence, operably linking the escort RNA sequence to the RNA guide sequence. In some embodiments, it may include one or more photolabile bonds or non-naturally occurring residues. e gRNAs of the invention can comprise one or more RNA linking sequences which can link an RNA aptamer and an gRNA and additional elements in any order. In one non-limiting example, an exg comprises a hydrolyzable aptamer linked to the 5' end of a protecting sequence, the protecting sequence joined at its 3' end to the 5' end of an gRNA. Such an arrangement provides a protecting sequence operating to enhance on-target specificity of the gRNA. In certain embodiments, the protecting sequence functions in a cell once the aptamer located at the 5' end is cleaved.

In one aspect, the aptamer sequence may be complementary to a target miRNA, which may or may not be present within a cell, so that only when the target miRNA is present is there binding of the escort RNA aptamer sequence to the target miRNA which results in cleavage of the gRNA by an RNA-induced silencing complex (RISC) within the cell.

Formation of a RISC through Guide Engineering

In some embodiments, the guide may be a protected guide (e.g. a pgRNA) or an escorted guide (e.g. an esgRNA) as described herein. Both of these, in some embodiments, make use of RISC. A RISC is a key component of RNAi. RISC (RNA-induced silencing complex) is a multiprotein, specifically a ribonucleoprotein, complex which incorporates one strand of a double-stranded RNA (dsRNA) fragment, such as small interfering RNA (siRNA) or microRNA (miRNA), which acts as a template for RISC to recognize a complementary messenger RNA (mRNA) transcript. The mRNA is thus cleaved by one of the components of the RISC.

As such, the formation of a RISC is advantageous in some embodiments. Guide RNAs according to various aspects of the present invention, including but not limited to protected and/or escorted guide RNAs, may be adapted to include RNA nucleotides that promote formation of a RISC, for example in combination with an siRNA or miRNA that may be provided or may, for instance, already be expressed in a cell. This may be useful, for instance, as a self-inactivating system to clear or degrade the guide.

Thus, the guide RNA may comprise a sequence complementary to a target miRNA or an siRNA, which may or may not be present within a cell. In this way, only when the miRNA or siRNA is present, for example through expression (by the cell or through human intervention), is there binding of the RNA sequence to the miRNA or siRNA which then results in cleavage of the guide RNA an RNA-induced silencing complex (RISC) within the cell. Therefore, in some embodiments, the guide RNA comprises an RNA sequence complementary to a target miRNA or siRNA, and binding of the guide RNA sequence to the target miRNA or siRNA results in cleavage of the guide RNA by an RNA-induced silencing complex (RISC) within the cell.

This is explained further below with specific reference to both protected and escorted guides.

RISC formation through use of Protected Guides

For example, a protected guide may be described in the following aspect: an engineered, non-naturally occurring composition comprising a Clustered Regularly Interspaced Short Palindromic Repeats (CRISPR)-CRISPR associated (Cas) (CRISPR-Cas) system having a protected guide RNA (pgRNA) polynucleotide sequence comprising (a) a protector sequence, (b) a direct repeat and (c) a guide sequence capable of hybridizing to a target sequence in a eukaryotic cell, wherein (a), (b), and (c) are arranged in a 5' to 3' orientation, wherein the protector sequence comprises two or more nucleotides that are non-complementary to the target sequence, wherein when transcribed, the guide sequence directs sequence-specific binding of a CRISPR complex to the target sequence, wherein the CRISPR complex comprises a Cpf1 protein complexed with (1) the guide sequence that is hybridized to the target sequence and wherein in the polynucleotide sequence and/or one or more of the guide RNAs are modified.

In one aspect, this protected guide system is used for secondary structure protection for 3' extensions to the gRNA. For example, Applicants extend the gRNA such that a miRNA binding site is introduced to make the gRNA only active when the miRNA binding site is processed and cleaved by the RISC complex machinery. This would not be possible without secondary structure protection since exonuclease processing would start from the 5' end and cut back towards the gRNA. By adding a small secondary structure loop 5' to the added miRNA site, then miRNA may be protected from exonuclease chew back.

RISC formation through use of Escorted Guides

In another example, an escorted guide may be described. In particular, an miRNA Inducible esgRNA is envisaged. Here the escort RNA aptamer sequence is complementary to a target miRNA, so that when the target miRNA is present in a cell incorporated into the RNA-induced silencing complex (RISC), there is binding of the escort RNA aptamer sequence to the target miRNA, which results in cleavage of the esgRNA by an RNA-induced silencing complex (RISC) within the cell.

In alternative embodiments, a wide variety of primary and secondary structures may be provided at the 3' end of the esgRNA, designed so that the RISC complex is able to access the miRNA binding site. An esgRNA may have first and second linker sequences, 3' to a protector sequence. In alternative embodiments, linkers 1 and 2 may for example each independently be 0, 1, 2, 3, or 4 nucleotides long, with a protector sequence of 0, 1 or 2 nucleotides in length.

In an exemplary embodiment, induction of esgRNA targeting may be illustrated using miR-122 in a HEK.293 cell system, in which miR-122 is not expressed natively. In the absence of exogenous miR-122, the protected esgRNAs do not mediate targeted EMX1.3 nuclease activity. When exogenous miR-122 is added (100 ng/well) targeted EMX1.3 cutting was observed (as distinct cleavage artifacts visible as electrophoretic variants on gels). This demonstrates that highly expressed endogenous miRNAs can be utilized in systems that provide genetically inducible sgRNAs. Any miRNA may be used in place of miRNA122, with a corresponding sequence readily determined.

For example, an sgRNA may be linked to an "escort" RNA aptamer sequence complementary to an endogenous target miRNA. The target miRNA may form an RNA-induced silencing complex (RISC) within the cell. When the target miRNA is present in a cell there is binding of the escort RNA aptamer sequence to the target miRNA, which results in cleavage of the esgRNA by the RNA-induced silencing complex (RISC) within the cell. Cleavage of the escort releases the active sgRNA.

For example, a protected guide may be described in the following aspect: a non-naturally occurring or engineered composition comprising an escorted single CRISPR-Cas9 guide RNA (esgRNA) comprising:

- an RNA guide sequence capable of hybridizing to a target sequence in a genomic locus of interest in a cell; and,
- an escort RNA aptamer sequence,
- wherein the escort RNA aptamer sequence comprises binding affinity for an aptamer ligand on or in the cell, or the escort RNA aptamer sequence is responsive to a localized aptamer effector on or in the cell,
- wherein the presence of the aptamer ligand or effector on or in the cell is spatially or temporally restricted.

The escort RNA aptamer sequence may be complementary to a target miRNA, which may or may not be present within a cell, so that only when the target miRNA is present is there binding of the escort RNA aptamer sequence to the target miRNA which results in cleavage of the esgRNA by an RNA-induced silencing complex (RISC) within the cell. Therefore, in some embodiments, the escort RNA aptamer sequence is complementary to a target miRNA, and binding of the escort RNA aptamer sequence to the target miRNA results in cleavage of the esgRNA by an RNA-induced silencing complex (RISC) within the cell.

In some embodiments, the (escort) aptamer sequence can be designed or engineered to target specific cell receptors. This allows for cell-specific delivery.

In some embodiments, the present gRNA are inducible and optionally the escort RNA aptamer sequence are inducible.

In some embodiments, the aptamer ligand or effector is light responsive, whether inducible or not. Preferred examples are inducibility achieved via the activation and binding of cryptochrome-2 and CIB1. The invention also contemplates energy sources such as electromagnetic radiation, sound energy or thermal energy to induce the guide. In some embodiments, a chemical inducible system (such as a ABI-PYL based system inducible by Abscisic Acid (ABA); a FKBP-FRB based system inducible by rapamycin (or related chemicals based on rapamycin); a GID1-GAI based system inducible by Gibberellin (GA)) is provided.

In some embodiments, a chemical inducible system can be an estrogen receptor (ER) based system inducible by 4-hydroxytamoxifen (40HT).

In some embodiments, the inducible system comprises the Transient receptor potential (TRP) ion channel. This system inducible by energy, heat or radio-wave. These TRP family proteins typically respond to different stimuli, including light and heat.

In some embodiments, electroporation is preferred as the energy source. In some embodiments, ultrasound is preferred as the energy source.

In some embodiments, aptamer-modified e gRNAs are provided. For example, by adding the aptamer C1, C1Min, Otter, or OtterMin to the gRNA backbone at the MS2 loop/tetraloop or stem loop 2. gRNAs modified with escort RNA aptamer sequence (in this case OtterMin and C1Min) improved gene editing activity by 25-50%. Accordingly, in some embodiments, gene editing activity can be increased and this may preferably be by at least 25% and most preferably by at least 50%.

In some embodiments, the addition of aptamers that up to 120 an din particular 117 nucleotides long is provided. Advantageously, this additional should not negatively affect gRNA activity, even if, in some embodiments, the gRNA may be only 100, 110 or 120 nucleotides long itself. Accordingly, large functional RNA secondary structures may be added to the sRNA backbone. In some embodiments, 10 to 200 nucleotides, or any integer range within that range may be added.

In some embodiments, 2-Fluoro modified nucleotides may be incorporated into the e gRNA, for example as part of the guide sequence, the aptamer sequence or an aptamer linker sequence.

In some embodiments, gRNAs can be functionalized with nucleic acid functionalities that promote activity within a specific cell type. For instance, gRNAs with aptamers that target the cell surface receptors, such as PSMA.

In some embodiments, near infrared light exposure is provided as the energy source for a responsive aptamer-effector system.

For minimization of toxicity and off-target effect, it will be important to control the concentration of Cas mRNA and guide RNA delivered. Optimal concentrations of Cas mRNA and guide RNA can be determined by testing different concentrations in a cellular or non-human eukaryote animal model and using deep sequencing the analyze the extent of modification at potential off-target genomic loci. Alternatively, to minimize the level of toxicity and off-target effect, Cas nickase mRNA (for example *S. pyogenes* Cas9 with the N580 according to SaCas9 protein A mutation) can be delivered with a pair of guide RNAs targeting a site of interest. Guide sequences and strategies to minimize toxicity and off-target effects can be as in WO 2014/093622 (PCT/US2013/074667); or, via mutation as herein.

In certain embodiments, the invention provides guide sequences which are modified in a manner which allows for formation of the CRISPR complex and successful binding to the target, while at the same time, not allowing for successful nuclease activity (i.e. without nuclease activity/without indel activity). For matters of explanation such modified guide sequences are referred to as “dead guides” or “dead guide sequences”. These dead guides or dead guide sequences can be thought of as catalytically inactive or conformationally inactive with regard to nuclease activity. Nuclease activity may be measured using surveyor analysis or deep sequencing as commonly used in the art, preferably surveyor analysis. Similarly, dead guide sequences may not sufficiently engage in productive base pairing with respect to the ability to promote catalytic activity or to distinguish on-target and off-target binding activity. Briefly, the surveyor assay involves purifying and amplifying a CRISPR target site for a gene and forming heteroduplexes with primers amplifying the CRISPR target site. After re-anneal, the products are treated with SURVEYOR nuclease and SURVEYOR enhancer S (Transgenomics) following the manufacturer’s recommended protocols, analyzed on gels, and quantified based upon relative band intensities.

The ability of a dead guide sequence to direct sequence-specific binding of a CRISPR complex to a target sequence may be assessed by any suitable assay. For example, the components of a CRISPR system sufficient to form a CRISPR complex, including the dead guide sequence to be tested, may be provided to a host cell having the corresponding target sequence, such as by transfection with vectors encoding the components of the CRISPR sequence, followed by an assessment of preferential cleavage within the target sequence, such as by Surveyor assay as described herein. Similarly, cleavage of a target polynucleotide sequence may be evaluated in a test tube by providing the target sequence, components of a CRISPR complex, including the dead guide sequence to be tested and a control guide sequence different from the test dead guide sequence, and comparing binding or rate of cleavage at the target sequence between the test and control guide sequence reactions. Other assays are possible, and will occur to those skilled in the art. A dead guide sequence may be selected to target any target sequence. In some embodiments, the target sequence is a sequence within a genome of a cell.

As explained further herein, several structural parameters allow for a proper framework to arrive at such dead guides. Dead guide sequences are shorter than respective guide sequences which result in active Cas9-specific indel formation. Dead guides are 5%, 10%, 20%, 30%, 40%, 50%, shorter than respective guides directed to the same Cas9 leading to active Cas9-specific indel formation.

In an embodiment of the invention, the first 15 nt of the dead guide match the target sequence. In another embodiment, first 14 nt of the dead guide match the target sequence. In another embodiment, the first 13 nt of the dead guide match the target sequence. In another embodiment first 12 nt of the dead guide match the target sequence. In another embodiment, first 11 nt of the dead guide match the target sequence. In another embodiment, the first 10 nt of the dead guide match the target sequence. In an embodiment of the invention the first 15 nt of the dead guide does not match an off-target sequence downstream from a CRISPR motif in the regulatory region of another gene locus. In other embodiments, the first 14 nt, or the first 13 nt of the dead guide, or the first 12 nt of the guide, or the first 11 nt of the dead guide, or the first 10 nt of the dead guide, does not match an off-target sequence downstream from a CRISPR motif in the regulatory region of another gene locus. In other embodiments, the first 15 nt, or 14 nt, or 13 nt, or 12 nt, or 11 nt of the dead guide do not match an off-target sequence downstream from a CRISPR motif in the genome.

In certain embodiments, the dead guide RNA includes additional nucleotides at the 3'-end that do not match the target sequence. Thus, a dead guide RNA that includes the first 15 nt, or 14 nt, or 13 nt, or 12 nt, or 11 nt downstream of a CRISPR motif can be extended in length at the 3' end to 12 nt, 13 nt, 14 nt, 15 nt, 16 nt, 17 nt, 18 nt, 19 nt, 20 nt, or longer.

In certain embodiments, an object of the current invention is to further enhance the specificity of effector protein given individual guide RNAs through thermodynamic tuning of the binding specificity of the guide RNA to target DNA. This is a general approach of introducing mismatches, elongation or truncation of the guide sequence to increase/decrease the number of complimentary bases vs. mismatched bases shared between a genomic target and its potential off-target loci, in order to give thermodynamic advantage to targeted genomic loci over genomic off-targets.

In one aspect, the invention provides for the guide sequence being modified by secondary structure to increase the specificity of the CRISPR-Cas system and whereby the secondary structure can protect against exonuclease activity and allow for 3' additions to the guide sequence.

In one aspect, the invention provides for hybridizing a "protector RNA" to a guide sequence, wherein the "protector RNA" is an RNA strand complementary to the 5' end of the guide RNA (gRNA), to thereby generate a partially double-stranded gRNA. In an embodiment of the invention, protecting the mismatched bases with a perfectly complementary protector sequence decreases the likelihood of target DNA binding to the mismatched base pairs at the 3' end. In embodiments of the invention, additional sequences comprising an extended length may also be present.

Guide RNA (gRNA) extensions matching the genomic target provide gRNA protection and enhance specificity. Extension of the gRNA with matching sequence distal to the end of the spacer seed for individual genomic targets is envisaged to provide enhanced specificity. Matching gRNA extensions that enhance specificity have been observed in cells without truncation. Prediction of gRNA structure accompanying these stable length extensions has shown that stable forms arise from protective states, where the extension forms a closed loop with the gRNA seed due to complimentary sequences in the spacer extension and the spacer seed. These results demonstrate that the protected guide concept also includes sequences matching the genomic target sequence distal of the 20mer spacer-binding region. Thermodynamic prediction can be used to predict completely matching or partially matching guide extensions that result in protected gRNA states. This extends the concept of protected gRNAs to interaction between X and Z, where X will generally be of length 17-20nt and Z is of length 1-30nt. Thermodynamic prediction can be used to determine the optimal extension state for Z, potentially introducing small numbers of mismatches in Z to promote the formation of protected conformations between X and Z. Throughout the present application, the terms "X" and seed length (SL) are used interchangeably with the term exposed length (EpL) which denotes the number of nucleotides available for target DNA to bind; the terms "Y" and protector length (PL) are used interchangeably to represent the length of the protector; and the terms "Z", "E", "E" and EL are used interchangeably to correspond to the term extended length (ExL) which represents the number of nucleotides by which the target sequence is extended.

An extension sequence which corresponds to the extended length (ExL) may optionally be attached directly to the guide sequence at the 3' end of the protected guide sequence. The extension sequence may be 2 to 12 nucleotides in length. Preferably ExL may be denoted as 0, 2, 4, 6, 8, 10 or 12 nucleotides in length. In a preferred embodiment the ExL is denoted as 0 or 4 nucleotides in length. In a more preferred embodiment the ExL is 4 nucleotides in length. The extension sequence may or may not be complementary to the target sequence.

An extension sequence may further optionally be attached directly to the guide sequence at the 5' end of the protected guide sequence as well as to the 3' end of a protecting sequence. As a result, the extension sequence serves as a linking sequence between the protected sequence and the protecting sequence. Without wishing to be bound by theory, such a link may position the protecting sequence near the protected sequence for improved binding of the protecting sequence to the protected sequence.

Addition of gRNA mismatches to the distal end of the gRNA can demonstrate enhanced specificity. The introduction of unprotected distal mismatches in Y or extension of the gRNA with distal mismatches (Z) can demonstrate enhanced specificity. This concept as mentioned is tied to X, Y, and Z components used in protected gRNAs. The unprotected mismatch concept may be further generalized to the concepts of X, Y, and Z described for protected guide RNAs.

Typically, in the context of an endogenous CRISPR system, formation of a CRISPR complex (comprising a guide sequence hybridized to a target sequence and complexed with one or more Cas proteins) results in cleavage of one or both strands in or near (e.g. within 1, 2, 3, 4, 5, 6, 7, 8, 9, 10, 20, 50, or more base pairs from) the target sequence. Without wishing to be bound by theory, the tracr sequence, which may comprise or consist of all or a portion of a wild-type tracr sequence (e.g. about or more than about 20, 26, 32, 45, 48, 54, 63, 67, 85, or more nucleotides of a wild-type tracr sequence), may also form part of a CRISPR complex, such as by hybridization along at least a portion of the tracr sequence to all or a portion of a tracr mate sequence that is operably linked to the guide sequence.

In some embodiments, guides of the invention comprise RNA. In certain embodiments, guides of the invention comprise DNA. In certain embodiments, guides of the invention comprise both RNA and DNA. In other words, guides of the invention may comprise both Ribonucleic acid (RNA) and/or Deoxyribonucleic acid (DNA). For areas where secondary structure is preferred or required, then Ribonucleic acid (RNA) is most useful. However, in other areas, such as a sequence complementary to the target sequence, then some or potentially all of the nucleotides may be Deoxyribonucleic acid (DNA). This may be designed subject to the functional requirements of the user. Blends of RNA to DNA may be about 100:0; 90:10; 80:20; 70:30; 60:40; 50:50; 40:60; 30:70; 20:80; 10:90; or 0:1000. Due to the utility of RNA secondary structure in some embodiments, the RNA:DNA ratio in the guide molecule may be 80:20; 70:30; 60:40; or 50:50. The Ribonucleic acid (RNA) and/or Deoxyribonucleic acid (DNA) may also be modified and so forth as described below.

Guides Comprising, for Example, Non-Naturally Occurring Nucleotides

In certain embodiments, guides of the invention comprise non-naturally occurring nucleic acids and/or non-naturally occurring nucleotides and/or nucleotide analogs, and/or chemically modified nucleotides (i.e. nucleotides comprising chemical modifications). Non-naturally occurring nucleic acids can include, for example, mixtures of naturally and non-naturally occurring nucleotides. Non-naturally occurring nucleotides and/or nucleotide analogs may be modified at the ribose, phosphate, and/or base moiety. In an embodiment of the invention, a guide nucleic acid comprises ribonucleotides and non-ribonucleotides. In one such embodiment, a guide comprises one or more ribonucleotides and one or more deoxyribonucleotides. In an embodiment of the invention, the guide comprises one or more non-naturally occurring nucleotide or nucleotide analog such as a nucleotide with phosphorothioate linkage, a locked nucleic acid (LNA) nucleotides comprising a methylene bridge between the 2' and 4' carbons of the ribose ring, or bridged nucleic acids (BNA). Other examples of modified nucleotides include 2'-O-methyl analogs, 2'-deoxy analogs, or 2'-fluoro analogs. Further examples of modified bases include, but are not limited to, 2-aminopurine, 5-bromouridine, pseudouridine, inosine, 7-methylguanosine. Examples of guide RNA chemical modifications include, without limitation, incorporation of 2'-O-methyl (M), 2'-O-methyl 3' phosphorothioate (MS), or 2'-O-methyl 3' thio-PACE (MSP) at one or more terminal nucleotides. Such chemically modified guides can comprise increased stability and increased activity as compared to unmodified guides, though on-target vs. off-target specificity is not predictable. (See, Hendel, 2015, Nat Biotechnol. 33(9):985-9, doi: 10.1038/nbt.3290, published online 29 Jun. 2015). In certain embodiments, a guide comprises ribonucleotides in a region that binds to a target DNA and one or more deoxyribonucleotides and/or nucleotide analogs in a region that binds to Cpf1. In an embodiment of the invention, deoxyribonucleotides and/or nucleotide analogs are incorporated in engineered guide structures, such as, without limitation, stem-loop regions.

Synthetically Linked Guides

In one aspect, the guide comprises a tracr sequence and a tracr mate sequence that are chemically linked or conjugated via a non-phosphodiester bond. In some embodiments, the tracr sequence and the tracr mate sequence are considered to be fused together or contiguous. In one aspect, the guide comprises a tracr sequence and a tracr mate sequence that are chemically linked or conjugated via a non-nucleotide loop. In some embodiments, the tracr and tracr mate sequences are joined via a non-phosphodiester covalent linker. Examples of the covalent linker include but are not limited to a chemical moiety selected from the group consisting of carbamates, ethers, esters, amides, imines, amidines, aminotrizines, hydrozone, disulfides, thioethers, thioesters, phosphorothioates, phosphorodithioates, sulfonamides, sulfonates, fulfones, sulfoxides, ureas, thioureas, hydrazide, oxime, triazole, photolabile linkages, C—C bond forming groups such as Diels-Alder cyclo-addition pairs or ring-closing metathesis pairs, and Michael reaction pairs.

In some embodiments, the tracr and tracr mate sequences are first synthesized using the standard phosphoramidite synthetic protocol (Herdewijn, P., ed., Methods in Molecular Biology Col 288, Oligonucleotide Synthesis: Methods and Applications, Humana Press, New Jersey (2012)). In some embodiments, the tracr or tracr mate sequences can be functionalized to contain an appropriate functional group for ligation using the standard protocol known in the art (Hermanson, G. T., Bioconjugate Techniques, Academic Press (2013)). Examples of functional groups include, but are not limited to, hydroxyl, amine, carboxylic acid, carboxylic acid halide, carboxylic acid active ester, aldehyde, carbonyl, chlorocarbonyl, imidazolylcarbonyl, hydrozide, semicarbazide, thio semicarbazide, thiol, maleimide, haloalkyl, sulfonyl, ally, propargyl, diene, alkyne, and azide. Once the tracr and the tracr mate sequences are functionalized, a covalent chemical bond or linkage can be formed between the two oligonucleotides. Examples of chemical bonds include, but are not limited to, those based on carbamates, ethers, esters, amides, imines, amidines, aminotrizines, hydrozone, disulfides, thioethers, thioesters, phosphorothioates, phosphorodithioates, sulfonamides, sulfonates, fulfones, sulfoxides, ureas, thioureas, hydrazide, oxime, triazole, photolabile linkages, C—C bond forming groups such as Diels-Alder cyclo-addition pairs or ring-closing metathesis pairs, and Michael reaction pairs.

In some embodiments, the tracr and tracr mate sequences can be chemically synthesized. The tracer and tracr mate alone/individually, synthesized together in the form of a fusion, or synthesized separately and chemically linked. In some embodiments, the chemical synthesis uses automated, solid-phase oligonucleotide synthesis machines with 2'-acetoxyethyl orthoester (2'-ACE) (Scaringe et al., J. Am. Chem. Soc. (1998) 120: 11820-11821; Scaringe, Methods Enzymol. (2000) 317: 3-18) or 2'-thionocarbamate (2'-TC) chemistry (Dellinger et al., J. Am. Chem. Soc. (2011) 133: 11540-11546; Hendel et al., Nat. Biotechnol. (2015) 33:985-989).

In some embodiments, the tracr and tracr mate sequences can be covalently linked using various bioconjugation reactions, loops, bridges, and non-nucleotide links via modifications of sugar, internucleotide phosphodiester bonds, purine and pyrimidine residues. Sletten et al., Angew. Chem. Int. Ed. (2009) 48:6974-6998; Manoharan, M. Curr. Opin. Chem. Biol. (2004) 8: 570-9; Behlke et al., Oligonucleotides (2008) 18: 305-19; Watts, et al., Drug. Discov. Today (2008) 13: 842-55; Shukla, et al., ChemMedChem (2010) 5: 328-49.

In some embodiments, the tracr and tracr mate sequences can be covalently linked using click chemistry. In some embodiments, the tracr and tracr mate sequences can be covalently linked using a triazole linker. In some embodiments, the tracr and tracr mate sequences can be covalently linked using Huisgen 1,3-dipolar cycloaddition reaction involving an alkyne and azide to yield a highly stable triazole linker (He et al., ChemBioChem (2015) 17: 1809-1812; WO 2016/186745). In some embodiments, the tracr and tracr mate sequences are covalently linked by ligating a 5'-hexyne tracrRNA and a 3'-azide crRNA. In some embodiments, either or both of the 5'-hexyne tracrRNA and a 3'-azide crRNA can be protected with 2'-acetoxyethyl orthoester (2'-ACE) group, which can be subsequently removed using Dharmacon protocol (Scaringe et al., J. Am. Chem. Soc. (1998) 120: 11820-11821; Scaringe, Methods Enzymol. (2000) 317: 3-18).

In some embodiments, the tracr and tracr mate sequences can be covalently linked via a linker (e.g., a non-nucleotide loop) that comprises a moiety such as spacers, attachments, bioconjugates, chromophores, reporter groups, dye labeled RNAs, and non-naturally occurring nucleotide analogues. More specifically, suitable spacers for purposes of this invention include, but are not limited to, polyethers (e.g., polyethylene glycols, polyalcohols, polypropylene glycol or mixtures of ethylene and propylene glycols), polyamines group (e.g., spennine, spermidine and polymeric derivatives thereof), polyesters (e.g., poly(ethyl acrylate)), polyphosphodiesters, alkylenes, and combinations thereof. Suitable attachments include any moiety that can be added to the linker to add additional properties to the linker, such as but not limited to, fluorescent labels. Suitable bioconjugates include, but are not limited to, peptides, glycosides, lipids, cholesterol, phospholipids, diacyl glycerols and dialkyl glycerols, fatty acids, hydrocarbons, enzyme substrates, steroids, biotin, digoxigenin, carbohydrates, polysaccharides. Suitable chromophores, reporter groups, and dye-labeled RNAs include, but are not limited to, fluorescent dyes such as fluorescein and rhodamine, chemiluminescent, electrochemiluminescent, and bioluminescent marker compounds. The design of example linkers conjugating two RNA components are also described in WO 2004/015075.

The linker (e.g., a non-nucleotide loop) can be of any length. In some embodiments, the linker has a length equivalent to about 0-16 nucleotides. In some embodiments, the linker has a length equivalent to about 0-8 nucleotides. In some embodiments, the linker has a length equivalent to about 0-4 nucleotides. In some embodiments, the linker has a length equivalent to about 2 nucleotides. Example linker design is also described in WO2011/008730.

A typical Type II Cas9 sgRNA comprises (in 5' to 3' direction): a guide sequence, a poly U tract, a first complimentary stretch (the "repeat"), a loop (tetraloop), a second complimentary stretch (the "anti-repeat" being complimentary to the repeat), a stem, and further stem loops and stems and a poly A (often poly U in RNA) tail (terminator). In preferred embodiments, certain aspects of guide architecture are retained, certain aspect of guide architecture cam be modified, for example by addition, subtraction, or substitution of features, whereas certain other aspects of guide architecture are maintained. Preferred locations for engineered sgRNA modifications, including but not limited to insertions, deletions, and substitutions include guide termini and regions of the sgRNA that are exposed when complexed with CRISPR protein and/or target, for example the tetraloop and/or loop2. Certain guide architecture and secondary structure may, as described herein, may utilized or encouraged in guides other than those specifically referred to as sgRNA.

In certain embodiments, guides of the invention comprise, for example are adapted or designed to include, one or more specific binding sites (e.g. comprising an aptamer or aptamer sequences such as MS2 or PP7, for example as described herein) for adaptor proteins. The adaptor proteins may comprise one or more functional domains (e.g. via fusion protein). When such a guide forms a CRISPR complex (i.e. CRISPR enzyme binding to guide and target) the adaptor proteins bind and, the functional domain associated with the adaptor protein is positioned in a spatial orientation which is advantageous for the attributed function to be effective. For example, if the functional domain is a transcription activator (e.g. VP64 or p65), the transcription activator is placed in a spatial orientation which allows it to affect the transcription of the target. Likewise, a transcription repressor (e.g. KRAB) will be advantageously positioned to affect the transcription of the target and a nuclease (e.g. Fok1) will be advantageously positioned to cleave or partially cleave the target. Suitable examples of aptamer are described herein, for example below. Suitable examples of functional domains are also described herein.

The skilled person will understand that modifications to the guide which allow for binding of the adaptor+functional domain but not proper positioning of the adaptor+functional domain (e.g. due to steric hindrance within the three dimensional structure of the CRISPR complex) are modifications which are not intended if the CRISPR complex is to be optimally formed or formed in a functional manner. In some embodiments, sub-optimal formation of the CRISPR complex may be useful.

The one or more modified guide may be modified at the tetra loop, the stem loop 1, stem loop 2, or stem loop 3, as described herein, preferably at either the tetra loop or stem loop 2, and most preferably at both the tetra loop and stem loop 2.

The repeat:anti repeat duplex will be apparent from the secondary structure of the sgRNA. It may be typically a first complimentary stretch after (in 5' to 3' direction) the poly U tract and before the tetraloop; and a second complimentary stretch after (in 5' to 3' direction) the tetraloop and before the poly A tract. The first complimentary stretch (the "repeat") is complimentary to the second complimentary stretch (the "anti-repeat"). As such, they Watson-Crick base pair to form a duplex of dsRNA when folded back on one another. As such, the anti-repeat sequence is the complimentary sequence of the repeat and in terms to A-U or C-G base pairing, but also in terms of the fact that the anti-repeat is in the reverse orientation due to the tetraloop.

In an embodiment of the invention, modification of guide architecture comprises replacing bases in stemloop 2. For example, in some embodiments, "actt" ("acuu" in RNA) and "aagt" ("aagu" in RNA) bases in stemloop2 are replaced with "cgcc" and "gcgg". In some embodiments, "actt" and "aagt" bases in stemloop2 are replaced with complimentary GC-rich regions of 4 nucleotides. In some embodiments, the complimentary GC-rich regions of 4 nucleotides are "cgcc" and "gcgg" (both in 5' to 3' direction). In some embodiments, the complimentary GC-rich regions of 4 nucleotides are "gcgg" and "cgcc" (both in 5' to 3' direction). Other combination of C and G in the complimentary GC-rich regions of 4 nucleotides will be apparent including CCCC and GGGG.

In one aspect, the stemloop 2, e.g., "ACTTgtttAAGT" (SEQ ID NO: 9) can be replaced by any "XXXXgtttYYYY" (SEQ ID NO: 10), e.g., where XXXX and YYYY represent any complementary sets of nucleotides that together will base pair to each other to create a stem.

In one aspect, the stem comprises at least about 4 bp comprising complementary X and Y sequences, although stems of more, e.g., 5, 6, 7, 8, 9, 10, 11 or 12 or fewer, e.g., 3, 2, base pairs are also contemplated. Thus, for example X2-12 and Y2-12 (wherein X and Y represent any complementary set of nucleotides) may be contemplated. In one aspect, the stem made of the X and Y nucleotides, together with the "gttt," will form a complete hairpin in the overall secondary structure; and, this may be advantageous and the amount of base pairs can be any amount that forms a complete hairpin. In one aspect, any complementary X:Y basepairing sequence (e.g., as to length) is tolerated, so long as the secondary structure of the entire sgRNA is preserved. In one aspect, the stem can be a form of X:Y basepairing that does not disrupt the secondary structure of the whole sgRNA in that it has a DR:tracr duplex, and 3 stemloops. In one aspect, the "gttt" tetraloop that connects ACTT and AAGT (or any alternative stem made of X:Y basepairs) can be any sequence of the same length (e.g., 4 basepair) or longer that does not interrupt the overall secondary structure of the sgRNA. In one aspect, the stemloop can be something that further lengthens stemloop2, e.g. can be MS2 aptamer. In one aspect, the stemloop3 "GGCACCGagtCGGTGC" (SEQ ID NO: 11) can likewise take on a "XXXXXXXagtYYYYYYY" (SEQ ID NO: 103) form, e.g., wherein X7 and Y7 represent any complementary sets of nucleotides that together will base pair to each other to create a stem. In one aspect, the stem comprises about 7 bp comprising complementary X and Y sequences, although stems of more or fewer basepairs are also contemplated. In one aspect, the stem made of the X and Y nucleotides, together with the "agt", will form a complete hairpin in the overall secondary structure. In one aspect, any complementary X:Y basepairing sequence is tolerated, so long as the secondary structure of the entire sgRNA is preserved. In one aspect, the stem can be a form of X:Y basepairing that doesn't disrupt the secondary structure of the whole sgRNA in that it has a DR:tracr duplex, and 3 stemloops. In one aspect, the "agt" sequence of the stemloop 3 can be extended or be replaced by an aptamer, e.g., a MS2 aptamer or sequence that otherwise generally preserves the architecture of stemloop3. In one aspect for alternative Stemloops 2 and/or 3, each X and Y pair can refer to any basepair. In one aspect, non-Watson Crick basepairing is contemplated, where such pairing otherwise generally preserves the architecture of the stemloop at that position.

In one aspect, the DR:tracrRNA duplex can be replaced with the form: gYYYYag(N)NNNNxxxxNNNN(AAN) uuRRRRu (SEQ ID NO: 12) (using standard IUPAC nomenclature for nucleotides), wherein (N) and (AAN) represent part of the bulge in the duplex, and "xxxx" represents a linker sequence. NNNN on the direct repeat can be anything so long as it basepairs with the corresponding NNNN portion of the tracrRNA. In one aspect, the DR:tracrRNA duplex can be connected by a linker of any length (xxxx . . . ), any base composition, as long as it doesn't alter the overall structure.

In one aspect, the sgRNA structural requirement is to have a duplex and 3 stemloops. In most aspects, the actual sequence requirement for many of the particular base requirements are lax, in that the architecture of the DR:tracrRNA duplex should be preserved, but the sequence that creates the architecture, i.e., the stems, loops, bulges, etc., may be altered.

The nucleic acid molecule encoding a Cas is advantageously codon optimized Cas. An example of a codon optimized sequence, is in this instance a sequence optimized for expression in a eukaryote, e.g., humans (i.e. being optimized for expression in humans), or for another eukaryote, animal or mammal as herein discussed; see, e.g., SaCas9 human codon optimized sequence in WO 2014/093622 (PCT/US2013/074667). Whilst this is preferred, it will be appreciated that other examples are possible and codon optimization for a host species other than human, or for codon optimization for specific organs is known. In some embodiments, an enzyme coding sequence encoding a Cas is codon optimized for expression in particular cells, such as eukaryotic cells. The eukaryotic cells may be those of or derived from a particular organism, such as a mammal, including but not limited to human, or non-human eukaryote or animal or mammal as herein discussed, e.g., mouse, rat, rabbit, dog, livestock, or non-human mammal or primate. In some embodiments, processes for modifying the germ line genetic identity of human beings and/or processes for modifying the genetic identity of animals which are likely to cause them suffering without any substantial medical benefit to man or animal, and also animals resulting from such processes, may be excluded. In general, codon optimization refers to a process of modifying a nucleic acid sequence for enhanced expression in the host cells of interest by replacing at least one codon (e.g. about or more than about 1, 2, 3, 4, 5, 10, 15, 20, 25, 50, or more codons) of the native sequence with codons that are more frequently or most frequently used in the genes of that host cell while maintaining the native amino acid sequence. Various species exhibit particular bias for certain codons of a particular amino acid. Codon bias (differences in codon usage between organisms) often correlates with the efficiency of translation of messenger RNA (mRNA), which is in turn believed to be dependent on, among other things, the properties of the codons being translated and the availability of particular transfer RNA (tRNA) molecules. The predominance of selected tRNAs in a cell is generally a reflection of the codons used most frequently in peptide synthesis. Accordingly, genes can be tailored for optimal gene expression in a given organism based on codon optimization. Codon usage tables are readily available, for example, at the "Codon Usage Database" available at www.kazusa.or.jp/codon/and these tables can be adapted in a number of ways. See Nakamura, Y., et al. "Codon usage tabulated from the international DNA sequence databases: status for the year 2000" Nucl. Acids Res. 28:292 (2000). Computer algorithms for codon optimizing a particular sequence for expression in a particular host cell are also available, such as Gene Forge (Aptagen; Jacobus, PA), are also available. In some embodiments, one or more codons (e.g. 1, 2, 3, 4, 5, 10, 15, 20, 25, 50, or more, or all codons) in a sequence encoding a Cas9 correspond to the most frequently used codon for a particular amino acid.

In certain embodiments, the methods as described herein may comprise providing a Cas (e.g. Cas9, Cpf1, C2c1, C2c2, C2c3, Cas13, group 29/30) transgenic cell in which one or more nucleic acids encoding one or more guide RNAs, and optionally the fusion protein according to the invention as described herein are provided or introduced operably connected in the cell with a regulatory element comprising a promoter of one or more gene of interest. As used herein, the term "Cas transgenic cell" refers to a cell, such as a eukaryotic cell, in which a Cas gene has been genomically integrated. The nature, type, or origin of the cell are not particularly limiting according to the present invention. Also the way how the Cas transgene is introduced in the cell is may vary and can be any method as is known in the art. In certain embodiments, the Cas transgenic cell is obtained by introducing the Cas transgene in an isolated cell. In certain other embodiments, the Cas transgenic cell is obtained by isolating cells from a Cas transgenic organism. By means of example, and without limitation, the Cas transgenic cell as referred to herein may be derived from a Cas transgenic eukaryote, such as a Cas knock-in eukaryote. Reference is made to WO 2014/093622 (PCT/US13/74667), incorporated herein by reference. Methods of US Patent Publication Nos. 20120017290 and 20110265198 assigned to Sangamo BioSciences, Inc. directed to targeting the Rosa locus may be modified to utilize the CRISPR Cas system of the present invention. Methods of US Patent Publication No. 20130236946 assigned to Cellectis directed to targeting the Rosa locus may also be modified to utilize the CRISPR Cas system of the present invention. By means of further example reference is made to Platt et. al. (Cell; 159(2):440-455 (2014)), describing a Cas9 knock-in mouse, which is incorporated herein by reference. The Cas transgene can further comprise a Lox-Stop-polyA-Lox(LSL) cassette thereby rendering Cas expression inducible by Cre recombinase. Alternatively, the Cas transgenic cell may be obtained by introducing the Cas transgene in an isolated cell. Delivery systems for transgenes are well known in the art. By means of example, the Cas9 transgene may be delivered in for instance eukaryotic cell by means of vector (e.g., AAV, adenovirus, lentivirus) and/or particle and/or nanoparticle delivery, as also described herein elsewhere.

It will be understood by the skilled person that the cell, such as the Cas transgenic cell, as referred to herein may comprise further genomic alterations besides having an integrated Cas gene or the mutations arising from the sequence specific action of Cas when complexed with RNA capable of guiding Cas to a target locus, such as for instance one or more oncogenic mutations, as for instance and without limitation described in Platt et al. (2014), Chen et al., (2014) or Kumar et al., (2009).

In some embodiments, the Cas sequence or fusion protein according to the invention as described herein is fused to one or more nuclear localization sequences (NLSs), such as about or more than about 1, 2, 3, 4, 5, 6, 7, 8, 9, 10, or more NLSs. In some embodiments, the Cas comprises about or more than about 1, 2, 3, 4, 5, 6, 7, 8, 9, 10, or more NLSs at or near the amino-terminus, about or more than about 1, 2, 3, 4, 5, 6, 7, 8, 9, 10, or more NLSs at or near the carboxy-terminus, or a combination of these (e.g. zero or at least one or more NLS at the amino-terminus and zero or at one or more NLS at the carboxy terminus). When more than one NLS is present, each may be selected independently of the others, such that a single NLS may be present in more than one copy and/or in combination with one or more other NLSs present in one or more copies. In a preferred embodiment of the invention, the Cas comprises at most 6 NLSs. In some embodiments, an NLS is considered near the N- or C-terminus when the nearest amino acid of the NLS is within about 1, 2, 3, 4, 5, 10, 15, 20, 25, 30, 40, 50, or more amino acids along the polypeptide chain from the N- or C-terminus. Non-limiting examples of NLSs include an NLS sequence derived from: the NLS of the SV40 virus large T-antigen, having the amino acid sequence PKKKRKV (SEQ ID NO: 13); the NLS from nucleoplasmin (e.g. the nucleoplasmin bipartite NLS with the sequence KRPAATKKAGQAKKKK) (SEQ ID NO: 14); the c-myc NLS having the amino acid sequence PAAKRVKLD (SEQ ID NO: 15) or RQRRNELKRSP (SEQ ID NO: 16); the hRNPA1 M9 NLS having the sequence NQSSNFGPMKGGNFGGRSSGPYGGGGQYFAKPRNQGGY (SEQ ID NO: 17); the sequence RMRIZFKNKGKDTAELRRRRVEVSVELRKAKKDEQILKRRNV (SEQ ID NO: 18) of the IBB domain from importin-alpha; the sequences VSRKRPRP (SEQ ID NO: 19) and PPKKARED (SEQ ID NO: 20) of the myoma T protein; the sequence PQPKKKPL (SEQ ID NO: 21) of human p53; the sequence SALIKKKKKMAP (SEQ ID NO: 22) of mouse c-abl IV; the sequences DRLRR (SEQ ID NO: 23) and PKQKKRK (SEQ ID NO: 24) of the influenza virus NS1; the sequence RKLKKKIKKL (SEQ ID NO: 25) of the Hepatitis virus delta antigen; the sequence REKKKFLKRR (SEQ ID NO: 26) of the mouse Mxl protein; the sequence KRKGDEVDGVDEVAKKKSKK (SEQ ID NO: 27) of the human poly(ADP-ribose) polymerase; and the sequence RKCLQAGMNLEARKTKK (SEQ ID NO: 28) of the steroid hormone receptors (human) glucocorticoid. In general, the one or more NLSs are of sufficient strength to drive accumulation of the Cas in a detectable amount in the nucleus of a eukaryotic cell. In general, strength of nuclear localization activity may derive from the number of NLSs in the Cas, the particular NLS(s) used, or a combination of these factors. Detection of accumulation in the nucleus may be performed by any suitable technique. For example, a detectable marker may be fused to the Cas, such that location within a cell may be visualized, such as in combination with a means for detecting the location of the nucleus (e.g. a stain specific for the nucleus such as DAPI). Cell nuclei may also be isolated from cells, the contents of which may then be analyzed by any suitable process for detecting protein, such as immunohistochemistry, Western blot, or enzyme activity assay. Accumulation in the nucleus may also be determined indirectly, such as by an assay for the effect of CRISPR complex formation (e.g. assay for DNA cleavage or mutation at the target sequence, or assay for altered gene expression activity affected by CRISPR complex formation and/or Cas enzyme activity), as compared to a control no exposed to the Cas9 or complex, or exposed to a Cas9 lacking the one or more NLSs. In other embodiments, no NLS is required.

In certain aspects the invention involves vectors, e.g. for delivering or introducing in a cell Cas (e.g. Cas9, Cpf1, C2c1, C2c2, C2c3, Cas13, group 29/30), the fusion protein according to the invention as described herein, and/or RNA capable of guiding Cas to a target locus (i.e. guide RNA), but also for propagating these components (e.g. in prokaryotic cells). A used herein, a "vector" is a tool that allows or facilitates the transfer of an entity from one environment to another. It is a replicon, such as a plasmid, phage, or cosmid, into which another DNA segment may be inserted so as to bring about the replication of the inserted segment. Generally, a vector is capable of replication when associated with the proper control elements. In general, the term "vector" refers to a nucleic acid molecule capable of transporting another nucleic acid to which it has been linked. Vectors include, but are not limited to, nucleic acid molecules that are single-stranded, double-stranded, or partially double-stranded; nucleic acid molecules that comprise one or more free ends, no free ends (e.g. circular); nucleic acid molecules that comprise DNA, RNA, or both; and other varieties of polynucleotides known in the art. One type of vector is a "plasmid," which refers to a circular double stranded DNA loop into which additional DNA segments can be inserted, such as by standard molecular cloning techniques. Another type of vector is a viral vector, wherein virally-derived DNA or RNA sequences are present in the vector for packaging into a virus (e.g. retroviruses, replication defective retroviruses, adenoviruses, replication defective adenoviruses, and adeno-associated viruses (AAVs)). Viral vectors also include polynucleotides carried by a virus for transfection into a host cell. Certain vectors are capable of autonomous replication in a host cell into which they are introduced (e.g. bacterial vectors having a bacterial origin of replication and episomal mammalian vectors). Other vectors (e.g., non-episomal mammalian vectors) are integrated into the genome of a host cell upon introduction into the host cell, and thereby are replicated along with the host genome. Moreover, certain vectors are capable of directing the expression of genes to which they are operatively-linked. Such vectors are referred to herein as "expression vectors." Common expression vectors of utility in recombinant DNA techniques are often in the form of plasmids.

Recombinant expression vectors can comprise a nucleic acid of the invention in a form suitable for expression of the nucleic acid in a host cell, which means that the recombinant expression vectors include one or more regulatory elements, which may be selected on the basis of the host cells to be used for expression, that is operatively-linked to the nucleic acid sequence to be expressed. Within a recombinant expression vector, "operably linked" is intended to mean that the nucleotide sequence of interest is linked to the regulatory element(s) in a manner that allows for expression of the nucleotide sequence (e.g. in an in vitro transcription/translation system or in a host cell when the vector is introduced into the host cell). With regards to recombination and cloning methods, mention is made of U.S. patent application Ser. No. 10/815,730, published Sep. 2, 2004 as US 2004-0171156 A1, the contents of which are herein incorporated by reference in their entirety.

The vector(s) can include the regulatory element(s), e.g., promoter(s). The vector(s) can comprise Cas encoding sequences, a fusion protein according to the invention as described herein, and/or a single, but possibly also can comprise at least 3 or 8 or 16 or 32 or 48 or 50 guide RNA(s) (e.g., gRNAs) encoding sequences, such as 1-2, 1-3, 1-4 1-5, 3-6, 3-7, 3-8, 3-9, 3-10, 3-8, 3-16, 3-30, 3-32, 3-48, 3-50 RNA(s) (e.g., gRNAs). In a single vector there can be a promoter for each RNA (e.g., gRNA), advantageously when there are up to about 16 RNA(s) (e.g., gRNAs); and, when a single vector provides for more than 16 RNA(s) (e.g., gRNAs), one or more promoter(s) can drive expression of more than one of the RNA(s) (e.g., gRNAs), e.g., when there are 32 RNA(s) (e.g., gRNAs), each promoter can drive expression of two RNA(s) (e.g., gRNAs), and when there are 48 RNA(s) (e.g., gRNAs), each promoter can drive expression of three RNA(s) (e.g., gRNAs). By simple arithmetic and well established cloning protocols and the teachings in this disclosure one skilled in the art can readily practice the invention as to the RNA(s) (e.g., gRNA(s) for a suitable exemplary vector such as AAV, and a suitable promoter such as the U6 promoter, e.g., U6—gRNAs. For example, the packaging limit of AAV is −4.7 kb. The length of a single U6—gRNA (plus restriction sites for cloning) is 361 bp. Therefore, the skilled person can readily fit about 12-16, e.g., 13 U6—gRNA cassettes in a single vector. This can be assembled by any suitable means, such as a golden gate strategy used for TALE assembly (www.genome-engineering.org/taleffectors/). The skilled person can also use a tandem guide strategy to increase the number of U6—gRNAs by approximately 1.5 times, e.g., to increase from 12-16, e.g., 13 to approximately 18-24, e.g., about 19 U6-gRNAs. Therefore, one skilled in the art can readily reach approximately 18-24, e.g., about 19 promoter-RNAs, e.g., U6-gRNAs in a single vector, e.g., an AAV vector. A further means for increasing the number of promoters and RNAs, e.g., gRNA(s) in a vector is to use a single promoter (e.g., U6) to express an array of RNAs, e.g., gRNAs separated by cleavable sequences. And an even further means for increasing the number of promoter-RNAs, e.g., gRNAs in a vector, is to express an array of promoter-RNAs, e.g., gRNAs separated by cleavable sequences in the intron of a coding sequence or gene; and, in this instance it is advantageous to use a polymerase II promoter, which can have increased expression and enable the transcription of long RNA in a tissue specific manner. (see, e.g., nar.oxfordjournals.org/content/34/7/e53.short, www.nature.com/mt/journal/v16/n9/abs/mt2008144a.html). In an advantageous embodiment, AAV may package U6 tandem gRNA targeting up to about 50 genes. Accordingly, from the knowledge in the art and the teachings in this disclosure the skilled person can readily make and use vector(s), e.g., a single vector, expressing multiple RNAs or guides or gRNAs under the control or operatively or functionally linked to one or more promoters-especially as to the numbers of RNAs or guides or gRNAs discussed herein, without any undue experimentation.

The guide RNA(s), e.g., gRNA(s) encoding sequences and/or Cas9 encoding sequences, can be functionally or operatively linked to regulatory element(s) and hence the regulatory element(s) drive expression. The promoter(s) can be constitutive promoter(s) and/or conditional promoter(s) and/or inducible promoter(s) and/or tissue specific promoter (s). The promoter can be selected from the group consisting of RNA polymerases, pol I, pol II, pol III, T7, U6, H1, retroviral Rous sarcoma virus (RSV) LTR promoter, the cytomegalovirus (CMV) promoter, the SV40 promoter, the dihydrofolate reductase promoter, the β-actin promoter, the phosphoglycerol kinase (PGK) promoter, and the EF1α promoter. An advantageous promoter is the promoter is U6.

As used herein, the term "crRNA" or "guide RNA" or "single guide RNA" or "gRNA" or "one or more nucleic acid components" of a CRISPR-Cas locus effector protein comprises any polynucleotide sequence having sufficient complementarity with a target nucleic acid sequence to hybridize with the target nucleic acid sequence and direct sequence-specific binding of a nucleic acid-targeting complex to the target nucleic acid sequence.

In certain embodiments, the CRISPR system as provided herein can make use of a crRNA or analogous polynucleotide comprising a guide sequence, wherein the polynucleotide is an RNA, a DNA or a mixture of RNA and DNA, and/or wherein the polynucleotide comprises one or more nucleotide analogs. The sequence can comprise any structure, including but not limited to a structure of a native crRNA, such as a bulge, a hairpin or a stem loop structure. In certain embodiments, the polynucleotide comprising the guide sequence forms a duplex with a second polynucleotide sequence which can be an RNA or a DNA sequence.

In certain embodiments, guides of the invention comprise non-naturally occurring nucleic acids and/or non-naturally occurring nucleotides and/or nucleotide analogs, and/or chemically modifications. Non-naturally occurring nucleic acids can include, for example, mixtures of naturally and non-naturally occurring nucleotides. Non-naturally occurring nucleotides and/or nucleotide analogs may be modified at the ribose, phosphate, and/or base moiety. In an embodiment of the invention, a guide nucleic acid comprises ribonucleotides and non-ribonucleotides. In one such embodiment, a guide comprises one or more ribonucleotides and one or more deoxyribonucleotides. In an embodiment of the invention, the guide comprises one or more non-naturally occurring nucleotide or nucleotide analog such as a nucleotide with phosphorothioate linkage, boranophosphate linkage, a locked nucleic acid (LNA) nucleotides comprising a methylene bridge between the 2' and 4' carbons of the ribose ring, or bridged nucleic acids (BNA). Other examples of modified nucleotides include 2'-O-methyl analogs, 2'-deoxy analogs, 2-thiouridine analogs, N6-methyladenosine analogs, or 2'-fluoro analogs. Further examples of modified bases include, but are not limited to, 2-aminopurine, 5-bromo-uridine, pseudouridine (ψ), $N^1$-methylpseudouridine ($me^1ψ$), 5-methoxyuridine(5moU), inosine, 7-methylguanosine.

In certain embodiments, use is made of chemically modified guide RNAs. Examples of guide RNA chemical modifications include, without limitation, incorporation of 2'-O-methyl (M), 2'-O-methyl 3'phosphorothioate (MS), S-constrained ethyl (cEt), or 2'-O-methyl 3'thioPACE (MSP) at one or more terminal nucleotides. Such chemically modified guide RNAs can comprise increased stability and increased activity as compared to unmodified guide RNAs, though on-target vs. off-target specificity is not predictable. (See, Hendel, 2015, Nat Biotechnol. 33(9):985-9, doi: 10.1038/nbt.3290, published online 29 Jun. 2015; Allerson et al., J. Med. Chem. 2005, 48:901-904; Bramsen et al., Front. Genet., 2012, 3:154; Deng et al., PNAS, 2015, 112:11870-11875; Sharma et al., MedChemComm., 2014, 5:1454-1471; Li et al., Nature Biomedical Engineering, 2017, 1, 0066 DOI:10.1038/s41551-017-0066). Chemically modified guide RNAs further include, without limitation, RNAs with phosphorothioate linkages and locked nucleic acid (LNA) nucleotides comprising a methylene bridge between the 2' and 4' carbons of the ribose ring.

In some embodiments, the degree of complementarity, when optimally aligned using a suitable alignment algorithm, is about or more than about 50%, 60%, 75%, 80%, 85%, 90%, 95%, 97.5%, 99%, or more. Optimal alignment may be determined with the use of any suitable algorithm for aligning sequences, non-limiting example of which include the Smith-Waterman algorithm, the Needleman-Wunsch algorithm, algorithms based on the Burrows-Wheeler Transform (e.g., the Burrows Wheeler Aligner), Clustal W, Clustal X, BLAT, Novoalign (Novocraft Technologies; available at www.novocraft.com), ELAND (Illumina, San Diego, CA), SOAP (available at soap.genomics.org.cn), and Maq (available at maq.sourceforge.net). The ability of a guide sequence (within a nucleic acid-targeting guide RNA) to direct sequence-specific binding of a nucleic acid-targeting complex to a target nucleic acid sequence may be assessed by any suitable assay. For example, the components of a nucleic acid-targeting CRISPR system sufficient to form a nucleic acid-targeting complex, including the guide sequence to be tested, may be provided to a host cell having the corresponding target nucleic acid sequence, such as by transfection with vectors encoding the components of the nucleic acid-targeting complex, followed by an assessment of preferential targeting (e.g., cleavage) within the target nucleic acid sequence, such as by Surveyor assay as described herein. Similarly, cleavage of a target nucleic acid sequence may be evaluated in a test tube by providing the target nucleic acid sequence, components of a nucleic acid-targeting complex, including the guide sequence to be tested and a control guide sequence different from the test guide sequence, and comparing binding or rate of cleavage at the target sequence between the test and control guide sequence reactions. Other assays are possible, and will occur to those skilled in the art. A guide sequence, and hence a nucleic acid-targeting guide RNA may be selected to target any target nucleic acid sequence.

In certain embodiments, the target sequence may be DNA. In certain embodiments, the target sequence may be an RNA sequence. In some embodiments, the target sequence may be a sequence within a RNA molecule selected from the group consisting of messenger RNA (mRNA), pre-mRNA, ribosomal RNA (rRNA), transfer RNA (tRNA), micro-RNA (miRNA), small interfering RNA (siRNA), small nuclear RNA (snRNA), small nucleolar RNA (snoRNA), double stranded RNA (dsRNA), non coding RNA (ncRNA), long non-coding RNA (lncRNA), and small cytoplasmatic RNA (scRNA). In some preferred embodiments, the target sequence may be a sequence within an RNA molecule selected from the group consisting of mRNA, pre-mRNA, and rRNA. In some preferred embodiments, the target sequence may be a sequence within a RNA molecule selected from the group consisting of ncRNA, and lncRNA. In some more preferred embodiments, the target sequence may be a sequence within an mRNA molecule or a pre-mRNA molecule.

In some embodiments, a nucleic acid-targeting guide is selected to reduce the degree secondary structure within the nucleic acid-targeting guide. In some embodiments, about or less than about 75%, 50%, 40%, 30%, 25%, 20%, 15%, 10%, 5%, 1%, or fewer of the nucleotides of the nucleic acid-targeting guide participate in self-complementary base pairing when optimally folded. Optimal folding may be determined by any suitable polynucleotide folding algorithm. Some programs are based on calculating the minimal Gibbs free energy. An example of one such algorithm is mFold, as described by Zuker and Stiegler (Nucleic Acids Res. 9 (1981), 133-148). Another example folding algorithm is the online webserver RNAfold, developed at Institute for Theoretical Chemistry at the University of Vienna, using the centroid structure prediction algorithm (see e.g., A.R. Gruber et al., 2008, Cell 106(1): 23-24; and PA Carr and GM Church, 2009, Nature Biotechnology 27(12): 1151-62).

In certain embodiments, a guide RNA or crRNA may comprise, consist essentially of, or consist of a direct repeat (DR) sequence and a guide sequence or spacer sequence. In certain embodiments, the guide RNA or crRNA may comprise, consist essentially of, or consist of a direct repeat sequence fused or linked to a guide sequence or spacer sequence. In certain embodiments, the direct repeat sequence may be located upstream (i.e., 5') from the guide sequence or spacer sequence. In other embodiments, the direct repeat sequence may be located downstream (i.e., 3') from the guide sequence or spacer sequence.

In certain embodiments, the crRNA comprises a stem loop, preferably a single stem loop. In certain embodiments, the direct repeat sequence forms a stem loop, preferably a single stem loop.

In certain embodiments, the spacer length of the guide RNA is from 15 to 35 nt. In certain embodiments, the spacer length of the guide RNA is at least 15 nucleotides. In certain embodiments, the spacer length is from 15 to 17 nt, e.g., 15, 16, or 17 nt, from 17 to 20 nt, e.g., 17, 18, 19, or 20 nt, from 20 to 24 nt, e.g., 20, 21, 22, 23, or 24 nt, from 23 to 25 nt, e.g., 23, 24, or 25 nt, from 24 to 27 nt, e.g., 24, 25, 26, or 27 nt, from 27-30 nt, e.g., 27, 28, 29, or 30 nt, from 30-35 nt, e.g., 30, 31, 32, 33, 34, or 35 nt, or 35 nt or longer.

A guide sequence may be selected to target any target sequence. In some embodiments, the target sequence is a sequence within a genome of a cell. Exemplary target sequences include those that are unique in the target genome. For example, for the *S. pyogenes* Cas9, a unique target sequence in a genome may include a Cas9 target site of the form MMMMMMMMNNNNNNNNNNNNXGG (SEQ ID NO: 29) where NNNNNNNNNNNNXGG (SEQ ID NO: 30) (N is A, G, T, or C; and X can be anything) has a single occurrence in the genome. A unique target sequence in a genome may include an *S. pyogenes* Cas9 target site of the form MMMMMMMMMNNNNNNNNNNNXGG (SEQ ID NO: 31) where NNNNNNNNNNNXGG (SEQ ID NO: 32) (N is A, G, T, or C; and X can be anything) has a single occurrence in the genome. For the *S. thermophilus* CRISPRI Cas9, a unique target sequence in a genome may include a Cas9 target site of the form MMMMMMMMMNNNNNNNNNNNNXXAGAAW (SEQ ID NO: 33) where NNNNNNNNNNNNXXAGAAW (SEQ ID NO: 34) (N is A, G, T, or C; X can be anything; and W is A or T) has a single occurrence in the genome. A unique target sequence in a genome may include an *S. thermophilus* CRISPRI Cas9 target site of the form MMMMMMMMMMNNNNNNNNNNNXXAGAAW (SEQ ID NO: 35) where NNNNNNNNNNNXXAGAAW (SEQ ID NO: 36) (N is A, G, T, or C; X can be anything; and W is A or T) has a single occurrence in the genome. For the *S. pyogenes* Cas9, a unique target sequence in a genome may include a Cas9 target site of the form MMMMMMMMNNNNNNNNNNNNXGGXG (SEQ ID NO: 37) where NNNNNNNNNNNNXGGXG (SEQ ID NO: 38) (N is A, G, T, or C; and X can be anything) has a single occurrence in the genome. A unique target sequence in a genome may include an *S. pyogenes* Cas9 target site of the form MMMMMMMMMNNNNNNNNNNNXGGXG (SEQ ID NO: 39) where NNNNNNNNNNNXGGXG (SEQ ID NO: 40) (N is A, G, T, or C; and X can be anything) has a single occurrence in the genome. In each of these sequences "M" may be A, G, T, or C, and need not be considered in identifying a sequence as unique. In some embodiments, a guide sequence is selected to reduce the degree secondary structure within the guide sequence. In some embodiments, about or less than about 75%, 50%, 40%, 30%, 25%, 20%, 15%, 10%, 5%, 1%, or fewer of the nucleotides of the guide sequence participate in self-complementary base pairing when optimally folded. Optimal folding may be determined by any suitable polynucleotide folding algorithm. Some programs are based on calculating the minimal Gibbs free energy. An example of one such algorithm is mFold, as described by Zuker and Stiegler (Nucleic Acids Res. 9 (1981), 133-148). Another example folding algorithm is the online webserver RNAfold, developed at Institute for Theoretical Chemistry at the University of Vienna, using the centroid structure prediction algorithm (see e.g., A.R. Gruber et al., 2008, Cell 106(1): 23-24; and PA Carr and GM Church, 2009, Nature Biotechnology 27(12): 1151-62).

In general, a tracr mate sequence includes any sequence that has sufficient complementarity with a tracr sequence to promote one or more of: (1) excision of a guide sequence flanked by tracr mate sequences in a cell containing the corresponding tracr sequence; and (2) formation of a CRISPR complex at a target sequence, wherein the CRISPR complex comprises the tracr mate sequence hybridized to the tracr sequence. In general, degree of complementarity is with reference to the optimal alignment of the tracr mate sequence and tracr sequence, along the length of the shorter of the two sequences. Optimal alignment may be determined by any suitable alignment algorithm, and may further account for secondary structures, such as self-complementarity within either the tracr sequence or tracr mate sequence. In some embodiments, the degree of complementarity between the tracr sequence and tracr mate sequence along the length of the shorter of the two when optimally aligned is about or more than about 25%, 30%, 40%, 50%, 60%, 70%, 80%, 90%, 95%, 97.5%, 99%, or higher. In some embodiments, the tracr sequence is about or more than about 5, 6, 7, 8, 9, 10, 11, 12, 13, 14, 15, 16, 17, 18, 19, 20, 25, 30, 40, 50, or more nucleotides in length. In some embodiments, the tracr sequence and tracr mate sequence are contained within a single transcript, such that hybridization between the two produces a transcript having a secondary structure, such as a hairpin. In an embodiment of the invention, the transcript or transcribed polynucleotide sequence has at least two or more hairpins. In preferred embodiments, the transcript has two, three, four or five hairpins. In a further embodiment of the invention, the transcript has at most five hairpins. In a hairpin structure the portion of the sequence 5' of the final "N" and upstream of the loop corresponds to the tracr mate sequence, and the portion of the sequence 3' of the loop corresponds to the tracr sequence Further non-limiting examples of single polynucleotides comprising a guide sequence, a tracr mate sequence, and a tracr sequence are as follows (listed 5' to 3'), where "N" represents a base of a guide sequence, the first block of lower case letters represent the tracr mate sequence, and the second block of lower case letters represent the tracr sequence, and the final poly-T sequence represents the transcription terminator: (1) NNNNNNNNNNNNNNN-NNNNNgtttttgtactctcaagatttaGAAAtaaatcttgcagaagctaca-aagataa ggcttcatgccgaaatcaacaccctgtcattttatggcag- ggtgtttt-cgttatttaaTTTTTT (SEQ ID NO: 41); (2) NNNNNNN-NNNNNNNNNNNNNgtttttgtactctcaGAAAtgcagaagctac-aaagataaggcttcatgccgaaatcaacaccctgtcattttatggcagggtgtttt-cgttatttaaTTTTTT (SEQ ID NO: 42); (3) NNNNNNNNNN-NNNNNNNNNNgtttttgtactctcaGAAAtgcagaagctacaaaga-taaggcttcatgccg aaatcaacaccctgtcattttatggcagggtgtTTTTTT (SEQ ID NO: 43); (4) NNNNNNNNNNNNNNNNN-NNNgttttagagctaGAAAtagcaagttaaaataaggctagtccgttat-caactt gaaaaagtggcaccgagtcggtgcTTTTTT (SEQ ID NO; 44); (5) NNNNNNNNNNNNNNNNNNNNgttttagagcta-GAAATAGcaagttaaaataaggctagtccgttatcaac ttgaaaaagtg TTTTTTT (SEQ ID NO: 45); and (6) NNNNNN-NNNNNNNNNNNNNNgttttagagctagAAATAGcaagt-taaaataaggctagtccgttatcaTT TTTTTT (SEQ ID NO: 46). In some embodiments, sequences (1) to (3) are used in combination with Cas9 from *S. thermophilus* CRISPRI. In some embodiments, sequences (4) to (6) are used in combination with Cas9 from *S. pyogenes*. In some embodiments, the tracr sequence is a separate transcript from a transcript comprising the tracr mate sequence.

In some embodiments, candidate tracrRNA may be subsequently predicted by sequences that fulfill any or all of the following criteria: 1. sequence homology to direct repeats (motif search in Geneious with up to 18-bp mismatches); 2. presence of a predicted Rho-independent transcriptional terminator in direction of transcription; and 3. stable hairpin secondary structure between tracrRNA and direct repeat. In some embodiments, 2 of these criteria may be used, for instance 1 and 2, 2 and 3, or 1 and 3. In some embodiments, all 3 criteria may be used.

In some embodiments, chimeric synthetic guide RNAs (gRNAs) designs may incorporate at least 12 bp of duplex structure between the direct repeat and tracrRNA.

For minimization of toxicity and off-target effect, it will be important to control the concentration of CRISPR enzyme mRNA and guide RNA delivered. Optimal concentrations of CRISPR enzyme mRNA and guide RNA can be determined by testing different concentrations in a cellular or non-human eukaryote animal model and using deep sequencing the analyze the extent of modification at potential off-target genomic loci. For example, for the guide sequence targeting 5'-GAGTCCGAGCAGAAGAAGAA-3' (SEQ ID NO: 47) in the EMX1 gene of the human genome, deep sequencing can be used to assess the level of modification at the following two off-target loci, 1: 5'-GAGTCCTAGCAGGAGAAGAA-3' (SEQ ID NO: 48) and 2: 5'-GAGTCTAAGCAGAAGAAGAA-3' (SEQ ID NO: 49). The concentration that gives the highest level of on-target modification while minimizing the level of off-target modification should be chosen for in vivo delivery. Alternatively, to minimize the level of toxicity and off-target effect, CRISPR enzyme nickase mRNA (for example *S. pyogenes* Cas9 with the D10A mutation) can be delivered with a pair of guide RNAs targeting a site of interest. The two guide RNAs need to be spaced as follows. Guide sequences and strategies to minimize toxicity and off-target effects can be as in WO 2014/093622 (PCT/US2013/074667).

The term "nucleic acid-targeting system", wherein nucleic acid is DNA or RNA, and in some aspects may also refer to DNA-RNA hybrids or derivatives thereof, refers collectively to transcripts and other elements involved in the expression of or directing the activity of DNA or RNA-targeting CRISPR-associated ("Cas") genes, which may include sequences encoding a DNA or RNA-targeting Cas effector protein and a DNA or RNA-targeting guide RNA comprising a CRISPR RNA (crRNA) sequence and (in some but not all systems) a trans-activating CRISPR/Cas system RNA (tracrRNA) sequence, or other sequences and transcripts from a DNA or RNA-targeting CRISPR locus. In general, a RNA-targeting system is characterized by elements that promote the formation of a DNA or RNA-targeting complex at the site of a target DNA or RNA sequence. In the context of formation of a DNA or RNA-targeting complex, "target sequence" refers to a DNA or RNA sequence to which a DNA or RNA-targeting guide RNA is designed to have complementarity, where hybridization between a target sequence and a RNA-targeting guide RNA promotes the formation of a RNA-targeting complex. In some embodiments, a target sequence is located in the nucleus or cytoplasm of a cell.

In an aspect of the invention, novel DNA targeting systems also referred to as DNA-targeting CRISPR/Cas or the CRISPR-Cas DNA-targeting system of the present application are based on identified Cas proteins which do not require the generation of customized proteins to target specific DNA sequences but rather a single effector protein or enzyme can be programmed by a RNA molecule to recognize a specific DNA target, in other words the enzyme can be recruited to a specific DNA target using said RNA molecule. The invention particularly relates to DNA targeting RNA-guided CRISPR/Cas systems.

In an aspect of the invention, novel RNA targeting systems also referred to as RNA- or RNA-targeting CRISPR/Cas or the CRISPR-Cas system RNA-targeting system of the present application are based on identified Cas effector proteins which do not require the generation of customized proteins to target specific RNA sequences but rather a single enzyme can be programmed by a RNA molecule to recognize a specific RNA target, in other words the enzyme can be recruited to a specific RNA target using said RNA molecule.

The nucleic acids-targeting systems, the vector systems, the vectors and the compositions described herein may be used in various nucleic acids-targeting applications, altering or modifying synthesis of a gene product, such as a protein, nucleic acids cleavage, nucleic acids editing, nucleic acids splicing; trafficking of target nucleic acids, tracing of target nucleic acids, isolation of target nucleic acids, visualization of target nucleic acids, etc.

Aspects of the invention also encompass methods and uses of the compositions and systems described herein in genome engineering, e.g. for altering or manipulating the expression of one or more genes or the one or more gene products, in prokaryotic or eukaryotic cells, in vitro, in vivo or ex vivo.

The CRISPR system is derived advantageously from a type II CRISPR system. In some embodiments, one or more elements of a CRISPR system is derived from a particular organism comprising an endogenous CRISPR system, such as *Streptococcus pyogenes*. The CRISPR system is a type II CRISPR system and the Cas enzyme is Cas9, which catalyzes DNA cleavage. Non-limiting examples of Cas proteins include Cas1, Cas1B, Cas2, Cas3, Cas4, Cas5, Cas6, Cas7, Cas8, Cas9 (also known as Csn1 and Csx12), Cas10, Csyl, Csy2, Csy3, Csel, Cse2, Cscl, Csc2, Csa5, Csn2, Csm2, Csm3, Csm4, Csm5, Csm6, Cmrl, Cmr3, Cmr4, Cmr5, Cmr6, Csb1, Csb2, Csb3, Csx17, Csx14, Csx10, Csx16, CsaX, Csx3, Csx1, Csx15, Csf1, Csf2, Csf3, Csf4, homologues thereof, or modified versions thereof.

In an embodiment, the Cas9 protein may be an ortholog of an organism of a genus which includes but is not limited to *Corynebacterium, Sutterella, Legionella, Treponema, Filifactor, Eubacterium, Streptococcus, Lactobacillus, Mycoplasma, Bacteroides, Flaviivola, Flavobacterium*, Sphaerochaeta, Azospirillum, *Gluconacetobacter, Neisseria, Roseburia, Parvibaculum, Staphylococcus, Nitratifractor, Mycoplasma* and *Campylobacter*. Species of an organism of such a genus can be as otherwise herein discussed.

Some methods of identifying orthologs of CRISPR-Cas system enzymes may involve identifying tracr sequences in genomes of interest. Identification of tracr sequences may relate to the following steps: Search for the direct repeats or tracr mate sequences in a database to identify a CRISPR region comprising a CRISPR enzyme. Search for homologous sequences in the CRISPR region flanking the CRISPR enzyme in both the sense and antisense directions. Look for transcriptional terminators and secondary structures. Identify any sequence that is not a direct repeat or a tracr mate sequence but has more than 50% identity to the direct repeat or tracr mate sequence as a potential tracr sequence. Take the potential tracr sequence and analyze for transcriptional terminator sequences associated therewith.

It will be appreciated that any of the functionalities described herein may be engineered into CRISPR enzymes from other orthologs, including chimeric enzymes comprising fragments from multiple orthologs. Examples of such orthologs are described elsewhere herein. Thus, chimeric enzymes may comprise fragments of CRISPR enzyme orthologs of an organism which includes but is not limited to *Corynebacterium, Sutterella, Legionella, Treponema, Filifactor, Eubacterium, Streptococcus, Lactobacillus, Mycoplasma, Bacteroides, Flaviivola, Flavobacterium*, Sphaerochaeta, Azospirillum, *Gluconacetobacter, Neisseria, Roseburia, Parvibaculum, Staphylococcus, Nitratifractor, Mycoplasma* and *Campylobacter*. A chimeric enzyme can comprise a first fragment and a second fragment, and the fragments can be of CRISPR enzyme orthologs of organisms of genuses herein mentioned or of species herein mentioned; advantageously the fragments are from CRISPR enzyme orthologs of different species.

In some embodiments, the unmodified CRISPR Cas enzyme has DNA and/or RNA cleavage activity. In some embodiments, the CRISPR enzyme directs cleavage of one or both strands at the location of a target sequence, such as within the target sequence and/or within the complement of the target sequence. In some embodiments, the CRISPR enzyme directs cleavage of one or both strands within about 1, 2, 3, 4, 5, 6, 7, 8, 9, 10, 15, 20, 25, 50, 100, 200, 500, or more base pairs from the first or last nucleotide of a target sequence. In some embodiments, a vector encodes a CRISPR enzyme that is mutated to with respect to a corresponding wild-type enzyme such that the mutated CRISPR enzyme lacks the ability to cleave one or both strands of a target polynucleotide containing a target sequence. For example, an aspartate-to-alanine substitution (D10A) in the RuvC I catalytic domain of Cas9 from *S. pyogenes* converts Cas9 from a nuclease that cleaves both strands to a nickase (cleaves a single strand). Other examples of mutations that render Cas9 a nickase include, without limitation, H840A, N854A, and N863A. As a further example, two or more catalytic domains of Cas9 (RuvC I, RuvC II, and RuvC III or the HNH domain) may be mutated to produce a mutated Cas9 substantially lacking all DNA cleavage activity. In some embodiments, a D10A mutation is combined with one or more of H840A, N854A, or N863A mutations to produce a Cas9 enzyme substantially lacking all DNA cleavage activity. In some embodiments, a CRISPR enzyme is considered to substantially lack all DNA cleavage activity when the DNA cleavage activity of the mutated enzyme is about no more than 25%, 10%, 5%, 1%, 0.1%, 0.01%, or less of the DNA cleavage activity of the non-mutated form of the enzyme; an example can be when the DNA cleavage activity of the mutated form is nil or negligible as compared with the non-mutated form. Where the enzyme is not SpCas9, mutations may be made at any or all residues corresponding to positions 10, 762, 840, 854, 863 and/or 986 of SpCas9 (which may be ascertained for instance by standard sequence comparison tools). In particular, any or all of the following mutations are preferred in SpCas9: D10A, E762A, H840A, N854A, N863A and/or D986A; as well as conservative substitution for any of the replacement amino acids is also envisaged. The same (or conservative substitutions of these mutations) at corresponding positions in other Cas9s are also preferred. Particularly preferred are D10 and H840 in SpCas9. However, in other CRISPR effectors, residues corresponding to SpCas9 D10 and H840 are also preferred. Orthologs of SpCas9 can be used in the practice of the invention. A Cas enzyme may be identified Cas9 as this can refer to the general class of enzymes that share homology to the biggest nuclease with multiple nuclease domains from the type II CRISPR system. Most preferably, the Cas9 enzyme is from, or is derived from, spCas9 (*S. pyogenes* Cas9) or saCas9 (*S. aureus* Cas9). StCas9" refers to wild type Cas9 from *S. thermophilus*, the protein sequence of which is given in the SwissProt database under accession number G3ECR1. Similarly, *S pyogenes* Cas9 or spCas9 is included in SwissProt under accession number Q99ZW2. By derived, Applicants mean that the derived enzyme is largely based, in the sense of having a high degree of sequence homology with, a wildtype enzyme, but that it has been mutated (modified) in some way as described herein. It will be appreciated that the terms Cas and CRISPR enzyme are generally used herein interchangeably, unless otherwise apparent. As mentioned above, many of the residue numberings used herein refer to the Cas9 enzyme from the type II CRISPR locus in *Streptococcus pyogenes*. However, it will be appreciated that this invention includes many more Cas9s from other species of microbes, such as SpCas9, SaCa9, St1Cas9 and so forth. Enzymatic action by Cas9 derived from Streptococcuspyogenes or any closely related Cas9 generates double stranded breaks at target site sequences which hybridize to 20 nucleotides of the guide sequence and that have a protospacer-adjacent motif (PAM) sequence (examples include NGG/NRG or a PAM that can be determined as described herein) following the 20 nucleotides of the target sequence. CRISPR activity through Cas9 for site-specific DNA recognition and cleavage is defined by the guide sequence, the tracr sequence that hybridizes in part to the guide sequence and the PAM sequence. More aspects of the CRISPR system are described in Karginov and Hannon, The CRISPR system: small RNA-guided defense in bacteria and archaea, Mole Cell 2010, January 15; 37(1): 7. The type II CRISPR locus from Streptococcuspyogenes SF370, which contains a cluster of four genes Cas9, Cas1, Cas2, and Csn1, as well as two non-coding RNA elements, tracrRNA and a characteristic array of repetitive sequences (direct repeats) interspaced by short stretches of non-repetitive sequences (spacers, about 30 bp each). In this system, targeted DNA double-strand break (DSB) is generated in four sequential steps. First, two non-coding RNAs, the pre-crRNA array and tracrRNA, are transcribed from the CRISPR locus. Second, tracrRNA hybridizes to the direct repeats of pre-crRNA, which is then processed into mature crRNAs containing individual spacer sequences. Third, the mature crRNA:tracrRNA complex directs Cas9 to the DNA target comprising, consisting essentially of, or consisting of the protospacer and the corresponding PAM via heteroduplex formation between the spacer region of the crRNA and the protospacer DNA. Finally, Cas9 mediates cleavage of target DNA upstream of PAM to create a DSB within the protospacer. A pre-crRNA array comprising, consisting essentially of, or consisting of a single spacer flanked by two direct repeats (DRs) is also encompassed by the term "tracr-mate sequences"). In certain embodiments, Cas9 may be constitutively present or inducibly present or conditionally present or administered or delivered. Cas9 optimization may be used to enhance function or to develop new functions, one can generate chimeric Cas9 proteins. And Cas9 may be used as a generic DNA binding protein.

Typically, in the context of an endogenous CRISPR system, formation of a CRISPR complex (comprising a guide sequence hybridized to a target sequence and complexed with one or more Cas proteins) results in cleavage of one or both strands in or near (e.g., within 1, 2, 3, 4, 5, 6, 7, 8, 9, 10, 20, 50, or more base pairs from) the target sequence. Without wishing to be bound by theory, the tracr sequence, which may comprise, consist essentially of, or consist of all or a portion of a wild-type tracr sequence (e.g., about or more than about 20, 26, 32, 45, 48, 54, 63, 67, 85, or more nucleotides of a wild-type tracr sequence), may also form part of a CRISPR complex, such as by hybridization along at least a portion of the tracr sequence to all or a portion of a tracr mate sequence that is operably linked to the guide sequence.

An example of a codon optimized sequence, is in this instance a sequence optimized for expression in a eukaryote, e.g., humans (i.e. being optimized for expression in humans), or for another eukaryote, animal or mammal as herein discussed; see, e.g., SaCas9 human codon optimized sequence in WO 2014/093622 (PCT/US2013/074667). While this is preferred, it will be appreciated that other examples are possible and codon optimization for a host species other than human, or for codon optimization for specific organs is known. In some embodiments, a coding sequence encoding a CRISPR enzyme is codon optimized for expression in particular cells, such as eukaryotic cells. The eukaryotic cells may be those of or derived from a particular organism, such as a mammal, including but not limited to human, or non-human eukaryote or animal or mammal as herein discussed, e.g., mouse, rat, rabbit, dog, livestock, or non-human mammal or primate. In some embodiments, processes for modifying the germ line genetic identity of human beings and/or processes for modifying the genetic identity of animals which are likely to cause them suffering without any substantial medical benefit to man or animal, and also animals resulting from such processes, may be excluded. In general, codon optimization refers to a process of modifying a nucleic acid sequence for enhanced expression in the host cells of interest by replacing at least one codon (e.g., about or more than about 1, 2, 3, 4, 5, 10, 15, 20, 25, 50, or more codons) of the native sequence with codons that are more frequently or most frequently used in the genes of that host cell while maintaining the native amino acid sequence. Various species exhibit particular bias for certain codons of a particular amino acid. Codon bias (differences in codon usage between organisms) often correlates with the efficiency of translation of messenger RNA (mRNA), which is in turn believed to be dependent on, among other things, the properties of the codons being translated and the availability of particular transfer RNA (tRNA) molecules. The predominance of selected tRNAs in a cell is generally a reflection of the codons used most frequently in peptide synthesis. Accordingly, genes can be tailored for optimal gene expression in a given organism based on codon optimization. Codon usage tables are readily available, for example, at the "Codon Usage Database" available at www.kazusa.or.jp/codon/and these tables can be adapted in a number of ways. See Nakamura, Y., et al. "Codon usage tabulated from the international DNA sequence databases: status for the year 2000" Nucl. Acids Res. 28:292 (2000). Computer algorithms for codon optimizing a particular sequence for expression in a particular host cell are also available, such as Gene Forge (Aptagen; Jacobus, PA), are also available. In some embodiments, one or more codons (e.g., 1, 2, 3, 4, 5, 10, 15, 20, 25, 50, or more, or all codons) in a sequence encoding a CRISPR enzyme correspond to the most frequently used codon for a particular amino acid.

In some embodiments, a vector encodes a CRISPR enzyme comprising one or more nuclear localization sequences (NLSs), such as about or more than about 1, 2, 3, 4, 5, 6, 7, 8, 9, 10, or more NLSs. In some embodiments, the CRISPR enzyme comprises about or more than about 1, 2, 3, 4, 5, 6, 7, 8, 9, 10, or more NLSs at or near the amino-terminus, about or more than about 1, 2, 3, 4, 5, 6, 7, 8, 9, 10, or more NLSs at or near the carboxy-terminus, or a combination of these (e.g., zero or at least one or more NLS at the amino-terminus and zero or at one or more NLS at the carboxy terminus). When more than one NLS is present, each may be selected independently of the others, such that a single NLS may be present in more than one copy and/or in combination with one or more other NLSs present in one or more copies. In a preferred embodiment of the invention, the CRISPR enzyme comprises at most 6 NLSs. In some embodiments, an NLS is considered near the N- or C-terminus when the nearest amino acid of the NLS is within about 1, 2, 3, 4, 5, 10, 15, 20, 25, 30, 40, 50, or more amino acids along the polypeptide chain from the N- or C-terminus. Non-limiting examples of NLSs include an NLS sequence derived from: the NLS of the SV40 virus large T-antigen, having the amino acid sequence PKKKRKV (SEQ ID NO: 13); the NLS from nucleoplasmin (e.g., the nucleoplasmin bipartite NLS with the sequence KRPAATKKAGQAKKKK (SEQ ID NO: 14)); the c-myc NLS having the amino acid sequence PAAKRVKLD (SEQ ID NO: 15) or RQRRNELKRSP (SEQ ID NO: 16); the hRNPA1 M9 NLS having the sequence NQSSNFGPM-KGGNFGGRSSGPYGGGGQYFAKPRNQGGY (SEQ ID NO: 17); the sequence RMRIZFKNKGKDTAEL-RRRRVEVSVELRKAKKDEQILKRRNV (SEQ ID NO: 18) of the IBB domain from importin-alpha; the sequences VSRKRPRP (SEQ ID NO: 19) and PPKKARED (SEQ ID NO: 20) of the myoma T protein; the sequence PQPKKKPL (SEQ ID NO: 21) of human p53; the sequence SALIK-KKKKMAP (SEQ ID NO: 22) of mouse c-abl IV; the sequences DRLRR (SEQ ID NO: 23) and PKQKKRK (SEQ ID NO: 24) of the influenza virus NS1; the sequence RKLKKKIKKL (SEQ ID NO: 25) of the Hepatitis virus delta antigen; the sequence REKKKFLKRR (SEQ ID NO: 26) of the mouse Mxl protein; the sequence KRKGDEVDGVDEVAKKKSKK (SEQ ID NO: 27) of the human poly(ADP-ribose) polymerase; and the sequence RKCLQAGMNLEARKTKK (SEQ ID NO: 28) of the steroid hormone receptors (human) glucocorticoid. In general, the one or more NLSs are of sufficient strength to drive accumulation of the CRISPR enzyme in a detectable amount in the nucleus of a eukaryotic cell. In general, strength of nuclear localization activity may derive from the number of NLSs in the CRISPR enzyme, the particular NLS(s) used, or a combination of these factors. Detection of accumulation in the nucleus may be performed by any suitable technique. For example, a detectable marker may be fused to the CRISPR enzyme, such that location within a cell may be visualized, such as in combination with a means for detecting the location of the nucleus (e.g., a stain specific for the nucleus such as DAPI). Cell nuclei may also be isolated from cells, the contents of which may then be analyzed by any suitable process for detecting protein, such as immunohistochemistry, Western blot, or enzyme activity assay. Accumulation in the nucleus may also be determined indirectly, such as by an assay for the effect of CRISPR complex formation (e.g., assay for DNA cleavage or mutation at the target sequence, or assay for altered gene expression activity affected by CRISPR complex formation and/or CRISPR enzyme activity), as compared to a control no exposed to the CRISPR enzyme or complex, or exposed to a CRISPR enzyme lacking the one or more NLSs.

Aspects of the invention relate to the expression of the gene product being decreased or a template polynucleotide being further introduced into the DNA molecule encoding the gene product or an intervening sequence being excised precisely by allowing the two 5' overhangs to reanneal and ligate or the activity or function of the gene product being altered or the expression of the gene product being increased. In an embodiment of the invention, the gene product is a protein. Only gRNA pairs creating 5' overhangs with less than 8 bp overlap between the guide sequences (offset greater than −8 bp) were able to mediate detectable indel formation. Importantly, each guide used in these assays is able to efficiently induce indels when paired with wildtype Cas9, indicating that the relative positions of the guide pairs are the most important parameters in predicting double nicking activity. Since Cas9n and Cas9H840A nick opposite strands of DNA, substitution of Cas9n with Cas9H840A with a given gRNA pair should have resulted in the inversion of the overhang type; but no indel formation is observed as with Cas9H840A indicating that Cas9H840A is a CRISPR enzyme substantially lacking all DNA cleavage activity (which is when the DNA cleavage activity of the mutated enzyme is about no more than 25%, 10%, 5%, 1%, 0.1%, 0.01%, or less of the DNA cleavage activity of the non-mutated form of the enzyme; whereby an example can be when the DNA cleavage activity of the mutated form is nil or negligible as compared with the non-mutated form, e.g., when no indel formation is observed as with Cas9H840A in the eukaryotic system in contrast to the biochemical or prokaryotic systems). Nonetheless, a pair of gRNAs that will generate a 5' overhang with Cas9n should in principle generate the corresponding 3' overhang instead, and double nicking. Therefore, gRNA pairs that lead to the generation of a 3' overhang with Cas9n can be used with another mutated Cas9 to generate a 5' overhang, and double nicking. Accordingly, in some embodiments, a recombination template is also provided. A recombination template may be a component of another vector as described herein, contained in a separate vector, or provided as a separate polynucleotide. In some embodiments, a recombination template is designed to serve as a template in homologous recombination, such as within or near a target sequence nicked or cleaved by a CRISPR enzyme as a part of a CRISPR complex. A template polynucleotide may be of any suitable length, such as about or more than about 10, 15, 20, 25, 50, 75, 100, 150, 200, 500, 1000, or more nucleotides in length. In some embodiments, the template polynucleotide is complementary to a portion of a polynucleotide comprising the target sequence. When optimally aligned, a template polynucleotide might overlap with one or more nucleotides of a target sequences (e.g., about or more than about 1, 5, 10, 15, 20, or more nucleotides). In some embodiments, when a template sequence and a polynucleotide comprising a target sequence are optimally aligned, the nearest nucleotide of the template polynucleotide is within about 1, 5, 10, 15, 20, 25, 50, 75, 100, 200, 300, 400, 500, 1000, 5000, 10000, or more nucleotides from the target sequence. In certain embodiments, said template comprises at least 250 nucleotides, preferably at least 500 nucleotides, more preferably at least 1000 nucleotides, at least 2000 nucleotides, at least 3000 nucleotides, at least 4000 nucleotides, at least 5000 nucleotides, at least 6000 nucleotides, at least 7000 nucleotides, at least 8000 nucleotides, at least 9000 nucleotides, or at least 10000 nucleotides. Large templates are in particular useful for transforming plants. (Large) templates may encode for particular traits, such as particular plant traits, and may be used for making transgenic or transformed plants. A template may include coding sequence for a particular gene (e.g. trait), and may include certain regulatory sequences (such as operably connected to to coding sequence), in particular promoters, enhancers, etc. CRISPR/Cas system generated transformed plants have already been generated in the art, such as for instance "Waxy corn" generated using CRISPR/Cas technology by DuPont Pioneer.

In some embodiments, one or more vectors driving expression of one or more elements of a CRISPR system are introduced into a host cell such that expression of the elements of the CRISPR system direct formation of a CRISPR complex at one or more target sites. For example, a Cas enzyme, a guide sequence linked to a tracr-mate sequence, and a tracr sequence could each be operably linked to separate regulatory elements on separate vectors. Or, RNA(s) of the CRISPR System can be delivered to a transgenic CRISPR effector animal or mammal, e.g., an animal or mammal that constitutively or inducibly or conditionally expresses Cas9; or an animal or mammal that is otherwise expressing CRISPR effector or has cells containing CRISPR effector, such as by way of prior administration thereto of a vector or vectors that code for and express in vivo CRISPR effector. Alternatively, two or more of the elements expressed from the same or different regulatory elements, may be combined in a single vector, with one or more additional vectors providing any components of the CRISPR system not included in the first vector. CRISPR system elements that are combined in a single vector may be arranged in any suitable orientation, such as one element located 5' with respect to ("upstream" of) or 3' with respect to ("downstream" of) a second element. The coding sequence of one element may be located on the same or opposite strand of the coding sequence of a second element, and oriented in the same or opposite direction. In some embodiments, a single promoter drives expression of a transcript encoding a CRISPR enzyme and one or more of the guide sequence, tracr mate sequence (optionally operably linked to the guide sequence), and a tracr sequence embedded within one or more intron sequences (e.g., each in a different intron, two or more in at least one intron, or all in a single intron). In some embodiments, the CRISPR enzyme, guide sequence, tracr mate sequence, and tracr sequence are operably linked to and expressed from the same promoter. Delivery vehicles, vectors, particles, nanoparticles, formulations and components thereof for expression of one or more elements of a CRISPR system are as used in the foregoing documents, such as WO 2014/093622 (PCT/US2013/074667). In some embodiments, a vector comprises one or more insertion sites, such as a restriction endonuclease recognition sequence (also referred to as a "cloning site"). In some embodiments, one or more insertion sites (e.g., about or more than about 1, 2, 3, 4, 5, 6, 7, 8, 9, 10, or more insertion sites) are located upstream and/or downstream of one or more sequence elements of one or more vectors. In some embodiments, a vector comprises an insertion site upstream of a tracr mate sequence, and optionally downstream of a regulatory element operably linked to the tracr mate sequence, such that following insertion of a guide sequence into the insertion site and upon expression the guide sequence directs sequence-specific binding of a CRISPR complex to a target sequence in a eukaryotic cell. In some embodiments, a vector comprises two or more insertion sites, each insertion site being located between two tracr mate sequences so as to allow insertion of a guide sequence at each site. In such an arrangement, the two or more guide sequences may comprise two or more copies of a single guide sequence, two or more different guide sequences, or combinations of these. When multiple different guide sequences are used, a single expression construct may be used to target CRISPR activity to multiple different, corresponding target sequences within a cell. For example, a single vector may comprise about or more than about 1, 2, 3, 4, 5, 6, 7, 8, 9, 10, 15, 20, or more guide sequences. In some embodiments, about or more than about 1, 2, 3, 4, 5, 6, 7, 8, 9, 10, or more such guide-sequence-containing vectors may be provided, and optionally delivered to a cell. In some embodiments, a vector comprises a regulatory element operably linked to an enzyme-coding sequence encoding a CRISPR enzyme. CRISPR enzyme or CRISPR enzyme mRNA or CRISPR guide RNA or RNA(s) can be delivered separately; and advantageously at least one of these is delivered via a nanoparticle complex. CRISPR enzyme mRNA can be delivered prior to the guide RNA to give time for CRISPR enzyme to be expressed. CRISPR enzyme mRNA might be administered 1-12 hours (preferably around 2-6 hours) prior to the administration of guide RNA. Alternatively, CRISPR enzyme mRNA and guide RNA can be administered together. Advantageously, a second booster dose of guide RNA can be administered 1-12 hours (preferably around 2-6 hours) after the initial administration of CRISPR enzyme mRNA+guide RNA. Additional administrations of CRISPR enzyme mRNA and/or guide RNA might be useful to achieve the most efficient levels of genome modification.

In one aspect, the invention provides methods for using one or more elements of a CRISPR system. The CRISPR complex of the invention provides an effective means for modifying a target polynucleotide. The CRISPR complex of the invention has a wide variety of utility including modifying (e.g., deleting, inserting, translocating, inactivating, activating) a target polynucleotide in a multiplicity of cell types. As such the CRISPR complex of the invention has a broad spectrum of applications in, e.g., gene therapy, drug screening, disease diagnosis, and prognosis. An exemplary CRISPR complex comprises a CRISPR enzyme complexed with a guide sequence hybridized to a target sequence within the target polynucleotide. The guide sequence is linked to a tracr mate sequence, which in turn hybridizes to a tracr sequence. In one embodiment, this invention provides a method of cleaving a target polynucleotide. The method comprises modifying a target polynucleotide using a CRISPR complex that binds to the target polynucleotide and effect cleavage of said target polynucleotide. Typically, the CRISPR complex of the invention, when introduced into a cell, creates a break (e.g., a single or a double strand break) in the genome sequence. For example, the method can be used to cleave a disease gene in a cell. The break created by the CRISPR complex can be repaired by a repair processes such as the error prone non-homologous end joining (NHEJ) pathway or the high fidelity homology-directed repair (HDR). During these repair process, an exogenous polynucleotide template can be introduced into the genome sequence. In some methods, the HDR process is used modify genome sequence. For example, an exogenous polynucleotide template comprising a sequence to be integrated flanked by an upstream sequence and a downstream sequence is introduced into a cell. The upstream and downstream sequences share sequence similarity with either side of the site of integration in the chromosome. Where desired, a donor polynucleotide can be DNA, e.g., a DNA plasmid, a bacterial artificial chromosome (BAC), a yeast artificial chromosome (YAC), a viral vector, a linear piece of DNA, a PCR fragment, a naked nucleic acid, or a nucleic acid complexed with a delivery vehicle such as a liposome or poloxamer. The exogenous polynucleotide template comprises a sequence to be integrated (e.g., a mutated gene). The sequence for integration may be a sequence endogenous or exogenous to the cell. Examples of a sequence to be integrated include polynucleotides encoding a protein or a non-coding RNA (e.g., a microRNA). Thus, the sequence for integration may be operably linked to an appropriate control sequence or sequences. Alternatively, the sequence to be integrated may provide a regulatory function. The upstream and downstream sequences in the exogenous polynucleotide template are selected to promote recombination between the chromosomal sequence of interest and the donor polynucleotide. The upstream sequence is a nucleic acid sequence that shares sequence similarity with the genome sequence upstream of the targeted site for integration. Similarly, the downstream sequence is a nucleic acid sequence that shares sequence similarity with the chromosomal sequence downstream of the targeted site of integration. The upstream and downstream sequences in the exogenous polynucleotide template can have 75%, 80%, 85%, 90%, 95%, or 100% sequence identity with the targeted genome sequence. Preferably, the upstream and downstream sequences in the exogenous polynucleotide template have about 95%, 96%, 97%, 98%, 99%, or 100% sequence identity with the targeted genome sequence. In some methods, the upstream and downstream sequences in the exogenous polynucleotide template have about 99% or 100% sequence identity with the targeted genome sequence. An upstream or downstream sequence may comprise from about 20 bp to about 2500 bp, for example, about 50, 100, 200, 300, 400, 500, 600, 700, 800, 900, 1000, 1100, 1200, 1300, 1400, 1500, 1600, 1700, 1800, 1900, 2000, 2100, 2200, 2300, 2400, or 2500 bp. In some methods, the exemplary upstream or downstream sequence have about 200 bp to about 2000 bp, about 600 bp to about 1000 bp, or more particularly about 700 bp to about 1000 bp. In some methods, the exogenous polynucleotide template may further comprise a marker. Such a marker may make it easy to screen for targeted integrations. Examples of suitable markers include restriction sites, fluorescent proteins, or selectable markers. The exogenous polynucleotide template of the invention can be constructed using recombinant techniques (see, for example, Sambrook et al., 2001 and Ausubel et al., 1996). In a method for modifying a target polynucleotide by integrating an exogenous polynucleotide template, a double stranded break is introduced into the genome sequence by the CRISPR complex, the break is repaired via homologous recombination an exogenous polynucleotide template such that the template is integrated into the genome. The presence of a double-stranded break facilitates integration of the template. In other embodiments, this invention provides a method of modifying expression of a polynucleotide in a eukaryotic cell. The method comprises increasing or decreasing expression of a target polynucleotide by using a CRISPR complex that binds to the polynucleotide. In some methods, a target polynucleotide can be inactivated to effect the modification of the expression in a cell. For example, upon the binding of a CRISPR complex to a target sequence in a cell, the target polynucleotide is inactivated such that the sequence is not transcribed, the coded protein is not produced, or the sequence does not function as the wild-type sequence does. For example, a protein or microRNA coding sequence may be inactivated such that the protein or microRNA or pre-microRNA transcript is not produced. In some methods, a control sequence can be inactivated such that it no longer functions as a control sequence. As used herein, "control sequence" refers to any nucleic acid sequence that effects the transcription, translation, or accessibility of a nucleic acid sequence. Examples of a control sequence include, a promoter, a transcription terminator, and an enhancer are control sequences. The target polynucleotide of a CRISPR complex can be any polynucleotide endogenous or exogenous to the eukaryotic cell. For example, the target polynucleotide can be a polynucleotide residing in the nucleus of the eukaryotic cell. The target polynucleotide can be a sequence coding a gene product (e.g., a protein) or a non-coding sequence (e.g., a regulatory polynucleotide or a junk DNA). Examples of target polynucleotides include a sequence associated with a signaling biochemical pathway, e.g., a signaling biochemical pathway-associated gene or polynucleotide. Examples of target polynucleotides include a disease associated gene or polynucleotide. A "disease-associated" gene or polynucleotide refers to any gene or polynucleotide which is yielding transcription or translation products at an abnormal level or in an abnormal form in cells derived from a disease-affected tissues compared with tissues or cells of a non disease control. It may be a gene that becomes expressed at an abnormally high level; it may be a gene that becomes expressed at an abnormally low level, where the altered expression correlates with the occurrence and/or progression of the disease. A disease-associated gene also refers to a gene possessing mutation(s) or genetic variation that is directly responsible or is in linkage disequilibrium with a gene(s) that is responsible for the etiology of a disease. The transcribed or translated products may be known or unknown, and may be at a normal or abnormal level. The target polynucleotide of a CRISPR complex can be any polynucleotide endogenous or exogenous to the eukaryotic cell. For example, the target polynucleotide can be a polynucleotide residing in the nucleus of the eukaryotic cell. The target polynucleotide can be a sequence coding a gene product (e.g., a protein) or a non-coding sequence (e.g., a regulatory polynucleotide or a junk DNA).

The target polynucleotide of a CRISPR complex can be any polynucleotide endogenous or exogenous to the eukaryotic cell. For example, the target polynucleotide can be a polynucleotide residing in the nucleus of the eukaryotic cell. The target polynucleotide can be a sequence coding a gene product (e.g., a protein) or a non-coding sequence (e.g., a regulatory polynucleotide or a junk DNA). The target can be a control element or a regulatory element or a promoter or an enhancer or a silencer. The promoter may, in some embodiments, be in the region of +200 bp or even +1000 bp from the TTS. In some embodiments, the regulatory region may be an enhancer. The enhancer is typically more than +1000 bp from the TTS. More in particular, expression of eukaryotic protein-coding genes generally is regulated through multiple cis-acting transcription-control regions. Some control elements are located close to the start site (promoter-proximal elements), whereas others lie more distant (enhancers and silencers) Promoters determine the site of transcription initiation and direct binding of RNA polymerase II. Three types of promoter sequences have been identified in eukaryotic DNA. The TATA box, the most common, is prevalent in rapidly transcribed genes. Initiator promoters infrequently are found in some genes, and CpG islands are characteristic of transcribed genes. Promoter-proximal elements occur within ≈200 base pairs of the start site. Several such elements, containing up to ≈20 base pairs, may help regulate a particular gene. Enhancers, which are usually ≈100-200 base pairs in length, contain multiple 8- to 20-bp control elements. They may be located from 200 base pairs to tens of kilobases upstream or downstream from a promoter, within an intron, or downstream from the final exon of a gene. Promoter-proximal elements and enhancers may be cell-type specific, functioning only in specific differentiated cell types. However, any of these regions can be the target sequence and are encompassed by the concept that the target can be a control element or a regulatory element or a promoter or an enhancer or a silencer.

Without wishing to be bound by theory, it is believed that the target sequence should be associated with a PAM (protospacer adjacent motif); that is, a short sequence recognized by the CRISPR complex. The precise sequence and length requirements for the PAM differ depending on the CRISPR enzyme used, but PAMs are typically 2-5 base pair sequences adjacent the protospacer (that is, the target sequence) Examples of PAM sequences are given in the examples section below, and the skilled person will be able to identify further PAM sequences for use with a given CRISPR enzyme. In some embodiments, the method comprises allowing a CRISPR complex to bind to the target polynucleotide to effect cleavage of said target polynucleotide thereby modifying the target polynucleotide, wherein the CRISPR complex comprises a CRISPR enzyme complexed with a guide sequence hybridized to a target sequence within said target polynucleotide, wherein said guide sequence is linked to a tracr mate sequence which in turn hybridizes to a tracr sequence. In one aspect, the invention provides a method of modifying expression of a polynucleotide in a eukaryotic cell. In some embodiments, the method comprises allowing a CRISPR complex to bind to the polynucleotide such that said binding results in increased or decreased expression of said polynucleotide; wherein the CRISPR complex comprises a CRISPR enzyme complexed with a guide sequence hybridized to a target sequence within said polynucleotide, wherein said guide sequence is linked to a tracr mate sequence which in turn hybridizes to a tracr sequence. Similar considerations and conditions apply as above for methods of modifying a target polynucleotide. In fact, these sampling, culturing and re-introduction options apply across the aspects of the present invention. In one aspect, the invention provides for methods of modifying a target polynucleotide in a eukaryotic cell, which may be in vivo, ex vivo or in vitro. In some embodiments, the method comprises sampling a cell or population of cells from a human or non-human animal, and modifying the cell or cells. Culturing may occur at any stage ex vivo. The cell or cells may even be re-introduced into the non-human animal or plant. For re-introduced cells it is particularly preferred that the cells are stem cells.

Indeed, in any aspect of the invention, the CRISPR complex may comprise a CRISPR enzyme complexed with a guide sequence hybridized to a target sequence, wherein said guide sequence may be linked to a tracr mate sequence which in turn may hybridize to a tracr sequence.

The invention relates to the engineering and optimization of systems, methods and compositions used for the control of gene expression involving sequence targeting, such as genome perturbation or gene-editing, including epigenetic modulation or modification, transcriptional or translational modulation, etc. that relate to the CRISPR-Cas system and components thereof. An advantage of the present methods is that the CRISPR system minimizes or avoids off-target binding and its resulting side effects. This is achieved using systems arranged to have a high degree of sequence specificity for the target DNA or RNA.

In relation to a CRISPR-Cas complex or system preferably, the tracr sequence has one or more hairpins and is 30 or more nucleotides in length, 40 or more nucleotides in length, or 50 or more nucleotides in length; the guide sequence is between 10 to 30 nucleotides in length, the CRISPR/Cas enzyme is a Type II CRISPR effector protein.

In one aspect, the invention provides a fusion protein comprising one or more destabilization domains (DD), one or more adaptor proteins capable of binding to a DNA- or RNA guided (endo)nuclease system guide RNA or guide DNA, such as in certain embodiments a CRISPR/Cas or argonaute system guide RNA (gRNA) or guide DNA (gDNA), and optionally one or more functional domains. In certain embodiments, the RNA-guided or DNA-guided (endo)nuclease (also called "effector protein") may itself also be associated with a destabilizing domain. Such non-naturally occurring or engineered effector protein associated with at least one destabilization domain (DD); and, for shorthand purposes, such a non-naturally occurring or engineered CRISPR enzyme associated with at least one destabilization domain (DD) is herein termed a "DD-effector". In one aspect, the invention provides an engineered, non-naturally occurring DD-CRISPR-Cas (or argonaute) system comprising a fusion protein according to the invention as defined herein associated with at least one destabilization domain, a CRISPR enzyme, wherein the CRISPR enzyme is a Cas protein, which is a type II DD-CRISPR Cas protein and guide RNA that targets a nucleic acid molecule such as a DNA or RNA molecule, whereby the guide RNA targets the nucleic acid molecule, e.g., DNA or RNA molecule. The nucleic acid molecule, e.g., DNA or RNA molecule can encode a gene product. In some embodiments the Cas protein may cleave the DNA molecule encoding the gene product. In some embodiments expression of the gene product is altered. The Cas protein and the guide RNA do not naturally occur together. The invention comprehends the guide RNA comprising a guide sequence fused to a tracr sequence in case the particular Cas protein requires the presence of a tracr. The invention further comprehends coding for the Cas protein being codon optimized for expression in a eukaryotic cell. In a preferred embodiment the eukaryotic cell is a mammalian cell and in a more preferred embodiment the mammalian cell is a human cell. Expression of the gene product may be decreased. The CRISPR enzyme may form part of a CRISPR-Cas system, which further comprises a guide RNA (gRNA) comprising a guide sequence capable of hybridizing to a target sequence in a genomic locus of interest in a cell. The gRNA may be functionalized such as being capable of binding to the fusion protein according to the invention, in particular binding to the adaptor protein of the fusion protein. In some embodiments, the functional CRISPR-Cas system binds to the target sequence. In some embodiments, the functional CRISPR-Cas system may edit the target sequence, e.g., the target sequence may comprise a genomic locus, and in some embodiments there may be an alteration of gene expression. In some embodiments, the functional CRISPR-Cas system may comprise further functional domains. In some embodiments, the invention provides a method for altering or modifying expression of a gene product. The method may comprise introducing into a cell containing a target nucleic acid, e.g., DNA or RNA molecule, or containing and expressing a target nucleic acid, e.g., DNA or RNA molecule; for instance, the target nucleic acid may encode a gene product or provide for expression of a gene product (e.g., a regulatory sequence).

The CRISPR enzyme may be a Cas9, Cpf1, C2c1, C2c2, C2c3, Cas13, or group 29/30. Alternatively, the CRISPR enzyme in the methods, compositions, and systems as described herein may be replaced by another DNA- or RNA-guided (endo)nuclease, such as argonaute. In some embodiments, the CRISPR enzyme is an Sp DD-Cas9. In some embodiments, the CRISPR enzyme is an Sa DD-Cas9. In some embodiments, the CRISPR enzyme is an St or Fn DD-Cas9, although other orthologs are envisaged. Sp and Sa DD-Cas9s are particularly preferred, in some embodiments. In some embodiments, the CRISPR enzyme cleave both strands of DNA to produce a double strand break (DSB). In some embodiments, the CRISPR enzyme is a nickase. In some embodiments, the CRISPR enzyme is a dual nickase. In some embodiments, the CRISPR enzyme is a deadCas, e.g., a Cas having substantially no nuclease activity, e.g., no more than 5% nuclease activity as compared with a wild-type Cas or Cas not having had mutations to it.

In some general embodiments, the fusion protein is associated with one or more functional domains.

In some general embodiments, the CRISPR enzyme is associated with one or more functional domains. In some more specific embodiments, the CRISPR enzyme is a deadCas and/or is associated with one or more functional domains.

In some embodiments, the CRISPR enzyme comprises a Rec2 or HD2 truncation. In some embodiments, the CRISPR enzyme is associated with the DD by way of a fusion protein. In some embodiments, the CRISPR enzyme is fused to the DD. In other words, the DD may be associated with the CRISPR enzyme by fusion with said CRISPR enzyme. In some embodiments, the enzyme may be considered to be a modified CRISPR enzyme, wherein the CRISPR enzyme is optionally fused to at least one destabilization domain (DD).

In some embodiments, the DD of the fusion protein according to the invention, or of the CRISPR enzyme may be associated therewith via a connector protein, for example using a system such as a marker system such as the streptavidin-biotin system. As such, provided is a fusion of a fusion protein according to the invention, or CRISPR enzyme with a connector protein specific for a high affinity ligand for that connector, whereas the DD is bound to said high affinity ligand. For example, streptavidin may be the connector fused to the fusion protein or CRISPR enzyme, while biotin may be bound to the DD. Upon co-localization, the streptavidin will bind to the biotin, thus connecting the fusion protein or CRISPR enzyme to the DD. For simplicity, a fusion of the fusion protein and/or CRISPR enzyme with the DD is preferred in some embodiments. In some embodiments, the fusion may be to the N-terminal end of the fusion protein or CRISPR enzyme. In some embodiments, at least one DD is fused to the N-terminus of the fusion protein or CRISPR enzyme. In some embodiments, the fusion may be to the C-terminal end of the fusion protein or CRISPR enzyme. In some embodiments, at least one DD is fused to the C-terminus of the fusion protein or CRISPR enzyme. In some embodiments, one DD may be fused to the N-terminal end of the fusion protein or CRISPR enzyme with another DD fused to the C-terminal of the fusion protein or CRISPR enzyme. In some embodiments, the fusion protein or CRISPR enzyme is associated with at least two DDs and wherein a first DD is fused to the N-terminus of the fusion protein or CRISPR enzyme and a second DD is fused to the C-terminus of the fusion protein or CRISPR enzyme, the first and second DDs being the same or different. In some embodiments, the fusion may be to the N-terminal end of the DD. In some embodiments, the fusion may be to the C-terminal end of the DD. In some embodiments, the fusion may between the C-terminal end of the fusion protein or CRISPR enzyme and the N-terminal end of the DD. In some embodiments, the fusion may between the C-terminal end of the DD and N-terminal end of the fusion protein or CRISPR enzyme. Less background was observed with a DD fused to the CRISPR protein comprising at least one N-terminal fusion than a DD comprising at least one C terminal fusion. Combining N- and C-terminal CRISPR protein fusions had the least background but lowest overall activity. Advantageously a DD is provided through at least one N-terminal fusion or at least one N terminal fusion plus at least one C-terminal fusion. And of course, a DD can be provided by at least one C-terminal fusion.

In some embodiments, the DD is ER50. A corresponding stabilizing ligand for this DD is, in some embodiments, 4HT. As such, in some embodiments, one of the at least one DDs is ER50 and a stabilizing ligand therefor is 4HT or CMP8. In some embodiments, the DD is DHFR50. A corresponding stabilizing ligand for this DD is, in some embodiments, TMP. As such, in some embodiments, one of the at least one DDs is DHFR50 and a stabilizing ligand therefor is TMP. In some embodiments, the DD is ER50. A corresponding stabilizing ligand for this DD is, in some embodiments, CMP8. CMP8 may therefore be an alternative stabilizing ligand to 4HT in the ER50 system. While it may be possible that CMP8 and 4HT can/should be used in a competitive matter, some cell types may be more susceptible to one or the other of these two ligands, and from this disclosure and the knowledge in the art the skilled person can use CMP8 and/or 4HT.

In some embodiments, one or two DDs may be fused to the N-terminal end of the fusion protein or CRISPR enzyme with one or two DDs fused to the C-terminal of the fusion protein or CRISPR enzyme. In some embodiments, the at least two DDs are associated with the fusion protein or CRISPR enzyme and the DDs are the same DD, i.e. the DDs are homologous. Thus, both (or two or more) of the DDs could be ER50 DDs. This is preferred in some embodiments. Alternatively, both (or two or more) of the DDs could be DHFR50 DDs. This is also preferred in some embodiments. In some embodiments, the at least two DDs are associated with the fusion protein or CRISPR enzyme and the DDs are different DDs, i.e. the DDs are heterologous. Thus, one of the DDS could be ER50 while one or more of the or any other DDs could be DHFR50. Having two or more DDs which are heterologous may be advantageous as it would provide a greater level of degradation control. A tandem fusion of more than one DD at the N or C-term may enhance degradation; and such a tandem fusion can be, for example ER50-ER50-adaptor (or CRISPR) protein or DHFR-DHFR-adaptor (or CRISPR). High levels of degradation occur in the absence of either stabilizing ligand, intermediate levels of degradation occur in the absence of one stabilizing ligand and the presence of the other (or another) stabilizing ligand, while low levels of degradation occur in the presence of both (or two of more) of the stabilizing ligands. Control may also be imparted by having an N-terminal ER50 DD and a C-terminal DHFR50 DD, or vice versa.

In some embodiments, the fusion of the fusion protein or CRISPR enzyme with the DD comprises a linker between the DD and the fusion protein or CRISPR enzyme. In some embodiments, the linker is a GlySer linker. In some embodiments, the fusion protein and/or CRISPR enzyme further comprises at least one Nuclear Export Signal (NES). In some embodiments, the fusion protein and/or CRISPR enzyme comprises two or more NESs. In some embodiments, the fusion protein and/or CRISPR enzyme comprises at least one Nuclear Localization Signal (NLS). This may be in addition to an NES. In some embodiments, the fusion protein and/or CRISPR enzyme comprises or consists essentially of or consists of a localization (nuclear import or export) signal as, or as part of, the linker between the fusion protein or CRISPR enzyme and the DD. HA or Flag tags are also within the ambit of the invention as linkers. Applicants use NLS and/or NES as linker and use Glycine Serine linkers as short as GS up to (GGGGS)3 (SEQ ID NO: 1).

In an aspect, the present invention provides a polynucleotide encoding the fusion protein according to the invention as described herein, minimally containing the DD and the adaptor protein, optionally a functional domain. In some embodiments, the encoded adaptor protein and associated DD are operably linked to a first regulatory element. In some embodiments, a DD is also encoded and is operably linked to a second regulatory element. Advantageously, the DD here is to "mop up" the stabilizing ligand and so it is advantageously the same DD (i.e. the same type of Domain) as that associated with the enzyme, e.g., as herein discussed (with it understood that the term "mop up" is meant in the sense of performing so as to contribute or conclude activity. In some embodiments, the first regulatory element is a promoter and may optionally include an enhancer. In some embodiments, the second regulatory element is a promoter and may optionally include an enhancer. In some embodiments, the first regulatory element is an early promoter. In some embodiments, the second regulatory element is a late promoter. In some embodiments, the second regulatory element is or comprises or consists essentially of an inducible control element, optionally the tet system, or a repressible control element, optionally the tetr system. An inducible promoter may be favorable e.g. rTTA to induce tet in the presence of doxycycline.

In an aspect, the present invention provides a means for delivering the DD-CRISPR-Cas complex of the invention or polynucleotides discussed herein, e.g., particle(s) delivering component(s) of the complex, vector(s) comprising the polynucleotide(s) discussed herein (e.g., encoding the CRISPR enzyme, the DD; providing RNA of the CRISPR-Cas complex). In some embodiments, the vector may be a plasmid or a viral vector such as AAV, or lentivirus. Transient transfection with plasmids, e.g., into HEK cells may be advantageous, especially given the size limitations of AAV and that while SpCas9 fits into AAV, one may reach an upper limit with additional coding as to the association with the DD(s).

Also provided is a model that constitutively expresses the fusion protein and/or CRISPR enzyme and associated DD. The organism may be a transgenic and may have been transfected the present vectors or may be the offspring of an organism so transfected. In a further aspect, the present invention provides compositions comprising the fusion protein and/or CRISPR enzyme and associated DD or the polynucleotides or vectors described herein. Also provides are CRISPR-Cas systems comprising guide RNAs.

Also provided is a method of treating a subject, e.g., a subject in need thereof, comprising inducing gene editing by transforming the subject with the polynucleotide encoding the system or any of the present vectors and administering stabilizing ligand to the subject. A suitable repair template may also be provided, for example delivered by a vector comprising said repair template. Also provided is a method of treating a subject, e.g., a subject in need thereof, comprising inducing transcriptional activation or repression by transforming the subject with the polynucleotide encoding the present system or any of the present vectors, wherein said polynucleotide or vector encodes or comprises the fusion protein (optionally comprising one or more functional (heterologous) domains, catalytically inactive CRISPR enzyme and optionally one or more associated functional domains; the method further comprising administering a stabilizing ligand to the subject. These methods may also include delivering and/or expressing excess DD to the subject. Where any treatment is occurring ex vivo, for example in a cell culture, then it will be appreciated that the term 'subject' may be replaced by the phrase "cell or cell culture."

Compositions comprising the present system for use in said method of treatment are also provided. A separate composition ay comprise the stabilizing ligand. A kit of parts may be provided including such compositions. Use of the present system in the manufacture of a medicament for such methods of treatment are also provided. Use of the present system in screening is also provided by the present invention, e.g., gain of function screens. Cells which are artificially forced to overexpress a gene are be able to down regulate the gene over time (re-establishing equilibrium) e.g. by negative feedback loops. By the time the screen starts the unregulated gene might be reduced again. Using an inducible CRISPR effector activator allows one to induce transcription right before the screen and therefore minimizes the chance of false negative hits. Accordingly, by use of the instant invention in screening, e.g., gain of function screens, the chance of false negative results may be minimized.

In one aspect, the invention provides an engineered, non-naturally occurring CRISPR-Cas or argonaute system comprising a fusion protein according to the invention as described herein, a Cas or argonaute protein (i.e. effector protein) and a guide RNA or guide DNA that targets a DNA or RNA molecule encoding a gene product in a cell, whereby the guide DNA/RNA targets the RNA/DNA molecule encoding the gene product and the Cas9 protein cleaves the DNA molecule encoding the gene product, whereby expression of the gene product is altered; and, wherein the effector protein and the guide DNA/RNA do not naturally occur together. The invention comprehends the guide RNA comprising a guide sequence fused to a tracr sequence if required for proper functionality of the effector protein. The Cas protein is a type II CRISPR-Cas protein and may be a Cas9, Cpf1, C2c1, C2c2, C2c3, Cas13, or group 29/30 protein. The invention further comprehends coding for the fusion protein and/or effector protein being codon optimized for expression in a eukaryotic cell. In a preferred embodiment the eukaryotic cell is a mammalian cell and in a more preferred embodiment the mammalian cell is a human cell. In a further embodiment of the invention, the expression of the gene product is decreased.

Where functional domains and the like are "associated" with one or other part of the enzyme, these are typically fusions. The term "associated with" is used here in respect of how one molecule 'associates' with respect to another, for example between parts of the fusion protein or CRISPR enzyme and a functional domain. The two may be considered to be tethered to each other. In the case of such protein-protein interactions, this association may be viewed in terms of recognition in the way an antibody recognizes an epitope. Alternatively, one protein may be associated with another protein via a fusion of the two, for instance one subunit being fused to another subunit. Fusion typically occurs by addition of the amino acid sequence of one to that of the other, for instance via splicing together of the nucleotide sequences that encode each protein or subunit. Alternatively, this may essentially be viewed as binding between two molecules or direct linkage, such as a fusion protein. In any event, the fusion protein may include a linker between the two subunits of interest (e.g. between the enzyme and the functional domain or between the adaptor protein and the functional domain). Thus, in some embodiments, the part of the fusion protein or CRISPR enzyme is associated with a functional domain by binding thereto. In other embodiments, the fusion protein and/or CRISPR enzyme is associated with a functional domain because the two are fused together, optionally via an intermediate linker. Examples of linkers include the GlySer linkers discussed herein. While a non covalent bound DD may be able to initiate degradation of the associated fusion protein or effector protein, proteasome degradation involves unwinding of the protein chain; and, a fusion is preferred as it can provide that the DD stays connected to fusion protein or effector protein upon degradation. However the fusion protein or CRISPR enzyme and DD are brought together, in the presence of a stabilizing ligand specific for the DD, a stabilization complex is formed. This complex comprises the stabilizing ligand bound to the DD. The complex also comprises the DD associated with the fusion protein and/or CRISPR enzyme. In the absence of said stabilizing ligand, degradation of the DD and its associated fusion protein or CRISPR enzyme is promoted.

Destabilizing domains have general utility to confer instability to a wide range of proteins; see, e.g., Miyazaki, J Am Chem Soc. Mar. 7, 2012; 134(9): 3942-3945, and Chung H Nature Chemical Biology Vol. 11 Sep. 2015 pgs 713-720, incorporated herein by reference. CMP8 or 4-hydroxytamoxifen can be destabilizing domains. More generally, a temperature-sensitive mutant of mammalian DHFR (DHFRts), a destabilizing residue by the N-end rule, was found to be stable at a permissive temperature but unstable at 37° C. The addition of methotrexate, a high-affinity ligand for mammalian DHFR, to cells expressing DHFRts inhibited degradation of the protein partially. This was an important demonstration that a small molecule ligand (i.e. "stabilizing ligand") can stabilize a protein otherwise targeted for degradation in cells. A rapamycin derivative was used to stabilize an unstable mutant of the FRB domain of mTOR (FRB*) and restore the function of the fused kinase, GSK-30.6,7 This system demonstrated that ligand-dependent stability represented an attractive strategy to regulate the function of a specific protein in a complex biological environment. A system to control protein activity can involve the DD becoming functional when the ubiquitin complementation occurs by rapamycin induced dimerization of FK506-binding protein and FKBP12. Mutants of human FKBP12 or ecDHFR protein can be engineered to be metabolically unstable in the absence of their high-affinity ligands, Shield-1 or trimethoprim (TMP), respectively. These mutants are some of the possible destabilizing domains (DDs) useful in the practice of the invention and instability of a DD as a fusion with a CRISPR enzyme confers to the CRISPR protein degradation of the entire fusion protein by the proteasome. Shield-1 and TMP bind to and stabilize the DD in a dose-dependent manner. The estrogen receptor ligand binding domain (ERLBD, residues 305-549 of ERS1) can also be engineered as a destabilizing domain. Since the estrogen receptor signaling pathway is involved in a variety of diseases such as breast cancer, the pathway has been widely studied and numerous agonist and antagonists of estrogen receptor have been developed. Thus, compatible pairs of ERLBD and drugs are known. There are ligands that bind to mutant but not wild-type forms of the ERLBD. By using one of these mutant domains encoding three mutations (L384M, M421G, G521R)12, it is possible to regulate the stability of an ERLBD-derived DD using a ligand that does not perturb endogenous estrogen-sensitive networks. An additional mutation (Y537S) can be introduced to further destabilize the ERLBD and to configure it as a potential DD candidate. This tetra-mutant is an advantageous DD development. The mutant ERLBD can be fused to a CRISPR enzyme and its stability can be regulated or perturbed using a ligand, whereby the CRISPR enzyme has a DD. Another DD can be a 12-kDa (107-amino-acid) tag based on a mutated FKBP protein, stabilized by Shieldi ligand; see, e.g., Nature Methods 5, (2008). For instance a DD can be a modified FK506 binding protein 12 (FKBP12) that binds to and is reversibly stabilized by a synthetic, biologically inert small molecule, Shield-1; see, e.g., Banaszynski LA, Chen L C, Maynard-Smith L A, Ooi A G, Wandless T J. A rapid, reversible, and tunable method to regulate protein function in living cells using synthetic small molecules. Cell. 2006; 126:995-1004; Banaszynski L A, Sellmyer M A, Contag C H, Wandless T J, Thorne S H. Chemical control of protein stability and function in living mice. Nat Med. 2008; 14:1123-1127; Maynard-Smith L A, Chen L C, Banaszynski L A, Ooi A G, Wandless T J. A directed approach for engineering conditional protein stability using biologically silent small molecules. The Journal of biological chemistry. 2007; 282:24866-24872; and Rodriguez, Chem Biol. Mar. 23, 2012; 19(3): 391-398-all of which are incorporated herein by reference and may be employed in the practice of the invention in selected a DD to associate with a fusion protein and/or optionally CRISPR enzyme in the practice of this invention. As can be seen, the knowledge in the art includes a number of DDs, and the DD can be associated with, e.g., fused to, advantageously with a linker, to a fusion protein or CRISPR enzyme, whereby the DD can be stabilized in the presence of a ligand and when there is the absence thereof the DD can become destabilized, whereby the fusion protein or CRISPR enzyme is entirely destabilized, or the DD can be stabilized in the absence of a ligand and when the ligand is present the DD can become destabilized; the DD allows the fusion protein or CRISPR enzyme and hence the CRISPR-Cas complex or system to be regulated or controlled-turned on or off so to speak, to thereby provide means for regulation or control of the system, e.g., in an in vivo or in vitro environment. For instance, when a protein of interest is expressed as a fusion with the DD tag, it is destabilized and rapidly degraded in the cell, e.g., by proteasomes. Thus, absence of stabilizing ligand leads to a DD associated fusion protein or effector protein being degraded. When a new DD is fused to a protein of interest, its instability is conferred to the protein of interest, resulting in the rapid degradation of the entire fusion protein. Peak activity for Cas proteins is sometimes beneficial to reduce off-target effects. Thus, short bursts of high activity are preferred. The present invention is able to provide such peaks. In some senses the system is inducible. In some other senses, the system repressed in the absence of stabilizing ligand and de-repressed in the presence of stabilizing ligand. Without wishing to be bound by any theory and without making any promises, other benefits of the invention may include that it is:

Dosable (in contrast to a system that turns on or off, e.g., can allow for variable CRISPR-Cas system or complex activity).

Orthogonal, e.g., a ligand only affects its cognate DD so two or more systems can operate independently, and/or the CRISPR enzymes can be from one or more orthologs.

Transportable, e.g., may work in different cell types or cell lines.

Rapid.

Temporal Control.

Able to reduce background or off target effector protein or effector protein toxicity or excess build up of effector protein by allowing the fusion protein or effector protein to be degraded, i.e. generally inactivating the system.

Cheap—the stabilizing ligands are widely available and typically not expensive.

While the DD can be at N and/or C terminal(s) of the fusion protein or CRISPR enzyme, including a DD at one or more sides of a split e.g. Cas9(N)-linker-DD-linker-Cas9(C) is also a way to introduce a DD. In some embodiments, if using only one terminal association of DD to the fusion protein or CRISPR enzyme is to be used, then it is preferred to use ER50 as the DD. In some embodiments, if using both N- and C-terminals, then use of either ER50 and/or DHFR50 is preferred. Particularly good results were seen with the N-terminal fusion, which is surprising. Having both N and C terminal fusion may be synergistic. The size of Destabilization Domain varies but is typically approx.—approx. 100-300 amino acids in size. The DD is preferably an engineered destabilizing protein domain. DDs and methods for making DDs, e.g., from a high affinity ligand and its ligand binding domain. The invention may be considered to be "orthogonal" as only the specific ligand will stabilize its respective (cognate) DD, it will have no effect on the stability of non-cognate DDs. A commercially available DD system is the ClonTech, ProteoTuner™ system; the stabilizing ligand is Shield1, which is also preferred for use in the present invention.

In some embodiments, the stabilizing ligand is a 'small molecule'. In some embodiments, the stabilizing ligand is cell-permeable. It has a high affinity for its corresponding DD. Suitable DD—stabilizing ligand pairs are known in the art. In general, the stabilizing ligand may be removed by:

Natural processing (e.g., proteasome degradation), e.g., in vivo;

Mopping up, e.g. ex vivo/cell culture, by:

Provision of a preferred binding partner; or

In certain embodiments, the stabilizing ligand may be conditionally or inducibly active or activatable. Accordingly, in certain embodiments, targeted activation of the stabilizing ligand is envisaged. The stabilizing ligand may for instance be provided in an inactive form (cf. prodrug), and may be activated upon suitable stimulus, such as inducible or conditional activation (e.g. particular cellular environment, addition of releasing agents, etc.)

In an aspect, the present invention provides a stabilizing ligand for a DD (i.e. a DD ligand) which is capable of being activated or deactivated. In an embodiment of the invention, the DD ligand is activated or inactivated in vivo. In an embodiment of the invention, the DD ligand is activated or inactivated in situ. In an embodiment of the invention, the DD ligand is activated or inactivated by an enzyme present or provided to a target cell or tissue. In one such embodiment, an ester is appended to a DD ligand such that the DD ligand is blocked from stabilizing and activating its destabilizing domain partner. When subject to esterase activity native to or artificially expressed in a cell or tissue of interest, the ester is cleaved from the DD ligand with the result that the DD ligand is activated and stabilizes its partner DD bound to or associated with a CRISPR system component. CRISPR system activity persists for as long as the DD ligand is present. In certain embodiments, the DD ligand is degradable, with the result that CRISPR system activity persists only for as long as the DD ligand is present.

In an embodiment of the invention, the DD ligand is activated or inactivated by EM radiation, including but not limited to visible light and infrared. In one embodiment, a photocaging system based on o-nitrobenzyl is employed. In one such embodiment a 6-nitroveratryl carbamate (NVOC) group is appended to trimethoprim, blocking binding to DHFR.

In certain embodiments, a boron-dipyrromethene (BODIPY)-based photocage is employed. Goswami, P. P. et al. J. Am. Chem. Soc. 137, 3783-3786 (2015) demonstrated photorelease of protecting groups derived from meso-substituted BODIPY dyes with green wavelengths >500 nm and showed that the photocages are functional in living *Drosophila* S2 cells. Other photocages include, without limitation, phenacyl, acridinyl, benzoinyl, coumarinyl, xanthenyl, and o-hydroxynaphthyl structures. Carling et al. Chem. Sci. 7, 2392-2398 (2016) functionalized the drugs paclitaxel, dexamethasone and chlorambucil with an amino-1,4-benzoquinone photocage which can be released by visible light in the 400-700 nm range. Gorka et al, J Am. Chem. Soc. 136, 14153-14159 (2014) reports a near-IR light-initiated uncaging reaction sequence based on readily synthesized C4'-dialkylamine-substituted heptamethine cyanines, which is biocompatible and initiated with low intensity light of about 690 nm.

The DD ligand can be adapted as to cellular location. Ibsen et al., Pharm. Res. 27, 1848-1860 (2010) describes a controllably activatable chemotherapy prodrug of DOX created by blocking its free amine group with a biotinylated photocleavable blocking group. The PCB included an ortho-nitrophenyl group for photo cleavability, and a biotin group for enhanced membrane interaction. Unlike DOX, DOX-PCB stayed in the cell cytoplasm, did not enter the nucleus, and did not stain the exposed DNA during mitosis. Horbert et al., ACS Chem. Biol, 10, 2099-2107 (2015) report on novel photoactivatable caged prodrugs of vemurafenib, a kinase inhibitor approved drug for treatment of BRAF-mutated melanoma. An LED reactor with an emission at 365 nm (long enough to avoid tissue damage) was used to irradiate solutions of the prodrugs and release the active drug.

In an embodiment of the invention, the activatable DD ligand is selected taking into account its half life such that when activated, the DD ligand binds to a CRISPR system-associated DD, thereby promoting the activity of the CRISPR system, followed by reduced activity of the CRISPR system as the DD ligand is degraded.

EM radiation can be delivered to cells and tissues by a variety of methods and devices. Example include, without limitation, endoscopes, catheters and other fiber optics, as well as implantable and swallowable devices. In one non-limiting embodiment, a 'PillCam' like device is used to provide visible or near-infrared illumination to the digestive tract. In certain embodiments, upconversion may be employed. Upconversion efficiently converts two or more low-energy excitation photons, which are generally near infrared (NIR) light, into a higher energy photon (i.e., having shorter wavelength such as NIR, visible, ultraviolet). Small upconversion nanoparticles are useful in theranostics due to properties such as non-blinking, non-photobleaching, absence of autofluorescence, low-toxicity, low photodamage to live cells, and the ability to introduce light in tissues. In particular, illumination at wavelengths to which tissues are relatively transparent may can be upconverted to shorter wavelengths useful for de-caging photocaged agents but to which tissues are relatively opaque. Upconversion nanocrystals are useful in diagnostics and imaging, biosensing, drug delivery, photoactivation, tissue engineering, and light activated therapy.

Provision of XS substrate (DD without fusion protein or CRISPR protein)

Advantageously, the DD may "mop up" the stabilizing ligand and so it is the same DD (i.e. the same type of DD) as that associated with the enzyme. By mopping up the stabilizing ligand with excess DD that is not associated with the fusion protein or CRISPR enzyme, greater degradation of the fusion protein or CRISPR enzyme will be seen. It is envisaged, without being bound by theory, that as additional or excess un-associated DD is added that the equilibrium will shift away from the stabilizing ligand complexing or binding to the DD associated with the fusion protein or CRISPR enzyme and instead move towards more of the stabilizing ligand complexing or binding to the free DD (i.e. that not associated with the fusion protein or CRISPR enzyme). Thus, provision of excess or additional unassociated (or free) DD is preferred when it is desired to reduce fusion protein or CRISPR enzyme activity through increased degradation of the fusion protein or CRISPR enzyme. An excess of free DD will bind residual ligand and also takes away bound ligand from fusion protein or DD-Cas fusion. Therefore it accelerates degradation and enhances temporal control of activity.

The present invention also contemplates use of the systems described herein to provide RNA-guided gene drives, for example in systems analogous to gene drives described in PCT Patent Publication WO 2015/105928. Further reference can be found for instance in Esvelt et al. (eLife 2014; 3:e03401; DOI: 10.7554/eLife.03401.001); Webber et al. (PNAS; 2015; 112(34):10565-10567); DeFrancesco (Nature Biotechnology, 2015, 33(10):1019-1021); DiCarlo et al. (Nature Biotechnology, 2015; 33: 1250-1255); Gantz et al. (PNAS; 2015; 112(49):E6736-E6743). Systems of this kind may for example provide methods for altering eukaryotic germline cells, by introducing into the germline cell a nucleic acid sequence encoding an RNA or DNA-guided DNA or RNA nuclease and one or more guide RNAs or guide DNAs. The guide RNAs/DNAs may be designed to be complementary to one or more target locations on (genomic) DNA or RNA of the germline cell. The nucleic acid sequence encoding the DNA/RNA guided DNA/RNA nuclease and the nucleic acid sequence encoding the guide RNAs/DNAs may be provided on constructs between flanking sequences, with promoters arranged such that the germline cell may express the nuclease and the guides, together with any desired cargo-encoding sequences that are also situated between the flanking sequences. The flanking sequences will typically include a sequence which is identical to a corresponding sequence on a selected target chromosome, so that the flanking sequences work with the components encoded by the construct to facilitate insertion of the foreign nucleic acid construct sequences into RNA or DNA at a target cut site by mechanisms such as homologous recombination, to render the germline cell homozygous for the foreign nucleic acid sequence. In this way, gene-drive systems are capable of introgressing desired cargo genes throughout a breeding population (Gantz et al., 2015, Highly efficient Cas9-mediated gene drive for population modification of the malaria vector mosquito *Anopheles stephensi*, PNAS 2015, published ahead of print Nov. 23, 2015, doi: 10.1073/pnas.1521077112; Esvelt et al., 2014, Concerning DNA- or RNA-guided gene drives for the alteration of wild populations eLife 2014;3:e03401). In select embodiments, target sequences may be selected which have few potential off-target sites in a genome. Targeting multiple sites within a target locus, using multiple guide RNAs, may increase the cutting frequency and hinder the evolution of drive resistant alleles. Truncated guide RNAs may reduce off-target cutting. Paired nickases may be used instead of a single nuclease, to further increase specificity. Gene drive constructs may include cargo sequences encoding transcriptional regulators, for example to activate homologous recombination genes and/or repress non-homologous end-joining. Target sites may be chosen within an essential gene, so that non-homologous end-joining events may cause lethality rather than creating a drive-resistant allele. The gene drive constructs can be engineered to function in a range of hosts at a range of temperatures (Cho et al. 2013, Rapid and Tunable Control of Protein Stability in *Caenorhabditis elegans* Using a Small Molecule, PLoS ONE 8(8): e72393. doi:10.1371/journal.pone.0072393).

In order to enforce the gene drive, then the stabilizing ligand will need to be present in the environment (such as the diet) of the host. In the absence of a stabilizing ligand, the fusion protein and optionally the effector protein will be degraded and no or reduced gene drive will be seen.

Attachment or association can be via a linker, e.g., a flexible glycine-serine (GlyGlyGlySer) (SEQ ID NO: 3) or $(GGGS)_3$ (SEQ ID NO: 4) or a rigid alpha-helical linker such as (Ala(GluAlaAlaAlaLys)Ala) (SEQ ID NO: 50). Linkers such as $(GGGGS)_3$ (SEQ ID NO: 1) are preferably used herein to separate protein or peptide domains. $(GGGGS)_3$ (SEQ ID NO: 1) is preferable because it is a relatively long linker (15 amino acids). The glycine residues are the most flexible and the serine residues enhance the chance that the linker is on the outside of the protein. $(GGGGS)_6$ (SEQ ID NO: 5) $(GGGGS)_9$ (SEQ ID NO: 51) or $(GGGGS)_{12}$ (SEQ ID NO: 52) may preferably be used as alternatives. Other preferred alternatives are (GGGGS)i (SEQ ID NO: 6), $(GGGGS)_2$ (SEQ ID NO: 53), $(GGGGS)_4$ (SEQ ID NO: 54), $(GGGGS)_5$(SEQ ID NO: 55), $(GGGGS)_7$ (SEQ ID NO: 56), $(GGGGS)_5$(SEQ ID NO: 57), $(GGGGS)_{10}$ (SEQ ID NO: 58), or (GGGGS)ii (SEQ ID NO: 59). Alternative linkers are available, but highly flexible linkers are thought to work best to allow for maximum opportunity for the fusion partners to come together. One alternative is that the NLS of nucleoplasmin can be used as a linker. For example, a linker can also be used between the fusion protein according to the invention as described herein (or the effector protein) and any functional domain. Again, a $(GGGGS)_3$ (SEQ ID NO: 1) linker may be used here (or the 6, 9, or 12 repeat versions therefore) or the NLS of nucleoplasmin can be used as a linker between fusion protein according to the invention as described herein (or the effector protein) and the functional domain.

In some embodiments, the CRISPR enzyme comprises a Rec2 or HD2 truncation. The Rec2 or HD2 domains are known in Sp Cas9 from the crystal structure provided by Nishimasu et al. and the herein cited materials; corresponding domains are envisaged in orthologs. Such mutants may be advantageous where there is a desire to reduce the package size as this can assist with delivery, especially with the larger Cas9s such as Sp Cas9.

It will be appreciated that truncation may include removal of the domain, in some embodiments. In some embodiments, the truncation includes replacement with a different amino acid sequence, for example a linker. In some embodiments, the linker is branched or otherwise allows for tethering of the DD and/or a functional domain to the fusion protein or CRISPR enzyme. Functional domains are discussed further herein. HD2, the Helical Domain 2, is dispensable (meaning that at least 10% functional CRISPR enzyme activity is retained, preferably at least 30% and most preferably at least 50% functional CRISPR enzyme activity is retained in the truncated CRISPR enzyme). An exemplary DNA sequence encoding it in Sp Cas9 is provided below and suitable equivalents will be readily apparent in orthologs of Sp via sequence comparison, using programs such as BLAST.

HD2 domain in Sp Cas9: CTGAACCCCGAC-AACAGCGACGTGGACAAGCTGTTCATCCAGCTG-GTGCAGACCTA CAACCAGCTGTTCGAGGAAAACC-CCATCAACGCCAGCGGCGTGGACGCCAAGGCCA TCCTGTCTGCCAGACTGAGCAAGAGCAGACGGC-TGGAAAATCTGATCGCCCAGCTGCCCGGCGAGAA-GAAGAATGGCCTGTTCGGAAACCTGATTGCCCTG-AGCCTGGGCCT GACCCCCAACTTCAAGAGCAAC-TTCGACCTGGCCGAGGATGCCAAACTGCAGCTGA GCAAGGACACCTACGACGACGACCTGGACAAC-CTGCTGGCCCAGATCGGCGACCAGTACGCCGAC-CTGTTTCTGGCCGCCAAGAACCTGTCCGACGCCA-TCCTGCTGAGCGAC ATCCTGAGAGTGAACACCG-AG (SEQ ID NO: 60)

In an aspect the invention involves a split CRISPR effector, providing an additional level of control on top of the DD fusion protein of the present invention, as in Zetsche et al (Zetsche et al., "A split-Cas9 architecture for inducible genome editing and transcription modulation," Nature Biotechnology 33:139-142, DOI:10.1038/nbt.3149 (Published online 2 Feb. 2015)). For example, the invention can provide a non-naturally occurring or engineered inducible CRISPR-Cas system, comprising: a first CRISPR enzyme fusion construct attached to a first half of an inducible dimer and a second CRISPR enzyme fusion construct attached to a second half of the inducible dimer, wherein the first CRISPR enzyme fusion construct comprises a first part of a CRISPR enzyme of the present invention and is operably linked to one or more nuclear localization signals, wherein the second CRISPR enzyme fusion construct comprises a second part of a CRISPR enzyme of the present invention is operably linked to one or more nuclear export signals, wherein contact with an inducer energy source brings the first and second halves of the inducible dimer together, wherein bringing the first and second halves of the inducible dimer together brings the first and second parts of the CRISPR enzyme together and thereby allows the first and second CRISPR enzyme fusion constructs to constitute a functional CRISPR-Cas system, wherein the CRISPR-Cas system comprises a guide RNA (gRNA) comprising a guide sequence capable of hybridizing to a target sequence in a genomic locus of interest in a cell, and wherein the functional CRISPR-Cas system binds to the target sequence and, optionally, edits the genomic locus to alter gene expression.

In an aspect of the invention in the inducible CRISPR-Cas system, the CRISPR enzyme comprises two parts of a split CRISPR enzyme. With regard to the inducible system, the terms CRISPR enzyme and split CRISPR enzyme may be used interchangeably. In an aspect of the invention in the inducible CRISPR-Cas system, the inducible dimer is or comprises or consists essentially of or consists of an inducible heterodimer. In an aspect, in inducible CRISPR-Cas system, the first half or a first portion or a first fragment of the inducible heterodimer is or comprises or consists of or consists essentially of an FKBP, optionally FKBP12. In an aspect of the invention, in the inducible CRISPR-Cas system, the second half or a second portion or a second fragment of the inducible heterodimer is or comprises or consists of or consists essentially of FRB. In an aspect of the invention, in the inducible CRISPR-Cas system, the arrangement of the first CRISPR enzyme fusion construct is or comprises or consists of or consists essentially of N-terminal Cas9 part-FRB—NES. In an aspect of the invention, in the inducible CRISPR-Cas system, the arrangement of the first CRISPR enzyme fusion construct is or comprises or consists of or consists essentially of NES-N-terminal Cas part-FRB—NES. In an aspect of the invention, in the inducible CRISPR-Cas system, the arrangement of the second CRISPR enzyme fusion construct is or comprises or consists essentially of or consists of C-terminal Cas part-FKBP-NLS. In an aspect the invention provides in the inducible CRISPR-Cas system, the arrangement of the second CRISPR enzyme fusion construct is or comprises or consists of or consists essentially of NLS-C-terminal Cas part-FKBP-NLS. In an aspect, in inducible CRISPR-Cas system there can be a linker that separates the Cas part from the half or portion or fragment of the inducible dimer. In an aspect, in the inducible CRISPR-Cas system, the inducer energy source is or comprises or consists essentially of or consists of rapamycin. In an aspect, in inducible CRISPR-Cas system, the inducible dimer is an inducible homodimer. In an aspect, in inducible CRISPR-Cas system, the CRISPR enzyme is Cas9, e.g., SpCas9 or SaCas9.

Inducer for Split Cas9: An inducer energy source may be considered to be simply an inducer or a dimerizing agent. The term 'inducer energy source' is used herein throughout for consistency. The inducer energy source (or inducer) acts to reconstitute the effector protein. In some embodiments, the inducer energy source brings the two parts of the effector together through the action of the two halves of the inducible dimer. The two halves of the inducible dimer therefore are brought tougher in the presence of the inducer energy source. The two halves of the dimer will not form into the dimer (dimerize) without the inducer energy source. Thus, the two halves of the inducible dimer cooperate with the inducer energy source to dimerize the dimer. This in turn reconstitutes the effector by bringing the first and second parts of the effector together. Suitable examples include rapamycin.

Split Position: In an aspect in inducible CRISPR-Cas system, the effector protein, such as the CRISPR effector, such as Cas9, Cpf1, C2c1, C2c2, C2c3, Cas13, Cas13, or group 29/30 or argonaute is split into two parts at any one of the following split points, according or with reference to SpCas9: a split position between 202A/2035; a split position between 255F/256D; a split position between 310E/311I; a split position between 534R/535K; a split position between 572E/573C; a split position between 7135/714G; a split position between 1003L/104E; a split position between 1054G/1055E; a split position between 1114N/1115S; a split position between 1152K/11535; a split position between 1245K/1246G; or a split between 1098 and 1099. Cas9 can be split into two distinct fragments, which reconstitute a functional full-length Cas9 nuclease when brought back together using chemical induction. The split Cas9 architecture will be useful for a variety of applications. For example, split Cas may enable genetic strategies for restricting Cas activity to intersectional cell populations by putting each fragment under a different tissue specific promoter. Additionally, different chemically inducible dimerization domains such as APA and gibberellin may also be employed. The split position or location is the point at which the first part of the Cas enzyme is separated from the second part. In some embodiments, the first will comprise or encode amino acids 1 to X, whilst the second part will comprise or encode amino acids X+1 to the end. In this example, the numbering is contiguous, but this may not always be necessary as amino acids (or the nucleotides encoding them) could be trimmed from the end of either of the split ends, provided that sufficient DNA binding activity and, if required, DNA nickase or cleavage activity is retained, for example at least 40%, 50%, 60%, 70%, 80%, 90% or 95% activity compared to wildtype Cas.

The exemplary numbering provided herein may be in reference to the wildtype protein, preferably the wildtype SpCas9 protein. However, it is envisaged that mutants of the wildtype SpCas9 protein can be used. For example, in the crystal data paper itself, a deadCas was used and these are preferred in some embodiments, see the discussion elsewhere herein. The numbering may also not follow exactly the Sp Cas9 numbering as, for instance, some N- or C-terminal truncations or deletions may be used, but this can be addressed suing standard sequence alignment tools. Orthologs are also preferred as a sequence alignment tool. Thus, the split position may be selected using ordinary skill in the art, for instance based on the crystal data provided in the herein cited materials. A number of split positions in SpCas9, which reconstitute Cas9 with inducible dimerization domains, include as tabulated below (showing Amino Acid position of split in Sp

| Fusion Side | Structure | Domain |
|---|---|---|
| 202A/203S | Outside loop | Rec 2 |
| 255F/256D | Outside loop | Rec 2 |
| 310E/311I | Outside loop | Rec 1 |
| 534R/535K | Outside loop | Rec 1 |
| 572E/573C | Unstructured | Rec 1 |
| 713S/714G | Unstructured | Rec 1 |
| 1003L/104E | Unstructured | RuvC3 |
| 1054G/1055E | Unstructured | RuvC3 |
| 1114N/1115S | Unstructured | PI |
| 1152K/1153S | Outside loop | PI |
| 1245K/1246G | Unstructured | PI |

The following split positions may also be advantageously employed (Amino Acid position of split in Sp Cas9 (1368 a.a. in total)):

| Split number | Amino Acid position of Sp Cas9 (1368 a.a. in total) | Domain | Split in Loop (L) or Unstructured Region (UR)? |
|---|---|---|---|
| 1 | 203 | Rec 2 | L |
| 2 | 256 | Rec 2 | L |
| 3 | 311 | Rec 1 | L |
| 4 | 535 | Rec 1 | L |
| 5 | 573 | Rec 1 | UR |
| 6 | 714 | Rec 1 | UR |
| 7 | 1004 | RuvC3 | UR |
| 8 | 1055 | RuvC3 | UR |
| 9 | 1115 | PI | UR |
| 10 | 1153 | PI | L |
| 11 | 1246 | PI | UR |

Identifying potential split sides is most simply done with the help of a crystal structure. For Sp mutants, it should be readily apparent what the corresponding position for, for example, a sequence alignment. For non-Sp enzymes one can use the crystal structure of an ortholog if a relatively high degree of homology exists between the ortholog and the intended Cas9.

The split position may be located within a region or loop. Preferably, the split position occurs where an interruption of the amino acid sequence does not result in the partial or full destruction of a structural feature (e.g. alpha-helixes or beta-sheets). Unstructured regions (regions that did not show up in the crystal structure because these regions are not structured enough to be "frozen" in a crystal) are often preferred options. Splits in all unstructured regions that are exposed on the surface of SpCas9 are envisioned in the practice of the invention. The positions within the unstructured regions or outside loops may not need to be exactly the numbers provided above, but may vary by, for example 1, 2, 3, 4, 5, 6, 7, 8, 9, or even 10 amino acids either side of the position given above, depending on the size of the loop, so long as the split position still falls within an unstructured region of outside loop.

A split in an outside loop of the Rec 2 domain is preferred in some embodiments. In other embodiments, a split in an outside loop of Rec 1 is preferred. In other embodiments, a split in an outside loop of PI is preferred. In other embodiments, a split in an unstructured region of Rec 1 is preferred. In other embodiments, a split in an unstructured region of RuvC3 is preferred. In other embodiments, a split in an unstructured region of PI is preferred.

Splits 4, 5 and 6 in Table 2 above are beneficial in one aspect, in that there is some advantage to keeping the two parts (either side of the split) roughly the same length for packing purposes. For example, it is thought to be easier to maintain stoichiometry between both pieces when the transcripts are about the same size.

The N- and C-term pieces of human codon-optimized *S. pyogenes* Cas9 may be fused to FRB and FKBP dimerization domains, respectively. This arrangement is preferred. They may be switched over (i.e. N-term to FKBP and C-term to FRB), this arrangement worked as well but there is a suggestion that this switched arrangement brings the two parts of the Cas9 further apart.

Linkers such as $(GGGGS)_3$ (SEQ ID NO: 1) are preferably used herein to separate the Cas fragment from the dimerization domain. $(GGGGS)_3$ (SEQ ID NO: 1) is preferable because it is a relatively long linker (15 amino acids). The glycine residues are the most flexible and the serine residues enhance the chance that the linker is on the outside of the protein. $(GGGGS)_6$ (SEQ ID NO: 5) $(GGGGS)_9$ (SEQ ID NO: 51) or $(GGGGS)_{12}$ (SEQ ID NO: 52) may preferably be used as alternatives. Other preferred alternatives are (GGGGS)i (SEQ ID NO: 6), $(GGGGS)_2$ (SEQ ID NO: 53), $(GGGGS)_4$ (SEQ ID NO: 54), $(GGGGS)_5$(SEQ ID NO: 55), $(GGGGS)_7$ (SEQ ID NO: 56), $(GGGGS)_5$(SEQ ID NO: 57), $(GGGGS)_{10}$ (SEQ ID NO: 58), or (GGGGS)ii (SEQ ID NO: 59). For example, $(GGGGS)_3$ (SEQ ID NO: 1) may be used between the N-term Cas fragment and FRB. Such a linker may also be used between FKB and the C-term Cas fragment. Alternative linkers are available, but highly flexible linkers are thought to work best to allow for maximum opportunity for the 2 parts of the Cas to come together and thus reconstitute Cas activity. One alternative is that the NLS of nucleoplasmin can be used as a linker. A linker, such as any of the linkers discussed herein, can also be used between the Cas and any functional domain. Again, a $(GGGGS)_3$ (SEQ ID NO: 1) linker may be used here (or the 6, 9, or 12 repeat versions therefore) or the NLS of nucleoplasmin can be used as a linker between Cas and the functional domain.

In some embodiments, the FRB/FKBP system is preferred. However, alternatives to the FRB/FKBP system are envisaged. For example the ABA and gibberellin system. Accordingly, preferred examples of the FKBP family are any one of the following inducible systems. FKBP which dimerizes with CalcineurinA (CNA), in the presence of FK506; FKBP which dimerizes with CyP-Fas, in the presence of FKCsA; FKBP which dimerizes with FRB, in the presence of Rapamycin; GyrB which dimerizes with GryB, in the presence of Coumermycin; GAI which dimerizes with GID1, in the presence of Gibberellin; or Snap-tag which dimerizes with HaloTag, in the presence of HaXS. Alternatives within the FKBP family itself are also preferred. For example, FKBP, which homo-dimerizes (i.e. one FKBP dimerizes with another FKBP) in the presence of FK1012. Thus, also provided is a non-naturally occurring or engineered inducible CRISPR-Cas system, comprising: a first CRISPR enzyme fusion construct attached to a first half of an inducible homodimer and a second CRISPR enzyme fusion construct attached to a second half of the inducible homodimer, wherein the first CRISPR enzyme fusion construct is operably linked to one or more nuclear localization signals, wherein the second CRISPR enzyme fusion construct is operably linked to a (optionally one or more) nuclear export signal(s), wherein contact with an inducer energy source brings the first and second halves of the inducible homodimer together, wherein bringing the first and second halves of the inducible homodimer together allows the first and second CRISPR enzyme fusion constructs to constitute a functional CRISPR-Cas system, wherein the CRISPR-Cas system comprises a guide RNA (gRNA) comprising a guide sequence capable of hybridizing to a target sequence in a genomic locus of interest in a cell, and wherein the functional CRISPR-Cas system binds to the target sequence and, optionally, edits the genomic locus to alter gene expression.

In one embodiment, the homodimer is preferably FKBP and the inducer energy source is preferably FK1012. In another embodiment, the homodimer is preferably GryB and the inducer energy source is preferably Coumermycin. In another embodiment, the homodimer is preferably ABA and the inducer energy source is preferably Gibberellin. In other embodiments, the dimer is a heterodimer. Preferred examples of heterodimers are any one of the following inducible systems: FKBP which dimerizes with CalcineurinA (CNA), in the presence of FK506; FKBP which dimerizes with CyP-Fas, in the presence of FKCsA; FKBP which dimerizes with FRB, in the presence of Rapamycin, in the presence of Coumermycin; GAI which dimerizes with GID1, in the presence of Gibberellin; or Snap-tag which dimerizes with HaloTag, in the presence of HaXS. FKBP/FRB is advantageous as it is well characterized and both domains are sufficiently small (<100 amino acids) to assist with packaging. Furthermore, rapamycin has been used for a long time and side effects are well understood. Large dimerization domains (>300 aa) should work too but may require longer linkers to make enable Cas reconstitution.

Teachings in Paulmurugan and Gambhir (Cancer Res, Aug. 15, 2005 65; 7413) may be used in combination with herein teachings to exemplify the FRB/FKBP/Rapamycin system in the practice of the invention; see also Crabtree et al. (Chemistry & Biology 13, 99-107, Jan 2006).

An inducer energy source may be considered to be simply an inducer or a dimerizing agent. The term 'inducer energy source' is used herein throughout for consistency. The inducer energy source (or inducer) acts to reconstitute the effector protein. In some embodiments, the inducer energy source brings the two parts of the effector protein together through the action of the two halves of the inducible dimer. The two halves of the inducible dimer therefore are brought tougher in the presence of the inducer energy source. The two halves of the dimer will not form into the dimer (dimerize) without the inducer energy source.

Thus, the two halves of the inducible dimer cooperate with the inducer energy source to dimerize the dimer. This in turn reconstitutes the Cas9 by bringing the first and second parts of the Cas9 together.

A single vector can be used. An expression cassette (plasmid) was constructed as follows. The split Cas construct was based on a first CRISPR enzyme fusion construct, flanked by NLSs, with FKBP fused to C terminal part of the split Cas via a GlySer linker; and a second CRISPR enzyme fusion construct, flanked by NESs, with FRB fused with the N terminal part of the split Cas via a GlySer linker. To separate the first and second CRISPR enzyme fusion constructs, P2A was used splitting on transcription. The Split Cass showed indel formation similar to wildtype in the presence of rapamycin, but markedly lower indel formation than the wildtype in the absence of rapamycin. Accordingly, a single vector is provided. The vector comprises: a first CRISPR enzyme fusion construct attached to a first half of an inducible dimer and a second CRISPR enzyme fusion construct attached to a second half of the inducible dimer, wherein the first CRISPR enzyme fusion construct is operably linked to one or more nuclear localization signals, wherein the second CRISPR enzyme fusion construct is operably linked to one or more nuclear export signals, wherein contact with an inducer energy source brings the first and second halves of the inducible heterodimer together, wherein bringing the first and second halves of the inducible heterodimer together allows the first and second CRISPR enzyme fusion constructs to constitute a functional CRISPR-Cas system, wherein the CRISPR-Cas system comprises a guide RNA (gRNA) comprising a guide sequence capable of hybridizing to a target sequence in a genomic locus of interest in a cell, and wherein the functional CRISPR-Cas system binds to the target sequence and, optionally, edits the genomic locus to alter gene expression. These elements are preferably provided on a single construct, for example an expression cassette.

The first CRISPR enzyme fusion construct is preferably flanked by at least one nuclear localization signal at each end. The second CRISPR enzyme fusion construct is preferably flanked by at least one nuclear export signal at each end.

Applicants have determined new split sites for SaCas9.

Table showing Amino Acid position of split in Sa Cas9 (1053 a.a. in total)

| Fusion Side | Structure | Domain |
|---|---|---|
| 430/431 | Unstructured loop | Between REC and NUC lobes (between 3'/C' terminal end of Rec Domain and 5'/N' terminal end of RuvCII domain). |
| 739/740 | Unstructured region | RuvCIII domain |

Table showing Amino Acid position of split in Sa Cas9 (1053 a.a. in total)

In some embodiments, with any Cas, the split is preferably positioned in an unstructured loop or an unstructured region.

In some embodiments, with split SaCas9, the split is preferably positioned at or around amino acid position 430 or 431, in particular between 430 and 431.

In some embodiments, with split SaCas9, the split is preferably positioned at or around amino acid position 739 or 740, in particular between 739 and 740.

With split SaCas9, a certain amount of variation should be tolerated on each side of each split. For example, for split point 1: −4 to +2 amino acid positions is ideal. In some embodiments, the split is positioned at (ideally C' terminal to) amino acid positions 426, 427, 428, 429 or 430. In some embodiments, the split is positioned at (ideally C' terminal to) amino acid positions 431, 432 or even 433. In some embodiments, the split is positioned at (ideally C' terminal to) amino acid positions 426-433.

Without being bound by theory, it is understood that any further towards the N' terminal than −4 and the split position gets too close to the gRNA. Further towards the C' terminal than +2 and the split position gets too close to an alpha-helix.

For split point 2: the split point at 739-740 may be moved within −7 to +4 amino acid positions. In some embodiments, the split is positioned at (ideally C' terminal to) amino acid positions 732, 733, 734, 735, 736, 737, 738, or 739. In some embodiments, the split is positioned at (ideally C' terminal to) amino acid positions 740, 471, 742, 743, 744 or even 745. In some embodiments, the split is positioned at (ideally C' terminal to) amino acid positions 732-745.

Without being bound by theory, it is understood that split 2 is located in the middle of an unstructured region flanked by alpha-helixes.

Corresponding positions in other orthologues are also envisaged

The promoter used for SaCas9 splits is CBh and bGHpA is the polyA signal in all constructs cloned so far and are planning to clone. However, we know that CMV, EF1alpha and EFS (minimal EF1α promoter) work well for SpCas9 and will also work for SaCas9.

In an aspect, the promoter used for SaCas9 splits is CBh. In other aspects, CMV, EF1alpha and EFS (minimal EF1α promoter) may be used as promoters. In an aspect, a polyA tail such as bGHpA may be used.

Also provided is a split SaCas9 with specific split points. In an aspect the invention provides a non-naturally occurring or engineered inducible CRISPR-Cas system, comprising: a first CRISPR enzyme fusion construct attached to a first half of an inducible dimer and a second CRISPR enzyme fusion construct attached to a second half of the inducible dimer,

- wherein the first CRISPR enzyme fusion construct comprises a first part of a CRISPR enzyme,
- wherein the second CRISPR enzyme fusion construct comprises a second part of a CRISPR enzyme,
- wherein contact with an inducer energy source brings the first and second halves of the inducible dimer together,
- wherein bringing the first and second halves of the inducible dimer together brings the first and second parts of the CRISPR enzyme together and thereby allows the first and second CRISPR enzyme fusion constructs to constitute a functional CRISPR-Cas system,
- wherein the CRISPR-Cas system comprises a guide RNA (gRNA) comprising a guide sequence capable of hybridizing to a target sequence in a genomic locus of interest in a cell, and
- wherein the functional CRISPR-Cas system binds to the target sequence and, optionally, edits the genomic locus to alter gene expression, and
- wherein the two parts of the Cas are split between amino acid positions amino acid positions 426-433 or amino acid positions 732-745, or positions corresponding thereto. In an aspect, the Cas9 is SaCas9. In an aspect, the Cas9 is an ortholog of SaCas9. In an aspect, the first CRISPR enzyme fusion construct comprises a first part of a CRISPR enzyme and is operably linked to one or more, preferably two or more nuclear localization signals (NLS). In an aspect, the first CRISPR enzyme fusion construct comprises a first part of a CRISPR enzyme and is operably linked to one or more, preferably two or more nuclear export signals (NES). In an aspect, the second CRISPR enzyme fusion construct comprises a second part of a CRISPR enzyme and is operably linked to one or more, preferably two or more nuclear localization signals. In an aspect, the second CRISPR enzyme fusion construct comprises a second part of a CRISPR enzyme and is operably linked to one or more, preferably two or more nuclear export signals. In an aspect, the first CRISPR enzyme fusion construct comprises a first part of a CRISPR enzyme and is operably linked to one or more, preferably two or more nuclear localization signals and the second CRISPR enzyme fusion construct comprises a second part of a CRISPR enzyme and is operably linked to one or more, preferably two or more nuclear export signals. In an aspect, the first CRISPR enzyme fusion construct comprises a first part of a CRISPR enzyme and is operably linked to one or more, preferably two or more nuclear export signals and the second CRISPR enzyme fusion construct comprises a second part of a CRISPR enzyme and is operably linked to one or more, preferably two or more nuclear localization signals.

In an aspect, two NLS are operably linked to one part, and one NES operably is operably linked to the other part. In a further aspect, one or two NLS are operably linked to one part, and one or two NES operably are also operably linked to the other part.

In addition as to Split Cas9, in an aspect, in the inducible CRISPR-Cas system, one or more functional domains, as discussed herein are associated, with one or both parts of the Cas enzyme. For example, the functional domains may optionally include a transcriptional activator, a transcriptional or a nuclease such as a Fok1 nuclease. Further examples are provided herein. In an aspect, in the inducible CRISPR-Cas system, the functional CRISPR-Cas system binds to the target sequence and the enzyme is a deadCas, optionally having a diminished nuclease activity of at least 97%, or 100% (or no more than 3% and advantageously 0% nuclease activity) as compared with the CRISPR enzyme not having the at least one mutation. In an aspect, in the inducible CRISPR-Cas system, the deadCas9 (CRISPR enzyme) comprises two or more mutations wherein two or more of D10, E762, H840, N854, N863, or D986 according to SpCas9 protein or any corresponding ortholog or N580 according to SaCas9 protein are mutated, or the CRISPR enzyme comprises at least one mutation, e.g., wherein at least H840 is mutated.

In some embodiments, the one or more DDs may be used. The or each DD may be associated with one of the two parts of the split CRISPR enzyme.

Where one DD is used, it is preferred in some embodiments, that the NES is associated with the same part of the split CRISPR enzyme as the DD. This may help to ensure cytoplasmic location of the DD.

Where more than one DD is used, it is preferred in some embodiments, that the NES is associated with the same part of the split CRISPR enzyme as at least one of the DDs. Again, this may help to ensure cytoplasmic location of the DD.

In some embodiments, where one part of the split CRISPR enzyme comprises two or more DDs, there may be one DD associated with the N-terminal of the split CRISPR enzyme and one DD associated with the C-terminal of the CRISPR enzyme.

In some embodiments, two DDs may be used. Both may be associated with the same part of the split CRISPR enzyme, or one DD may be associated with one part of the split CRISPR enzyme (N- or C-terminal) and the other DD may be associated with the other part of the split CRISPR enzyme (N- or C-terminal).

In some embodiments, three DDs may be used. All three may be associated with the same part of the split CRISPR enzyme (N- or C-terminal or a mixture), or one DD may be associated with one part of the split CRISPR enzyme (N- or C-terminal) and the other two DDs may be associated with the other part of the split CRISPR enzyme (N- or C-terminal or a mixture).

In some embodiments, four DDs may be used. All four may be associated with the same part of the split CRISPR enzyme (N- or C-terminal or a mixture), or one DD may be associated with one part of the split CRISPR enzyme (N- or C-terminal) and the other three DDs may be associated with the other part of the split CRISPR enzyme (N- or C-terminal or a mixture).

In some embodiments, four DDs may be used and two DDs may be associated with one part of the split CRISPR enzyme (N- or C-terminal or a mixture) and the other two DDs may be associated with the other part of the split CRISPR enzyme (N- or C-terminal or a mixture). In some embodiments using four DDs, one DD may be associated with each end of the two split CRISPR enzyme parts. This paired approach is preferred as it allows one DD at each end of both parts of the split CRISPR enzyme.

As such, in some embodiments, one DD is associated with the N-terminal of the first part of the split CRISPR enzyme and one DD is associated with the C-terminal of the first part of the CRISPR enzyme; and one DD is associated with the N-terminal of the second part of the split CRISPR enzyme and one DD is associated with the C-terminal of the second part of the CRISPR enzyme. The invention further comprehends and an aspect of the invention provides, a polynucleotide encoding the inducible CRISPR-Cas system as herein discussed.

One guide with a first aptamer/RNA-binding protein pair can be linked or fused to an activator, while a second guide with a second aptamer/RNA-binding protein pair can be linked or fused to a repressor. The guides are for different targets (loci), so this allows one gene to be activated and one repressed. For example, the following schematic shows such an approach: Guide 1-MS2 aptamer-------MS2 RNA-binding protein fused to DD-------VP64 activator; and Guide 2-PP7 aptamer-------PP7 RNA-binding protein fused to DD-------SID4X repressor.

The present invention also relates to orthogonal PP7/MS2 gene targeting. In this example, gRNA targeting different loci are modified with distinct RNA loops in order to recruit MS2-VP64 or PP7-SID4X, which activate and repress their target loci, respectively. PP7 is the RNA-binding coat protein of the bacteriophage *Pseudomonas*. Like MS2, it binds a specific RNA sequence and secondary structure. The PP7 RNA-recognition motif is distinct from that of MS2. Consequently, PP7 and MS2 can be multiplexed to mediate distinct effects at different genomic loci simultaneously. For example, an gRNA targeting locus A can be modified with MS2 loops, recruiting MS2-VP64 activators, while another gRNA targeting locus B can be modified with PP7 loops, recruiting PP7-SID4X repressor domains. In the same cell, dead effector proteins can thus mediate orthogonal, locus-specific modifications. This principle can be extended to incorporate other orthogonal RNA-binding proteins such as Q-beta.

A PP7 variant may be used in some embodiments. For example, Applicants found that the PP7 *Pseudomonas* bacteriophage coat protein (with amino acids 68-69 mutated to SG and amino acids 70-75 deleted from the wild type protein as described in Wu, Bin, Jeffrey A. Chao, and Robert H. Singer. "Fluorescence fluctuation spectroscopy enables quantitative imaging of single mRNAs in living cells. "Biophysical journal 102.12 (2012): 2936-2944. and Chao, Jeffrey A., et al. "Structural basis for the coevolution of a viral RNA-protein complex." Nature structural & molecular biology 15.1 (2007): 103-105.), worked well. As such, in some embodiments, where the adaptor protein is an RNA-binding protein and that RNA-binding protein is PP7, the PP7 may be the variant described above, i.e. with amino acids 68-69 mutated to SG and/or amino acids 70-75 deleted from the wild type protein.

Similarly, an MS2 variant may also be used, such as the N55 mutant, especially the N55K mutant. This is the N55K mutant of the MS2 bacteriophage coat protein (shown to have higher binding affinity than wild type MS2 in Lim, F., M. Spingola, and D. S. Peabody. "Altering the RNA binding specificity of a translational repressor." Journal of Biological Chemistry 269.12 (1994): 9006-9010.)

An alternative option for orthogonal repression includes incorporating non-coding RNA loops with transactive repressive function into the guide (either at similar positions to the MS2/PP7 loops integrated into the guide or at the 3' terminus of the guide). For instance, guides were designed with non-coding (but known to be repressive) RNA loops (e.g., using the Alu repressor (in RNA) that interferes with RNA polymerase II in mammalian cells). The Alu RNA sequence was located: in place of the MS2 RNA sequences as used herein (e.g., at tetraloop and/or stem loop 2); and/or at 3' terminus of the guide. This gives possible combinations of MS2, PP7 or Alu at the tetraloop and/or stemloop 2 positions, as well as, optionally, addition of Alu at the 3' end of the guide (with or without a linker).

The use of two different aptamers (each associated with a distinct RNA) allows an activator-adaptor protein fusion and a repressor-adaptor protein fusion to be used, with different guides, to activate expression of one gene, while repressing another. They, along with their different guides can be administered together, or substantially together, in a multiplexed approach. A large number of such modified guides can be used all at the same time, for example 10 or 20 or 30 and so forth, while only one (or at least a minimal number) of CRISPR effectors to be delivered, as a comparatively small number of effectors can be used with a large number modified guides. The adaptor protein may be associated (preferably linked or fused to) one or more activators or one or more repressors. For example, the adaptor protein may be associated with a first activator and a second activator. The first and second activators may be the same, but they are preferably different activators. For example, one might be VP64, while the other might be p65, although these are just examples and other transcriptional activators are envisaged. Three or more or even four or more activators (or repressors) may be used, but package size may limit the number being higher than 5 different functional domains. Linkers are preferably used, over a direct fusion to the adaptor protein, where two or more functional domains are associated with the adaptor protein. Suitable linkers might include the Gly-Ser linker.

It is also envisaged that the enzyme-guide complex as a whole may be associated with two or more functional domains. For example, there may be two or more functional domains associated with the fusion protein or enzyme, or preferably there may be two or more functional domains associated with the guide (via one or more adaptor proteins), or there may be one or more functional domains associated with the enzyme and one or more functional domains associated with the guide (via one or more adaptor proteins).

The fusion between the adaptor protein and the activator or repressor may include a linker. For example, GlySer linkers GGGS (SEQ ID NO: 3) can be used. They can be used in repeats of 3 ($(GGGGS)_3$ (SEQ ID NO: 1)) or 6, 9 or even 12 or more, to provide suitable lengths, as required. Linkers can be used between the RNA-binding protein and the functional domain (activator or repressor), or between the CRISPR Enzyme (Cas9) and the functional domain (activator or repressor). The linkers the user to engineer appropriate amounts of "mechanical flexibility".

The invention comprehends a DD-CRISPR Cas complex comprising a DD-fusion protein (optionally comprising one or more further functional domains), a CRISPR enzyme or argonaute (optionally also comprising a DD and/or functional domain) and a guide RNA (gRNA) or guide DNA (gDNA), wherein the CRISPR enzyme/argonaute comprises at least one mutation, such that the CRISPR enzyme has no more than 5% of the nuclease activity of the CRISPR enzyme not having the at least one mutation and, optional, at least one or more nuclear localization sequences; the guide RNA/DNA comprises a guide sequence capable of hybridizing to a target sequence in a genomic locus of interest in a cell; and wherein: the CRISPR enzyme is optionally associated with one or more functional domains; and at least one loop of the gRNA/gDNA is modified by the insertion of distinct RNA/DNA sequence(s) that bind to one or more adaptor proteins, and wherein the adaptor protein is associated with at least one DD, and optionally with one or more additional functional domain; or the CRISPR enzyme is associated with one or more functional domains and at least one loop of the gRNA is modified by the insertion of distinct RNA sequence(s) that bind to one or more adaptor proteins, and wherein the adaptor protein is associated with one or more DD and optionally one or more functional domains. The invention comprehends the use of modified guides such as in Konermann et al., "Genome-scale transcription activation by an engineered CRISPR-Cas9 complex," doi:10.1038/nature14136, incorporated herein by reference, or PCT/US14/70175, filed Dec. 12, 2014.

In some embodiments, one or more functional domains are associated with an adaptor protein, for example as used with the modified guides of Konermann et al. (Nature 517, 583-588, 29 Jan. 2015).

For the purposes of the following discussion, reference to a functional domain could be a functional domain associated with the CRISPR enzyme/argonaute or a functional domain associated with the adaptor protein.

In some embodiments, the one or more functional domains is an NLS (Nuclear Localization Sequence) or an NES (Nuclear Export Signal). In some embodiments, the one or more functional domains is a transcriptional activation domain comprises VP64, p65, MyoD1, HSF1, RTA, SET7/9 and a histone acetyltransferase. Other references herein to activation (or activator) domains in respect of those associated with the CRISPR enzyme include any known transcriptional activation domain and specifically VP64, p65, MyoD1, HSF1, RTA, SET7/9 or a histone acetyltransferase.

In some embodiments, the one or more functional domains is a transcriptional repressor domain. In some embodiments, the transcriptional repressor domain is a KRAB domain. In some embodiments, the transcriptional repressor domain is a NuE domain, NcoR domain, SID domain or a SID4X domain.

In some embodiments, the one or more functional domains have one or more activities comprising methylase activity, demethylase activity, transcription activation activity, transcription repression activity, transcription release factor activity, histone modification activity, RNA cleavage activity, DNA cleavage activity, DNA integration activity or nucleic acid binding activity.

In some embodiments, the one or more functional domains are selected from transcription or translation activator, transcription or translation repressor, (DNA or RNA), argonaute, methyltransferase, methylase, demethylase, DNA hydroxylmethylase, histone acetylase, histone deacetylases, transcription or translation release factor domain, histone modification domain, nuclease, single-strand RNA cleavage domain, double-strand RNA cleavage domain, single-strand DNA cleavage domain, double-strand DNA cleavage domain, nucleic acid binding domain, a protein acetyltransferase, a protein deacetylase, a protein methyltransferase, a protein deaminase, a protein kinase, a protein phosphatase, transposase, integrase, recombinase, resolvase, invertase, protease, repressor, activator, nuclear-localization signal, nuclear export signal, transcription-regulatory protein (or transcription complex recruiting) domain, cellular uptake activity associated domain, nucleic acid binding domain, antibody presentation domain, histone modifying enzymes, recruiter of histone modifying enzymes; inhibitor of histone modifying enzymes, histone methyltransferase, histone demethylase, histone kinase, histone phosphatase, histone ribosylase, histone deribosylase, histone ubiquitinase, histone deubiquitinase, histone biotinase, histone tail protease, HDACs, histone methyltransferases (HMTs), histone acetyltransferase (HAT) inhibitors, HDAC and HMT recruiting proteins, HDAC effector Domains, HDAC recruiter effector domains, histone methyltransferase (HMT) effector domains, histone methyltransferase (HMT) recruiter effector domains, histone acetyltransferase inhibitor effector domains, or domains having molecular switch activity or chemical inducibility or light inducibility.

Histone modifying domains are also preferred in some embodiments. Exemplary histone modifying domains are discussed below. Transposase domains, HR (Homologous Recombination) machinery domains, recombinase domains, and/or integrase domains are also preferred as the present functional domains. In some embodiments, DNA integration activity includes HR machinery domains, integrase domains, recombinase domains and/or transposase domains. Histone acetyltransferases are preferred in some embodiments.

In some embodiments, the DNA cleavage activity is due to a nuclease. In some embodiments, the nuclease comprises a Fok1 nuclease.

In some embodiments, the one or more functional domains is attached to the CRISPR enzyme/argonaute so that upon binding to the gRNA and target the functional domain is in a spatial orientation allowing for the functional domain to function in its attributed function.

In some embodiments, the one or more functional domains is attached to the adaptor protein so that upon binding of the CRISPR enzyme to the gRNA and target, the functional domain is in a spatial orientation allowing for the functional domain to function in its attributed function.

In an aspect the invention provides a composition as herein discussed wherein the one or more functional domains is attached to the CRISPR enzyme or adaptor protein via a linker, optionally a GlySer linker, as discussed herein.

Endogenous transcriptional repression is often mediated by chromatin modifying enzymes such as histone methyltransferases (TINMTs) and deacetylases (TIDACs). Repressive histone effector domains are known and an exemplary list is provided below. In the exemplary table, preferencewas givento proteins and functional truncations ofsmall sizeto facilitate efficient viral packaging (for instance via AAV). In general, however, the domains may include TDACs, histone methyltransferases (TIN/Ts), and histone acetyltransferase (HAT) inhibitors, as well as TIDAC and HMN/T recruiting proteins. The functional domain may be or include, in some embodiments, HDAC Effector Domains, XDAC Recruiter Effector Domains, Histone Methyltransferase (TINMT) Effector Domains, Hi stone Methyltransferase (THM/T) Recruiter Effector Domains, or Histone Acetyltransferase Inhibitor Effector Domains.

| Subtype/ Complex | Name | Substrate (if known) | Modification (if known) | Organism | Full size (aa) | Selected truncation (aa) | Final size (aa) | Catalytic domain |
|---|---|---|---|---|---|---|---|---|
| HDAC I | HDAC8 | — | — | *X. laevis* | 325 | 1-325 | 325 | 1-272: HDAC |
| HDAC I | RPD3 | — | — | *S. cerevisiae* | 433 | 19-340 | 322 (Vannier) | 19-331: HDAC |
| HDAC IV | MesoLo4 | — | — | *M. loti* | 300 | 1-300 (Gregoretti) | 300 | — |
| HDAC IV | HDAC11 | — | — | *H. sapiens* | 347 | 1-347 (Gao) | 347 | 14-326: HDAC |
| HD2 | HDT1 | — | — | *A. thaliana* | 245 | 1-211 (Wu) | 211 | — |
| SIRT I | SIRT3 | H3K9Ac H4K16Ac H3K56Ac | — | *H. sapiens* | 399 | 143-399 (Scher) | 257 | 126-382: SIRT |
| SIRT I | HST2 | — | — | *C. albicans* | 331 | 1-331 (Hnisz) | 331 | — |
| SIRT I | CobB | — | — | *E. coli* (K12) | 242 | 1-242 (Landry) | 242 | — |
| SIRT I | HST2 | — | — | *S. cerevisiae* | 357 | 8-298 (Wilson) | 291 | — |
| SIRT III | SIRT5 | H4K8Ac H4K16Ac | — | *H. sapiens* | 310 | 37-310 (Gertz) | 274 | 41-309: SIRT |
| SIRT III | Sir2A | — | — | *P. falciparum* | 273 | 1-273 (Zhu) | 273 | 19-273: SIRT |
| SIRT IV | SIRT6 | H3K9Ac H3K56Ac | — | *H. sapiens* | 355 | 1-289 (Tennen) | 289 | 35-274: SIRT |

Accordingly, the repressor domains of the present invention may be selected from histone methyltransferases (HMNTs), histone deacetylases (HIDACs), histone acetyltransferase (HAT) inhibitors, as well as HIDAC and HMNT recruiting proteins.

The HIDAC domain may be any of those in the table above, namely: HIDAC8, RPD3, MesoLo4, HIDAC1 1, HIDT1, SIRT3, HST2, CobB, HST2, SIRT5, Sir2A, or SIRT6.

In some embodiment, the functional domain may be a tDAC Recruiter Effector Domain. Preferred examples include those in the Table below, namely MeCP2, MBD2b, Sin3a, NcoR, SALL1, RCOR1. NcoR is exemplified in the present Examples and, although preferred, it is envisaged that others in the class will also be useful.

Table of HDAC Recruiter Effector Domains

| Subtype/ Complex | Name | Substrate (if known) | Modification (if known) | Organism | Full size (aa) | Selected truncation (aa) | Final size (aa) | Catalytic domain |
|---|---|---|---|---|---|---|---|---|
| Sin3a | MeCP2 | — | — | *R. norvegicus* | 492 | 207-492 (Nan) | 286 | — |
| Sin3a | MBD2b | — | — | *H. sapiens* | 262 | 45-262 (Boeke) | 218 | — |

-continued

Table of HDAC Recruiter Effector Domains

| Subtype/ Complex | Name | Substrate (if known) | Modification (if known) | Organism | Full size (aa) | Selected truncation (aa) | Final size (aa) | Catalytic domain |
|---|---|---|---|---|---|---|---|---|
| Sin3a | Sin3a | — | — | *H. sapiens* | 1273 | 524-851 (Laherty) | 328 | 627-829: HDAC1 interaction |
| NcoR | NcoR | — | — | *H. sapiens* | 2440 | 420-488 (Zhang) | 69 | — |
| NuRD | SALL1 | — | — | *M. musculus* | 1322 | 1-93 (Lauberth) | 93 | — |
| CoREST | RCOR1 | — | — | *H. sapiens* | 482 | 81-300 (Gu, Ouyang) | 220 | — |

In some embodiment, the functional domain may be a Methyltransferase (TNT) Effector Domain. Preferred examples include those in the Table below, namely NUE, vSET, ETIMT2/G9A, SUV39H1, dim-5, KYP, SUVR4, SET4, SET1, SETD8, and TgSET8. NUE is exemplified in the present Examples and, although preferred, it is envisaged that others in the class will also be useful.

Table of Histone Methyltransferase (HMT) Effector Domains

| Subtype/ Complex | Name | Substrate (if known) | Modification (if known) | Organism | Full size (aa) | Selected truncation (aa) | Final size (aa) | Catalytic domain |
|---|---|---|---|---|---|---|---|---|
| SET | NUE | H2B, H3, H4 | — | *C. trachomatis* | 219 | 1-219 (Pennini) | 219 | — |
| SET | vSET | — | H3K27me3 | *P. bursaria* chlorella virus | 119 | 1-119 (Mujtaba) | 119 | 4-112: SET2 |
| SUV39 family | EHMT2/ G9A | H1.4K2, H3K9, H3K27 | H3K9me1/2, H1K25me1 | *M. musculus* | 1263 | 969-1263 (Tachibana | 295 | 1025-1233: preSET, SET, postSET |
| SUV39 | SUV39H1 | — | H3K9me2/3 | *H. sapiens* | 412 | 79-412 (Snowden) | 334 | 172-412: preSET, SET, postSET |
| Suvar3-9 | dim-5 | — | H3K9me3 | *N. crassa* | 331 | 1-331 (Rathert) | 331 | 77-331: preSET, SET, postSET |
| Suvar3-9 (SUVH subfamily) | KYP | — | H3K9me1/2 | *A. thaliana* | 624 | 335-601 | 267 (Jackson) | |
| Suvar3-9 (SUVR subfamily | SUVR4 | H3K9me1 | H3K9me2/3 | *A. thaliana* | 492 | 180-492 | 313 (Thorstensen) | 192-462: preSET, SET, postSET |
| Suvar4-20 | SET4 | — | H4K20me3 | *C. elegans* | 288 | 1-288 (Vielle) | 288 | — |
| SET8 | SET1 | — | H4K20me1 | *C. elegans* | 242 | 1-242 (Vielle) | 242 | — |
| SET8 | SETD8 | — | H4K20me1 | *H. sapiens* | 393 | 185-393 | 209 (Couture) | 256-382: SET |
| SET8 | TgSET8 | — | H4K20me1/2/ 3 | *T. gondii* | 1893 | 1590-1893 (Sautel) | 304 | 1749-1884: SET |

In some embodiment, the functional domain may be a Histone Methyltransferase (TINMT) Recruiter Effector Domain. Preferred examples include those in the Table below, namely Hp11a, PIIF 19, and NIPP 1.

Table of Histone Methyltransferase (HMT) Recruiter Effector Domains

| Subtype/ Complex | Name | Substrate (if known) | Modification (if known) | Organism | Full size (aa) | Selected truncation (aa) | Final size (aa) | Catalytic domain |
|---|---|---|---|---|---|---|---|---|
| — | Hp1a | — | H3K9me3 | *M. musculus* | 191 | 73-191 | 119 (Hathaway | 121-179: chromoshadow |
| — | PHF19 | — | H3K27me3 | *H. sapiens* | 580 | (1-250) + GGSG linker + (500-580) (SEQ ID NO: 61) | 335 (Ballaré) | 163-250: PHD2 |
| — | NIPP1 | — | H3K27me3 | *H. sapiens* | 351 | 1-329 (Jin) | 329 | 310-329: EED |

In some embodiment, the functional domain may be Histone Acetyltransferase Inhibitor Effector Domain. Preferred examples include SET/TAF-103 listed in the Table below.

Table of Histone Acetyltransferase Inhibitor Effector Domains

| Subtype/ Complex | Name | Substrate (if known) | Modification (if known) | Organism | Full size (aa) | Selected truncation (aa) | Final size (aa) | Catalytic domain |
|---|---|---|---|---|---|---|---|---|
| — | SET/TAF-1β | — | — | *M. musculus* | 289 | 1-289 (Cervoni) | 289 | — |

It is also preferred to target endogenous (regulatory) control elements (such as enhancers and silencers) in addition to a promoter or promoter-proximal elements. Thus, the invention can also be used to target endogenous control elements (including enhancers and silencers) in addition to targeting of the promoter. These control elements can be located upstream and downstream of the transcriptional start site (TSS), starting from 200 bp from the TSS to 100kb away. Targeting of known control elements can be used to activate or repress the gene of interest. In some cases, a single control element can influence the transcription of multiple target genes. Targeting of a single control element could therefore be used to control the transcription of multiple genes simultaneously.

Targeting of putative control elements on the other hand (e.g. by tiling the region of the putative control element as well as 200 bp up to 100 kB around the element) can be used as a means to verify such elements (by measuring the transcription of the gene of interest) or to detect novel control elements (e.g. by tiling 100kb upstream and downstream of the TSS of the gene of interest). In addition, targeting of putative control elements can be useful in the context of understanding genetic causes of disease. Many mutations and common SNP variants associated with disease phenotypes are located outside coding regions. Targeting of such regions with either the activation or repression systems described herein can be followed by readout of transcription of either a) a set of putative targets (e.g. a set of genes located in closest proximity to the control element) or b) whole-transcriptome readout by e.g. RNAseq or microarray. This would allow for the identification of likely candidate genes involved in the disease phenotype. Such candidate genes could be useful as novel drug targets.

Histone acetyltransferase (HAT) inhibitors are mentioned herein. However, an alternative in some embodiments is for the one or more functional domains to comprise an acetyltransferase, preferably a histone acetyltransferase. These are useful in the field of epigenomics, for example in methods of interrogating the epigenome. Methods of interrogating the epigenome may include, for example, targeting epigenomic sequences. Targeting epigenomic sequences may include the guide being directed to an epigenomic target sequence. Epigenomic target sequence may include, in some embodiments, include a promoter, silencer or an enhancer sequence.

Use of a functional domain linked to a fusion protein according to the invention as described herein, and/or a CRISPR-Cas enzyme/argonaute as described herein, preferably a dead-Cas/argonaute, to target epigenomic sequences can be used to activate or repress promoters, silencer or enhancers.

Examples of acetyltransferases are known but may include, in some embodiments, histone acetyltransferases. In some embodiments, the histone acetyltransferase may comprise the catalytic core of the human acetyltransferase p300 (Gerbasch & Reddy, Nature Biotech 6th April 2015).

In some preferred embodiments, the functional domain is linked to a fusion protein according to the invention and/or dead-Cas9 enzyme to target and activate epigenomic sequences such as promoters or enhancers. One or more guides directed to such promoters or enhancers may also be provided to direct the binding of the CRISPR enzyme to such promoters or enhancers.

The term "associated with" is used here in relation to the association of the functional domain to the CRISPR enzyme or the adaptor protein. It is used in respect of how one molecule 'associates' with respect to another, for example between an adaptor protein and a functional domain, or between the CRISPR enzyme and a functional domain. In the case of such protein-protein interactions, this association may be viewed in terms of recognition in the way an antibody recognizes an epitope. Alternatively, one protein may be associated with another protein via a fusion of the two, for instance one subunit being fused to another subunit. Fusion typically occurs by addition of the amino acid sequence of one to that of the other, for instance via splicing together of the nucleotide sequences that encode each protein or subunit. Alternatively, this may essentially be viewed as binding between two molecules or direct linkage, such as a fusion protein. In any event, the fusion protein may include a linker between the two subunits of interest (i.e. between the enzyme and the functional domain or between the adaptor protein and the functional domain). Thus, in some embodiments, the CRISPR enzyme or adaptor protein is associated with a functional domain by binding thereto. In other embodiments, the CRISPR enzyme or adaptor protein is associated with a functional domain because the two are fused together, optionally via an intermediate linker.

Attachment of a functional domain or fusion protein can be via a linker, e.g., a flexible glycine-serine (GlyGlyGlySer) (SEQ ID NO: 6) or (GGGS)3 (SEQ ID NO: 4) or a rigid alpha-helical linker such as (Ala(GluAlaAlaAlaLys)Ala) (SEQ ID NO: 50). Linkers such as (GGGGS)3 (SEQ ID NO: 1) are preferably used herein to separate protein or peptide domains. (GGGGS)3 (SEQ ID NO: 1) is preferable because it is a relatively long linker (15 amino acids). The glycine residues are the most flexible and the serine residues enhance the chance that the linker is on the outside of the protein. (GGGGS)6 (SEQ ID NO: 5), (GGGGS)9 (SEQ ID NO: 51), or (GGGGS)12 (SEQ ID NO: 52) may preferably be used as alternatives. Other preferred alternatives are (GGGGS)1 (SEQ ID NO: 6), (GGGGS)2 (SEQ ID NO: 53), (GGGGS)4 (SEQ ID NO: 54), (GGGGS)5 (SEQ ID NO: 55), (GGGGS)7 (SEQ ID NO: 56), (GGGGS)8 (SEQ ID NO: 57), (GGGGS)10 (SEQ ID NO: 58), or (GGGGS)11 (SEQ ID NO: 59). Alternative linkers are available, but highly flexible linkers are thought to work best to allow for maximum opportunity for the 2 parts of the Cas9 to come together and thus reconstitute Cas9 activity. One alternative is that the NLS of nucleoplasmin can be used as a linker. For example, a linker can also be used between the Cas9 and any functional domain. Again, a (GGGGS)3 (SEQ ID NO: 1) linker may be used here (or the 6, 9, or 12 repeat versions therefore) or the NLS of nucleoplasmin can be used as a linker between Cas9 and the functional domain.

It is also preferred to target endogenous (regulatory) control elements (such as enhancers and silencers) in addition to a promoter or promoter-proximal elements. Thus, the invention can also be used to target endogenous control elements (including enhancers and silencers) in addition to targeting of the promoter. These control elements can be located upstream and downstream of the transcriptional start site (TSS), starting from 200 bp from the TSS to 100kb away. Targeting of known control elements can be used to activate or repress the gene of interest. In some cases, a single control element can influence the transcription of multiple target genes. Targeting of a single control element could therefore be used to control the transcription of multiple genes simultaneously.

Targeting of putative control elements on the other hand (e.g. by tiling the region of the putative control element as well as 200 bp up to 100 kB around the element) can be used as a means to verify such elements (by measuring the transcription of the gene of interest) or to detect novel control elements (e.g. by tiling 100kb upstream and downstream of the TSS of the gene of interest). In addition, targeting of putative control elements can be useful in the context of understanding genetic causes of disease. Many mutations and common SNP variants associated with disease phenotypes are located outside coding regions. Targeting of such regions with either the activation or repression systems described herein can be followed by readout of transcription of either a) a set of putative targets (e.g. a set of genes located in closest proximity to the control element) or b) whole-transcriptome readout by e.g. RNAseq or microarray. This would allow for the identification of likely candidate genes involved in the disease phenotype. Such candidate genes could be useful as novel drug targets.

The term "associated with" is used here in relation to the association of the functional domain to the CRISPR enzyme or the adaptor protein. It is used in respect of how one molecule 'associates' with respect to another, for example between an adaptor protein and a functional domain, or between the CRISPR enzyme and a functional domain. In the case of such protein-protein interactions, this association may be viewed in terms of recognition in the way an antibody recognizes an epitope. Alternatively, one protein may be associated with another protein via a fusion of the two, for instance one subunit being fused to another subunit. Fusion typically occurs by addition of the amino acid sequence of one to that of the other, for instance via splicing together of the nucleotide sequences that encode each protein or subunit. Alternatively, this may essentially be viewed as binding between two molecules or direct linkage, such as a fusion protein. In any event, the fusion protein may include a linker between the two subunits of interest (i.e. between the enzyme and the functional domain or between the adaptor protein and the functional domain). Thus, in some embodiments, the CRISPR enzyme or adaptor protein is associated with a functional domain by binding thereto. In other embodiments, the CRISPR enzyme or adaptor protein is associated with a functional domain because the two are fused together, optionally via an intermediate linker.

In an embodiment, nucleic acid molecule(s) encoding the DNA-targeting effector protein, in particular Cas9 or an ortholog or homolog thereof, may be codon-optimized for expression in a eukaryotic cell. A eukaryote can be as herein discussed. Nucleic acid molecule(s) can be engineered or non-naturally occurring.

In an embodiment, the DNA-targeting effector protein, in particular Cas9, may comprise one or more mutations (and hence nucleic acid molecule(s) coding for same may have mutation(s). The mutations may be artificially introduced mutations and may include but are not limited to one or more mutations in a catalytic domain. Examples of catalytic domains with reference to a Cas9 enzyme may include but are not limited to RuvC I, RuvC II, RuvC III and HNH domains.

In an embodiment, the Type II protein such as Cas9 may comprise one or more mutations. The mutations may be artificially introduced mutations and may include but are not limited to one or more mutations in a catalytic domain, to provide a nickase, for example. Examples of catalytic domains with reference to a Cas enzyme may include but are not limited to RuvC I, RuvC II, RuvC III, and HNH domains.

In an embodiment, the effector protein such as Cas9 may be used as a generic nucleic acid binding protein with fusion to or being operably linked to a functional domain. Exemplary functional domains may include but are not limited to translational initiator, translational activator, translational repressor, nucleases, in particular ribonucleases, a spliceosome, beads, a light inducible/controllable domain or a chemically inducible/controllable domain.

In some embodiments, the unmodified nucleic acid-targeting effector protein may have cleavage activity. In some embodiments, the DNA- or RNA-targeting effector protein may direct cleavage of one or both nucleic acid strands at the location of or near a target sequence, such as within the target sequence and/or within the complement of the target sequence or at sequences associated with the target sequence. In some embodiments, the nucleic acid-targeting effector protein may direct cleavage of one or both DNA or RNA strands within about 1, 2, 3, 4, 5, 6, 7, 8, 9, 10, 15, 20, 25, 50, 100, 200, 500, or more base pairs from the first or last nucleotide of a target sequence. In some embodiments, the cleavage may be blunt, i.e., generating blunt ends. In some embodiments, the cleavage may be staggered, i.e., generating sticky ends. In some embodiments, the cleavage may be a staggered cut with a 5' overhang, e.g., a 5' overhang of 1 to 5 nucleotides. In some embodiments, the cleavage may be a staggered cut with a 3' overhang, e.g., a 3' overhang of 1 to 5 nucleotides. In some embodiments, a vector encodes a nucleic acid-targeting effector protein that may be mutated with respect to a corresponding wild-type enzyme such that the mutated nucleic acid-targeting effector protein lacks the ability to cleave one or both DNA or RNA strands of a target polynucleotide containing a target sequence. As a further example, two or more catalytic domains of Cas9 (RuvC I, RuvC II, and RuvC III or the HNH domain) may be mutated to produce a mutated Cas substantially lacking all RNA cleavage activity. As described herein, corresponding catalytic domains of a effector protein may also be mutated to produce a mutated effector protein lacking all DNA or RNA cleavage activity or having substantially reduced DNA or RNA cleavage activity. In some embodiments, a nucleic acid-targeting effector protein may be considered to substantially lack all DNA or RNA cleavage activity when the DNA or RNA cleavage activity of the mutated enzyme is about no more than 25%, 10%, 5%, 1%, 0.1%, 0.01%, or less of the nucleic acid cleavage activity of the non-mutated form of the enzyme; an example can be when the nucleic acid cleavage activity of the mutated form is nil or negligible as compared with the non-mutated form. An effector protein may be identified with reference to the general class of enzymes that share homology to the biggest nuclease with multiple nuclease domains from the Type II CRISPR system. Most preferably, the effector protein is a Type II protein such as Cas9. By derived, Applicants mean that the derived enzyme is largely based, in the sense of having a high degree of sequence homology with, a wildtype enzyme, but that it has been mutated (modified) in some way as known in the art or as described herein.

Again, it will be appreciated that the terms Cas9 and CRISPR enzyme and CRISPR protein and Cas9 protein and CRISPR effector or CRISPR effector protein, or effector (protein) in general are generally used interchangeably and at all points of reference herein refer by analogy to novel CRISPR effector proteins further described in this application, unless otherwise apparent. As mentioned above, many of the residue numberings used herein refer to the effector protein from the Type II CRISPR locus. However, it will be appreciated that this invention includes many more effector proteins from other species of microbes.

In certain embodiments, the effector protein may be constitutively present or inducibly present or conditionally present or administered or delivered. Effector protein optimization may be used to enhance function or to develop new functions, one can generate chimeric effector proteins. And effector proteins may be used as a generic nucleic acid binding protein.

Typically, in the context of an endogenous nucleic acid-targeting system, formation of a nucleic acid-targeting complex (comprising a guide RNA hybridized to a target sequence and complexed with one or more nucleic acid-targeting effector proteins) results in cleavage of one or both DNA or RNA strands in or near (e.g., within 1, 2, 3, 4, 5, 6, 7, 8, 9, 10, 20, 50, or more base pairs from) the target sequence. As used herein the term "sequence(s) associated with a target locus of interest" refers to sequences near the vicinity of the target sequence (e.g. within 1, 2, 3, 4, 5, 6, 7, 8, 9, 10, 20, 50, or more base pairs from the target sequence, wherein the target sequence is comprised within a target locus of interest).

An example of a codon optimized sequence, is in this instance a sequence optimized for expression in a eukaryote, e.g., humans (i.e. being optimized for expression in humans), or for another eukaryote, animal or mammal as herein discussed; see, e.g., SaCas9 human codon optimized sequence in WO 2014/093622 (PCT/US2013/074667) as an example of a codon optimized sequence (from knowledge in the art and this disclosure, codon optimizing coding nucleic acid molecule(s), especially as to effector protein (e.g., Cas9) is within the ambit of the skilled artisan). Whilst this is preferred, it will be appreciated that other examples are possible and codon optimization for a host species other than human, or for codon optimization for specific organs is known. In some embodiments, an enzyme coding sequence encoding a DNA- or RNA-targeting Cas protein is codon optimized for expression in particular cells, such as eukaryotic cells. The eukaryotic cells may be those of or derived from a particular organism, such as a mammal, including but not limited to human, or non-human eukaryote or animal or mammal as herein discussed, e.g., mouse, rat, rabbit, dog, livestock, or non-human mammal or primate. In some embodiments, processes for modifying the germ line genetic identity of human beings and/or processes for modifying the genetic identity of animals which are likely to cause them suffering without any substantial medical benefit to man or animal, and also animals resulting from such processes, may be excluded. In general, codon optimization refers to a process of modifying a nucleic acid sequence for enhanced expression in the host cells of interest by replacing at least one codon (e.g., about or more than about 1, 2, 3, 4, 5, 10, 15, 20, 25, 50, or more codons) of the native sequence with codons that are more frequently or most frequently used in the genes of that host cell while maintaining the native amino acid sequence. Various species exhibit particular bias for certain codons of a particular amino acid. Codon bias (differences in codon usage between organisms) often correlates with the efficiency of translation of messenger RNA (mRNA), which is in turn believed to be dependent on, among other things, the properties of the codons being translated and the availability of particular transfer RNA (tRNA) molecules. The predominance of selected tRNAs in a cell is generally a reflection of the codons used most frequently in peptide synthesis. Accordingly, genes can be tailored for optimal gene expression in a given organism based on codon optimization. Codon usage tables are readily available, for example, at the "Codon Usage Database" available at www.kazusa.or.jp/codon/and these tables can be adapted in a number of ways. See Nakamura, Y., et al. "Codon usage tabulated from the international DNA sequence databases: status for the year 2000" Nucl. Acids Res. 28:292 (2000). Computer algorithms for codon optimizing a particular sequence for expression in a particular host cell are also available, such as Gene Forge (Aptagen; Jacobus, P A), are also available. In some embodiments, one or more codons (e.g., 1, 2, 3, 4, 5, 10, 15, 20, 25, 50, or more, or all codons) in a sequence encoding a DNA/RNA-targeting Cas protein corresponds to the most frequently used codon for a particular amino acid.

In one aspect, the invention provides methods for using one or more elements of a nucleic acid-targeting system. The nucleic acid-targeting complex of the invention provides an effective means for modifying a target DNA (single or double stranded, linear or super-coiled). The nucleic acid-targeting complex of the invention has a wide variety of utility including modifying (e.g., deleting, inserting, translocating, inactivating, activating) a target DNA in a multiplicity of cell types. As such the nucleic acid-targeting complex of the invention has a broad spectrum of applications in, e.g., gene therapy, drug screening, disease diagnosis, and prognosis. An exemplary nucleic acid-targeting complex comprises a DNA- or RNA-targeting effector protein complexed with a guide RNA or guide DNA hybridized to a target sequence within the target locus of interest.

In one embodiment, this invention provides a method of cleaving a target DNA that encodes an RNA or of cleaving an RNA. The method may comprise modifying a target DNA or RNA using a nucleic acid-targeting complex that binds to the target DNA or RNA and effect cleavage of said target DNA or RNA. The (encoded) RNA can be any RNA endogenous or exogenous to the eukaryotic cell. For example, the target RNA can be a RNA residing in the nucleus of the eukaryotic cell. The target RNA can be a sequence (e.g., mRNA or pre-mRNA) coding a gene product (e.g., a protein) or a non-coding sequence (e.g., ncRNA, lncRNA, tRNA, or rRNA). Examples of encoded RNA include a sequence associated with a signaling biochemical pathway, e.g., a signaling biochemical pathway-associated RNA. Examples of encoded RNA include a disease associated RNA. A "disease-associated" RNA refers to any RNA which is yielding translation products at an abnormal level or in an abnormal form in cells derived from a disease-affected tissues compared with tissues or cells of a non disease control. It may be a RNA transcribed from a gene that becomes expressed at an abnormally high level; it may be a RNA transcribed from a gene that becomes expressed at an abnormally low level, where the altered expression correlates with the occurrence and/or progression of the disease. A disease-associated RNA also refers to a RNA transcribed from a gene possessing mutation(s) or genetic variation that is directly responsible or is in linkage disequilibrium with a gene(s) that is responsible for the etiology of a disease. The translated products may be known or unknown, and may be at a normal or abnormal level. The encoded RNA of a DNA-targeting complex can be any RNA endogenous or exogenous to the eukaryotic cell. For example, the target RNA can be a RNA residing in the nucleus of the eukaryotic cell. The encoded RNA can be a sequence (e.g., mRNA or pre-mRNA) coding a gene product (e.g., a protein) or a non-coding sequence (e.g., ncRNA, lncRNA, tRNA, or rRNA).

In some embodiments, the method may comprise allowing a nucleic acid-targeting complex to bind to the target DNA or RNA to effect cleavage of said target DNA or RNA thereby modifying the target DNA o RNA, wherein the nucleic acid-targeting complex comprises a nucleic acid-targeting effector protein complexed with a guide RNA hybridized to a target sequence within said target DNA or RNA. In one aspect, the invention provides a method of modifying expression of DNA or RNA in a eukaryotic cell. In some embodiments, the method comprises allowing a nucleic acid-targeting complex to bind to the DNA or RNA such that said binding results in increased or decreased expression of said DNA or RNA; wherein the nucleic acid-targeting complex comprises a nucleic acid-targeting effector protein complexed with a guide RNA. Similar considerations and conditions apply as above for methods of modifying a target DNA or RNA. In fact, these sampling, culturing and re-introduction options apply across the aspects of the present invention. In one aspect, the invention provides for methods of modifying a target DNA or RNA in a eukaryotic cell, which may be in vivo, ex vivo or in vitro. In some embodiments, the method comprises sampling a cell or population of cells from a human or non-human animal, and modifying the cell or cells. Culturing may occur at any stage ex vivo. The cell or cells may even be re-introduced into the non-human animal or plant. For re-introduced cells it is particularly preferred that the cells are stem cells.

Indeed, in any aspect of the invention, the nucleic acid-targeting complex may comprise a nucleic acid-targeting effector protein complexed with a guide RNA hybridized to a target sequence.

The invention relates to the engineering and optimization of systems, methods and compositions used for the control of gene expression involving DNA or RNA sequence targeting, that relate to the nucleic acid-targeting system according to the invention as described herein, i.e. one or more fusion protein of the invention, a CRISPR effector or argonaute, and a gRNA or gDNA (and optionally a tracr RNA when required) and components thereof. An advantage of the present methods is that the system minimizes or avoids off-target binding and its resulting side effects. This is achieved using systems arranged to have a high degree of sequence specificity for the target DNA or RNA. In relation to a nucleic acid-targeting complex or system preferably, the tracr sequence (when required) has one or more hairpins and is 30 or more nucleotides in length, 40 or more nucleotides in length, or 50 or more nucleotides in length; the crRNA sequence is between 10 to 30 nucleotides in length, the nucleic acid-targeting effector protein is a Type II CRISPR effector protein, such as Cas9, Cpf1, C2c1, C2c2, C2c3, Cas13, or group 29/30.

Crystallization of CRISPR-Cas9 and Characterization of Crystal Structure

The crystals of the CRISPR protein can be obtained by techniques of protein crystallography, including batch, liquid bridge, dialysis, vapor diffusion and hanging drop methods. Generally, the crystals of the invention are grown by dissolving substantially pure CRISPR-Cas9 and a nucleic acid molecule to which it binds in an aqueous buffer containing a precipitant at a concentration just below that necessary to precipitate. Water is removed by controlled evaporation to produce precipitating conditions, which are maintained until crystal growth ceases. The crystal structure information is described in U.S. provisional applications 61/915,251 filed Dec. 12, 2013, 61/930,214 filed on Jan. 22, 2014, 61/980,012 filed Apr. 15, 2014 and international application PCT/US2014/069925, filed Dec. 12, 2014; and Nishimasu et al, "Crystal Structure of Cas9 in Complex with Guide RNA and Target DNA," Cell 156(5):935-949, DOI: dx.doi.org/10.1016/j.cell.2014.02.001 (2014), each and all of which are incorporated herein by reference.

Uses of the Crystals, Crystal Structure and Atomic Structure Co-Ordinates: The crystals of the Cas, and particularly the atomic structure co-ordinates obtained therefrom, have a wide variety of uses. The crystals and structure co-ordinates are particularly useful for identifying compounds (nucleic acid molecules) that bind to CRISPR-Cas, and CRISPR-Cas that can bind to particular compounds (nucleic acid molecules). Thus, the structure co-ordinates described herein can be used as phasing models in determining the crystal structures of additional synthetic or mutated CRISPR-Cas, Cas, nickases, binding domains. The provision of the crystal structure of CRISPR-Cas complexed with a nucleic acid molecule as applied in conjunction with the herein teachings provides the skilled artisan with a detailed insight into the mechanisms of action of CRISPR-Cas. This insight provides a means to design modified CRISPR-Cas, such as by attaching thereto a functional group, such as a repressor or activator. While one can attach a functional group such as a repressor or activator to the N or C terminal of CRISPR-Cas, the crystal structure demonstrates that the N terminal seems obscured or hidden, whereas the C terminal is more available for a functional group such as repressor or activator. Moreover, the crystal structure demonstrates that there is a flexible loop between approximately CRISPR-Cas9 (*S. pyogenes*) residues 534-676 which is suitable for attachment of a functional group such as an activator or repressor. Attachment can be via a linker, e.g., a flexible glycine-serine (GlyGlyGlySer) (SEQ ID NO: 3) or $(GGGS)_3$ (SEQ ID NO: 4) or a rigid alpha-helical linker such as (Ala(GluAlaAlaAlaLys)Ala) (SEQ ID NO: 50). In addition to the flexible loop there is also a nuclease or H3 region, an H2 region and a helical region. By "helix" or "helical", is meant a helix as known in the art, including, but not limited to an alpha-helix. Additionally, the term helix or helical may also be used to indicate a c-terminal helical element with an N-terminal turn.

The provision of the crystal structure of CRISPR-Cas complexed with a nucleic acid molecule allows a novel approach for drug or compound discovery, identification, and design for compounds that can bind to CRISPR-Cas and thus the invention provides tools useful in diagnosis, treatment, or prevention of conditions or diseases of multicellular organisms, e.g., algae, plants, invertebrates, fish, amphibians, reptiles, avians, mammals; for example domesticated plants, animals (e.g., production animals such as swine, bovine, chicken; companion animal such as felines, canines, rodents (rabbit, gerbil, hamster); laboratory animals such as mouse, rat), and humans.

In any event, the determination of the three-dimensional structure of CRISPR-Cas (*S. pyogenes* Cas9) complex provides a basis for the design of new and specific nucleic acid molecules that bind to CRISPR-Cas (e.g., *S. pyogenes* Cas9), as well as the design of new CRISPR-Cas9 systems, such as by way of modification of the CRISPR-Cas system to bind to various nucleic acid molecules, by way of modification of the CRISPR-Cas system to have linked thereto to any one or more of various functional groups that may interact with each other, with the CRISPR-Cas (e.g., an inducible system that provides for self-activation and/or self-termination of function), with the nucleic acid molecule nucleic acid molecules (e.g., the functional group may be a regulatory or functional domain which may be selected from the group consisting of a transcriptional repressor, a transcriptional activator, a nuclease domain, a DNA methyl transferase, a protein acetyltransferase, a protein deacetylase, a protein methyltransferase, a protein deaminase, a protein kinase, and a protein phosphatase; and, in some aspects, the functional domain is an epigenetic regulator; see, e.g., Zhang et al., U.S. Pat. No. 8,507,272, and it is again mentioned that it and all documents cited herein and all appln cited documents are hereby incorporated herein by reference), by way of modification of Cas, by way of novel nickases). Indeed, the herewith CRISPR-Cas (*S. pyogenes* Cas9) crystal structure has a multitude of uses. For example, from knowing the three-dimensional structure of CRISPR-Cas (*S. pyogenes* Cas9) crystal structure, computer modelling programs may be used to design or identify different molecules expected to interact with possible or confirmed sites such as binding sites or other structural or functional features of the CRISPR-Cas system (e.g., *S. pyogenes* Cas9). Compound that potentially bind ("binder") can be examined through the use of computer modeling using a docking program. Docking programs are known; for example GRAM, DOCK or AUTODOCK (see Walters et al. Drug Discovery Today, vol. 3, no. 4 (1998), 160-178, and Dunbrack et al. Folding and Design 2 (1997), 27-42). This procedure can include computer fitting of potential binders ascertain how well the shape and the chemical structure of the potential binder will bind to a CRISPR-Cas system (e.g., *S. pyogenes* Cas9). Computer-assisted, manual examination of the active site or binding site of a CRISPR-Cas system (e.g., *S. pyogenes* Cas9) may be performed. Programs such as GRID (P. Goodford, J. Med. Chem, 1985, 28, 849-57)-a program that determines probable interaction sites between molecules with various functional groups—may also be used to analyze the active site or binding site to predict partial structures of binding compounds. Computer programs can be employed to estimate the attraction, repulsion or steric hindrance of the two binding partners, e.g., CRISPR-Cas system (e.g., *S. pyogenes* Cas9) and a candidate nucleic acid molecule or a nucleic acid molecule and a candidate CRISPR-Cas system (e.g., *S. pyogenes* Cas9); and the CRISPR-Cas crystal structure (*S. pyogenes* Cas9) herewith enables such methods. Generally, the tighter the fit, the fewer the steric hindrances, and the greater the attractive forces, the more potent the potential binder, since these properties are consistent with a tighter binding constant. Furthermore, the more specificity in the design of a candidate CRISPR-Cas system (e.g., *S. pyogenes* Cas9), the more likely it is that it will not interact with off-target molecules as well. Also, "wet" methods are enabled by the instant invention. For example, in an aspect, the invention provides for a method for determining the structure of a binder (e.g., target nucleic acid molecule) of a candidate CRISPR-Cas system (e.g., *S. pyogenes* Cas9) bound to the candidate CRISPR-Cas9 system (e.g., *S. pyogenes* Cas9), said method comprising, (a) providing a first crystal of a candidate CRISPR-Cas system (*S. pyogenes* Cas9) according to the invention or a second crystal of a candidate a candidate CRISPR-Cas9 system (e.g., *S. pyogenes* Cas9), (b) contacting the first crystal or second crystal with said binder under conditions whereby a complex may form; and (c) determining the structure of said a candidate (e.g., CRISPR-Cas9 system (e.g., *S. pyogenes* Cas9) or CRISPR-Cas system (*S. pyogenes* Cas9) complex. The second crystal may have essentially the same coordinates discussed herein, however due to minor alterations in CRISPR-Cas system (e.g., from the Cas9 of such a system being e.g., *S. pyogenes* Cas9 versus being *S. pyogenes* Cas9), wherein "e.g., *S. pyogenes* Cas9" indicates that the Cas9 is a Cas9 and can be of or derived from *S. pyogenes* or an ortholog thereof), the crystal may form in a different space group.

The invention further involves, in place of or in addition to "in silico" methods, other "wet" methods, including high throughput screening of a binder (e.g., target nucleic acid molecule) and a candidate CRISPR-Cas system (e.g., *S. pyogenes* Cas9), or a candidate binder (e.g., target nucleic acid molecule) and a CRISPR-Cas system (e.g., *S. pyogenes* Cas9), or a candidate binder (e.g., target nucleic acid molecule) and a candidate CRISPR-Cas system (e.g., *S. pyogenes* Cas9) (the foregoing CRISPR-Cas9 system(s) with or without one or more functional group(s)), to select compounds with binding activity. Those pairs of binder and CRISPR-Cas system which show binding activity may be selected and further crystallized with the CRISPR-Cas crystal having a structure herein, e.g., by co-crystallization or by soaking, for X-ray analysis. The resulting X-ray structure may be compared with that of the Cas Crystal Structure for a variety of purposes, e.g., for areas of overlap. Having designed, identified, or selected possible pairs of binder and CRISPR-Cas system by determining those which have favorable fitting properties, e.g., predicted strong attraction based on the pairs of binder and CRISPR-Cas crystal structure data herein, these possible pairs can then be screened by "wet" methods for activity. Consequently, in an aspect the invention can involve: obtaining or synthesizing the possible pairs; and contacting a binder (e.g., target nucleic acid molecule) and a candidate CRISPR-Cas system (e.g., *S. pyogenes* Cas9), or a candidate binder (e.g., target nucleic acid molecule) and a CRISPR-Cas system (e.g., *S. pyogenes* Cas9), or a candidate binder (e.g., target nucleic acid molecule) and a candidate CRISPR-Cas system (e.g., *S. pyogenes* Cas9) (the foregoing CRISPR-Cas9 system(s) with or without one or more functional group(s)) to determine ability to bind. In the latter step, the contacting is advantageously under conditions to determine function. Instead of, or in addition to, performing such an assay, the invention may comprise: obtaining or synthesizing complex (es) from said contacting and analyzing the complex(es), e.g., by X-ray diffraction or NMR or other means, to determine the ability to bind or interact. Detailed structural information can then be obtained about the binding, and in light of this information, adjustments can be made to the structure or functionality of a candidate CRISPR-Cas system or components thereof. These steps may be repeated and re-repeated as necessary. Alternatively or additionally, potential CRISPR-Cas systems from or in the foregoing methods can be with nucleic acid molecules in vivo, including without limitation by way of administration to an organism (including non-human animal and human) to ascertain or confirm function, including whether a desired outcome (e.g., reduction of symptoms, treatment) results therefrom.

The invention further involves a method of determining three dimensional structures of CRISPR-Cas systems or complex(es) of unknown structure by using the structural co-ordinates of the CRISPR effector Crystal Structure. For example, if X-ray crystallographic or NMR spectroscopic data are provided for a CRISPR-Cas system or complex of unknown crystal structure, the structure of a CRISPR-Cas complex may be used to interpret that data to provide a likely structure for the unknown system or complex by such techniques as by phase modeling in the case of X-ray crystallography. Thus, an inventive method can comprise: aligning a representation of the CRISPR-Cas system or complex having an unknown crystal structure with an analogous representation of the CRISPR-Cas system and complex of the crystal structure herein to match homologous or analogous regions (e.g., homologous or analogous sequences); modeling the structure of the matched homologous or analogous regions (e.g., sequences) of the CRISPR-Cas system or complex of unknown crystal structure based on the structure of the Cas Crystal Structure of the corresponding regions (e.g., sequences); and, determining a conformation (e.g. taking into consideration favorable interactions should be formed so that a low energy conformation is formed) for the unknown crystal structure which substantially preserves the structure of said matched homologous regions. "Homologous regions" describes, for example as to amino acids, amino acid residues in two sequences that are identical or have similar, e.g., aliphatic, aromatic, polar, negatively charged, or positively charged, side-chain chemical groups. Homologous regions as to nucleic acid molecules can include at least 85% or 86% or 87% or 88% or 89% or 90% or 91% or 92% or 93% or 94% or 95% or 96% or 97% or 98% or 99% homology or identity. Identical and similar regions are sometimes described as being respectively "invariant" and "conserved" by those skilled in the art. Homology modeling is a technique that is well known to those skilled in the art (see, e.g., Greer, Science vol. 228 (1985) 1055, and Blundell et al. Eur J Biochem vol 172 (1988), 513). The computer representation of the conserved regions of the CRISPR-Cas crystal structure and those of a CRISPR-Cas system of unknown crystal structure aid in the prediction and determination of the crystal structure of the CRISPR-Cas system of unknown crystal structure.

Further still, the aspects of the invention which employ the CRISPR-Cas crystal structure in silico may be equally applied to new CRISPR-Cas crystal structures divined by using the herein-referenced CRISPR-Cas crystal structure. In this fashion, a library of CRISPR-Cas crystal structures can be obtained. Rational CRISPR-Cas system design is thus provided by the instant invention. For instance, having determined a conformation or crystal structure of a CRISPR-Cas system or complex, by the methods described herein, such a conformation may be used in a computer-based methods herein for determining the conformation or crystal structure of other CRISPR-Cas systems or complexes whose crystal structures are yet unknown. Data from all of these crystal structures can be in a database, and the herein methods can be more robust by having herein comparisons involving the herein crystal structure or portions thereof be with respect to one or more crystal structures in the library. The invention further provides systems, such as computer systems, intended to generate structures and/or perform rational design of a CRISPR-Cas system or complex. The system can contain: atomic co-ordinate data according to the herein-referenced Crystal Structure or be derived therefrom e.g., by modeling, said data defining the three-dimensional structure of a CRISPR-Cas system or complex or at least one domain or sub-domain thereof, or structure factor data therefor, said structure factor data being derivable from the atomic co-ordinate data of the herein-referenced Crystal Structure. The invention also involves computer readable media with: atomic co-ordinate data according to the herein-referenced Crystal Structure or derived therefrom e.g., by homology modeling, said data defining the three-dimensional structure of a CRISPR-Cas system or complex or at least one domain or sub-domain thereof, or structure factor data therefor, said structure factor data being derivable from the atomic co-ordinate data of the herein-referenced Crystal Structure. "Computer readable media" refers to any media which can be read and accessed directly by a computer, and includes, but is not limited to: magnetic storage media; optical storage media; electrical storage media; cloud storage and hybrids of these categories. By providing such computer readable media, the atomic co-ordinate data can be routinely accessed for modeling or other "in silico" methods. The invention further comprehends methods of doing business by providing access to such computer readable media, for instance on a subscription basis, via the Internet or a global communication/computer network; or, the computer system can be available to a user, on a subscription basis. A "computer system" refers to the hardware means, software means and data storage means used to analyze the atomic co-ordinate data of the present invention. The minimum hardware means of computer-based systems of the invention may comprise a central processing unit (CPU), input means, output means, and data storage means. Desirably, a display or monitor is provided to visualize structure data. The invention further comprehends methods of transmitting information obtained in any method or step thereof described herein or any information described herein, e.g., via telecommunications, telephone, mass communications, mass media, presentations, internet, email, etc. The crystal structures of the invention can be analyzed to generate Fourier electron density map(s) of CRISPR-Cas systems or complexes; advantageously, the three-dimensional structure being as defined by the atomic co-ordinate data according to the herein-referenced Crystal Structure. Fourier electron density maps can be calculated based on X-ray diffraction patterns. These maps can then be used to determine aspects of binding or other interactions. Electron density maps can be calculated using known programs such as those from the CCP4 computer package (Collaborative Computing Project, No. 4. The CCP4 Suite: Programs for Protein Crystallography, Acta Crystallographica, D50, 1994, 760-763). For map visualization and model building programs such as "QUANTA" (1994, San Diego, Calif.: Molecular Simulations, Jones et al., Acta Crystallography A47 (1991), 110-119) can be used.

The herein-referenced Crystal Structure gives atomic co-ordinate data for a CRISPR-Cas9 (*S. pyogenes*), and lists each atom by a unique number; the chemical element and its position for each amino acid residue (as determined by electron density maps and antibody sequence comparisons), the amino acid residue in which the element is located, the chain identifier, the number of the residue, co-ordinates (e.g., X, Y, Z) which define with respect to the crystallographic axes the atomic position (in angstroms) of the respective atom, the occupancy of the atom in the respective position, "B", isotropic displacement parameter (in angstroms$^2$) which accounts for movement of the atom around its atomic center, and atomic number.

In particular embodiments of the invention, the conformational variations in the crystal structures of the CRISPR-Cas system or of components of the CRISPR-Cas provide important and critical information about the flexibility or movement of protein structure regions relative to nucleotide (RNA or DNA) structure regions that may be important for CRISPR-Cas system function. The structural information provided for Cas9 (e.g. *S. pyogenes* Cas9) as the CRISPR enzyme in the present application may be used to further engineer and optimize the CRISPR-Cas system and this may be extrapolated to interrogate structure-function relationships in other CRISPR enzyme systems as well. An aspect of the invention relates to the crystal structure of *S. pyogenes* Cas9 in complex with gRNA and its target DNA at 2.4 A resolution. The structure revealed a bilobed architecture composed of target recognition and nuclease lobes, accommodating a gRNA:DNA duplex in a positively-charged groove at their interface. The recognition lobe is essential for gRNA and DNA binding and the nuclease lobe contains the HNH and RuvC nuclease domains, which are properly positioned for the cleavage of complementary and non-complementary strands of the target DNA, respectively. This high-resolution structure and the functional analyses provided herein elucidate the molecular mechanism of RNA-guided DNA targeting by Cas9, and provides an abundance of information for generating optimized CRISPR-Cas systems and components thereof.

In particular embodiments of the invention, the crystal structure provides a critical step towards understanding the molecular mechanism of RNA-guided DNA targeting by the CRISPR effector. The structural and functional analyses herein provide a useful scaffold for rational engineering of CRISPR/Cas-based genome modulating technologies and may provide guidance as to CRISPR effector-mediated recognition of PAM sequences on the target DNA/RNA or mismatch tolerance between the gRNA:DNA (or RNA) duplex. Aspects of the invention also relate to truncation mutants, e.g. an *S. pyogenes* Cas9 truncation mutant may facilitate packaging of CRISPR effector into size-constrained viral vectors for in vivo and therapeutic applications. Similarly, future engineering of the PAM Interacting (PI) domain may allow programing of PAM specificity, improve target site recognition fidelity, and increase the versatility of the CRISPR/Cas genome/transcriptome engineering platform.

Accordingly, while the herein-referenced crystal structure may be used in conjunction with the herein disclosure, and in conjunction with the herein invention, the herein invention of protected guides and the utility thereof could not have been predicted from the herein-referenced crystal structure.

The invention comprehends optimized functional CRISPR-Cas enzyme systems. In particular the CRISPR enzyme comprises one or more mutations that converts it to a DNA binding protein to which functional domains exhibiting a function of interest may be recruited or appended or inserted or attached. In certain embodiments, the CRISPR enzyme comprises one or more mutations which include but are not limited to D10A, E762A, H840A, N854A, N863A or D986A (based on the amino acid position numbering of a *S. pyogenes* Cas9) and/or the one or more mutations is in a RuvC1 or HNH domain of the CRISPR enzyme or is a mutation as otherwise as discussed herein. In some embodiments, the CRISPR enzyme has one or more mutations in a catalytic domain, wherein when transcribed, the tracr mate sequence hybridizes to the tracr sequence and the guide sequence directs sequence-specific binding of a CRISPR complex to the target sequence, and wherein the enzyme further comprises a functional domain.

The structural information provided herein allows for interrogation of gRNA (or chimeric RNA) interaction with the target DNA and the CRISPR enzyme (e.g. Cas9) permitting engineering or alteration of gRNA structure to optimize functionality of the entire CRISPR-Cas system. For example, loops of the gRNA may be extended, without colliding with the Cas9 protein by the insertion of distinct RNA loop(s) or distinct sequence(s) that may recruit adaptor proteins that can bind to the distinct RNA loop(s) or distinct sequence(s). The adaptor proteins may include but are not limited to orthogonal RNA-binding protein/aptamer combinations that exist within the diversity of bacteriophage coat proteins. A list of such coat proteins includes, but is not limited to: Qβ, F2, GA, fr, JP501, M12, R17, BZ13, JP34, JP500, KU1, M11, MX1, TW18, VK, SP, FI, ID2, NL95, TW19, AP205, ϕCb5, ϕCb8r, ϕCb12r, ϕCb23r, 7s and PRR1. These adaptor proteins or orthogonal RNA binding proteins can further recruit effector proteins or fusions which comprise one or more functional domains. In some embodiments, the functional domain may be selected from the group consisting of: transposase domain, integrase domain, recombinase domain, resolvase domain, invertase domain, protease domain, DNA methyltransferase domain, DNA hydroxylmethylase domain, DNA demethylase domain, histone acetylase domain, histone deacetylases domain, nuclease domain, repressor domain, activator domain, nuclear-localization signal domains, transcription-regulatory protein (or transcription complex recruiting) domain, cellular uptake activity associated domain, nucleic acid binding domain, antibody presentation domain, histone modifying enzymes, recruiter of histone modifying enzymes; inhibitor of histone modifying enzymes, histone methyltransferase, histone demethylase, histone kinase, histone phosphatase, histone ribosylase, histone deribosylase, histone ubiquitinase, histone deubiquitinase, histone biotinase and histone tail protease.

In some preferred embodiments, the functional domain is a transcriptional activation domain, preferably VP64. In some embodiments, the functional domain is a transcription repression domain, preferably KRAB. In some embodiments, the transcription repression domain is SID, or concatemers of SID (eg SID4X). In some embodiments, the functional domain is an epigenetic modifying domain, such that an epigenetic modifying enzyme is provided. In some embodiments, the functional domain is an activation domain, which may be the P65 activation domain.

In one aspect surveyor analysis is used for identification of indel activity/nuclease activity. In general survey analysis includes extraction of genomic DNA, PCR amplification of the genomic region flanking the CRISPR target site, purification of products, re-annealing to enable heteroduplex formation. After re-annealing, products are treated with SURVEYOR nuclease and SURVEYOR enhancer S (Transgenomics) following the manufacturer's recommended protocol. Analysis may be performed with polyacrylamide gels according to known methods. Quantification may be based on relative band intensities.

Delivery Generally

Gene Editing or Altering a Target Loci with CRISPR Effectors

The double strand break or single strand break in one of the strands advantageously should be sufficiently close to target position such that correction occurs. In an embodiment, the distance is not more than 50, 100, 200, 300, 350 or 400 nucleotides. While not wishing to be bound by theory, it is believed that the break should be sufficiently close to target position such that the break is within the region that is subject to exonuclease-mediated removal during end resection. If the distance between the target position and a break is too great, the mutation may not be included in the end resection and, therefore, may not be corrected, as the template nucleic acid sequence may only be used to correct sequence within the end resection region.

In an embodiment, in which a guide RNA and a Type II molecule, in particular Cas9, Cpf1, C2c1, C2c2, C2c3, Cas13, group 29/30 or an ortholog or homolog thereof, preferably a CRISPR effector induce a double strand break for the purpose of inducing HDR-mediated correction, the cleavage site is between 0-200 bp (e.g., 0 to 175, 0 to 150, 0 to 125, 0 to 100, 0 to 75, 0 to 50, 0 to 25, 25 to 200, 25 to 175, 25 to 150, 25 to 125, 25 to 100, 25 to 75, 25 to 50, 50 to 200, 50 to 175, 50 to 150, 50 to 125, 50 to 100, 50 to 75, 75 to 200, 75 to 175, 75 to 150, 75 to 1 25, 75 to 100 bp) away from the target position. In an embodiment, the cleavage site is between 0-100 bp (e.g., 0 to 75, 0 to 50, 0 to 25, 25 to 100, 25 to 75, 25 to 50, 50 to 100, 50 to 75 or 75 to 100 bp) away from the target position. In a further embodiment, two or more guide RNAs complexing with CRISPR effector or an ortholog or homolog thereof, may be used to induce multiplexed breaks for purpose of inducing HDR-mediated correction.

The homology arm should extend at least as far as the region in which end resection may occur, e.g., in order to allow the resected single stranded overhang to find a complementary region within the donor template. The overall length could be limited by parameters such as plasmid size or viral packaging limits. In an embodiment, a homology arm may not extend into repeated elements. Exemplary homology arm lengths include a least 50, 100, 250, 500, 750 or 1000 nucleotides.

Target position, as used herein, refers to a site on a target nucleic acid or target gene (e.g., the chromosome) that is modified by a CRISPR/Cas molecule-dependent process. For example, the target position can be a modified CRISPR effector molecule cleavage of the target nucleic acid and template nucleic acid directed modification, e.g., correction, of the target position. In an embodiment, a target position can be a site between two nucleotides, e.g., adjacent nucleotides, on the target nucleic acid into which one or more nucleotides is added. The target position may comprise one or more nucleotides that are altered, e.g., corrected, by a template nucleic acid. In an embodiment, the target position is within a target sequence (e.g., the sequence to which the guide RNA binds). In an embodiment, a target position is upstream or downstream of a target sequence (e.g., the sequence to which the guide RNA binds).

A template nucleic acid, as that term is used herein, refers to a nucleic acid sequence which can be used in conjunction with a CRISPR effector and a guide RNA molecule to alter the structure of a target position. In an embodiment, the target nucleic acid is modified to have some or all of the sequence of the template nucleic acid, typically at or near cleavage site(s). In an embodiment, the template nucleic acid is single stranded. In an alternate embodiment, the template nucleic acid is double stranded. In an embodiment, the template nucleic acid is DNA, e.g., double stranded DNA. In an alternate embodiment, the template nucleic acid is single stranded DNA.

In an embodiment, the template nucleic acid alters the structure of the target position by participating in homologous recombination. In an embodiment, the template nucleic acid alters the sequence of the target position. In an embodiment, the template nucleic acid results in the incorporation of a modified, or non-naturally occurring base into the target nucleic acid.

The template sequence may undergo a breakage mediated or catalyzed recombination with the target sequence. In an embodiment, the template nucleic acid may include sequence that corresponds to a site on the target sequence that is cleaved by a CRISPR/Cas system mediated cleavage event. In an embodiment, the template nucleic acid may include sequence that corresponds to both, a first site on the target sequence that is cleaved in a first CRISPR/Cas system mediated event, and a second site on the target sequence that is cleaved in a second CRISPR/Cas system mediated event.

In certain embodiments, the template nucleic acid can include sequence which results in an alteration in the coding sequence of a translated sequence, e.g., one which results in the substitution of one amino acid for another in a protein product, e.g., transforming a mutant allele into a wild type allele, transforming a wild type allele into a mutant allele, and/or introducing a stop codon, insertion of an amino acid residue, deletion of an amino acid residue, or a nonsense mutation. In certain embodiments, the template nucleic acid can include sequence which results in an alteration in a non-coding sequence, e.g., an alteration in an exon or in a 5' or 3' non-translated or non-transcribed region. Such alterations include an alteration in a control element, e.g., a promoter, enhancer, and an alteration in a cis-acting or trans-acting control element.

A template nucleic acid having homology with a target position in a target gene may be used to alter the structure of a target sequence. The template sequence may be used to alter an unwanted structure, e.g., an unwanted or mutant nucleotide. The template nucleic acid may include sequence which, when integrated, results in: decreasing the activity of a positive control element; increasing the activity of a positive control element; decreasing the activity of a negative control element; increasing the activity of a negative control element; decreasing the expression of a gene; increasing the expression of a gene; increasing resistance to a disorder or disease; increasing resistance to viral entry; correcting a mutation or altering an unwanted amino acid residue conferring, increasing, abolishing or decreasing a biological property of a gene product, e.g., increasing the enzymatic activity of an enzyme, or increasing the ability of a gene product to interact with another molecule.

The template nucleic acid may include sequence which results in: a change in sequence of 1, 2, 3, 4, 5, 6, 7, 8, 9, 10, 11, 12 or more nucleotides of the target sequence. In an embodiment, the template nucleic acid may be 20+/−10, 30+/−10, 40+/−10, 50+/−10, 60+/−10, 70+/−10, 80+/−10, 90+/−10, 100+/−10, 110+/−10, 120+/−10, 130+/−10, 140+/−10, 150+/−10, 160+/−10, 170+/−10, 180+/−10, 190+/−10, 200+/−10, 210+/−10, of 220+/−10 nucleotides in length. In an embodiment, the template nucleic acid may be 30+/−20, 40+/−20, 50+/−20, 60+/−20, 70+/−20, 80+/−20, 90+/−20, 100+/−20, 110+/−20, 120+/−20, 130+/−20, 140+/−20, 150+/−20, 160+/−20, 170+/−20, 180+/−20, 190+/−20, 200+/−20, 210+/−20, of 220+/−20 nucleotides in length. In an embodiment, the template nucleic acid is 10 to 1,000, 20 to 900, 30 to 800, 40 to 700, 50 to 600, 50 to 500, 50 to 400, 50 to 300, 50 to 200, or 50 to 100 nucleotides in length.

A template nucleic acid comprises the following components: [5' homology arm]-[replacement sequence]-[3' homology arm]. The homology arms provide for recombination into the chromosome, thus replacing the undesired element, e.g., a mutation or signature, with the replacement sequence. In an embodiment, the homology arms flank the most distal cleavage sites. In an embodiment, the 3' end of the 5' homology arm is the position next to the 5' end of the replacement sequence. In an embodiment, the 5' homology arm can extend at least 10, 20, 30, 40, 50, 100, 200, 300, 400, 500, 600, 700, 800, 900, 1000, 1500, or 2000 nucleotides 5' from the 5' end of the replacement sequence. In an embodiment, the 5' end of the 3' homology arm is the position next to the 3' end of the replacement sequence. In an embodiment, the 3' homology arm can extend at least 10, 20, 30, 40, 50, 100, 200, 300, 400, 500, 600, 700, 800, 900, 1000, 1500, or 2000 nucleotides 3' from the 3' end of the replacement sequence.

In certain embodiments, one or both homology arms may be shortened to avoid including certain sequence repeat elements. For example, a 5' homology arm may be shortened to avoid a sequence repeat element. In other embodiments, a 3' homology arm may be shortened to avoid a sequence repeat element. In some embodiments, both the 5' and the 3' homology arms may be shortened to avoid including certain sequence repeat elements.

In certain embodiments, a template nucleic acids for correcting a mutation may designed for use as a single-stranded oligonucleotide. When using a single-stranded oligonucleotide, 5' and 3' homology arms may range up to about 200 base pairs (bp) in length, e.g., at least 25, 50, 75, 100, 125, 150, 175, or 200 bp in length.

Cas Effector Protein Complex System Promoted Non-Homologous End-Joining

In certain embodiments, nuclease-induced non-homologous end-joining (NHEJ) can be used to target gene-specific knockouts. Nuclease-induced NHEJ can also be used to remove (e.g., delete) sequence in a gene of interest. Generally, NHEJ repairs a double-strand break in the DNA by joining together the two ends; however, generally, the original sequence is restored only if two compatible ends, exactly as they were formed by the double-strand break, are perfectly ligated. The DNA ends of the double-strand break are frequently the subject of enzymatic processing, resulting in the addition or removal of nucleotides, at one or both strands, prior to rejoining of the ends. This results in the presence of insertion and/or deletion (indel) mutations in the DNA sequence at the site of the NHEJ repair. Two-thirds of these mutations typically alter the reading frame and, therefore, produce a non-functional protein. Additionally, mutations that maintain the reading frame, but which insert or delete a significant amount of sequence, can destroy functionality of the protein. This is locus dependent as mutations in critical functional domains are likely less tolerable than mutations in non-critical regions of the protein. The indel mutations generated by NHEJ are unpredictable in nature; however, at a given break site certain indel sequences are favored and are over represented in the population, likely due to small regions of microhomology. The lengths of deletions can vary widely; most commonly in the 1-50 bp range, but they can easily be greater than 50 bp, e.g., they can easily reach greater than about 100-200 bp. Insertions tend to be shorter and often include short duplications of the sequence immediately surrounding the break site. However, it is possible to obtain large insertions, and in these cases, the inserted sequence has often been traced to other regions of the genome or to plasmid DNA present in the cells.

Because NHEJ is a mutagenic process, it may also be used to delete small sequence motifs as long as the generation of a specific final sequence is not required. If a double-strand break is targeted near to a short target sequence, the deletion mutations caused by the NHEJ repair often span, and therefore remove, the unwanted nucleotides. For the deletion of larger DNA segments, introducing two double-strand breaks, one on each side of the sequence, can result in NHEJ between the ends with removal of the entire intervening sequence. Both of these approaches can be used to delete specific DNA sequences; however, the error-prone nature of NHEJ may still produce indel mutations at the site of repair.

Both double strand cleaving Type II molecule, in particular Cas9 or an ortholog or homolog thereof, preferably Cas9 molecules and single strand, or nickase, Type II molecule, in particular Cas9 or an ortholog or homolog thereof, preferably Cas9 molecules can be used in the methods and compositions described herein to generate NHEJ-mediated indels. NHEJ-mediated indels targeted to the gene, e.g., a coding region, e.g., an early coding region of a gene of interest can be used to knockout (i.e., eliminate expression of) a gene of interest. For example, early coding region of a gene of interest includes sequence immediately following a transcription start site, within a first exon of the coding sequence, or within 500 bp of the transcription start site (e.g., less than 500, 450, 400, 350, 300, 250, 200, 150, 100 or 50 bp).

In an embodiment, in which a guide RNA and Type II molecule, in particular CRISPR effector generates a double strand break for the purpose of inducing NHEJ-mediated indels, a guide RNA may be configured to position one double-strand break in close proximity to a nucleotide of the target position. In an embodiment, the cleavage site may be between 0-500 bp away from the target position (e.g., less than 500, 400, 300, 200, 100, 50, 40, 30, 25, 20, 15, 10, 9, 8, 7, 6, 5, 4, 3, 2 or 1 bp from the target position).

In an embodiment, in which two guide RNAs complexing with CRISPR effectors, such as preferably nickases induce two single strand breaks for the purpose of inducing NHEJ-mediated indels, two guide RNAs may be configured to position two single-strand breaks to provide for NHEJ repair a nucleotide of the target position.

Cas Effector Protein Complexes Can Deliver Functional Effectors

Unlike CRISPR-Cas-mediated gene knockout, which permanently eliminates expression by mutating the gene at the DNA level, CRISPR-Cas transcriptional or translational upregulation or knockdown allows for temporary reduction of gene expression through the use of artificial transcription factors (activators or repressors). Mutating key residues in both DNA cleavage domains of the Cas protein results in the generation of a catalytically inactive Cas. A catalytically inactive Cas complexes with a guide RNA and localizes to the DNA or RNA sequence specified by that guide RNA's targeting domain, however, it does not cleave the target DNA or RNA. Fusion of the inactive Cas protein to an effector domain, e.g., a transcription/translation repression domain, enables recruitment of the effector to any DNA/RNA site specified by the guide RNA. In certain embodiments, Cas9 may be fused to a transcriptional/translational repression domain and recruited to the promoter region of a gene. Especially for gene repression, it is contemplated herein that blocking the binding site of an endogenous transcription/translation factor would aid in downregulating gene expression. In another embodiment, an inactive Cas can be fused to a chromatin modifying protein. Altering chromatin status can result in decreased expression of the target gene.

In an embodiment, a guide RNA molecule can be targeted to a known transcription response elements (e.g., promoters, enhancers, etc.), a known upstream activating sequences, and/or sequences of unknown or known function that are suspected of being able to control expression of the target DNA.

In some methods, a target polynucleotide can be inactivated to effect the modification of the expression in a cell. For example, upon the binding of a CRISPR complex to a target sequence in a cell, the target polynucleotide is inactivated such that the sequence is not transcribed, the coded protein is not produced, or the sequence does not function as the wild-type sequence does. For example, a protein or microRNA coding sequence may be inactivated such that the protein is not produced.

In certain embodiments, the CRISPR enzyme comprises one or more mutations selected from the group consisting of D917A, E1006A and D1225A and/or the one or more mutations is in a RuvC domain of the CRISPR enzyme or is a mutation as otherwise as discussed herein. In some embodiments, the CRISPR enzyme has one or more mutations in a catalytic domain, wherein when transcribed, the direct repeat sequence forms a single stem loop and the guide sequence directs sequence-specific binding of a CRISPR complex to the target sequence, and wherein the enzyme further comprises a functional domain. In some embodiments, the functional domain is a transcriptional activation domain, preferably VP64. In some embodiments, the functional domain is a transcription repression domain, preferably KRAB. In some embodiments, the transcription repression domain is SID, or concatemers of SID (eg SID4X). In some embodiments, the functional domain is an epigenetic modifying domain, such that an epigenetic modifying enzyme is provided. In some embodiments, the functional domain is an activation domain, which may be the P65 activation domain.

Delivery of the CRISPR-Cas Complex or Components Thereof

Through this disclosure and the knowledge in the art, TALEs, CRISPR-Cas system, specifically the novel CRISPR systems or argonaute based systems described herein, or components thereof or nucleic acid molecules thereof (including, for instance HDR template) or nucleic acid molecules encoding or providing components thereof may be delivered by a delivery system herein described both generally and in detail.

Vector delivery, e.g., plasmid, viral delivery: The CRISPR enzyme/argonaute and/or any of the present RNAs or DNAs, for instance a guide RNA, and/or the fusion protein according to the invention as described herein can be delivered using any suitable vector, e.g., plasmid or viral vectors, such as adeno associated virus (AAV), lentivirus, adenovirus or other viral vector types, or combinations thereof. CRISPR effector, fusion protein, and/or one or more guide RNAs can be packaged into one or more vectors, e.g., plasmid or viral vectors. In some embodiments, the vector, e.g., plasmid or viral vector is delivered to the tissue of interest by, for example, an intramuscular injection, while other times the delivery is via intravenous, transdermal, intranasal, oral, mucosal, or other delivery methods. Such delivery may be either via a single dose, or multiple doses. One skilled in the art understands that the actual dosage to be delivered herein may vary greatly depending upon a variety of factors, such as the vector choice, the target cell, organism, or tissue, the general condition of the subject to be treated, the degree of transformation/modification sought, the administration route, the administration mode, the type of transformation/modification sought, etc.

Such a dosage may further contain, for example, a carrier (water, saline, ethanol, glycerol, lactose, sucrose, calcium phosphate, gelatin, dextran, agar, pectin, peanut oil, sesame oil, etc.), a diluent, a pharmaceutically-acceptable carrier (e.g., phosphate-buffered saline), a pharmaceutically-acceptable excipient, and/or other compounds known in the art. The dosage may further contain one or more pharmaceutically acceptable salts such as, for example, a mineral acid salt such as a hydrochloride, a hydrobromide, a phosphate, a sulfate, etc.; and the salts of organic acids such as acetates, propionates, malonates, benzoates, etc. Additionally, auxiliary substances, such as wetting or emulsifying agents, pH buffering substances, gels or gelling materials, flavorings, colorants, microspheres, polymers, suspension agents, etc. may also be present herein. In addition, one or more other conventional pharmaceutical ingredients, such as preservatives, humectants, suspending agents, surfactants, antioxidants, anticaking agents, fillers, chelating agents, coating agents, chemical stabilizers, etc. may also be present, especially if the dosage form is a reconstitutable form. Suitable exemplary ingredients include microcrystalline cellulose, carboxymethylcellulose sodium, polysorbate 80, phenylethyl alcohol, chlorobutanol, potassium sorbate, sorbic acid, sulfur dioxide, propyl gallate, the parabens, ethyl vanillin, glycerin, phenol, parachlorophenol, gelatin, albumin and a combination thereof. A thorough discussion of pharmaceutically acceptable excipients is available in REMINGTON-S PHARMACEUTICAL SCIENCES (Mack Pub. Co., N.J. 1991) which is incorporated by reference herein.

In an embodiment herein the delivery is via an adenovirus, which may be at a single booster dose containing at least $1\times10^5$ particles (also referred to as particle units, pu) of adenoviral vector. In an embodiment herein, the dose preferably is at least about $1\times10^6$ particles (for example, about $1\times10^6$-$1\times10^{12}$ particles), more preferably at least about $1\times10^7$ particles, more preferably at least about $1\times10^8$ particles (e.g., about $1\times10^8$-$1\times10^{10}$ particles or about $1\times10^8$-$1\times10^{12}$ particles), and most preferably at least about $1\times10^{10}$ particles (e.g., about $1\times10^9$-$1\times10^{10}$ particles or about $1\times10^9$-$1\times10^{12}$ particles), or even at least about $1\times10^{10}$ particles (e.g., about $1\times10^{10}$-$1\times10^{12}$ particles) of the adenoviral vector. Alternatively, the dose comprises no more than about $1\times10^{14}$ particles, preferably no more than about $1\times10^3$ particles, even more preferably no more than about $1\times10^{12}$ particles, even more preferably no more than about $1\times10^{11}$ particles, and most preferably no more than about $1\times10^{10}$ particles (e.g., no more than about $1\times10^9$ articles). Thus, the dose may contain a single dose of adenoviral vector with, for example, about $1\times10^6$ particle units (pu), about $2\times10^6$ pu, about $4\times10^6$ pu, about $1\times10^7$ pu, about $2\times10^7$ pu, about $4\times10^7$ pu, about $1\times10^8$ pu, about $2\times10^8$ pu, about $4\times10^8$ pu, about $1\times10^9$ pu, about $2\times10^9$ pu, about $4\times10^9$ pu, about $1\times10^{10}$ pu, about $2\times10^{10}$ pu, about $4\times10^{10}$ pu, about 1×10" pu, about $2\times10^{11}$ pu, about 4×10" pu, about $1\times10^{12}$ pu, about $2\times10^{12}$ pu, or about $4\times10^{12}$ pu of adenoviral vector. See, for example, the adenoviral vectors in U.S. Pat. No. 8,454,972 B2 to Nabel, et. al., granted on Jun. 4, 2013; incorporated by reference herein, and the dosages at col 29, lines 36-58 thereof. In an embodiment herein, the adenovirus is delivered via multiple doses.

In an embodiment herein, the delivery is via an AAV. A therapeutically effective dosage for in vivo delivery of the AAV to a human is believed to be in the range of from about 20 to about 50 ml of saline solution containing from about $1\times10^{10}$ to about $1\times10^{10}$ functional AAV/ml solution. The dosage may be adjusted to balance the therapeutic benefit against any side effects. In an embodiment herein, the AAV dose is generally in the range of concentrations of from about $1\times10^5$ to $1\times10^{50}$ genomes AAV, from about $1\times10^8$ to $1\times10^{20}$ genomes AAV, from about $1\times10^{10}$ to about $1\times10^{16}$ genomes, or about $1\times10^{11}$ to about $1\times10^{16}$ genomes AAV. A human dosage may be about $1\times10^{13}$ genomes AAV. Such concentrations may be delivered in from about 0.001 ml to about 100 ml, about 0.05 to about 50 ml, or about 10 to about 25 ml of a carrier solution. Other effective dosages can be readily established by one of ordinary skill in the art through routine trials establishing dose response curves. See, for example, U.S. Pat. No. 8,404,658 B2 to Hajjar, et al., granted on Mar. 26, 2013, at col. 27, lines 45-60.

In an embodiment herein the delivery is via a plasmid. In such plasmid compositions, the dosage should be a sufficient amount of plasmid to elicit a response. For instance, suitable quantities of plasmid DNA in plasmid compositions can be from about 0.1 to about 2 mg, or from about 1 g to about 10 g per 70 kg individual. Plasmids of the invention will generally comprise (i) a promoter; (ii) a sequence encoding a CRISPR enzyme, operably linked to said promoter; (iii) a selectable marker; (iv) an origin of replication; and (v) a transcription terminator downstream of and operably linked to (ii). The plasmid can also encode the RNA components of a CRISPR complex, but one or more of these may instead be encoded on a different vector.

The doses herein are based on an average 70 kg individual. The frequency of administration is within the ambit of the medical or veterinary practitioner (e.g., physician, veterinarian), or scientist skilled in the art. It is also noted that mice used in experiments are typically about 20g and from mice experiments one can scale up to a 70 kg individual.

In some embodiments the RNA molecules of the invention are delivered in liposome or lipofectin formulations and the like and can be prepared by methods well known to those skilled in the art. Such methods are described, for example, in U.S. Pat. Nos. 5,593,972, 5,589,466, and 5,580,859, which are herein incorporated by reference. Delivery systems aimed specifically at the enhanced and improved delivery of siRNA into mammalian cells have been developed, (see, for example, Shen et al FEBS Let. 2003, 539: 111-114; Xia et al., Nat. Biotech. 2002, 20:1006-1010; Reich et al., Mol. Vision. 2003, 9: 210-216; Sorensen et al., J. Mol. Biol. 2003, 327: 761-766; Lewis et al., Nat. Gen. 2002, 32: 107-108 and Simeoni et al., NAR 2003, 31, 11: 2717-2724) and may be applied to the present invention. siRNA has recently been successfully used for inhibition of gene expression in primates (see for example. Tolentino et al., Retina 24(4):660 which may also be applied to the present invention.

Indeed, RNA delivery is a useful method of in vivo delivery. It is possible to deliver Cas9 and gRNA (and, for instance, HR repair template) into cells using liposomes or nanoparticles. Thus delivery of the CRISPR enzyme, such as a Cas9 and/or delivery of the RNAs of the invention may be in RNA form and via microvesicles, liposomes or nanoparticles. For example, Cas9 mRNA and gRNA can be packaged into liposomal particles for delivery in vivo. Liposomal transfection reagents such as lipofectamine from Life Technologies and other reagents on the market can effectively deliver RNA molecules into the liver.

Means of delivery of RNA also preferred include delivery of RNA via nanoparticles (Cho, S., Goldberg, M., Son, S., Xu, Q., Yang, F., Mei, Y., Bogatyrev, S., Langer, R. and Anderson, D., Lipid-like nanoparticles for small interfering RNA delivery to endothelial cells, Advanced Functional Materials, 19: 3112-3118, 2010) or exosomes (Schroeder, A., Levins, C., Cortez, C., Langer, R., and Anderson, D., Lipid-based nanotherapeutics for siRNA delivery, Journal of Internal Medicine, 267: 9-21, 2010, PMID: 20059641). Indeed, exosomes have been shown to be particularly useful in delivery siRNA, a system with some parallels to the CRISPR system. For instance, El-Andaloussi S, et al. ("Exosome-mediated delivery of siRNA in vitro and in vivo." Nat Protoc. 2012 December; 7(12):2112-26. doi: 10.1038/nprot.2012.131. Epub 2012 Nov 15.) describe how exosomes are promising tools for drug delivery across different biological barriers and can be harnessed for delivery of siRNA in vitro and in vivo. Their approach is to generate targeted exosomes through transfection of an expression vector, comprising an exosomal protein fused with a peptide ligand. The exosomes are then purify and characterized from transfected cell supernatant, then RNA is loaded into the exosomes. Delivery or administration according to the invention can be performed with exosomes, in particular but not limited to the brain. Vitamin E (α-tocopherol) may be conjugated with CRISPR Cas and delivered to the brain along with high density lipoprotein (HDL), for example in a similar manner as was done by Uno et al. (HUMAN GENE THERAPY 22:711-719 (June 2011)) for delivering short-interfering RNA (siRNA) to the brain. Mice were infused via Osmotic minipumps (model 1007D; Alzet, Cupertino, CA) filled with phosphate-buffered saline (PBS) or free Toc-siBACE or Toc-siBACE/HDL and connected with Brain Infusion Kit 3 (Alzet). A brain-infusion cannula was placed about 0.5 mm posterior to the bregma at midline for infusion into the dorsal third ventricle. Uno et al. found that as little as 3 nmol of Toc-siRNA with HDL could induce a target reduction in comparable degree by the same ICV infusion method. A similar dosage of CRISPR Cas9 conjugated to α-tocopherol and co-administered with HDL targeted to the brain may be contemplated for humans in the present invention, for example, about 3 nmol to about 3 μmol of CRISPR Cas9 targeted to the brain may be contemplated. Zou et al. ((HUMAN GENE THERAPY 22:465-475 (April 2011)) describes a method of lentiviral-mediated delivery of short-hairpin RNAs targeting PKC7 for in vivo gene silencing in the spinal cord of rats. Zou et al. administered about 10 μl of a recombinant lentivirus having a titer of $1\times10^9$ transducing units (TU)/ml by an intrathecal catheter. A similar dosage of CRISPR Cas9 expressed in a lentiviral vector targeted to the brain may be contemplated for humans in the present invention, for example, about 10-50 ml of CRISPR Cas targeted to the brain in a lentivirus having a titer of $1\times10^9$ transducing units (TU)/ml may be contemplated.

In terms of local delivery to the brain, this can be achieved in various ways. For instance, material can be delivered intrastriatally e.g., by injection. Injection can be performed stereotactically via a craniotomy.

Enhancing NHEJ or HR efficiency is also helpful for delivery. It is preferred that NHEJ efficiency is enhanced by co-expressing end-processing enzymes such as Trex2 (Dumitrache et al. Genetics. 2011 August; 188(4): 787-797). It is preferred that HR efficiency is increased by transiently inhibiting NHEJ machineries such as Ku70 and Ku86. HR efficiency can also be increased by co-expressing prokaryotic or eukaryotic homologous recombination enzymes such as RecBCD, RecA.

Packaging and Promoters generally

Ways to package Cas and/or fusion protein coding nucleic acid molecules, e.g., DNA, into vectors, e.g., viral vectors, to mediate genome modification in vivo include:

- To achieve NHEJ-mediated gene knockout:
- Single virus vector:
  - Vector containing two or more expression cassettes:
  - Promoter-Cas/fusion protein coding nucleic acid molecule-terminator
  - Promoter-gRNA1-terminator
  - Promoter-gRNA2-terminator
  - Promoter-gRNA(N)-terminator (up to size limit of vector)
- Double virus vector:
  - Vector 1 containing one expression cassette for driving the expression of Cas/fusion protein
  - Promoter-Cas/fusion protein coding nucleic acid molecule-terminator
  - Vector 2 containing one more expression cassettes for driving the expression of one or more guide RNAs
  - Promoter-gRNA1-terminator
  - Promoter-gRNA(N)-terminator (up to size limit of vector)
- To mediate homology-directed repair.

In addition to the single and double virus vector approaches described above, an additional vector is used to deliver a homology-direct repair template.

The promoter used to drive Cas/fusion protein coding nucleic acid molecule expression can include: AAV ITR can serve as a promoter: this is advantageous for eliminating the need for an additional promoter element (which can take up space in the vector). The additional space freed up can be used to drive the expression of additional elements (gRNA, etc.). Also, ITR activity is relatively weaker, so can be used to reduce potential toxicity due to over expression of Cas/fusion protein.

For ubiquitous expression, can use promoters: CMV, CAG, CBh, PGK, SV40, Ferritin heavy or light chains, etc.

For brain or other CNS expression, can use promoters: SynapsinI for all neurons, CaMKIIalpha for excitatory neurons, GAD67 or GAD65 or VGAT for GABAergic neurons, etc.

For liver expression, can use Albumin promoter.

For lung expression, can use SP-B.

For endothelial cells, can use ICAM.

For hematopoietic cells can use IFNbeta or CD45.

For Osteoblasts can use OG-2.

The promoter used to drive guide RNA can include:

Pol III promoters such as U6 or H1

Use of Pol II promoter and intronic cassettes to express Guide RNA

Adeno associated virus (AAV)

Cas protein, fusion protein, and one or more guide RNA can be delivered using adeno associated virus (AAV), lentivirus, adenovirus or other plasmid or viral vector types, in particular, using formulations and doses from, for example, U.S. Pat. No. 8,454,972 (formulations, doses for adenovirus), U.S. Pat. No. 8,404,658 (formulations, doses for AAV) and U.S. Pat. No. 5,846,946 (formulations, doses for DNA plasmids) and from clinical trials and publications regarding the clinical trials involving lentivirus, AAV and adenovirus. For examples, for AAV, the route of administration, formulation and dose can be as in U.S. Pat. No. 8,454,972 and as in clinical trials involving AAV. For Adenovirus, the route of administration, formulation and dose can be as in U.S. Pat. No. 8,404,658 and as in clinical trials involving adenovirus. For plasmid delivery, the route of administration, formulation and dose can be as in U.S. Pat. No. 5,846,946 and as in clinical studies involving plasmids. Doses may be based on or extrapolated to an average 70 kg individual (e.g., a male adult human), and can be adjusted for patients, subjects, mammals of different weight and species. Frequency of administration is within the ambit of the medical or veterinary practitioner (e.g., physician, veterinarian), depending on usual factors including the age, sex, general health, other conditions of the patient or subject and the particular condition or symptoms being addressed. The viral vectors can be injected into the tissue of interest. For cell-type specific genome modification, the expression of Cas9 can be driven by a cell-type specific promoter. For example, liver-specific expression might use the Albumin promoter and neuron-specific expression (e.g., for targeting CNS disorders) might use the Synapsin I promoter.

In terms of in vivo delivery, AAV is advantageous over other viral vectors for a couple of reasons:

- Low toxicity (this may be due to the purification method not requiring ultracentrifugation of cell particles that can activate the immune response) and
- Low probability of causing insertional mutagenesis because it does not integrate into the host genome.

AAV has a packaging limit of 4.5 or 4.75 Kb. This means that Cas protein as well as a promoter and transcription terminator have to be all fit into the same viral vector. Constructs larger than 4.5 or 4.75 Kb will lead to significantly reduced virus production. SpCas9 is quite large, the gene itself is over 4.1 Kb, which makes it difficult for packing into AAV. Therefore embodiments of the invention include utilizing homologs of Cas9 that are shorter. For example:

| Species | Cas9 Size |
|---|---|
| *Corynebacterium diphtheriae* | 3252 |
| *Eubacterium ventriosum* | 3321 |
| *Streptococcus pasteurianus* | 3390 |
| *Lactobacillus farciminis* | 3378 |
| *Sphaerochaeta globus* | 3537 |
| *Azospirillum* B510 | 3504 |
| *Gluconacetobacter diazotrophicus* | 3150 |
| *Neisseria cinerea* | 3246 |
| *Roseburia intestinalis* | 3420 |
| *Parvibaculum lavamentivorans* | 3111 |
| *Staphylococcus aureus* | 3159 |
| *Nitratifractor salsuginis* DSM 16511 | 3396 |
| *Campylobacter lari* CF89-12 | 3009 |
| *Streptococcus thermophilus* LMD-9 | 3396 |

These species are therefore, in general, preferred Cas9 species.

As to AAV, the AAV can be AAV1, AAV2, AAV5 or any combination thereof. One can select the AAV of the AAV with regard to the cells to be targeted; e.g., one can select AAV serotypes 1, 2, 5 or a hybrid capsid AAV1, AAV2, AAV5 or any combination thereof for targeting brain or neuronal cells; and one can select AAV4 for targeting cardiac tissue. AAV8 is useful for delivery to the liver. The herein promoters and vectors are preferred individually. A tabulation of certain AAV serotypes as to these cells (see Grimm, D. et al, J. Virol. 82: 5887-5911 (2008)) is as follows:

| Cell Line | AAV-1 | AAV-2 | AAV-3 | AAV-4 | AAV-5 | AAV-6 | AAV-8 | AAV-9 |
|---|---|---|---|---|---|---|---|---|
| Huh-7 | 13 | 100 | 2.5 | 0.0 | 0.1 | 10 | 0.7 | 0.0 |
| HEK293 | 25 | 100 | 2.5 | 0.1 | 0.1 | 5 | 0.7 | 0.1 |
| HeLa | 3 | 100 | 2.0 | 0.1 | 6.7 | 1 | 0.2 | 0.1 |
| HepG2 | 3 | 100 | 16.7 | 0.3 | 1.7 | 5 | 0.3 | ND |
| Hep1A | 20 | 100 | 0.2 | 1.0 | 0.1 | 1 | 0.2 | 0.0 |
| 911 | 17 | 100 | 11 | 0.2 | 0.1 | 17 | 0.1 | ND |
| CHO | 100 | 100 | 14 | 1.4 | 333 | 50 | 10 | 1.0 |
| COS | 33 | 100 | 33 | 3.3 | 5.0 | 14 | 2.0 | 0.5 |
| MeWo | 10 | 100 | 20 | 0.3 | 6.7 | 10 | 1.0 | 0.2 |
| NIH3T3 | 10 | 100 | 2.9 | 2.9 | 0.3 | 10 | 0.3 | ND |
| A549 | 14 | 100 | 20 | ND | 0.5 | 10 | 0.5 | 0.1 |
| HT1180 | 20 | 100 | 10 | 0.1 | 0.3 | 33 | 0.5 | 0.1 |
| Monocytes | 1111 | 100 | ND | ND | 125 | 1429 | ND | ND |
| Immature DC | 2500 | 100 | ND | ND | 222 | 2857 | ND | ND |
| Mature DC | 2222 | 100 | ND | ND | 333 | 3333 | ND | ND |

Lentivirus

Lentiviruses are complex retroviruses that have the ability to infect and express their genes in both mitotic and post-mitotic cells. The most commonly known lentivirus is the human immunodeficiency virus (HIV), which uses the envelope glycoproteins of other viruses to target a broad range of cell types.

Lentiviruses may be prepared as follows. After cloning pCasES10 (which contains a lentiviral transfer plasmid backbone), HEK293FT at low passage (p=5) were seeded in a T-75 flask to 50% confluence the day before transfection in DMEM with 10% fetal bovine serum and without antibiotics. After 20 hours, media was changed to OptiMEM (serum-free) media and transfection was done 4 hours later. Cells were transfected with 10 μg of lentiviral transfer plasmid (pCasES10) and the following packaging plasmids: 5 μg of pMD2.G (VSV-g pseudotype), and 7.5 μg of psPAX2 (gag/pol/rev/tat). Transfection was done in 4 mL OptiMEM with a cationic lipid delivery agent (50 μL Lipofectamine 2000 and 100 μl Plus reagent). After 6 hours, the media was changed to antibiotic-free DMEM with 10% fetal bovine serum. These methods use serum during cell culture, but serum-free methods are preferred.

Lentivirus may be purified as follows. Viral supernatants were harvested after 48 hours. Supernatants were first cleared of debris and filtered through a 0.45 um low protein binding (PVDF) filter. They were then spun in a ultracentrifuge for 2 hours at 24,000 rpm. Viral pellets were resuspended in 50 μl of DMEM overnight at 4° C. They were then aliquoted and immediately frozen at −80° C.

In another embodiment, minimal non-primate lentiviral vectors based on the equine infectious anemia virus (EIAV) are also contemplated, especially for ocular gene therapy (see, e.g., Balagaan, J Gene Med 2006; 8: 275-285). In another embodiment, RetinoStat®, an equine infectious anemia virus-based lentiviral gene therapy vector that expresses angiostatic proteins endostatin and angiostatin that is delivered via a subretinal injection for the treatment of the web form of age-related macular degeneration is also contemplated (see, e.g., Binley et al., HUMAN GENE THERAPY 23:980-991 (September 2012)) and this vector may be modified for the CRISPR-Cas system of the present invention.

In another embodiment, self-inactivating lentiviral vectors with an siRNA targeting a common exon shared by HIV tat/rev, a nucleolar-localizing TAR decoy, and an anti-CCR5-specific hammerhead ribozyme (see, e.g., DiGiusto et al. (2010) Sci Transl Med 2:36ra43) may be used and/or adapted to the CRISPR-Cas system of the present invention.

A minimum of $2.5\times10^6$ CD34+ cells per kilogram patient weight may be collected and prestimulated for 16 to 20 hours in X-VIVO 15 medium (Lonza) containing 2 μmol/L-glutamine, stem cell factor (100 ng/ml), Flt-3 ligand (Flt-3L) (100 ng/ml), and thrombopoietin (10 ng/ml) (CellGenix) at a density of $2\times10^6$ cells/ml. Prestimulated cells may be transduced with lentiviral at a multiplicity of infection of 5 for 16 to 24 hours in 75-$cm^2$ tissue culture flasks coated with fibronectin (25 mg/$cm^2$) (RetroNectin,Takara Bio Inc.).

Lentiviral vectors have been disclosed as in the treatment for Parkinson's Disease, see, e.g., US Patent Publication No. 20120295960 and U.S. Pat. Nos. 7,303,910 and 7,351,585. Lentiviral vectors have also been disclosed for the treatment of ocular diseases, see e.g., US Patent Publication Nos. 20060281180, 20090007284, US20110117189; US20090017543; US20070054961, US20100317109. Lentiviral vectors have also been disclosed for delivery to the brain, see, e.g., US Patent Publication Nos. US20110293571; US20110293571, US20040013648, US20070025970, US20090111106 and U.S. Pat. No. 7,259,015.

RNA Delivery

RNA delivery: The effector protein, for instance a CRISPR protein or argonaute protein, the fusion protein according to the invention as described herein, and/or any of the present RNAs, for instance a guide RNA, can also be delivered in the form of RNA. Cas/fusion protein mRNA can be generated using in vitro transcription. For example, Cas/fusion protein mRNA can be synthesized using a PCR cassette containing the following elements: T7_promoter-kozak sequence (GCCACC)-Cas or fusion protein -3' UTR from beta globin-polyA tail (a string of 120 or more adenines). The cassette can be used for transcription by T7 polymerase. Guide RNAs can also be transcribed using in vitro transcription from a cassette containing T7_promoter-GG-guide RNA sequence.

To enhance expression and reduce possible toxicity, the CRISPR enzyme-coding sequence and/or the guide RNA can be modified to include one or more modified nucleoside e.g., using pseudo-U or 5-Methyl-C.

mRNA delivery methods are especially promising for liver delivery currently.

Much clinical work on RNA delivery has focused on RNAi or antisense, but these systems can be adapted for delivery of RNA for implementing the present invention. References below to RNAi etc. should be read accordingly.

Particle Delivery Systems and/or Formulations:

Several types of particle delivery systems and/or formulations are known to be useful in a diverse spectrum of biomedical applications. In general, a particle is defined as a small object that behaves as a whole unit with respect to its transport and properties. Particles are further classified according to diameter. Coarse particles cover a range between 2,500 and 10,000 nanometers. Fine particles are sized between 100 and 2,500 nanometers. Ultrafine particles, or nanoparticles, are generally between 1 and 100 nanometers in size. The basis of the 100-nm limit is the fact that novel properties that differentiate particles from the bulk material typically develop at a critical length scale of under 100 nm.

As used herein, a particle delivery system/formulation is defined as any biological delivery system/formulation which includes a particle in accordance with the present invention. A particle in accordance with the present invention is any entity having a greatest dimension (e.g. diameter) of less than 100 microns (pm). In some embodiments, inventive particles have a greatest dimension of less than 10 μm. In some embodiments, inventive particles have a greatest dimension of less than 2000 nanometers (nm). In some embodiments, inventive particles have a greatest dimension of less than 1000 nanometers (nm). In some embodiments, inventive particles have a greatest dimension of less than 900 nm, 800 nm, 700 nm, 600 nm, 500 nm, 400 nm, 300 nm, 200 nm, or 100 nm. Typically, inventive particles have a greatest dimension (e.g., diameter) of 500 nm or less. In some embodiments, inventive particles have a greatest dimension (e.g., diameter) of 250 nm or less. In some embodiments, inventive particles have a greatest dimension (e.g., diameter) of 200 nm or less. In some embodiments, inventive particles have a greatest dimension (e.g., diameter) of 150 nm or less. In some embodiments, inventive particles have a greatest dimension (e.g., diameter) of 100 nm or less. Smaller particles, e.g., having a greatest dimension of 50 nm or less are used in some embodiments of the invention. In some embodiments, inventive particles have a greatest dimension ranging between 25 nm and 200 nm.

Particle characterization (including e.g., characterizing morphology, dimension, etc.) is done using a variety of different techniques. Common techniques are electron microscopy (TEM, SEM), atomic force microscopy (AFM), dynamic light scattering (DLS), X-ray photoelectron spectroscopy (XPS), powder X-ray diffraction (XRD), Fourier transform infrared spectroscopy (FTIR), matrix-assisted laser desorption/ionization time-of-flight mass spectrometry (MALDI-TOF), ultraviolet-visible spectroscopy, dual polarisation interferometry and nuclear magnetic resonance (NMR). Characterization (dimension measurements) may be made as to native particles (i.e., preloading) or after loading of the cargo (herein cargo refers to e.g., one or more components of CRISPR-Cas system e.g., CRISPR enzyme or mRNA or guide RNA, or any combination thereof, and may include additional carriers and/or excipients) to provide particles of an optimal size for delivery for any in vitro, ex vivo and/or in vivo application of the present invention. In certain preferred embodiments, particle dimension (e.g., diameter) characterization is based on measurements using dynamic laser scattering (DLS). Mention is made of U.S. Pat. Nos. 8,709,843; 6,007,845; 5,855,913; 5,985,309; 5,543,158; and the publication by James E. Dahlman and Carmen Barnes et al. Nature Nanotechnology (2014) published online 11 May 2014, doi:10.1038/nnano.2014.84, concerning particles, methods of making and using them and measurements thereof.

Particles delivery systems within the scope of the present invention may be provided in any form, including but not limited to solid, semi-solid, emulsion, or colloidal particles. As such any of the delivery systems described herein, including but not limited to, e.g., lipid-based systems, liposomes, micelles, microvesicles, exosomes, or gene gun may be provided as particle delivery systems within the scope of the present invention.

Particles

CRISPR enzyme mRNA, fusion protein according to the invention as described herein, and/or guide RNA may be delivered simultaneously using particles or lipid envelopes; for instance, CRISPR enzyme/fusion protein and gRNA of the invention, e.g., as a complex, can be delivered via a particle as in Dahlman et al., WO2015089419 A2 and documents cited therein, such as 7C1 (see, e.g., James E. Dahlman and Carmen Barnes et al. Nature Nanotechnology (2014) published online 11 May 2014, doi:10.1038/nnano.2014.84), e.g., delivery particle comprising lipid or lipidoid and hydrophilic polymer, e.g., cationic lipid and hydrophilic polymer, for instance wherein the cationic lipid comprises 1,2-dioleoyl-3-trimethylammonium-propane (DOTAP) or 1,2-ditetradecanoyl-sn-glycero-3-phosphocholine (DMPC) and/or wherein the hydrophilic polymer comprises ethylene glycol or polyethylene glycol (PEG); and/or wherein the particle further comprises cholesterol (e.g., particle from formulation 1=DOTAP 100, DMPC 0, PEG 0, Cholesterol 0; formulation number 2=DOTAP 90, DMPC 0, PEG 10, Cholesterol 0; formulation number 3=DOTAP 90, DMPC 0, PEG 5, Cholesterol 5), wherein particles are formed using an efficient, multistep process wherein first, effector protein and RNA are mixed together, e.g., at a 1:1 molar ratio, e.g., at room temperature, e.g., for 30 minutes, e.g., in sterile, nuclease free 1X PBS; and separately, DOTAP, DMPC, PEG, and cholesterol as applicable for the formulation are dissolved in alcohol, e.g., 100% ethanol; and, the two solutions are mixed together to form particles containing the complexes).

Nucleic acid-targeting effector proteins (such as a Type II protein such as Cas9) mRNA and guide RNA may be delivered simultaneously using particles or lipid envelopes.

For example, Su X, Fricke J, Kavanagh DG, Irvine DJ ("In vitro and in vivo mRNA delivery using lipid-enveloped pH-responsive polymer nanoparticles" Mol Pharm. 2011 Jun. 6; 8(3):774-87. doi: 10.1021/mp100390w. Epub 2011 Apr 1) describes biodegradable core-shell structured nanoparticles with a poly(O-amino ester) (PBAE) core enveloped by a phospholipid bilayer shell. These were developed for in vivo mRNA delivery. The pH-responsive PBAE component was chosen to promote endosome disruption, while the lipid surface layer was selected to minimize toxicity of the polycation core. Such are, therefore, preferred for delivering RNA of the present invention.

In one embodiment, particles based on self assembling bioadhesive polymers are contemplated, which may be applied to oral delivery of peptides, intravenous delivery of peptides and nasal delivery of peptides, all to the brain. Other embodiments, such as oral absorption and ocular delivery of hydrophobic drugs are also contemplated. The molecular envelope technology involves an engineered polymer envelope which is protected and delivered to the site of the disease (see, e.g., Mazza, M. et al. ACS Nano, 2013. 7(2): 1016-1026; Siew, A., et al. Mol Pharm, 2012. 9(1):14-28; Lalatsa, A., et al. J Contr Rel, 2012. 161(2):523-36; Lalatsa, A., et al., Mol Pharm, 2012. 9(6):1665-80; Lalatsa, A., et al. Mol Pharm, 2012. 9(6):1764-74; Garrett, N. L., et al. J Biophotonics, 2012. 5(5-6):458-68; Garrett, N. L., et al. J Raman Spect, 2012. 43(5):681-688; Ahmad, S., et al. J Royal Soc Interface 2010. 7:S423-33; Uchegbu, I. F. Expert Opin Drug Deliv, 2006. 3(5):629-40; Qu, X.,et al. Biomacromolecules, 2006. 7(12):3452-9 and Uchegbu, I. F., et al. Int J Pharm, 2001.224:185-199). Doses of about 5 mg/kg are contemplated, with single or multiple doses, depending on the target tissue.

In one embodiment, particles that can deliver RNA to a cancer cell to stop tumor growth developed by Dan Anderson's lab at MIT may be used and/or adapted to the CRISPR Cas system of the present invention. In particular, the Anderson lab developed fully automated, combinatorial systems for the synthesis, purification, characterization, and formulation of new biomaterials and nanoformulations. See, e.g., Alabi et al., Proc Natl Acad Sci USA. 2013 Aug. 6; 110(32):12881-6; Zhang et al., Adv Mater. 2013 Sep. 6; 25(33):4641-5; Jiang et al., Nano Lett. 2013 Mar. 13; 13(3):1059-64; Karagiannis et al., ACS Nano. 2012 Oct. 23; 6(10):8484-7; Whitehead et al., ACS Nano. 2012 Aug. 28; 6(8):6922-9 and Lee et al., Nat Nanotechnol. 2012 Jun. 3; 7(6):389-93. US patent application 20110293703 relates to lipidoid compounds are also particularly useful in the administration of polynucleotides, which may be applied to deliver the CRISPR Cas system of the present invention. In one aspect, the aminoalcohol lipidoid compounds are combined with an agent to be delivered to a cell or a subject to form microparticles, nanoparticles, liposomes, or micelles. The agent to be delivered by the particles, liposomes, or micelles may be in the form of a gas, liquid, or solid, and the agent may be a polynucleotide, protein, peptide, or small molecule. The aminoalcohol lipidoid compounds may be combined with other aminoalcohol lipidoid compounds, polymers (synthetic or natural), surfactants, cholesterol, carbohydrates, proteins, lipids, etc. to form the particles. These particles may then optionally be combined with a pharmaceutical excipient to form a pharmaceutical composition.

US Patent Publication No. 20110293703 also provides methods of preparing the aminoalcohol lipidoid compounds. One or more equivalents of an amine are allowed to react with one or more equivalents of an epoxide-terminated compound under suitable conditions to form an aminoalcohol lipidoid compound of the present invention. In certain embodiments, all the amino groups of the amine are fully reacted with the epoxide-terminated compound to form tertiary amines. In other embodiments, all the amino groups of the amine are not fully reacted with the epoxide-terminated compound to form tertiary amines thereby resulting in primary or secondary amines in the aminoalcohol lipidoid compound. These primary or secondary amines are left as is or may be reacted with another electrophile such as a different epoxide-terminated compound. As will be appreciated by one skilled in the art, reacting an amine with less than excess of epoxide-terminated compound will result in a plurality of different aminoalcohol lipidoid compounds with various numbers of tails. Certain amines may be fully functionalized with two epoxide-derived compound tails while other molecules will not be completely functionalized with epoxide-derived compound tails. For example, a diamine or polyamine may include one, two, three, or four epoxide-derived compound tails off the various amino moieties of the molecule resulting in primary, secondary, and tertiary amines. In certain embodiments, all the amino groups are not fully functionalized. In certain embodiments, two of the same types of epoxide-terminated compounds are used. In other embodiments, two or more different epoxide-terminated compounds are used. The synthesis of the aminoalcohol lipidoid compounds is performed with or without solvent, and the synthesis may be performed at higher temperatures ranging from 30-100° C., preferably at approximately 50-90° C. The prepared aminoalcohol lipidoid compounds may be optionally purified. For example, the mixture of aminoalcohol lipidoid compounds may be purified to yield an aminoalcohol lipidoid compound with a particular number of epoxide-derived compound tails. Or the mixture may be purified to yield a particular stereo- or regioisomer. The aminoalcohol lipidoid compounds may also be alkylated using an alkyl halide (e.g., methyl iodide) or other alkylating agent, and/or they may be acylated.

US Patent Publication No. 20110293703 also provides libraries of aminoalcohol lipidoid compounds prepared by the inventive methods. These aminoalcohol lipidoid compounds may be prepared and/or screened using high-throughput techniques involving liquid handlers, robots, microtiter plates, computers, etc. In certain embodiments, the aminoalcohol lipidoid compounds are screened for their ability to transfect polynucleotides or other agents (e.g., proteins, peptides, small molecules) into the cell.

US Patent Publication No. 20130302401 relates to a class of poly(beta-amino alcohols) (PBAAs) has been prepared using combinatorial polymerization. The inventive PBAAs may be used in biotechnology and biomedical applications as coatings (such as coatings of films or multilayer films for medical devices or implants), additives, materials, excipients, non-biofouling agents, micropatterning agents, and cellular encapsulation agents. When used as surface coatings, these PBAAs elicited different levels of inflammation, both in vitro and in vivo, depending on their chemical structures. The large chemical diversity of this class of materials allowed us to identify polymer coatings that inhibit macrophage activation in vitro. Furthermore, these coatings reduce the recruitment of inflammatory cells, and reduce fibrosis, following the subcutaneous implantation of carboxylated polystyrene microparticles. These polymers may be used to form polyelectrolyte complex capsules for cell encapsulation. The invention may also have many other biological applications such as antimicrobial coatings, DNA or siRNA delivery, and stem cell tissue engineering. The teachings of US Patent Publication No. 20130302401 may be applied to the CRISPR Cas system of the present invention.

In another embodiment, lipid nanoparticles (LNPs) are contemplated. An antitransthyretin small interfering RNA has been encapsulated in lipid nanoparticles and delivered to humans (see, e.g., Coelho et al., N Engl J Med 2013; 369:819-29), and such a system may be adapted and applied to the CRISPR Cas system of the present invention. Doses of about 0.01 to about 1 mg per kg of body weight administered intravenously are contemplated. Medications to reduce the risk of infusion-related reactions are contemplated, such as dexamethasone, acetaminophen, diphenhydramine or cetirizine, and ranitidine are contemplated. Multiple doses of about 0.3 mg per kilogram every 4 weeks for five doses are also contemplated.

LNPs have been shown to be highly effective in delivering siRNAs to the liver (see, e.g., Tabernero et al., Cancer Discovery, April 2013, Vol. 3, No. 4, pages 363-470) and are therefore contemplated for delivering RNA encoding CRISPR Cas to the liver. A dosage of about four doses of 6 mg/kg of the LNP every two weeks may be contemplated. Tabernero et al. demonstrated that tumor regression was observed after the first 2 cycles of LNPs dosed at 0.7 mg/kg, and by the end of 6 cycles the patient had achieved a partial response with complete regression of the lymph node metastasis and substantial shrinkage of the liver tumors. A complete response was obtained after 40 doses in this patient, who has remained in remission and completed treatment after receiving doses over 26 months. Two patients with RCC and extrahepatic sites of disease including kidney, lung, and lymph nodes that were progressing following prior therapy with VEGF pathway inhibitors had stable disease at all sites for approximately 8 to 12 months, and a patient with PNET and liver metastases continued on the extension study for 18 months (36 doses) with stable disease.

However, the charge of the LNP must be taken into consideration. As cationic lipids combined with negatively charged lipids to induce nonbilayer structures that facilitate intracellular delivery. Because charged LNPs are rapidly cleared from circulation following intravenous injection, ionizable cationic lipids with pKa values below 7 were developed (see, e.g., Rosin et al, Molecular Therapy, vol. 19, no. 12, pages 1286-2200, Dec. 2011). Negatively charged polymers such as RNA may be loaded into LNPs at low pH values (e.g., pH 4) where the ionizable lipids display a positive charge. However, at physiological pH values, the LNPs exhibit a low surface charge compatible with longer circulation times. Four species of ionizable cationic lipids have been focused upon, namely 1,2-dilineoyl-3-dimethylammonium-propane (DLinDAP), 1,2-dilinoleyloxy-3-N,N-dimethylaminopropane (DLinDMA), 1,2-dilinoleyloxy-keto-N,N-dimethyl-3-aminopropane (DLinKDMA), and 1,2-dilinoleyl-4-(2-dimethylaminoethyl)-[1,3]-dioxolane (DLinKC2-DMA). It has been shown that LNP siRNA systems containing these lipids exhibit remarkably different gene silencing properties in hepatocytes in vivo, with potencies varying according to the series DLinKC2-DMA>DLinKDMA>DLinDMA>>DLinDAP employing a Factor VII gene silencing model (see, e.g., Rosin et al, Molecular Therapy, vol. 19, no. 12, pages 1286-2200, Dec. 2011). A dosage of 1 g/ml of LNP or CRISPR-Cas RNA in or associated with the LNP may be contemplated, especially for a formulation containing DLinKC2-DMA.

Preparation of LNPs and CRISPR Cas encapsulation may be used and/or adapted from Rosin et al, Molecular Therapy, vol. 19, no. 12, pages 1286-2200, Dec. 2011). The cationic lipids 1,2-dilineoyl-3-dimethylammonium-propane (DLinDAP), 1,2-dilinoleyloxy-3-N,N-dimethylaminopropane (DLinDMA), 1,2-dilinoleyloxyketo-N,N-dimethyl-3-aminopropane (DLinK-DMA), 1,2-dilinoleyl-4-(2-dimethylaminoethyl)-[1,3]-dioxolane (DLinKC2-DMA), (3-o-[2"-(methoxypolyethyleneglycol 2000) succinoyl]-1,2-dimyristoyl-sn-glycol (PEG-S-DMG), and R-3-[(o-methoxy-poly(ethylene glycol)2000) carbamoyl]-1,2-dimyristyloxypropyl-3-amine (PEG-C-DOMG) may be provided by Tekmira Pharmaceuticals (Vancouver, Canada) or synthesized. Cholesterol may be purchased from Sigma (St Louis, MO). The specific CRISPR Cas RNA may be encapsulated in LNPs containing DLinDAP, DLinDMA, DLinK-DMA, and DLinKC2-DMA (cationic lipid:DSPC: CHOL: PEGS-DMG or PEG-C-DOMG at 40:10:40:10 molar ratios). When required, 0.2% SP-DiOC18 (Invitrogen, Burlington, Canada) may be incorporated to assess cellular uptake, intracellular delivery, and biodistribution. Encapsulation may be performed by dissolving lipid mixtures comprised of cationic lipid:DSPC:cholesterol:PEG-c-DOMG (40:10:40:10 molar ratio) in ethanol to a final lipid concentration of 10 mmol/1. This ethanol solution of lipid may be added drop-wise to 50 mmol/1 citrate, pH 4.0 to form multilamellar vesicles to produce a final concentration of 30% ethanol vol/vol. Large unilamellar vesicles may be formed following extrusion of multilamellar vesicles through two stacked 80 nm Nuclepore polycarbonate filters using the Extruder (Northern Lipids, Vancouver, Canada). Encapsulation may be achieved by adding RNA dissolved at 2 mg/ml in 50 mmol/1 citrate, pH 4.0 containing 30% ethanol vol/vol drop-wise to extruded preformed large unilamellar vesicles and incubation at 31° C. for 30 minutes with constant mixing to a final RNA/lipid weight ratio of 0.06/1 wt/wt. Removal of ethanol and neutralization of formulation buffer were performed by dialysis against phosphate-buffered saline (PBS), pH 7.4 for 16 hours using Spectra/Por 2 regenerated cellulose dialysis membranes. Nanoparticle size distribution may be determined by dynamic light scattering using a NICOMP 370 particle sizer, the vesicle/intensity modes, and Gaussian fitting (Nicomp Particle Sizing, Santa Barbara, CA). The particle size for all three LNP systems may be −70 nm in diameter. RNA encapsulation efficiency may be determined by removal of free RNA using VivaPureD MiniH columns (Sartorius Stedim Biotech) from samples collected before and after dialysis. The encapsulated RNA may be extracted from the eluted nanoparticles and quantified at 260 nm. RNA to lipid ratio was determined by measurement of cholesterol content in vesicles using the Cholesterol E enzymatic assay from Wako Chemicals USA (Richmond, VA). In conjunction with the herein discussion of LNPs and PEG lipids, PEGylated liposomes or LNPs are likewise suitable for delivery of a CRISPR-Cas system or components thereof.

Preparation of large LNPs may be used and/or adapted from Rosin et al, Molecular Therapy, vol. 19, no. 12, pages 1286-2200, Dec. 2011. A lipid premix solution (20.4 mg/ml total lipid concentration) may be prepared in ethanol containing DLinKC2-DMA, DSPC, and cholesterol at 50:10:38.5 molar ratios. Sodium acetate may be added to the lipid premix at a molar ratio of 0.75:1 (sodium acetate:DLinKC2-DMA). The lipids may be subsequently hydrated by combining the mixture with 1.85 volumes of citrate buffer (10 mmol/1, pH 3.0) with vigorous stirring, resulting in spontaneous liposome formation in aqueous buffer containing 35% ethanol. The liposome solution may be incubated at 37° C. to allow for time-dependent increase in particle size. Aliquots may be removed at various times during incubation to investigate changes in liposome size by dynamic light scattering (Zetasizer Nano ZS, Malvern Instruments, Worcestershire, UK). Once the desired particle size is achieved, an aqueous PEG lipid solution (stock=10 mg/ml PEG-DMG in 35% (vol/vol) ethanol) may be added to the liposome mixture to yield a final PEG molar concentration of 3.5% of total lipid. Upon addition of PEG-lipids, the liposomes should their size, effectively quenching further growth. RNA may then be added to the empty liposomes at an RNA to total lipid ratio of approximately 1:10 (wt:wt), followed by incubation for 30 minutes at 37° C. to form loaded LNPs. The mixture may be subsequently dialyzed overnight in PBS and filtered with a 0.45-am syringe filter.

Spherical Nucleic Acid (SNA™) constructs and other nanoparticles (particularly gold nanoparticles) are also contemplated as a means to delivery CRISPR-Cas system to intended targets. Significant data show that AuraSense Therapeutics' Spherical Nucleic Acid (SNA™) constructs, based upon nucleic acid-functionalized gold nanoparticles, are useful.

Literature that may be employed in conjunction with herein teachings include: Cutler et al., J. Am. Chem. Soc. 2011 133:9254-9257, Hao et al., Small. 2011 7:3158-3162, Zhang et al., ACS Nano. 2011 5:6962-6970, Cutler et al., J. Am. Chem. Soc. 2012 134:1376-1391, Young et al., Nano Lett. 2012 12:3867-71, Zheng et al., Proc. Natl. Acad. Sci. USA. 2012 109:11975-80, Mirkin, Nanomedicine 2012 7:635-638 Zhang et al., J. Am. Chem. Soc. 2012 134:16488-1691, Weintraub, Nature 2013 495:S14-S16, Choi et al., Proc. Natl. Acad. Sci. USA. 2013 110(19):7625-7630, Jensen et al., Sci. Transl. Med. 5, 209ra152 (2013) and Mirkin, et al., Small, 10:186-192.

Self-assembling nanoparticles with RNA may be constructed with polyethyleneimine (PEI) that is PEGylated with an Arg-Gly-Asp (RGD) peptide ligand attached at the distal end of the polyethylene glycol (PEG). This system has been used, for example, as a means to target tumor neovasculature expressing integrins and deliver siRNA inhibiting vascular endothelial growth factor receptor-2 (VEGF R2) expression and thereby achieve tumor angiogenesis (see, e.g., Schiffelers et al., Nucleic Acids Research, 2004, Vol. 32, No. 19). Nanoplexes may be prepared by mixing equal volumes of aqueous solutions of cationic polymer and nucleic acid to give a net molar excess of ionizable nitrogen (polymer) to phosphate (nucleic acid) over the range of 2 to 6. The electrostatic interactions between cationic polymers and nucleic acid resulted in the formation of polyplexes with average particle size distribution of about 100 nm, hence referred to here as nanoplexes. A dosage of about 100 to 200 mg of CRISPR Cas9 is envisioned for delivery in the self-assembling nanoparticles of Schiffelers et al.

The nanoplexes of Bartlett et al. (PNAS, Sep. 25, 2007, vol. 104, no. 39) may also be applied to the present invention. The nanoplexes of Bartlett et al. are prepared by mixing equal volumes of aqueous solutions of cationic polymer and nucleic acid to give a net molar excess of ionizable nitrogen (polymer) to phosphate (nucleic acid) over the range of 2 to 6. The electrostatic interactions between cationic polymers and nucleic acid resulted in the formation of polyplexes with average particle size distribution of about 100 nm, hence referred to here as nanoplexes. The DOTA-siRNA of Bartlett et al. was synthesized as follows: 1,4,7,10-tetraazacyclododecane-1,4,7,10-tetraacetic acid mono(N-hydroxysuccinimide ester) (DOTA-NHS ester) was ordered from Macrocyclics (Dallas, TX). The amine modified RNA sense strand with a 100-fold molar excess of DOTA-NHS-ester in carbonate buffer (pH 9) was added to a microcentrifuge tube. The contents were reacted by stirring for 4 h at room temperature. The DOTA-RNAsense conjugate was ethanol-precipitated, resuspended in water, and annealed to the unmodified antisense strand to yield DOTA-siRNA. All liquids were pretreated with Chelex-100 (Bio-Rad, Hercules, CA) to remove trace metal contaminants. Tf-targeted and nontargeted siRNA nanoparticles may be formed by using cyclodextrin-containing polycations. Typically, nanoparticles were formed in water at a charge ratio of 3 (+/−) and an siRNA concentration of 0.5 g/liter. One percent of the adamantane-PEG molecules on the surface of the targeted nanoparticles were modified with Tf (adamantane-PEG-Tf). The nanoparticles were suspended in a 5% (wt/vol) glucose carrier solution for injection.

Davis et al. (Nature, Vol 464, 15 Apr. 2010) conducts a RNA clinical trial that uses a targeted nanoparticle-delivery system (clinical trial registration number NCT00689065). Patients with solid cancers refractory to standard-of-care therapies are administered doses of targeted nanoparticles on days 1, 3, 8 and 10 of a 21-day cycle by a 30-min intravenous infusion. The nanoparticles comprise, consist essentially of, or consist of a synthetic delivery system containing: (1) a linear, cyclodextrin-based polymer (CDP), (2) a human transferrin protein (TF) targeting ligand displayed on the exterior of the nanoparticle to engage TF receptors (TFR) on the surface of the cancer cells, (3) a hydrophilic polymer (polyethylene glycol (PEG) used to promote nanoparticle stability in biological fluids), and (4) siRNA designed to reduce the expression of the RRM2 (sequence used in the clinic was previously denoted siR2B+5). The TFR has long been known to be upregulated in malignant cells, and RRM2 is an established anti-cancer target. These nanoparticles (clinical version denoted as CALAA-01) have been shown to be well tolerated in multi-dosing studies in non-human primates. Although a single patient with chronic myeloid leukaemia has been administered siRNA by liposomal delivery, Davis et al.'s clinical trial is the initial human trial to systemically deliver siRNA with a targeted delivery system and to treat patients with solid cancer. To ascertain whether the targeted delivery system can provide effective delivery of functional siRNA to human tumors, Davis et al. investigated biopsies from three patients from three different dosing cohorts; patients A, B and C, all of whom had metastatic melanoma and received CALAA-01 doses of 18, 24 and 30 mg $m^{-2}$ siRNA, respectively. Similar doses may also be contemplated for the CRISPR Cas system of the present invention. The delivery of the invention may be achieved with nanoparticles containing a linear, cyclodextrin-based polymer (CDP), a human transferrin protein (TF) targeting ligand displayed on the exterior of the nanoparticle to engage TF receptors (TFR) on the surface of the cancer cells and/or a hydrophilic polymer (for example, polyethylene glycol (PEG) used to promote nanoparticle stability in biological fluids).

In terms of this invention, it is preferred to have one or more components of CRISPR complex, e.g., CRISPR enzyme, fusion protein according to the invention as described herein or mRNA or guide RNA delivered using nanoparticles or lipid envelopes. Other delivery systems or vectors are may be used in conjunction with the nanoparticle aspects of the invention.

In general, a "nanoparticle" refers to any particle having a diameter of less than 1000 nm. In certain preferred embodiments, nanoparticles of the invention have a greatest dimension (e.g., diameter) of 500 nm or less. In other preferred embodiments, nanoparticles of the invention have a greatest dimension ranging between 25 nm and 200 nm. In other preferred embodiments, nanoparticles of the invention have a greatest dimension of 100 nm or less. In other preferred embodiments, nanoparticles of the invention have a greatest dimension ranging between 35 nm and 60 nm.

Nanoparticles encompassed in the present invention may be provided in different forms, e.g., as solid nanoparticles (e.g., metal such as silver, gold, iron, titanium), non-metal, lipid-based solids, polymers), suspensions of nanoparticles, or combinations thereof. Metal, dielectric, and semiconductor nanoparticles may be prepared, as well as hybrid structures (e.g., core-shell nanoparticles). Nanoparticles made of semiconducting material may also be labeled quantum dots if they are small enough (typically sub 10 nm) that quantization of electronic energy levels occurs. Such nanoscale particles are used in biomedical applications as drug carriers or imaging agents and may be adapted for similar purposes in the present invention.

Semi-solid and soft nanoparticles have been manufactured, and are within the scope of the present invention. A prototype nanoparticle of semi-solid nature is the liposome. Various types of liposome nanoparticles are currently used clinically as delivery systems for anticancer drugs and vaccines. Nanoparticles with one half hydrophilic and the other half hydrophobic are termed Janus particles and are particularly effective for stabilizing emulsions. They can self-assemble at water/oil interfaces and act as solid surfactants.

U.S. Pat. No. 8,709,843, incorporated herein by reference, provides a drug delivery system for targeted delivery of therapeutic agent-containing particles to tissues, cells, and intracellular compartments. The invention provides targeted particles comprising polymer conjugated to a surfactant, hydrophilic polymer or lipid.

U.S. Pat. No. 6,007,845, incorporated herein by reference, provides particles which have a core of a multiblock copolymer formed by covalently linking a multifunctional compound with one or more hydrophobic polymers and one or more hydrophilic polymers, and contain a biologically active material.

U.S. Pat. No. 5,855,913, incorporated herein by reference, provides a particulate composition having aerodynamically light particles having a tap density of less than 0.4 g/cm3 with a mean diameter of between 5 μm and 30 μm, incorporating a surfactant on the surface thereof for drug delivery to the pulmonary system.

U.S. Pat. No. 5,985,309, incorporated herein by reference, provides particles incorporating a surfactant and/or a hydrophilic or hydrophobic complex of a positively or negatively charged therapeutic or diagnostic agent and a charged molecule of opposite charge for delivery to the pulmonary system.

U.S. Pat. No. 5,543,158, incorporated herein by reference, provides biodegradable injectable nanoparticles having a biodegradable solid core containing a biologically active material and poly(alkylene glycol) moieties on the surface.

WO2012135025 (also published as US20120251560), incorporated herein by reference, describes conjugated polyethyleneimine (PEI) polymers and conjugated aza-macrocycles (collectively referred to as "conjugated lipomer" or "lipomers"). In certain embodiments, it can envisioned that such conjugated lipomers can be used in the context of the CRISPR-Cas system to achieve in vitro, ex vivo and in vivo genomic perturbations to modify gene expression, including modulation of protein expression.

In one embodiment, the nanoparticle may be epoxide-modified lipid-polymer, advantageously 7C1 (see, e.g., James E. Dahlman and Carmen Barnes et al. Nature Nanotechnology (2014) published online 11 May 2014, doi: 10.1038/nnano.2014.84). C71 was synthesized by reacting C15 epoxide-terminated lipids with PEI600 at a 14:1 molar ratio, and was formulated with C14PEG2000 to produce nanoparticles (diameter between 35 and 60 nm) that were stable in PBS solution for at least 40 days.

An epoxide-modified lipid-polymer may be utilized to deliver the CRISPR-Cas system of the present invention to pulmonary, cardiovascular or renal cells, however, one of skill in the art may adapt the system to deliver to other target organs. Dosage ranging from about 0.05 to about 0.6 mg/kg are envisioned. Dosages over several days or weeks are also envisioned, with a total dosage of about 2 mg/kg.

Exosomes

Exosomes are endogenous nano-vesicles that transport RNAs and proteins, and which can deliver RNA to the brain and other target organs. To reduce immunogenicity, Alvarez-Erviti et al. (2011, Nat Biotechnol 29: 341) used self-derived dendritic cells for exosome production. Targeting to the brain was achieved by engineering the dendritic cells to express Lamp2b, an exosomal membrane protein, fused to the neuron-specific RVG peptide. Purified exosomes were loaded with exogenous RNA by electroporation. Intravenously injected RVG-targeted exosomes delivered GAPDH siRNA specifically to neurons, microglia, oligodendrocytes in the brain, resulting in a specific gene knockdown. Pre-exposure to RVG exosomes did not attenuate knockdown, and non-specific uptake in other tissues was not observed. The therapeutic potential of exosome-mediated siRNA delivery was demonstrated by the strong mRNA (60%) and protein (62%) knockdown of BACE1, a therapeutic target in Alzheimer's disease.

To obtain a pool of immunologically inert exosomes, Alvarez-Erviti et al. harvested bone marrow from inbred C57BL/6 mice with a homogenous major histocompatibility complex (MHC) haplotype. As immature dendritic cells produce large quantities of exosomes devoid of T-cell activators such as MHC-II and CD86, Alvarez-Erviti et al. selected for dendritic cells with granulocyte/macrophage-colony stimulating factor (GM-CSF) for 7 d. Exosomes were purified from the culture supernatant the following day using well-established ultracentrifugation protocols. The exosomes produced were physically homogenous, with a size distribution peaking at 80 nm in diameter as determined by nanoparticle tracking analysis (NTA) and electron microscopy. Alvarez-Erviti et al. obtained 6-12 μg of exosomes (measured based on protein concentration) per $10^6$ cells.

Next, Alvarez-Erviti et al. investigated the possibility of loading modified exosomes with exogenous cargoes using electroporation protocols adapted for nanoscale applications. As electroporation for membrane particles at the nanometer scale is not well-characterized, nonspecific Cy5-labeled RNA was used for the empirical optimization of the electroporation protocol. The amount of encapsulated RNA was assayed after ultracentrifugation and lysis of exosomes. Electroporation at 400 V and 125 μF resulted in the greatest retention of RNA and was used for all subsequent experiments.

Alvarez-Erviti et al. administered 150 μg of each BACE1 siRNA encapsulated in 150 μg of RVG exosomes to normal C57BL/6 mice and compared the knockdown efficiency to four controls: untreated mice, mice injected with RVG exosomes only, mice injected with BACE1 siRNA complexed to an in vivo cationic liposome reagent and mice injected with BACE1 siRNA complexed to RVG-9R, the RVG peptide conjugated to 9 D-arginines that electrostatically binds to the siRNA. Cortical tissue samples were analyzed 3 d after administration and a significant protein knockdown (45%, $P<0.05$, versus 62%, $P<0.01$) in both siRNA-RVG-9R-treated and siRNA-RVG exosome-treated mice was observed, resulting from a significant decrease in BACE1 mRNA levels (66% [+ or -]15%, $P<0.001$ and 61% [+ or -]13% respectively, $P<0.01$). Moreover, Applicants demonstrated a significant decrease (55%, $P<0.05$) in the total [beta]-amyloid 1-42 levels, a main component of the amyloid plaques in Alzheimer's pathology, in the RVG-exosome-treated animals. The decrease observed was greater than the β-amyloid 1-40 decrease demonstrated in normal mice after intraventricular injection of BACE1 inhibitors. Alvarez-Erviti et al. carried out 5'-rapid amplification of cDNA ends (RACE) on BACE1 cleavage product, which provided evidence of RNAi-mediated knockdown by the siRNA.

Finally, Alvarez-Erviti et al. investigated whether RNA-RVG exosomes induced immune responses in vivo by assessing IL-6, IP-10, TNFα and IFN-α serum concentrations. Following exosome treatment, nonsignificant changes in all cytokines were registered similar to siRNA-transfection reagent treatment in contrast to siRNA-RVG-9R, which potently stimulated IL-6 secretion, confirming the immunologically inert profile of the exosome treatment. Given that exosomes encapsulate only 20% of siRNA, delivery with RVG-exosome appears to be more efficient than RVG-9R delivery as comparable mRNA knockdown and greater protein knockdown was achieved with fivefold less siRNA without the corresponding level of immune stimulation. This experiment demonstrated the therapeutic potential of RVG-exosome technology, which is potentially suited for long-term silencing of genes related to neurodegenerative diseases. The exosome delivery system of Alvarez-Erviti et al. may be applied to deliver the CRISPR-Cas system of the present invention to therapeutic targets, especially neurodegenerative diseases. A dosage of about 100 to 1000 mg of CRISPR Cas9 encapsulated in about 100 to 1000 mg of RVG exosomes may be contemplated for the present invention.

El-Andaloussi et al. (Nature Protocols 7,2112-2126 (2012)) discloses how exosomes derived from cultured cells can be harnessed for delivery of RNA in vitro and in vivo. This protocol first describes the generation of targeted exosomes through transfection of an expression vector, comprising an exosomal protein fused with a peptide ligand. Next, El-Andaloussi et al. explain how to purify and characterize exosomes from transfected cell supernatant. Next, El-Andaloussi et al. detail crucial steps for loading RNA into exosomes. Finally, El-Andaloussi et al. outline how to use exosomes to efficiently deliver RNA in vitro and in vivo in mouse brain. Examples of anticipated results in which exosome-mediated RNA delivery is evaluated by functional assays and imaging are also provided. The entire protocol takes ~3 weeks. Delivery or administration according to the invention may be performed using exosomes produced from self-derived dendritic cells. From the herein teachings, this can be employed in the practice of the invention.

In another embodiment, the plasma exosomes of Wahlgren et al. (Nucleic Acids Research, 2012, Vol. 40, No. 17 e130) are contemplated. Exosomes are nano-sized vesicles (30-90 nm in size) produced by many cell types, including dendritic cells (DC), B cells, T cells, mast cells, epithelial cells and tumor cells. These vesicles are formed by inward budding of late endosomes and are then released to the extracellular environment upon fusion with the plasma membrane. Because exosomes naturally carry RNA between cells, this property may be useful in gene therapy, and from this disclosure can be employed in the practice of the instant invention.

Exosomes from plasma can be prepared by centrifugation of buffy coat at 900 μg for 20 min to isolate the plasma followed by harvesting cell supernatants, centrifuging at 300 μg for 10 min to eliminate cells and at 16 500 μg for 30 min followed by filtration through a 0.22 mm filter. Exosomes are pelleted by ultracentrifugation at 120 000 μg for 70 min. Chemical transfection of siRNA into exosomes is carried out according to the manufacturer's instructions in RNAi Human/Mouse Starter Kit (Qiagen, Hilden, Germany). siRNA is added to 100 ml PBS at a final concentration of 2 mmol/ml. After adding HiPerFect transfection reagent, the mixture is incubated for 10 min at RT. In order to remove the excess of micelles, the exosomes are re-isolated using aldehyde/sulfate latex beads. The chemical transfection of CRISPR Cas9 into exosomes may be conducted similarly to siRNA. The exosomes may be co-cultured with monocytes and lymphocytes isolated from the peripheral blood of healthy donors. Therefore, it may be contemplated that exosomes containing CRISPR Cas9 may be introduced to monocytes and lymphocytes of and autologously reintroduced into a human. Accordingly, delivery or administration according to the invention may be performed using plasma exosomes.

Liposomes

Delivery or administration according to the invention can be performed with liposomes. Liposomes are spherical vesicle structures composed of a uni- or multilamellar lipid bilayer surrounding internal aqueous compartments and a relatively impermeable outer lipophilic phospholipid bilayer. Liposomes have gained considerable attention as drug delivery carriers because they are biocompatible, nontoxic, can deliver both hydrophilic and lipophilic drug molecules, protect their cargo from degradation by plasma enzymes, and transport their load across biological membranes and the blood brain barrier (BBB) (see, e.g., Spuch and Navarro, Journal of Drug Delivery, vol. 2011, Article ID 469679, 12 pages, 2011. doi:10.1155/2011/469679 for review).

Liposomes can be made from several different types of lipids; however, phospholipids are most commonly used to generate liposomes as drug carriers. Although liposome formation is spontaneous when a lipid film is mixed with an aqueous solution, it can also be expedited by applying force in the form of shaking by using a homogenizer, sonicator, or an extrusion apparatus (see, e.g., Spuch and Navarro, Journal of Drug Delivery, vol. 2011, Article ID 469679, 12 pages, 2011. doi:10.1155/2011/469679 for review).

Several other additives may be added to liposomes in order to modify their structure and properties. For instance, either cholesterol or sphingomyelin may be added to the liposomal mixture in order to help stabilize the liposomal structure and to prevent the leakage of the liposomal inner cargo. Further, liposomes are prepared from hydrogenated egg phosphatidylcholine or egg phosphatidylcholine, cholesterol, and dicetyl phosphate, and their mean vesicle sizes were adjusted to about 50 and 100 nm. (see, e.g., Spuch and Navarro, Journal of Drug Delivery, vol. 2011, Article ID 469679, 12 pages, 2011. doi:10.1155/2011/469679 for review).

A liposome formulation may be mainly comprised of natural phospholipids and lipids such as 1,2-distearoyl-sn-glycero-3-phosphatidyl choline (DSPC), sphingomyelin, egg phosphatidylcholines and monosialoganglioside. Since this formulation is made up of phospholipids only, liposomal formulations have encountered many challenges, one of the ones being the instability in plasma. Several attempts to overcome these challenges have been made, specifically in the manipulation of the lipid membrane. One of these attempts focused on the manipulation of cholesterol. Addition of cholesterol to conventional formulations reduces rapid release of the encapsulated bioactive compound into the plasma or 1,2-dioleoyl-sn-glycero-3-phosphoethanolamine (DOPE) increases the stability (see, e.g., Spuch and Navarro, Journal of Drug Delivery, vol. 2011, Article ID 469679, 12 pages, 2011. doi:10.1155/2011/469679 for review).

In a particularly advantageous embodiment, Trojan Horse liposomes (also known as Molecular Trojan Horses) are desirable and protocols may be found at cshprotocols.cshlp.org/content/2010/4/pdb.prot5407.long. These particles allow delivery of a transgene to the entire brain after an intravascular injection. Without being bound by limitation, it is believed that neutral lipid particles with specific antibodies conjugated to surface allow crossing of the blood brain barrier via endocytosis. Applicant postulates utilizing Trojan Horse Liposomes to deliver the CRISPR family of nucleases to the brain via an intravascular injection, which would allow whole brain transgenic animals without the need for embryonic manipulation. About 1-5 g of DNA or RNA may be contemplated for in vivo administration in liposomes.

In another embodiment, the CRISPR Cas system or components thereof may be administered in liposomes, such as a stable nucleic-acid-lipid particle (SNALP) (see, e.g., Morrissey et al., Nature Biotechnology, Vol. 23, No. 8, August 2005). Daily intravenous injections of about 1, 3 or 5 mg/kg/day of a specific CRISPR Cas targeted in a SNALP are contemplated. The daily treatment may be over about three days and then weekly for about five weeks. In another embodiment, a specific CRISPR Cas encapsulated SNALP) administered by intravenous injection to at doses of about 1 or 2.5 mg/kg are also contemplated (see, e.g., Zimmerman et al., Nature Letters, Vol. 441, 4 May 2006). The SNALP formulation may contain the lipids 3-N-[(methoxypoly(ethylene glycol) 2000) carbamoyl]-1,2-dimyristyloxy-propylamine (PEG-C-DMA), 1,2-dilinoleyloxy-N,N-dimethyl-3-aminopropane (DLinDMA), 1,2-distearoyl-sn-glycero-3-phosphocholine (DSPC) and cholesterol, in a 2:40:10:48 molar percent ratio (see, e.g., Zimmerman et al., Nature Letters, Vol. 441, 4 May 2006).

In another embodiment, stable nucleic-acid-lipid particles (SNALPs) have proven to be effective delivery molecules to highly vascularized HepG2-derived liver tumors but not in poorly vascularized HCT-116 derived liver tumors (see, e.g., Li, Gene Therapy (2012) 19, 775-780). The SNALP liposomes may be prepared by formulating D-Lin-DMA and PEG-C-DMA with distearoylphosphatidylcholine (DSPC), Cholesterol and siRNA using a 25:1 lipid/siRNA ratio and a 48/40/10/2 molar ratio of Cholesterol/D-Lin-DMA/DSPC/PEG-C-DMA. The resulted SNALP liposomes are about 80-100 nm in size.

In yet another embodiment, a SNALP may comprise synthetic cholesterol (Sigma-Aldrich, St Louis, MO, USA), dipalmitoylphosphatidylcholine (Avanti Polar Lipids, Alabaster, AL, USA), 3-N-[(methoxypoly poly(ethylene glycol) 2000)carbamoyl]-1,2-dimyristyloxypropylamine, and cationic 1,2-dilinoleyloxy-3-N,N-dimethylaminopropane (see, e.g., Geisbert et al., Lancet 2010; 375: 1896-905). A dosage of about 2 mg/kg total CRISPR Cas9 per dose administered as, for example, a bolus intravenous infusion may be contemplated.

In yet another embodiment, a SNALP may comprise synthetic cholesterol (Sigma-Aldrich), 1,2-distearoyl-sn-glycero-3-phosphocholine (DSPC; Avanti Polar Lipids Inc.), PEG-cDMA, and 1,2-dilinoleyloxy-3-(N,N-dimethyl)aminopropane (DLinDMA) (see, e.g., Judge, J. Clin. Invest. 119:661-673 (2009)). Formulations used for in vivo studies may comprise a final lipid/RNA mass ratio of about 9:1.

The safety profile of RNAi nanomedicines has been reviewed by Barros and Gollob of Alnylam Pharmaceuticals (see, e.g., Advanced Drug Delivery Reviews 64 (2012) 1730-1737). The stable nucleic acid lipid particle (SNALP) is comprised of four different lipids an ionizable lipid (DLinDMA) that is cationic at low pH, a neutral helper lipid, cholesterol, and a diffusible polyethylene glycol (PEG)-lipid. The particle is approximately 80 nm in diameter and is charge-neutral at physiologic pH. During formulation, the ionizable lipid serves to condense lipid with the anionic RNA during particle formation. When positively charged under increasingly acidic endosomal conditions, the ionizable lipid also mediates the fusion of SNALP with the endosomal membrane enabling release of RNA into the cytoplasm. The PEG-lipid stabilizes the particle and reduces aggregation during formulation, and subsequently provides a neutral hydrophilic exterior that improves pharmacokinetic properties.

To date, two clinical programs have been initiated using SNALP formulations with RNA. Tekmira Pharmaceuticals recently completed a phase I single-dose study of SNALP-ApoB in adult volunteers with elevated LDL cholesterol. ApoB is predominantly expressed in the liver and jejunum and is essential for the assembly and secretion of VLDL and LDL. Seventeen subjects received a single dose of SNALP-ApoB (dose escalation across 7 dose levels). There was no evidence of liver toxicity (anticipated as the potential dose-limiting toxicity based on preclinical studies). One (of two) subjects at the highest dose experienced flu-like symptoms consistent with immune system stimulation, and the decision was made to conclude the trial.

Alnylam Pharmaceuticals has similarly advanced ALN-TTRO1, which employs the SNALP technology described above and targets hepatocyte production of both mutant and wild-type TTR to treat TTR amyloidosis (ATTR). Three ATTR syndromes have been described: familial amyloidotic polyneuropathy (FAP) and familial amyloidotic cardiomyopathy (FAC) both caused by autosomal dominant mutations in TTR; and senile systemic amyloidosis (SSA) cause by wildtype TTR. A placebo-controlled, single dose-escalation phase I trial of ALN-TTRO1 was recently completed in patients with ATTR. ALN-TTRO1 was administered as a 15-minute IV infusion to 31 patients (23 with study drug and 8 with placebo) within a dose range of 0.01 to 1.0 mg/kg (based on siRNA). Treatment was well tolerated with no significant increases in liver function tests. Infusion-related reactions were noted in 3 of 23 patients at>0.4 mg/kg; all responded to slowing of the infusion rate and all continued on study. Minimal and transient elevations of serum cytokines IL-6, IP-10 and IL-lra were noted in two patients at the highest dose of 1 mg/kg (as anticipated from preclinical and NHP studies). Lowering of serum TTR, the expected pharmacodynamics effect of ALN-TTR01, was observed at 1 mg/kg.

In yet another embodiment, a SNALP may be made by solubilizing a cationic lipid, DSPC, cholesterol and PEG-lipid e.g., in ethanol, e.g., at a molar ratio of 40:10:40:10, respectively (see, Semple et al., Nature Biotechnology, Volume 28 Number 2 Feb. 2010, pp. 172-177). The lipid mixture was added to an aqueous buffer (50 mM citrate, pH 4) with mixing to a final ethanol and lipid concentration of 30% (vol/vol) and 6.1 mg/ml, respectively, and allowed to equilibrate at 22° C. for 2 min before extrusion. The hydrated lipids were extruded through two stacked 80 nm pore-sized filters (Nuclepore) at 22° C. using a Lipex Extruder (Northern Lipids) until a vesicle diameter of 70-90 nm, as determined by dynamic light scattering analysis, was obtained. This generally required 1-3 passes. The siRNA (solubilized in a 50 mM citrate, pH 4 aqueous solution containing 30% ethanol) was added to the pre-equilibrated (35° C.) vesicles at a rate of −5 ml/min with mixing. After a final target siRNA/lipid ratio of 0.06 (wt/wt) was reached, the mixture was incubated for a further 30 min at 35° C. to allow vesicle reorganization and encapsulation of the siRNA. The ethanol was then removed and the external buffer replaced with PBS (155 mM NaCl, 3 mM $Na_2HPO_4$, 1 mM $KH_2PO_4$, pH 7.5) by either dialysis or tangential flow diafiltration. siRNA were encapsulated in SNALP using a controlled step-wise dilution method process. The lipid constituents of KC2-SNALP were DLin-KC2-DMA (cationic lipid), dipalmitoylphosphatidylcholine (DPPC; Avanti Polar Lipids), synthetic cholesterol (Sigma) and PEG-C-DMA used at a molar ratio of 57.1:7.1:34.3:1.4. Upon formation of the loaded particles, SNALP were dialyzed against PBS and filter sterilized through a 0.2 m filter before use. Mean particle sizes were 75-85 nm and 90-95% of the siRNA was encapsulated within the lipid particles. The final siRNA/lipid ratio in formulations used for in vivo testing was −0.15 (wt/wt). LNP-siRNA systems containing Factor VII siRNA were diluted to the appropriate concentrations in sterile PBS immediately before use and the formulations were administered intravenously through the lateral tail vein in a total volume of 10 ml/kg. This method and these delivery systems may be extrapolated to the CRISPR Cas9 system of the present invention.

Other Lipids

Other cationic lipids, such as amino lipid 2,2-dilinoleyl-4-dimethylaminoethyl-[1,3]-dioxolane (DLin-KC2-DMA) may be utilized to encapsulate CRISPR Cas9 or components thereof or nucleic acid molecule(s) coding therefor e.g., similar to SiRNA (see, e.g., Jayaraman, Angew. Chem. Int. Ed. 2012, 51, 8529-8533), and hence may be employed in the practice of the invention. A preformed vesicle with the following lipid composition may be contemplated: amino lipid, distearoylphosphatidylcholine (DSPC), cholesterol and (R)-2,3-bis(octadecyloxy) propyl-1-(methoxy poly(ethylene glycol)2000)propylcarbamate (PEG-lipid) in the molar ratio 40/10/40/10, respectively, and a FVII siRNA/total lipid ratio of approximately 0.05 (w/w). To ensure a narrow particle size distribution in the range of 70-90 nm and a low polydispersity index of 0.11±0.04 (n=56), the particles may be extruded up to three times through 80 nm membranes prior to adding the guide RNA. Particles containing the highly potent amino lipid 16 may be used, in which the molar ratio of the four lipid components 16, DSPC, cholesterol and PEG-lipid (50/10/38.5/1.5) which may be further optimized to enhance in vivo activity.

Michael S D Kormann et al. ("Expression of therapeutic proteins after delivery of chemically modified mRNA in mice: Nature Biotechnology, Volume: 29, Pages: 154-157 (2011)) describes the use of lipid envelopes to deliver RNA. Use of lipid envelopes is also preferred in the present invention.

In another embodiment, lipids may be formulated with the CRISPR Cas system of the present invention or component (s) thereof or nucleic acid molecule(s) coding therefor to form lipid nanoparticles (LNPs). Lipids include, but are not limited to, DLin-KC2-DMA4, C12-200 and colipids distearoylphosphatidyl choline, cholesterol, and PEG-DMG may be formulated with CRISPR Cas instead of siRNA (see, e.g., Novobrantseva, Molecular Therapy-Nucleic Acids (2012) 1, e4; doi:10.1038/mtna.2011.3) using a spontaneous vesicle formation procedure. The component molar ratio may be about 50/10/38.5/1.5 (DLin-KC2-DMA or C12-200/distearoylphosphatidyl choline/cholesterol/PEG-DMG). The final lipid:siRNA weight ratio may be-12:1 and 9:1 in the case of DLin-KC2-DMA and C12-200 lipid nanoparticles (LNPs), respectively. The formulations may have mean particle diameters of −80 nm with >90% entrapment efficiency. A 3 mg/kg dose may be contemplated.

Tekmira has a portfolio of approximately 95 patent families, in the U.S. and abroad, that are directed to various aspects of LNPs and LNP formulations (see, e.g., U.S. Pat. Nos. 7,982,027; 7,799,565; 8,058,069; 8,283,333; 7,901,708; 7,745,651; 7,803,397; 8,101,741; 8,188,263; 7,915,399; 8,236,943 and 7,838,658 and European Pat. Nos 1766035; 1519714; 1781593 and 1664316), all of which may be used and/or adapted to the present invention.

The CRISPR Cas system or components thereof or nucleic acid molecule(s) coding therefor may be delivered encapsulated in PLGA Microspheres such as that further described in US published applications 20130252281 and 20130245107 and 20130244279 (assigned to Moderna Therapeutics) which relate to aspects of formulation of compositions comprising modified nucleic acid molecules which may encode a protein, a protein precursor, or a partially or fully processed form of the protein or a protein precursor. The formulation may have a molar ratio 50:10:38.5:1.5-3.0 (cationic lipid:fusogenic lipid:cholesterol:PEG lipid). The PEG lipid may be selected from, but is not limited to PEG-c-DOMG, PEG-DMG. The fusogenic lipid may be DSPC. See also, Schrum et al., Delivery and Formulation of Engineered Nucleic Acids, US published application 20120251618.

Nanomerics' technology addresses bioavailability challenges for a broad range of therapeutics, including low molecular weight hydrophobic drugs, peptides, and nucleic acid based therapeutics (plasmid, siRNA, miRNA). Specific administration routes for which the technology has demonstrated clear advantages include the oral route, transport across the blood-brain-barrier, delivery to solid tumors, as well as to the eye. See, e.g., Mazza et al., 2013, ACS Nano. 2013 Feb. 26; 7(2):1016-26; Uchegbu and Siew, 2013, J Pharm Sci. 102(2):305-10 and Lalatsa et al., 2012, J Control Release. 2012 Jul. 20; 161(2):523-36.

US Patent Publication No. 20050019923 describes cationic dendrimers for delivering bioactive molecules, such as polynucleotide molecules, peptides and polypeptides and/or pharmaceutical agents, to a mammalian body. The dendrimers are suitable for targeting the delivery of the bioactive molecules to, for example, the liver, spleen, lung, kidney or heart (or even the brain). Dendrimers are synthetic 3-dimensional macromolecules that are prepared in a step-wise fashion from simple branched monomer units, the nature and functionality of which can be easily controlled and varied. Dendrimers are synthesized from the repeated addition of building blocks to a multifunctional core (divergent approach to synthesis), or towards a multifunctional core (convergent approach to synthesis) and each addition of a 3-dimensional shell of building blocks leads to the formation of a higher generation of the dendrimers. Polypropylenimine dendrimers start from a diaminobutane core to which is added twice the number of amino groups by a double Michael addition of acrylonitrile to the primary amines followed by the hydrogenation of the nitriles. This results in a doubling of the amino groups. Polypropylenimine dendrimers contain 100% protonable nitrogens and up to 64 terminal amino groups (generation 5, DAB 64). Protonable groups are usually amine groups which are able to accept protons at neutral pH. The use of dendrimers as gene delivery agents has largely focused on the use of the polyamidoamine. and phosphorous containing compounds with a mixture of amine/amide or N—P($O_2$)S as the conjugating units respectively with no work being reported on the use of the lower generation polypropylenimine dendrimers for gene delivery. Polypropylenimine dendrimers have also been studied as pH sensitive controlled release systems for drug delivery and for their encapsulation of guest molecules when chemically modified by peripheral amino acid groups. The cytotoxicity and interaction of polypropylenimine dendrimers with DNA as well as the transfection efficacy of DAB 64 has also been studied.

US Patent Publication No. 20050019923 is based upon the observation that, contrary to earlier reports, cationic dendrimers, such as polypropylenimine dendrimers, display suitable properties, such as specific targeting and low toxicity, for use in the targeted delivery of bioactive molecules, such as genetic material. In addition, derivatives of the cationic dendrimer also display suitable properties for the targeted delivery of bioactive molecules. See also, Bioactive Polymers, US published application 20080267903, which discloses "Various polymers, including cationic polyamine polymers and dendrimeric polymers, are shown to possess anti-proliferative activity, and may therefore be useful for treatment of disorders characterised by undesirable cellular proliferation such as neoplasms and tumors, inflammatory disorders (including autoimmune disorders), psoriasis and atherosclerosis. The polymers may be used alone as active agents, or as delivery vehicles for other therapeutic agents, such as drug molecules or nucleic acids for gene therapy. In such cases, the polymers' own intrinsic anti-tumor activity may complement the activity of the agent to be delivered." The disclosures of these patent publications may be employed in conjunction with herein teachings for delivery of CRISPR Cas system(s) or component(s) thereof or nucleic acid molecule(s) coding therefor.

Supercharged Proteins

Supercharged proteins are a class of engineered or naturally occurring proteins with unusually high positive or negative net theoretical charge and may be employed in delivery of CRISPR Cas system(s) or component(s) thereof or nucleic acid molecule(s) coding therefor. Both supernegatively and superpositively charged proteins exhibit a remarkable ability to withstand thermally or chemically induced aggregation. Superpositively charged proteins are also able to penetrate mammalian cells. Associating cargo with these proteins, such as plasmid DNA, RNA, or other proteins, can enable the functional delivery of these macromolecules into mammalian cells both in vitro and in vivo. David Liu's lab reported the creation and characterization of supercharged proteins in 2007 (Lawrence et al., 2007, Journal of the American Chemical Society 129, 10110-10112).

The nonviral delivery of RNA and plasmid DNA into mammalian cells are valuable both for research and therapeutic applications (Akinc et al., 2010, Nat. Biotech. 26, 561-569). Purified+36 GFP protein (or other superpositively charged protein) is mixed with RNAs in the appropriate serum-free media and allowed to complex prior addition to cells. Inclusion of serum at this stage inhibits formation of the supercharged protein-RNA complexes and reduces the effectiveness of the treatment. The following protocol has been found to be effective for a variety of cell lines (McNaughton et al., 2009, Proc. Natl. Acad. Sci. USA 106, 6111-6116). However, pilot experiments varying the dose of protein and RNA should be performed to optimize the procedure for specific cell lines.

(1) One day before treatment, plate $1\times10^5$ cells per well in a 48-well plate.

(2) On the day of treatment, dilute purified+36 GFP protein in serum free media to a final concentration 200 nM. Add RNA to a final concentration of 50 nM. Vortex to mix and incubate at room temperature for 10 min.

(3) During incubation, aspirate media from cells and wash once with PBS.

(4) Following incubation of +36 GFP and RNA, add the protein-RNA complexes to cells.

(5) Incubate cells with complexes at 37° C. for 4 h.

(6) Following incubation, aspirate the media and wash three times with 20 U/mL heparin PBS. Incubate cells with serum-containing media for a further 48 h or longer depending upon the assay for activity.

(7) Analyze cells by immunoblot, qPCR, phenotypic assay, or other appropriate method.

David Liu's lab has further found+36 GFP to be an effective plasmid delivery reagent in a range of cells. As plasmid DNA is a larger cargo than siRNA, proportionately more+36 GFP protein is required to effectively complex plasmids. For effective plasmid delivery Applicants have developed a variant of +36 GFP bearing a C-terminal HA2 peptide tag, a known endosome-disrupting peptide derived from the influenza virus hemagglutinin protein. The following protocol has been effective in a variety of cells, but as above it is advised that plasmid DNA and supercharged protein doses be optimized for specific cell lines and delivery applications.

(1) One day before treatment, plate $1\times10^5$ per well in a 48-well plate.

(2) On the day of treatment, dilute purified 36 GFP protein in serum free media to a final concentration 2 mM. Add 1 mg of plasmid DNA. Vortex to mix and incubate at room temperature for 10 min.

(3) During incubation, aspirate media from cells and wash once with PBS.

(4) Following incubation of 36 GFP and plasmid DNA, gently add the protein-DNA complexes to cells.

(5) Incubate cells with complexes at 37° C. for 4 h.

(6) Following incubation, aspirate the media and wash with PBS. Incubate cells in serum-containing media and incubate for a further 24-48 h.

(7) Analyze plasmid delivery (e.g., by plasmid-driven gene expression) as appropriate.

See also, e.g., McNaughton et al., Proc. Natl. Acad. Sci. USA 106, 6111-6116 (2009); Cronican et al., ACS Chemical Biology 5, 747-752 (2010); Cronican et al., Chemistry & Biology 18, 833-838 (2011); Thompson et al., Methods in Enzymology 503, 293-319 (2012); Thompson, D. B., et al., Chemistry & Biology 19 (7), 831-843 (2012). The methods of the super charged proteins may be used and/or adapted for delivery of the CRISPR Cas system of the present invention. These systems of Dr. Lui and documents herein in in conjunction with herein teachints can be employed in the delivery of CRISPR Cas system(s) or component(s) thereof or nucleic acid molecule(s) coding therefor.

Cell Penetrating Peptides (CPPs)

In yet another embodiment, cell penetrating peptides (CPPs) are contemplated for the delivery of the CRISPR Cas system. CPPs are short peptides that facilitate cellular uptake of various molecular cargo (from nano-size particles to small chemical molecules and large fragments of DNA). The term "cargo" as used herein includes but is not limited to the group consisting of therapeutic agents, diagnostic probes, peptides, nucleic acids, antisense oligonucleotides, plasmids, proteins, particles including nanoparticles, liposomes, chromophores, small molecules and radioactive materials. In aspects of the invention, the cargo may also comprise any component of the CRISPR Cas system or the entire functional CRISPR Cas system. Aspects of the present invention further provide methods for delivering a desired cargo into a subject comprising: (a) preparing a complex comprising the cell penetrating peptide of the present invention and a desired cargo, and (b) orally, intraarticularly, intraperitoneally, intrathecally, intraarterially, intranasally, intraparenchymally, subcutaneously, intramuscularly, intravenously, dermally, intrarectally, or topically administering the complex to a subject. The cargo is associated with the peptides either through chemical linkage via covalent bonds or through non-covalent interactions.

The function of the CPPs are to deliver the cargo into cells, a process that commonly occurs through endocytosis with the cargo delivered to the endosomes of living mammalian cells. Cell-penetrating peptides are of different sizes, amino acid sequences, and charges but all CPPs have one distinct characteristic, which is the ability to translocate the plasma membrane and facilitate the delivery of various molecular cargoes to the cytoplasm or an organelle. CPP translocation may be classified into three main entry mechanisms: direct penetration in the membrane, endocytosis-mediated entry, and translocation through the formation of a transitory structure. CPPs have found numerous applications in medicine as drug delivery agents in the treatment of different diseases including cancer and virus inhibitors, as well as contrast agents for cell labeling. Examples of the latter include acting as a carrier for GFP, MRI contrast agents, or quantum dots. CPPs hold great potential as in vitro and in vivo delivery vectors for use in research and medicine. CPPs typically have an amino acid composition that either contains a high relative abundance of positively charged amino acids such as lysine or arginine or has sequences that contain an alternating pattern of polar/charged amino acids and non-polar, hydrophobic amino acids. These two types of structures are referred to as polycationic or amphipathic, respectively. A third class of CPPs are the hydrophobic peptides, containing only apolar residues, with low net charge or have hydrophobic amino acid groups that are crucial for cellular uptake. One of the initial CPPs discovered was the trans-activating transcriptional activator (Tat) from Human Immunodeficiency Virus 1 (HIV-1) which was found to be efficiently taken up from the surrounding media by numerous cell types in culture. Since then, the number of known CPPs has expanded considerably and small molecule synthetic analogues with more effective protein transduction properties have been generated. CPPs include but are not limited to Penetratin, Tat (48-60), Transportan, and (R-AhX-R4) (SEQ ID NO: 62) (Ahx=aminohexanoyl).

U.S. Pat. No. 8,372,951, provides a CPP derived from eosinophil cationic protein (ECP) which exhibits highly cell-penetrating efficiency and low toxicity. Aspects of delivering the CPP with its cargo into a vertebrate subject are also provided. Further aspects of CPPs and their delivery are described in U.S. Pat. Nos. 8,575,305; 8;614,194, 8,044,019. CPPs can be used to deliver the CRISPR-Cas system or components thereof. That CPPs can be employed to deliver the CRISPR-Cas system or components thereof is also provided in the manuscript "Gene disruption by cell-penetrating peptide-mediated delivery of Cas9 protein and guide RNA", by Suresh Ramakrishna, Abu-Bonsrah Kwaku Dad, Jagadish Beloor, et al. Genome Res. 2014 Apr 2. [Epub ahead of print], incorporated by reference in its entirety, wherein it is demonstrated that treatment with CPP-conjugated recombinant Cas9 protein and CPP-complexed guide RNAs lead to endogenous gene disruptions in human cell lines. In the paper the Cas9 protein was conjugated to CPP via a thioether bond, whereas the guide RNA was complexed with CPP, forming condensed, positively charged particles. It was shown that simultaneous and sequential treatment of human cells, including embryonic stem cells, dermal fibroblasts, HEK293T cells, HeLa cells, and embryonic carcinoma cells, with the modified Cas9 and guide RNA led to efficient gene disruptions with reduced off-target mutations relative to plasmid transfections.

Implantable Devices

In another embodiment, implantable devices are also contemplated for delivery of the CRISPR Cas system or component(s) thereof or nucleic acid molecule(s) coding therefor. For example, US Patent Publication 20110195123 discloses an implantable medical device which elutes a drug locally and in prolonged period is provided, including several types of such a device, the treatment modes of implementation and methods of implantation. The device comprising of polymeric substrate, such as a matrix for example, that is used as the device body, and drugs, and in some cases additional scaffolding materials, such as metals or additional polymers, and materials to enhance visibility and imaging. An implantable delivery device can be advantageous in providing release locally and over a prolonged period, where drug is released directly to the extracellular matrix (ECM) of the diseased area such as tumor, inflammation, degeneration or for symptomatic objectives, or to injured smooth muscle cells, or for prevention. One kind of drug is RNA, as disclosed above, and this system may be used and/or adapted to the CRISPR Cas system of the present invention. The modes of implantation in some embodiments are existing implantation procedures that are developed and used today for other treatments, including brachytherapy and needle biopsy. In such cases the dimensions of the new implant described in this invention are similar to the original implant. Typically a few devices are implanted during the same treatment procedure.

US Patent Publication 20110195123 provides a drug delivery implantable or insertable system, including systems applicable to a cavity such as the abdominal cavity and/or any other type of administration in which the drug delivery system is not anchored or attached, comprising a biostable and/or degradable and/or bioabsorbable polymeric substrate, which may for example optionally be a matrix. It should be noted that the term "insertion" also includes implantation. The drug delivery system is preferably implemented as a "Loder" as described in US Patent Publication 20110195123.

The polymer or plurality of polymers are biocompatible, incorporating an agent and/or plurality of agents, enabling the release of agent at a controlled rate, wherein the total volume of the polymeric substrate, such as a matrix for example, in some embodiments is optionally and preferably no greater than a maximum volume that permits a therapeutic level of the agent to be reached. As a non-limiting example, such a volume is preferably within the range of 0.1 $m^3$ to 1000 $mm^3$, as required by the volume for the agent load. The Loder may optionally be larger, for example when incorporated with a device whose size is determined by functionality, for example and without limitation, a knee joint, an intra-uterine or cervical ring and the like.

The drug delivery system (for delivering the composition) is designed in some embodiments to preferably employ degradable polymers, wherein the main release mechanism is bulk erosion; or in some embodiments, non degradable, or slowly degraded polymers are used, wherein the main release mechanism is diffusion rather than bulk erosion, so that the outer part functions as membrane, and its internal part functions as a drug reservoir, which practically is not affected by the surroundings for an extended period (for example from about a week to about a few months). Combinations of different polymers with different release mechanisms may also optionally be used. The concentration gradient at the surface is preferably maintained effectively constant during a significant period of the total drug releasing period, and therefore the diffusion rate is effectively constant (termed "zero mode" diffusion). By the term "constant" it is meant a diffusion rate that is preferably maintained above the lower threshold of therapeutic effectiveness, but which may still optionally feature an initial burst and/or may fluctuate, for example increasing and decreasing to a certain degree. The diffusion rate is preferably so maintained for a prolonged period, and it can be considered constant to a certain level to optimize the therapeutically effective period, for example the effective silencing period.

The drug delivery system optionally and preferably is designed to shield the nucleotide based therapeutic agent from degradation, whether chemical in nature or due to attack from enzymes and other factors in the body of the subject.

The drug delivery system as described in US Patent Publication 20110195123 is optionally associated with sensing and/or activation appliances that are operated at and/or after implantation of the device, by non and/or minimally invasive methods of activation and/or acceleration/deceleration, for example optionally including but not limited to thermal heating and cooling, laser beams, and ultrasonic, including focused ultrasound and/or RF (radiofrequency) methods or devices.

According to some embodiments of US Patent Publication 20110195123, the site for local delivery may optionally include target sites characterized by high abnormal proliferation of cells, and suppressed apoptosis, including tumors, active and/or chronic inflammation and infection including autoimmune diseases states, degenerating tissue including muscle and nervous tissue, chronic pain, degenerative sites, and location of bone fractures and other wound locations for enhancement of regeneration of tissue, and injured cardiac, smooth and striated muscle.

The site for implantation of the composition, or target site, preferably features a radius, area and/or volume that is sufficiently small for targeted local delivery. For example, the target site optionally has a diameter in a range of from about 0.1 mm to about 5 cm.

The location of the target site is preferably selected for maximum therapeutic efficacy. For example, the composition of the drug delivery system (optionally with a device for implantation as described above) is optionally and preferably implanted within or in the proximity of a tumor environment, or the blood supply associated thereof.

For example the composition (optionally with the device) is optionally implanted within or in the proximity to pancreas, prostate, breast, liver, via the nipple, within the vascular system and so forth.

The target location is optionally selected from the group comprising, consisting essentially of, or consisting of (as non-limiting examples only, as optionally any site within the body may be suitable for implanting a Loder): 1. brain at degenerative sites like in Parkinson or Alzheimer disease at the basal ganglia, white and gray matter; 2. spine as in the case of amyotrophic lateral sclerosis (ALS); 3. uterine cervix to prevent HPV infection; 4. active and chronic inflammatory joints; 5. dermis as in the case of psoriasis; 6. sympathetic and sensoric nervous sites for analgesic effect; 7. Intra osseous implantation; 8. acute and chronic infection sites; 9. Intra vaginal; 10. Inner ear--auditory system, labyrinth of the inner ear, vestibular system; 11. Intra tracheal; 12. Intra-cardiac; coronary, epicardiac; 13. urinary bladder; 14. biliary system; 15. parenchymal tissue including and not limited to the kidney, liver, spleen; 16. lymph nodes; 17. salivary glands; 18. dental gums; 19. Intra-articular (into joints); 20. Intra-ocular; 21. Brain tissue; 22. Brain ventricles; 23. Cavities, including abdominal cavity (for example but without limitation, for ovary cancer); 24. Intra esophageal and 25. Intra rectal.

Optionally insertion of the system (for example a device containing the composition) is associated with injection of material to the ECM at the target site and the vicinity of that site to affect local pH and/or temperature and/or other biological factors affecting the diffusion of the drug and/or drug kinetics in the ECM, of the target site and the vicinity of such a site.

Optionally, according to some embodiments, the release of said agent could be associated with sensing and/or activation appliances that are operated prior and/or at and/or after insertion, by non and/or minimally invasive and/or else methods of activation and/or acceleration/deceleration, including laser beam, radiation, thermal heating and cooling, and ultrasonic, including focused ultrasound and/or RF (radiofrequency) methods or devices, and chemical activators.

According to other embodiments of US Patent Publication 20110195123, the drug preferably comprises a RNA, for example for localized cancer cases in breast, pancreas, brain, kidney, bladder, lung, and prostate as described below. Although exemplified with RNAi, many drugs are applicable to be encapsulated in Loder, and can be used in association with this invention, as long as such drugs can be encapsulated with the Loder substrate, such as a matrix for example, and this system may be used and/or adapted to deliver the CRISPR Cas system of the present invention.

As another example of a specific application, neuro and muscular degenerative diseases develop due to abnormal gene expression. Local delivery of RNAs may have therapeutic properties for interfering with such abnormal gene expression. Local delivery of anti apoptotic, anti inflammatory and anti degenerative drugs including small drugs and macromolecules may also optionally be therapeutic. In such cases the Loder is applied for prolonged release at constant rate and/or through a dedicated device that is implanted separately. All of this may be used and/or adapted to the CRISPR Cas system of the present invention.

As yet another example of a specific application, psychiatric and cognitive disorders are treated with gene modifiers. Gene knockdown is a treatment option. Loders locally delivering agents to central nervous system sites are therapeutic options for psychiatric and cognitive disorders including but not limited to psychosis, bi-polar diseases, neurotic disorders and behavioral maladies. The Loders could also deliver locally drugs including small drugs and macromolecules upon implantation at specific brain sites. All of this may be used and/or adapted to the CRISPR Cas system of the present invention.

As another example of a specific application, silencing of innate and/or adaptive immune mediators at local sites enables the prevention of organ transplant rejection. Local delivery of RNAs and immunomodulating reagents with the Loder implanted into the transplanted organ and/or the implanted site renders local immune suppression by repelling immune cells such as CD8 activated against the transplanted organ. All of this may be used and/or adapted to the CRISPR Cas system of the present invention.

As another example of a specific application, vascular growth factors including VEGFs and angiogenin and others are essential for neovascularization. Local delivery of the factors, peptides, peptidomimetics, or suppressing their repressors is an important therapeutic modality; silencing the repressors and local delivery of the factors, peptides, macromolecules and small drugs stimulating angiogenesis with the Loder is therapeutic for peripheral, systemic and cardiac vascular disease.

The method of insertion, such as implantation, may optionally already be used for other types of tissue implantation and/or for insertions and/or for sampling tissues, optionally without modifications, or alternatively optionally only with non-major modifications in such methods. Such methods optionally include but are not limited to brachytherapy methods, biopsy, endoscopy with and/or without ultrasound, such as ERCP, stereotactic methods into the brain tissue, Laparoscopy, including implantation with a laparoscope into joints, abdominal organs, the bladder wall and body cavity.

Implantable device technology herein discussed can be employed with herein teachings and hence by this disclosure and the knowledge in the art, CRISPR-Cas system or components thereof or nucleic acid molecules thereof or encoding or providing components may be delivered via an implantable device.

Patient-Specific Screening Methods

A CRISPR-Cas or argonaute system that targets nucleotide, e.g., trinucleotide repeats can be used to screen patients or patent samples for the presence of such repeats. The repeats can be the target of the RNA of the CRISPR-Cas system, and if there is binding thereto by the CRISPR-Cas system, that binding can be detected, to thereby indicate that such a repeat is present. Thus, a CRISPR-Cas system can be used to screen patients or patient samples for the presence of the repeat. The patient can then be administered suitable compound(s) to address the condition; or, can be administered a CRISPR-Cas system to bind to and cause insertion, deletion or mutation and alleviate the condition.

CRISPR Effector Protein mRNA and Guide RNA

CRISPR enzyme mRNA/argonaute mRNA, fusion protein mRNA and guide RNA might also be delivered separately. CRISPR enzyme/fusion protein mRNA can be delivered prior to the guide RNA to give time for CRISPR enzyme/fusion protein to be expressed. CRISPR enzyme/fusion protein mRNA might be administered 1-12 hours (preferably around 2-6 hours) prior to the administration of guide RNA.

Alternatively, CRISPR enzyme/fusion protein mRNA and guide RNA can be administered together. Advantageously, a second booster dose of guide RNA can be administered 1-12 hours (preferably around 2-6 hours) after the initial administration of CRISPR enzyme/fusion protein mRNA+guide RNA.

The CRISPR effector protein of the present invention, i.e. a Cas9 effector protein is sometimes referred to herein as a CRISPR Enzyme. It will be appreciated that the effector protein is based on or derived from an enzyme, so the term 'effector protein' certainly includes 'enzyme' in some embodiments. However, it will also be appreciated that the effector protein may, as required in some embodiments, have DNA or RNA binding, but not necessarily cutting or nicking, activity, including a dead-Cas effector protein function.

Additional administrations of CRISPR enzyme/fusion protein mRNA and/or guide RNA might be useful to achieve the most efficient levels of genome modification. In some embodiments, phenotypic alteration is preferably the result of genome modification when a genetic disease is targeted, especially in methods of therapy and preferably where a repair template is provided to correct or alter the phenotype.

In some embodiments diseases that may be targeted include those concerned with disease-causing splice defects.

In some embodiments, cellular targets include Hemopoietic Stem/Progenitor Cells (CD34+); Human T cells; and Eye (retinal cells)—for example photoreceptor precursor cells.

In some embodiments Gene targets include: Human Beta Globin—HBB (for treating Sickle Cell Anemia, including by stimulating gene-conversion (using closely related HBD gene as an endogenous template)); CD3 (T-Cells); and CEP920 —retina (eye).

In some embodiments disease targets also include: cancer; Sickle Cell Anemia (based on a point mutation); HIV; Beta-Thalassemia; and ophthalmic or ocular disease—for example Leber Congenital Amaurosis (LCA)-causing Splice Defect.

In some embodiments delivery methods include: Cationic Lipid Mediated "direct" delivery of Enzyme-Guide complex (RiboNucleoProtein) and electroporation of plasmid DNA.

Inventive methods can further comprise delivery of templates, such as repair templates, which may be dsODN or ssODN, see below. Delivery of templates may be via the cotemporaneous or separate from delivery of any or all the CRISPR enzyme, guide, tracr mate or tracrRNA and via the same delivery mechanism or different. In some embodiments, it is preferred that the template is delivered together with the guide, tracr mate and/or tracrRNA and, preferably, also the CRISPR enzyme. An example may be an AAV vector where the CRISPR enzyme is SaCas9 (with the N580 mutation).

Inventive methods can further comprise: (a) delivering to the cell a double-stranded oligodeoxynucleotide (dsODN) comprising overhangs complimentary to the overhangs created by said double strand break, wherein said dsODN is integrated into the locus of interest; or -(b) delivering to the cell a single-stranded oligodeoxynucleotide (ssODN), wherein said ssODN acts as a template for homology directed repair of said double strand break. Inventive methods can be for the prevention or treatment of disease in an individual, optionally wherein said disease is caused by a defect in said locus of interest. Inventive methods can be conducted in vivo in the individual or ex vivo on a cell taken from the individual, optionally wherein said cell is returned to the individual.

For minimization of toxicity and off-target effect, it will be important to control the concentration of CRISPR enzyme mRNA and guide RNA delivered. Optimal concentrations of CRISPR enzyme mRNA and guide RNA can be determined by testing different concentrations in a cellular or animal model and using deep sequencing the analyze the extent of modification at potential off-target genomic loci. For example, for the guide sequence targeting 5'-GAGTCCGAGCAGAAGAAGAA-3' (SEQ ID NO: 47) in the EMX1 gene of the human genome, deep sequencing can be used to assess the level of modification at the following two off-target loci, 1: 5'-GAGTCCTAGCAG-GAGAAGAA-3' (SEQ ID NO: 48) and 2: 5'-GAGTCTAAGCAGAAGAAGAA-3' (SEQ ID NO: 49). The concentration that gives the highest level of on-target modification while minimizing the level of off-target modification should be chosen for in vivo delivery.

Inducible Systems

In some embodiments, a CRISPR enzyme, gRNA, or fusion protein according to the invention as defined herein may form a component of an inducible system. The inducible nature of the system would allow for spatiotemporal control of gene editing or gene expression using a form of energy. The form of energy may include but is not limited to electromagnetic radiation, sound energy, chemical energy and thermal energy. Examples of inducible system include tetracycline inducible promoters (Tet-On or Tet-Off), small molecule two-hybrid transcription activations systems (FKBP, ABA, etc), or light inducible systems (Phytochrome, LOV domains, or cryptochrome).In one embodiment, the CRISPR enzyme may be a part of a Light Inducible Transcriptional Effector (LITE) to direct changes in transcriptional activity in a sequence-specific manner. The components of a LITE may include a CRISPR enzyme, a light-responsive cytochrome heterodimer (e.g. from *Arabidopsis thaliana*), and a transcriptional activation/repression domain. Further examples of inducible DNA binding proteins and methods for their use are provided in U.S. 61/736,465, U.S. 61/721,283 and WO 2014/018423, which is hereby incorporated by reference in its entirety.

Self-Inactivating Systems

Once all copies of a gene in the genome of a cell have been edited, continued CRISRP/Cas expression in that cell is no longer necessary. Indeed, sustained expression would be undesirable in case of off-target effects at unintended genomic sites, etc. Thus time-limited expression would be useful. Inducible expression offers one approach, but in addition Applicants have engineered a Self-Inactivating CRISPR-Cas system that relies on the use of a non-coding guide target sequence within the CRISPR vector itself. Thus, after expression begins, the CRISPR system will lead to its own destruction, but before destruction is complete it will have time to edit the genomic copies of the target gene (which, with a normal point mutation in a diploid cell, requires at most two edits). Simply, the self inactivating CRISPR-Cas system includes additional RNA (i.e., guide RNA) that targets the coding sequence for the CRISPR enzyme itself and/or the fusion protein according to the invention as described herein or that targets one or more non-coding guide target sequences complementary to unique sequences present in one or more of the following:

(a) within the promoter driving expression of the non-coding RNA elements,
(b) within the promoter driving expression of the CRISPR effector gene/fusion protein,
(c) within 100 bp of the ATG translational start codon in the CRISPR effector/fusion protein coding sequence,
(d) within the inverted terminal repeat (iTR) of a viral delivery vector, e.g., in the AAV genome.

Furthermore, that RNA can be delivered via a vector, e.g., a separate vector or the same vector that is encoding the CRISPR complex. When provided by a separate vector, the CRISPR RNA that targets Cas/fusion protein/gRNA expression can be administered sequentially or simultaneously. When administered sequentially, the CRISPR RNA that targets Cas/fusion protein/gRNA expression is to be delivered after the CRISPR/fusion protein/gRNA RNA that is intended for e.g. gene editing or gene engineering. This period may be a period of minutes (e.g. 5 minutes, 10 minutes, 20 minutes, 30 minutes, 45 minutes, 60 minutes). This period may be a period of hours (e.g. 2 hours, 4 hours, 6 hours, 8 hours, 12 hours, 24 hours). This period may be a period of days (e.g. 2 days, 3 days, 4 days, 7 days). This period may be a period of weeks (e.g. 2 weeks, 3 weeks, 4 weeks). This period may be a period of months (e.g. 2 months, 4 months, 8 months, 12 months). This period may be a period of years (2 years, 3 years, 4 years). In this fashion, the Cas enzyme associates with a first gRNA/chiRNA capable of hybridizing to a first target, such as a genomic locus or loci of interest and undertakes the function (s) desired of the CRISPR-Cas system (e.g., gene engineering); and subsequently the Cas enzyme may then associate with the second gRNA/chiRNA capable of hybridizing to the sequence comprising at least part of the Cas or CRISPR cassette. Where the gRNA/chiRNA targets the sequences encoding expression of the Cas protein, the enzyme becomes impeded and the system becomes self inactivating. In the same manner, CRISPR RNA that targets Cas expression applied via, for example liposome, lipofection, particles, microvesicles as explained herein, may be administered sequentially or simultaneously. Similarly, self-inactivation may be used for inactivation of one or more guide RNA used to target one or more targets.

In some aspects, a single gRNA is provided that is capable of hybridization to a sequence downstream of a CRISPR effector/fusion protein start codon, whereby after a period of time there is a loss of the CRISPR enzyme/fusion protein expression. In some aspects, one or more gRNA(s) are provided that are capable of hybridization to one or more coding or non-coding regions of the polynucleotide encoding the CRISPR-Cas system, whereby after a period of time there is a inactivation of one or more, or in some cases all, of the CRISPR-Cas system. In some aspects of the system, and not to be limited by theory, the cell may comprise a plurality of CRISPR-Cas complexes, wherein a first subset of CRISPR complexes comprise a first chiRNA capable of targeting a genomic locus or loci to be edited, and a second subset of CRISPR complexes comprise at least one second chiRNA capable of targeting the polynucleotide encoding the CRISPR-Cas system, wherein the first subset of CRISPR-Cas complexes mediate editing of the targeted genomic locus or loci and the second subset of CRISPR complexes eventually inactivate the CRISPR-Cas system, thereby inactivating further CRISPR-Cas expression in the cell.

Thus the invention provides a CRISPR-Cas system comprising one or more vectors for delivery to a eukaryotic cell, wherein the vector(s) encode(s): (i) a CRISPR enzyme; (ii) a first guide RNA capable of hybridizing to a target sequence in the cell; (iii) a second guide RNA capable of hybridizing to one or more target sequence(s) in the vector which encodes the CRISPR enzyme; (iv) at least one tracr mate sequence; and (v) at least one tracr sequence (if or where applicable), The first and second complexes can use the same tracr and tracr mate, thus differing only by the guide sequence, wherein, when expressed within the cell: the first guide RNA directs sequence-specific binding of a first CRISPR complex to the target sequence in the cell; the second guide RNA directs sequence-specific binding of a second CRISPR complex to the target sequence in the vector which encodes the CRISPR enzyme; the CRISPR complexes comprise (a) a tracr mate sequence hybridised to a tracr sequence (if applicable) and (b) a CRISPR enzyme bound to a guide RNA, such that a guide RNA can hybridize to its target sequence; and the second CRISPR complex inactivates the CRISPR-Cas system to prevent continued expression of the CRISPR enzyme by the cell.

Further characteristics of the vector(s), the encoded enzyme, the guide sequences, etc. are disclosed elsewhere herein. For instance, one or both of the guide sequence(s) can be part of a chiRNA sequence which provides the guide, tracr mate and tracr sequences (where applicable) within a single RNA, such that the system can encode (i) a CRISPR enzyme; (ii) a first chiRNA comprising a sequence capable of hybridizing to a first target sequence in the cell, a first tracr mate sequence, and a first tracr sequence; (iii) a second guide RNA capable of hybridizing to the vector which encodes the CRISPR enzyme, a second tracr mate sequence, and a second tracr sequence. Similarly, the enzyme can include one or more NLS, etc.

The various coding sequences (CRISPR enzyme, guide RNAs, tracr mate and optionally tracr) can be included on a single vector or on multiple vectors. For instance, it is possible to encode the enzyme on one vector and the various RNA sequences on another vector, or to encode the enzyme and one chiRNA on one vector, and the remaining chiRNA on another vector, or any other permutation. In general, a system using a total of one or two different vectors is preferred.

Where multiple vectors are used, it is possible to deliver them in unequal numbers, and ideally with an excess of a vector which encodes the first guide RNA relative to the second guide RNA, thereby assisting in delaying final inactivation of the CRISPR system until genome editing has had a chance to occur.

The first guide RNA can target any target sequence of interest within a genome or alternatively transcriptome, as described elsewhere herein. The second guide RNA targets a sequence within the vector which encodes the CRISPR Cas enzyme, and thereby inactivates the enzyme's expression from that vector. Thus the target sequence in the vector must be capable of inactivating expression. Suitable target sequences can be, for instance, near to or within the translational start codon for the Cas coding sequence, in a non-coding sequence in the promoter driving expression of the non-coding RNA elements, within the promoter driving expression of the Cas gene, within 100 bp of the ATG translational start codon in the Cas coding sequence, and/or within the inverted terminal repeat (iTR) of a viral delivery vector, e.g., in the AAV genome. A double stranded break near this region can induce a frame shift in the Cas coding sequence, causing a loss of protein expression. An alternative target sequence for the "self-inactivating" guide RNA would aim to edit/inactivate regulatory regions/sequences needed for the expression of the CRISPR-Cas system or for the stability of the vector. For instance, if the promoter for the Cas9 coding sequence is disrupted then transcription can be inhibited or prevented. Similarly, if a vector includes sequences for replication, maintenance or stability then it is possible to target these. For instance, in a AAV vector a useful target sequence is within the iTR. Other useful sequences to target can be promoter sequences, polyadenylation sites, etc.

Furthermore, if the guide RNAs are expressed in array format, the "self-inactivating" guide RNAs that target both promoters simultaneously will result in the excision of the intervening nucleotides from within the CRISPR-Cas expression construct, effectively leading to its complete inactivation. Similarly, excision of the intervening nucleotides will result where the guide RNAs target both ITRs, or targets two or more other CRISPR-Cas components simultaneously. Self-inactivation as explained herein is applicable, in general, with CRISPR-Cas9 systems in order to provide regulation of the CRISPR-Cas9. For example, self-inactivation as explained herein may be applied to the CRISPR repair of mutations, for example expansion disorders, as explained herein. As a result of this self-inactivation, CRISPR repair is only transiently active.

Addition of non-targeting nucleotides to the 5' end (e.g. 1-10 nucleotides, preferably 1-5 nucleotides) of the "self-inactivating" guide RNA can be used to delay its processing and/or modify its efficiency as a means of ensuring editing at the targeted genomic locus prior to CRISPR-Cas shutdown.

In one aspect of the self-inactivating AAV-CRISPR-Cas system, plasmids that co-express one or more gRNA targeting genomic sequences of interest (e.g. 1-2, 1-5, 1-10, 1-15, 1-20, 1-30) may be established with "self-inactivating" gRNAs that target an SpCas9 sequence at or near the engineered ATG start site (e.g. within 5 nucleotides, within 15 nucleotides, within 30 nucleotides, within 50 nucleotides, within 100 nucleotides). A regulatory sequence in the U6 promoter region can also be targeted with an gRNA. The U6-driven gRNAs may be designed in an array format such that multiple gRNA sequences can be simultaneously released. When first delivered into target tissue/cells (left cell) gRNAs begin to accumulate while Ca9 levels rise in the nucleus. Cas complexes with all of the gRNAs to mediate genome editing and self-inactivation of the CRISPR-Cas plasmids.

One aspect of a self-inactivating CRISPR-Cas system is expression of singly or in tandem array format from 1 up to 4 or more different guide sequences; e.g. up to about 20 or about 30 guides sequences. Each individual self inactivating guide sequence may target a different target. Such may be processed from, e.g. one chimeric pol3 transcript. Pol3 promoters such as U6 or H1 promoters may be used. Pol2 promoters such as those mentioned throughout herein. Inverted terminal repeat (iTR) sequences may flank the Pol3 promoter—gRNA(s)-Pol2 promoter-Cas.

One aspect of a chimeric, tandem array transcript is that one or more guide(s) edit the one or more target(s) while one or more self inactivating guides inactivate the CRISPR/Cas system. Thus, for example, the described CRISPR-Cas system for repairing expansion disorders may be directly combined with the self-inactivating CRISPR-Cas system described herein. Such a system may, for example, have two guides directed to the target region for repair as well as at least a third guide directed to self-inactivation of the CRISPR-Cas. Reference is made to Application Ser. No. PCT/US2014/069897, entitled "Compositions And Methods Of Use Of Crispr-Cas Systems In Nucleotide Repeat Disorders," published Dec. 12, 2014 as WO/2015/089351.

The guide RNA may be a control guide. For example it may be engineered to target a nucleic acid sequence encoding the CRISPR Enzyme itself, as described in US2015232881A1, the disclosure of which is hereby incorporated by reference. In some embodiments, a system or composition may be provided with just the guide RNA engineered to target the nucleic acid sequence encoding the CRISPR Enzyme. In addition, the system or composition may be provided with the guide RNA engineered to target the nucleic acid sequence encoding the CRISPR Enzyme, as well as nucleic acid sequence encoding the CRISPR Enzyme and, optionally a second guide RNA and, further optionally, a repair template. The second guide RNA may be the primary target of the CRISPR system or composition (such a therapeutic, diagnostic, knock out etc. as defined herein). In this way, the system or composition is self-inactivating.

This is exemplified in relation to Cas9 in US2015232881A1 (also published as WO2015070083 (Al), referenced elsewhere herein).

Kits

In one aspect, the invention provides kits containing any one or more of the elements disclosed in the above methods and compositions. In some embodiments, the kit comprises a vector system and instructions for using the kit. In some embodiments, the vector system comprises (a) a first regulatory element operably linked to a tracr mate (i.e. direct repeat) sequence and one or more insertion sites for inserting a guide sequence upstream of the tracr mate sequence, wherein when expressed, the guide sequence directs sequence-specific binding of a CRISPR complex to a target sequence in a eukaryotic cell, wherein the CRISPR complex comprises a CRISPR enzyme complexed with (1) the guide sequence that is hybridized to the target sequence, and (2) the tracr mate sequence that is hybridized to the tracr sequence if applicable; and/or (b) a second regulatory element operably linked to an enzyme-coding sequence encoding said CRISPR enzyme comprising a nuclear localization sequence and/or (c) a third regulatory element operably linked to sequence encoding the fusion protein according to the invention as described herein, optionally comprising a nuclear localization sequence or NES. Elements may be provide individually or in combinations, and may be provided in any suitable container, such as a vial, a bottle, or a tube. The kits may include the gRNA and the unbound protector strand as described herein. The kits may include the gRNA with the protector strand bound to at least partially to the guide sequence (i.e. pgRNA). Thus the kits may include the pgRNA in the form of a partially double stranded nucleotide sequence as described here. In some embodiments, the kit includes instructions in one or more languages, for example in more than one language. The instructions may be specific to the applications and methods described herein.

In some embodiments, a kit comprises one or more reagents for use in a process utilizing one or more of the elements described herein. Reagents may be provided in any suitable container. For example, a kit may provide one or more reaction or storage buffers. Reagents may be provided in a form that is usable in a particular assay, or in a form that requires addition of one or more other components before use (e.g. in concentrate or lyophilized form). A buffer can be any buffer, including but not limited to a sodium carbonate buffer, a sodium bicarbonate buffer, a borate buffer, a Tris buffer, a MOPS buffer, a HEPES buffer, and combinations thereof. In some embodiments, the buffer is alkaline. In some embodiments, the buffer has a pH from about 7 to about 10. In some embodiments, the kit comprises one or more oligonucleotides corresponding to a guide sequence for insertion into a vector so as to operably link the guide sequence and a regulatory element. In some embodiments, the kit comprises a homologous recombination template polynucleotide. In some embodiments, the kit comprises one or more of the vectors and/or one or more of the polynucleotides described herein. The kit may advantageously allow to provide all elements of the systems of the invention.

In one aspect, the invention provides methods for using one or more elements of a CRISPR system. The CRISPR complex of the invention provides an effective means for modifying a target polynucleotide. The CRISPR complex of the invention has a wide variety of utility including modifying (e.g., deleting, inserting, translocating, inactivating, activating) a target polynucleotide in a multiplicity of cell types. As such the CRISPR complex of the invention has a broad spectrum of applications in, e.g., gene therapy, drug screening, disease diagnosis, and prognosis. An exemplary CRISPR complex comprises a CRISPR effector protein complexed with a guide sequence hybridized to a target sequence within the target polynucleotide. In certain embodiments, a direct repeat sequence is linked to the guide sequence.

In one embodiment, this invention provides a method of cleaving a target polynucleotide. The method comprises modifying a target polynucleotide using a CRISPR complex that binds to the target polynucleotide and effect cleavage of said target polynucleotide. Typically, the CRISPR complex of the invention, when introduced into a cell, creates a break (e.g., a single or a double strand break) in the genome sequence. For example, the method can be used to cleave a disease gene in a cell.

The break created by the CRISPR complex can be repaired by a repair processes such as the error prone non-homologous end joining (NHEJ) pathway or the high fidelity homology directed repair (HDR). During these repair process, an exogenous polynucleotide template can be introduced into the genome sequence. In some methods, the HDR process is used to modify genome sequence. For example, an exogenous polynucleotide template comprising a sequence to be integrated flanked by an upstream sequence and a downstream sequence is introduced into a cell. The upstream and downstream sequences share sequence similarity with either side of the site of integration in the chromosome.

Where desired, a donor polynucleotide can be DNA, e.g., a DNA plasmid, a bacterial artificial chromosome (BAC), a yeast artificial chromosome (YAC), a viral vector, a linear piece of DNA, a PCR fragment, a naked nucleic acid, or a nucleic acid complexed with a delivery vehicle such as a liposome or poloxamer.

The exogenous polynucleotide template comprises a sequence to be integrated (e.g., a mutated gene). The sequence for integration may be a sequence endogenous or exogenous to the cell. Examples of a sequence to be integrated include polynucleotides encoding a protein or a non-coding RNA (e.g., a microRNA). Thus, the sequence for integration may be operably linked to an appropriate control sequence or sequences. Alternatively, the sequence to be integrated may provide a regulatory function.

The upstream and downstream sequences in the exogenous polynucleotide template are selected to promote recombination between the chromosomal sequence of interest and the donor polynucleotide. The upstream sequence is a nucleic acid sequence that shares sequence similarity with the genome sequence upstream of the targeted site for integration. Similarly, the downstream sequence is a nucleic acid sequence that shares sequence similarity with the chromosomal sequence downstream of the targeted site of integration. The upstream and downstream sequences in the exogenous polynucleotide template can have 75%, 80%, 85%, 90%, 95%, or 100% sequence identity with the targeted genome sequence. Preferably, the upstream and downstream sequences in the exogenous polynucleotide template have about 95%, 96%, 97%, 98%, 99%, or 100% sequence identity with the targeted genome sequence. In some methods, the upstream and downstream sequences in the exogenous polynucleotide template have about 99% or 100% sequence identity with the targeted genome sequence.

An upstream or downstream sequence may comprise from about 20 bp to about 2500 bp, for example, about 50, 100, 200, 300, 400, 500, 600, 700, 800, 900, 1000, 1100, 1200, 1300, 1400, 1500, 1600, 1700, 1800, 1900, 2000, 2100, 2200, 2300, 2400, or 2500 bp. In some methods, the exemplary upstream or downstream sequence have about 200 bp to about 2000 bp, about 600 bp to about 1000 bp, or more particularly about 700 bp to about 1000 bp.

In some methods, the exogenous polynucleotide template may further comprise a marker. Such a marker may make it easy to screen for targeted integrations. Examples of suitable markers include restriction sites, fluorescent proteins, or selectable markers. The exogenous polynucleotide template of the invention can be constructed using recombinant techniques (see, for example, Sambrook et al., 2001 and Ausubel et al., 1996).

In an exemplary method for modifying a target polynucleotide by integrating an exogenous polynucleotide template, a double stranded break is introduced into the genome sequence by the CRISPR complex, the break is repaired via homologous recombination an exogenous polynucleotide template such that the template is integrated into the genome. The presence of a double-stranded break facilitates integration of the template.

In other embodiments, this invention provides a method of modifying expression of a polynucleotide in a eukaryotic cell. The method comprises increasing or decreasing expression of a target polynucleotide by using a CRISPR complex that binds to the polynucleotide.

In some methods, a target polynucleotide can be inactivated to effect the modification of the expression in a cell. For example, upon the binding of a CRISPR complex to a target sequence in a cell, the target polynucleotide is inactivated such that the sequence is not transcribed, the coded protein is not produced, or the sequence does not function as the wild-type sequence does. For example, a protein or microRNA coding sequence may be inactivated such that the protein is not produced.

In some methods, a control sequence can be inactivated such that it no longer functions as a control sequence. As used herein, "control sequence" refers to any nucleic acid sequence that effects the transcription, translation, or accessibility of a nucleic acid sequence. Examples of a control sequence include, a promoter, a transcription terminator, and an enhancer are control sequences. The inactivated target sequence may include a deletion mutation (i.e., deletion of one or more nucleotides), an insertion mutation (i.e., insertion of one or more nucleotides), or a nonsense mutation (i.e., substitution of a single nucleotide for another nucleotide such that a stop codon is introduced). In some methods, the inactivation of a target sequence results in "knockout" of the target sequence.

Modifying a Target with CRISPR-Cas System or Complex

In one aspect, the invention provides for methods of modifying a target polynucleotide in a eukaryotic cell, which may be in vivo, ex vivo or in vitro. In some embodiments, the method comprises sampling a cell or population of cells from a human or non-human animal or plant (including micro-algae), and modifying the cell or cells. Culturing may occur at any stage ex vivo. The cell or cells may even be re-introduced into the non-human animal or plant. For re-introduced cells it is particularly preferred that the cells are stem cells.

In some embodiments, the method comprises allowing a CRISPR complex to bind to the target polynucleotide to effect cleavage of said target polynucleotide thereby modifying the target polynucleotide, wherein the CRISPR complex comprises a CRISPR enzyme complexed with a guide sequence hybridized or hybridizable to a target sequence within said target polynucleotide, wherein said guide sequence is linked to a tracr mate sequence which in turn hybridizes to a tracr sequence (if and where applicable), optionally as well as the fusion protein according to the invention as described herein.

In one aspect, the invention provides a method of modifying expression of a polynucleotide in a eukaryotic cell. In some embodiments, the method comprises allowing a CRISPR complex to bind to the polynucleotide such that said binding results in increased or decreased expression of said polynucleotide; wherein the CRISPR complex comprises a CRISPR enzyme complexed with a guide sequence hybridized or hybridizable to a target sequence within said polynucleotide, wherein said guide sequence is linked to a tracr mate sequence which in turn hybridizes to a tracr sequence (if and where applicable)), optionally as well as the fusion protein according to the invention as described herein. Similar considerations and conditions apply as above for methods of modifying a target polynucleotide. In fact, these sampling, culturing and re-introduction options apply across the aspects of the present invention.

Indeed, in any aspect of the invention, the CRISPR complex may comprise a CRISPR enzyme complexed with a guide sequence hybridized or hybridizable to a target sequence, wherein said guide sequence may be linked to a tracr mate sequence which in turn may hybridize to a tracr sequence (if and where applicable), optionally as well as the fusion protein according to the invention as described herein. Similar considerations and conditions apply as above for methods of modifying a target polynucleotide.

In plants, pathogens are often host-specific. For example, *Fusarium oxysporum* f. sp. *lycopersici* causes tomato wilt but attacks only tomato, and *F. oxysporum* f *dianthus Puccinia graminis* f. sp. *tritici* attacks only wheat. Plants have existing and induced defenses to resist most pathogens. Mutations and recombination events across plant generations lead to genetic variability that gives rise to susceptibility, especially as pathogens reproduce with more frequency than plants. In plants there can be non-host resistance, e.g., the host and pathogen are incompatible. There can also be Horizontal Resistance, e.g., partial resistance against all races of a pathogen, typically controlled by many genes and Vertical Resistance, e.g., complete resistance to some races of a pathogen but not to other races, typically controlled by a few genes. In a Gene-for-Gene level, plants and pathogens evolve together, and the genetic changes in one balance changes in other. Accordingly, using Natural Variability, breeders combine most useful genes for Yield, Quality, Uniformity, Hardiness, Resistance. The sources of resistance genes include native or foreign Varieties, Heirloom Varieties, Wild Plant Relatives, and Induced Mutations, e.g., treating plant material with mutagenic agents. Using the present invention, plant breeders are provided with a new tool to induce mutations. Accordingly, one skilled in the art can analyze the genome of sources of resistance genes, and in Varieties having desired characteristics or traits employ the present invention to induce the rise of resistance genes, with more precision than previous mutagenic agents and hence accelerate and improve plant breeding programs.

Similar considerations and conditions apply as above for methods of modifying a target polynucleotide. Thus in any of the non-naturally-occurring CRISPR enzymes described herein comprise at least one modification and whereby the enzyme has certain improved capabilities. In particular, any of the enzymes are capable of forming a CRISPR complex with a guide RNA. When such a complex forms, the guide RNA is capable of binding to a target polynucleotide sequence and the enzyme is capable of modifying a target locus. In addition, the enzyme in the CRISPR complex has reduced capability of modifying one or more off-target loci as compared to an unmodified enzyme.

In addition, the modified CRISPR enzymes described herein encompass enzymes whereby in the CRISPR complex the enzyme has increased capability of modifying the one or more target loci as compared to an unmodified enzyme. Such function may be provided separate to or provided in combination with the above-described function of reduced capability of modifying one or more off-target loci. Any such enzymes may be provided with any of the further modifications to the CRISPR enzyme as described herein, such as in combination with any activity provided by one or more associated heterologous functional domains, any further mutations to reduce nuclease activity and the like.

In advantageous embodiments of the invention, the modified CRISPR enzyme is provided with reduced capability of modifying one or more off-target loci as compared to an unmodified enzyme and increased capability of modifying the one or more target loci as compared to an unmodified enzyme. In combination with further modifications to the enzyme, significantly enhanced specificity may be achieved. For example, combination of such advantageous embodiments with one or more additional mutations is provided wherein the one or more additional mutations are in one or more catalytically active domains. Such further catalytic mutations may confer nickase functionality as described in detail elsewhere herein. In such enzymes, enhanced specificity may be achieved due to an improved specificity in terms of enzyme activity. By means of example, and without limitation, enhanced specificity may be obtained (with reference to SpCas9) by one or more of the following mutations: K855A, K810A/K1003A/R1060A, K848A/K1003A/R1060A, or D1135V/G1218R/R1335E/T1337R.

Modifications to reduce off-target effects and/or enhance on-target effects as described above may be made to amino acid residues located in a positively-charged region/groove situated between the RuvC-III and HNH domains. It will be appreciated that any of the functional effects described above may be achieved by modification of amino acids within the aforementioned groove but also by modification of amino acids adjacent to or outside of that groove.

Additional functionalities which may be engineered into modified CRISPR enzymes as described herein include the following. 1. modified CRISPR enzymes that disrupt DNA:protein interactions without affecting protein tertiary or secondary structure. This includes residues that contact any part of the RNA:DNA duplex. 2. modified CRISPR enzymes that weaken intra-protein interactions holding CRISPR effector in conformation essential for nuclease cutting in response to DNA binding (on or off target). For example: a modification that mildly inhibits, but still allows, the nuclease conformation of the HNH domain (positioned at the scissile phosphate). 3. modified CRISPR enzymes that strengthen intra-protein interactions holding CRISPR effector in a conformation inhibiting nuclease activity in response to DNA binding (on or off targets). For example: a modification that stabilizes the HNH domain in a conformation away from the scissile phosphate. Any such additional functional enhancement may be provided in combination with any other modification to the CRISPR enzyme as described in detail elsewhere herein.

Any of the herein described improved functionalities may be made to any CRISPR enzyme, such as a Cas9 enzyme. Cas9 enzymes described herein are in preferred embodiments derived from Cas9 enzymes from *S. pyogenes* and *S. aureus*. However, it will be appreciated that any of the functionalities described herein may be engineered into Cas9 enzymes from other orthologs, including chimeric enzymes comprising fragments from multiple orthologs.

Nucleic acids, amino acids and proteins, Regulatory sequences, Vectors, etc

The invention uses nucleic acids to bind (single stranded or double stranded) target DNA or RNA sequences, or alternatively DNA/RNA hybrid sequence. This is advantageous as nucleic acids are much easier and cheaper to produce than proteins, and the specificity can be varied according to the length of the stretch where homology is sought. Complex 3-D positioning of multiple fingers, for example is not required. The terms "polynucleotide", "nucleotide", "nucleotide sequence", "nucleic acid" and "oligonucleotide" are used interchangeably. They refer to a polymeric form of nucleotides of any length, either deoxyribonucleotides or ribonucleotides, or analogs thereof. Polynucleotides may have any three dimensional structure, and may perform any function, known or unknown. The following are non-limiting examples of polynucleotides: coding or non-coding regions of a gene or gene fragment, loci (locus) defined from linkage analysis, exons, introns, messenger RNA (mRNA), transfer RNA, ribosomal RNA, short interfering RNA (siRNA), short-hairpin RNA (shRNA), micro-RNA (miRNA), ribozymes, cDNA, recombinant polynucleotides, branched polynucleotides, plasmids, vectors, isolated DNA of any sequence, isolated RNA of any sequence, nucleic acid probes, and primers. The term also encompasses nucleic-acid-like structures with synthetic backbones, see, e.g., Eckstein, 1991; Baserga et al., 1992; Milligan, 1993; WO 97/03211; WO 96/39154; Mata, 1997; Strauss-Soukup, 1997; and Samstag, 1996. A polynucleotide may comprise one or more modified nucleotides, such as methylated nucleotides and nucleotide analogs. If present, modifications to the nucleotide structure may be imparted before or after assembly of the polymer. The sequence of nucleotides may be interrupted by non-nucleotide components. A polynucleotide may be further modified after polymerization, such as by conjugation with a labeling component.

In aspects of the invention the terms "chimeric RNA", "chimeric guide RNA", "guide RNA", "single guide RNA" and "synthetic guide RNA" are used interchangeably and refer to the polynucleotide sequence comprising the guide sequence, the tracr sequence and the tracr mate sequence. The skilled person will understand that some CRISPR effector proteins do not require a tracr RNA for activity (e.g. Cpf1). It will therefore be understood that reference to "tracr" is only applicable for CRISPR effectors that actually require a tracr. The term "guide sequence" refers to the about 20 bp sequence within the guide RNA that specifies the target site and may be used interchangeably with the terms "guide" or "spacer". The term "tracr mate sequence" may also be used interchangeably with the term "direct repeat(s) ".

As used herein the term "wild type" is a term of the art understood by skilled persons and means the typical form of an organism, strain, gene or characteristic as it occurs in nature as distinguished from mutant or variant forms. A "wild type" can be a base line.

As used herein the term "variant" should be taken to mean the exhibition of qualities that have a pattern that deviates from what occurs in nature.

The terms "non-naturally occurring" or "engineered" are used interchangeably and indicate the involvement of the hand of man. The terms, when referring to nucleic acid molecules or polypeptides mean that the nucleic acid molecule or the polypeptide is at least substantially free from at least one other component with which they are naturally associated in nature and as found in nature.

"Complementarity" refers to the ability of a nucleic acid to form hydrogen bond(s) with another nucleic acid sequence by either traditional Watson-Crick base pairing or other non-traditional types. A percent complementarity indicates the percentage of residues in a nucleic acid molecule which can form hydrogen bonds (e.g., Watson-Crick base pairing) with a second nucleic acid sequence (e.g., 5, 6, 7, 8, 9, 10 out of 10 being 50%, 60%, 70%, 80%, 90%, and 100% complementary). "Perfectly complementary" means that all the contiguous residues of a nucleic acid sequence will hydrogen bond with the same number of contiguous residues in a second nucleic acid sequence. "Substantially complementary" as used herein refers to a degree of complementarity that is at least 60%, 65%, 70%, 75%, 80%, 85%, 90%, 95%, 97%, 98%, 99%, or 100% over a region of 8, 9, 10, 11, 12, 13, 14, 15, 16, 17, 18, 19, 20, 21, 22, 23, 24, 25, 30, 35, 40, 45, 50, or more nucleotides, or refers to two nucleic acids that hybridize under stringent conditions.

As used herein, "stringent conditions" for hybridization refer to conditions under which a nucleic acid having complementarity to a target sequence predominantly hybridizes with the target sequence, and substantially does not hybridize to non-target sequences. Stringent conditions are generally sequence-dependent, and vary depending on a number of factors. In general, the longer the sequence, the higher the temperature at which the sequence specifically hybridizes to its target sequence. Non-limiting examples of stringent conditions are described in detail in Tijssen (1993), Laboratory Techniques In Biochemistry And Molecular Biology-Hybridization With Nucleic Acid Probes Part I, Second Chapter "Overview of principles of hybridization and the strategy of nucleic acid probe assay", Elsevier, N.Y. Where reference is made to a polynucleotide sequence, then complementary or partially complementary sequences are also envisaged. These are preferably capable of hybridizing to the reference sequence under highly stringent conditions. Generally, in order to maximize the hybridization rate, relatively low-stringency hybridization conditions are selected: about 20 to 25° C. lower than the thermal melting point ($T_m$). The $T_m$ is the temperature at which 50% of specific target sequence hybridizes to a perfectly complementary probe in solution at a defined ionic strength and pH. Generally, in order to require at least about 85% nucleotide complementarity of hybridized sequences, highly stringent washing conditions are selected to be about 5 to 15° C. lower than the $T_m$. In order to require at least about 70% nucleotide complementarity of hybridized sequences, moderately-stringent washing conditions are selected to be about 15 to 30° C. lower than the $T_m$. Highly permissive (very low stringency) washing conditions may be as low as 50° C. below the $T_m$, allowing a high level of mis-matching between hybridized sequences. Those skilled in the art will recognize that other physical and chemical parameters in the hybridization and wash stages can also be altered to affect the outcome of a detectable hybridization signal from a specific level of homology between target and probe sequences. Preferred highly stringent conditions comprise incubation in 50% formamide, 5×SSC, and 1% SDS at 42° C., or incubation in 5×SSC and 1% SDS at 65° C., with wash in 0.2×SSC and 0.1% SDS at 65° C.

"Hybridization" refers to a reaction in which one or more polynucleotides react to form a complex that is stabilized via hydrogen bonding between the bases of the nucleotide residues. The hydrogen bonding may occur by Watson Crick base pairing, Hoogstein binding, or in any other sequence specific manner. The complex may comprise two strands forming a duplex structure, three or more strands forming a multi stranded complex, a single self hybridizing strand, or any combination of these. A hybridization reaction may constitute a step in a more extensive process, such as the initiation of PCR, or the cleavage of a polynucleotide by an enzyme. A sequence capable of hybridizing with a given sequence is referred to as the "complement" of the given sequence.

As used herein, the term "locus" (plural loci) is the specific location of a gene or DNA or alternatively RNA sequence on a chromosome or other polynucleic acid sequence (e.g. mRNA). A "gene" refers to stretches of DNA or RNA that encode a polypeptide or an RNA chain that has functional role to play in an organism and hence is the molecular unit of heredity in living organisms. For the purpose of this invention it may be considered that genes include regions which regulate the production of the gene product, whether or not such regulatory sequences are adjacent to coding and/or transcribed sequences. Accordingly, a gene includes, but is not necessarily limited to, promoter sequences, terminators, translational regulatory sequences such as ribosome binding sites and internal ribosome entry sites, enhancers, silencers, insulators, boundary elements, replication origins, matrix attachment sites and locus control regions. As used herein, "expression of a genomic locus" or "gene expression" is the process by which information from a gene is used in the synthesis of a functional gene product. The products of gene expression are often proteins, but in non-protein coding genes such as rRNA genes or tRNA genes, the product is functional RNA. The process of gene expression is used by all known life—eukaryotes (including multicellular organisms), prokaryotes (bacteria and archaea) and viruses to generate functional products to survive. As used herein "expression" of a gene or nucleic acid encompasses not only cellular gene expression, but also the transcription and translation of nucleic acid(s) in cloning systems and in any other context.

As used herein, "expression" refers to the process by which a polynucleotide is transcribed from a DNA template (such as into and mRNA or other RNA transcript) and/or the process by which a transcribed mRNA is subsequently translated into peptides, polypeptides, or proteins. Transcripts and encoded polypeptides may be collectively referred to as "gene product." If the polynucleotide is derived from genomic DNA, expression may include splicing of the mRNA in a eukaryotic cell.

The terms "polypeptide", "peptide" and "protein" are used interchangeably herein to refer to polymers of amino acids of any length. The polymer may be linear or branched, it may comprise modified amino acids, and it may be interrupted by non amino acids. The terms also encompass an amino acid polymer that has been modified; for example, disulfide bond formation, glycosylation, lipidation, acetylation, phosphorylation, or any other manipulation, such as conjugation with a labeling component. As used herein the term "amino acid" includes natural and/or unnatural or synthetic amino acids, including glycine and both the D or L optical isomers, and amino acid analogs and peptidomimetics.

As used herein, the term "domain" or "protein domain" refers to a part of a protein sequence that may exist and function independently of the rest of the protein chain. As described in aspects of the invention, sequence identity is related to sequence homology. Homology comparisons may be conducted by eye, or more usually, with the aid of readily available sequence comparison programs. These commercially available computer programs may calculate percent (%) homology between two or more sequences and may also calculate the sequence identity shared by two or more amino acid or nucleic acid sequences.

In aspects of the invention the term "guide RNA", refers to the polynucleotide sequence comprising one or more of a putative or identified tracr sequence and a putative or identified crRNA sequence or guide sequence. In particular embodiments, the "guide RNA" comprises a putative or identified crRNA sequence or guide sequence. In further embodiments, the guide RNA does not comprise a putative or identified tracr sequence.

As used herein the term "wild type" is a term of the art understood by skilled persons and means the typical form of an organism, strain, gene or characteristic as it occurs in nature as distinguished from mutant or variant forms. A "wild type" can be a base line.

As used herein the term "variant" should be taken to mean the exhibition of qualities that have a pattern that deviates from what occurs in nature.

The terms "non-naturally occurring" or "engineered" are used interchangeably and indicate the involvement of the hand of man. The terms, when referring to nucleic acid molecules or polypeptides mean that the nucleic acid molecule or the polypeptide is at least substantially free from at least one other component with which they are naturally associated in nature and as found in nature. In all aspects and embodiments, whether they include these terms or not, it will be understood that, preferably, the may be optional and thus preferably included or not preferably not included. Furthermore, the terms "non-naturally occurring" and "engineered" may be used interchangeably and so can therefore be used alone or in combination and one or other may replace mention of both together. In particular, "engineered" is preferred in place of "non-naturally occurring" or "non-naturally occurring and/or engineered." It will be understood that the fusion proteins according to the invention as described herein are "non-naturally occurring" or "engineered".

Sequence homologies may be generated by any of a number of computer programs known in the art, for example BLAST or FASTA, etc. A suitable computer program for carrying out such an alignment is the GCG Wisconsin Bestfit package (University of Wisconsin, U.S.A; Devereux et al., 1984, Nucleic Acids Research 12:387). Examples of other software than may perform sequence comparisons include, but are not limited to, the BLAST package (see Ausubel et al., 1999 ibid—Chapter 18), FASTA (Atschul et al., 1990, J. Mol. Biol., 403-410) and the GENEWORKS suite of comparison tools. Both BLAST and FASTA are available for offline and online searching (see Ausubel et al., 1999 ibid, pages 7-58 to 7-60). However it is preferred to use the GCG Bestfit program. Percentage (%) sequence homology may be calculated over contiguous sequences, i.e., one sequence is aligned with the other sequence and each amino acid or nucleotide in one sequence is directly compared with the corresponding amino acid or nucleotide in the other sequence, one residue at a time. This is called an "ungapped" alignment. Typically, such ungapped alignments are performed only over a relatively short number of residues. Although this is a very simple and consistent method, it fails to take into consideration that, for example, in an otherwise identical pair of sequences, one insertion or deletion may cause the following amino acid residues to be put out of alignment, thus potentially resulting in a large reduction in % homology when a global alignment is performed. Consequently, most sequence comparison methods are designed to produce optimal alignments that take into consideration possible insertions and deletions without unduly penalizing the overall homology or identity score. This is achieved by inserting "gaps" in the sequence alignment to try to maximize local homology or identity. However, these more complex methods assign "gap penalties" to each gap that occurs in the alignment so that, for the same number of identical amino acids, a sequence alignment with as few gaps as possible-reflecting higher relatedness between the two compared sequences—may achieve a higher score than one with many gaps. "Affinity gap costs" are typically used that charge a relatively high cost for the existence of a gap and a smaller penalty for each subsequent residue in the gap. This is the most commonly used gap scoring system. High gap penalties may, of course, produce optimized alignments with fewer gaps. Most alignment programs allow the gap penalties to be modified. However, it is preferred to use the default values when using such software for sequence comparisons. For example, when using the GCG Wisconsin Bestfit package the default gap penalty for amino acid sequences is −12 for a gap and −4 for each extension. Calculation of maximum % homology therefore first requires the production of an optimal alignment, taking into consideration gap penalties. A suitable computer program for carrying out such an alignment is the GCG Wisconsin Bestfit package (Devereux et al., 1984 *Nuc. Acids Research* 12 p387). Examples of other software than may perform sequence comparisons include, but are not limited to, the BLAST package (see Ausubel et al., 1999 *Short Protocols in Molecular Biology*, 4$^{th}$ Ed.—Chapter 18), FASTA (Altschul et al., 1990 J. Mol. Biol. 403-410) and the GENEWORKS suite of comparison tools. Both BLAST and FASTA are available for offline and online searching (see Ausubel et al., 1999, Short Protocols in Molecular Biology, pages 7-58 to 7-60). However, for some applications, it is preferred to use the GCG Bestfit program. A new tool, called BLAST 2 Sequences is also available for comparing protein and nucleotide sequences (see *FEMSMicrobiolLett.* 1999 174 (2): 247-50; *FEMS Microbiol Lett.* 1999 177(1): 187-8 and the website of the National Center for Biotechnology information at the website of the National Institutes for Health). Although the final % homology may be measured in terms of identity, the alignment process itself is typically not based on an all-or-nothing pair comparison. Instead, a scaled similarity score matrix is generally used that assigns scores to each pair-wise comparison based on chemical similarity or evolutionary distance. An example of such a matrix commonly used is the BLOSUM62 matrix—the default matrix for the BLAST suite of programs. GCG Wisconsin programs generally use either the public default values or a custom symbol comparison table, if supplied (see user manual for further details). For some applications, it is preferred to use the public default values for the GCG package, or in the case of other software, the default matrix, such as BLOSUM62. Alternatively, percentage homologies may be calculated using the multiple alignment feature in DNASIS™ (Hitachi Software), based on an algorithm, analogous to CLUSTAL (Higgins DG & Sharp PM (1988), Gene 73(1), 237-244). Once the software has produced an optimal alignment, it is possible to calculate % homology, preferably % sequence identity. The software typically does this as part of the sequence comparison and generates a numerical result. The sequences may also have deletions, insertions or substitutions of amino acid residues which produce a silent change and result in a functionally equivalent substance. Deliberate amino acid substitutions may be made on the basis of similarity in amino acid properties (such as polarity, charge, solubility, hydrophobicity, hydrophilicity, and/or the amphipathic nature of the residues) and it is therefore useful to group amino acids together in functional groups. Amino acids may be grouped together based on the properties of their side chains alone. However, it is more useful to include mutation data as well. The sets of amino acids thus derived are likely to be conserved for structural reasons. These sets may be described in the form of a Venn diagram (Livingstone C.D. and Barton G.J. (1993) "Protein sequence alignments: a strategy for the hierarchical analysis of residue conservation" Comput. Appl. Biosci. 9: 745-756) (Taylor W.R. (1986) "The classification of amino acid conservation" J Theor. Biol. 119; 205-218). Conservative substitutions may be made, for example according to the table below which describes a generally accepted Venn diagram grouping of amino acids.

| Set | | Sub-set | |
|---|---|---|---|
| Hydrophobic | F W Y H K M I L V A G C (SEQ ID NO: 104) | Aromatic | F W Y H (SEQ ID NO: 105) |
| | | Aliphatic | I L V |
| Polar | W Y H K R E D C S T N Q (SEQ ID NO: 106) | Charged | H K R E D (SEQ ID NO: 107) |
| | | Positively charged | H K R |
| | | Negatively charged | E D |
| Small | V C A G S P T N D (SEQ ID NO: 108) | Tiny | A G S |

The terms "subject," "individual," and "patient" are used interchangeably herein to refer to a vertebrate, preferably a mammal, more preferably a human. Mammals include, but are not limited to, murines, simians, humans, farm animals, sport animals, and pets. Tissues, cells and their progeny of a biological entity obtained in vivo or cultured in vitro are also encompassed.

The terms "therapeutic agent", "therapeutic capable agent" or "treatment agent" are used interchangeably and refer to a molecule or compound that confers some beneficial effect upon administration to a subject. The beneficial effect includes enablement of diagnostic determinations; amelioration of a disease, symptom, disorder, or pathological condition; reducing or preventing the onset of a disease, symptom, disorder or condition; and generally counteracting a disease, symptom, disorder or pathological condition.

As used herein, "treatment" or "treating," or "palliating" or "ameliorating" are used interchangeably. These terms refer to an approach for obtaining beneficial or desired results including but not limited to a therapeutic benefit and/or a prophylactic benefit. By therapeutic benefit is meant any therapeutically relevant improvement in or effect on one or more diseases, conditions, or symptoms under treatment. For prophylactic benefit, the compositions may be administered to a subject at risk of developing a particular disease, condition, or symptom, or to a subject reporting one or more of the physiological symptoms of a disease, even though the disease, condition, or symptom may not have yet been manifested.

The term "effective amount" or "therapeutically effective amount" refers to the amount of an agent that is sufficient to effect beneficial or desired results. The therapeutically effective amount may vary depending upon one or more of: the subject and disease condition being treated, the weight and age of the subject, the severity of the disease condition, the manner of administration and the like, which can readily be determined by one of ordinary skill in the art. The term also applies to a dose that will provide an image for detection by any one of the imaging methods described herein. The specific dose may vary depending on one or more of: the particular agent chosen, the dosing regimen to be followed, whether it is administered in combination with other compounds, timing of administration, the tissue to be imaged, and the physical delivery system in which it is carried.

The practice of the present invention employs, unless otherwise indicated, conventional techniques of immunology, biochemistry, chemistry, molecular biology, microbiology, cell biology, genomics and recombinant DNA, which are within the skill of the art. See Sambrook, Fritsch and Maniatis, MOLECULAR CLONING: A LABORATORY MANUAL, 2nd edition (1989); CURRENT PROTOCOLS IN MOLECULAR BIOLOGY (F. M. Ausubel, et al. eds., (1987)); the series METHODS IN ENZYMOLOGY (Academic Press, Inc.): PCR 2: A PRACTICAL APPROACH (M.J. MacPherson, B. D. Hames and G. R. Taylor eds. (1995)), Harlow and Lane, eds. (1988) ANTIBODIES, A LABORATORY MANUAL, and ANIMAL CELL CULTURE (R.I. Freshney, ed. (1987)).

Several aspects of the invention relate to vector systems comprising one or more vectors, or vectors as such. Vectors can be designed for expression of CRISPR transcripts (e.g. nucleic acid transcripts, proteins, or enzymes) in prokaryotic or eukaryotic cells. For example, CRISPR transcripts can be expressed in bacterial cells such as *Escherichia coli*, insect cells (using baculovirus expression vectors), yeast cells, or mammalian cells. Suitable host cells are discussed further in Goeddel, GENE EXPRESSION TECHNOLOGY: METHODS IN ENZYMOLOGY 185, Academic Press, San Diego, Calif (1990). Alternatively, the recombinant expression vector can be transcribed and translated in vitro, for example using T7 promoter regulatory sequences and T7 polymerase.

Embodiments of the invention include sequences (both polynucleotide or polypeptide) which may comprise homologous substitution (substitution and replacement are both used herein to mean the interchange of an existing amino acid residue or nucleotide, with an alternative residue or nucleotide) that may occur i.e., like-for-like substitution in the case of amino acids such as basic for basic, acidic for acidic, polar for polar, etc. Non-homologous substitution may also occur i.e., from one class of residue to another or alternatively involving the inclusion of unnatural amino acids such as ornithine (hereinafter referred to as Z), diaminobutyric acid ornithine (hereinafter referred to as B), norleucine ornithine (hereinafter referred to as O), pyridylalanine, thienylalanine, naphthylalanine and phenylglycine. Variant amino acid sequences may include suitable spacer groups that may be inserted between any two amino acid residues of the sequence including alkyl groups such as methyl, ethyl or propyl groups in addition to amino acid spacers such as glycine or P-alanine residues. A further form of variation, which involves the presence of one or more amino acid residues in peptoid form, may be well understood by those skilled in the art. For the avoidance of doubt, "the peptoid form" is used to refer to variant amino acid residues wherein the a-carbon substituent group is on the residue's nitrogen atom rather than the a-carbon. Processes for preparing peptides in the peptoid form are known in the art, for example Simon R J et al., PNAS (1992) 89(20), 9367-9371 and Horwell DC, Trends Biotechnol. (1995) 13(4), 132-134.

Homology modelling: Corresponding residues in other CRISPR effector orthologs can be identified by the methods of Zhang et al., 2012 (Nature; 490(7421): 556-60) and Chen et al., 2015 (PLoS Comput Biol; 11(5): e1004248)-a computational protein-protein interaction (PPI) method to predict interactions mediated by domain-motif interfaces. PrePPI (Predicting PPI), a structure based PPI prediction method, combines structural evidence with non-structural evidence using a Bayesian statistical framework. The method involves taking a pair a query proteins and using structural alignment to identify structural representatives that correspond to either their experimentally determined structures or homology models. Structural alignment is further used to identify both close and remote structural neighbors by considering global and local geometric relationships. Whenever two neighbors of the structural representatives form a complex reported in the Protein Data Bank, this defines a template for modelling the interaction between the two query proteins. Models of the complex are created by superimposing the representative structures on their corresponding structural neighbor in the template. This approach is further described in Dey et al., 2013 (Prot Sci; 22: 359-66).

For purpose of this invention, amplification means any method employing a primer and a polymerase capable of replicating a target sequence with reasonable fidelity. Amplification may be carried out by natural or recombinant DNA polymerases such as TaqGold™, T7 DNA polymerase, Klenow fragment of *E. coli* DNA polymerase, and reverse transcriptase. A preferred amplification method is PCR.

In certain aspects the invention involves vectors. A used herein, a "vector" is a tool that allows or facilitates the transfer of an entity from one environment to another. It is a replicon, such as a plasmid, phage, or cosmid, into which another DNA segment may be inserted so as to bring about the replication of the inserted segment. Generally, a vector is capable of replication when associated with the proper control elements. In general, the term "vector" refers to a nucleic acid molecule capable of transporting another nucleic acid to which it has been linked. Vectors include, but are not limited to, nucleic acid molecules that are single-stranded, double-stranded, or partially double-stranded; nucleic acid molecules that comprise one or more free ends, no free ends (e.g., circular); nucleic acid molecules that comprise DNA, RNA, or both; and other varieties of polynucleotides known in the art. One type of vector is a "plasmid," which refers to a circular double stranded DNA loop into which additional DNA segments can be inserted, such as by standard molecular cloning techniques. Another type of vector is a viral vector, wherein virally-derived DNA or RNA sequences are present in the vector for packaging into a virus (e.g., retroviruses, replication defective retroviruses, adenoviruses, replication defective adenoviruses, and adeno-associated viruses (AAVs)). Viral vectors also include polynucleotides carried by a virus for transfection into a host cell. Certain vectors are capable of autonomous replication in a host cell into which they are introduced (e.g., bacterial vectors having a bacterial origin of replication and episomal mammalian vectors). Other vectors (e.g., non-episomal mammalian vectors) are integrated into the genome of a host cell upon introduction into the host cell, and thereby are replicated along with the host genome. Moreover, certain vectors are capable of directing the expression of genes to which they are operatively-linked. Such vectors are referred to herein as "expression vectors." Common expression vectors of utility in recombinant DNA techniques are often in the form of plasmids.

Recombinant expression vectors can comprise a nucleic acid of the invention in a form suitable for expression of the nucleic acid in a host cell, which means that the recombinant expression vectors include one or more regulatory elements, which may be selected on the basis of the host cells to be used for expression, that is operatively-linked to the nucleic acid sequence to be expressed. Within a recombinant expression vector, "operably linked" is intended to mean that the nucleotide sequence of interest is linked to the regulatory element(s) in a manner that allows for expression of the nucleotide sequence (e.g., in an in vitro transcription/translation system or in a host cell when the vector is introduced into the host cell). With regards to recombination and cloning methods, mention is made of U.S. patent application Ser. No. 10/815,730, published Sep. 2, 2004 as US 2004-0171156 A1, the contents of which are herein incorporated by reference in their entirety.

Aspects of the invention relate to bicistronic vectors for chimeric RNA and Cas9. Bicistronic expression vectors for chimeric RNA and Cas9 are preferred. In general and particularly in this embodiment Cas9 is preferably driven by the CBh promoter. The chimeric RNA may preferably be driven by a Pol III promoter, such as a U6 promoter. Ideally the two are combined. The chimeric guide RNA typically comprises, consists essentially of, or consists of a 20 bp guide sequence (Ns) and this may be joined to the tracr sequence (running from the first "U" of the lower strand to the end of the transcript). The tracr sequence may be truncated at various positions as indicated. The guide and tracr sequences are separated by the tracr-mate sequence, which may be GUUUUAGAGCUA (SEQ ID NO: 63). This may be followed by the loop sequence GAAA as shown. Both of these are preferred examples. Applicants have demonstrated Cas9-mediated indels at the human EMX] and PVALB loci by SURVEYOR assays. ChiRNAs are indicated by their "+n" designation, and crRNA refers to a hybrid RNA where guide and tracr sequences are expressed as separate transcripts. Throughout this application, chimeric RNA may also be called single guide, or synthetic guide RNA (gRNA).

In some embodiments, a loop in the guide RNA is provided. This may be a stem loop or a tetra loop. The loop is preferably GAAA, but it is not limited to this sequence or indeed to being only 4 bp in length. Indeed, preferred loop forming sequences for use in hairpin structures are four nucleotides in length, and most preferably have the sequence GAAA. However, longer or shorter loop sequences may be used, as may alternative sequences. The sequences preferably include a nucleotide triplet (for example, AAA), and an additional nucleotide (for example C or G). Examples of loop forming sequences include CAAA and AAAG. In practicing any of the methods disclosed herein, a suitable vector can be introduced to a cell or an embryo via one or more methods known in the art, including without limitation, microinjection, electroporation, sonoporation, biolistics, calcium phosphate-mediated transfection, cationic transfection, liposome transfection, dendrimer transfection, heat shock transfection, nucleofection transfection, magnetofection, lipofection, impalefection, optical transfection, proprietary agent-enhanced uptake of nucleic acids, and delivery via liposomes, immunoliposomes, virosomes, or artificial virions. In some methods, the vector is introduced into an embryo by microinjection. The vector or vectors may be microinjected into the nucleus or the cytoplasm of the embryo. In some methods, the vector or vectors may be introduced into a cell by nucleofection.

The term "regulatory element" is intended to include promoters, enhancers, internal ribosomal entry sites (IRES), and other expression control elements (e.g., transcription termination signals, such as polyadenylation signals and poly-U sequences). Such regulatory elements are described, for example, in Goeddel, GENE EXPRESSION TECHNOLOGY: METHODS IN ENZYMOLOGY 185, Academic Press, San Diego, Calif. (1990). Regulatory elements include those that direct constitutive expression of a nucleotide sequence in many types of host cell and those that direct expression of the nucleotide sequence only in certain host cells (e.g., tissue-specific regulatory sequences). A tissue-specific promoter may direct expression primarily in a desired tissue of interest, such as muscle, neuron, bone, skin, blood, specific organs (e.g., liver, pancreas), or particular cell types (e.g., lymphocytes). Regulatory elements may also direct expression in a temporal-dependent manner, such as in a cell-cycle dependent or developmental stage-dependent manner, which may or may not also be tissue or cell-type specific. In some embodiments, a vector comprises one or more pol III promoter (e.g., 1, 2, 3, 4, 5, or more pol III promoters), one or more pol II promoters (e.g., 1, 2, 3, 4, 5, or more pol II promoters), one or more pol I promoters (e.g., 1, 2, 3, 4, 5, or more pol I promoters), or combinations thereof. Examples of pol III promoters include, but are not limited to, U6 and H1 promoters. Examples of pol II promoters include, but are not limited to, the retroviral Rous sarcoma virus (RSV) LTR promoter (optionally with the RSV enhancer), the cytomegalovirus (CMV) promoter (optionally with the CMV enhancer) [see, e.g., Boshart et al, Cell, 41:521-530 (1985)], the SV40 promoter, the dihydrofolate reductase promoter, the j-actin promoter, the phosphoglycerol kinase (PGK) promoter, and the EF1α promoter. Also encompassed by the term "regulatory element" are enhancer elements, such as WPRE; CMV enhancers; the R-U5' segment in LTR of HTLV-I (Mol. Cell. Biol., Vol. 8(1), p. 466-472, 1988); SV40 enhancer; and the intron sequence between exons 2 and 3 of rabbit β-globin (Proc. Natl. Acad. Sci. USA., Vol. 78(3), p. 1527-31, 1981). It will be appreciated by those skilled in the art that the design of the expression vector can depend on such factors as the choice of the host cell to be transformed, the level of expression desired, etc. A vector can be introduced into host cells to thereby produce transcripts, proteins, or peptides, including fusion proteins or peptides, encoded by nucleic acids as described herein (e.g., clustered regularly interspersed short palindromic repeats (CRISPR) transcripts, proteins, enzymes, mutant forms thereof, fusion proteins thereof, etc.). With regards to regulatory sequences, mention is made of U.S. patent application Ser. No. 10/491,026, the contents of which are incorporated by reference herein in their entirety. With regards to promoters, mention is made of PCT publication WO 2011/028929 and U.S. application Ser. No. 12/511,940, the contents of which are incorporated by reference herein in their entirety.

Vectors can be designed for expression of CRISPR transcripts (e.g., nucleic acid transcripts, proteins, or enzymes) in prokaryotic or eukaryotic cells. For example, CRISPR transcripts can be expressed in bacterial cells such as *Escherichia coli*, insect cells (using baculovirus expression vectors), yeast cells, or mammalian cells. Suitable host cells are discussed further in Goeddel, GENE EXPRESSION TECHNOLOGY: METHODS IN ENZYMOLOGY 185, Academic Press, San Diego, Calif (1990). Alternatively, the recombinant expression vector can be transcribed and translated in vitro, for example using T7 promoter regulatory sequences and T7 polymerase.

Vectors may be introduced and propagated in a prokaryote or prokaryotic cell. In some embodiments, a prokaryote is used to amplify copies of a vector to be introduced into a eukaryotic cell or as an intermediate vector in the production of a vector to be introduced into a eukaryotic cell (e.g., amplifying a plasmid as part of a viral vector packaging system). In some embodiments, a prokaryote is used to amplify copies of a vector and express one or more nucleic acids, such as to provide a source of one or more proteins for delivery to a host cell or host organism. Expression of proteins in prokaryotes is most often carried out in *Escherichia coli* with vectors containing constitutive or inducible promoters directing the expression of either fusion or non-fusion proteins. Fusion vectors add a number of amino acids to a protein encoded therein, such as to the amino terminus of the recombinant protein. Such fusion vectors may serve one or more purposes, such as: (i) to increase expression of recombinant protein; (ii) to increase the solubility of the recombinant protein; and (iii) to aid in the purification of the recombinant protein by acting as a ligand in affinity purification. Often, in fusion expression vectors, a proteolytic cleavage site is introduced at the junction of the fusion moiety and the recombinant protein to enable separation of the recombinant protein from the fusion moiety subsequent to purification of the fusion protein. Such enzymes, and their cognate recognition sequences, include Factor Xa, thrombin and enterokinase. Example fusion expression vectors include pGEX (Pharmacia Biotech Inc; Smith and Johnson, 1988. Gene 67: 31-40), pMAL (New England Biolabs, Beverly, Mass.) and pRIT5 (Pharmacia, Piscataway, N.J.) that fuse glutathione S-transferase (GST), maltose E binding protein, or protein A, respectively, to the target recombinant protein.

Examples of suitable inducible non-fusion *E. coli* expression vectors include pTrc (Amrann et al., (1988) Gene 69:301-315) and pET lid (Studier et al., GENE EXPRESSION TECHNOLOGY: METHODS IN ENZYMOLOGY 185, Academic Press, San Diego, Calif. (1990) 60-89).

In some embodiments, a vector is a yeast expression vector. Examples of vectors for expression in yeast *Saccharomyces cerevisiae* include pYepSecl (Baldari, et al., 1987. *EMBO J.* 6: 229-234), pMFa (Kuijan and Herskowitz, 1982. Cell30: 933-943), pJRY88 (Schultz et al., 1987. *Gene* 54: 113-123), pYES2 (Invitrogen Corporation, San Diego, Calif.), and picZ (InVitrogen Corp, San Diego, Calif.).

In some embodiments, a vector drives protein expression in insect cells using baculovirus expression vectors. Baculovirus vectors available for expression of proteins in cultured insect cells (e.g., SF9 cells) include the pAc series (Smith, et al., 1983. *Mol. Cell. Biol.* 3: 2156-2165) and the pVL series (Luckow and Summers, 1989. *Virology* 170: 31-39).

In some embodiments, a vector is capable of driving expression of one or more sequences in mammalian cells using a mammalian expression vector. Examples of mammalian expression vectors include pCDM8 (Seed, 1987. *Nature* 329: 840) and pMT2PC (Kaufman, et al., 1987. *EMBO J.* 6: 187-195). When used in mammalian cells, the expression vector's control functions are typically provided by one or more regulatory elements. For example, commonly used promoters are derived from polyoma, adenovirus 2, cytomegalovirus, simian virus 40, and others disclosed herein and known in the art. For other suitable expression systems for both prokaryotic and eukaryotic cells see, e.g., Chapters 16 and 17 of Sambrook, et al., *MOLECULAR CLONING: A LABORATORY MANUAL*. 2nd ed., Cold Spring Harbor Laboratory, Cold Spring Harbor Laboratory Press, Cold Spring Harbor, N.Y., 1989.

In some embodiments, the recombinant mammalian expression vector is capable of directing expression of the nucleic acid preferentially in a particular cell type (e.g., tissue-specific regulatory elements are used to express the nucleic acid). Tissue-specific regulatory elements are known in the art. Non-limiting examples of suitable tissue-specific promoters include the albumin promoter (liver-specific; Pinkert, et al., 1987. *Genes Dev.* 1: 268-277), lymphoid-specific promoters (Calame and Eaton, 1988. *Adv. Immunol.* 43: 235-275), in particular promoters of T cell receptors (Winoto and Baltimore, 1989. *EMBO J.* 8: 729-733) and immunoglobulins (Baneiji, et al., 1983. *Cell* 33: 729-740; Queen and Baltimore, 1983. *Cell* 33: 741-748), neuron-specific promoters (e.g., the neurofilament promoter; Byrne and Ruddle, 1989. *Proc. Natl. Acad. Sci. USA* 86: 5473-5477), pancreas-specific promoters (Edlund, et al., 1985. *Science* 230: 912-916), and mammary gland-specific promoters (e.g., milk whey promoter; U.S. Pat. No. 4,873,316 and European Application Publication No. 264,166). Developmentally-regulated promoters are also encompassed, e.g., the murine hox promoters (Kessel and Gruss, 1990. *Science* 249: 374-379) and the a-fetoprotein promoter (Campes and Tilghman, 1989. *Genes Dev.* 3: 537-546). With regards to these prokaryotic and eukaryotic vectors, mention is made of U.S. Pat. No. 6,750,059, the contents of which are incorporated by reference herein in their entirety. Other embodiments of the invention may relate to the use of viral vectors, with regards to which mention is made of U.S. patent application Ser. No. 13/092,085, the contents of which are incorporated by reference herein in their entirety. Tissue-specific regulatory elements are known in the art and in this regard, mention is made of U.S. Pat. No. 7,776,321, the contents of which are incorporated by reference herein in their entirety.

In some embodiments, a regulatory element is operably linked to one or more elements of a CRISPR system so as to drive expression of the one or more elements of the CRISPR system. In general, CRISPRs (Clustered Regularly Interspaced Short Palindromic Repeats), also known as SPIDRs (Spacer Interspersed Direct Repeats), constitute a family of DNA loci that are usually specific to a particular bacterial species. The CRISPR locus comprises a distinct class of interspersed short sequence repeats (SSRs) that were recognized in *E. coli* (Ishino et al., *J. Bacteriol.*, 169:5429-5433 [1987]; and Nakata et al., *J. Bacteriol.*, 171:3553-3556 [1989]), and associated genes. Similar interspersed SSRs have been identified in *Haloferax mediterranei, Streptococcus pyogenes, Anabaena*, and *Mycobacterium tuberculosis* (See, Groenen et al., *Mol. Microbiol.*, 10:1057-1065 [1993]; Hoe et al., *Emerg. Infect. Dis.*, 5:254-263 [1999]; Masepohl et al., *Biochim. Biophys. Acta* 1307:26-30 [1996]; and Mojica et al., *Mol. Microbiol.*, 17:85-93 [1995]). The CRISPR loci typically differ from other SSRs by the structure of the repeats, which have been termed short regularly spaced repeats (SRSRs) (Janssen et al., *OMICS J. Integ. Biol.*, 6:23-33 [2002]; and Mojica et al., *Mol. Microbiol.*, 36:244-246 [2000]). In general, the repeats are short elements that occur in clusters that are regularly spaced by unique intervening sequences with a substantially constant length (Mojica et al., [2000], supra). Although the repeat sequences are highly conserved between strains, the number of interspersed repeats and the sequences of the spacer regions typically differ from strain to strain (van Embden et al., *J. Bacteriol.*, 182:2393-2401 [2000]). CRISPR loci have been identified in more than 40 prokaryotes (See e.g., Jansen et al., *Mol. Microbiol.*, 43:1565-1575 [2002]; and Mojica et al., [2005]) including, but not limited to Aeropyrum, *Pyrobaculum, Sulfolobus, Archaeoglobus, Haloarcula, Methanobacterium, Methanococcus, Methanosarcina, Methanopyrus, Pyrococcus*, Picrophilus, Thermoplasma, *Corynebacterium, Mycobacterium, Streptomyces, Aquifex, Porphyromonas, Chlorobium, Thermus, Bacillus, Listeria, Staphylococcus, Clostridium, Thermoanaerobacter, Mycoplasma, Fusobacterium*, Azoarcus, Chromobacterium, *Neisseria, Nitrosomonas, Desulfovibrio, Geobacter, Myxococcus, Campylobacter, Wolinella, Acinetobacter, Erwinia, Escherichia, Legionella, Methylococcus, Pasteurella, Photobacterium, Salmonella, Xanthomonas, Yersinia, Treponema*, and *Thermotoga*.

In general, "CRISPR system" refers collectively to transcripts and other elements involved in the expression of or directing the activity of CRISPR-associated ("Cas") genes, including sequences encoding a Cas gene, a tracr (trans-activating CRISPR) sequence (e.g. tracrRNA or an active partial tracrRNA; where applicable), a tracr-mate sequence (encompassing a "direct repeat" and a tracrRNA-processed partial direct repeat in the context of an endogenous CRISPR system; where applicable), a guide sequence (also referred to as a "spacer" in the context of an endogenous CRISPR system), or other sequences and transcripts from a CRISPR locus. In some embodiments, one or more elements of a CRISPR system is derived from a type I, type II, or type III CRISPR system. In some embodiments, one or more elements of a CRISPR system is derived from a particular organism comprising an endogenous CRISPR system, such as Streptococcuspyogenes. In general, a CRISPR system is characterized by elements that promote the formation of a CRISPR complex at the site of a target sequence (also referred to as a protospacer in the context of an endogenous CRISPR system). In the context of formation of a CRISPR complex, "target sequence" refers to a sequence to which a guide sequence is designed to have complementarity, where hybridization between a target sequence and a guide sequence promotes the formation of a CRISPR complex. Full complementarity is not necessarily required, provided there is sufficient complementarity to cause hybridization and promote formation of a CRISPR complex. A target sequence may comprise any polynucleotide, such as DNA or RNA polynucleotides. In some embodiments, a target sequence is located in the nucleus or cytoplasm of a cell. In some embodiments, the target sequence may be within an organelle of a eukaryotic cell, for example, mitochondrion or chloroplast. A sequence or template that may be used for recombination into the targeted locus comprising the target sequences is referred to as an "editing template" or "editing polynucleotide" or "editing sequence". In aspects of the invention, an exogenous template polynucleotide may be referred to as an editing template. In an aspect of the invention the recombination is homologous recombination.

Typically, in the context of an endogenous CRISPR system, formation of a CRISPR complex (comprising a guide sequence hybridized to a target sequence and complexed with one or more Cas proteins) results in cleavage of one or both strands in or near (e.g. within 1, 2, 3, 4, 5, 6, 7, 8, 9, 10, 20, 50, or more base pairs from) the target sequence. Without wishing to be bound by theory, the tracr sequence (where applicable), which may comprise or consist of all or a portion of a wild-type tracr sequence (e.g. about or more than about 20, 26, 32, 45, 48, 54, 63, 67, 85, or more nucleotides of a wild-type tracr sequence), may also form part of a CRISPR complex, such as by hybridization along at least a portion of the tracr sequence to all or a portion of a tracr mate sequence that is operably linked to the guide sequence. In some embodiments, the tracr sequence has sufficient complementarity to a tracr mate sequence to hybridize and participate in formation of a CRISPR complex. As with the target sequence, it is believed that complete complementarity is not needed, provided there is sufficient to be functional. In some embodiments, the tracr sequence has at least 50%, 60%, 70%, 80%, 90%, 95% or 99% of sequence complementarity along the length of the tracr mate sequence when optimally aligned. In some embodiments, one or more vectors driving expression of one or more elements of a CRISPR system are introduced into a host cell such that expression of the elements of the CRISPR system direct formation of a CRISPR complex at one or more target sites. For example, a Cas9 enzyme, a guide sequence linked to a tracr-mate sequence, and a tracr sequence could each be operably linked to separate regulatory elements on separate vectors. Alternatively, two or more of the elements expressed from the same or different regulatory elements, may be combined in a single vector, with one or more additional vectors providing any components of the CRISPR system not included in the first vector. CRISPR system elements that are combined in a single vector may be arranged in any suitable orientation, such as one element located 5' with respect to ("upstream" of) or 3' with respect to ("downstream" of) a second element. The coding sequence of one element may be located on the same or opposite strand of the coding sequence of a second element, and oriented in the same or opposite direction. In some embodiments, a single promoter drives expression of a transcript encoding a CRISPR enzyme and one or more of the guide sequence, tracr mate sequence (optionally operably linked to the guide sequence), and a tracr sequence embedded within one or more intron sequences (e.g. each in a different intron, two or more in at least one intron, or all in a single intron). In some embodiments, the CRISPR enzyme, guide sequence, tracr mate sequence, and tracr sequence (where applicable) are operably linked to and expressed from the same promoter.

In some embodiments, a vector comprises one or more insertion sites, such as a restriction endonuclease recognition sequence (also referred to as a "cloning site"). In some embodiments, one or more insertion sites (e.g. about or more than about 1, 2, 3, 4, 5, 6, 7, 8, 9, 10, or more insertion sites) are located upstream and/or downstream of one or more sequence elements of one or more vectors. In some embodiments, a vector comprises an insertion site upstream of a tracr mate sequence, and optionally downstream of a regulatory element operably linked to the tracr mate sequence, such that following insertion of a guide sequence into the insertion site and upon expression the guide sequence directs sequence-specific binding of a CRISPR complex to a target sequence in a eukaryotic cell. In some embodiments, a vector comprises two or more insertion sites, each insertion site being located between two tracr mate sequences so as to allow insertion of a guide sequence at each site. In such an arrangement, the two or more guide sequences may comprise two or more copies of a single guide sequence, two or more different guide sequences, or combinations of these. When multiple different guide sequences are used, a single expression construct may be used to target CRISPR activity to multiple different, corresponding target sequences within a cell. For example, a single vector may comprise about or more than about 1, 2, 3, 4, 5, 6, 7, 8, 9, 10, 15, 20, or more guide sequences. In some embodiments, about or more than about 1, 2, 3, 4, 5, 6, 7, 8, 9, 10, or more such guide-sequence-containing vectors may be provided, and optionally delivered to a cell.

In some embodiments, a vector comprises a regulatory element operably linked to an enzyme-coding sequence encoding a CRISPR protein (i.e. CRISPR/Cas system effector or CRISPR effector). These enzymes are known; for example, the amino acid sequence of *S. pyogenes* Cas9 protein may be found in the SwissProt database under accession number Q99ZW2. In some embodiments, the unmodified CRISPR enzyme has DNA cleavage activity, such as Cas9. The CRISPR enzyme is Cas9, and may be Cas9 from *S. pyogenes* or *S. pneumoniae*. In some embodiments, the CRISPR enzyme directs cleavage of one or both strands at the location of a target sequence, such as within the target sequence and/or within the complement of the target sequence. In some embodiments, the CRISPR enzyme directs cleavage of one or both strands within about 1, 2, 3, 4, 5, 6, 7, 8, 9, 10, 15, 20, 25, 50, 100, 200, 500, or more base pairs from the first or last nucleotide of a target sequence. In some embodiments, a vector encodes a CRISPR enzyme that is mutated to with respect to a corresponding wild-type enzyme such that the mutated CRISPR enzyme lacks the ability to cleave one or both strands of a target polynucleotide containing a target sequence. For example, an aspartate-to-alanine substitution (D10A) in the RuvC I catalytic domain of Cas9 from *S. pyogenes* converts Cas9 from a nuclease that cleaves both strands to a nickase (cleaves a single strand). Other examples of mutations that render Cas9 a nickase include, without limitation, H840A, N854A, and N863A. In some embodiments, a Cas9 nickase may be used in combination with guide sequenc(es), e.g., two guide sequences, which target respectively sense and antisense strands of the DNA target. This combination allows both strands to be nicked and used to induce NHEJ. Applicants have demonstrated (data not shown) the efficacy of two nickase targets (i.e., gRNAs targeted at the same location but to different strands of DNA) in inducing mutagenic NHEJ. A single nickase (Cas9-D10A with a single gRNA) is unable to induce NHEJ and create indels but Applicants have shown that double nickase (Cas9-D10A and two gRNAs targeted to different strands at the same location) can do so in human embryonic stem cells (hESCs). The efficiency is about 50% of nuclease (i.e., regular Cas9 without D10 mutation) in hESCs.

As a further example, two or more catalytic domains of Cas9 (RuvC I, RuvC II, and RuvC III) may be mutated to produce a mutated Cas9 substantially lacking all DNA cleavage activity. In some embodiments, a D10A mutation is combined with one or more of H840A, N854A, or N863A mutations to produce a Cas9 enzyme substantially lacking all DNA cleavage activity. In some embodiments, a CRISPR enzyme is considered to substantially lack all DNA cleavage activity when the DNA cleavage activity of the mutated enzyme is less than about 25%, 10%, 5%, 1%, 0.1%, 0.01%, or lower with respect to its non-mutated form. Other mutations may be useful; where the Cas9 or other CRISPR enzyme is from a species other than *S. pyogenes*, mutations in corresponding amino acids may be made to achieve similar effects.

In some embodiments, a coding sequence encoding a CRISPR enzyme is codon optimized for expression in particular cells, such as eukaryotic cells. The eukaryotic cells may be those of or derived from a particular organism, such as a mammal, including but not limited to human, mouse, rat, rabbit, dog, or non-human primate. In general, codon optimization refers to a process of modifying a nucleic acid sequence for enhanced expression in the host cells of interest by replacing at least one codon (e.g. about or more than about 1, 2, 3, 4, 5, 10, 15, 20, 25, 50, or more codons) of the native sequence with codons that are more frequently or most frequently used in the genes of that host cell while maintaining the native amino acid sequence. Various species exhibit particular bias for certain codons of a particular amino acid. Codon bias (differences in codon usage between organisms) often correlates with the efficiency of translation of messenger RNA (mRNA), which is in turn believed to be dependent on, among other things, the properties of the codons being translated and the availability of particular transfer RNA (tRNA) molecules. The predominance of selected tRNAs in a cell is generally a reflection of the codons used most frequently in peptide synthesis. Accordingly, genes can be tailored for optimal gene expression in a given organism based on codon optimization. Codon usage tables are readily available, for example, at the "Codon Usage Database", and these tables can be adapted in a number of ways. See Nakamura, Y., et al. "Codon usage tabulated from the international DNA sequence databases: status for the year 2000" *Nucl. Acids Res.* 28:292 (2000). Computer algorithms for codon optimizing a particular sequence for expression in a particular host cell are also available, such as Gene Forge (Aptagen; Jacobus, PA), are also available. In some embodiments, one or more codons (e.g. 1, 2, 3, 4, 5, 10, 15, 20, 25, 50, or more, or all codons) in a sequence encoding a CRISPR enzyme correspond to the most frequently used codon for a particular amino acid.

In some embodiments, a vector encodes a CRISPR enzyme comprising one or more nuclear localization sequences (NLSs) or nuclear export signals (NESs), such as about or more than about 1, 2, 3, 4, 5, 6, 7, 8, 9, 10, or more NLSs or NESs. In some embodiments, the CRISPR enzyme comprises about or more than about 1, 2, 3, 4, 5, 6, 7, 8, 9, 10, or more NLSs or NESs at or near the amino-terminus, about or more than about 1, 2, 3, 4, 5, 6, 7, 8, 9, 10, or more NLSs or NESs at or near the carboxy-terminus, or a combination of these (e.g. one or more NLS or NES at the amino-terminus and one or more NLS or NES at the carboxy terminus). When more than one NLS or NES is present, each may be selected independently of the others, such that a single NLS or NES may be present in more than one copy and/or in combination with one or more other NLSs present in one or more copies. In a preferred embodiment of the invention, the CRISPR enzyme comprises at most 6 NLSs or NESs. In some embodiments, an NLS or NES is considered near the N- or C-terminus when the nearest amino acid of the NLS or NES is within about 1, 2, 3, 4, 5, 10, 15, 20, 25, 30, 40, 50, or more amino acids along the polypeptide chain from the N- or C-terminus. Typically, an NLS consists of one or more short sequences of positively charged lysines or arginines exposed on the protein surface, but other types of NLS are known. Non-limiting examples of NLSs include an NLS sequence derived from: the NLS of the SV40 virus large T-antigen, having the amino acid sequence PKKKRKV (SEQ ID NO: 13); the NLS from nucleoplasmin (e.g. the nucleoplasmin bipartite NLS with the sequence KRPAATKKAGQAKKKK (SEQ ID NO: 14)); the c-myc NLS having the amino acid sequence PAAKRVKLD (SEQ ID NO: 15 or RQRRNELKRSP (SEQ ID NO: 16); the hRNPA1 M9 NLS having the sequence NQSSNFGPMKGGNFGGRSSGPYGGGGQYFAKPRNQGGY (SEQ ID NO: 17); the sequence RMRIZFKNKGKDTAELRRRRVEVSVELRKAKKDEQILKRRNV (SEQ ID NO: 18) of the IBB domain from importin-alpha; the sequences VSRKRPRP (SEQ ID NO: 19) and PPKKARED (SEQ ID NO: 20) of the myoma T protein; the sequence PQPKKKPL (SEQ ID NO: 21) of human p53; the sequence SALIKKKKKMAP (SEQ ID NO: 22) of mouse c-abl IV; the sequences DRLRR (SEQ ID NO: 23) and PKQKKRK (SEQ ID NO: 24) of the influenza virus NS1; the sequence RKLKKKIKKL (SEQ ID NO: 25) of the Hepatitis virus delta antigen; the sequence REKKKFLKRR (SEQ ID NO: 26) of the mouse Mx1 protein; the sequence KRKGDEVDGVDEVAKKKSKK (SEQ ID NO: 27) of the human poly(ADP-ribose) polymerase; and the sequence RKCLQAGMNLEARKTKK (SEQ ID NO: 28) of the steroid hormone receptors (human) glucocorticoid.

In general, the one or more NLSs or NESs are of sufficient strength to drive accumulation of the CRISPR enzyme in a detectable amount respectively in the nucleus or cytoplasm of a eukaryotic cell. In general, strength of nuclear/cytoplasmic localization activity may derive from the number of NLSs or NESs in the CRISPR enzyme, the particular NLS(s) or NESs used, or a combination of these factors. Detection of accumulation in the nucleus may be performed by any suitable technique. For example, a detectable marker may be fused to the CRISPR enzyme, such that location within a cell may be visualized, such as in combination with a means for detecting the location of the nucleus (e.g. a stain specific for the nucleus such as DAPI). Examples of detectable markers include fluorescent proteins (such as Green fluorescent proteins, or GFP; RFP; CFP), and epitope tags (HA tag, flag tag, SNAP tag). Cell nuclei may also be isolated from cells, the contents of which may then be analyzed by any suitable process for detecting protein, such as immunohistochemistry, Western blot, or enzyme activity assay. Accumulation in the nucleus may also be determined indirectly, such as by an assay for the effect of CRISPR complex formation (e.g. assay for DNA cleavage or mutation at the target sequence, or assay for altered gene expression activity affected by CRISPR complex formation and/or CRISPR enzyme activity), as compared to a control no exposed to the CRISPR enzyme or complex, or exposed to a CRISPR enzyme lacking the one or more NLSs or NESs.

In general, a guide sequence is any polynucleotide sequence having sufficient complementarity with a target polynucleotide sequence to hybridize with the target sequence and direct sequence-specific binding of a CRISPR complex to the target sequence. In some embodiments, the degree of complementarity between a guide sequence and its corresponding target sequence, when optimally aligned using a suitable alignment algorithm, is about or more than about 50%, 60%, 75%, 80%, 85%, 90%, 95%, 97.5%, 99%, or more. Optimal alignment may be determined with the use of any suitable algorithm for aligning sequences, non-limiting example of which include the Smith-Waterman algorithm, the Needleman-Wunsch algorithm, algorithms based on the Burrows-Wheeler Transform (e.g. the Burrows Wheeler Aligner), Clustal W, Clustal X, BLAT, Novoalign (Novocraft Technologies, ELAND (Illumina, San Diego, CA), SOAP (available at soap.genomics.org.cn), and Maq (available at maq.sourceforge.net). In some embodiments, a guide sequence is about or more than about 5, 10, 11, 12, 13, 14, 15, 16, 17, 18, 19, 20, 21, 22, 23, 24, 25, 26, 27, 28, 29, 30, 35, 40, 45, 50, 75, or more nucleotides in length. In some embodiments, a guide sequence is less than about 75, 50, 45, 40, 35, 30, 25, 20, 15, 12, or fewer nucleotides in length. The ability of a guide sequence to direct sequence-specific binding of a CRISPR complex to a target sequence may be assessed by any suitable assay. For example, the components of a CRISPR system sufficient to form a CRISPR complex, including the guide sequence to be tested, may be provided to a host cell having the corresponding target sequence, such as by transfection with vectors encoding the components of the CRISPR sequence, followed by an assessment of preferential cleavage within the target sequence, such as by Surveyor assay as described herein. Similarly, cleavage of a target polynucleotide sequence may be evaluated in a test tube by providing the target sequence, components of a CRISPR complex, including the guide sequence to be tested and a control guide sequence different from the test guide sequence, and comparing binding or rate of cleavage at the target sequence between the test and control guide sequence reactions. Other assays are possible, and will occur to those skilled in the art.

A guide sequence may be selected to target any target sequence. In some embodiments, the target sequence is a sequence within a genome of a cell. Exemplary target sequences include those that are unique in the target genome. For example, for the *S. pyogenes* Cas9, a unique target sequence in a genome may include a Cas9 target site of the form MMMMMMMMNNNNNNNNNNNNXGG (SEQ ID NO: 29) where NNNNNNNNNNNNXGG (SEQ ID NO: 30) (N is A, G, T, or C; and X can be anything) has a single occurrence in the genome. A unique target sequence in a genome may include an *S. pyogenes* Cas9 target site of the form MMMMMMMMMNNNNNNNNNNNXGG (SEQ ID NO: 31) where NNNNNNNNNNNXGG (SEQ ID NO: 32) (N is A, G, T, or C; and X can be anything) has a single occurrence in the genome. For the *S. thermophilus* CRISPRI Cas9, a unique target sequence in a genome may include a Cas9 target site of the form MMMMMMMMNNNNNNNNNNNNXXAGAAW (SEQ ID NO: 33) where NNNNNNNNNNNNXXAGAAW (SEQ ID NO: 34) (N is A, G, T, or C; X can be anything; and W is A or T) has a single occurrence in the genome. A unique target sequence in a genome may include an *S. thermophilus* CRISPRI Cas9 target site of the form MMMMMMMMMNNNNNNNNNNNXXAGAAW (SEQ ID NO: 35) where NNNNNNNNNNNXXAGAAW (SEQ ID NO: 36) (N is A, G, T, or C; X can be anything; and W is A or T) has a single occurrence in the genome. For the *S. pyogenes* Cas9, a unique target sequence in a genome may include a Cas9 target site of the form MMMMMMMMNNNNNNNNNNNNXGGXG (SEQ ID NO: 37) where NNNNNNNNNNNNXGGXG (SEQ ID NO: 38) (N is A, G, T, or C; and X can be anything) has a single occurrence in the genome. A unique target sequence in a genome may include an *S. pyogenes* Cas9 target site of the form MMMMMMMMMNNNNNNNNNNNXGGXG (SEQ ID NO: 39) where NNNNNNNNNNNXGGXG (SEQ ID NO: 40) (N is A, G, T, or C; and X can be anything) has a single occurrence in the genome. In each of these sequences "M" may be A, G, T, or C, and need not be considered in identifying a sequence as unique.

In some embodiments, a guide sequence is selected to reduce the degree of secondary structure within the guide sequence. Secondary structure may be determined by any suitable polynucleotide folding algorithm. Some programs are based on calculating the minimal Gibbs free energy. An example of one such algorithm is mFold, as described by Zuker and Stiegler (*Nucleic Acids Res.* 9 (1981), 133-148). Another example folding algorithm is the online webserver RNAfold, developed at Institute for Theoretical Chemistry at the University of Vienna, using the centroid structure prediction algorithm (see e.g. A.R. Gruber et al., 2008, *Cell* 106(1): 23-24; and PA Carr and GM Church, 2009, *Nature Biotechnology* 27(12): 1151-62). Further algorithms may be found in U.S. application Ser. No. 61/836,080; incorporated herein by reference.

In general, a tracr mate sequence includes any sequence that has sufficient complementarity with a tracr sequence to promote one or more of: (1) excision of a guide sequence flanked by tracr mate sequences in a cell containing the corresponding tracr sequence; and (2) formation of a CRISPR complex at a target sequence, wherein the CRISPR complex comprises the tracr mate sequence hybridized to the tracr sequence. In general, degree of complementarity is with reference to the optimal alignment of the tracr mate sequence and tracr sequence, along the length of the shorter of the two sequences. Optimal alignment may be determined by any suitable alignment algorithm, and may further account for secondary structures, such as self-complementarity within either the tracr sequence or tracr mate sequence. In some embodiments, the degree of complementarity between the tracr sequence and tracr mate sequence along the length of the shorter of the two when optimally aligned is about or more than about 25%, 30%, 40%, 50%, 60%, 70%, 80%, 90%, 95%, 97.5%, 99%, or higher. In some embodiments, the tracr sequence is about or more than about 5, 6, 7, 8, 9, 10, 11, 12, 13, 14, 15, 16, 17, 18, 19, 20, 25, 30, 40, 50, or more nucleotides in length. In some embodiments, the tracr sequence and tracr mate sequence are contained within a single transcript, such that hybridization between the two produces a transcript having a secondary structure, such as a hairpin. Preferred loop forming sequences for use in hairpin structures are four nucleotides in length, and most preferably have the sequence GAAA. However, longer or shorter loop sequences may be used, as may alternative sequences. The sequences preferably include a nucleotide triplet (for example, AAA), and an additional nucleotide (for example C or G). Examples of loop forming sequences include CAAA and AAAG. In an embodiment of the invention, the transcript or transcribed polynucleotide sequence has at least two or more hairpins. In preferred embodiments, the transcript has two, three, four or five hairpins. In a further embodiment of the invention, the transcript has at most five hairpins. In some embodiments, the single transcript further includes a transcription termination sequence; preferably this is a polyT sequence, for example six T nucleotides. An example of such a hairpin structure is where the portion of the sequence 5' of the final "N" and upstream of the loop corresponds to the tracr mate sequence, and the portion of the sequence 3' of the loop corresponds to the tracr sequence. Further non-limiting examples of single polynucleotides comprising a guide sequence, a tracr mate sequence, and a tracr sequence are as follows (listed 5' to 3'), where "N" represents a base of a guide sequence, the first block of lower case letters represent the tracr mate sequence, and the second block of lower case letters represent the tracr sequence, and the final poly-T sequence represents the transcription terminator: (1) NNNNNNNNNNNNNNNNNNNNgtttttgtactctcaagatttaGAAAtaaatcttgcagaagctacaaagataaggcttcatgccgaaatcaacaccctgtcattttatggcagggtgttttcgttatttaaTTTTTT (SEQ ID NO: 41); (2) NNNNNNNNNNNNNNNNNNNNgtttttgtactctcaGAAAtgcagaagctacaaagataaggcttcatgccg- aaatca acaccctgtcattttatggcagggtgttttcgttatttaaTTTTTT (SEQ ID NO: 42); (3) NNNNNNNNNNNNNNNNNNNNgtttttgtactctcaGAAAtgcagaagctacaaagataaggcttcatgccgaaatca acaccctgtcattttatggcagggtgtTTTTTT (SEQ ID NO: 43); (4) NNNNNNNNNNNNNNNNNNNNgttttagagctaGAAAtagcaagttaaaataaggctagtccgttatcaacttgaaaa agtggcaccgagtcggtgc TTTTTT (SEQ ID NO: 44); (5) NNNNNNNNN-NNNNNNNNNNNgttttagagctaGAAATAGcaagttaaaat-aaggctagtccgttatcaacttgaa aaagtgTTTTTTT (SEQ ID NO: 45); and (6) NNNNNNNNNNNNNNNNNNNNgttttaga-gctagAAATAGcaagttaaaataaggctagtccgttatcaTTTTT TTT (SEQ ID NO: 46). In some embodiments, sequences (1) to (3) are used in combination with Cas9 from *S. thermophilus* CRISPRI. In some embodiments, sequences (4) to (6) are used in combination with Cas9 from *S. pyogenes*. In some embodiments, the tracr sequence is a separate transcript from a transcript comprising the tracr mate sequence.

In some embodiments, a recombination template is also provided. A recombination template may be a component of another vector as described herein, contained in a separate vector, or provided as a separate polynucleotide. In some embodiments, a recombination template is designed to serve as a template in homologous recombination, such as within or near a target sequence nicked or cleaved by a CRISPR enzyme as a part of a CRISPR complex. A template polynucleotide may be of any suitable length, such as about or more than about 10, 15, 20, 25, 50, 75, 100, 150, 200, 500, 1000, or more nucleotides in length. In some embodiments, the template polynucleotide is complementary to a portion of a polynucleotide comprising the target sequence. When optimally aligned, a template polynucleotide might overlap with one or more nucleotides of a target sequences (e.g. about or more than about 1, 5, 10, 15, 20, 25, 30, 35, 40, 45, 50, 60, 70, 80, 90, 100 or more nucleotides). In some embodiments, when a template sequence and a polynucleotide comprising a target sequence are optimally aligned, the nearest nucleotide of the template polynucleotide is within about 1, 5, 10, 15, 20, 25, 50, 75, 100, 200, 300, 400, 500, 1000, 5000, 10000, or more nucleotides from the target sequence.

In some embodiments, the CRISPR enzyme is part of a fusion protein comprising one or more heterologous protein domains (e.g., about or more than about 1, 2, 3, 4, 5, 6, 7, 8, 9, 10, or more domains in addition to the CRISPR enzyme). A CRISPR enzyme fusion protein may comprise any additional protein sequence, and optionally a linker sequence between any two domains. Examples of protein domains that may be fused to a CRISPR enzyme include, without limitation, epitope tags, reporter gene sequences, and protein domains having one or more of the following activities: methylase activity, demethylase activity, transcription activation activity, transcription repression activity, transcription release factor activity, histone modification activity, RNA cleavage activity and nucleic acid binding activity. Non-limiting examples of epitope tags include histidine (His) tags, V5 tags, FLAG tags, influenza hemagglutinin (HA) tags, Myc tags, VSV-G tags, and thioredoxin (Trx) tags. Examples of reporter genes include, but are not limited to, glutathione-S-transferase (GST), horseradish peroxidase (HRP), chloramphenicol acetyltransferase (CAT) beta-galactosidase, beta-glucuronidase, luciferase, green fluorescent protein (GFP), HcRed, DsRed, cyan fluorescent protein (CFP), yellow fluorescent protein (YFP), and autofluorescent proteins including blue fluorescent protein (BFP). A CRISPR enzyme may be fused to a gene sequence encoding a protein or a fragment of a protein that bind DNA molecules or bind other cellular molecules, including but not limited to maltose binding protein (MBP), S-tag, Lex A DNA binding domain (DBD) fusions, GAL4 DNA binding domain fusions, and herpes simplex virus (HSV) BP16 protein fusions. Additional domains that may form part of a fusion protein comprising a CRISPR enzyme are described in US20110059502, incorporated herein by reference. In some embodiments, a tagged CRISPR enzyme is used to identify the location of a target sequence.

In some aspects, the invention provides methods comprising delivering one or more polynucleotides, such as or one or more vectors as described herein, one or more transcripts thereof, and/or one or proteins transcribed therefrom, to a host cell. In some aspects, the invention further provides cells produced by such methods, and organisms (such as animals, plants, or fungi) comprising or produced from such cells. In some embodiments, a CRISPR enzyme in combination with (and optionally complexed with) a guide sequence is delivered to a cell. Conventional viral and non-viral based gene transfer methods can be used to introduce nucleic acids in mammalian cells or target tissues. Such methods can be used to administer nucleic acids encoding components of a CRISPR system to cells in culture, or in a host organism. Non-viral vector delivery systems include DNA plasmids, RNA (e.g. a transcript of a vector described herein), naked nucleic acid, and nucleic acid complexed with a delivery vehicle, such as a liposome. Viral vector delivery systems include DNA and RNA viruses, which have either episomal or integrated genomes after delivery to the cell. For a review of gene therapy procedures, see Anderson, *Science* 256:808-813 (1992); *Nabel & Felgner, TIBTECH* 11:211-217 (1993); *Mitani & Caskey, TIBTECH* 11:162-166 (1993); *Dillon, TIBTECH* 11:167-175 (1993); Miller, *Nature* 357:455-460 (1992); *Van Brunt, Biotechnology* 6(10):1149-1154 (1988); Vigne, *Restorative Neurology and Neuroscience* 8:35-36 (1995); Kremer & Perricaudet, *British Medical Bulletin* 51(1):31-44 (1995); Haddada et al., in *Current Topics in Microbiology and Immunology*, Doerfler and Bohm (eds) (1995); and Yu et al., *Gene Therapy* 1:13-26 (1994).

Methods of non-viral delivery of nucleic acids include lipofection, nucleofection, microinjection, biolistics, virosomes, liposomes, immunoliposomes, polycation or lipid: nucleic acid conjugates, naked DNA, artificial virions, and agent-enhanced uptake of DNA. Lipofection is described in e.g., U.S. Pat. Nos. 5,049,386, 4,946,787; and 4,897,355) and lipofection reagents are sold commercially (e.g., Transfectam™ and Lipofectin™). Cationic and neutral lipids that are suitable for efficient receptor-recognition lipofection of polynucleotides include those of Felgner, WO 91/17424; WO 91/16024. Delivery can be to cells (e.g. in vitro or ex vivo administration) or target tissues (e.g. in vivo administration).

The preparation of lipid:nucleic acid complexes, including targeted liposomes such as immunolipid complexes, is well known to one of skill in the art (see, e.g., Crystal, *Science* 270:404-410 (1995); Blaese et al., *Cancer Gene Ther.* 2:291-297 (1995); Behr et al., *Bioconjugate Chem.* 5:382-389 (1994); Remy et al., *Bioconjugate Chem.* 5:647-654 (1994); Gao et al., *Gene Therapy* 2:710-722 (1995); Ahmad et al., *Cancer Res.* 52:4817-4820 (1992); U.S. Pat. Nos. 4,186,183, 4,217,344, 4,235,871, 4,261,975, 4,485,054, 4,501,728, 4,774,085, 4,837,028, and 4,946,787).

The use of RNA or DNA viral based systems for the delivery of nucleic acids takes advantage of highly evolved processes for targeting a virus to specific cells in the body and trafficking the viral payload to the nucleus. Viral vectors can be administered directly to patients (in vivo) or they can be used to treat cells in vitro, and the modified cells may optionally be administered to patients (ex vivo). Conventional viral based systems could include retroviral, lentivirus, adenoviral, adeno-associated and herpes simplex virus vectors for gene transfer. Integration in the host genome is possible with the retrovirus, lentivirus, and adeno-associated virus gene transfer methods, often resulting in long term expression of the inserted transgene. Additionally, high transduction efficiencies have been observed in many different cell types and target tissues.

The tropism of a retrovirus can be altered by incorporating foreign envelope proteins, expanding the potential target population of target cells. Lentiviral vectors are retroviral vectors that are able to transduce or infect non-dividing cells and typically produce high viral titers. Selection of a retroviral gene transfer system would therefore depend on the target tissue. Retroviral vectors are comprised of cis-acting long terminal repeats with packaging capacity for up to 6-10 kb of foreign sequence. The minimum cis-acting LTRs are sufficient for replication and packaging of the vectors, which are then used to integrate the therapeutic gene into the target cell to provide permanent transgene expression. Widely used retroviral vectors include those based upon murine leukemia virus (MuLV), gibbon ape leukemia virus (GaLV), Simian Immunodeficiency virus (SIV), human Immunodeficiency virus (HIV), and combinations thereof (see, e.g., Buchscher et al., *J. Virol.* 66:2731-2739 (1992); Johann et al., *J. Virol.* 66:1635-1640 (1992); Sommnerfelt et al., *Virol.* 176:58-59 (1990); Wilson et al., *J. Virol.* 63:2374-2378 (1989); Miller et al., *J. Virol.* 65:2220-2224 (1991); PCT/US94/05700).In applications where transient expression is preferred, adenoviral based systems may be used. Adenoviral based vectors are capable of very high transduction efficiency in many cell types and do not require cell division. With such vectors, high titer and levels of expression have been obtained. This vector can be produced in large quantities in a relatively simple system. Adeno-associated virus ("AAV") vectors may also be used to transduce cells with target nucleic acids, e.g., in the in vitro production of nucleic acids and peptides, and for in vivo and ex vivo gene therapy procedures (see, e.g., West et al., *Virology* 160:38-47 (1987); U.S. Pat. No. 4,797,368; WO 93/24641; Kotin, Human Gene Therapy 5:793-801 (1994); *Muzyczka, J. Clin. Invest.* 94:1351 (1994). Construction of recombinant AAV vectors are described in a number of publications, including U.S. Pat. No. 5,173,414; Tratschin et al., *Mol. Cell. Biol.* 5:3251-3260 (1985); Tratschin, et al., *Mol. Cell. Biol.* 4:2072-2081 (1984); *Hermonat & Muzyczka, PNAS* 81:6466-6470 (1984); and Samulski et al., *J. Virol.* 63:03822-3828 (1989).

Packaging cells are typically used to form virus particles that are capable of infecting a host cell. Such cells include 293 cells, which package adenovirus, and W2 cells or PA317 cells, which package retrovirus. Viral vectors used in gene therapy are usually generated by producing a cell line that packages a nucleic acid vector into a viral particle. The vectors typically contain the minimal viral sequences required for packaging and subsequent integration into a host, other viral sequences being replaced by an expression cassette for the polynucleotide(s) to be expressed. The missing viral functions are typically supplied in trans by the packaging cell line. For example, AAV vectors used in gene therapy typically only possess ITR sequences from the AAV genome which are required for packaging and integration into the host genome. Viral DNA is packaged in a cell line, which contains a helper plasmid encoding the other AAV genes, namely rep and cap, but lacking ITR sequences. The cell line may also be infected with adenovirus as a helper. The helper virus promotes replication of the AAV vector and expression of AAV genes from the helper plasmid. The helper plasmid is not packaged in significant amounts due to a lack of ITR sequences. Contamination with adenovirus can be reduced by, e.g., heat treatment to which adenovirus is more sensitive than AAV. Additional methods for the delivery of nucleic acids to cells are known to those skilled in the art. See, for example, US20030087817, incorporated herein by reference.

In some embodiments, a host cell is transiently or non-transiently transfected with one or more vectors described herein. In some embodiments, a cell is transfected as it naturally occurs in a subject. In some embodiments, a cell that is transfected is taken from a subject. In some embodiments, the cell is derived from cells taken from a subject, such as a cell line. A wide variety of cell lines for tissue culture are known in the art. Examples of cell lines include, but are not limited to, C8161, CCRF-CEM, MOLT, mIMCD-3, NHDF, HeLa-S3, Huh1, Huh4, Huh7, HUVEC, HASMC, HEKn, HEKa, MiaPaCell, Panc1, PC-3, TF1, CTLL-2, C1R, Rat6, CV1, RPTE, A10, T24, J82, A375, ARH-77, Calul, SW480, SW620, SKOV3, SK-UT, CaCo2, P388D1, SEM-K2, WEHI-231, HB56, TIB55, Jurkat, J45.01, LRMB, Bcl-1, BC-3, IC21, DLD2, Raw264.7, NRK, NRK-52E, MRC5, MEF, Hep G2, HeLa B, HeLa T4, COS, COS-1, COS-6, COS-M6A, BS-C-1 monkey kidney epithelial, BALB/3T3 mouse embryo fibroblast, 3T3 Swiss, 3T3-L1, 132-d5 human fetal fibroblasts; 10.1 mouse fibroblasts, 293-T, 3T3, 721, 9L, A2780, A2780ADR, A2780cis, A172, A20, A253, A431, A-549, ALC, B16, B35, BCP-1 cells, BEAS-2B, bEnd.3, BHK-21, BR 293, BxPC3, C3H-10T1/2, C6/36, Cal-27, CHO, CHO-7, CHO-IR, CHO-K1, CHO-K2, CHO-T, CHO Dhfr −/−, COR-L23, COR-L23/CPR, COR-L23/5010, COR-L23/R23, COS-7, COV-434, CML T1, CMT, CT26, D17, DH82, DU145, DuCaP, EL4, EM2, EM3, EMT6/AR1, EMT6/AR10.0, FM3, H1299, H69, HB54, HB55, HCA2, HEK-293, HeLa, Hepalclc7, HL-60, HMEC, HT-29, Jurkat, JY cells, K562 cells, Ku812, KCL22, KG1, KYO1, LNCap, Ma-Mel 1-48, MC-38, MCF-7, MCF-10A, MDA-MB-231, MDA-MB-468, MDA-MB-435, MDCK II, MDCK II, MOR/0.2R, MONO-MAC 6, MTD-1A, MyEnd, NCI-H69/CPR, NCI-H69/LX10, NCI-H69/LX20, NCI-H69/LX4, NIH-3T3, NALM-1, NW-145, OPCN/OPCT cell lines, Peer, PNT-1A/PNT 2, RenCa, RIN-5F, RMA/RMAS, Saos-2 cells, Sf-9, SkBr3, T2, T-47D, T84, THP1 cell line, U373, U87, U937, VCaP, Vero cells, WM39, WT-49, X63, YAC-1, YAR, and transgenic varieties thereof. Cell lines are available from a variety of sources known to those with skill in the art (see, e.g., the American Type Culture Collection (ATCC) (Manassas, Va.)). In some embodiments, a cell transfected with one or more vectors described herein is used to establish a new cell line comprising one or more vector-derived sequences. In some embodiments, a cell transiently transfected with the components of a CRISPR system as described herein (such as by transient transfection of one or more vectors, or transfection with RNA), and modified through the activity of a CRISPR complex, is used to establish a new cell line comprising cells containing the modification but lacking any other exogenous sequence. In some embodiments, cells transiently or non-transiently transfected with one or more vectors described herein, or cell lines derived from such cells are used in assessing one or more test compounds.

In some embodiments, one or more vectors described herein are used to produce a non-human transgenic animal or transgenic plant. In some embodiments, the transgenic animal is a mammal, such as a mouse, rat, or rabbit. In certain embodiments, the organism or subject is a plant. In certain embodiments, the organism or subject or plant is algae. Methods for producing transgenic plants and animals are known in the art, and generally begin with a method of cell transfection, such as described herein.

In one aspect, the invention provides for methods of modifying a target polynucleotide in a eukaryotic cell. In some embodiments, the method comprises allowing a CRISPR complex to bind to the target polynucleotide to effect cleavage of said target polynucleotide thereby modifying the target polynucleotide, wherein the CRISPR complex comprises a CRISPR enzyme complexed with a guide sequence hybridized to a target sequence within said target polynucleotide, wherein said guide sequence is linked to a tracr mate sequence which in turn hybridizes to a tracr sequence (where applicable).

In one aspect, the invention provides a method of modifying expression of a polynucleotide in a eukaryotic cell. In some embodiments, the method comprises allowing a CRISPR complex to bind to the polynucleotide such that said binding results in increased or decreased expression of said polynucleotide; wherein the CRISPR complex comprises a CRISPR enzyme complexed with a guide sequence hybridized to a target sequence within said polynucleotide, wherein said guide sequence is linked to a tracr mate sequence which in turn hybridizes to a tracr sequence (where applicable).

With recent advances in crop genomics, the ability to use CRISPR-Cas systems to perform efficient and cost effective gene editing and manipulation will allow the rapid selection and comparison of single and multiplexed genetic manipulations to transform such genomes for improved production and enhanced traits. In this regard reference is made to US patents and publications: U.S. Pat. No. 6,603,061-*Agrobacterium*-Mediated Plant Transformation Method; U.S. Pat. No. 7,868,149-Plant Genome Sequences and Uses Thereof and US 2009/0100536-Transgenic Plants with Enhanced Agronomic Traits, all the contents and disclosure of each of which are herein incorporated by reference in their entirety. In the practice of the invention, the contents and disclosure of Morrell et al "Crop genomics:advances and applications" *Nat Rev Genet.* 2011 Dec. 29; 13(2):85-96 are also herein incorporated by reference in their entirety. In an advantageous embodiment of the invention, the CRISPR/Cas9 system is used to engineer microalgae. Accordingly, reference herein to animal cells may also apply, mutatis mutandis, to plant cells unless otherwise apparent.

The practice of the present invention employs, unless otherwise indicated, conventional techniques of immunology, biochemistry, chemistry, molecular biology, microbiology, cell biology, genomics and recombinant DNA, which are within the skill of the art. See Sambrook, Fritsch and Maniatis, *MOLECULAR CLONING: A LABORATORY MANUAL,* 2nd edition (1989); CURRENT PROTOCOLS IN MOLECULAR BIOLOGY (F. M. Ausubel, et al. eds., (1987)); the series METHODS IN ENZYMOLOGY (Academic Press, Inc.): PCR 2: A PRACTICAL APPROACH (M. J. MacPherson, B. D. Hames and G. R. Taylor eds. (1995)), Harlow and Lane, eds. (1988) ANTIBODIES, A LABORATORY MANUAL, and ANIMAL CELL CULTURE (R.I. *Freshney, ed.* (1987)).

Models of Genetic and Epiuenetic Conditions

A method of the invention may be used to create a plant, an animal or cell that may be used to model and/or study genetic or epigenetic conditions of interest, such as a through a model of mutations of interest or a as a disease model. As used herein, "disease" refers to a disease, disorder, or indication in a subject. For example, a method of the invention may be used to create an animal or cell that comprises a modification in one or more nucleic acid sequences associated with a disease, or a plant, animal or cell in which the expression of one or more nucleic acid sequences associated with a disease are altered. Such a nucleic acid sequence may encode a disease associated protein sequence or may be a disease associated control sequence. Accordingly, it is understood that in embodiments of the invention, a plant, subject, patient, organism or cell can be a non-human subject, patient, organism or cell. Thus, the invention provides a plant, animal or cell, produced by the present methods, or a progeny thereof. The progeny may be a clone of the produced plant or animal, or may result from sexual reproduction by crossing with other individuals of the same species to introgress further desirable traits into their offspring. The cell may be in vivo or ex vivo in the cases of multicellular organisms, particularly animals or plants. In the instance where the cell is in cultured, a cell line may be established if appropriate culturing conditions are met and preferably if the cell is suitably adapted for this purpose (for instance a stem cell). Bacterial cell lines produced by the invention are also envisaged. Hence, cell lines are also envisaged.

In some methods, the disease model can be used to study the effects of mutations on the animal or cell and development and/or progression of the disease using measures commonly used in the study of the disease. Alternatively, such a disease model is useful for studying the effect of a pharmaceutically active compound on the disease.

In some methods, the disease model can be used to assess the efficacy of a potential gene therapy strategy. That is, a disease-associated gene or polynucleotide can be modified such that the disease development and/or progression is inhibited or reduced. In particular, the method comprises modifying a disease-associated gene or polynucleotide such that an altered protein is produced and, as a result, the animal or cell has an altered response. Accordingly, in some methods, a genetically modified animal may be compared with an animal predisposed to development of the disease such that the effect of the gene therapy event may be assessed.

In another embodiment, this invention provides a method of developing a biologically active agent that modulates a cell signaling event associated with a disease gene. The method comprises contacting a test compound with a cell comprising one or more vectors that drive expression of one or more of a CRISPR enzyme, a guide sequence linked to a tracr mate sequence, and a tracr sequence; and detecting a change in a readout that is indicative of a reduction or an augmentation of a cell signaling event associated with, e.g., a mutation in a disease gene contained in the cell.

A cell model or animal model can be constructed in combination with the method of the invention for screening a cellular function change. Such a model may be used to study the effects of a genome sequence modified by the CRISPR complex of the invention on a cellular function of interest. For example, a cellular function model may be used to study the effect of a modified genome sequence on intracellular signaling or extracellular signaling. Alternatively, a cellular function model may be used to study the effects of a modified genome sequence on sensory perception. In some such models, one or more genome sequences associated with a signaling biochemical pathway in the model are modified.

Several disease models have been specifically investigated. These include de novo autism risk genes CHD8, KATNAL2, and SCN2A; and the syndromic autism (Angelman Syndrome) gene UBE3A. These genes and resulting autism models are of course preferred, but serve to show the broad applicability of the invention across genes and corresponding models.

An altered expression of one or more genome sequences associated with a signaling biochemical pathway can be determined by assaying for a difference in the mRNA levels of the corresponding genes between the test model cell and a control cell, when they are contacted with a candidate agent. Alternatively, the differential expression of the sequences associated with a signaling biochemical pathway is determined by detecting a difference in the level of the encoded polypeptide or gene product.

To assay for an agent-induced alteration in the level of mRNA transcripts or corresponding polynucleotides, nucleic acid contained in a sample is first extracted according to standard methods in the art. For instance, mRNA can be isolated using various lytic enzymes or chemical solutions according to the procedures set forth in Sambrook et al. (1989), or extracted by nucleic-acid-binding resins following the accompanying instructions provided by the manufacturers. The mRNA contained in the extracted nucleic acid sample is then detected by amplification procedures or conventional hybridization assays (e.g. Northern blot analysis) according to methods widely known in the art or based on the methods exemplified herein.

For purpose of this invention, amplification means any method employing a primer and a polymerase capable of replicating a target sequence with reasonable fidelity. Amplification may be carried out by natural or recombinant DNA polymerases such as TaqGold™, T7 DNA polymerase, Klenow fragment of *E. coli* DNA polymerase, and reverse transcriptase. A preferred amplification method is PCR. In particular, the isolated RNA can be subjected to a reverse transcription assay that is coupled with a quantitative polymerase chain reaction (RT-PCR) in order to quantify the expression level of a sequence associated with a signaling biochemical pathway.

Detection of the gene expression level can be conducted in real time in an amplification assay. In one aspect, the amplified products can be directly visualized with fluorescent DNA-binding agents including but not limited to DNA intercalators and DNA groove binders. Because the amount of the intercalators incorporated into the double-stranded DNA molecules is typically proportional to the amount of the amplified DNA products, one can conveniently determine the amount of the amplified products by quantifying the fluorescence of the intercalated dye using conventional optical systems in the art. DNA-binding dye suitable for this application include SYBR green, SYBR blue, DAPI, propidium iodine, Hoeste, SYBR gold, ethidium bromide, acridines, proflavine, acridine orange, acriflavine, fluorcoumanin, ellipticine, daunomycin, chloroquine, distamycin D, chromomycin, homidium, mithramycin, ruthenium polypyridyls, anthramycin, and the like.

In another aspect, other fluorescent labels such as sequence specific probes can be employed in the amplification reaction to facilitate the detection and quantification of the amplified products. Probe-based quantitative amplification relies on the sequence-specific detection of a desired amplified product. It utilizes fluorescent, target-specific probes (e.g., TaqMan® probes) resulting in increased specificity and sensitivity. Methods for performing probe-based quantitative amplification are well established in the art and are taught in U.S. Pat. No. 5,210,015.

In yet another aspect, conventional hybridization assays using hybridization probes that share sequence homology with sequences associated with a signaling biochemical pathway can be performed. Typically, probes are allowed to form stable complexes with the sequences associated with a signaling biochemical pathway contained within the biological sample derived from the test subject in a hybridization reaction. It will be appreciated by one of skill in the art that where antisense is used as the probe nucleic acid, the target polynucleotides provided in the sample are chosen to be complementary to sequences of the antisense nucleic acids. Conversely, where the nucleotide probe is a sense nucleic acid, the target polynucleotide is selected to be complementary to sequences of the sense nucleic acid.

Hybridization can be performed under conditions of various stringency. Suitable hybridization conditions for the practice of the present invention are such that the recognition interaction between the probe and sequences associated with a signaling biochemical pathway is both sufficiently specific and sufficiently stable. Conditions that increase the stringency of a hybridization reaction are widely known and published in the art. See, for example, (Sambrook, et al., (1989); Nonradioactive In Situ Hybridization Application Manual, Boehringer Mannheim, second edition). The hybridization assay can be formed using probes immobilized on any solid support, including but are not limited to nitrocellulose, glass, silicon, and a variety of gene arrays. A preferred hybridization assay is conducted on high-density gene chips as described in U.S. Pat. No. 5,445,934.

For a convenient detection of the probe-target complexes formed during the hybridization assay, the nucleotide probes are conjugated to a detectable label. Detectable labels suitable for use in the present invention include any composition detectable by photochemical, biochemical, spectroscopic, immunochemical, electrical, optical or chemical means. A wide variety of appropriate detectable labels are known in the art, which include fluorescent or chemiluminescent labels, radioactive isotope labels, enzymatic or other ligands. In preferred embodiments, one will likely desire to employ a fluorescent label or an enzyme tag, such as digoxigenin, 8-galactosidase, urease, alkaline phosphatase or peroxidase, avidin/biotin complex.

The detection methods used to detect or quantify the hybridization intensity will typically depend upon the label selected above. For example, radiolabels may be detected using photographic film or a phosphoimager. Fluorescent markers may be detected and quantified using a photodetector to detect emitted light. Enzymatic labels are typically detected by providing the enzyme with a substrate and measuring the reaction product produced by the action of the enzyme on the substrate; and finally colorimetric labels are detected by simply visualizing the colored label.

An agent-induced change in expression of sequences associated with a signaling biochemical pathway can also be determined by examining the corresponding gene products. Determining the protein level typically involves (a) contacting the protein contained in a biological sample with an agent that specifically bind to a protein associated with a signaling biochemical pathway; and (b) identifying any agent:protein complex so formed. In one aspect of this embodiment, the agent that specifically binds a protein associated with a signaling biochemical pathway is an antibody, preferably a monoclonal antibody.

The reaction is performed by contacting the agent with a sample of the proteins associated with a signaling biochemical pathway derived from the test samples under conditions that will allow a complex to form between the agent and the proteins associated with a signaling biochemical pathway. The formation of the complex can be detected directly or indirectly according to standard procedures in the art. In the direct detection method, the agents are supplied with a detectable label and unreacted agents may be removed from the complex; the amount of remaining label thereby indicating the amount of complex formed. For such method, it is preferable to select labels that remain attached to the agents even during stringent washing conditions. It is preferable that the label does not interfere with the binding reaction. In the alternative, an indirect detection procedure may use an agent that contains a label introduced either chemically or enzymatically. A desirable label generally does not interfere with binding or the stability of the resulting agent:polypeptide complex. However, the label is typically designed to be accessible to an antibody for an effective binding and hence generating a detectable signal.

A wide variety of labels suitable for detecting protein levels are known in the art. Non-limiting examples include radioisotopes, enzymes, colloidal metals, fluorescent compounds, bioluminescent compounds, and chemiluminescent compounds.

The amount of agent:polypeptide complexes formed during the binding reaction can be quantified by standard quantitative assays. As illustrated above, the formation of agent:polypeptide complex can be measured directly by the amount of label remained at the site of binding. In an alternative, the protein associated with a signaling biochemical pathway is tested for its ability to compete with a labeled analog for binding sites on the specific agent. In this competitive assay, the amount of label captured is inversely proportional to the amount of protein sequences associated with a signaling biochemical pathway present in a test sample.

A number of techniques for protein analysis based on the general principles outlined above are available in the art. They include but are not limited to radioimmunoassays, ELISA (enzyme linked immunoradiometric assays), "sandwich" immunoassays, immunoradiometric assays, in situ immunoassays (using e.g., colloidal gold, enzyme or radioisotope labels), western blot analysis, immunoprecipitation assays, immunofluorescent assays, and SDS-PAGE.

Antibodies that specifically recognize or bind to proteins associated with a signaling biochemical pathway are preferable for conducting the aforementioned protein analyses. Where desired, antibodies that recognize a specific type of post-translational modifications (e.g., signaling biochemical pathway inducible modifications) can be used. Post-translational modifications include but are not limited to glycosylation, lipidation, acetylation, and phosphorylation. These antibodies may be purchased from commercial vendors. For example, anti-phosphotyrosine antibodies that specifically recognize tyrosine-phosphorylated proteins are available from a number of vendors including Invitrogen and Perkin Elmer. Anti-phosphotyrosine antibodies are particularly useful in detecting proteins that are differentially phosphorylated on their tyrosine residues in response to an ER stress. Such proteins include but are not limited to eukaryotic translation initiation factor 2 alpha (eIF-2a). Alternatively, these antibodies can be generated using conventional polyclonal or monoclonal antibody technologies by immunizing a host animal or an antibody-producing cell with a target protein that exhibits the desired post-translational modification.

In practicing the subject method, it may be desirable to discern the expression pattern of an protein associated with a signaling biochemical pathway in different bodily tissue, in different cell types, and/or in different subcellular structures. These studies can be performed with the use of tissue-specific, cell-specific or subcellular structure specific antibodies capable of binding to protein markers that are preferentially expressed in certain tissues, cell types, or subcellular structures.

An altered expression of a gene associated with a signaling biochemical pathway can also be determined by examining a change in activity of the gene product relative to a control cell. The assay for an agent-induced change in the activity of a protein associated with a signaling biochemical pathway will dependent on the biological activity and/or the signal transduction pathway that is under investigation. For example, where the protein is a kinase, a change in its ability to phosphorylate the downstream substrate(s) can be determined by a variety of assays known in the art. Representative assays include but are not limited to immunoblotting and immunoprecipitation with antibodies such as anti-phosphotyrosine antibodies that recognize phosphorylated proteins. In addition, kinase activity can be detected by high throughput chemiluminescent assays such as AlphaScreen™ (available from Perkin Elmer) and eTag™ assay (Chan-Hui, et al. (2003) *Clinical Immunology* 111: 162-174).

Where the protein associated with a signaling biochemical pathway is part of a signaling cascade leading to a fluctuation of intracellular pH condition, pH sensitive molecules such as fluorescent pH dyes can be used as the reporter molecules. In another example where the protein associated with a signaling biochemical pathway is an ion channel, fluctuations in membrane potential and/or intracellular ion concentration can be monitored. A number of commercial kits and high-throughput devices are particularly suited for a rapid and robust screening for modulators of ion channels. Representative instruments include FLIPR™ (Molecular Devices, Inc.) and VIPR (Aurora Biosciences). These instruments are capable of detecting reactions in over 1000 sample wells of a microplate simultaneously, and providing real-time measurement and functional data within a second or even a minisecond.

In practicing any of the methods disclosed herein, a suitable vector can be introduced to a cell or an embryo via one or more methods known in the art, including without limitation, microinjection, electroporation, sonoporation, biolistics, calcium phosphate-mediated transfection, cationic transfection, liposome transfection, dendrimer transfection, heat shock transfection, nucleofection transfection, magnetofection, lipofection, impalefection, optical transfection, proprietary agent-enhanced uptake of nucleic acids, and delivery via liposomes, immunoliposomes, virosomes, or artificial virions. In some methods, the vector is introduced into an embryo by microinjection. The vector or vectors may be microinjected into the nucleus or the cytoplasm of the embryo. In some methods, the vector or vectors may be introduced into a cell by nucleofection.

The target polynucleotide of a CRISPR complex can be any DNA or RNA polynucleotide endogenous or exogenous to the eukaryotic cell. For example, the target polynucleotide can be a polynucleotide residing in the nucleus of the eukaryotic cell. The target polynucleotide can be a sequence coding a gene product (e.g., a protein) or a non-coding sequence (e.g., a regulatory polynucleotide or a junk DNA).

Examples of target polynucleotides include a sequence associated with a signaling biochemical pathway, e.g., a signaling biochemical pathway-associated gene or polynucleotide. Examples of target polynucleotides include a disease associated gene or polynucleotide. A "disease-associated" gene or polynucleotide refers to any gene or polynucleotide which is yielding transcription or translation products at an abnormal level or in an abnormal form in cells derived from a disease-affected tissues compared with tissues or cells of a non disease control. It may be a gene that becomes expressed at an abnormally high level; it may be a gene that becomes expressed at an abnormally low level, where the altered expression correlates with the occurrence and/or progression of the disease. A disease-associated gene also refers to a gene possessing mutation(s) or genetic variation that is directly responsible or is in linkage disequilibrium with a gene(s) that is responsible for the etiology of a disease. The transcribed or translated products may be known or unknown, and may be at a normal or abnormal level.

The target polynucleotide of a CRISPR complex can be any DNA or RNA polynucleotide endogenous or exogenous to the eukaryotic cell. For example, the target polynucleotide can be a polynucleotide residing in the nucleus of the eukaryotic cell. The target polynucleotide can be a sequence coding a gene product (e.g., a protein) or a non-coding sequence (e.g., a regulatory polynucleotide or a junk DNA). Without wishing to be bound by theory, it is believed that the target sequence should be associated with a PAM (protospacer adjacent motif); that is, a short sequence recognized by the CRISPR complex. The precise sequence and length requirements for the PAM differ depending on the CRISPR enzyme used, but PAMs are typically 2-5 base pair sequences adjacent the protospacer (that is, the target sequence) Examples of PAM sequences are given in the examples section below, and the skilled person will be able to identify further PAM sequences for use with a given CRISPR enzyme.

The target polynucleotide of a CRISPR complex may include a number of disease-associated genes and polynucleotides as well as signaling biochemical pathway-associated genes and polynucleotides as listed in U.S. provisional patent applications 61/736,527 and 61/748,427 both entitled SYSTEMS METHODS AND COMPOSITIONS FOR SEQUENCE MANIPULATION filed on Dec. 12, 2012 and Jan. 2, 2013, respectively, and PCT Application PCT/US2013/074667, entitled DELIVERY, ENGINEERING AND OPTIMIZATION OF SYSTEMS, METHODS AND COMPOSITIONS FOR SEQUENCE MANIPULATION AND THERAPEUTIC APPLICATIONS, filed Dec. 12, 2013, the contents of all of which are herein incorporated by reference in their entirety.

Examples of target polynucleotides include a sequence associated with a signaling biochemical pathway, e.g., a signaling biochemical pathway-associated gene or polynucleotide. Examples of target polynucleotides include a disease associated gene or polynucleotide. A "disease-associated" gene or polynucleotide refers to any gene or polynucleotide which is yielding transcription or translation products at an abnormal level or in an abnormal form in cells derived from a disease-affected tissues compared with tissues or cells of a non disease control. It may be a gene that becomes expressed at an abnormally high level; it may be a gene that becomes expressed at an abnormally low level, where the altered expression correlates with the occurrence and/or progression of the disease. A disease-associated gene also refers to a gene possessing mutation(s) or genetic variation that is directly responsible or is in linkage disequilibrium with a gene(s) that is responsible for the etiology of a disease. The transcribed or translated products may be known or unknown, and may be at a normal or abnormal level.

Genome-Wide Knock-out Screening

The CRISPR-Cas proteins and systems described herein can be used to perform efficient and cost effective functional genomic screens. Such screens can utilize CRISPR-Cas genome wide libraries. Such screens and libraries can provide for determining the function of genes, cellular pathways genes are involved in, and how any alteration in gene expression can result in a particular biological process. An advantage of the present invention is that the CRISPR system avoids off-target binding and its resulting side effects. This is achieved using systems arranged to have a high degree of sequence specificity for the target DNA.

A genome wide library may comprise a plurality of CRISPR-Cas system guide RNAs, as described herein, comprising guide sequences that are capable of targeting a plurality of target sequences in a plurality of genomic loci in a population of eukaryotic cells. The population of cells may be a population of embryonic stem (ES) cells. The target sequence in the genomic locus may be a non-coding sequence. The non-coding sequence may be an intron, regulatory sequence, splice site, 3' UTR, 5' UTR, or polyadenylation signal. Gene function of one or more gene products may be altered by said targeting. The targeting may result in a knockout of gene function. The targeting of a gene product may comprise more than one guide RNA. A gene product may be targeted by 2, 3, 4, 5, 6, 7, 8, 9, or 10 guide RNAs, preferably 3 to 4 per gene. Off-target modifications may be minimized by exploiting the staggered double strand breaks generated by Cas9 effector protein complexes or by utilizing methods analogous to those used in CRISPR-Cas9 systems. (See, e.g., DNA targeting specificity of RNA-guided Cas9 nucleases. Hsu, P., Scott, D., Weinstein, J., Ran, FA., Konermann, S., Agarwala, V., Li, Y., Fine, E., Wu, X., Shalem, O., Cradick, TJ., Marraffini, LA., Bao, G., & Zhang, F. *Nat Biotechnol* doi:10.1038/nbt.2647 (2013)), incorporated herein by reference. The targeting may be of about 100 or more sequences. The targeting may be of about 1000 or more sequences. The targeting may be of about 20,000 or more sequences. The targeting may be of the entire genome. The targeting may be of a panel of target sequences focused on a relevant or desirable pathway. The pathway may be an immune pathway. The pathway may be a cell division pathway.

One aspect of the invention comprehends a genome wide library that may comprise a plurality of CRISPR-Cas system guide RNAs that may comprise guide sequences that are capable of targeting a plurality of target sequences in a plurality of genomic loci, wherein said targeting results in a knockout of gene function. This library may potentially comprise guide RNAs that target each and every gene in the genome of an organism.

In some embodiments of the invention the organism or subject is a eukaryote (including mammal including human) or a non-human eukaryote or a non-human animal or a non-human mammal. In some embodiments, the organism or subject is a non-human animal, and may be an arthropod, for example, an insect, or may be a nematode. In some methods of the invention the organism or subject is a plant. In some methods of the invention the organism or subject is a mammal or a non-human mammal. A non-human mammal may be for example a rodent (preferably a mouse or a rat), an ungulate, or a primate. In some methods of the invention the organism or subject is algae, including microalgae, or is a fungus.

The knockout of gene function may comprise: introducing into each cell in the population of cells a vector system of one or more vectors comprising an engineered, non-naturally occurring CRISPR-Cas system comprising I. a Cas9 protein, and II. one or more guide RNAs, wherein components I and II may be same or on different vectors of the system, integrating components I and II into each cell, wherein the guide sequence targets a unique gene in each cell, wherein the Cas9 protein is operably linked to a regulatory element, wherein when transcribed, the guide RNA comprising the guide sequence directs sequence-specific binding of a CRISPR-Cas system to a target sequence in the genomic loci of the unique gene, inducing cleavage of the genomic loci by the Cas9 protein, and confirming different knockout mutations in a plurality of unique genes in each cell of the population of cells thereby generating a gene knockout cell library. The invention comprehends that the population of cells is a population of eukaryotic cells, and in a preferred embodiment, the population of cells is a population of embryonic stem (ES) cells.

The one or more vectors may be plasmid vectors. The vector may be a single vector comprising Cas9, a gRNA, and optionally, a selection marker into target cells. Not being bound by a theory, the ability to simultaneously deliver Cas9 and gRNA through a single vector enables application to any cell type of interest, without the need to first generate cell lines that express Cas9. The regulatory element may be an inducible promoter. The inducible promoter may be a doxycycline inducible promoter. In some methods of the invention the expression of the guide sequence is under the control of the T7 promoter and is driven by the expression of T7 polymerase. The confirming of different knockout mutations may be by whole exome sequencing. The knockout mutation may be achieved in 100 or more unique genes. The knockout mutation may be achieved in 1000 or more unique genes. The knockout mutation may be achieved in 20,000 or more unique genes. The knockout mutation may be achieved in the entire genome. The knockout of gene function may be achieved in a plurality of unique genes which function in a particular physiological pathway or condition. The pathway or condition may be an immune pathway or condition. The pathway or condition may be a cell division pathway or condition.

The invention also provides kits that comprise the genome wide libraries mentioned herein. The kit may comprise a single container comprising vectors or plasmids comprising the library of the invention. The kit may also comprise a panel comprising a selection of unique CRISPR-Cas system guide RNAs comprising guide sequences from the library of the invention, wherein the selection is indicative of a particular physiological condition. The invention comprehends that the targeting is of about 100 or more sequences, about 1000 or more sequences or about 20,000 or more sequences or the entire genome. Furthermore, a panel of target sequences may be focused on a relevant or desirable pathway, such as an immune pathway or cell division.

In an additional aspect of the invention, a Cas9 enzyme may comprise one or more mutations and may be used as a generic DNA binding protein with or without fusion to a functional domain. The mutations may be artificially introduced mutations or gain- or loss-of-function mutations. The mutations may include but are not limited to mutations in one of the catalytic domains (D10 and H840) in the RuvC and HNH catalytic domains, respectively. Further mutations have been characterized. In one aspect of the invention, the functional domain may be a transcriptional activation domain, which may be VP64. In other aspects of the invention, the functional domain may be a transcriptional repressor domain, which may be KRAB or SID4X. Other aspects of the invention relate to the mutated Cas 9 enzyme being fused to domains which include but are not limited to a transcriptional activator, repressor, a recombinase, a transposase, a histone remodeler, a demethylase, a DNA methyltransferase, a cryptochrome, a light inducible/controllable domain or a chemically inducible/controllable domain. Some methods of the invention can include inducing expression of targeted genes. In one embodiment, inducing expression by targeting a plurality of target sequences in a plurality of genomic loci in a population of eukaryotic cells is by use of a functional domain.

Useful in the practice of the instant invention, reference is made to:

Genome-Scale CRISPR-Cas9 Knockout Screening in Human Cells. Shalem, O., Sanjana, N E., Hartenian, E., Shi, X., Scott, D A., Mikkelson, T., Heckl, D., Ebert, B L., Root, D E., Doench, J G., Zhang, F. Science Dec 12. (2013). [*Epub ahead of print*]; Published in final edited form as: *Science*. 2014 Jan. 3; 343(6166): 84-87.

Shalem et al. involves a new way to interrogate gene function on a genome-wide scale. Their studies showed that delivery of a genome-scale CRISPR-Cas9 knockout (GeCKO) library targeted 18,080 genes with 64,751 unique guide sequences enabled both negative and positive selection screening in human cells. First, the authors showed use of the GeCKO library to identify genes essential for cell viability in cancer and pluripotent stem cells. Next, in a melanoma model, the authors screened for genes whose loss is involved in resistance to vemurafenib, a therapeutic that inhibits mutant protein kinase BRAF. Their studies showed that the highest-ranking candidates included previously validated genes NF1 and MED12 as well as novel hits NF2, CUL3, TADA2B, and TADA1. The authors observed a high level of consistency between independent guide RNAs targeting the same gene and a high rate of hit confirmation, and thus demonstrated the promise of genome-scale screening with Cas9.

Reference is also made to US patent publication number US 20140357530; and PCT Patent Publication WO 2014093701, hereby incorporated herein by reference. Reference is also made to NIH Press Release of Oct. 22, 2015 entitled, "Researchers identify potential alternative to CRISPR-Cas genome editing tools: New Cas enzymes shed light on evolution of CRISPR-Cas systems, which is incorporated by reference.

It will be appreciated that the above aspects and embodiments can be adapted as suited for transcriptome analysis, e.g. transcriptome-Wide Knock-down Screening, in case the CRISPR effector is an RNA targeting CRISPR protein.

Functional Alteration and Screening

In another aspect, the present invention provides for a method of functional evaluation and screening of genes. The use of the CRISPR system of the present invention to precisely deliver functional domains, to activate or repress genes or to alter epigenetic state by precisely altering the methylation site on a specific locus of interest, can be with one or more guide RNAs applied to a single cell or population of cells or with a library applied to genome in a pool of cells ex vivo or in vivo comprising the administration or expression of a library comprising a plurality of guide RNAs (gRNAs) and wherein the screening further comprises use of a CRISPR effector protein, wherein the CRISPR complex comprising the CRISPR effector protein is modified to comprise a heterologous functional domain. In an aspect the invention provides a method for screening a genome comprising the administration to a host or expression in a host in vivo of a library. In an aspect the invention provides a method as herein discussed further comprising an activator administered to the host or expressed in the host. In an aspect the invention provides a method as herein discussed wherein the activator is attached to a CRISPR effector protein. In an aspect the invention provides a method as herein discussed wherein the activator is attached to the N terminus or the C terminus of the CRISPR effector protein. In an aspect the invention provides a method as herein discussed wherein the activator is attached to a gRNA loop. In an aspect the invention provides a method as herein discussed further comprising a repressor administered to the host or expressed in the host. In an aspect the invention provides a method as herein discussed, wherein the screening comprises affecting and detecting gene activation, gene inhibition, or cleavage in the locus.

In an aspect, the invention provides efficient on-target activity and minimizes off target activity. In an aspect, the invention provides efficient on-target cleavage by CRISPR effector protein and minimizes off-target cleavage by the CRISPR effector protein. In an aspect, the invention provides guide specific binding of CRISPR effector protein at a gene locus without DNA or RNA cleavage. Accordingly, in an aspect, the invention provides target-specific gene regulation. In an aspect, the invention provides guide specific binding of CRISPR effector protein at a gene locus without DNA or RNA cleavage. Accordingly, in an aspect, the invention provides for cleavage at one gene locus and gene regulation at a different gene locus using a single CRISPR effector protein. In an aspect, the invention provides orthogonal activation and/or inhibition and/or cleavage of multiple targets using one or more CRISPR effector protein and/or enzyme.

In an aspect the invention provides a method as herein discussed, wherein the host is a eukaryotic cell. In an aspect the invention provides a method as herein discussed, wherein the host is a mammalian cell. In an aspect the invention provides a method as herein discussed, wherein the host is a non-human eukaryote. In an aspect the invention provides a method as herein discussed, wherein the non-human eukaryote is a non-human mammal. In an aspect the invention provides a method as herein discussed, wherein the non-human mammal is a mouse. An aspect the invention provides a method as herein discussed comprising the delivery of the CRISPR effector protein complexes or component(s) thereof or nucleic acid molecule(s) coding therefor, wherein said nucleic acid molecule(s) are operatively linked to regulatory sequence(s) and expressed in vivo. In an aspect the invention provides a method as herein discussed wherein the expressing in vivo is via a lentivirus, an adenovirus, or an AAV. In an aspect the invention provides a method as herein discussed wherein the delivery is via a particle, a nanoparticle, a lipid or a cell penetrating peptide (CPP).

In an aspect the invention provides a pair of CRISPR complexes comprising a CRISPR effector protein, each comprising a guide RNA (gRNA) comprising a guide sequence capable of hybridizing to a target sequence in a genomic locus of interest in a cell, wherein at least one loop of each gRNA is modified by the insertion of distinct RNA sequence(s) that bind to one or more adaptor proteins, and wherein the adaptor protein is associated with one or more functional domains, wherein each gRNA of each CRISPR effector protein complex comprises a functional domain having a DNA cleavage activity. In an aspect the invention provides paired CRISPR effector protein complexes as herein-discussed, wherein the DNA cleavage activity is due to a Fok1 nuclease.

In an aspect the invention provides a method for cutting a target sequence in a genomic locus of interest comprising delivery to a cell of the CRISPR effector protein complexes or component(s) thereof or nucleic acid molecule(s) coding therefor, wherein said nucleic acid molecule(s) are operatively linked to regulatory sequence(s) and expressed in vivo. In an aspect the invention provides a method as herein-discussed wherein the delivery is via a lentivirus, an adenovirus, or an AAV. In an aspect the invention provides a method as herein-discussed or paired CRISPR effector protein complexes as herein-discussed wherein the target sequence for a first complex of the pair is on a first strand of double stranded DNA and the target sequence for a second complex of the pair is on a second strand of double stranded DNA. In an aspect the invention provides a method as herein-discussed or paired CRISPR effector protein complexes as herein-discussed wherein the target sequences of the first and second complexes are in proximity to each other such that the DNA is cut in a manner that facilitates homology directed repair. In an aspect a herein method can further include introducing into the cell template DNA. In an aspect a herein method or herein paired CRISPR effector protein complexes can involve wherein each CRISPR effector protein complex has a CRISPR effector enzyme that is mutated such that it has no more than about 5% of the nuclease activity of the CRISPR effector enzyme that is not mutated.

In an aspect the invention provides a guide DNA or guide RNA, composition, library, method or complex as herein-discussed wherein the gRNA is modified to have at least one non-coding functional loop, e.g., wherein the at least one non-coding functional loop is repressive; for instance, wherein the at least one non-coding functional loop comprises Alu.

In one aspect, the invention provides a method for altering or modifying expression of a gene product. The said method may comprise introducing into a cell containing and expressing a DNA molecule encoding the gene product an engineered, non-naturally occurring CRISPR system comprising a CRISPR effector protein and guide RNA that targets the DNA molecule, whereby the guide RNA targets the DNA molecule encoding the gene product and the Cas9 effector protein cleaves the DNA molecule encoding the gene product, whereby expression of the gene product is altered; and, wherein the CRISPR effector protein and the guide RNA do not naturally occur together. The invention comprehends the guide RNA comprising a guide sequence linked to a direct repeat sequence. The invention further comprehends the CRISPR effector protein being codon optimized for expression in a Eukaryotic cell. In a preferred embodiment the Eukaryotic cell is a mammalian cell and in a more preferred embodiment the mammalian cell is a human cell. In a further embodiment of the invention, the expression of the gene product is decreased.

In some embodiments, one or more functional domains are associated with the CRISPR enzyme, for example a Type II Cas9 enzyme. Preferred agents in the context of this invention comprise a CRISPR/Cas system or complex. In certain embodiments, the CRISPR/Cas system or complex is a class 2 CRISPR/Cas system. In certain embodiments, said CRISPR/Cas system or complex is a type II, type V, or type VI CRISPR/Cas system or complex. The CRISPR/Cas system does not require the generation of customized proteins to target specific sequences but rather a single Cas protein can be programmed by an RNA guide (gRNA) to recognize a specific nucleic acid target, in other words the Cas enzyme protein can be recruited to a specific nucleic acid target locus (which may comprise or consist of RNA and/or DNA) of interest using said short RNA guide.

In some embodiments, one or more functional domains are associated with an adaptor protein, for example as used with the modified guides of Konnerman et al. (*Nature* 517, 583-588, 29 Jan. 2015).

In some embodiments, one or more functional domains are associated with an dead gRNA (dRNA). In some embodiments, a dRNA complex with active CRISPR directs gene regulation by a functional domain at on gene locus while an gRNA directs DNA cleavage by the active CRISPR at another locus, for example as described by Dahlman et al., 'Orthogonal gene control with a catalytically active Cas9 nuclease' (in press). In some embodiments, dRNAs are selected to maximize selectivity of regulation for a gene locus of interest compared to off-target regulation. In some embodiments, dRNAs are selected to maximize target gene regulation and minimize target cleavage.

For the purposes of the following discussion, reference to a functional domain could be a functional domain associated with the CRISPR enzyme or a functional domain associated with the adaptor protein.

In the practice of the invention, loops of the gRNA may be extended, without colliding with the CRISPR protein by the insertion of distinct RNA loop(s) or distinct sequence(s) that may recruit adaptor proteins that can bind to the distinct RNA loop(s) or distinct sequence(s). The adaptor proteins may include but are not limited to orthogonal RNA-binding protein/aptamer combinations that exist within the diversity of bacteriophage coat proteins. A list of such coat proteins includes, but is not limited to: Qβ, F2, GA, fr, JP501, M12, R17, BZ13, JP34, JP500, KU1, M11, MX1, TW18, VK, SP, FI, ID2, NL95, TW19, AP205, ϕCb5, ϕCbSr, ϕCb12r, ϕCb23r, 7s and PRR1. These adaptor proteins or orthogonal RNA binding proteins can further recruit effector proteins or fusions which comprise one or more functional domains. In some embodiments, the functional domain may be selected from the group consisting of: transposase domain, integrase domain, recombinase domain, resolvase domain, invertase domain, protease domain, DNA methyltransferase domain, DNA hydroxylmethylase domain, DNA demethylase domain, histone acetylase domain, histone deacetylases domain, nuclease domain, repressor domain, activator domain, nuclear-localization signal domains, transcription-regulatory protein (or transcription complex recruiting) domain, cellular uptake activity associated domain, nucleic acid binding domain, antibody presentation domain, histone modifying enzymes, recruiter of histone modifying enzymes; inhibitor of histone modifying enzymes, histone methyltransferase, histone demethylase, histone kinase, histone phosphatase, histone ribosylase, histone deribosylase, histone ubiquitinase, histone deubiquitinase, histone biotinase and histone tail protease. In some preferred embodiments, the functional domain is a transcriptional activation domain, such as, without limitation, VP64, p65, MyoD1, HSF1, RTA, SET7/9 or a histone acetyltransferase. In some embodiments, the functional domain is a transcription repression domain, preferably KRAB. In some embodiments, the transcription repression domain is SID, or concatemers of SID (e.g SID4X). In some embodiments, the functional domain is an epigenetic modifying domain, such that an epigenetic modifying enzyme is provided. In some embodiments, the functional domain is an activation domain, which may be the P65 activation domain.

Saturating Mutagenesis

CRISPR-Cas System(s) can be used to perform saturating or deep scanning mutagenesis of genomic loci in conjunction with a cellular phenotype—for instance, for determining critical minimal features and discrete vulnerabilities of functional elements required for gene expression, drug resistance, and reversal of disease. By saturating or deep scanning mutagenesis is meant that every or essentially every DNA base is cut within the genomic loci. A library of CRISPR-Cas guide RNAs may be introduced into a population of cells. The library may be introduced, such that each cell receives a guide RNA (gRNA). In the case where the library is introduced by transduction of a viral vector, as described herein, a low multiplicity of infection (MOI) is used. The library may include gRNAs targeting every sequence upstream of a (protospacer adjacent motif) (PAM) sequence in a genomic locus. The library may include at least 100 non-overlapping genomic sequences upstream of a PAM sequence for every 1000 base pairs within the genomic locus. The library may include gRNAs targeting sequences upstream of at least one different PAM sequence. The CRISPR-Cas System(s) may include more than one Cas protein. Any Cas protein as described herein, including orthologues or engineered Cas proteins that recognize different PAM sequences may be used. The frequency of off target sites for a gRNA may be less than 500. Off target scores may be generated to select gRNAs with the lowest off target sites. Any phenotype determined to be associated with cutting at a gRNA target site may be confirmed by using gRNA's targeting the same site in a single experiment. Validation of a target site may also be performed by using a nickase Cas9, as described herein, and two gRNAs targeting the genomic site of interest. Not being bound by a theory, a target site is a true hit if the change in phenotype is observed in validation experiments.

The genomic loci may include at least one continuous genomic region. The at least one continuous genomic region may comprise up to the entire genome. The at least one continuous genomic region may comprise a functional element of the genome. The functional element may be within a non-coding region, coding gene, intronic region, promoter, or enhancer. The at least one continuous genomic region may comprise at least 1 kb, preferably at least 50 kb of genomic DNA. The at least one continuous genomic region may comprise a transcription factor binding site. The at least one continuous genomic region may comprise a region of DNase I hypersensitivity. The at least one continuous genomic region may comprise a transcription enhancer or repressor element. The at least one continuous genomic region may comprise a site enriched for an epigenetic signature. The at least one continuous genomic DNA region may comprise an epigenetic insulator. The at least one continuous genomic region may comprise two or more continuous genomic regions that physically interact. Genomic regions that interact may be determined by '4C technology'. 4C technology allows the screening of the entire genome in an unbiased manner for DNA segments that physically interact with a DNA fragment of choice, as is described in Zhao et al. ((2006) *Nat Genet* 38, 1341-7) and in U.S. Pat. No. 8,642,295, both incorporated herein by reference in its entirety. The epigenetic signature may be histone acetylation, histone methylation, histone ubiquitination, histone phosphorylation, DNA methylation, or a lack thereof.

CRISPR-Cas System(s) for saturating or deep scanning mutagenesis can be used in a population of cells. The CRISPR-Cas System(s) can be used in eukaryotic cells, including but not limited to mammalian and plant cells. The population of cells may be prokaryotic cells. The population of eukaryotic cells may be a population of embryonic stem (ES) cells, neuronal cells, epithelial cells, immune cells, endocrine cells, muscle cells, erythrocytes, lymphocytes, plant cells, or yeast cells.

In one aspect, the present invention provides for a method of screening for functional elements associated with a change in a phenotype. The library may be introduced into a population of cells that are adapted to contain a Cas protein. The cells may be sorted into at least two groups based on the phenotype. The phenotype may be expression of a gene, cell growth, or cell viability. The relative representation of the guide RNAs present in each group are determined, whereby genomic sites associated with the change in phenotype are determined by the representation of guide RNAs present in each group. The change in phenotype may be a change in expression of a gene of interest. The gene of interest may be upregulated, downregulated, or knocked out. The cells may be sorted into a high expression group and a low expression group. The population of cells may include a reporter construct that is used to determine the phenotype. The reporter construct may include a detectable marker. Cells may be sorted by use of the detectable marker.

In another aspect, the present invention provides for a method of screening for genomic sites associated with resistance to a chemical compound. The chemical compound may be a drug or pesticide. The library may be introduced into a population of cells that are adapted to contain a Cas protein, wherein each cell of the population contains no more than one guide RNA; the population of cells are treated with the chemical compound; and the representation of guide RNAs are determined after treatment with the chemical compound at a later time point as compared to an early time point, whereby genomic sites associated with resistance to the chemical compound are determined by enrichment of guide RNAs. Representation of gRNAs may be determined by deep sequencing methods.

Useful in the practice of the instant invention, reference is made to the article entitled BCL11A enhancer dissection by Cas9-mediated in situ saturating mutagenesis. Canver, M.C., Smith, E.C., Sher, F., Pinello, L., Sanjana, N. E., Shalem, O., Chen, D. D., Schupp, P.G., Vinjamur, D. S., Garcia, S. P., Luc, S., Kurita, R., Nakamura, Y., Fujiwara, Y., Maeda, T., Yuan, G., Zhang, F., Orkin, S. H., & Bauer, D. E. DOI: 10.1038/naturel5521, published online Sep. 16, 2015, the article is herein incorporated by reference and discussed briefly below: >Canver et al. describes novel pooled CRISPR-Cas9 guide RNA libraries to perform in situ saturating mutagenesis of the human and mouse BCL11A erythroid enhancers previously identified as an enhancer associated with fetal hemoglobin (HbF) level and whose mouse ortholog is necessary for erythroid BCL11A expression. This approach revealed critical minimal features and discrete vulnerabilities of these enhancers. Through editing of primary human progenitors and mouse transgenesis, the authors validated the BCL11A erythroid enhancer as a target for HbF reinduction. The authors generated a detailed enhancer map that informs therapeutic genome editing.

Method of Using CRISPR-Cas Systems to Modify a Cell or Organism

The invention in some embodiments comprehends a method of modifying a cell or organism. The cell may be a prokaryotic cell or a eukaryotic cell. The cell may be a mammalian cell. The mammalian cell many be a non-human primate, bovine, porcine, rodent or mouse cell. The cell may be a non-mammalian eukaryotic cell such as poultry, fish or shrimp. The cell may also be a plant cell. The plant cell may be of a crop plant such as cassava, corn, sorghum, wheat, or rice. The plant cell may also be of an algae, tree or vegetable. The modification introduced to the cell by the present invention may be such that the cell and progeny of the cell are altered for improved production of biologic products such as an antibody, starch, alcohol or other desired cellular output. The modification introduced to the cell by the present invention may be such that the cell and progeny of the cell include an alteration that changes the biologic product produced.

The system may comprise one or more different vectors. In an aspect of the invention, the Cas protein is codon optimized for expression the desired cell type, preferentially a eukaryotic cell, preferably a mammalian cell or a human cell.

Packaging cells are typically used to form virus particles that are capable of infecting a host cell. Such cells include 293 cells, which package adenovirus, and W2 cells or PA317 cells, which package retrovirus. Viral vectors used in gene therapy are usually generated by producing a cell line that packages a nucleic acid vector into a viral particle. The vectors typically contain the minimal viral sequences required for packaging and subsequent integration into a host, other viral sequences being replaced by an expression cassette for the polynucleotide(s) to be expressed. The missing viral functions are typically supplied in trans by the packaging cell line. For example, AAV vectors used in gene therapy typically only possess ITR sequences from the AAV genome which are required for packaging and integration into the host genome. Viral DNA is packaged in a cell line, which contains a helper plasmid encoding the other AAV genes, namely rep and cap, but lacking ITR sequences. The cell line may also be infected with adenovirus as a helper. The helper virus promotes replication of the AAV vector and expression of AAV genes from the helper plasmid. The helper plasmid is not packaged in significant amounts due to a lack of ITR sequences. Contamination with adenovirus can be reduced by, e.g., heat treatment to which adenovirus is more sensitive than AAV. Additional methods for the delivery of nucleic acids to cells are known to those skilled in the art. See, for example, US20030087817, incorporated herein by reference.

In some embodiments, a host cell is transiently or non-transiently transfected with one or more vectors described herein. In some embodiments, a cell is transfected as it naturally occurs in a subject. In some embodiments, a cell that is transfected is taken from a subject. In some embodiments, the cell is derived from cells taken from a subject, such as a cell line. A wide variety of cell lines for tissue culture are known in the art. Examples of cell lines include, but are not limited to, C8161, CCRF-CEM, MOLT, mIMCD-3, NHDF, HeLa-S3, Huh1, Huh4, Huh7, HUVEC, HASMC, HEKn, HEKa, MiaPaCell, Panc1, PC-3, TF1, CTLL-2, CIR, Rat6, CV1, RPTE, A10, T24, J82, A375, ARH-77, Calul, SW480, SW620, SKOV3, SK-UT, CaCo2, P388D1, SEM-K2, WEHI-231, HB56, TIB55, Jurkat, J45.01, LRMB, Bcl-1, BC-3, IC21, DLD2, Raw264.7, NRK, NRK-52E, MRC5, MEF, Hep G2, HeLa B, HeLa T4, COS, COS-1, COS-6, COS-M6A, BS-C-1 monkey kidney epithelial, BALB/3T3 mouse embryo fibroblast, 3T3 Swiss, 3T3-L1, 132-d5 human fetal fibroblasts; 10.1 mouse fibroblasts, 293-T, 3T3, 721, 9L, A2780, A2780ADR, A2780cis, A172, A20, A253, A431, A-549, ALC, B16, B35, BCP-1 cells, BEAS-2B, bEnd.3, BHK-21, BR 293, BxPC3, C3H-1OT1/2, C6/36, Cal-27, CHO, CHO-7, CHO-IR, CHO-K1, CHO-K2, CHO-T, CHO Dhfr −/−, COR-L23, COR-L23/CPR, COR-L23/5010, COR-L23/R23, COS-7, COV-434, CML T1, CMT, CT26, D17, DH82, DU145, DuCaP, EL4, EM2, EM3, EMT6/AR1, EMT6/AR10.0, FM3, H1299, H69, HB54, HB55, HCA2, HEK-293, HeLa, Hepalclc7, HL-60, HMEC, HT-29, Jurkat, JY cells, K562 cells, Ku812, KCL22, KG1, KYO1, LNCap, Ma-Mel 1-48, MC-38, MCF-7, MCF-10A, MDA-MB-231, MDA-MB-468, MDA-MB-435, MDCK II, MDCK II, MOR/0.2R, MONO-MAC 6, MTD-1A, MyEnd, NCI-H69/CPR, NCI-H69/LX10, NCI-H69/LX20, NCI-H69/LX4, NIH-3T3, NALM-1, NW-145, OPCN/OPCT cell lines, Peer, PNT-1A/PNT 2, RenCa, RIN-5F, RMA/RMAS, Saos-2 cells, Sf-9, SkBr3, T2, T-47D, T84, THP1 cell line, U373, U87, U937, VCaP, Vero cells, WM39, WT-49, X63, YAC-1, YAR, and transgenic varieties thereof. Cell lines are available from a variety of sources known to those with skill in the art (see, e.g., the American Type Culture Collection (ATCC) (Manassas, Va.)). In some embodiments, a cell transfected with one or more vectors described herein is used to establish a new cell line comprising one or more vector-derived sequences. In some embodiments, a cell transiently transfected with the components of a nucleic acid-targeting system as described herein (such as by transient transfection of one or more vectors, or transfection with RNA), and modified through the activity of a nucleic acid-targeting complex, is used to establish a new cell line comprising cells containing the modification but lacking any other exogenous sequence. In some embodiments, cells transiently or non-transiently transfected with one or more vectors described herein, or cell lines derived from such cells are used in assessing one or more test compounds.

In some embodiments, one or more vectors described herein are used to produce a non-human transgenic animal or transgenic plant. In some embodiments, the transgenic animal is a mammal, such as a mouse, rat, or rabbit. In certain embodiments, the organism or subject is a plant. In certain embodiments, the organism or subject or plant is algae. Methods for producing transgenic plants and animals are known in the art, and generally begin with a method of cell transfection, such as described herein.

In one aspect, the invention provides for methods of modifying a target polynucleotide in a eukaryotic cell. In some embodiments, the method comprises allowing a nucleic acid-targeting complex to bind to the target polynucleotide to effect cleavage of said target polynucleotide thereby modifying the target polynucleotide, wherein the nucleic acid-targeting complex comprises a nucleic acid-targeting effector protein complexed with a guide RNA hybridized to a target sequence within said target polynucleotide.

In one aspect, the invention provides a method of modifying expression of a polynucleotide in a eukaryotic cell. In some embodiments, the method comprises allowing a nucleic acid-targeting complex to bind to the polynucleotide such that said binding results in increased or decreased expression of said polynucleotide; wherein the nucleic acid-targeting complex comprises a nucleic acid-targeting effector protein complexed with a guide RNA hybridized to a target sequence within said polynucleotide.

CRISPR Systems Can Be Used In Plants

CRISPR-Cas system(s) (e.g., single or multiplexed) can be used in conjunction with recent advances in crop genomics. Such CRISPR-Cas system(s) can be used to perform efficient and cost effective plant gene or genome interrogation or editing or manipulation—for instance, for rapid investigation and/or selection and/or interrogations and/or comparison and/or manipulations and/or transformation of plant genes or genomes; e.g., to create, identify, develop, optimize, or confer trait(s) or characteristic(s) to plant(s) or to transform a plant genome. There can accordingly be improved production of plants, new plants with new combinations of traits or characteristics or new plants with enhanced traits. Such CRISPR-Cas system(s) can be used with regard to plants in Site-Directed Integration (SDI) or Gene Editing (GE) or any Near Reverse Breeding (NRB) or Reverse Breeding (RB) techniques. With respect to use of the CRISPR-Cas system in plants, mention is made of the University of Arizona website "CRISPR-PLANT" (www.genome.arizona.edu/crispr/) (supported by Penn State and AGI). Embodiments of the invention can be used in genome editing in plants or where RNAi or similar genome editing techniques have been used previously; see, e.g., Nekrasov, "Plant genome editing made easy: targeted mutagenesis in model and crop plants using the CRISPR/Cas system," Plant Methods 2013, 9:39 (doi:10.1186/1746-4811-9-39); Brooks, "Efficient gene editing in tomato in the first generation using the CRISPR/Cas9 system," Plant Physiology September 2014 pp 114.247577; Shan, "Targeted genome modification of crop plants using a CRISPR-Cas system," Nature Biotechnology 31, 686-688 (2013); Feng, "Efficient genome editing in plants using a CRISPR/Cas system," *Cell Research* (2013) 23:1229-1232. doi: 10.1038/cr.2013.114; published online 20 Aug. 2013; Xie, "RNA-guided genome editing in plants using a CRISPR-Cas system," *Mol Plant.* 2013 November; 6(6):1975-83. doi: 10.1093/mp/sstl19. Epub 2013 Aug 17; Xu, "Gene targeting using the *Agrobacterium tumefaciens*-mediated CRISPR-Cas system in rice," Rice 2014, 7:5 (2014), Zhou et al., "Exploiting SNPs for biallelic CRISPR mutations in the outcrossing woody perennial *Populus* reveals 4-coumarate: CoA ligase specificity and Redundancy," New Phytologist (2015) (Forum) 1-4 (available online only at www.newphytologist.com); Caliando et al, "Targeted DNA degradation using a CRISPR device stably carried in the host genome, *NATURE COMMUNICATIONS* 6:6989, DOI: 10.1038/ncomms7989, www.nature.com/naturecommunications DOI: 10.1038/ncomms7989; U.S. Pat. No. 6,603,061-*Agrobacterium*-Mediated Plant Transformation Method; U.S. Pat. No. 7,868,149-Plant Genome Sequences and Uses Thereof and US 2009/0100536-Transgenic Plants with Enhanced Agronomic Traits, all the contents and disclosure of each of which are herein incorporated by reference in their entirety. In the practice of the invention, the contents and disclosure of Morrell et al "Crop genomics: advances and applications," *Nat Rev Genet.* 2011 Dec. 29; 13(2):85-96; each of which is incorporated by reference herein including as to how herein embodiments may be used as to plants. Accordingly, reference herein to animal cells may also apply, mutatis mutandis, to plant cells unless otherwise apparent; and, the enzymes herein having reduced off-target effects and systems employing such enzymes can be used in plant applications, including those mentioned herein.

Sugano et al. (*Plant Cell Physiol.* 2014 March;55(3):475-81. doi: 10.1093/pcp/pcu014. Epub 2014 Jan 18) reports the application of CRISPR/Cas9 to targeted mutagenesis in the liverwort Marchantia *polymorpha* L., which has emerged as a model species for studying land plant evolution. The U6 promoter of M. *polymorpha* was identified and cloned to express the gRNA. The target sequence of the gRNA was designed to disrupt the gene encoding auxin response factor 1 (ARF1) in M. *polymorpha.* Using *Agrobacterium*-mediated transformation, Sugano et al. isolated stable mutants in the gametophyte generation of M. *polymorpha*. CRISPR/Cas9-based site-directed mutagenesis in vivo was achieved using either the Cauliflower mosaic virus 35S or M. *polymorpha* EF1α promoter to express Cas9. Isolated mutant individuals showing an auxin-resistant phenotype were not chimeric. Moreover, stable mutants were produced by asexual reproduction of T1 plants. Multiple arfl alleles were easily established using CRISPR/Cas9-based targeted mutagenesis. The methods of Sugano et al. may be applied to the CRISPR Cas system of the present invention.

Kabadi et al. (*Nucleic Acids Res.* 2014 Oct. 29; 42(19): e147. doi: 10.1093/nar/gku749. Epub 2014 Aug 13) developed a single lentiviral system to express a Cas9 variant, a reporter gene and up to four gRNAs from independent RNA polymerase III promoters that are incorporated into the vector by a convenient Golden Gate cloning method. Each gRNA was efficiently expressed and can mediate multiplex gene editing and sustained transcriptional activation in immortalized and primary human cells. The methods of Kabadi et al. may be applied to the CRISPR Cas system of the present invention.

Ling et al. (*BMC Plant Biology* 2014, 14:327) developed a CRISPR/Cas9 binary vector set based on the pGreen or pCAMBIA backbone, as well as a gRNA This toolkit requires no restriction enzymes besides BsaI to generate final constructs harboring maize-codon optimized Cas9 and one or more gRNAs with high efficiency in as little as one cloning step. The toolkit was validated using maize protoplasts, transgenic maize lines, and transgenic *Arabidopsis* lines and was shown to exhibit high efficiency and specificity. More importantly, using this toolkit, targeted mutations of three *Arabidopsis* genes were detected in transgenic seedlings of the T1 generation. Moreover, the multiple-gene mutations could be inherited by the next generation. (guide RNA) module vector set, as a toolkit for multiplex genome editing in plants. The toolbox of Lin et al. may be applied to the CRISPR Cas system of the present invention.

Protocols for targeted plant genome editing via CRISPR/Cas9 are also available in volume 1284 of the series Methods in Molecular Biology pp 239-255 10 Feb. 2015. A detailed procedure to design, construct, and evaluate dual gRNAs for plant codon optimized Cas9 (pcoCas9) mediated genome editing using *Arabidopsis thaliana* and *Nicotiana benthamiana* protoplasts s model cellular systems are described. Strategies to apply the CRISPR/Cas9 system to generating targeted genome modifications in whole plants are also discussed. The protocols described in the chapter may be applied to the CRISPR Cas system of the present invention.

Ma et al. (*Mol Plant.* 2015 Aug. 3; 8(8):1274-84. doi: 10.1016/j.molp.2015.04.007) reports robust CRISPR/Cas9 vector system, utilizing a plant codon optimized Cas9 gene, for convenient and high-efficiency multiplex genome editing in monocot and dicot plants. Ma et al. designed PCR-based procedures to rapidly generate multiple gRNA expression cassettes, which can be assembled into the binary CRISPR/Cas9 vectors in one round of cloning by Golden Gate ligation or Gibson Assembly. With this system, Ma et al. edited 46 target sites in rice with an average 85.4% rate of mutation, mostly in biallelic and homozygous status. Ma et al. provide examples of loss-of-function gene mutations in TO rice and T1 *Arabidopsis* plants by simultaneous targeting of multiple (up to eight) members of a gene family, multiple genes in a biosynthetic pathway, or multiple sites in a single gene. The methods of Ma et al. may be applied to the CRISPR Cas system of the present invention.

Lowder et al. (*Plant Physiol.* 2015 Aug 21. pii: pp. 00636.2015) also developed a CRISPR/Cas9 toolbox enables multiplex genome editing and transcriptional regulation of expressed, silenced or non-coding genes in plants. This toolbox provides researchers with a protocol and reagents to quickly and efficiently assemble functional CRISPR/Cas9 T-DNA constructs for monocots and dicots using Golden Gate and Gateway cloning methods. It comes with a full suite of capabilities, including multiplexed gene editing and transcriptional activation or repression of plant endogenous genes. T-DNA based transformation technology is fundamental to modern plant biotechnology, genetics, molecular biology and physiology. As such, Applicants developed a method for the assembly of Cas9 (WT, nickase or dCas9) and gRNA(s) into a T-DNA destination-vector of interest. The assembly method is based on both Golden Gate assembly and MultiSite Gateway recombination. Three modules are required for assembly. The first module is a Cas9 entry vector, which contains promoterless Cas9 or its derivative genes flanked by attL1 and attR5 sites. The second module is a gRNA entry vector which contains entry gRNA expression cassettes flanked by attL5 and attL2 sites. The third module includes attR1-attR2-containing destination T-DNA vectors that provide promoters of choice for Cas9 expression. The toolbox of Lowder et al. may be applied to the CRISPR Cas system of the present invention.

In an advantageous embodiment, the plant may be a tree. The present invention may also utilize the herein disclosed CRISPR Cas system for herbaceous systems (see, e.g., Belhaj et al., *Plant Methods* 9: 39 and Harrison et al., *Genes & Development* 28: 1859-1872). In a particularly advantageous embodiment, the CRISPR Cas system of the present invention may target single nucleotide polymorphisms (SNPs) in trees (see, e.g., Zhou et al., New Phytologist, Volume 208, Issue 2, pages 298-301, October 2015). In the Zhou et al. study, the authors applied a CRISPR Cas system in the woody perennial *Populus* using the 4-coumarate:CoA ligase (4CL) gene family as a case study and achieved 100% mutational efficiency for two 4CL genes targeted, with every transformant examined carrying biallelic modifications. In the Zhou et al., study, the CRISPR/Cas9 system was highly sensitive to single nucleotide polymorphisms (SNPs), as cleavage for a third 4CL gene was abolished due to SNPs in the target sequence.

The methods of Zhou et al. (New Phytologist, Volume 208, Issue 2, pages 298-301, October 2015) may be applied to the present invention as follows. Two 4CL genes, 4CL1 and 4CL2, associated with lignin and flavonoid biosynthesis, respectively are targeted for CRISPR/Cas9 editing. The *Populus tremula*×alba clone 717-1B4 routinely used for transformation is divergent from the genome-sequenced *Populus trichocarpa*. Therefore, the 4CL1 and 4CL2 gRNAs designed from the reference genome are interrogated with in-house 717 RNA-Seq data to ensure the absence of SNPs which could limit Cas efficiency. A third gRNA designed for 4CL5, a genome duplicate of 4CL1, is also included. The corresponding 717 sequence harbors one SNP in each allele near/within the PAM, both of which are expected to abolish targeting by the 4CL5-gRNA. All three gRNA target sites are located within the first exon. For 717 transformation, the gRNA is expressed from the *Medicago* U6.6 promoter, along with a human codon-optimized Cas under control of the CaMV 35S promoter in a binary vector. Transformation with the Cas-only vector can serve as a control. Randomly selected 4CL1 and 4CL2 lines are subjected to amplicon-sequencing. The data is then processed and biallelic mutations are confirmed in all cases.

In plants, pathogens are often host-specific. For example, *Fusarium oxysporum* f. sp. *lycopersici* causes tomato wilt but attacks only tomato, and *F. oxysporum* f *dianthus Puccinia graminis* f. sp. *tritici* attacks only wheat. Plants have existing and induced defenses to resist most pathogens. Mutations and recombination events across plant generations lead to genetic variability that gives rise to susceptibility, especially as pathogens reproduce with more frequency than plants. In plants there can be non-host resistance, e.g., the host and pathogen are incompatible. There can also be Horizontal Resistance, e.g., partial resistance against all races of a pathogen, typically controlled by many genes and Vertical Resistance, e.g., complete resistance to some races of a pathogen but not to other races, typically controlled by a few genes. In a Gene-for-Gene level, plants and pathogens evolve together, and the genetic changes in one balance changes in other. Accordingly, using Natural Variability, breeders combine most useful genes for Yield, Quality, Uniformity, Hardiness, Resistance. The sources of resistance genes include native or foreign Varieties, Heirloom Varieties, Wild Plant Relatives, and Induced Mutations, e.g., treating plant material with mutagenic agents. Using the present invention, plant breeders are provided with a new tool to induce mutations. Accordingly, one skilled in the art can analyze the genome of sources of resistance genes, and in Varieties having desired characteristics or traits employ the present invention to induce the rise of resistance genes, with more precision than previous mutagenic agents and hence accelerate and improve plant breeding programs.

CRISPR Systems Can Be Used In Non-Human Organisms/Animals

The present application may also be extended to other agricultural applications such as, for example, farm and production animals. For example, pigs have many features that make them attractive as biomedical models, especially in regenerative medicine. In particular, pigs with severe combined immunodeficiency (SCID) may provide useful models for regenerative medicine, xenotransplantation, and tumor development and will aid in developing therapies for human SCID patients. Lee et al., (*Proc Natl Acad Sci USA*. 2014 May 20;111(20):7260-5) utilized a reporter-guided transcription activator-like effector nuclease (TALEN) system to generated targeted modifications of recombination activating gene (RAG) 2 in somatic cells at high efficiency, including some that affected both alleles. CRISPR Cas may be applied to a similar system.

The methods of Lee et al., (*Proc Natl Acad Sci USA*. 2014 May 20;111(20):7260-5) may be applied to the present invention as follows. Mutated pigs are produced by targeted modification of RAG2 in fetal fibroblast cells followed by SCNT and embryo transfer. Constructs coding for CRISPR Cas and a reporter are electroporated into fetal-derived fibroblast cells. After 48 h, transfected cells expressing the green fluorescent protein are sorted into individual wells of a 96-well plate at an estimated dilution of a single cell per well. Targeted modification of RAG2 are screened by amplifying a genomic DNA fragment flanking any CRISPR Cas cutting sites followed by sequencing the PCR products. After screening and ensuring lack of off-site mutations, cells carrying targeted modification of RAG2 are used for SCNT. The polar body, along with a portion of the adjacent cytoplasm of oocyte, presumably containing the metaphase II plate, are removed, and a donor cell are placed in the perivitelline. The reconstructed embryos are then electrically operated to fuse the donor cell with the oocyte and then chemically activated. The activated embryos are incubated in Porcine Zygote Medium 3 (PZM3) with 0.5 μM Scriptaid (S7817; Sigma-Aldrich) for 14-16 h. Embryos are then washed to remove the Scriptaid and cultured in PZM3 until they were transferred into the oviducts of surrogate pigs.

The present invention is also applicable to modifying SNPs of other animals, such as cows. Tan et al. (*Proc Natl Acad Sci USA*. 2013 Oct. 8; 110(41): 16526-16531) expanded the livestock gene editing toolbox to include transcription activator-like (TAL) effector nuclease (TALEN)- and clustered regularly interspaced short palindromic repeats (CRISPR)/Cas9-stimulated homology-directed repair (HDR) using plasmid, rAAV, and oligonucleotide templates. Gene specific gRNA sequences were cloned into the Church lab gRNA vector (Addgene ID: 41824) according to their methods (*Mali* P, et al. (2013) RNA-Guided Human Genome Engineering via Cas9. *Science* 339(6121):823-826). The Cas9 nuclease was provided either by co-transfection of the hCas9 plasmid (Addgene ID: 41815) or mRNA synthesized from RCIScript-hCas9. This RCIScript-hCas9 was constructed by sub-cloning the XbaI-AgeI fragment from the hCas9 plasmid (encompassing the hCas9 cDNA) into the RCIScript plasmid.

Heo et al. (*Stem Cells Dev.* 2015 Feb. 1; 24(3):393-402. doi: 10.1089/scd.2014.0278. Epub 2014 Nov 3) reported highly efficient gene targeting in the bovine genome using bovine pluripotent cells and clustered regularly interspaced short palindromic repeat (CRISPR)/Cas9 nuclease. First, Heo et al. generate induced pluripotent stem cells (iPSCs) from bovine somatic fibroblasts by the ectopic expression of yamanaka factors and GSK30 and MEK inhibitor (2i) treatment. Heo et al. observed that these bovine iPSCs are highly similar to naive pluripotent stem cells with regard to gene expression and developmental potential in teratomas. Moreover, CRISPR/Cas9 nuclease, which was specific for the bovine NANOG locus, showed highly efficient editing of the bovine genome in bovine iPSCs and embryos.

Igenity® provides a profile analysis of animals, such as cows, to perform and transmit traits of economic traits of economic importance, such as carcass composition, carcass quality, maternal and reproductive traits and average daily gain. The analysis of a comprehensive Igenity® profile begins with the discovery of DNA markers (most often single nucleotide polymorphisms or SNPs). All the markers behind the Igenity® profile were discovered by independent scientists at research institutions, including universities, research organizations, and government entities such as USDA. Markers are then analyzed at Igenity® in validation populations. Igenity® uses multiple resource populations that represent various production environments and biological types, often working with industry partners from the seedstock, cow-calf, feedlot and/or packing segments of the beef industry to collect phenotypes that are not commonly available. Cattle genome databases are widely available, see, e.g., the NAGRP Cattle Genome Coordination Program www.animalgenome.org/cattle/maps/db.html). Thus, the present invention may be applied to target bovine SNPs. One of skill in the art may utilize the above protocols for targeting SNPs and apply them to bovine SNPs as described, for example, by Tan et al. or Heo et al.

Therapeutic Targeting with RNA-Guided Effector Protein Complex

As will be apparent, it is envisaged that the present system can be used to target any polynucleotide sequence of interest. The invention provides a non-naturally occurring or engineered composition, or one or more polynucleotides encoding components of said composition, or vector or delivery systems comprising one or more polynucleotides encoding components of said composition for use in a modifying a target cell in vivo, ex vivo or in vitro and, may be conducted in a manner alters the cell such that once modified the progeny or cell line of the CRISPR modified cell retains the altered phenotype. The modified cells and progeny may be part of a multi-cellular organism such as a plant or animal with ex vivo or in vivo application of CRISPR system to desired cell types. The CRISPR invention may be a therapeutic method of treatment. The therapeutic method of treatment may comprise gene or genome editing, or gene therapy.

Treating Pathogens, Like Bacterial, Fungal and Parasitic Pathogens

The present invention may also be applied to treat bacterial, fungal and parasitic pathogens. Most research efforts have focused on developing new antibiotics, which once developed, would nevertheless be subject to the same problems of drug resistance. The invention provides novel CRISPR-based alternatives which overcome those difficulties. Furthermore, unlike existing antibiotics, CRISPR-based treatments can be made pathogen specific, inducing bacterial cell death of a target pathogen while avoiding beneficial bacteria.

Jiang et al. ("RNA-guided editing of bacterial genomes using CRISPR-Cas systems," Nature Biotechnology vol. 31, p. 233-9, March 2013) used a CRISPR-Cas9 system to mutate or kill *S. pneumoniae* and *E. coli*. The work, which introduced precise mutations into the genomes, relied on dual-RNA:Cas9-directed cleavage at the targeted genomic site to kill unmutated cells and circumvented the need for selectable markers or counter-selection systems. CRISPR systems have be used to reverse antibiotic resistance and eliminate the transfer of resistance between strains. Bickard et al. showed that Cas9, reprogrammed to target virulence genes, kills virulent, but not avirulent, *S. aureus*. Reprogramming the nuclease to target antibiotic resistance genes destroyed staphylococcal plasmids that harbor antibiotic resistance genes and immunized against the spread of plasmid-borne resistance genes. (see, Bikard et al., "Exploiting CRISPR-Cas nucleases to produce sequence-specific antimicrobials," *Nature Biotechnology* vol. 32, 1146-1150, doi: 10.1038/nbt.3043, published online 5 Oct. 2014.) Bikard showed that CRISPR-Cas9 antimicrobials function in vivo to kill *S. aureus* in a mouse skin colonization model. Similarly, Yosef et al used a CRISPR system to target genes encoding enzymes that confer resistance to P-lactam antibiotics (see Yousef et al., "Temperate and lytic bacteriophages programmed to sensitize and kill antibiotic-resistant bacteria," *Proc. Natl. Acad. Sci. USA*, vol. 112, p. 7267-7272, doi: 10.1073/pnas.1500107112 published online May 18, 2015).

CRISPR systems can be used to edit genomes of parasites that are resistant to other genetic approaches. For example, a CRISPR-Cas9 system was shown to introduce double-stranded breaks into the in the *Plasmodium* yoeiii genome (see, Zhang et al., "*Efficient Editing of Malaria Parasite Genome Using the CRISPR/Cas9 System," mBio*. vol. 5, e01414-14, Jul-Aug 2014). Ghorbal et al. ("Genome editing in the human malaria parasite *Plasmodium falciparum* using the CRISPR-Cas9 system," Nature Biotechnology, vol. 32, p. 819-821, doi: 10.1038/nbt.2925, published online Jun. 1, 2014) modified the sequences of two genes, orcl and kelch13, which have putative roles in gene silencing and emerging resistance to artemisinin, respectively. Parasites that were altered at the appropriate sites were recovered with very high efficiency, despite there being no direct selection for the modification, indicating that neutral or even deleterious mutations can be generated using this system. CRISPR-Cas9 is also used to modify the genomes of other pathogenic parasites, including *Toxoplasma gondii* (see Shen et al., "Efficient gene disruption in diverse strains of *Toxoplasma gondii* using CRISPR/CAS9," mBio vol. 5:e01114-14, 2014; and Sidik et al., "Efficient Genome Engineering of *Toxoplasma gondii* Using CRISPR/Cas9," *PLoS One* vol. 9, e100450, doi: 10.1371/journal-.pone.0100450, published online Jun. 27, 2014).

Vyas et al. ("A *Candida albicans* CRISPR system permits genetic engineering of essential genes and gene families," Science Advances, vol. 1, e1500248, DOI: 10.1126/sciadv.1500248, Apr. 3, 2015) employed a CRISPR system to overcome long-standing obstacles to genetic engineering in *C. albicans* and efficiently mutate in a single experiment both copies of several different genes. In an organism where several mechanisms contribute to drug resistance, Vyas produced homozygous double mutants that no longer displayed the hyper-resistance to fluconazole or cycloheximide displayed by the parental clinical isolate Can90. Vyas also obtained homozygous loss-of-function mutations in essential genes of *C. albicans* by creating conditional alleles. Null alleles of DCR1, which is required for ribosomal RNA processing, are lethal at low temperature but viable at high temperature. Vyas used a repair template that introduced a nonsense mutation and isolated dcrl dcr]mutants that failed to grow at 16° C.

The CRISPR system of the present invention for use in *P. falciparum* by disrupting chromosomal loci. Ghorbal et al. ("Genome editing in the human malaria parasite *Plasmodium falciparum* using the CRISPR-Cas9 system", Nature Biotechnology, 32, 819-821 (2014), DOI: 10.1038/nbt.2925, Jun. 1, 2014) employed a CRISPR system to introduce specific gene knockouts and single-nucleotide substitutions in the malaria genome. To adapt the CRISPR-Cas9 system to *P. falciparum*, Ghorbal et al. generated expression vectors for under the control of plasmoidal regulatory elements in the pUF1-Cas9 episome that also carries the drug-selectable marker dhodh, which gives resistance to DSM1, a *P. falciparum* dihydroorotate dehydrogenase (PfDHODH) inhibitor and for transcription of the gRNA, used *P. falciparum* U6 small nuclear (sn)RNA regulatory elements placing the guide RNA and the donor DNA template for homologous recombination repair on the same plasmid, pL7. See also, Zhang C. et al. ("Efficient editing of malaria parasite genome using the CRISPR/Cas9 system", MBio, 2014 Jul 1; 5(4): E01414-14, doi: 10.1 128/MbIO.01414-14) and Wagner et al. ("Efficient CRISPR-Cas9-mediated genome editing in *Plasmodium falciparum*:, Nature Methods 11, 915-918 (2014), DOI: 10.1038/nmeth.3063).

Treating Pathouens, Like Viral Pathouens Such as HIV

Cas-mediated genome editing might be used to introduce protective mutations in somatic tissues to combat nongenetic or complex diseases. For example, NHEJ-mediated inactivation of the CCR5 receptor in lymphocytes (Lombardo et al., *Nat Biotechnol.* 2007 November; 25(11):1298-306) may be a viable strategy for circumventing HIV infection, whereas deletion of PCSK9 (Cohen et al., *Nat Genet.* 2005 February; 37(2):161-5) or angiopoietin (Musunuru et al., *N Engl J Med.* 2010 Dec. 2; 363(23):2220-7) may provide therapeutic effects against statin-resistant hypercholesterolemia or hyperlipidemia. Although these targets may be also addressed using siRNA-mediated protein knockdown, a unique advantage of NHEJ-mediated gene inactivation is the ability to achieve permanent therapeutic benefit without the need for continuing treatment. As with all gene therapies, it will of course be important to establish that each proposed therapeutic use has a favorable benefit-risk ratio.

Hydrodynamic delivery of plasmid DNA encoding Cas9 and guide RNA along with a repair template into the liver of an adult mouse model of tyrosinemia was shown to be able to correct the mutant Fah gene and rescue expression of the wild-type Fah protein in-1 out of 250 cells (*Nat Biotechnol.*

2014 June; 32(6):551-3). In addition, clinical trials successfully used ZF nucleases to combat HIV infection by ex vivo knockout of the CCR5 receptor. In all patients, HIV DNA levels decreased, and in one out of four patients, HIV RNA became undetectable (Tebas et al., *N Engl J Med.* 2014 Mar. 6; 370(10):901-10). Both of these results demonstrate the promise of programmable nucleases as a new therapeutic platform.

In another embodiment, self-inactivating lentiviral vectors with an siRNA targeting a common exon shared by HIV tat/rev, a nucleolar-localizing TAR decoy, and an anti-CCR5-specific hammerhead ribozyme (see, e.g., DiGiusto et al. (2010) *Sci Transl Med* 2:36ra43) may be used and/or adapted to the CRISPR-Cas system of the present invention. A minimum of $2.5\times10^6$ CD34+ cells per kilogram patient weight may be collected and prestimulated for 16 to 20 hours in X-VIVO 15 medium (Lonza) containing 2 μmol/L-glutamine, stem cell factor (100 ng/ml), Flt-3 ligand (Flt-3L) (100 ng/ml), and thrombopoietin (10 ng/ml) (CellGenix) at a density of $2\times10^6$ cells/ml. Prestimulated cells may be transduced with lentiviral at a multiplicity of infection of 5 for 16 to 24 hours in 75-$cm^2$ tissue culture flasks coated with fibronectin (25 $mg/cm^2$) (RetroNectin,Takara Bio Inc.).

With the knowledge in the art and the teachings in this disclosure the skilled person can correct HSCs as to immunodeficiency condition such as HIV/AIDS comprising contacting an HSC with a CRISPR-Cas9 system that targets and knocks out CCR5. An guide RNA (and advantageously a dual guide approach, e.g., a pair of different guide RNAs; for instance, guide RNAs targeting of two clinically relevant genes, B2M and CCR5, in primary human CD4+ T cells and CD34+hematopoietic stem and progenitor cells (HSPCs)) that targets and knocks out CCR5-and-Cas9 protein containing particle is contacted with HSCs. The so contacted cells can be administered; and optionally treated/expanded; cf. Cartier. See also Kiem, "Hematopoietic stem cell-based gene therapy for HIV disease," Cell Stem Cell. Feb. 3, 2012; 10(2): 137-147; incorporated herein by reference along with the documents it cites; Mandal et al, "Efficient Ablation of Genes in Human Hematopoietic Stem and Effector Cells using CRISPR/Cas9," Cell Stem Cell, Volume 15, Issue 5, p643-652, 6 Nov. 2014; incorporated herein by reference along with the documents it cites. Mention is also made of Ebina, "CRISPR/Cas9 system to suppress HIV-1 expression by editing HIV-1 integrated proviral DNA" SCIENTIFIC REPORTS |3: 2510| DOI: 10.1038/srep02510, incorporated herein by reference along with the documents it cites, as another means for combatting HIV/AIDS using a CRISPR-Cas9 system.

The rationale for genome editing for HIV treatment originates from the observation that individuals homozygous for loss of function mutations in CCR5, a cellular co-receptor for the virus, are highly resistant to infection and otherwise healthy, suggesting that mimicking this mutation with genome editing could be a safe and effective therapeutic strategy [Liu, R., et al. *Cell* 86, 367-377 (1996)]. This idea was clinically validated when an HIV infected patient was given an allogeneic bone marrow transplant from a donor homozygous for a loss of function CCR5 mutation, resulting in undetectable levels of HIV and restoration of normal CD4 T-cell counts [Hutter, G., et al. The New England journal of medicine 360, 692-698 (2009)]. Although bone marrow transplantation is not a realistic treatment strategy for most HIV patients, due to cost and potential graft vs. host disease, HIV therapies that convert a patient's own T-cells into CCR5 are desirable.

Early studies using ZFNs and NHEJ to knockout CCR5 in humanized mouse models of HIV showed that transplantation of CCR5 edited CD4 T cells improved viral load and CD4 T-cell counts [Perez, E. E., et al. Nature biotechnology 26, 808-816 (2008)]. Importantly, these models also showed that HIV infection resulted in selection for CCR5 null cells, suggesting that editing confers a fitness advantage and potentially allowing a small number of edited cells to create a therapeutic effect.

As a result of this and other promising preclinical studies, genome editing therapy that knocks out CCR5 in patient T cells has now been tested in humans [Holt, N., et al. Nature biotechnology 28, 839-847 (2010); Li, L., et al. *Molecular therapy. the journal of the American Society of Gene Therapy* 21, 1259-1269 (2013)]. In a recent phase I clinical trial, CD4+ T cells from patients with HIV were removed, edited with ZFNs designed to knockout the CCR5 gene, and autologously transplanted back into patients [Tebas, P., et al. The New England journal of medicine 370, 901-910 (2014)].

In another study (Mandal et al., Cell Stem Cell, Volume 15, Issue 5, p643-652, 6 Nov. 2014), CRISPR-Cas9 has targeted two clinical relevant genes, B2M and CCR5, in human CD4+ T cells and CD34+hematopoietic stem and progenitor cells (HSPCs). Use of single RNA guides led to highly efficient mutagenesis in HSPCs but not in T cells. A dual guide approach improved gene deletion efficacy in both cell types. HSPCs that had undergone genome editing with CRISPR-Cas9 retained multilineage potential. Predicted on- and off-target mutations were examined via target capture sequencing in HSPCs and low levels of off-target mutagenesis were observed at only one site. These results demonstrate that CRISPR-Cas9 can efficiently ablate genes in HSPCs with minimal off-target mutagenesis, which have broad applicability for hematopoietic cell-based therapy.

Wang et al. (*PLoS One.* 2014 Dec. 26; 9(12):e115987. doi: 10.1371/journal.pone.0115987) silenced CCR5 via CRISPR associated protein 9 (Cas9) and single guided RNAs (guide RNAs) with lentiviral vectors expressing Cas9 and CCR5 guide RNAs. Wang et al. showed that a single round transduction of lentiviral vectors expressing Cas9 and CCR5 guide RNAs into HIV-1 susceptible human CD4+ cells yields high frequencies of CCR5 gene disruption. CCR5 gene-disrupted cells are not only resistant to R5-tropic HIV-1, including transmitted/founder (T/F) HIV-1 isolates, but also have selective advantage over CCR5 gene-undisrupted cells during R5-tropic HIV-1 infection. Genome mutations at potential off-target sites that are highly homologous to these CCR5 guide RNAs in stably transduced cells even at 84 days post transduction were not detected by a T7 endonuclease I assay.

Fine et al. (*Sci Rep.* 2015 Jul. 1; 5:10777. doi: 10.1038/srep10777) identified a two-cassette system expressing pieces of the *S. pyogenes* Cas9 (SpCas9) protein which splice together in cellular to form a functional protein capable of site-specific DNA cleavage. With specific CRISPR guide strands, Fine et al. demonstrated the efficacy of this system in cleaving the HBB and CCR5 genes in human HEK-293T cells as a single Cas9 and as a pair of Cas9 nickases. The trans-spliced SpCas9 (tsSpCas9) displayed ~35% of the nuclease activity compared with the wild-type SpCas9 (wtSpCas9) at standard transfection doses, but had substantially decreased activity at lower dosing levels. The greatly reduced open reading frame length of the tsSpCas9 relative to wtSpCas9 potentially allows for more complex and longer genetic elements to be packaged into an AAV vector including tissue-specific promoters, multiplexed guide RNA expression, and effector domain fusions to SpCas9.

Li et al. (*J Gen Virol.* 2015 August; 96(8):2381-93. doi: 10.1099/vir.0.000139. Epub 2015 Apr 8) demonstrated that CRISPR-Cas9 can efficiently mediate the editing of the CCR5 locus in cell lines, resulting in the knockout of CCR5 expression on the cell surface. Next-generation sequencing revealed that various mutations were introduced around the predicted cleavage site of CCR5. For each of the three most effective guide RNAs that were analyzed, no significant off-target effects were detected at the 15 top-scoring potential sites. By constructing chimeric Ad5F35 adenoviruses carrying CRISPR-Cas9 components, Li et al. efficiently transduced primary CD4+T-lymphocytes and disrupted CCR5 expression, and the positively transduced cells were conferred with HIV-1 resistance.

Mention is made of WO 2015/148670 and through the teachings herein the invention comprehends methods and materials of this document applied in conjunction with the teachings herein. In an aspect of gene therapy, methods and compositions for editing of a target sequence related to or in connection with Human Immunodeficiency Virus (HIV) and Acquired Immunodeficiency Syndrome (AIDS) are comprehended. In a related aspect, the invention described herein comprehends prevention and treatment of HIV infection and AIDS, by introducing one or more mutations in the gene for C—C chemokine receptor type 5 (CCR5). The CCR5 gene is also known as CKR5, CCR-5, CD195, CKR-5, CCCKR5, CMKBR5, IDDM22, and CC-CKR-5. In a further aspect, the invention described herein comprehends provide for prevention or reduction of HIV infection and/or prevention or reduction of the ability for HIV to enter host cells, e.g., in subjects who are already infected. Exemplary host cells for HIV include, but are not limited to, CD4 cells, T cells, gut associated lymphatic tissue (GALT), macrophages, dendritic cells, myeloid precursor cell, and microglia. Viral entry into the host cells requires interaction of the viral glycoproteins gp41 and gp120 with both the CD4 receptor and a co-receptor, e.g., CCR5. If a co-receptor, e.g., CCR5, is not present on the surface of the host cells, the virus cannot bind and enter the host cells. The progress of the disease is thus impeded. By knocking out or knocking down CCR5 in the host cells, e.g., by introducing a protective mutation (such as a CCR5 delta 32 mutation), entry of the HIV virus into the host cells is prevented.

One of skill in the art may utilize the above studies of, for example, Holt, N., et al. Nature biotechnology 28, 839-847 (2010), Li, L., et al. *Molecular therapy: the journal of the American Society of Gene Therapy* 21, 1259-1269 (2013), Mandal et al., Cell Stem Cell, Volume 15, Issue 5, p643-652, 6 Nov. 2014, Wang et al. (*PLoS One.* 2014 Dec. 26; 9(12):e115987. doi: 10.1371/journal.pone.0115987), Fine et al. (*Sci Rep.* 2015 Jul. 1; 5:10777. doi: 10.1038/srep10777) and Li et al. (*J Gen Virol.* 2015 August; 96(8):2381-93. doi: 10.1099/vir.0.000139. Epub 2015 Apr 8) for targeting CCR5 with the CRISPR Cas system of the present invention.

Treating Pathouens, Like Viral Pathogens, Such as HBV

The present invention may also be applied to treat hepatitis B virus (HBV). However, the CRISPR Cas system must be adapted to avoid the shortcomings of RNAi, such as the risk of oversatring endogenous small RNA pathways, by for example, optimizing dose and sequence (see, e.g., Grimm et al., *Nature* vol. 441, 26 May 2006). For example, low doses, such as about 1-10×$10^{14}$ particles per human are contemplated. In another embodiment, the CRISPR Cas system directed against HBV may be administered in liposomes, such as a stable nucleic-acid-lipid particle (SNALP) (see, e.g., Morrissey et al., *Nature Biotechnology*, Vol. 23, No. 8, August 2005). Daily intravenous injections of about 1, 3 or 5 mg/kg/day of CRISPR Cas targeted to HBV RNA in a SNALP are contemplated. The daily treatment may be over about three days and then weekly for about five weeks. In another embodiment, the system of Chen et al. (*Gene Therapy* (2007) 14, 11-19) may be used and/or adapted for the CRISPR Cas system of the present invention. Chen et al. use a double-stranded adeno associated virus 8-pseudotyped vector (dsAAV2/8) to deliver shRNA. A single administration of dsAAV2/8 vector (1×$10^{12}$ vector genomes per mouse), carrying HBV-specific shRNA, effectively suppressed the steady level of HBV protein, mRNA and replicative DNA in liver of HBV transgenic mice, leading to up to 2-3 $\log_{10}$ decrease in HBV load in the circulation. Significant HBV suppression sustained for at least 120 days after vector administration. The therapeutic effect of shRNA was target sequence dependent and did not involve activation of interferon. For the present invention, a CRISPR Cas system directed to HBV may be cloned into an AAV vector, such as a dsAAV2/8 vector and administered to a human, for example, at a dosage of about 1×$10^{15}$ vector genomes to about 1×$10^{16}$ vector genomes per human. In another embodiment, the method of Wooddell et al. (*Molecular Therapy* vol. 21 no. 5, 973-985 May 2013) may be used and/or adapted to the CRISPR Cas system of the present invention. Woodell et al. show that simple coinjection of a hepatocyte-targeted, N-acetylgalactosamine-conjugated melittin-like peptide (NAG-MLP) with a liver-tropic cholesterol-conjugated siRNA (chol-siRNA) targeting coagulation factor VII (F7) results in efficient F7 knockdown in mice and nonhuman primates without changes in clinical chemistry or induction of cytokines. Using transient and transgenic mouse models of HBV infection, Wooddell et al. show that a single coinjection of NAG-MLP with potent chol-siRNAs targeting conserved HBV sequences resulted in multilog repression of viral RNA, proteins, and viral DNA with long duration of effect. Intravenous coinjections, for example, of about 6 mg/kg of NAG-MLP and 6 mg/kg of HBV specific CRISPR Cas may be envisioned for the present invention. In the alternative, about 3 mg/kg of NAG-MLP and 3 mg/kg of HBV specific CRISPR Cas may be delivered on day one, followed by administration of about 2-3 mg/kg of NAG-MLP and 2-3 mg/kg of HBV specific CRISPR Cas two weeks later.

Lin et al. (*Mol Ther Nucleic Acids.* 2014 Aug. 19; 3:e186. doi: 10.1038/mtna.2014.38) designed eight gRNAs against HBV of genotype A. With the HBV-specific gRNAs, the CRISPR-Cas9 system significantly reduced the production of HBV core and surface proteins in Huh-7 cells transfected with an HBV-expression vector. Among eight screened gRNAs, two effective ones were identified. One gRNA targeting the conserved HBV sequence acted against different genotypes. Using a hydrodynamics-HBV persistence mouse model, Lin et al. further demonstrated that this system could cleave the intrahepatic HBV genome-containing plasmid and facilitate its clearance in vivo, resulting in reduction of serum surface antigen levels. These data suggest that the CRISPR-Cas9 system could disrupt the HBV-expressing templates both in vitro and in vivo, indicating its potential in eradicating persistent HBV infection.

Dong et al. (*Antiviral Res.* 2015 June;118:110-7. doi: 10.1016/j.antiviral.2015.03.015. Epub 2015 Apr 3) used the CRISPR-Cas9 system to target the HBV genome and efficiently inhibit HBV infection. Dong et al. synthesized four single-guide RNAs (guide RNAs) targeting the conserved regions of HBV. The expression of these guide RNAS with Cas9 reduced the viral production in Huh7 cells as well as in HBV-replication cell HepG2.2.15. Dong et al. further demonstrated that CRISPR-Cas9 direct cleavage and cleavage-mediated mutagenesis occurred in HBV cccDNA of transfected cells. In the mouse model carrying HBV cccDNA, injection of guide RNA-Cas9 plasmids via rapid tail vein resulted in the low level of cccDNA and HBV protein.

Liu et al. (*J Gen Virol.* 2015 August; 96(8):2252-61. doi: 10.1099/vir.0.000159. Epub 2015 Apr 22) designed eight guide RNAs (gRNAs) that targeted the conserved regions of different HBV genotypes, which could significantly inhibit HBV replication both in vitro and in vivo to investigate the possibility of using the CRISPR-Cas9 system to disrupt the HBV DNA templates. The HBV-specific gRNA/Cas9 system could inhibit the replication of HBV of different genotypes in cells, and the viral DNA was significantly reduced by a single gRNA/Cas9 system and cleared by a combination of different gRNA/Cas9 systems.

Wang et al. (*World J Gastroenterol.* 2015 Aug. 28; 21(32): 9554-65. doi: 10.3748/wjg.v21.i32.9554) designed 15 gRNAs against HBV of genotypes A-D. Eleven combinations of two above gRNAs (dual-gRNAs) covering the regulatory region of HBV were chosen. The efficiency of each gRNA and 11 dual-gRNAs on the suppression of HBV (genotypes A-D) replication was examined by the measurement of HBV surface antigen (HBsAg) or e antigen (HBeAg) in the culture supernatant. The destruction of HBV-expressing vector was examined in HuH7 cells co-transfected with dual-gRNAs and HBV-expressing vector using polymerase chain reaction (PCR) and sequencing method, and the destruction of cccDNA was examined in HepAD38 cells using KCl precipitation, plasmid-safe ATP-dependent DNase (PSAD) digestion, rolling circle amplification and quantitative PCR combined method. The cytotoxicity of these gRNAs was assessed by a mitochondrial tetrazolium assay. All of gRNAs could significantly reduce HBsAg or HBeAg production in the culture supernatant, which was dependent on the region in which gRNA against. All of dual gRNAs could efficiently suppress HBsAg and/or HBeAg production for HBV of genotypes A-D, and the efficacy of dual gRNAs in suppressing HBsAg and/or HBeAg production was significantly increased when compared to the single gRNA used alone. Furthermore, by PCR direct sequencing Applicants confirmed that these dual gRNAs could specifically destroy HBV expressing template by removing the fragment between the cleavage sites of the two used gRNAs. Most importantly, gRNA-5 and gRNA-12 combination not only could efficiently suppressing HBsAg and/or HBeAg production, but also destroy the cccDNA reservoirs in HepAD38 cells.

Karimova et al. (*Sci Rep.* 2015 Sep. 3; 5:13734. doi: 10.1038/srep13734) identified cross-genotype conserved HBV sequences in the S and X region of the HBV genome that were targeted for specific and effective cleavage by a Cas9 nickase. This approach disrupted not only episomal cccDNA and chromosomally integrated HBV target sites in reporter cell lines, but also HBV replication in chronically and de novo infected hepatoma cell lines.

One of skill in the art may utilize the above studies of, for example, Lin et al. (*Mol Ther Nucleic Acids.* 2014 Aug. 19; 3:e186. doi: 10.1038/mtna.2014.38), Dong et al. (*Antiviral Res.* 2015 Jun;118:110-7. doi: 10.1016/j.antiviral.2015.03.015. Epub 2015 Apr 3), Liu et al. (*J Gen Virol.* 2015 Aug;96(8):2252-61. doi: 10.1099/vir.0.000159. Epub 2015 Apr 22), Wang et al. (*World J Gastroenterol.* 2015 Aug. 28; 21(32):9554-65. doi: 10.3748/wjg.v21.i32.9554) and Karimova et al. (*Sci Rep.* 2015 Sep. 3; 5:13734. doi: 10.1038/srep13734) for targeting HBV with the CRISPR Cas system of the present invention.

The present invention may also be applied to treat pathogens, e.g. bacterial, fungal and parasitic pathogens. Most research efforts have focused on developing new antibiotics, which once developed, would nevertheless be subject to the same problems of drug resistance. The invention provides novel CRISPR-based alternatives which overcome those difficulties. Furthermore, unlike existing antibiotics, CRISPR-based treatments can be made pathogen specific, inducing bacterial cell death of a target pathogen while avoiding beneficial bacteria.

Jiang et al. ("RNA-guided editing of bacterial genomes using CRISPR-Cas systems," Nature Biotechnology vol. 31, p. 233-9, March 2013) used a CRISPR-Cas9 system to mutate or kill *S. pneumoniae* and *E. coli*. The work, which introduced precise mutations into the genomes, relied on dual-RNA:Cas9-directed cleavage at the targeted genomic site to kill unmutated cells and circumvented the need for selectable markers or counter-selection systems. CRISPR systems have be used to reverse antibiotic resistance and eliminate the transfer of resistance between strains. Bickard et al. showed that Cas9, reprogrammed to target virulence genes, kills virulent, but not avirulent, *S. aureus*. Reprogramming the nuclease to target antibiotic resistance genes destroyed staphylococcal plasmids that harbor antibiotic resistance genes and immunized against the spread of plasmid-borne resistance genes. (see, Bikard et al., "Exploiting CRISPR-Cas nucleases to produce sequence-specific antimicrobials," *Nature Biotechnology* vol. 32, 1146-1150, doi: 10.1038/nbt.3043, published online 5 Oct. 2014.) Bikard showed that CRISPR-Cas9 antimicrobials function in vivo to kill *S. aureus* in a mouse skin colonization model. Similarly, Yosef et al used a CRISPR system to target genes encoding enzymes that confer resistance to P-lactam antibiotics (see Yousef et al., "Temperate and lytic bacteriophages programmed to sensitize and kill antibiotic-resistant bacteria," *Proc. Natl. Acad. Sci. USA*, vol. 112, p. 7267-7272, doi: 10.1073/pnas.1500107112 published online May 18, 2015).

CRISPR systems can be used to edit genomes of parasites that are resistant to other genetic approaches. For example, a CRISPR-Cas9 system was shown to introduce double-stranded breaks into the in the *Plasmodium* yoeiii genome (see, Zhang et al., "*Efficient Editing of Malaria Parasite Genome Using the CRISPR/Cas*9 *System,*" *mBio*. vol. 5, e01414-14, Jul-Aug 2014). Ghorbal et al. ("Genome editing in the human malaria parasite *Plasmodium falciparum* using the CRISPR-Cas9 system," Nature Biotechnology, vol. 32, p. 819-821, doi: 10.1038/nbt.2925, published online Jun. 1, 2014) modified the sequences of two genes, orcl and kelch13, which have putative roles in gene silencing and emerging resistance to artemisinin, respectively. Parasites that were altered at the appropriate sites were recovered with very high efficiency, despite there being no direct selection for the modification, indicating that neutral or even deleterious mutations can be generated using this system. CRISPR-Cas9 is also used to modify the genomes of other pathogenic parasites, including *Toxoplasma gondii* (see Shen et al., "Efficient gene disruption in diverse strains of *Toxoplasma gondii* using CRISPR/CAS9," mBio vol. 5:e01114-14, 2014; and Sidik et al., "Efficient Genome Engineering of *Toxoplasma gondii* Using CRISPR/Cas9," *PLoS One* vol. 9, e100450, doi: 10.1371/journal-.pone.0100450, published online Jun. 27, 2014).

Vyas et al. ("A *Candida albicans* CRISPR system permits genetic engineering of essential genes and gene families," Science Advances, vol. 1, e1500248, DOI: 10.1126/sciadv.1500248, Apr. 3, 2015) employed a CRISPR system to overcome long-standing obstacles to genetic engineering in *C. albicans* and efficiently mutate in a single experiment both copies of several different genes. In an organism where several mechanisms contribute to drug resistance, Vyas produced homozygous double mutants that no longer displayed the hyper-resistance to fluconazole or cycloheximide displayed by the parental clinical isolate Can90. Vyas also obtained homozygous loss-of-function mutations in essential genes of *C. albicans* by creating conditional alleles. Null alleles of DCR1, which is required for ribosomal RNA processing, are lethal at low temperature but viable at high temperature. Vyas used a repair template that introduced a nonsense mutation and isolated dcrl dcr]mutants that failed to grow at 16° C. Treating Diseases with Genetic or Epiuenetic Aspects The CRISPR-Cas systems of the present invention can be used to correct genetic mutations that were previously attempted with limited success using TALEN and ZFN and have been identified as potential targets for CRISPR/Cas systems, including as in published applications of Editas Medicine describing methods to use Cas9 systems to target loci to therapeutically address diseases with gene therapy, including, WO 2015/048577 CRISPR-RELATED METHODS AND COMPOSITIONS of Gluckmann et al.; WO 2015/070083 CRISPR-RELATED METHODS AND COMPOSITIONS WITH GOVERNING gRNAS of Glucksmann et al.

Mention is made of WO 2015/153780 CRISPR/CAS-RELATED METHODS AND COMPOSITIONS FOR TREATING USHER SYNDROME AND RETINITIS PIGMENTOSA of Maeder et al. Through the teachings herein the invention comprehends methods and materials of these documents applied in conjunction with the teachings herein. In an aspect of ocular and auditory gene therapy, methods and compositions for treating Usher Syndrome and Retinitis-Pigmentosa may be adapted to the CRISPR-Cas system of the present invention (see, e.g., WO 2015/134812). In an embodiment, the WO 2015/134812 involves a treatment or delaying the onset or progression of Usher Syndrome type IIA (USH2A, USH11A) and retinitis pigmentosa 39 (RP39) by gene editing, e.g., using CRISPR-Cas9 mediated methods to correct the guanine deletion at position 2299 in the USH2A gene (e.g., replace the deleted guanine residue at position 2299 in the USH2A gene). In a related aspect, a mutation is targeted by cleaving with either one or more nuclease, one or more nickase, or a combination thereof, e.g., to induce HDR with a donor template that corrects the point mutation (e.g., the single nucleotide, e.g., guanine, deletion). The alteration or correction of the mutant USH2A gene can be mediated by any mechanism. Exemplary mechanisms that can be associated with the alteration (e.g., correction) of the mutant HSH2A gene include, but are not limited to, non-homologous end joining, microhomology-mediated end joining (MMEJ), homology-directed repair (e.g., endogenous donor template mediated), SDSA (synthesis dependent strand annealing), single-strand annealing or single strand invasion. In an embodiment, the method used for treating Usher Syndrome and Retinitis-Pigmentosa can include acquiring knowledge of the mutation carried by the subject, e.g., by sequencing the appropriate portion of the USH2A gene.

Mention is also made of WO 2015/138510 and through the teachings herein the invention (using a CRISPR-Cas system) comprehends providing a treatment or delaying the onset or progression of Leber's Congenital Amaurosis 10 (LCA 10). LCA 10 is caused by a mutation in the CEP290 gene, e.g., a c.2991+1655, adenine to guanine mutation in the CEP290 gene which gives rise to a cryptic splice site in intron 26. This is a mutation at nucleotide 1655 of intron 26 of CEP290, e.g., an A to G mutation. CEP290 is also known as: CT87; MKS4; POC3; rdl6; BBS14; JBTS5; LCAJO; NPHP6; SLSN6; and 3H11Ag (see, e.g., WO 2015/138510). In an aspect of gene therapy, the invention involves introducing one or more breaks near the site of the LCA target position (e.g., c.2991+1655; A to G) in at least one allele of the CEP290 gene. Altering the LCA10 target position refers to (1) break-induced introduction of an indel (also referred to herein as NHEJ-mediated introduction of an indel) in close proximity to or including a LCA10 target position (e.g., c.2991+1655A to G), or (2) break-induced deletion (also referred to herein as NHEJ-mediated deletion) of genomic sequence including the mutation at a LCA10 target position (e.g., c.2991+1655A to G). Both approaches give rise to the loss or destruction of the cryptic splice site resulting from the mutation at the LCA 10 target position.

In an aspect, the invention (using a CRISPR-Cas system) comprehends providing a treatment or delaying the onset or progression of Leber's Congenital Amaurosis 10 (LCA 10). LCA 10 is caused by a mutation in the CEP290 gene, e.g., a c.2991+1655, adenine to guanine mutation in the CEP290 gene which gives rise to a cryptic splice site in intron 26. This is a mutation at nucleotide 1655 of intron 26 of CEP290, e.g., an A to G mutation. CEP290 is also known as: CT87; MKS4; POC3; rdl6; BBS14; JBTS5; LCAJO; NPHP6; SLSN6; and 3H11Ag (see, e.g., WO 2015/138510). In an aspect of gene therapy, the invention involves introducing one or more breaks near the site of the LCA target position (e.g., c.2991+1655; A to G) in at least one allele of the CEP290 gene. Altering the LCA10 target position refers to (1) break-induced introduction of an indel (also referred to herein as NHEJ-mediated introduction of an indel) in close proximity to or including a LCA10 target position (e.g., c.2991+1655A to G), or (2) break-induced deletion (also referred to herein as NHEJ-mediated deletion) of genomic sequence including the mutation at a LCA10 target position (e.g., c.2991+1655A to G). Both approaches give rise to the loss or destruction of the cryptic splice site resulting from the mutation at the LCA 10 target position.

Researchers are contemplating whether gene therapies could be employed to treat a wide range of diseases. The CRISPR systems of the present invention based on CRISPR effector protein are envisioned for such therapeutic uses, including, but noted limited to further exemplified targeted areas and with delivery methods as below. Some examples of conditions or diseases that might be usefully treated using the present system are included in the examples of genes and references included herein and are currently associated with those conditions are also provided there. The genes and conditions exemplified are not exhaustive.

Treating Diseases of the Circulatory System

The present invention also contemplates delivering the CRISPR-Cas system, specifically the novel CRISPR effector protein systems described herein, to the blood or hematopoietic stem cells (HSC). The plasma exosomes of Wahlgren et al. (*Nucleic Acids Research,* 2012, Vol. 40, No. 17 e130) were previously described and may be utilized to deliver the CRISPR Cas system to the blood. The nucleic acid-targeting system of the present invention is also contemplated to treat hemoglobinopathies, such as thalassemias and sickle cell disease. See, e.g., International Patent Publication No. WO 2013/126794 for potential targets that may be targeted by the CRISPR Cas system of the present invention. Target sequences identified in US Patent Publication Nos. 20110225664, 20110091441, 20100229252, 20090271881 and 20090222937 may be of interest as to the present invention.

Drakopoulou, "Review Article, The Ongoing Challenge of Hematopoietic Stem Cell-Based Gene Therapy for 0-Thalassemia," Stem Cells International, Volume 2011, Article ID 987980, 10 pages, doi:10.4061/2011/987980, incorporated herein by reference along with the documents it cites, as if set out in full, discuss modifying HSCs using a lentivirus that delivers a gene for β-globin or γ-globin. In contrast to using lentivirus, with the knowledge in the art and the teachings in this disclosure, the skilled person can correct HSCs as to β-Thalassemia using a CRISPR-Cas system that targets and corrects the mutation (e.g., with a suitable HDR template that delivers a coding sequence for β-globin or γ-globin, advantageously non-sickling β-globin or γ-globin); specifically, the guide RNA can target mutation that give rise to β-Thalassemia, and the HDR can provide coding for proper expression of β-globin or γ-globin. A guide RNA that targets the mutation-and-Cas protein containing particle is contacted with HSCs carrying the mutation. The particle also can contain a suitable HDR template to correct the mutation for proper expression of β-globin or γ-globin; or the HSC can be contacted with a second particle or a vector that contains or delivers the HDR template. The so contacted cells can be administered; and optionally treated/expanded; cf. Cartier. In this regard mention is made of: Cavazzana, "Outcomes of Gene Therapy for β-Thalassemia Major via Transplantation of Autologous Hematopoietic Stem Cells Transduced Ex Vivo with a Lentiviral $\beta^{A-T87Q}$-Globin Vector." tif2014.org/abstractFiles/Jean %20Antoine %20Ribeil_Abstract.pdf; Cavazzana-Calvo, "Transfusion independence and HMGA2 activation after gene therapy of human β-thalassaemia", *Nature* 467, 318-322 (16 Sep. 2010) doi:10.1038/nature09328; Nienhuis, "Development of Gene Therapy for Thalassemia, Cold Spring Harbor Perspectives in Medicine, doi: 10.1101/cshperspect.a011833 (2012), LentiGlobin BB305, a lentiviral vector containing an engineered β-globin gene (βA-T87Q); and Xie et al., "Seamless gene correction of β-thalassaemia mutations in patient-specific iPSCs using CRISPR/Cas9 and piggyback" *Genome Research* gr.173427.114 (2014) www.genome.org/cgi/doi/10.1101/gr.173427.114 (Cold Spring Harbor Laboratory Press); that is the subject of Cavazzana work involving human β-thalassaemia and the subject of the Xie work, are all incorporated herein by reference, together with all documents cited therein or associated therewith. In the instant invention, the HDR template can provide for the HSC to express an engineered β-globin gene (e.g., PA-T87Q), or β-globin as in Xie.

Xu et al. (*Sci Rep.* 2015 Jul. 9; 5:12065. doi: 10.1038/srep12065) have designed TALENs and CRISPR-Cas9 to directly target the intron2 mutation site IVS2-654 in the globin gene. Xu et al. observed different frequencies of double-strand breaks (DSBs) at IVS2-654 loci using TALENs and CRISPR-Cas9, and TALENs mediated a higher homologous gene targeting efficiency compared to CRISPR-Cas9 when combined with the piggyBac transposon donor. In addition, more obvious off-target events were observed for CRISPR-Cas9 compared to TALENs. Finally, TALENs-corrected iPSC clones were selected for erythroblast differentiation using the OP9 co-culture system and detected relatively higher transcription of HBB than the uncorrected cells.

Song et al. (*Stem Cells Dev.* 2015 May 1;24(9):1053-65. doi: 10.1089/scd.2014.0347. Epub 2015 Feb 5) used CRISPR/Cas9 to correct β-Thal iPSCs; gene-corrected cells exhibit normal karyotypes and full pluripotency as human embryonic stem cells (hESCs) showed no off-targeting effects. Then, Song et al. evaluated the differentiation efficiency of the gene-corrected β-Thal iPSCs. Song et al. found that during hematopoietic differentiation, gene-corrected β-Thal iPSCs showed an increased embryoid body ratio and various hematopoietic progenitor cell percentages. More importantly, the gene-corrected β-Thal iPSC lines restored HBB expression and reduced reactive oxygen species production compared with the uncorrected group. Song et al.'s study suggested that hematopoietic differentiation efficiency of β-Thal iPSCs was greatly improved once corrected by the CRISPR-Cas9 system. Similar methods may be performed utilizing the CRISPR-Cas systems described herein, e.g. systems comprising CRISPR effector proteins.

Mention is made of WO 2015/148860, through the teachings herein the invention comprehends methods and materials of these documents applied in conjunction with the teachings herein. In an aspect of blood-related disease gene therapy, methods and compositions for treating beta thalassemia may be adapted to the CRISPR-Cas system of the present invention (see, e.g., WO 2015/148860). In an embodiment, WO 2015/148860 involves the treatment or prevention of beta thalassemia, or its symptoms, e.g., by altering the gene for B-cell CLL/lymphoma 11A (BCL11A). The BCL11A gene is also known as B-cell CLL/lymphoma 11A, BCL11A-L, BCL11A-S, BCL1 1AXL, CTIP 1, HBFQTL5 and ZNF. BCL11A encodes a zinc-finger protein that is involved in the regulation of globin gene expression. By altering the BCL11A gene (e.g., one or both alleles of the BCL11A gene), the levels of gamma globin can be increased. Gamma globin can replace beta globin in the hemoglobin complex and effectively carry oxygen to tissues, thereby ameliorating beta thalassemia disease phenotypes.

Sickle cell anemia is an autosomal recessive genetic disease in which red blood cells become sickle-shaped. It is caused by a single base substitution in the β-globin gene, which is located on the short arm of chromosome 11. As a result, valine is produced instead of glutamic acid causing the production of sickle hemoglobin (HbS). This results in the formation of a distorted shape of the erythrocytes. Due to this abnormal shape, small blood vessels can be blocked, causing serious damage to the bone, spleen and skin tissues. This may lead to episodes of pain, frequent infections, hand-foot syndrome or even multiple organ failure. The distorted erythrocytes are also more susceptible to hemolysis, which leads to serious anemia. As in the case of β-thalassaemia, sickle cell anemia can be corrected by modifying HSCs with the CRISPR-Cas system. The system allows the specific editing of the cell's genome by cutting its DNA and then letting it repair itself. The CRISPR protein is inserted and directed by a RNA guide to the mutated point and then it cuts the DNA at that point. Simultaneously, a healthy version of the sequence is inserted. This sequence is used by the cell's own repair system to fix the induced cut. In this way, the CRISPR-Cas allows the correction of the mutation in the previously obtained stem cells. With the knowledge in the art and the teachings in this disclosure, the skilled person can correct HSCs as to sickle cell anemia using a CRISPR-Cas system that targets and corrects the mutation (e.g., with a suitable HDR template that delivers a coding sequence for β-globin, advantageously non-sickling p-globin); specifically, the guide RNA can target mutation that give rise to sickle cell anemia, and the HDR can provide coding for proper expression of β-globin. An guide RNA that targets the mutation-and-Cas protein containing particle is contacted with HSCs carrying the mutation. The particle also can contain a suitable HDR template to correct the mutation for proper expression of β-globin; or the HSC can be contacted with a second particle or a vector that contains or delivers the HDR template. The so contacted cells can be administered; and optionally treated/expanded; cf. Cartier. The HDR template can provide for the HSC to express an engineered β-globin gene (e.g., RA-T87Q), or β-globin as in Xie.

Mention is also made of WO 2015/148863 and through the teachings herein the invention comprehends methods and materials of these documents which may be adapted to the CRISPR-Cas system of the present invention. In an aspect of treating and preventing sickle cell disease, which is an inherited hematologic disease, WO 2015/148863 comprehends altering the BCL11A gene. By altering the BCL11A gene (e.g., one or both alleles of the BCL11A gene), the levels of gamma globin can be increased. Gamma globin can replace beta globin in the hemoglobin complex and effectively carry oxygen to tissues, thereby ameliorating sickle cell disease phenotypes.

Williams, "Broadening the Indications for Hematopoietic Stem Cell Genetic Therapies," Cell Stem Cell 13:263-264 (2013), incorporated herein by reference along with the documents it cites, as if set out in full, report lentivirus-mediated gene transfer into HSC/P cells from patients with the lysosomal storage disease metachromatic leukodystrophy disease (MLLD), a genetic disease caused by deficiency of arylsulfatase A (ARSA), resulting in nerve demyelination; and lentivirus-mediated gene transfer into HSCs of patients with Wiskott-Aldrich syndrome (WAS) (patients with defective WAS protein, an effector of the small GTPase CDC42 that regulates cytoskeletal function in blood cell lineages and thus suffer from immune deficiency with recurrent infections, autoimmune symptoms, and thrombocytopenia with abnormally small and dysfunctional platelets leading to excessive bleeding and an increased risk of leukemia and lymphoma). In contrast to using lentivirus, with the knowledge in the art and the teachings in this disclosure, the skilled person can correct HSCs as to MLD (deficiency of arylsulfatase A (ARSA)) using a CRISPR-Cas system that targets and corrects the mutation (deficiency of arylsulfatase A (ARSA)) (e.g., with a suitable HDR template that delivers a coding sequence for ARSA); specifically, the guide RNA can target mutation that gives rise to MLD (deficient ARSA), and the HDR can provide coding for proper expression of ARSA. A guide RNA that targets the mutation-and-Cas protein containing particle is contacted with HSCs carrying the mutation. The particle also can contain a suitable HDR template to correct the mutation for proper expression of ARSA; or the HSC can be contacted with a second particle or a vector that contains or delivers the HDR template. The so contacted cells can be administered; and optionally treated/expanded; cf. Cartier. In contrast to using lentivirus, with the knowledge in the art and the teachings in this disclosure, the skilled person can correct HSCs as to WAS using a CRISPR-Cas system that targets and corrects the mutation (deficiency of WAS protein) (e.g., with a suitable HDR template that delivers a coding sequence for WAS protein); specifically, the guide RNA can target mutation that gives rise to WAS (deficient WAS protein), and the HDR can provide coding for proper expression of WAS protein. A guide RNA that targets the mutation-and-CRISPR protein containing particle is contacted with HSCs carrying the mutation. The particle also can contain a suitable HDR template to correct the mutation for proper expression of WAS protein; or the HSC can be contacted with a second particle or a vector that contains or delivers the HDR template. The so contacted cells can be administered; and optionally treated/expanded; cf. Cartier.

Targeted deletion, therapeutic applications: Targeted deletion of genes may be preferred. Preferred are, therefore, genes involved in immunodeficiency disorder, hematologic condition, or genetic lysosomal storage disease, e.g., Hemophilia B, SCID, SCID-X1, ADA-SCID, Hereditary tyrosinemia, β-thalassemia, X-linked CGD, Wiskott-Aldrich syndrome, Fanconi anemia, adrenoleukodystrophy (ALD), metachromatic leukodystrophy (MLD), HIV/AIDS, other metabolic disorders, genes encoding mis-folded proteins involved in diseases, genes leading to loss-of-function involved in diseases; generally, mutations that can be targeted in an HSC, using any herein-discussed delivery system, with the particle system considered advantageous.

In an aspect of the invention, methods and compositions which involve editing a target nucleic acid sequence, or modulating expression of a target nucleic acid sequence, and applications thereof in connection with cancer immunotherapy are comprehended by adapting the CRISPR-Cas system of the present invention. Reference is made to the application of gene therapy in WO 2015/161276 which involves methods and compositions which can be used to affect T-cell proliferation, survival and/or function by altering one or more T-cell expressed genes, e.g., one or more of FAS, BID, CTLA4, PDCD1, CBLB, PTPN6, TRAC and/or TRBC genes. In a related aspect, T-cell proliferation can be affected by altering one or moreT-cell expressed genes, e.g., the CBLB and/or PTPN6 gene, FAS and/or BID gene, CTLA4 and/or PDCDI and/or TRAC and/or TRBC gene.

Chimeric antigen receptor (CAR)19 T-cells exhibit anti-leukemic effects in patient malignancies. However, leukemia patients often do not have enough T-cells to collect, meaning that treatment must involve modified T cells from donors. Accordingly, there is interest in establishing a bank of donor T-cells. Qasim et al. ("First Clinical Application of Talen Engineered Universal CAR19 T Cells in B-ALL" ASH 57th Annual Meeting and Exposition, Dec. 5-8, 2015, Abstract 2046 (ash.confex.com/ash/2015/webprogram/Paper81653.html published online November 2015) discusses modifying CAR19 T cells to eliminate the risk of graft-versus-host disease through the disruption of T-cell receptor expression and CD52 targeting. Furthermore, CD52 cells were targeted such that they became insensitive to Alemtuzumab, and thus allowed Alemtuzumab to prevent host-mediated rejection of human leukocyte antigen (HLA) mismatched CAR19 T-cells. Investigators used third generation self-inactivating lentiviral vector encoding a 4g7 CAR19 (CD19 scFv-4-1BB-CD3) linked to RQR8, then electroporated cells with two pairs of TALEN mRNA for multiplex targeting for both the T-cell receptor (TCR) alpha constant chain locus and the CD52 gene locus. Cells which were still expressing TCR following ex vivo expansion were depleted using CliniMacs α/β TCR depletion, yielding a T-cell product (UCART19) with <1% TCR expression, 85% of which expressed CAR19, and 64% becoming CD52 negative. The modified CAR19 T cells were administered to treat a patient's relapsed acute lymphoblastic leukemia. The teachings provided herein provide effective methods for modifying cells, for example to remove or modulate CD52 or other targets, thus can be used in conjunction with modification of administration of T cells or other cells to patients to treat malignancies.

Watts, "Hematopoietic Stem Cell Expansion and Gene Therapy" Cytotherapy 13(10):1164-1171. doi:10.3109/14653249.2011.620748 (2011), incorporated herein by reference along with the documents it cites, as if set out in full, discusses hematopoietic stem cell (HSC) gene therapy, e.g., virus-mediated HSC gene therapy, as an highly attractive treatment option for many disorders including hematologic conditions, immunodeficiencies including HIV/AIDS, and other genetic disorders like lysosomal storage diseases, including SCID-X1, ADA-SCID, 0-thalassemia, X-linked CGD, Wiskott-Aldrich syndrome, Fanconi anemia, adrenoleukodystrophy (ALD), and metachromatic leukodystrophy (MLD).

US Patent Publication Nos. 20110225664, 20110091441, 20100229252, 20090271881 and 20090222937 assigned to Cellectis, relates to CREI variants, wherein at least one of the two I-CreI monomers has at least two substitutions, one in each of the two functional subdomains of the LAGLIDADG (SEQ ID NO: 64) core domain situated respectively from positions 26 to 40 and 44 to 77 of I-CreI, said variant being able to cleave a DNA target sequence from the human interleukin-2 receptor gamma chain (IL2RG) gene also named common cytokine receptor gamma chain gene or gamma C gene. The target sequences identified in US Patent Publication Nos. 20110225664, 20110091441, 20100229252, 20090271881 and 20090222937 may be utilized for the nucleic acid-targeting system of the present invention.

Severe Combined Immune Deficiency (SCID) results from a defect in lymphocytes T maturation, always associated with a functional defect in lymphocytes B (Cavazzana-Calvo et al., *Annu. Rev. Med.,* 2005, 56, 585-602; Fischer et al., *Immunol. Rev.,* 2005, 203, 98-109). Overall incidence is estimated to 1 in 75 000 births. Patients with untreated SCID are subject to multiple opportunist micro-organism infections, and do generally not live beyond one year. SCID can be treated by allogenic hematopoietic stem cell transfer, from a familial donor. Histocompatibility with the donor can vary widely. In the case of Adenosine Deaminase (ADA) deficiency, one of the SCID forms, patients can be treated by injection of recombinant Adenosine Deaminase enzyme.

Since the ADA gene has been shown to be mutated in SCID patients (Giblett et al., *Lancet,* 1972, 2, 1067-1069), several other genes involved in SCID have been identified (Cavazzana-Calvo et al., *Annu. Rev. Med.,* 2005, 56, 585-602; Fischer et al., *Immunol. Rev.,* 2005, 203, 98-109). There are four major causes for SCID: (i) the most frequent form of SCID, SCID-X1 (X-linked SCID or X-SCID), is caused by mutation in the IL2RG gene, resulting in the absence of mature T lymphocytes and NK cells. IL2RG encodes the gamma C protein (Noguchi, et al., *Cell,* 1993, 73, 147-157), a common component of at least five interleukin receptor complexes. These receptors activate several targets through the JAK3 kinase (Macchi et al., *Nature,* 1995, 377, 65-68), which inactivation results in the same syndrome as gamma C inactivation; (ii) mutation in the ADA gene results in a defect in purine metabolism that is lethal for lymphocyte precursors, which in turn results in the quasi absence of B, T and NK cells; (iii) V(D)J recombination is an essential step in the maturation of immunoglobulins and T lymphocytes receptors (TCRs). Mutations in Recombination Activating Gene 1 and 2 (RAG1 and RAG2) and Artemis, three genes involved in this process, result in the absence of mature T and B lymphocytes; and (iv) Mutations in other genes such as CD45, involved in T cell specific signaling have also been reported, although they represent a minority of cases (Cavazzana-Calvo et al., *Annu. Rev. Med.,* 2005, 56, 585-602; Fischer et al., *Immunol. Rev.,* 2005, 203, 98-109). Since when their genetic bases have been identified, the different SCID forms have become a paradigm for gene therapy approaches (Fischer et al., *Immunol. Rev.,* 2005, 203, 98-109) for two major reasons. First, as in all blood diseases, an ex vivo treatment can be envisioned. Hematopoietic Stem Cells (HSCs) can be recovered from bone marrow, and keep their pluripotent properties for a few cell divisions. Therefore, they can be treated in vitro, and then reinjected into the patient, where they repopulate the bone marrow. Second, since the maturation of lymphocytes is impaired in SCID patients, corrected cells have a selective advantage. Therefore, a small number of corrected cells can restore a functional immune system. This hypothesis was validated several times by (i) the partial restoration of immune functions associated with the reversion of mutations in SCID patients (Hirschhorn et al., *Nat. Genet.,* 1996, 13, 290-295; Stephan et al., *N. Engl. J. Med.,* 1996, 335, 1563-1567; Bousso et al., *Proc. Natl., Acad. Sci. USA,* 2000, 97, 274-278; Wada et al., *Proc. Natl. Acad. Sci. USA,* 2001, 98, 8697-8702; Nishikomori et al., *Blood,* 2004, 103, 4565-4572), (ii) the correction of SCID-X1 deficiencies in vitro in hematopoietic cells (Candotti et al., *Blood,* 1996, 87, 3097-3102; Cavazzana-Calvo et al., *Blood,* 1996, Blood, 88, 3901-3909; Taylor et al., *Blood,* 1996, 87, 3103-3107; Hacein-Bey et al., *Blood,* 1998, 92, 4090-4097), (iii) the correction of SCID-X1 (Soudais et al., *Blood,* 2000, 95, 3071-3077; Tsai et al., *Blood,* 2002, 100, 72-79), JAK-3 (Bunting et al., *Nat. Med.,* 1998, 4, 58-64; Bunting et al., *Hum. Gene Ther.,* 2000, 11, 2353-2364) and RAG2 (Yates et al., *Blood,* 2002, 100, 3942-3949) deficiencies in vivo in animal models and (iv) by the result of gene therapy clinical trials (Cavazzana-Calvo et al., *Science,* 2000, 288, 669-672; Aiuti et al., *Nat. Med.,* 2002; 8, 423-425; Gaspar et al., *Lancet,* 2004, 364, 2181-2187).

US Patent Publication No. 20110182867 assigned to the Children's Medical Center Corporation and the President and Fellows of Harvard College relates to methods and uses of modulating fetal hemoglobin expression (HbF) in a hematopoietic progenitor cells via inhibitors of BCL11A expression or activity, such as RNAi and antibodies. The targets disclosed in US Patent Publication No. 20110182867, such as BCL11A, may be targeted by the CRISPR Cas system of the present invention for modulating fetal hemoglobin expression. See also Bauer et al. (*Science* 11 *Oct.* 2013: Vol. 342 no. 6155 pp. 253-257) and Xu et al. (*Science* 18 *Nov.* 2011: Vol. 334 no. 6058 pp. 993-996) for additional BCL11A targets.

With the knowledge in the art and the teachings in this disclosure, the skilled person can correct HSCs as to a genetic hematologic disorder, e.g., β-Thalassemia, Hemophilia, or a genetic lysosomal storage disease.

Treating Disease of the Brain, Central Nervous and Immune Systems

The present invention also contemplates delivering the CRISPR-Cas system to the brain or neurons. For example, RNA interference (RNAi) offers therapeutic potential for this disorder by reducing the expression of HTT, the disease-causing gene of Huntington's disease (see, e.g., McBride et al., *Molecular Therapy* vol. 19 no. 12 Dec. 2011, pp. 2152-2162), therefore Applicant postulates that it may be used and/or adapted to the CRISPR-Cas system. The CRISPR-Cas system may be generated using an algorithm to reduce the off-targeting potential of antisense sequences. The CRISPR-Cas sequences may target either a sequence in exon 52 of mouse, rhesus or human huntingtin and expressed in a viral vector, such as AAV. Animals, including humans, may be injected with about three microinjections per hemisphere (six injections total): the first 1 mm rostral to the anterior commissure (12 μl) and the two remaining injections (12 μl and 10 μl, respectively) spaced 3 and 6 mm caudal to the first injection with 1e12 vg/ml of AAV at a rate of about 1 l/minute, and the needle was left in place for an additional 5 minutes to allow the injectate to diffuse from the needle tip.

DiFiglia et al. (*PNAS*, Oct. 23, 2007, vol. 104, no. 43, 17204-17209) observed that single administration into the adult striatum of an siRNA targeting Htt can silence mutant Htt, attenuate neuronal pathology, and delay the abnormal behavioral phenotype observed in a rapid-onset, viral transgenic mouse model of HD. DiFiglia injected mice intrastriatally with 2 μl of Cy3-labeled cc-siRNA-Htt or unconjugated siRNA-Htt at 10 M. A similar dosage of CRISPR Cas targeted to Htt may be contemplated for humans in the present invention, for example, about 5-10 ml of 10 M CRISPR Cas targeted to Htt may be injected intrastriatally.

In another example, Boudreau et al. (*Molecular Therapy* vol. 17 no. 6 Jun. 2009) injects 5 μl of recombinant AAV serotype 2/1 vectors expressing htt-specific RNAi virus (at $4\times10^{12}$ viral genomes/ml) into the striatum. A similar dosage of CRISPR Cas targeted to Htt may be contemplated for humans in the present invention, for example, about 10-20 ml of $4\times10^{12}$ viral genomes/ml) CRISPR Cas targeted to Htt may be injected intrastriatally.

In another example, a CRISPR Cas targeted to HTT may be administered continuously (see, e.g., Yu et al., *Cell* 150, 895-908, Aug. 31, 2012). Yu et al. utilizes osmotic pumps delivering 0.25 ml/hr (Model 2004) to deliver 300 mg/day of ss-siRNA or phosphate-buffered saline (PBS) (Sigma Aldrich) for 28 days, and pumps designed to deliver 0.5 l/hr (Model 2002) were used to deliver 75 mg/day of the positive control MOE ASO for 14 days. Pumps (Durect Corporation) were filled with ss-siRNA or MOE diluted in sterile PBS and then incubated at 37% C for 24 or 48 (Model 2004) hours prior to implantation. Mice were anesthetized with 2.5% isoflurane, and a midline incision was made at the base of the skull. Using stereotaxic guides, a cannula was implanted into the right lateral ventricle and secured with Loctite adhesive. A catheter attached to an Alzet osmotic mini pump was attached to the cannula, and the pump was placed subcutaneously in the midscapular area. The incision was closed with 5.0 nylon sutures. A similar dosage of CRISPR Cas targeted to Htt may be contemplated for humans in the present invention, for example, about 500 to 1000 g/day CRISPR Cas targeted to Htt may be administered.

In another example of continuous infusion, Stiles et al. (*Experimental Neurology* 233 (2012) 463-471) implanted an intraparenchymal catheter with a titanium needle tip into the right putamen. The catheter was connected to a SynchroMed® II Pump (Medtronic Neurological, Minneapolis, MN) subcutaneously implanted in the abdomen. After a 7 day infusion of phosphate buffered saline at 6 μL/day, pumps were re-filled with test article and programmed for continuous delivery for 7 days. About 2.3 to 11.52 mg/d of siRNA were infused at varying infusion rates of about 0.1 to 0.5 L/min. A similar dosage of CRISPR Cas targeted to Htt may be contemplated for humans in the present invention, for example, about 20 to 200 mg/day CRISPR Cas targeted to Htt may be administered. In another example, the methods of US Patent Publication No. 20130253040 assigned to Sangamo may also be also be adapted from TALES to the nucleic acid-targeting system of the present invention for treating Huntington's Disease.

A further aspect of the invention relates to utilizing the CRISPR-Cas system for correcting defects in the EMP2A and EMP2B genes that have been identified to be associated with Lafora disease. Lafora disease is an autosomal recessive condition which is characterized by progressive myoclonus epilepsy which may start as epileptic seizures in adolescence. A few cases of the disease may be caused by mutations in genes yet to be identified. The disease causes seizures, muscle spasms, difficulty walking, dementia, and eventually death. There is currently no therapy that has proven effective against disease progression. Other genetic abnormalities associated with epilepsy may also be targeted by the CRISPR-Cas system and the underlying genetics is further described in Genetics of Epilepsy and Genetic Epilepsies, edited by Giuliano Avanzini, Jeffrey L. Noebels, Mariani Foundation Paediatric Neurology:20; 2009).

The methods of US Patent Publication No. 20110158957 assigned to Sangamo BioSciences, Inc. involved in inactivating T cell receptor (TCR) genes may also be modified to the CRISPR Cas system of the present invention. In another example, the methods of US Patent Publication No. 20100311124 assigned to Sangamo BioSciences, Inc. and US Patent Publication No. 20110225664 assigned to Cellectis, which are both involved in inactivating glutamine synthetase gene expression genes may also be modified to the CRISPR Cas system of the present invention.

Treating Hearing Diseases

The present invention also contemplates delivering the CRISPR-Cas system to one or both ears.

Researchers are looking into whether gene therapy could be used to aid current deafness treatments—namely, cochlear implants. Deafness is often caused by lost or damaged hair cells that cannot relay signals to auditory neurons. In such cases, cochlear implants may be used to respond to sound and transmit electrical signals to the nerve cells. But these neurons often degenerate and retract from the cochlea as fewer growth factors are released by impaired hair cells.

US patent application 20120328580 describes injection of a pharmaceutical composition into the ear (e.g., auricular administration), such as into the luminae of the cochlea (e.g., the Scala media, Sc vestibule, and Sc tympani), e.g., using a syringe, e.g., a single-dose syringe. For example, one or more of the compounds described herein can be administered by intratympanic injection (e.g., into the middle ear), and/or injections into the outer, middle, and/or inner ear. Such methods are routinely used in the art, for example, for the administration of steroids and antibiotics into human ears. Injection can be, for example, through the round window of the ear or through the cochlear capsule. Other inner ear administration methods are known in the art (see, e.g., Salt and Plontke, *Drug Discovery Today,* 10:1299-1306, 2005).

In another mode of administration, the pharmaceutical composition can be administered in situ, via a catheter or pump. A catheter or pump can, for example, direct a pharmaceutical composition into the cochlear luminae or the round window of the ear and/or the lumen of the colon. Exemplary drug delivery apparatus and methods suitable for administering one or more of the compounds described herein into an ear, e.g., a human ear, are described by McKenna et al., (U.S. Publication No. 2006/0030837) and Jacobsen et al., (U.S. Pat. No. 7,206,639). In some embodiments, a catheter or pump can be positioned, e.g., in the ear (e.g., the outer, middle, and/or inner ear) of a patient during a surgical procedure. In some embodiments, a catheter or pump can be positioned, e.g., in the ear (e.g., the outer, middle, and/or inner ear) of a patient without the need for a surgical procedure.

Alternatively or in addition, one or more of the compounds described herein can be administered in combination with a mechanical device such as a cochlear implant or a hearing aid, which is worn in the outer ear. An exemplary cochlear implant that is suitable for use with the present invention is described by Edge et al., (U.S. Publication No. 2007/0093878).

In some embodiments, the modes of administration described above may be combined in any order and can be simultaneous or interspersed.

Alternatively or in addition, the present invention may be administered according to any one of the Food and Drug Administration approved methods, for example, as described in CDER Data Standards Manual, version number 004 (which is available at fda.give/cder/dsm/DRG/drg00301.htm).

In general, the cell therapy methods described in US patent application 20120328580 can be used to promote complete or partial differentiation of a cell to or towards a mature cell type of the inner ear (e.g., a hair cell) in vitro. Cells resulting from such methods can then be transplanted or implanted into a patient in need of such treatment. The cell culture methods required to practice these methods, including methods for identifying and selecting suitable cell types, methods for promoting complete or partial differentiation of selected cells, methods for identifying complete or partially differentiated cell types, and methods for implanting complete or partially differentiated cells are described below.

Cells suitable for use in the present invention include, but are not limited to, cells that are capable of differentiating completely or partially into a mature cell of the inner ear, e.g., a hair cell (e.g., an inner and/or outer hair cell), when contacted, e.g., in vitro, with one or more of the compounds described herein. Exemplary cells that are capable of differentiating into a hair cell include, but are not limited to stem cells (e.g., inner ear stem cells, adult stem cells, bone marrow derived stem cells, embryonic stem cells, mesenchymal stem cells, skin stem cells, iPS cells, and fat derived stem cells), progenitor cells (e.g., inner ear progenitor cells), support cells (e.g., Deiters' cells, pillar cells, inner phalangeal cells, tectal cells and Hensen's cells), and/or germ cells. The use of stem cells for the replacement of inner ear sensory cells is described in Li et al., (U.S. Publication No. 2005/0287127) and Li et al., (U.S. patent Ser. No. 11/953,797). The use of bone marrow derived stem cells for the replacement of inner ear sensory cells is described in Edge et al., PCT/US2007/084654. iPS cells are described, e.g., at Takahashi et al., Cell, Volume 131, Issue 5, Pages 861-872 (2007); *Takahashi and Yamanaka, Cell* 126, 663-76 (2006); Okita et al., *Nature* 448, 260-262 (2007); Yu, J. et al., *Science* 318(5858):1917-1920 (2007); Nakagawa et al., *Nat. Biotechnol.* 26:101-106 (2008); and Zaehres and Scholer, Cell 131(5):834-835 (2007). Such suitable cells can be identified by analyzing (e.g., qualitatively or quantitatively) the presence of one or more tissue specific genes. For example, gene expression can be detected by detecting the protein product of one or more tissue-specific genes. Protein detection techniques involve staining proteins (e.g., using cell extracts or whole cells) using antibodies against the appropriate antigen. In this case, the appropriate antigen is the protein product of the tissue-specific gene expression. Although, in principle, a first antibody (i.e., the antibody that binds the antigen) can be labeled, it is more common (and improves the visualization) to use a second antibody directed against the first (e.g., an anti-IgG). This second antibody is conjugated either with fluorochromes, or appropriate enzymes for colorimetric reactions, or gold beads (for electron microscopy), or with the biotin-avidin system, so that the location of the primary antibody, and thus the antigen, can be recognized.

The CRISPR Cas molecules of the present invention may be delivered to the ear by direct application of pharmaceutical composition to the outer ear, with compositions modified from US Published application, 20110142917. In some embodiments the pharmaceutical composition is applied to the ear canal. Delivery to the ear may also be referred to as aural or otic delivery.

In some embodiments the RNA molecules of the invention are delivered in liposome or lipofectin formulations and the like and can be prepared by methods well known to those skilled in the art. Such methods are described, for example, in U.S. Pat. Nos. 5,593,972, 5,589,466, and 5,580,859, which are herein incorporated by reference.

Delivery systems aimed specifically at the enhanced and improved delivery of siRNA into mammalian cells have been developed, (see, for example, Shen et al *FEBS Let.* 2003, 539:111-114; Xia et al., *Nat. Biotech.* 2002, 20:1006-1010; Reich et al., *Mol. Vision.* 2003, 9: 210-216; Sorensen et al., *J. Mol. Biol.* 2003, 327: 761-766; Lewis et al., *Nat. Gen.* 2002, 32: 107-108 and Simeoni et al., NAR 2003, 31, 11: 2717-2724) and may be applied to the present invention. siRNA has recently been successfully used for inhibition of gene expression in primates (see for example Tolentino et al., *Retina* 24(4):660 which may also be applied to the present invention).

Qi et al. discloses methods for efficient siRNA transfection to the inner ear through the intact round window by a novel protein delivery technology which may be applied to the nucleic acid-targeting system of the present invention (see, e.g., Qi et al., *Gene Therapy* (2013), 1-9). In particular, a TAT double stranded RNA-binding domains (TAT-DRBDs), which can transfect Cy3-labeled siRNA into cells of the inner ear, including the inner and outer hair cells, *crista ampullaris*, macula utriculi and macula sacculi, through intact round-window permeation was successful for delivering double stranded siRNAs in vivo for treating various inner ear ailments and preservation of hearing function. About 40 μl of 10 mM RNA may be contemplated as the dosage for administration to the ear.

According to Rejali et al. (*Hear Res.* 2007 June;228(1-2):180-7), cochlear implant function can be improved by good preservation of the spiral ganglion neurons, which are the target of electrical stimulation by the implant and brain derived neurotrophic factor (BDNF) has previously been shown to enhance spiral ganglion survival in experimentally deafened ears. Rejali et al. tested a modified design of the cochlear implant electrode that includes a coating of fibroblast cells transduced by a viral vector with a BDNF gene insert. To accomplish this type of ex vivo gene transfer, Rejali et al. transduced guinea pig fibroblasts with an adenovirus with a BDNF gene cassette insert, and determined that these cells secreted BDNF and then attached BDNF-secreting cells to the cochlear implant electrode via an agarose gel, and implanted the electrode in the scala tympani. Rejali et al. determined that the BDNF expressing electrodes were able to preserve significantly more spiral ganglion neurons in the basal turns of the cochlea after 48 days of implantation when compared to control electrodes and demonstrated the feasibility of combining cochlear implant therapy with ex vivo gene transfer for enhancing spiral ganglion neuron survival. Such a system may be applied to the nucleic acid-targeting system of the present invention for delivery to the ear.

Mukherjea et al. (Antioxidants & Redox Signaling, Volume 13, Number 5, 2010) document that knockdown of NOX3 using short interfering (si) RNA abrogated cisplatin ototoxicity, as evidenced by protection of OHCs from damage and reduced threshold shifts in auditory brainstem responses (ABRs). Different doses of siNOX3 (0.3, 0.6, and 0.9 μg) were administered to rats and NOX3 expression was evaluated by real time RT-PCR. The lowest dose of NOX3 siRNA used (0.3 μg) did not show any inhibition of NOX3 mRNA when compared to transtympanic administration of scrambled siRNA or untreated *cochleae*. However, administration of the higher doses of NOX3 siRNA (0.6 and 0.9 μg) reduced NOX3 expression compared to control scrambled siRNA. Such a system may be applied to the CRISPR Cas system of the present invention for transtympanic administration with a dosage of about 2 mg to about 4 mg of CRISPR Cas for administration to a human. Jung et al. (*Molecular Therapy*, vol. 21 no. 4, 834-841 Apr. 2013) demonstrate that Hes5 levels in the utricle decreased after the application of siRNA and that the number of hair cells in these utricles was significantly larger than following control treatment. The data suggest that siRNA technology may be useful for inducing repair and regeneration in the inner ear and that the Notch signaling pathway is a potentially useful target for specific gene expression inhibition. Jung et al. injected 8 μg of Hes5 siRNA in 2 μl volume, prepared by adding sterile normal saline to the lyophilized siRNA to a vestibular epithelium of the ear. Such a system may be applied to the nucleic acid-targeting system of the present invention for administration to the vestibular epithelium of the ear with a dosage of about 1 to about 30 mg of CRISPR Cas for administration to a human.

Treating Diseases of the Eye

The present invention also contemplates delivering the CRISPR-Cas system to one or both eyes.

In yet another aspect of the invention, the CRISPR-Cas system may be used to correct ocular defects that arise from several genetic mutations further described in Genetic Diseases of the Eye, Second Edition, edited by Elias I. Traboulsi, Oxford University *Press,* 2012.

For administration to the eye, lentiviral vectors, in particular equine infectious anemia viruses (EIAV) are particularly preferred.

In another embodiment, minimal non-primate lentiviral vectors based on the equine infectious anemia virus (EIAV) are also contemplated, especially for ocular gene therapy (see, e.g., Balagaan, *J Gene Med* 2006; 8: 275-285, Published online 21 Nov. 2005 in Wiley InterScience (www.interscience.wiley.com). DOI: 10.1002/jgm.845). The vectors are contemplated to have cytomegalovirus (CMV) promoter driving expression of the target gene. Intracameral, subretinal, intraocular and intravitreal injections are all contemplated (see, e.g., Balagaan, *J Gene Med* 2006; 8: 275-285, Published online 21 Nov. 2005 in Wiley InterScience (www.interscience.wiley.com). DOI: 10.1002/jgm.845). Intraocular injections may be performed with the aid of an operating microscope. For subretinal and intravitreal injections, eyes may be prolapsed by gentle digital pressure and fundi visualised using a contact lens system consisting of a drop of a coupling medium solution on the cornea covered with a glass microscope slide coverslip. For subretinal injections, the tip of a 10-mm 34-gauge needle, mounted on a 5 μl Hamilton syringe may be advanced under direct visualisation through the superior equatorial sclera tangentially towards the posterior pole until the aperture of the needle was visible in the subretinal space. Then, 2 μl of vector suspension may be injected to produce a superior bullous retinal detachment, thus confirming subretinal vector administration. This approach creates a self-sealing sclerotomy allowing the vector suspension to be retained in the subretinal space until it is absorbed by the RPE, usually within 48 h of the procedure. This procedure may be repeated in the inferior hemisphere to produce an inferior retinal detachment. This technique results in the exposure of approximately 70% of neurosensory retina and RPE to the vector suspension. For intravitreal injections, the needle tip may be advanced through the sclera 1 mm posterior to the corneoscleral limbus and 2 μl of vector suspension injected into the vitreous cavity. For intracameral injections, the needle tip may be advanced through a corneoscleral limbal paracentesis, directed towards the central cornea, and 2 μl of vector suspension may be injected. For intracameral injections, the needle tip may be advanced through a corneoscleral limbal paracentesis, directed towards the central cornea, and 2 μl of vector suspension may be injected. These vectors may be injected at titres of either $1.0\text{-}1.4\times10^{10}$ or $1.0\text{-}1.4\times10^{9}$ transducing units (TU)/ml.

In another embodiment, RetinoStat®, an equine infectious anemia virus-based lentiviral gene therapy vector that expresses angiostatic proteins endostatin and angiostatin that is delivered via a subretinal injection for the treatment of the web form of age-related macular degeneration is also contemplated (see, e.g., Binley et al., *HUMAN GENE THERAPY* 23:980-991 (September 2012)). Such a vector may be modified for the CRISPR-Cas system of the present invention. Each eye may be treated with either RetinoStat® at a dose of $1.1\times10^{5}$ transducing units per eye (TU/eye) in a total volume of 100 μl.

In an embodiment, mention is made of WO 2015/153780 which comprehends providing a treatment or prevention of Primary Open Angle Glaucoma (POAG) by targeting the coding sequence of the MYOC gene. Some of the target mutations which give rise to POAG include, but are not limited to, P370 (e.g. P370L); 1477 (e.g., I477N or I477S); T377 (e.g., TE77R); Q368 (Q368stop)—all in the MYOC gene. The target mutation also may include a mutational hotspot between amino acid sequence positions 246-252 in the MYOC gene. In an embodiment, the target mutation is a mutational hotspot between amino acid sequence positions, e.g., amino acids 368-380, amino acids 368-370+377-380, amino acids 364-380, or amino acids 347-380 in the MYOC gene. In an embodiment, the target mutation is a mutational hotspot between amino acid sequence positions 423-437 (e.g., amino acids 423-426, amino acids 423-427 and amino acids 423-437) in the MYOC gene. In an embodiment, the target mutation is a mutational hotspot between amino acid sequence positions 477-502 in the MYOC gene (see, e.g., WO 2015/153780).

In another embodiment, an El-, partial E3-, E4-deleted adenoviral vector may be contemplated for delivery to the eye. Twenty-eight patients with advanced neovascular age related macular degeneration (AMD) were given a single intravitreous injection of an El-, partial E3-, E4-deleted adenoviral vector expressing human pigment epithelium-derived factor (AdPEDF.ll) (see, e.g., Campochiaro et al., *Human Gene Therapy* 17:167-176 (February 2006)). Doses ranging from $10^{6}$ to $109^{9.5}$ particle units (PU) were investigated and there were no serious adverse events related to AdPEDF.ll and no dose-limiting toxicities (see, e.g., Campochiaro et al., *Human Gene Therapy* 17:167-176 (February 2006)). Adenoviral vector mediated ocular gene transfer appears to be a viable approach for the treatment of ocular disorders and could be applied to the CRISPR Cas system.

In another embodiment, the sd-rxRNA® system of Rxi Pharmaceuticals may be used and/or adapted for delivering CRISPR Cas to the eye. In this system, a single intravitreal administration of 3 μg of sd-rxRNA results in sequence-specific reduction of PPIB mRNA levels for 14 days. The sd-rxRNA® system may be applied to the nucleic acid-targeting system of the present invention, contemplating a dose of about 3 to 20 mg of CRISPR administered to a human.

Millington-Ward et al. (*Molecular Therapy*, vol. 19 no. 4, 642-649 Apr. 2011) describes adeno-associated virus (AAV) vectors to deliver an RNA interference (RNAi)-based rhodopsin suppressor and a codon-modified rhodopsin replacement gene resistant to suppression due to nucleotide alterations at degenerate positions over the RNAi target site. An injection of either $6.0\times10^{8}$ vp or $1.8\times10^{10}$ vp AAV were subretinally injected into the eyes by Millington-Ward et al. The AAV vectors of Millington-Ward et al. may be applied to the CRISPR Cas system of the present invention, contemplating a dose of about 2×10" to about $6\times10^{13}$ vp administered to a human.

Dalkara et al. (*Sci Transl Med* 5, 189ra76 (2013)) also relates to in vivo directed evolution to fashion an AAV vector that delivers wild-type versions of defective genes throughout the retina after noninjurious injection into the eyes' vitreous humor. Dalkara describes a 7mer peptide display library and an AAV library constructed by DNA shuffling of cap genes from AAV1, 2, 4, 5, 6, 8, and 9. The rcAAV libraries and rAAV vectors expressing GFP under a CAG or Rho promoter were packaged and deoxyribonuclease-resistant genomic titers were obtained through quantitative PCR. The libraries were pooled, and two rounds of evolution were performed, each consisting of initial library diversification followed by three in vivo selection steps. In each such step, P30 rho-GFP mice were intravitreally injected with 2 ml of iodixanol-purified, phosphate-buffered saline (PBS)-dialyzed library with a genomic titer of about $1\times10^{12}$ vg/ml. The AAV vectors of Dalkara et al. may be applied to the nucleic acid-targeting system of the present invention, contemplating a dose of about $1\times10^{15}$ to about $1\times10^{16}$ vg/ml administered to a human.

In another embodiment, the rhodopsin gene may be targeted for the treatment of retinitis pigmentosa (RP), wherein the system of US Patent Publication No. 20120204282 assigned to Sangamo BioSciences, Inc. may be modified in accordance of the CRISPR Cas system of the present invention.

In another embodiment, the methods of US Patent Publication No. 20130183282 assigned to Cellectis, which is directed to methods of cleaving a target sequence from the human rhodopsin gene, may also be modified to the nucleic acid-targeting system of the present invention.

US Patent Publication No. 20130202678 assigned to Academia *Sinica* relates to methods for treating retinopathies and sight-threatening ophthalmologic disorders relating to delivering of the Puf-A gene (which is expressed in retinal ganglion and pigmented cells of eye tissues and displays a unique anti-apoptotic activity) to the sub-retinal or intravitreal space in the eye. In particular, desirable targets are zgc:193933, prdmla, spata2, tex10, rbb4, ddx3, zp2.2, Blimp-1 and HtrA2, all of which may be targeted by the nucleic acid-targeting system of the present invention.

Wu (Cell Stem Cell,13:659-62, 2013) designed a guide RNA that led Cas9 to a single base pair mutation that causes cataracts in mice, where it induced DNA cleavage. Then using either the other wild-type allele or oligos given to the zygotes repair mechanisms corrected the sequence of the broken allele and corrected the cataract-causing genetic defect in mutant mouse.

US Patent Publication No. 20120159653, describes use of zinc finger nucleases to genetically modify cells, animals and proteins associated with macular degeneration (MD). Macular degeneration (MD) is the primary cause of visual impairment in the elderly, but is also a hallmark symptom of childhood diseases such as Stargardt disease, Sorsby fundus, and fatal childhood neurodegenerative diseases, with an age of onset as young as infancy. Macular degeneration results in a loss of vision in the center of the visual field (the macula) because of damage to the retina. Currently existing animal models do not recapitulate major hallmarks of the disease as it is observed in humans. The available animal models comprising mutant genes encoding proteins associated with MD also produce highly variable phenotypes, making translations to human disease and therapy development problematic.

One aspect of US Patent Publication No. 20120159653 relates to editing of any chromosomal sequences that encode proteins associated with MD which may be applied to the nucleic acid-targeting system of the present invention. The proteins associated with MD are typically selected based on an experimental association of the protein associated with MD to an MD disorder. For example, the production rate or circulating concentration of a protein associated with MD may be elevated or depressed in a population having an MD disorder relative to a population lacking the MD disorder. Differences in protein levels may be assessed using proteomic techniques including but not limited to Western blot, immunohistochemical staining, enzyme linked immunosorbent assay (ELISA), and mass spectrometry. Alternatively, the proteins associated with MD may be identified by obtaining gene expression profiles of the genes encoding the proteins using genomic techniques including but not limited to DNA microarray analysis, serial analysis of gene expression (SAGE), and quantitative real-time polymerase chain reaction (Q-PCR).

By way of non-limiting example, proteins associated with MD include but are not limited to the following proteins: (ABCA4) ATP-binding cassette, sub-family A (ABC1), member 4 ACHM1 achromatopsia (rod monochromacy) 1 ApoE Apolipoprotein E (ApoE) C1QTNF5 (CTRP5) C1q and tumor necrosis factor related protein 5 (ClQTNF5) C2 Complement component 2 (C2) C3 Complement components (C3) CCL2 Chemokine (C—C motif) Ligand 2 (CCL2) CCR2 Chemokine (C—C motif) receptor 2 (CCR2) CD36 Cluster of Differentiation 36 CFB Complement factor B CFH Complement factor CFH H CFHR1 complement factor H-related 1 CFHR3 complement factor H-related 3 CNGB3 cyclic nucleotide gated channel beta 3 CP ceruloplasmin (CP) CRP C reactive protein (CRP) CST3 cystatin C or cystatin 3 (CST3) CTSD Cathepsin D (CTSD) CX3CR1 chemokine (C-X3-C motif) receptor 1 ELOVL4 Elongation of very long chain fatty acids 4 ERCC6 excision repair crosscomplementing rodent repair deficiency, complementation group 6 FBLN5 Fibulin-5 FBLN5 Fibulin 5 FBLN6 Fibulin 6 FSCN2 fascin (FSCN2) HMCN1 Hemicentin 1 HMCN1 hemicentin 1 HTRA1 HtrA serine peptidase 1 (HTRA1) HTRA1 HtrA serine peptidase 1 IL-6 Interleukin 6 IL-8 Interleukin 8 LOC387715 Hypothetical protein PLEKHA1 Pleckstrin homology domain containing family A member 1 (PLEKHA1) PROM1 Prominin 1(PROM1 or CD133) PRPH2 Peripherin-2 RPGR retinitis pigmentosa GTPase regulator SERPING1 serpin peptidase inhibitor, clade G, member 1 (C1-inhibitor) TCOF1 Treacle TIMP3 Metalloproteinase inhibitor 3 (TIMP3) TLR3 Toll-like receptor 3.

The identity of the protein associated with MD whose chromosomal sequence is edited can and will vary. In preferred embodiments, the proteins associated with MD whose chromosomal sequence is edited may be the ATP-binding cassette, sub-family A (ABC1) member 4 protein (ABCA4) encoded by the ABCR gene, the apolipoprotein E protein (APOE) encoded by the APOE gene, the chemokine (C—C motif) Ligand 2 protein (CCL2) encoded by the CCL2 gene, the chemokine (C—C motif) receptor 2 protein (CCR2) encoded by the CCR2 gene, the ceruloplasmin protein (CP) encoded by the CP gene, the cathepsin D protein (CTSD) encoded by the CTSD gene, or the metalloproteinase inhibitor 3 protein (TIMP3) encoded by the TIMP3 gene. In an exemplary embodiment, the genetically modified animal is a rat, and the edited chromosomal sequence encoding the protein associated with MD may be: (ABCA4) ATP binding cassette, NM_000350 sub-family A (ABC1), member 4 APOE Apolipoprotein E NM_138828 (APOE) CCL2 Chemokine (C—C NM_031530 motif) Ligand 2 (CCL2) CCR2 Chemokine (C—C NM_021866 motif) receptor 2 (CCR2) CP ceruloplasmin (CP) NM_012532 CTSD Cathepsin D (CTSD) NM_134334 TIMP3 Metalloproteinase NM_012886 inhibitor 3 (TIMP3) The animal or cell may comprise 1, 2, 3, 4, 5, 6, 7 or more disrupted chromosomal sequences encoding a protein associated with MD and zero, 1, 2, 3, 4, 5, 6, 7 or more chromosomally integrated sequences encoding the disrupted protein associated with MD.

The edited or integrated chromosomal sequence may be modified to encode an altered protein associated with MD. Several mutations in MD-related chromosomal sequences have been associated with MD. Non-limiting examples of mutations in chromosomal sequences associated with MD include those that may cause MD including in the ABCR protein, E471K (i.e. glutamate at position 471 is changed to lysine), Ri 129L (i.e. arginine at position 1129 is changed to leucine), T1428M (i.e. threonine at position 1428 is changed to methionine), R1517S (i.e. arginine at position 1517 is changed to serine), I1562T (i.e. isoleucine at position 1562 is changed to threonine), and G1578R (i.e. glycine at position 1578 is changed to arginine); in the CCR2 protein, V64I (i.e. valine at position 192 is changed to isoleucine); in CP protein, G969B (i.e. glycine at position 969 is changed to asparagine or aspartate); in TIMP3 protein, S156C (i.e. serine at position 156 is changed to cysteine), G166C (i.e. glycine at position 166 is changed to cysteine), G167C (i.e. glycine at position 167 is changed to cysteine), Y168C (i.e. tyrosine at position 168 is changed to cysteine), S170C (i.e. serine at position 170 is changed to cysteine), Y172C (i.e. tyrosine at position 172 is changed to cysteine) and S181C (i.e. serine at position 181 is changed to cysteine). Other associations of genetic variants in MD-associated genes and disease are known in the art.

Treating Circulatory and Muscular Diseases

The present invention also contemplates delivering the CRISPR-Cas system described herein, e.g. Cas9 effector protein systems, to the heart. For the heart, a myocardium tropic adeno-associated virus (AAVM) is preferred, in particular AAVM41 which showed preferential gene transfer in the heart (see, e.g., Lin-Yanga et al., *PNAS*, Mar. 10, 2009, vol. 106, no. 10). Administration may be systemic or local. A dosage of about $1\text{-}10\times10^{14}$ vector genomes are contemplated for systemic administration. See also, e.g., Eulalio et al. (2012) *Nature* 492: 376 and Somasuntharam et al. (2013) *Biomaterials* 34: 7790.

For example, US Patent Publication No. 20110023139, describes use of zinc finger nucleases to genetically modify cells, animals and proteins associated with cardiovascular disease. Cardiovascular diseases generally include high blood pressure, heart attacks, heart failure, and stroke and TIA. Any chromosomal sequence involved in cardiovascular disease or the protein encoded by any chromosomal sequence involved in cardiovascular disease may be utilized in the methods described in this disclosure. The cardiovascular-related proteins are typically selected based on an experimental association of the cardiovascular-related protein to the development of cardiovascular disease. For example, the production rate or circulating concentration of a cardiovascular-related protein may be elevated or depressed in a population having a cardiovascular disorder relative to a population lacking the cardiovascular disorder. Differences in protein levels may be assessed using proteomic techniques including but not limited to Western blot, immunohistochemical staining, enzyme linked immunosorbent assay (ELISA), and mass spectrometry. Alternatively, the cardiovascular-related proteins may be identified by obtaining gene expression profiles of the genes encoding the proteins using genomic techniques including but not limited to DNA microarray analysis, serial analysis of gene expression (SAGE), and quantitative real-time polymerase chain reaction (Q-PCR).

Treating Diseases of the Liver and Kidney

The present invention also contemplates delivering the CRISPR-Cas system described herein, e.g. Cas9 effector protein systems, to the liver and/or kidney. Delivery strategies to induce cellular uptake of the therapeutic nucleic acid include physical force or vector systems such as viral-, lipid- or complex-based delivery, or nanocarriers. From the initial applications with less possible clinical relevance, when nucleic acids were addressed to renal cells with hydrodynamic high pressure injection systemically, a wide range of gene therapeutic viral and non-viral carriers have been applied already to target posttranscriptional events in different animal kidney disease models in vivo (Csaba Revesz and Peter Hamar (2011). Delivery Methods to Target RNAs in the Kidney, Gene Therapy Applications, Prof. Chunsheng Kang (Ed.), ISBN: 978-953-307-541-9, InTech, Available from: www.intechopen.com/books/gene-therapy-applications/delivery-methods-to-target-rnas-inthe-kidney). Delivery methods to the kidney may include those in Yuan et al. (*Am J Physiol Renal Physiol* 295: F605-F617, 2008) investigated whether in vivo delivery of small interfering RNAs (siRNAs) targeting the 12/15-lipoxygenase (12/15-LO) pathway of arachidonate acid metabolism can ameliorate renal injury and diabetic nephropathy (DN) in a streptozotocin injected mouse model of type 1 diabetes. To achieve greater in vivo access and siRNA expression in the kidney, Yuan et al. used double-stranded 12/15-LO siRNA oligonucleotides conjugated with cholesterol. About 400 μg of siRNA was injected subcutaneously into mice. The method of Yuang et al. may be applied to the CRISPR Cas system of the present invention contemplating a 1-2 g subcutaneous injection of CRISPR Cas conjugated with cholesterol to a human for delivery to the kidneys.

Molitoris et al. (*J Am Soc Nephrol* 20: 1754-1764, 2009) exploited proximal tubule cells (PTCs), as the site of oligonucleotide reabsorption within the kidney to test the efficacy of siRNA targeted to p53, a pivotal protein in the apoptotic pathway, to prevent kidney injury. Naked synthetic siRNA to p53 injected intravenously 4 h after ischemic injury maximally protected both PTCs and kidney function. Molitoris et al.'s data indicates that rapid delivery of siRNA to proximal tubule cells follows intravenous administration. For dose-response analysis, rats were injected with doses of siP53, 0.33; 1, 3, or 5 mg/kg, given at the same four time points, resulting in cumulative doses of 1.32; 4, 12, and 20 mg/kg, respectively. All siRNA doses tested produced a SCr reducing effect on day one with higher doses being effective over approximately five days compared with PBS-treated ischemic control rats. The 12 and 20 mg/kg cumulative doses provided the best protective effect. The method of Molitoris et al. may be applied to the nucleic acid-targeting system of the present invention contemplating 12 and 20 mg/kg cumulative doses to a human for delivery to the kidneys.

Thompson et al. (Nucleic Acid Therapeutics, Volume 22, Number 4, 2012) reports the toxicological and pharmacokinetic properties of the synthetic, small interfering RNA I5NP following intravenous administration in rodents and nonhuman primates. I5NP is designed to act via the RNA interference (RNAi) pathway to temporarily inhibit expression of the pro-apoptotic protein p53 and is being developed to protect cells from acute ischemia/reperfusion injuries such as acute kidney injury that can occur during major cardiac surgery and delayed graft function that can occur following renal transplantation. Doses of 800 mg/kg I5NP in rodents, and 1,000 mg/kg I5NP in nonhuman primates, were required to elicit adverse effects, which in the monkey were isolated to direct effects on the blood that included a sub-clinical activation of complement and slightly increased clotting times. In the rat, no additional adverse effects were observed with a rat analogue of I5NP, indicating that the effects likely represent class effects of synthetic RNA duplexes rather than toxicity related to the intended pharmacologic activity of I5NP. Taken together, these data support clinical testing of intravenous administration of I5NP for the preservation of renal function following acute ischemia/reperfusion injury. The no observed adverse effect level (NOAEL) in the monkey was 500 mg/kg. No effects on cardiovascular, respiratory, and neurologic parameters were observed in monkeys following i.v. administration at dose levels up to 25 mg/kg. Therefore, a similar dosage may be contemplated for intravenous administration of CRISPR Cas to the kidneys of a human.

Shimizu et al. (*J Am Soc Nephrol* 21: 622-633, 2010) developed a system to target delivery of siRNAs to glomeruli via poly(ethylene glycol)-poly(L-lysine)-based vehicles. The siRNA/nanocarrier complex was approximately 10 to 20 nm in diameter, a size that would allow it to move across the fenestrated endothelium to access to the mesangium. After intraperitoneal injection of fluorescence-labeled siRNA/nanocarrier complexes, Shimizu et al. detected siRNAs in the blood circulation for a prolonged time. Repeated intraperitoneal administration of a mitogen-activated protein kinase 1 (MAPK1) siRNA/nanocarrier complex suppressed glomerular MAPK1 mRNA and protein expression in a mouse model of glomerulonephritis. For the investigation of siRNA accumulation, Cy5-labeled siRNAs complexed with PIC nanocarriers (0.5 ml, 5 nmol of siRNA content), naked Cy5-labeled siRNAs (0.5 ml, 5 nmol), or Cy5-labeled siRNAs encapsulated in HVJ-E (0.5 ml, 5 nmol of siRNA content) were administrated to BALBc mice. The method of Shimizu et al. may be applied to the nucleic acid-targeting system of the present invention contemplating a dose of about of 10-20 mol CRISPR Cas complexed with nanocarriers in about 1-2 liters to a human for intraperitoneal administration and delivery to the kidneys.

Treating Epithelial and Lung Diseases

The present invention also contemplates delivering the CRISPR-Cas system described herein, e.g. Cas9 systems, to one or both lungs.

Although AAV-2-based vectors were originally proposed for CFTR delivery to CF airways, other serotypes such as AAV-1, AAV-5, AAV-6, and AAV-9 exhibit improved gene transfer efficiency in a variety of models of the lung epithelium (see, e.g., Li et al., *Molecular Therapy*, vol. 17 no. 12, 2067-277 Dec. 2009). AAV-1 was demonstrated to be ~100-fold more efficient than AAV-2 and AAV-5 at transducing human airway epithelial cells in vitro,5 although AAV-1 transduced murine tracheal airway epithelia in vivo with an efficiency equal to that of AAV-5. Other studies have shown that AAV-5 is 50-fold more efficient than AAV-2 at gene delivery to human airway epithelium (HAE) in vitro and significantly more efficient in the mouse lung airway epithelium in vivo. AAV-6 has also been shown to be more efficient than AAV-2 in human airway epithelial cells in vitro and murine airways in vivo.8 The more recent isolate, AAV-9, was shown to display greater gene transfer efficiency than AAV-5 in murine nasal and alveolar epithelia in vivo with gene expression detected for over 9 months suggesting AAV may enable long-term gene expression in vivo, a desirable property for a CFTR gene delivery vector. Furthermore, it was demonstrated that AAV-9 could be readministered to the murine lung with no loss of CFTR expression and minimal immune consequences. CF and non-CF HAE cultures may be inoculated on the apical surface with 100 1 μl of AAV vectors for hours (see, e.g., Li et al., *Molecular Therapy*, vol. 17 no. 12, 2067-277 Dec. 2009). The MOI may vary from $1\times10^3$ to $4\times10^5$ vector genomes/cell, depending on virus concentration and purposes of the experiments. The above cited vectors are contemplated for the delivery and/or administration of the invention.

Zamora et al. (*Am J Respir Crit Care Med* Vol 183. pp 531-538, 2011) reported an example of the application of an RNA interference therapeutic to the treatment of human infectious disease and also a randomized trial of an antiviral drug in respiratory syncytial virus (RSV)-infected lung transplant recipients. Zamora et al. performed a randomized, double-blind, placebo controlled trial in LTX recipients with RSV respiratory tract infection. Patients were permitted to receive standard of care for RSV. Aerosolized ALN-RSVO1 (0.6 mg/kg) or placebo was administered daily for 3 days. This study demonstrates that an RNAi therapeutic targeting RSV can be safely administered to LTX recipients with RSV infection. Three daily doses of ALN-RSVO1 did not result in any exacerbation of respiratory tract symptoms or impairment of lung function and did not exhibit any systemic proinflammatory effects, such as induction of cytokines or CRP. Pharmacokinetics showed only low, transient systemic exposure after inhalation, consistent with preclinical animal data showing that ALN-RSVO1, administered intravenously or by inhalation, is rapidly cleared from the circulation through exonuclease mediated digestion and renal excretion. The method of Zamora et al. may be applied to the nucleic acid-targeting system of the present invention and an aerosolized CRISPR Cas, for example with a dosage of 0.6 mg/kg, may be contemplated for the present invention.

Schwank et al. (*Cell Stem Cell,* 13:653-58, 2013) used CRISPR-Cas9 to correct a defect associated with cystic fibrosis in human stem cells. The team's target was the gene for an ion channel, cystic fibrosis transmembrane conductor receptor (CFTR). A deletion in CFTR causes the protein to misfold in cystic fibrosis patients. Using cultured intestinal stem cells developed from cell samples from two children with cystic fibrosis, Schwank et al. were able to correct the defect using CRISPR along with a donor plasmid containing the reparative sequence to be inserted. The researchers then grew the cells into intestinal "organoids," or miniature guts, and showed that they functioned normally. In this case, about half of clonal organoids underwent the proper genetic correction.

Treating Diseases of the Muscular System

The present invention also contemplates delivering the CRISPR-Cas system described herein, e.g. Cas9 systems, to muscle(s).

Bortolanza et al. (*Molecular Therapy* vol. 19 no. 11, 2055-264 Nov. 2011) shows that systemic delivery of RNA interference expression cassettes in the FRG1 mouse, after the onset of facioscapulohumeral muscular dystrophy (FSHD), led to a dose-dependent long-term FRG1 knockdown without signs of toxicity. Bortolanza et al. found that a single intravenous injection of $5\times10^{12}$ vg of rAAV6-sh1FRG1 rescues muscle histopathology and muscle function of FRG1 mice. In detail, 200 μl containing $2\times10^{12}$ or $5\times10^{12}$ vg of vector in physiological solution were injected into the tail vein using a 25-gauge Terumo syringe. The method of Bortolanza et al. may be applied to an AAV expressing CRISPR Cas and injected into humans at a dosage of about $2\times10^{15}$ or $2\times10^{16}$ vg of vector.

Dumonceaux et al. (*Molecular Therapy* vol. 18 no. 5, 881-887 May 2010) inhibit the myostatin pathway using the technique of RNA interference directed against the myostatin receptor AcvRIIb mRNA (sh-AcvRIIb). The restoration of a quasi-dystrophin was mediated by the vectorized U7 exon-skipping technique (U7-DYS). Adeno-associated vectors carrying either the sh-AcvrIIb construct alone, the U7-DYS construct alone, or a combination of both constructs were injected in the tibialis anterior (TA) muscle of dystrophic mdx mice. The injections were performed with 10" AAV viral genomes. The method of Dumonceaux et al. may be applied to an AAV expressing CRISPR Cas and injected into humans, for example, at a dosage of about $10^{14}$ to about $10^{15}$ vg of vector.

Kinouchi et al. (*Gene Therapy* (2008) 15, 1126-1130) report the effectiveness of in vivo siRNA delivery into skeletal muscles of normal or diseased mice through nanoparticle formation of chemically unmodified siRNAs with atelocollagen (ATCOL). ATCOL-mediated local application of siRNA targeting myostatin, a negative regulator of skeletal muscle growth, in mouse skeletal muscles or intravenously, caused a marked increase in the muscle mass within a few weeks after application. These results imply that ATCOL-mediated application of siRNAs is a powerful tool for future therapeutic use for diseases including muscular atrophy. MstsiRNAs (final concentration, 10 mM) were mixed with ATCOL (final concentration for local administration, 0.5%) (AteloGene, Kohken, Tokyo, Japan) according to the manufacturer's instructions. After anesthesia of mice (20-week-old male C57BL/6) by Nembutal (25 mg/kg, i.p.), the Mst-siRNA/ATCOL complex was injected into the masseter and biceps femoris muscles. The method of Kinouchi et al. may be applied to CRISPR Cas and injected into a human, for example, at a dosage of about 500 to 1000 ml of a 40 M solution into the muscle. Hagstrom et al. (*Molecular Therapy* Vol. 10, No. 2, August 2004) describe an intravascular, nonviral methodology that enables efficient and repeatable delivery of nucleic acids to muscle cells (myofibers) throughout the limb muscles of mammals. The procedure involves the injection of naked plasmid DNA or siRNA into a distal vein of a limb that is transiently isolated by a tourniquet or blood pressure cuff. Nucleic acid delivery to myofibers is facilitated by its rapid injection in sufficient volume to enable extravasation of the nucleic acid solution into muscle tissue. High levels of transgene expression in skeletal muscle were achieved in both small and large animals with minimal toxicity. Evidence of siRNA delivery to limb muscle was also obtained. For plasmid DNA intravenous injection into a rhesus monkey, a three way stopcock was connected to two syringe pumps (Model PHD 2000; Harvard Instruments), each loaded with a single syringe. Five minutes after a papaverine injection, pDNA (15.5 to 25.7 mg in 40-100 ml saline) was injected at a rate of 1.7 or 2.0 ml/s. This could be scaled up for plasmid DNA expressing CRISPR Cas of the present invention with an injection of about 300 to 500 mg in 800 to 2000 ml saline for a human. For adenoviral vector injections into a rat, $2\times10^{9}$ infectious particles were injected in 3 ml of normal saline solution (NSS). This could be scaled up for an adenoviral vector expressing CRISPR Cas of the present invention with an injection of about $1\times10^{13}$ infectious particles were injected in 10 liters of NSS for a human. For siRNA, a rat was injected into the great saphenous vein with 12.5 μg of a siRNA and a primate was injected into the great saphenous vein with 750 μg of a siRNA. This could be scaled up for a CRISPR Cas of the present invention, for example, with an injection of about 15 to about 50 mg into the great saphenous vein of a human.

See also, for example, WO2013163628 A2, Genetic Correction of Mutated Genes, published application of Duke University describes efforts to correct, for example, a frameshift mutation which causes a premature stop codon and a truncated gene product that can be corrected via nuclease mediated non-homologous end joining such as those responsible for Duchenne Muscular Dystrophy, ("DMD") a recessive, fatal, X-linked disorder that results in muscle degeneration due to mutations in the dystrophin gene. The majority of dystrophin mutations that cause DMD are deletions of exons that disrupt the reading frame and cause premature translation termination in the dystrophin gene. Dystrophin is a cytoplasmic protein that provides structural stability to the dystroglycan complex of the cell membrane that is responsible for regulating muscle cell integrity and function. The dystrophin gene or "DMD gene" as used interchangeably herein is 2.2 megabases at locus Xp21. The primary transcription measures about 2,400 kb with the mature mRNA being about 14 kb. 79 exons code for the protein which is over 3500 amino acids. Exon 51 is frequently adjacent to frame-disrupting deletions in DMD patients and has been targeted in clinical trials for oligonucleotide-based exon skipping. A clinical trial for the exon 51 skipping compound eteplirsen recently reported a significant functional benefit across 48 weeks, with an average of 47% dystrophin positive fibers compared to baseline. Mutations in exon 51 are ideally suited for permanent correction by NHEJ-based genome editing.

The methods of US Patent Publication No. 20130145487 assigned to Cellectis, which relates to meganuclease variants to cleave a target sequence from the human dystrophin gene (DMD), may also be modified to for the nucleic acid-targeting system of the present invention.

Treating Diseases of the Skin

The present invention also contemplates delivering the CRISPR-Cas system described herein, e.g. Cas9 effector protein systems, to the skin.

Hickerson et al. (*Molecular Therapy-Nucleic Acids* (2013) 2, e129) relates to a motorized microneedle array skin delivery device for delivering self-delivery (sd)-siRNA to human and murine skin. The primary challenge to translating siRNA-based skin therapeutics to the clinic is the development of effective delivery systems. Substantial effort has been invested in a variety of skin delivery technologies with limited success. In a clinical study in which skin was treated with siRNA, the exquisite pain associated with the hypodermic needle injection precluded enrollment of additional patients in the trial, highlighting the need for improved, more "patient-friendly" (i.e., little or no pain) delivery approaches. Microneedles represent an efficient way to deliver large charged cargos including siRNAs across the primary barrier, the stratum corneum, and are generally regarded as less painful than conventional hypodermic needles. Motorized "stamp type" microneedle devices, including the motorized microneedle array (MMNA) device used by Hickerson et al., have been shown to be safe in hairless mice studies and cause little or no pain as evidenced by (i) widespread use in the cosmetic industry and (ii) limited testing in which nearly all volunteers found use of the device to be much less painful than a flu shot, suggesting siRNA delivery using this device will result in much less pain than was experienced in the previous clinical trial using hypodermic needle injections. The MMNA device (marketed as Triple-M or Tri-M by Bomtech Electronic Co, Seoul, South Korea) was adapted for delivery of siRNA to mouse and human skin. sd-siRNA solution (up to 300 μl of 0.1 mg/ml RNA) was introduced into the chamber of the disposable Tri-M needle cartridge (Bomtech), which was set to a depth of 0.1 mm. For treating human skin, deidentified skin (obtained immediately following surgical procedures) was manually stretched and pinned to a cork platform before treatment. All intradermal injections were performed using an insulin syringe with a 28-gauge 0.5-inch needle. The MMNA device and method of Hickerson et al. could be used and/or adapted to deliver the CRISPR Cas of the present invention, for example, at a dosage of up to 300 μl of 0.1 mg/ml CRISPR Cas to the skin.

Leachman et al. (*Molecular Therapy*, vol. 18 no. 2, 442-446 Feb. 2010) relates to a phase Ib clinical trial for treatment of a rare skin disorder pachyonychia congenita (PC), an autosomal dominant syndrome that includes a disabling plantar keratoderma, utilizing the first short-interfering RNA (siRNA)-based therapeutic for skin. This siRNA, called TD101, specifically and potently targets the keratin 6a (K6a) N171K mutant mRNA without affecting wild-type K6a mRNA.

Zheng et al. (*PNAS*, Jul. 24, 2012, vol. 109, no. 30, 11975-11980) show that spherical nucleic acid nanoparticle conjugates (SNA-NCs), gold cores surrounded by a dense shell of highly oriented, covalently immobilized siRNA, freely penetrate almost 100% of keratinocytes in vitro, mouse skin, and human epidermis within hours after application. Zheng et al. demonstrated that a single application of 25 nM epidermal growth factor receptor (EGFR) SNA-NCs for 60 h demonstrate effective gene knockdown in human skin. A similar dosage may be contemplated for CRISPR Cas immobilized in SNA-NCs for administration to the skin.

General Gene Therapy Considerations

Examples of disease-associated genes and polynucleotides and disease specific information is available from McKusick-Nathans Institute of Genetic Medicine, Johns Hopkins University (Baltimore, Md.) and National Center for Biotechnology Information, National Library of Medicine (Bethesda, Md.), available on the World Wide Web.

Mutations in these genes and pathways can result in production of improper proteins or proteins in improper amounts which affect function. Further examples of genes, diseases and proteins are hereby incorporated by reference from U.S. Provisional application 61/736,527 filed Dec. 12, 2012. Such genes, proteins and pathways may be the target polynucleotide of a CRISPR complex of the present invention.

Embodiments of the invention also relate to methods and compositions related to knocking out genes, amplifying genes and repairing particular mutations associated with DNA repeat instability and neurological disorders (Robert D. Wells, Tetsuo Ashizawa, Genetic Instabilities and Neurological Diseases, Second Edition, Academic Press, Oct. 13, 2011-Medical). Specific aspects of tandem repeat sequences have been found to be responsible for more than twenty human diseases (New insights into repeat instability: role of RNADNA hybrids. McIvor E I, Polak U, Napierala M. RNA Biol. 2010 Sep-Oct;7(5):551-8). The present effector protein systems may be harnessed to correct these defects of genomic instability.

Several further aspects of the invention relate to correcting defects associated with a wide range of genetic diseases which are further described on the website of the National Institutes of Health under the topic subsection Genetic Disorders (website at health.nih.gov/topic/GeneticDisorders). The genetic brain diseases may include but are not limited to Adrenoleukodystrophy, Agenesis of the Corpus Callosum, Aicardi Syndrome, Alpers' Disease, Alzheimer's Disease, Barth Syndrome, Batten Disease, CADASIL, Cerebellar Degeneration, Fabry's Disease, Gerstmann-Straussler-Scheinker Disease, Huntington's Disease and other Triplet Repeat Disorders, Leigh's Disease, Lesch-Nyhan Syndrome, Menkes Disease, Mitochondrial Myopathies and NINDS Colpocephaly. These diseases are further described on the website of the National Institutes of Health under the subsection Genetic Brain Disorders.

Selected Other Conditions

Herpes Simplex Virus 1 and 2

In some embodiments, the treatment, prophylaxis or diagnosis of HSV-1 (Herpes Simplex Virus 1) is provided. The target is preferably the UL19, UL30, UL48 or UL50 gene in HSV-1. This is described in WO2015153789, the disclosure of which is hereby incorporated by reference.

In other embodiments, the treatment, prophylaxis or diagnosis of HSV-2 (Herpes Simplex Virus 2) is provided. The target is preferably the UL19, UL30, UL48 or UL50 gene in HSV-2. This is described in WO2015153791, the disclosure of which is hereby incorporated by reference.

As the invention in certain embodiments involves DD-CRISPR enzymes, DD-Cas, DD-Cas9, DD-CRISPR-Cas or CRISPR-Cas systems or complexes, the terms "CRISPR", "Cas", "Cas9", "CRISPR system", "CRISPR complex", "CRISPR-Cas", "CRISPR-Cas9" or the like, without the prefix "DD" may be considered as having the prefix DD, especially when the context permits so that the disclosure is reading on DD embodiments. Thus, in one aspect, the invention provides methods for using one or more elements of a CRISPR system (which can be read as DD-CRISPR system and/or CRISPR system"). The CRISPR complex of the invention provides an effective means for modifying a target polynucleotide. The CRISPR complex of the invention has a wide variety of utility including modifying (e.g., deleting, inserting, translocating, inactivating, activating) a target polynucleotide in a multiplicity of cell types. As such the CRISPR complex of the invention has a broad spectrum of applications in, e.g., gene therapy, drug screening, disease diagnosis, and prognosis.

CRISPR/Cas systems general

With respect to general information on CRISPR-Cas Systems, With respect to general information on CRISPR-Cas Systems, components thereof, and delivery of such components, including methods, materials, delivery vehicles, vectors, particles, AAV, and making and using thereof, including as to amounts and formulations, all useful in the practice of the instant invention, reference is made to: U.S. Pat. Nos. 8,697,359, 8,771,945, 8,795,965, 8,865,406, 8,871,445, 8,889,356, 8,889,418, 8,895,308, 8,906,616, 8,932,814, 8,945,839, 8,993,233 and 8,999,641; US Patent Publications US 2014-0310830 (U.S. application Ser. No. 14/105,031), US 2014-0287938 A1 (U.S. application Ser. No. 14/213,991), US 2014-0273234 A1 (U.S. application Ser. No. 14/293,674), US 2014-0273232 A1 (U.S. application Ser. No. 14/290,575), US 2014-0273231 (U.S. application Ser. No. 14/259,420), US 2014-0256046 A1 (U.S. application Ser. No. 14/226,274), US 2014-0248702 A1 (U.S. application Ser. No. 14/258,458), US 2014-0242700 A1 (U.S. application Ser. No. 14/222,930), US 2014-0242699 A1 (U.S. application Ser. No. 14/183,512), US 2014-0242664 A1 (U.S. application Ser. No. 14/104,990), US 2014-0234972 A1 (U.S. application Ser. No. 14/183,471), US 2014-0227787 A1 (U.S. application Ser. No. 14/256,912), US 2014-0189896 A1 (U.S. application Ser. No. 14/105,035), US 2014-0186958 (U.S. application Ser. No. 14/105,017), US 2014-0186919 A1 (U.S. application Ser. No. 14/104,977), US 2014-0186843 A1 (U.S. application Ser. No. 14/104,900), US 2014-0179770 A1 (U.S. application Ser. No. 14/104,837) and US 2014-0179006 A1 (U.S. application Ser. No. 14/183,486), US 2014-0170753 (U.S. application Ser. No. 14/183,429); US 2015-0184139 (U.S. application Ser. No. 14/324,960); U.S. Ser. No. 14/054,414 European Patent Applications EP 2 771 468 (EP13818570.7), EP 2 764 103 (EP13824232.6), and EP 2 784 162 (EP14170383.5); and PCT Patent Publications WO 2014/093661 (PCT/US2013/074743), WO 2014/093694 (PCT/US2013/074790), WO 2014/093595 (PCT/US2013/074611), WO 2014/093718 (PCT/US2013/074825), WO 2014/093709 (PCT/US2013/074812), WO 2014/093622 (PCT/US2013/074667), WO 2014/093635 (PCT/US2013/074691), WO 2014/093655 (PCT/US2013/074736), WO 2014/093712 (PCT/US2013/074819), WO 2014/093701 (PCT/US2013/074800), WO 2014/018423 (PCT/US2013/051418), WO 2014/204723 (PCT/US2014/041790), WO 2014/204724 (PCT/US2014/041800), WO 2014/204725 (PCT/US2014/041803), WO 2014/204726 (PCT/US2014/041804), WO 2014/204727 (PCT/US2014/041806), WO 2014/204728 (PCT/US2014/041808), WO 2014/204729 (PCT/US2014/041809), WO 2015/089351 (PCT/US2014/069897), WO 2015/089354 (PCT/US2014/069902), WO 2015/089364 (PCT/US2014/069925), WO 2015/089427 (PCT/US2014/070068), WO 2015/089462 (PCT/US2014/070127), WO 2015/089419 (PCT/US2014/070057), WO 2015/089465 (PCT/US2014/070135), WO 2015/089486 (PCT/US2014/070175), PCT/US2015/051691, PCT/US2015/051830. Reference is also made to U.S. provisional patent applications 61/758,468; 61/802,174; 61/806,375; 61/814,263; 61/819,803 and 61/828,130, filed on Jan. 30, 2013; Mar. 15, 2013; Mar. 28, 2013; Apr. 20, 2013; May 6, 2013 and May 28, 2013 respectively. Reference is also made to U.S. provisional patent application 61/836,123, filed on Jun. 17, 2013. Reference is additionally made to U.S. provisional patent applications 61/835,931, 61/835,936, 61/835,973, 61/836,080, 61/836,101, and 61/836,127, each filed Jun. 17, 2013. Further reference is made to U.S. provisional patent applications 61/862,468 and 61/862,355 filed on Aug. 5, 2013; 61/871,301 filed on Aug. 28, 2013; 61/960,777 filed on Sep. 25, 2013 and 61/961,980 filed on Oct. 28, 2013. Reference is yet further made to: PCT/US2014/62558 filed Oct. 28, 2014, and U.S. Provisional Patent Applications Ser. Nos. 61/915,148, 61/915,150, 61/915,153, 61/915,203, 61/915,251, 61/915,301, 61/915,267, 61/915,260, and 61/915,397, each filed Dec. 12, 2013; 61/757,972 and 61/768,959, filed on Jan. 29, 2013 and Feb. 25, 2013; 62/010,888 and 62/010,879, both filed Jun. 11, 2014; 62/010,329, 62/010,439 and 62/010,441, each filed Jun. 10, 2014; 61/939,228 and 61/939,242, each filed Feb. 12, 2014; 61/980,012, filed April 15,2014; 62/038,358, filed Aug. 17, 2014; 62/055,484, 62/055,460 and 62/055,487, each filed Sep. 25, 2014; and 62/069,243, filed Oct. 27, 2014. Reference is made to PCT application designating, inter alia, the United States, application No. PCT/US14/41806, filed Jun. 10, 2014. Reference is made to U.S. provisional patent application 61/930,214 filed on Jan. 22, 2014. Reference is made to PCT application designating, inter alia, the United States, application No. PCT/US14/41806, filed Jun. 10, 2014.

Mention is also made of U.S. application 62/180,709, 17-Jun-15, PROTECTED GUIDE RNAS (PGRNAS); U.S. application 62/091,455, filed, 12-Dec-14, PROTECTED GUIDE RNAS (PGRNAS); U.S. application 62/096,708, 24-Dec-14, PROTECTED GUIDE RNAS (PGRNAS); U.S. applications 62/091,462, 12-Dec-14, 62/096,324, 23-Dec-14, 62/180,681, 17 Jun. 2015, and 62/237,496, 5 Oct. 2015, DEAD GUIDES FOR CRISPR TRANSCRIPTION FACTORS; U.S. application 62/091,456, 12-Dec-14 and 62/180,692, 17 Jun. 2015, ESCORTED AND FUNCTIONALIZED GUIDES FOR CRISPR-CAS SYSTEMS; U.S. application 62/091,461, 12-Dec-14, DELIVERY, USE AND THERAPEUTIC APPLICATIONS OF THE CRISPR-CAS SYSTEMS AND COMPOSITIONS FOR GENOME EDITING AS TO HEMATOPOIETIC STEM CELLS (HSCs); U.S. application 62/094,903, 19-Dec-14, UNBIASED IDENTIFICATION OF DOUBLE-STRAND BREAKS AND GENOMIC REARRANGEMENT BY GENOME-WISE INSERT CAPTURE SEQUENCING; U.S. application 62/096,761, 24-Dec-14, ENGINEERING OF SYSTEMS, METHODS AND OPTIMIZED ENZYME AND GUIDE SCAFFOLDS FOR SEQUENCE MANIPULATION; U.S. application 62/098,059, 30-Dec-14, 62/181,641, 18 Jun. 2015, and 62/181,667, 18 Jun. 2015, RNA-TARGETING SYSTEM; U.S. application 62/096,656, 24-Dec-14 and 62/181,151, 17 Jun. 2015, CRISPR HAVING OR ASSOCIATED WITH DESTABILIZATION DOMAINS; U.S. application 62/096,697, 24-Dec-14, CRISPR HAVING OR ASSOCIATED WITH AAV; U.S. application 62/098,158, 30-Dec-14, ENGINEERED CRISPR COMPLEX INSERTIONAL TARGETING SYSTEMS; U.S. application 62/151,052, 22-Apr-15, CELLULAR TARGETING FOR EXTRACELLULAR EXOSOMAL REPORTING; U.S. application 62/054,490, 24-Sep-14, DELIVERY, USE AND THERAPEUTIC APPLICATIONS OF THE CRISPR-CAS SYSTEMS AND COMPOSITIONS FOR TARGETING DISORDERS AND DISEASES USING PARTICLE DELIVERY COMPONENTS; U.S. application 61/939,154, 12-FEB-14, SYSTEMS, METHODS AND COMPOSITIONS FOR SEQUENCE MANIPULATION WITH OPTIMIZED FUNCTIONAL CRISPR-CAS SYSTEMS; U.S. application 62/055,484, 25-Sep-14, SYSTEMS, METHODS AND COMPOSITIONS FOR SEQUENCE MANIPULATION WITH OPTIMIZED FUNCTIONAL CRISPR-CAS SYSTEMS; U.S. application 62/087,537, 4-Dec-14, SYSTEMS, METHODS AND COMPOSITIONS FOR SEQUENCE MANIPULATION WITH OPTIMIZED FUNCTIONAL CRISPR-CAS SYSTEMS; U.S. application 62/054,651, 24-Sep-14, DELIVERY, USE AND THERAPEUTIC APPLICATIONS OF THE CRISPR-CAS SYSTEMS AND COMPOSITIONS FOR MODELING COMPETITION OF MULTIPLE CANCER MUTATIONS IN VIVO; U.S. application 62/067,886, 23-Oct-14, DELIVERY, USE AND THERAPEUTIC APPLICATIONS OF THE CRISPR-CAS SYSTEMS AND COMPOSITIONS FOR MODELING COMPETITION OF MULTIPLE CANCER MUTATIONS IN VIVO; U.S. applications 62/054,675, 24-Sep-14 and 62/181,002, 17 Jun. 2015, DELIVERY, USE AND THERAPEUTIC APPLICATIONS OF THE CRISPR-CAS SYSTEMS AND COMPOSITIONS IN NEURONAL CELLS/TISSUES; U.S. application 62/054,528, 24-Sep-14, DELIVERY, USE AND THERAPEUTIC APPLICATIONS OF THE CRISPR-CAS SYSTEMS AND COMPOSITIONS IN IMMUNE DISEASES OR DISORDERS; U.S. application 62/055,454, 25-Sep-14, DELIVERY, USE AND THERAPEUTIC APPLICATIONS OF THE CRISPR-CAS SYSTEMS AND COMPOSITIONS FOR TARGETING DISORDERS AND DISEASES USING CELL PENETRATION PEPTIDES (CPP); U.S. application 62/055,460, 25-Sep-14, MULTIFUNCTIONAL-CRISPR COMPLEXES AND/OR OPTIMIZED ENZYME LINKED FUNCTIONAL-CRISPR COMPLEXES; U.S. application 62/087,475, 4-Dec-14 and 62/181,690, 18 Jun. 2015, FUNCTIONAL SCREENING WITH OPTIMIZED FUNCTIONAL CRISPR-CAS SYSTEMS; U.S. application 62/055,487, 25-Sep-14, FUNCTIONAL SCREENING WITH OPTIMIZED FUNCTIONAL CRISPR-CAS SYSTEMS; U.S. application 62/087,546, 4-Dec-14 and 62/181,687, 18 Jun. 2015, MULTIFUNCTIONAL CRISPR COMPLEXES AND/OR OPTIMIZED ENZYME LINKED FUNCTIONAL-CRISPR COMPLEXES; and U.S. application 62/098,285, 30-Dec-14, CRISPR MEDIATED IN VIVO MODELING AND GENETIC SCREENING OF TUMOR GROWTH AND METASTASIS.

Mention is made of U.S. applications 62/181,659, 18 Jun. 2015 and 62/207,318, 19-Aug-2015, ENGINEERING AND OPTIMIZATION OF SYSTEMS, METHODS, ENZYME AND GUIDE SCAFFOLDS OF CAS9 ORTHOLOGS AND VARIANTS FOR SEQUENCE MANIPULATION. Mention is made of U.S. applications 62/181,663, 18 Jun. 2015 and 62/245,264, 22 Oct. 2015, NOVEL CRISPR ENZYMES AND SYSTEMS, U.S. applications 62/181,675, 18 Jun. 2015, filed 22 Oct. 2015, NOVEL CRISPR ENZYMES AND SYSTEMS, U.S. application 62/232,067, 24 Sep. 2015, U.S. application 62/205,733, 16 Aug. 2015, U.S. application 62/201,542, 5 Aug. 2015, U.S. application 62/193,507, 16 Jul. 2015, and U.S. application 62/181,739, 18 Jun. 2015, each entitled NOVEL CRISPR ENZYMES AND SYSTEMS and of U.S. application 62/245,270, 22 Oct. 2015, NOVEL CRISPR ENZYMES AND SYSTEMS. Mention is also made of U.S. application 61/939,256, 12 Feb. 2014, and WO 2015/089473 (PCT/US2014/070152), 12 Dec. 2014, each entitled ENGINEERING OF SYSTEMS, METHODS AND OPTIMIZED GUIDE COMPOSITIONS WITH NEW ARCHITECTURES FOR SEQUENCE MANIPULATION. Mention is also made of PCT/US2015/045504, 15 Aug. 2015, U.S. application 62/180,699, 17 Jun. 2015, and U.S. application 62/038,358, 17 Aug. 2014, each entitled GENOME EDITING USING CAS9 NICKASES.

With respect to destabilizing domains, mention is made of U.S. application 62/096,656 filed 24 Dec. 2014, U.S. application 62/181,151 filed 17 Jun. 2015, and International application PCT/US2015/067177, filed 21 Dec. 2015, each entitled CRISPR HAVING OR ASSOCIATED WITH DESTABILIZATION DOMAINS.

Also with respect to general information on CRISPR-Cas Systems, mention is made of the following (also hereby incorporated herein by reference): Cong, L., Ran, F. A., Cox, D., Lin, S., Barretto, R., Habib, N., Hsu, P.D., Wu, X., Jiang, W., Marraffini, L. A., & Zhang, F. Science Feb 15;339 (6121):819-23 (2013); RNA-guided editing of bacterial genomes using CRISPR-Cas systems. Jiang W., Bikard D., Cox D., Zhang F, Marraffini L A. *Nat Biotechnol* Mar;31 (3):233-9 (2013); One-Step Generation of Mice Carrying Mutations in Multiple Genes by CRISPR/Cas-Mediated Genome Engineering. Wang H., Yang H., Shivalila C S., Dawlaty M M., *Cheng A W., Zhang F., Jaenisch R. Cell* May 9;153(4):910-8 (2013); Optical control of mammalian endogenous transcription and epigenetic states. Konermann S, Brigham M D, Trevino A E, Hsu P D, Heidenreich M, Cong L, Platt R J, Scott D A, Church G M, Zhang F. *Nature.* 2013 Aug. 22; 500(7463):472-6. doi: 10.1038/Nature12466. Epub 2013 Aug 23; Double Nicking by RNA-Guided CRISPR Cas9 for Enhanced Genome Editing Specificity. Ran, F A., Hsu, P D., Lin, C Y., Gootenberg, J S., Konermann, S., Trevino, A E., Scott, D A., Inoue, A., Matoba, S., Zhang, Y., & Zhang, F. Cell Aug 28. pii: S0092-8674(13) 01015-5. (2013); DNA targeting specificity of RNA-guided Cas9 nucleases. Hsu, P., Scott, D., Weinstein, J., Ran, F A., Konermann, S., Agarwala, V., Li, Y., Fine, E., Wu, X., Shalem, O., Cradick, T J., Marraffini, L A., Bao, G., & Zhang, F. *Nat Biotechnol* doi:10.1038/nbt.2647 (2013); Genome engineering using the CRISPR-Cas9 system. Ran, F A., Hsu, P D., Wright, J., Agarwala, V., Scott, D A., Zhang, F. Nature Protocols Nov;8(11):2281-308. (2013); Genome-Scale CRISPR-Cas9 Knockout Screening in Human Cells. Shalem, O., Sanjana, N E., Hartenian, E., Shi, X., Scott, D A., Mikkelson, T., Heckl, D., Ebert, B L., *Root, D E., Doench, J G., Zhang, F. Science* Dec 12. (2013). [Epub ahead of print]; Crystal structure of cas9 in complex with guide RNA and target DNA. Nishimasu, H., Ran, F A., Hsu, P D., Konermann, S., Shehata, S I., Dohmae, N., Ishitani, R., Zhang, F., Nureki, O. Cell Feb 27. (2014). 156(5):935-49; Genome-wide binding of the CRISPR endonuclease Cas9 in mammalian cells. Wu X., Scott D A., Kriz A J., Chiu A C., Hsu P D., Dadon D B., Cheng A W., Trevino A E., Konermann S., Chen S., Jaenisch R., Zhang F., Sharp P A. *Nat Biotechnol.* (2014) Apr 20. doi: 10.1038/nbt.2889; CRISPR-Cas9 Knockin Mice for Genome Editing and Cancer Modeling, Platt et al., *Cell* 159(2): 440-455 (2014) DOI: 10.1016/j.cell.2014.09.014; Development and Applications of CRISPR-Cas9 for Genome Engineering, Hsu et al, *Cell* 157, 1262-1278 (Jun. 5, 2014) (Hsu 2014); Genetic screens in human cells using the CRISPR/Cas9 system, Wang et al., *Science.* 2014 January 3; 343(6166): 80-84. doi:10.1126/science.1246981; Rational design of highly active gRNAs for CRISPR-Cas9-mediated gene inactivation, Doench et al., *Nature Biotechnology* 32(12):1262-7 (2014) published online 3 Sep. 2014; doi:10.1038/nbt.3026, and In vivo interrogation of gene function in the mammalian brain using CRISPR-Cas9, Swiech et al, *Nature Biotechnology* 33, 102-106 (2015) published online 19 Oct. 2014; doi:10.1038/nbt.3055, Cpf1 Is a Single RNA-Guided Endonuclease of a Class 2 CRISPR-Cas System, Zetsche et al., *Cell* 163, 1-13 (2015); Discovery and Functional Characterization of Diverse Class 2 CRISPR-Cas Systems, Shmakov et al., *Mol Cell* 60(3): 385-397 (2015); C2c2 is a single-component programmable RNA-guided RNA-targeting CRISPR effector, Abudayyeh et al, *Science* (2016) published online Jun. 2, 2016 doi: 10.1 126/science.aaf5573; Maji et al., *Nat. Chem. Biol.* (2017) published online 13 Oct. 2016; doi.

Each of these publications, patents, patent publications, and applications, and all documents cited therein or during their prosecution ("appln cited documents") and all documents cited or referenced in the appln cited documents, together with any instructions, descriptions, product specifications, and product sheets for any products mentioned therein or in any document therein and incorporated by reference herein, are hereby incorporated herein by reference, and may be employed in the practice of the invention. All documents (e.g., these patents, patent publications and applications and the appln cited documents) are incorporated herein by reference to the same extent as if each individual document was specifically and individually indicated to be incorporated by reference.

The present invention will be further illustrated in the following Examples which are given for illustration purposes only and are not intended to limit the invention in any way.

EXAMPLES

Example 1: Materials and Methods

Reagents and plasmids. Trimethoprim was purchased from Alfa Aesar (J63053). (Z)-4-Hydroxytamoxifen was purchased from Sigma Aldrich (H7904). Lipofectamine 2000 (Life Technologies) was used as a transfecting agent according to the manufacturer's protocol. Plasmid sequences for destabilized domain Cas9 and transcriptional effector constructs are included in the Supplementary Information.

Cell culture. All cells were cultured at 37° C. in a 5% CO2 atmosphere. HEK293T cells (Life Technologies) used in transcriptional activation experiments were cultured in Dulbecco's modified Eagle's medium (CellGro) supplemented with 10% fetal bovine serum (CellGro) and 1% penicillin/streptomycin/glutamine (CellGro). HEK293T cells used in surveyor assays and nuclease specificity experiments and U20S.eGFP-PEST cells stably integrated with an eGFP-PEST25 fusion gene were maintained in Dulbecco's modified Eagle's medium (Life Technologies) supplemented with 10% FBS, 1× penicillin/streptomycin/glutamax (Life Technologies) and 400 g/mL of the selection antibiotic G418 (for the U20S.eGFP-PEST cells).

Cells were Continuously Maintained at <90% Confluency.

Transcription activation experiments and quantitative RT-PCR analyses. Transient transfections of HEK293T cells (750,000 cells, 6-well format) were performed with an equivalent mass of each plasmid (dCas9, destabilized domain effector, and gRNA) for a total mass of 5 g of plasmid DNA. 24 h post-transfection, cells were treated with the appropriate dose of DD-stabilizing small molecule(s), as indicated, for 18 h prior to harvest and subsequent RNA extraction using the EZNA Total RNA Kit I (Omega). For reversibility experiments, cells were treated 24 h post-transfection with 100 nM TMP for 18 h, at which point cells were treated with fresh media either containing 100 nM TMP or lacking TMP. Post-media swap, cells were incubated for the indicated times in fresh media prior to harvest and subsequent RNA extraction using the EZNA Total RNA Kit I (Omega). qPCR reactions were performed on cDNA prepared from 1000 ng of total cellular RNA using the High-Capacity cDNA Reverse Transcription Kit (Applied Biosystems). TaqMan qPCR probes (Life Technologies, Table 1) or other primers (Table 2) and Fast Advanced Master Mix (Life Technologies) were used in 5 1 multiplexed reactions and 384-well format in a Light Cycler 480 II Real-Time PCR machine. All measurements were performed at least in triplicate. Data were analyzed using the LightCycler® 480 Software, Version 1.5 (Roche) by the ΔΔCt method: target gene Ct values (FAM dye) were normalized to GAPDH Ct values (VIC dye), and fold-changes in target gene expression were normalized to RFP-transfected experimental controls. Analyzed data are reported as the mean±95% confidence interval.

TABLE 1

TaqMan ® probes used for qPCR assays.

| Gene | ID |
|---|---|
| ASCL1 | Hs00269932_m1 |
| IL1RN | Hs00893626_m1 |

TABLE 2

Primers used for SYBR Universal Master Mix qPCR assays.

| Gene | Forward Primer | Reverse Primer |
|---|---|---|
| RPLP2 (housekeeping) | CGTCGCCTCCTACCTGCT SEQ ID NO: 65 | CCATTCAGCTCACTGATAACCTTG SEQ ID NO: 67 |
| NANOG | GATTTGTGGGCCTGAAGAAA SEQ ID NO: 66 | CAGATCCATGGAGGAAGGAA SEQ ID NO: 68 |

Next-generation sequencing of Cas9-mediated genome modifications. HEK293T cells (130,000 cells, 24-well format) were transiently transfected with 400 ng of the indicated Cas9 plasmid and 100 ng of the EMX1 gRNA expression plasmid in the presence or absence of TMP or 40HT, as appropriate. peGFP-N1 transfec-tion was used as a control. Genomic DNA was extracted 72 h post-transfection using the QuickExtract™ DNA extraction kit (Epicentre) by incubating the cell suspension at 65° C. for 15 min, 68° C. for 15 min and 98° C. for 10 min. Next-generation sequencing samples were prepared via two-step PCR (see Table 3) following a reported protocol 18. In the first step, PCR was performed using primers that introduced a priming sequence for the second-step PCR that amplified the target gene of interest. The second-step PCR attached Illumina P5 adapters with barcodes, after which PCR products were isolated via gel purification. DNA concentrations were determined using the Qubit® dsDNA HS Assay Kit (Life Technologies) and processed for NGS analysis using the MiSeq Reagent Kit v2 300 (Illumina) according to the manufacturer's protocol.

TABLE 3

Primers used to generate amplicons for next-generation sequencing (off-target mismatches underlined).

| Gene | Name | Target (5'-Sequence-3') | PAM (5'-Sequence-3') | Forward Primers (5'-Sequence-3') | Reverse Primers (5'-Sequence-3') |
|---|---|---|---|---|---|
| EMX1 | EMX1(1) | GAGTCCGAGCAGAAGAAGAA (SEQ ID NO: 69) | GGG | CCATCTCATCCCTGCGTGTCTCcCAAAGTACAAACGGCAGAAGC (SEQ ID NO: 77) | CCATCTCATCCCTGCGTGTCTCcGTTGCCCACCCTAGTCATTG (SEQ ID NO: 85) |
| | OT1 | GAGTTAGAGCAGAAGAAGAA (SEQ ID NO: 70) | AGG | CCATCTCATCCCTGCGTGTCTCcTTCTGAGGGCTGCTACCTGT (SEQ ID NO: 78) | CCATCTCATCCCTGCGTGTCTCcGCCCAATCATTGATGCTTTT (SEQ ID NO: 86) |
| | OT2 | GAGTCTAAGCAGAAGAAGAA (SEQ ID NO: 71) | GAG | CCATCTCATCCCTGCGTGTCTCcCACGGCCTTTGCAAATAGAG (SEQ ID NO: 79) | CCATCTCATCCCTGCGTGTCTCcGGCTTTCACAAGGATGCAGT (SEQ ID NO: 87) |
| | OT3 | GAGTCCTAGCAGGAGAAGAA (SEQ ID NO: 72) | GAG | CCATCTCATCCCTGCGTGTCTCcCCAGACTCAGTAAAGCCTGGA (SEQ ID NO: 80) | CCATCTCATCCCTGCGTGTCTCcTGGCCCCAGTCTCTCTTCTA (SEQ ID NO: 88) |
| | OT4 | AAGTCTGAGCACAAGAAGAA (SEQ ID NO: 73) | TGG | CCATCTCATCCCTGCGTGTCTCcGTTCTGACATTCCTCCTGAGGGA (SEQ ID NO: 81) | CCATCTCATCCCTGCGTGTCTCcATGGCTTACATATTTATTAGATAAAATGTATTCC (SEQ ID NO: 89) |
| | OT5 | GAGGCCGAGCAGAAGAAAGA (SEQ ID NO: 74) | CGG | CCATCTCATCCCTGCGTGTCTCcTGGGAGAGAGACCCCTTCTT (SEQ ID NO: 82) | CCATCTCATCCCTGCGTGTCTCcTCCTGCTCTCACTTAGACTTTCTC (SEQ ID NO: 90) |
| VEGFA | VEGF A(1) | GGTGAGTGAGTGTGTGCGTG (SEQ ID NO: 75) | TGG | CCATCTCATCCCTGCGTGTCTCcGCGTCTTCGAGAGTGAGGAC (SEQ ID NO: 83) | CCATCTCATCCCTGCGTGTCTCcGGGGAGAGGGACACACAGAT (SEQ ID NO: 91) |
| | OT1 | GCTGAGTGAGTGTATGCGTG (SEQ ID NO: 76) | TGG | CCATCTCATCCCTGCGTGTCTCcGCCCATTTCTCCTTTGAGGT (SEQ ID NO: 84) | CCATCTCATCCCTGCGTGTCTCcAGCCACAGAGGTGGAGACTG (SEQ ID NO: 92) |

Analysis of Cas9 nuclease activity via disruption of genomic eGFP-PEST. Approximately 200,000 U2OS.eGFP-PEST cells were nucleofected in duplicate with 500 ng of Cas9 and gRNA expressing plasmids along with a Td-tomato-encoding plasmid using the SE Cell Line 4D-Nucleofector™ X Kit (Lonza) according to the manufacturer's protocol. Approximately 30,000 transfected cells/well in 6 replicates were plated in a 96-well plate (Corning® 3904 clear bottom 96-well plate). The indicated quantities of TMP or 40HT were added for 48 h followed by processing for imaging. Cells were fixed using 4% paraformaldehyde and imaged with the HCS NuclearMask™ Blue Stain (Life Technologies) as the nuclear counter-staining agent. Imaging was performed with an IXM 137204 ImageXpress Automated High Content Microscope (Molecular Devices) at 4× magnification under three excitation channels (blue, green and red) with 12 acquiring sites per well. Images were analyzed in the MetaXpress software and data were plotted using GraphPad Prism 6.

Plasmid Sequences

DHFR.Cas9:

(SEQ ID NO: 93)

atggccccaaagaagaagcggaaggtcggtatccacggagtcccagcag
ccggatccatcagtctgattgcggcgttagcggtagattacgttatcgg
catggaaaacgccatgccgtggaacctgcctgccgatctcgcctggttt
aaacgcaacaccttaaataaacccgtgattatgggccgccatacctggg
aatcaatcggtcgtccgttgccaggacgcaaaaatattatcctcagcag
tcaaccgagtacggacgatcgcgtaacgtgggtgaagtcggtggatgaa
gccatcgcggcgtgtggtgacgtaccagaaatcatggtgattggcggcg
gtcgcgttattgaacagttcttgccaaaagcgcaaaaactgtatctgac
gcatatcgacgcagaagtggaaggcgacacccatttcccggattacgag
ccggatgactgggaatcggtattcagcgaattccacgatgctgatgcgc
agaactctcacagctattgctttgagattctggagcggcgaggaagcgg
aagcggatccgacaagaagtacagcatcggcctggacatcggcaccaac -continued tctgtgggctgggccgtgatcaccgacgagtacaaggtgcccagcaaga aattcaaggtgctgggcaacaccgaccggcacagcatcaagaagaacct gatcggagccctgctgttcgacagcggcgaaacagccgaggccacccgg ctgaagagaaccgccagaagaagatacaccagacggaagaaccggatct gctatctgcaagagatcttcagcaacgagatggccaaggtggacgacag cttcttccacagactggaagagtccttcctggtggaagaggataagaag cacgagcggcaccccatcttcggcaacatcgtggacgaggtggcctacc acgagaagtaccccaccatctaccacctgagaaagaaactggtggacag caccgacaaggccgacctgcggctgatctatctggccctggcccacatg atcaagttccggggccacttcctgatcgagggcgacctgaaccccgaca acagcgacgtggacaagctgttcatccagctggtgcagacctacaacca gctgttcgaggaaaaccccatcaacgccagcggcgtggacgccaaggcc atcctgtctgccagactgagcaagagcagacggctggaaaatctgatcg cccagctgcccggcgagaagaagaatggcctgttcggaaacctgattgc cctgagcctgggcctgacccccaacttcaagagcaacttcgacctggcc gaggatgccaaactgcagctgagcaaggacacctacgacgacgacctgg acaacctgctggcccagatcggcgaccagtacgccgacctgtttctggc cgccaagaacctgtccgacgccatcctgctgagcgacatcctgagagtg aacaccgagatcaccaaggcccccctgagcgcctctatgatcaagagat acgacgagcaccaccaggacctgaccctgctgaaagctctcgtgcggca gcagctgcctgagaagtacaaagagattttcttcgaccagagcaagaac ggctacgccggctacattgacggcggagccagccaggaagagttctaca agttcatcaagcccatcctggaaaagatggacggcaccgaggaactgct cgtgaagctgaacagagaggacctgctgcggaagcagcggaccttcgac aacggcagcatccccccaccagatccacctgggagagctgcacgccattc tgcggcggcaggaagattttttacccattcctgaaggacaaccgggaaaa gatcgagaagatcctgaccttccgcatcccctactacgtgggccctctg gccaggggaaacagcagattcgcctggatgaccagaaagagcgaggaaa ccatcacccccctggaacttcgaggaagtggtggacaagggcgcttccgc ccagagcttcatcgagcggatgaccaacttcgataagaacctgcccaac gagaaggtgctgcccaagcacagcctgctgtacgagtacttcaccgtgt ataacgagctgaccaaagtgaaatacgtgaccgagggaatgagaaagcc cgccttcctgagcggcgagcagaaaaaggccatcgtggacctgctgttc aagaccaaccggaaagtgaccgtgaagcagctgaaagaggactacttca agaaaatcgagtgcttcgactccgtggaaatctccggcgtggaagatcg gttcaacgcctccctgggcacataccacgatctgctgaaaattatcaag gacaaggacttcctggacaatgaggaaaacgaggacattctggaagata tcgtgctgaccctgacactgtttgaggacagagagatgatcgaggaacg gctgaaaacctatgcccacctgttcgacgacaaagtgatgaagcagctg aagcggcggagatacaccggctggggcaggctgagccggaagctgatca -continued acggcatccgggacaagcagtccggcaagacaatcctggatttcctgaa gtccgacggcttcgccaacagaaacttcatgcagctgatccacgacgac agcctgacctttaaagaggacatccagaaagcccaggtgtccggccagg gcgatagcctgcacgagcacattgccaatctggccggcagccccgccat taagaagggcatcctgcagacagtgaaggtggtggacgagctcgtgaaa gtgatgggccggcacaagcccgagaacatcgtgatcgaaatggccagag agaaccagaccacccagaagggacagaagaacagccgcgagagaatgaa gcggatcgaagagggcatcaaagagctgggcagccagatcctgaaagaa caccccgtggaaaacacccagctgcagaacgagaagctgtacctgtact acctgcagaatgggggatatgtacgtggaccaggaactggacatcaac cggctgtccgactacgatgtggaccatatcgtgcctcagagctttctga aggacgactccatcgacaacaaggtgctgaccagaagcgacaagaaccg gggcaagagcgacaacgtgccctccgaagaggtcgtgaagaagatgaag aactactggcggcagctgctgaacgccaagctgattacccagagaaagt tcgacaatctgaccaaggccgagagaggcggcctgagcgaactggataa ggccggcttcatcaagagacagctggtggaaacccggcagatcacaaag cacgtggcacagatcctggactcccggatgaacactaagtacgacgaga atgacaagctgatccgggaagtgaaagtgatcaccctgaagtccaagct ggtgtccgatttccggaaggatttccagttttacaaagtgcgcgagatc aacaactaccaccacgcccacgacgcctacctgaacgccgtcgtgggaa ccgccctgatcaaaaagtaccctaagctggaaagcgagttcgtgtacgg cgactacaaggtgtacgacgtgcggaagatgatcgccaagagcgagcag gaaatcggcaaggctaccgccaagtacttcttctacagcaacatcatga actttttcaagaccgagattaccctggccaacggcgagatccggaagcg gcctctgatcgagacaaacggcgaaaccggggagatcgtgtgggataag ggccgggattttgccaccgtgcggaaagtgctgagcatgccccaagtga atatcgtgaaaaagaccgaggtgcagacaggcggcttcagcaaagagtc tatcctgcccaagaggaacagcgataagctgatcgccagaaagaaggac tgggaccctaagaagtacggcggcttcgacagccccaccgtggcctatt ctgtgctggtggtggccaaagtggaaaagggcaagtccaagaaactgaa gagtgtgaaagagctgctggggatcaccatcatggaaagaagcagcttc gagaagaatcccatcgactttctggaagccaagggctacaaagaagtga aaaaggacctgatcatcaagctgcctaagtactccctgttcgagctgga aaacggccggaagagaatgctggcctctgccggcgaactgcagaaggga aacgaactggccctgccctccaaatatgtgaacttcctgtacctggcca gccactatgagaagctgaagggctcccccgaggataatgagcagaaaca gctgtttgtggaacagcacaagcactacctggacgagatcatcgagcag atcagcgagttctccaagagagtgatcctggccgacgctaatctggaca aagtgctgtccgcctacaacaagcaccgggataagcccatcagagagca ggccgagaatatcatccacctgtttaccctgaccaatctgggagcccct gccgccttcaagtactttgacaccaccatcgaccggaagaggtacacca -continued gcaccaaagaggtgctggacgccaccctgatccaccagagcatcaccgg cctgtacgagacacggatcgacctgtctcagctgggaggcgacaaaagg ccggcggccacgaaaaaggccggccaggcaaaaaagaaaaagtaa Cas9.DHFR:

(SEQ ID NO: 94)

atggccccaaagaagaagcggaaggtcggtatccacggagtcccagcag ccgacaagaagtacagcatcggcctggacatcggcaccaactctgtggg ctgggccgtgatcaccgacgagtacaaggtgcccagcaagaaattcaag gtgctgggcaacaccgaccggcacagcatcaagaagaacctgatcggag ccctgctgttcgacagcggcgaaacagccgaggccacccggctgaagag aaccgccagaagaagatacaccagacggaagaaccggatctgctatctg caagagatcttcagcaacgagatggccaaggtggacgacagcttcttcc acagactggaagagtccttcctggtggaagaggataagaagcacgagcg gcacccccatcttcggcaacatcgtggacgaggtggcctaccacgagaag taccccaccatctaccacctgagaaagaaactggtggacagcaccgaca aggccgacctgcggctgatctatctggccctggcccacatgatcaagtt ccggggccacttcctgatcgagggcgacctgaaccccgacaacagcgac gtggacaagctgttcatccagctggtgcagacctacaaccagctgttcg aggaaaaccccatcaacgccagcggcgtggacgccaaggccatcctgtc tgccagactgagcaagagcagacggctggaaaatctgatcgcccagctg cccggcgagaagaagaatggcctgttcggaaacctgattgccctgagcc tgggcctgacccccaacttcaagagcaacttcgacctggccgaggatgc caaactgcagctgagcaaggacacctacgacgacgacctggacaacctg ctggcccagatcggcgaccagtacgccgacctgtttctggccgccaaga acctgtccgacgccatcctgctgagcgacatcctgagagtgaacaccga gatcaccaaggcccccctgagcgcctctatgatcaagagatacgacgag caccaccaggacctgaccctgctgaaagctctcgtgcggcagcagctgc ctgagaagtacaaagagattttcttcgaccagagcaagaacggctacgc cggctacattgacggcggagccagccaggaagagttctacaagttcatc aagcccatcctggaaaagatggacggcaccgaggaactgctcgtgaagc tgaacagagaggacctgctgcggaagcagcggaccttcgacaacggcag catcccccaccagatccacctgggagagctgcacgccattctgcggcgg caggaagatttttacccattcctgaaggacaaccgggaaaagatcgaga agatcctgaccttccgcatcccctactacgtgggccctctggccagggg aaacagcagattcgcctggatgaccagaaagagcgaggaaaccatcacc ccctggaacttcgaggaagtggtggacaagggcgcttccgcccagagct tcatcgagcggatgaccaacttcgataagaacctgcccaacgagaaggt gctgcccaagcacagcctgctgtacgagtacttcaccgtgtataacgag ctgaccaaagtgaaatacgtgaccgagggaatgagaaagcccgccttcc tgagcggcgagcagaaaaaggccatcgtggacctgctgttcaagaccaa ccggaaagtgaccgtgaagcagctgaaagaggactacttcaagaaaatc gagtgcttcgactccgtggaaatctccggcgtggaagatcggttcaacg cctccctgggcacataccacgatctgctgaaaattatcaaggacaagga cttcctggacaatgaggaaaacgaggacattctggaagatatcgtgctg accctgacactgtttgaggacagagagatgatcgaggaacggctgaaaa cctatgcccacctgttcgacgacaaagtgatgaagcagctgaagcggcg gagatacaccggctggggcaggctgagccggaagctgatcaacggcatc cgggacaagcagtccggcaagacaatcctggatttcctgaagtccgacg gcttcgccaacagaaacttcatgcagctgatccacgacgacagcctgac ctttaaagaggacatccagaaagcccaggtgtccggccagggcgatagc ctgcacgagcacattgccaatctggccggcagccccgccattaagaagg gcatcctgcagacagtgaaggtggtggacgagctcgtgaaagtgatggg ccggcacaagcccgagaacatcgtgatcgaaatggccagagagaaccag accacccagaagggacagaagaacagccgcgagagaatgaagcggatcg aagagggcatcaaagagctgggcagccagatcctgaaagaacaccccgt ggaaaacacccagctgcagaacgagaagctgtacctgtactacctgcag aatgggggggatatgtacgtggaccaggaactggacatcaaccggctgtc cgactacgatgtggaccatatcgtgcctcagagctttctgaaggacgac tccatcgacaacaaggtgctgaccagaagcgacaagaaccggggcaaga gcgacaacgtgccctccgaagaggtcgtgaagaagatgaagaactactg gcggcagctgctgaacgccaagctgattacccagagaaagttcgacaat ctgaccaaggccgagagaggcggcctgagcgaactggataaggccggct tcatcaagagacagctggtggaaacccggcagatcacaaagcacgtggc acagatcctggactcccggatgaacactaagtacgacgagaatgacaag ctgatccgggaagtgaaagtgatcaccctgaagtccaagctggtgtccg atttccggaaggatttccagttttacaaagtgcgcgagatcaacaacta ccaccacgcccacgacgcctacctgaacgccgtcgtgggaaccgccctg atcaaaaagtaccctaagctggaaagcgagttcgtgtacggcgactaca aggtgtacgacgtgcggaagatgatcgccaagagcgagcaggaaatcgg caaggctaccgccaagtacttcttctacagcaacatcatgaactttttc aagaccgagattaccctggccaacggcgagatccggaagcggcctctga tcgagacaaacggcgaaaccggggagatcgtgtgggataagggccggga ttttgccaccgtgcggaaagtgctgagcatgccccaagtgaatatcgtg aaaaagaccgaggtgcagacaggcggcttcagcaaagagtctatcctgc ccaagaggaacagcgataagctgatcgccagaaagaaggactgggaccc taagaagtacggcggcttcgacagccccaccgtggcctattctgtgctg gtggtggccaaagtggaaaagggcaagtccaagaaactgaagagtgtga aagagctgctggggatcaccatcatggaaagaagcagcttcgagaagaa tcccatcgactttctggaagccaagggctacaaagaagtgaaaaaggac ctgatcatcaagctgcctaagtactccctgttcgagctggaaaacggcc -continued ggaagagaatgctggcctctgccggcgaactgcagaagggaaacgaact ggccctgccctccaaatatgtgaacttcctgtacctggccagccactat gagaagctgaagggctcccccgaggataatgagcagaaacagctgtttg tggaacagcacaagcactacctggacgagatcatcgagcagatcagcga gttctccaagagagtgatcctggccgacgctaatctggacaaagtgctg tccgcctacaacaagcaccgggataagcccatcagagagcaggccgaga atatcatccacctgtttaccctgaccaatctgggagcccctgccgcctt caagtactttgacaccaccatcgaccggaagaggtacaccagcaccaaa gaggtgctggacgccaccctgatccaccagagcatcaccggcctgtacg agacacggatcgacctgtctcagctgggaggcgacaaaggccggcggc cacgaaaaaggccggccaggcaaaaaagaaaaagatcagtctgattgcg gcgttagcggtagatcacgttatcggcatggaaaccgtcatgccgtgga acctgcctgccgatctcgcctggtttaaacgcaacaccttaaataaacc cgtgattatgggccgccatacctgggaatcaatcggtcgtccgttgcca ggacgcaaaaatattatcctcagcagtcaaccgagtacggacgatcgcg taacgtgggtgaagtcggtggatgaagccatcgcggcgtgtggtgacgt accagaaatcatggttattggcggcggtcgcgtttatgaacagttcttg ccaaaagcgcaaaaactgtatctgacgcatatcgacgcagaagtggaag gcgacacccatttcccggattacgagccggatgactgggaatcggtatt cagcgaattccacgatgctgatgcgcagaactctcacagctattgcttt gagattctggagcggcgataa DHFR.Cas9.DHFR:

(SEQ ID NO: 95)

atggccccaaagaagaagcggaaggtcggtatccacggagtcccagcag ccggatccatcagtctgattgcggcgttagcggtagattacgttatcgg catggaaaacgccatgccgtggaacctgcctgccgatctcgcctggttt aaacgcaacaccttaaataaacccgtgattatgggccgccatacctggg aatcaatcggtcgtccgttgccaggacgcaaaaatattatcctcagcag tcaaccgagtacggacgatcgcgtaacgtgggtgaagtcggtggatgaa gccatcgcggcgtgtggtgacgtaccagaaatcatggtgattggcggcg gtcgcgttattgaacagttcttgccaaaagcgcaaaaactgtatctgac gcatatcgacgcagaagtggaaggcgacacccatttcccggattacgag ccggatgactgggaatcggtattcagcgaattccacgatgctgatgcgc agaactctcacagctattgctttgagattctggagcggcgaggaagcgg aagcggatccgacaagaagtacagcatcggcctggacatcggcaccaac tctgtgggctgggccgtgatcaccgacgagtacaaggtgcccagcaaga aattcaaggtgctgggcaacaccgaccggcacagcatcaagaagaacct gatcggagccctgctgttcgacagcggcgaaacagccgaggccacccgg ctgaagagaaccgccagaagaagatacaccagacggaagaaccggatct gctatctgcaagagatcttcagcaacgagatggccaaggtggacgacag cttcttccacagactggaagagtccttcctggtggaagaggataagaag cacgagcggcaccccatcttcggcaacatcgtggacgaggtggcctacc acgagaagtaccccaccatctaccacctgagaaagaaactggtggacag caccgacaaggccgacctgcggctgatctatctggccctggcccacatg atcaagttccggggccacttcctgatcgagggcgacctgaaccccgaca acagcgacgtggacaagctgttcatccagctggtgcagacctacaacca gctgttcgaggaaaaccccatcaacgccagcggcgtggacgccaaggcc atcctgtctgccagactgagcaagagcagacggctggaaaatctgatcg cccagctgcccggcgagaagaagaatggcctgttcggaaacctgattgc cctgagcctgggcctgacccccaacttcaagagcaacttcgacctggcc gaggatgccaaactgcagctgagcaaggacacctacgacgacgacctgg acaacctgctggcccagatcggcgaccagtacgccgacctgtttctggc cgccaagaacctgtccgacgccatcctgctgagcgacatcctgagagtg aacaccgagatcaccaaggcccccctgagcgcctctatgatcaagagat acgacgagcaccaccaggacctgaccctgctgaaagctctcgtgcggca gcagctgcctgagaagtacaaagagattttcttcgaccagagcaagaac ggctacgccggctacattgacggcggagccagccaggaagagttctaca agttcatcaagcccatcctggaaaagatggacggcaccgaggaactgct cgtgaagctgaacagagaggacctgctgcggaagcagcggaccttcgac aacggcagcatcccccaccagatccacctgggagagctgcacgccattc tgcggcggcaggaagatttttacccattcctgaaggacaaccgggaaaa gatcgagaagatcctgaccttccgcatcccctactacgtgggccctctg gccaggggaaacagcagattcgcctggatgaccagaaagagcgaggaaa ccatcaccccctggaacttcgaggaagtggtggacaagggcgcttccgc ccagagcttcatcgagcggatgaccaacttcgataagaacctgcccaac gagaaggtgctgcccaagcacagcctgctgtacgagtacttcaccgtgt ataacgagctgaccaaagtgaaatacgtgaccgagggaatgagaaagcc cgccttcctgagcggcgagcagaaaaaggccatcgtggacctgctgttc aagaccaaccggaaagtgaccgtgaagcagctgaaagaggactacttca agaaaatcgagtgcttcgactccgtggaaatctccggcgtggaagatcg gttcaacgcctccctgggcacataccacgatctgctgaaaattatcaag gacaaggacttcctggacaatgaggaaaacgaggacattctggaagata tcgtgctgaccctgacactgtttgaggacagagagatgatcgaggaacg gctgaaaacctatgcccacctgttcgacgacaaagtgatgaagcagctg aagcggcggagatacaccggctggggcaggctgagccggaagctgatca acggcatccgggacaagcagtccggcaagacaatcctggatttcctgaa gtccgacggcttcgccaacagaaacttcatgcagctgatccacgacgac agcctgacctttaaagaggacatccagaaagcccaggtgtccggccagg gcgatagcctgcacgagcacattgccaatctggccggcagccccgccat taagaagggcatcctgcagacagtgaaggtggtggacgagctcgtgaaa gtgatgggccggcacaagcccgagaacatcgtgatcgaaatggccagag -continued agaaccagaccacccagaagggacagaagaacagccgcgagagaatgaa
gcggatcgaagagggcatcaaagagctgggcagccagatcctgaaagaa
caccccgtggaaaacacccagctgcagaacgagaagctgtacctgtact
acctgcagaatgggggatatgtacgtggaccaggaactggacatcaac
cggctgtccgactacgatgtggaccatatcgtgcctcagagctttctga
aggacgactccatcgacaacaaggtgctgaccagaagcgacaagaaccg
gggcaagagcgacaacgtgccctccgaagaggtcgtgaagaagatgaag
aactactggcggcagctgctgaacgccaagctgattacccagagaaagt
tcgacaatctgaccaaggccgagagaggcggcctgagcgaactggataa
ggccggcttcatcaagagacagctggtggaaacccggcagatcacaaag
cacgtggcacagatcctggactcccggatgaacactaagtacgacgaga
atgacaagctgatccgggaagtgaaagtgatcaccctgaagtccaagct
ggtgtccgatttccggaaggatttccagttttacaaagtgcgcgagatc
aacaactaccaccacgcccacgacgcctacctgaacgccgtcgtgggaa
ccgccctgatcaaaaagtaccctaagctggaaagcgagttcgtgtacgg
cgactacaaggtgtacgacgtgcggaagatgatcgccaagagcgagcag
gaaatcggcaaggctaccgccaagtacttcttctacagcaacatcatga
actttttcaagaccgagattaccctggccaacggcgagatccggaagcg
gcctctgatcgagacaaacggcgaaaccggggagatcgtgtgggataag
ggccgggattttgccaccgtgcggaaagtgctgagcatgccccaagtga
atatcgtgaaaaagaccgaggtgcagacaggcggcttcagcaaagagtc
tatcctgcccaagaggaacagcgataagctgatcgccagaaagaaggac
tgggaccctaagaagtacggcggcttcgacagccccaccgtggcctatt
ctgtgctggtggtggccaaagtggaaaagggcaagtccaagaaactgaa -continued gagtgtgaaagagctgctggggatcaccatcatggaaagaagcagcttc
gagaagaatcccatcgactttctggaagccaagggctacaaagaagtga
aaaaggacctgatcatcaagctgcctaagtactccctgttcgagctgga
aaacggccggaagagaatgctggcctctgccggcgaactgcagaaggga
aacgaactggccctgccctccaaatatgtgaacttcctgtacctggcca
gccactatgagaagctgaagggctcccccgaggataatgagcagaaaca
gctgtttgtggaacagcacaagcactacctggacgagatcatcgagcag
atcagcgagttctccaagagagtgatcctggccgacgctaatctggaca
aagtgctgtccgcctacaacaagcaccgggataagcccatcagagagca
ggccgagaatatcatccacctgtttaccctgaccaatctgggagcccct
gccgccttcaagtactttgacaccaccatcgaccggaagaggtacacca
gcaccaaagaggtgctggacgccaccctgatccaccagagcatcaccgg
cctgtacgagacacggatcgacctgtctcagctgggaggcgacaaaagg
ccggcggccacgaaaaaggccggccaggcaaaaaagaaaaagatcagtc
tgattgcggcgttagcggtagatcacgttatcggcatggaaaccgtcat
gccgtggaacctgcctgccgatctcgcctggtttaaacgcaacacctta
aataaacccgtgattatgggccgccatacctgggaatcaatcggtcgtc
cgttgccaggacgcaaaaatattatcctcagcagtcaaccgagtacgga
cgatcgcgtaacgtgggtgaagtcggtggatgaagccatcgcggcgtgt
ggtgacgtaccagaaatcatggttattggcggcggtcgcgtttatgaac
agttcttgccaaaagcgcaaaaactgtatctgacgcatatcgacgcaga
agtggaaggcgacacccatttcccggattacgagccggatgactgggaa
tcggtattcagcgaattccacgatgctgatgcgcagaactctcacagct
attgctttgagattctggagcggcgataa ER50.Cas9:

(SEQ ID NO: 96)

atggccccaaagaagaagcggaaggtcggtatccacggagtcccagcagccggatccagccttgccctgtcactta
cagccgaccagatggtttccgcgcttctcgacgctgaacctccaattctctattccgaatacgacccaaccaggccgttctccgaggcatcta
tgatgggtctgctgacaaatctggcagacagggaactggtgcacatgatcaattgggcgaagcgcgtacccggattcgtcgatcttgcactc
catgatcaggtgcacttgctggagtgcgcttggatggagatcctcatgatcgggctggtgtggcggagtatggaacaccccggcaagttgc
tgtttgcgcctaacctcctgttggacaggaaccaggggaaatgtgtggagggcggtgtggaaatctttgacatgctcctcgctacctcaagc
cggtttaggatgatgaatctgcagggcgaagagttcgtgtgtctcaaatctatcatactgttgaacagcggagtctacaccttcctctccagtac
tctgaaatctctggaggagaaagatcatatccatcgcgtgctggacaagataaccgacacgttgattcacttgatggccaaagctgggctca
ctctgcaacaacaacatcagcgactggcacagctgttgctgattttgagccacattcggcacatgtccagcaagagaatggagcacctctat
agtatgaagtgcaagaacgtcgtaccccctgtcagatctgcttcttgaaatgcttgatgcccaccggctgggaagcggaagcggatccgaca
agaagtacagcatcggcctggacatcggcaccaactctgtgggctgggccgtgatcaccgacgagtacaaggtgcccagcaagaaattc
aaggtgctgggcaacaccgaccggcacagcatcaagaagaacctgatcggagccctgctgttcgacagcggcgaaacagccgaggcc
acccggctgaagagaaccgccagaagaagatacaccagacggaagaaccggatctgctatctgcaagagatcttcagcaacgagatgg
ccaaggtggacgacagcttcttccacagactggaagagtccttcctggtggaagaggataagaagcacgagcggcaccccatcttcggca
acatcgtggacgaggtggcctaccacgagaagtaccccaccatctaccacctgagaaagaaactggtggacagcaccgacaaggccga -continued cctgcggctgatctatctggccctggcccacatgatcaagttccggggccacttcctgatcgagggcgacctgaaccccgacaacagcga
cgtggacaagctgttcatccagctggtgcagacctacaaccagctgttcgaggaaaaccccatcaacgccagcggcgtggacgccaagg
ccatcctgtctgccagactgagcaagagcagacggctggaaaatctgatcgcccagctgcccggcgagaagaagaatggcctgttcgga
aacctgattgccctgagcctgggcctgacccccaacttcaagagcaacttcgacctggccgaggatgccaaactgcagctgagcaaggac
acctacgacgacgacctggacaacctgctggcccagatcggcgaccagtacgccgacctgtttctggccgccaagaacctgtccgacgc
catcctgctgagcgacatcctgagagtgaacaccgagatcaccaaggcccccctgagcgcctctatgatcaagagatacgacgagcacca
ccaggacctgaccctgctgaaagctctcgtgcggcagcagctgcctgagaagtacaaagagattttcttcgaccagagcaagaacggcta
cgccggctacattgacggcggagccagccaggaagagttctacaagttcatcaagcccatcctggaaaagatggacggcaccgaggaac
tgctcgtgaagctgaacagagaggacctgctgcggaagcagcggaccttcgacaacggcagcatcccccaccagatccacctgggaga
gctgcacgccattctgcggcggcaggaagatttttacccattcctgaaggacaaccgggaaaagatcgagaagatcctgaccttccgcatc
ccctactacgtgggccctctggccaggggaaacagcagattcgcctggatgaccagaaagagcgaggaaaccatcaccccctggaactt
cgaggaagtggtggacaagggcgcttccgcccagagcttcatcgagcggatgaccaacttcgataagaacctgcccaacgagaaggtgc
tgcccaagcacagcctgctgtacgagtacttcaccgtgtataacgagctgaccaaagtgaaatacgtgaccgagggaatgagaaagcccg
ccttcctgagcggcgagcagaaaaaggccatcgtggacctgctgttcaagaccaaccggaaagtgaccgtgaagcagctgaaagagga
ctacttcaagaaaatcgagtgcttcgactccgtggaaatctccggcgtggaagatcggttcaacgcctccctgggcacataccacgatctgc
tgaaaattatcaaggacaaggacttcctggacaatgaggaaaacgaggacattctggaagatatcgtgctgaccctgacactgtttgaggac
agagagatgatcgaggaacggctgaaaacctatgcccacctgttcgacgacaaagtgatgaagcagctgaagcggcggagatacaccg
gctggggcaggctgagccggaagctgatcaacggcatccgggacaagcagtccggcaagacaatcctggatttcctgaagtccgacgg
cttcgccaacagaaacttcatgcagctgatccacgacgacagcctgacctttaaagaggacatccagaaagcccaggtgtccggccaggg
cgatagcctgcacgagcacattgccaatctggccggcagccccgccattaagaagggcatcctgcagacagtgaaggtggtggacgagc
tcgtgaaagtgatgggccggcacaagcccgagaacatcgtgatcgaaatggccagagagaaccagaccacccagaagggacagaaga
acagccgcgagagaatgaagcggatcgaagagggcatcaaagagctgggcagccagatcctgaaagaacaccccgtggaaaacaccc
agctgcagaacgagaagctgtacctgtactacctgcagaatgggggatatgtacgtggaccaggaactggacatcaaccggctgtccg
actacgatgtggaccatatcgtgcctcagagctttctgaaggacgactccatcgacaacaaggtgctgaccagaagcgacaagaaccggg
gcaagagcgacaacgtgccctccgaagaggtcgtgaagaagatgaagaactactggcggcagctgctgaacgccaagctgattaccca
gagaaagttcgacaatctgaccaaggccgagagaggcggcctgagcgaactggataaggccggcttcatcaagagacagctggtggaa
acccggcagatcacaaagcacgtggcacagatcctggactcccggatgaacactaagtacgacgagaatgacaagctgatccgggaagt
gaaagtgatcaccctgaagtccaagctggtgtccgatttccggaaggatttccagttttacaaagtgcgcgagatcaacaactaccaccacg
cccacgacgcctacctgaacgccgtcgtgggaaccgccctgatcaaaaagtaccctaagctggaaagcgagttcgtgtacggcgactaca
aggtgtacgacgtgcggaagatgatcgccaagagcgagcaggaaatcggcaaggctaccgccaagtacttcttctacagcaacatcatga
actttttcaagaccgagattaccctggccaacggcgagatccggaagcggcctctgatcgagacaaacggcgaaaccggggagatcgtgt
gggataagggccgggattttgccaccgtgcggaaagtgctgagcatgccccaagtgaatatcgtgaaaaagaccgaggtgcagacaggc
ggcttcagcaaagagtctatcctgcccaagaggaacagcgataagctgatcgccagaaagaaggactgggaccctaagaagtacggcg
gcttcgacagccccaccgtggcctattctgtgctggtggtggccaaagtggaaaagggcaagtccaagaaactgaagagtgtgaaagagc
tgctggggatcaccatcatggaaagaagcagcttcgagaagaatcccatcgactttctggaagccaagggctacaaagaagtgaaaaagg
acctgatcatcaagctgcctaagtactccctgttcgagctggaaaacggccggaagagaatgctggcctctgccggcgaactgcagaagg
gaaacgaactggccctgccctccaaatatgtgaacttcctgtacctggccagccactatgagaagctgaagggctcccccgaggataatga
gcagaaacagctgtttgtggaacagcacaagcactacctggacgagatcatcgagcagatcagcgagttctccaagagagtgatcctggc
cgacgctaatctggacaaagtgctgtccgcctacaacaagcaccgggataagcccatcagagagcaggccgagaatatcatccacctgttt
accctgaccaatctgggagcccctgccgccttcaagtactttgacaccaccatcgaccggaagaggtacaccagcaccaaagaggtgctg -continued gacgccaccctgatccaccagagcatcaccggcctgtacgagacacggatcgacctgtctcagctgggaggcgacaaaaggccggcgg ccacgaaaaaggccggccaggcaaaaaagaaaaagtaa Cas9.ER50:

(SEQ ID NO: 97)

atggccccaaagaagaagcggaaggtcggtatccacggagtcccagcagccgacaagaagtacagcatcggcct ggacatcggcaccaactctgtgggctgggccgtgatcaccgacgagtacaaggtgcccagcaagaaattcaaggtgctgggcaacaccg accggcacagcatcaagaagaacctgatcggagccctgctgttcgacagcggcgaaacagccgaggccacccggctgaagagaaccg ccagaagaagatacaccagacggaagaaccggatctgctatctgcaagagatcttcagcaacgagatggccaaggtggacgacagcttct tccacagactggaagagtccttcctggtggaagaggataagaagcacgagcggcaccccatcttcggcaacatcgtggacgaggtggcc taccacgagaagtaccccaccatctaccacctgagaaagaaactggtggacagcaccgacaaggccgacctgcggctgatctatctggcc ctggcccacatgatcaagttccggggccacttcctgatcgagggcgacctgaaccccgacaacagcgacgtggacaagctgttcatccag ctggtgcagacctacaaccagctgttcgaggaaaaccccatcaacgccagcggcgtggacgccaaggccatcctgtctgccagactgag caagagcagacggctggaaaatctgatcgcccagctgcccggcgagaagaagaatggcctgttcggaaacctgattgccctgagcctgg gcctgacccccaacttcaagagcaacttcgacctggccgaggatgccaaactgcagctgagcaaggacacctacgacgacgacctggac aacctgctggcccagatcggcgaccagtacgccgacctgtttctggccgccaagaacctgtccgacgccatcctgctgagcgacatcctg agagtgaacaccgagatcaccaaggcccccctgagcgcctctatgatcaagagatacgacgagcaccaccaggacctgaccctgctgaa agctctcgtgcggcagcagctgcctgagaagtacaaagagattttcttcgaccagagcaagaacggctacgccggctacattgacggcgg agccagccaggaagagttctacaagttcatcaagcccatcctggaaaagatggacggcaccgaggaactgctcgtgaagctgaacagag aggacctgctgcggaagcagcggaccttcgacaacggcagcatcccccaccagatccacctgggagagctgcacgccattctgcggcg gcaggaagatttttacccattcctgaaggacaaccgggaaaagatcgagaagatcctgaccttccgcatcccctactacgtgggccctctgg ccaggggaaacagcagattcgcctggatgaccagaaagagcgaggaaaccatcaccccctggaacttcgaggaagtggtggacaagg gcgcttccgcccagagcttcatcgagcggatgaccaacttcgataagaacctgcccaacgagaaggtgctgcccaagcacagcctgctgt acgagtacttcaccgtgtataacgagctgaccaaagtgaaatacgtgaccgagggaatgagaaagcccgccttcctgagcggcgagcag aaaaaggccatcgtggacctgctgttcaagaccaaccggaaagtgaccgtgaagcagctgaaagaggactacttcaagaaaatcgagtgc ttcgactccgtggaaatctccggcgtggaagatcggttcaacgcctccctgggcacataccacgatctgctgaaaattatcaaggacaagga cttcctggacaatgaggaaaacgaggacattctggaagatatcgtgctgaccctgacactgtttgaggacagagagatgatcgaggaacgg ctgaaaacctatgcccacctgttcgacgacaaagtgatgaagcagctgaagcggcggagatacaccggctggggcaggctgagccgga agctgatcaacggcatccgggacaagcagtccggcaagacaatcctggatttcctgaagtccgacggcttcgccaacagaaacttcatgca gctgatccacgacgacagcctgacctttaaagaggacatccagaaagcccaggtgtccggccagggcgatagcctgcacgagcacattg ccaatctggccggcagccccgccattaagaagggcatcctgcagacagtgaaggtggtggacgagctcgtgaaagtgatgggccggca caagcccgagaacatcgtgatcgaaatggccagagagaaccagaccacccagaagggacagaagaacagccgcgagagaatgaagc ggatcgaagagggcatcaaagagctgggcagccagatcctgaaagaacaccccgtggaaaacacccagctgcagaacgagaagctgt acctgtactacctgcagaatgggggggatatgtacgtggaccaggaactggacatcaaccggctgtccgactacgatgtggaccatatcgt gcctcagagctttctgaaggacgactccatcgacaacaaggtgctgaccagaagcgacaagaaccggggcaagagcgacaacgtgccc tccgaagaggtcgtgaagaagatgaagaactactggcggcagctgctgaacgccaagctgattacccagagaaagttcgacaatctgacc aaggccgagagaggcggcctgagcgaactggataaggccggcttcatcaagagacagctggtggaaacccggcagatcacaaagcac gtggcacagatcctggactcccggatgaacactaagtacgacgagaatgacaagctgatccgggaagtgaaagtgatcaccctgaagtcc aagctggtgtccgatttccggaaggatttccagttttacaaagtgcgcgagatcaacaactaccaccacgcccacgacgcctacctgaacgc cgtcgtgggaaccgccctgatcaaaaagtaccctaagctggaaagcgagttcgtgtacggcgactacaaggtgtacgacgtgcggaagat gatcgccaagagcgagcaggaaatcggcaaggctaccgccaagtacttcttctacagcaacatcatgaactttttcaagaccgagattaccc -continued tggccaacggcgagatccggaagcggcctctgatcgagacaaacggcgaaaccggggagatcgtgtgggataagggccgggattttgc caccgtgcggaaagtgctgagcatgccccaagtgaatatcgtgaaaaagaccgaggtgcagacaggcggcttcagcaaagagtctatcct gcccaagaggaacagcgataagctgatcgccagaaagaaggactgggaccctaagaagtacggcggcttcgacagccccaccgtggc ctattctgtgctggtggtggccaaagtggaaaagggcaagtccaagaaactgaagagtgtgaaagagctgctggggatcaccatcatgga aagaagcagcttcgagaagaatcccatcgactttctggaagccaagggctacaaagaagtgaaaaaggacctgatcatcaagctgcctaa gtactccctgttcgagctggaaaacggccggaagagaatgctggcctctgccggcgaactgcagaagggaaacgaactggccctgccct ccaaatatgtgaacttcctgtacctggccagccactatgagaagctgaagggctcccccgaggataatgagcagaaacagctgtttgtgga acagcacaagcactacctggacgagatcatcgagcagatcagcgagttctccaagagagtgatcctggccgacgctaatctggacaaagt gctgtccgcctacaacaagcaccgggataagcccatcagagagcaggccgagaatatcatccacctgtttaccctgaccaatctgggagc ccctgccgccttcaagtactttgacaccaccatcgaccggaagaggtacaccagcaccaaagaggtgctggacgccaccctgatccacca gagcatcaccggcctgtacgagacacggatcgacctgtctcagctgggaggcgacaaaaggccggcggccacgaaaaaggccggcca ggcaaaaaagaaaaagagccttgccctgtcacttacagccgaccagatggtttccgcgcttctcgacgctgaacctccaattctctattccga atacgacccaaccaggccgttctccgaggcatctatgatgggtctgctgacaaatctggcagacagggaactggtgcacatgatcaattgg gcgaagcgcgtacccggattcgtcgatcttgcactccatgatcaggtgcacttgctggagtgcgcttggatggagatcctcatgatcgggct ggtgtggcggagtatggaacaccccggcaagttgctgtttgcgcctaacctcctgttggacaggaaccaggggaaatgtgtggagggcgg tgtggaaatctttgacatgctcctcgctacctcaagccggtttaggatgatgaatctgcagggcgaagagttcgtgtgtctcaaatctatcatac tgttgaacagcggagtctacaccttcctctccagtactctgaaatctctggaggagaaagatcatatccatcgcgtgctggacaagataaccg acacgttgattcacttgatggccaaagctgggctcactctgcaacaacaacatcagcgactggcacagctgttgctgattttgagccacattc ggcacatgtccagcaagagaatggagcacctctatagtatgaagtgcaagaacgtcgtacccctgtcagatctgcttcttgaaatgcttgatg cccaccggctgtaa ER50.Cas9.ER50:

(SEQ ID NO: 98)

atggccccaaagaagaagcggaaggtcggtatccacggagtcccagcagccggatccagccttgccctgtcactta cagccgaccagatggtttccgcgcttctcgacgctgaacctccaattctctattccgaatacgacccaaccaggccgttctccgaggcatcta tgatgggtctgctgacaaatctggcagacagggaactggtgcacatgatcaattgggcgaagcgcgtacccggattcgtcgatcttgcactc catgatcaggtgcacttgctggagtgcgcttggatggagatcctcatgatcgggctggtgtggcggagtatggaacaccccggcaagttgc tgtttgcgcctaacctcctgttggacaggaaccaggggaaatgtgtggagggcggtgtggaaatctttgacatgctcctcgctacctcaagc cggtttaggatgatgaatctgcagggcgaagagttcgtgtgtctcaaatctatcatactgttgaacagcggagtctacaccttcctctccagtac tctgaaatctctggaggagaaagatcatatccatcgcgtgctggacaagataaccgacacgttgattcacttgatggccaaagctgggctca ctctgcaacaacaacatcagcgactggcacagctgttgctgattttgagccacattcggcacatgtccagcaagagaatggagcacctctat agtatgaagtgcaagaacgtcgtacccctgtcagatctgcttcttgaaatgcttgatgcccaccggctgggaagcggaagcggatccgaca agaagtacagcatcggcctggacatcggcaccaactctgtgggctgggccgtgatcaccgacgagtacaaggtgcccagcaagaaattc aaggtgctgggcaacaccgaccggcacagcatcaagaagaacctgatcggagccctgctgttcgacagcggcgaaacagccgaggcc acccggctgaagagaaccgccagaagaagatacaccagacggaagaaccggatctgctatctgcaagagatcttcagcaacgagatgg ccaaggtggacgacagcttcttccacagactggaagagtccttcctggtggaagaggataagaagcacgagcggcaccccatcttcggca acatcgtggacgaggtggcctaccacgagaagtaccccaccatctaccacctgagaaagaaactggtggacagcaccgacaaggccga cctgcggctgatctatctggccctggcccacatgatcaagttccggggccacttcctgatcgagggcgacctgaaccccgacaacagcga cgtggacaagctgttcatccagctggtgcagacctacaaccagctgttcgaggaaaaccccatcaacgccagcggcgtggacgccaagg ccatcctgtctgccagactgagcaagagcagacggctggaaaatctgatcgcccagctgcccggcgagaagaagaatggcctgttcgga aacctgattgccctgagcctgggcctgacccccaacttcaagagcaacttcgacctggccgaggatgccaaactgcagctgagcaaggac -continued acctacgacgacgacctggacaacctgctggcccagatcggcgaccagtacgccgacctgtttctggccgccaagaacctgtccgacgc
catcctgctgagcgacatcctgagagtgaacaccgagatcaccaaggcccccctgagcgcctctatgatcaagagatacgacgagcacca
ccaggacctgaccctgctgaaagctctcgtgcggcagcagctgcctgagaagtacaaagagattttcttcgaccagagcaagaacggcta
cgccggctacattgacggcggagccagccaggaagagttctacaagttcatcaagcccatcctggaaaagatggacggcaccgaggaac
tgctcgtgaagctgaacagagaggacctgctgcggaagcagcggaccttcgacaacggcagcatcccccaccagatccacctgggaga
gctgcacgccattctgcggcggcaggaagatttttacccattcctgaaggacaaccgggaaaagatcgagaagatcctgaccttccgcatc
ccctactacgtgggccctctggccaggggaaacagcagattcgcctggatgaccagaaagagcgaggaaaccatcacccccctggaactt
cgaggaagtggtggacaagggcgcttccgcccagagcttcatcgagcggatgaccaacttcgataagaacctgcccaacgagaaggtgc
tgcccaagcacagcctgctgtacgagtacttcaccgtgtataacgagctgaccaaagtgaaatacgtgaccgagggaatgagaaagcccg
ccttcctgagcggcgagcagaaaaaggccatcgtggacctgctgttcaagaccaaccggaaagtgaccgtgaagcagctgaaagagga
ctacttcaagaaaatcgagtgcttcgactccgtggaaatctccggcgtggaagatcggttcaacgcctccctgggcacataccacgatctgc
tgaaaattatcaaggacaaggacttcctggacaatgaggaaaacgaggacattctggaagatatcgtgctgaccctgacactgtttgaggac
agagagatgatcgaggaacggctgaaaacctatgcccacctgttcgacgacaaagtgatgaagcagctgaagcggcggagatacaccg
gctggggcaggctgagccggaagctgatcaacggcatccgggacaagcagtccggcaagacaatcctggatttcctgaagtccgacgg
cttcgccaacagaaacttcatgcagctgatccacgacgacagcctgacctttaaagaggacatccagaaagcccaggtgtccggccaggg
cgatagcctgcacgagcacattgccaatctggccggcagccccgccattaagaagggcatcctgcagacagtgaaggtggtggacgagc
tcgtgaaagtgatgggccggcacaagcccgagaacatcgtgatcgaaatggccagagagaaccagaccacccagaagggacagaaga
acagccgcgagagaatgaagcggatcgaagagggcatcaaagagctgggcagccagatcctgaaagaacaccccgtggaaaacaccc
agctgcagaacgagaagctgtacctgtactacctgcagaatgggggatatgtacgtggaccaggaactggacatcaaccggctgtccg
actacgatgtggaccatatcgtgcctcagagctttctgaaggacgactccatcgacaacaaggtgctgaccagaagcgacaagaaccggg
gcaagagcgacaacgtgccctccgaagaggtcgtgaagaagatgaagaactactggcggcagctgctgaacgccaagctgattaccca
gagaaagttcgacaatctgaccaaggccgagagaggcggcctgagcgaactggataaggccggcttcatcaagagacagctggtggaa
acccggcagatcacaaagcacgtggcacagatcctggactcccggatgaacactaagtacgacgagaatgacaagctgatccgggaagt
gaaagtgatcaccctgaagtccaagctggtgtccgatttccggaaggatttccagttttacaaagtgcgcgagatcaacaactaccaccacg
cccacgacgcctacctgaacgccgtcgtgggaaccgccctgatcaaaaagtaccctaagctggaaagcgagttcgtgtacggcgactaca
aggtgtacgacgtgcggaagatgatcgccaagagcgagcaggaaatcggcaaggctaccgccaagtacttcttctacagcaacatcatga
actttttcaagaccgagattaccctggccaacggcgagatccggaagcggcctctgatcgagacaaacggcgaaaccggggagatcgtgt
gggataagggccgggattttgccaccgtgcggaaagtgctgagcatgccccaagtgaatatcgtgaaaaagaccgaggtgcagacaggc
ggcttcagcaaagagtctatcctgcccaagaggaacagcgataagctgatcgccagaaagaaggactgggaccctaagaagtacggcg
gcttcgacagccccaccgtggcctattctgtgctggtggtggccaaagtggaaaagggcaagtccaagaaactgaagagtgtgaaagagc
tgctggggatcaccatcatggaaagaagcagcttcgagaagaatcccatcgactttctggaagccaagggctacaaagaagtgaaaaagg
acctgatcatcaagctgcctaagtactccctgttcgagctggaaaacggccggaagagaatgctggcctctgccggcgaactgcagaagg
gaaacgaactggccctgccctccaaatatgtgaacttcctgtacctggccagccactatgagaagctgaagggctcccccgaggataatga
gcagaaacagctgtttgtggaacagcacaagcactacctggacgagatcatcgagcagatcagcgagttctccaagagagtgatcctggc
cgacgctaatctggacaaagtgctgtccgcctacaacaagcaccgggataagcccatcagagagcaggccgagaatatcatccacctgttt
accctgaccaatctgggagcccctgccgccttcaagtactttgacaccaccatcgaccggaagaggtacaccagcaccaaagaggtgctg
gacgccaccctgatccaccagagcatcaccggcctgtacgagacacggatcgacctgtctcagctgggaggcgacaaaaggccggcgg
ccacgaaaaaggccggccaggcaaaaaagaaaaagagccttgccctgtcacttacagccgaccagatggtttccgcgcttctcgacgctg
aacctccaattctctattccgaatacgacccaaccaggccgttctccgaggcatctatgatgggtctgctgacaaatctggcagacagggaa
ctggtgcacatgatcaattgggcgaagcgcgtacccggattcgtcgatcttgcactccatgatcaggtgcacttgctggagtgcgcttggatg
gagatcctcatgatcgggctggtgtggcggagtatggaacaccccggcaagttgctgtttgcgcctaacctcctgttggacaggaaccagg -continued ggaaatgtgtggagggcggtgtggaaatctttgacatgctcctcgctacctcaagccggtttaggatgatgaatctgcagggcgaagagttc gtgtgtctcaaatctatcatactgttgaacagcggagtctacaccttcctctccagtactctgaaatctctggaggagaaagatcatatccatcg cgtgctggacaagataaccgacacgttgattcacttgatggccaaagctgggctcactctgcaacaacaacatcagcgactggcacagctg ttgctgattttgagccacattcggcacatgtccagcaagagaatggagcacctctatagtatgaagtgcaagaacgtcgtacccctgtcagat ctgcttcttgaaatgcttgatgcccaccggctgtaa

DHFR.PP7.VP64:

(SEQ ID NO: 99)

atgatcagtctgattgcggcgttagcggtagattacgttatcggcatgga aaacgccatgccgtggaacctgcctgccgatctcgcctggtttaaacgca acaccttaaataaacccgtgattatgggccgccatacctgggaatcaatc ggtcgtccgttgccaggacgcaaaaatattatcctcagcagtcaaccgag tacggacgatcgcgtaacgtgggtgaagtcggtggatgaagccatcgcgg cgtgtggtgacgtaccagaaatcatggtgattggcggcggtcgcgttatt gaacagttcttgccaaaagcgcaaaaactgtatctgacgcatatcgacgc agaagtggaaggcgacacccatttcccggattacgagccggatgactggg aatcggtattcagcgaattccacgatgctgatgcgcagaactctcacagc tattgctttgagattctggagcggcgaggtggaggaggttcaggaggtgg aggctctggaggtggaggcagctccaaaaccatcgttctttcggtcggcg aggctactcgcactctgactgagatccagtccaccgcagaccgtcagatc ttcgaagagaaggtcgggcctctggtgggtcggctgcgcctcacggcttc gctccgtcaaaacggagccaagaccgcgtatcgcgtcaacctaaaactgg atcaggcggacgtcgttgattccggacttccgaaagtgcgctacactcag gtatggtcgcacgacgtgacaatcgttgcgaatagcaccgaggcctcgcg caaatcgttgtacgatttgaccaagtccctcgtcgcgacctcgcaggtcg aagatcttgtcgtcaaccttgtgccgctgggccgtagcgctggaggaggt ggaagcggaggaggaggaagcggaggaggaggtagcggacctaagaaaaa gaggaaggtggcggccgctggatccggacgggctgacgcattggacgatt ttgatctggatatgctgggaagtgacgccctcgatgattttgaccttgac atgcttggttcggatgcccttgatgactttgacctcgacatgctcggcag tgacgcccttgatgatttcgacctggacatgctgtaa

ER50.MS2.P65.HSF1:

(SEQ ID NO: 100)

atgagccttgccctgtcacttacagccgaccagatggtttccgcgcttct cgacgctgaacctccaattctctattccgaatacgacccaaccaggccgt tctccgaggcatctatgatgggtctgctgacaaatctggcagacagggaa ctggtgcacatgatcaattgggcgaagcgcgtacccggattcgtcgatct tgcactccatgatcaggtgcacttgctggagtgcgcttggatggagatcc tcatgatcgggctggtgtggcggagtatggaacaccccggcaagttgctg tttgcgcctaacctcctgttggacaggaaccaggggaaatgtgtggaggg -continued cggtgtggaaatctttgacatgctcctcgctacctcaagccggtttagga tgatgaatctgcagggcgaagagttcgtgtgtctcaaatctatcatactg ttgaacagcggagtctacaccttcctctccagtactctgaaatctctgga ggagaaagatcatatccatcgcgtgctggacaagataaccgacacgttga ttcacttgatggccaaagctgggctcactctgcaacaacaacatcagcga ctggcacagctgttgctgattttgagccacattcggcacatgtccagcaa gagaatggagcacctctatagtatgaagtgcaagaacgtcgtacccctgt cagatctgcttcttgaaatgcttgatgcccaccggctgggtggaggaggt tcaggaggtggaggctctggaggtggaggcagcgcttcaaactttactca gttcgtgctcgtggacaatggtgggacaggggatgtgacagtggctcctt ctaatttcgctaatggggggcagagtggatcagctccaactcacggagcc aggcctacaaggtgacatgcagcgtcaggcagtctagtgcccagaagaga aagtataccatcaaggtggaggtccccaaagtggctacccagacagtggg cggagtcgaactgcctgtcgccgcttggaggtcctacctgaacatggagc tcactatcccaattttcgctaccaattctgactgtgaactcatcgtgaag gcaatgcaggggctcctcaaagacggtaatcctatcccttccgccatcgc cgctaactcaggtatctacagcgctggaggaggtggaagcggaggaggag gaagcggaggaggaggtagcggacctaagaaaaagaggaaggtggcggcc gctggatccccttcagggcagatcagcaaccaggccctggctctggcccc tagctccgctccagtgctggcccagactatggtgccctctagtgctatgg tgcctctggcccagccacctgctccagcccctgtgctgaccccaggacca ccccagtcactgagcgctccagtgcccaagtctacacaggccggcgaggg gactctgagtgaagctctgctgcacctgcagttcgacgctgatgaggacc tgggagctctgctggggaacagcaccgatcccggagtgttcacagatctg gcctccgtggacaactctgagtttcagcagctgctgaatcagggcgtgtc catgtctcatagtacagccgaaccaatgctgatggagtaccccgaagcca ttacccggctggtgaccggcagccagcggcccccgaccccgctccaact ccctgggaaccagcggcctgcctaatgggctgtccggagatgaagactt ctcaagcatcgctgatatggactttagtgccctgctgtcacagatttcct ctagtgggcagggaggaggtggaagcggcttcagcgtggacaccagtgcc ctgctggacctgttcagcccctcggtgaccgtgcccgacatgagcctgcc tgaccttgacagcagcctggccagtatccaagagctcctgtctccccagg agccccccaggcctcccgaggcagagaacagcagcccggattcagggaag cagctggtgcactacacagcgcagccgctgttcctgctggaccccggctc -continued cgtggacaccgggagcaacgacctgccggtgctgtttgagctgggagagg gctcctacttctccgaaggggacggcttcgccgaggaccccaccatctcc ctgctgacaggctcggagcctcccaaagccaaggaccccactgtctccta a Constructs containing modified sequences of destabilization domains are provided below. The modified destabilizations domains (indicated by underlining) are compatible (i.e. functioning) with low temperatures, such as body temperatures of cold-blooded animals. These constructs, in particular the modified destabilization domains can be used in gene drive experiments.

(SEQ ID NO: 101)

TGCCCACGGAGACGTCAAaccggtGGATCTAATTCAATTAGAGACTAATT

CAATTAGAGCTAATTCAATTAGGATCCAAGCTTATCGATTTCGAACCCTCGACCGCC

GGAGTATAAATAGAGGCGCTTCGTCTACGGAGCGACAATTCAATTCAAACAAGCAA

AGTGAACACGTCGCTAAGCGAAAGCTAAGCAAATAAACAAGCGCAGCTGAACAAG

CTAAACAATCGGCTCGAAGCCGGTCGCCACCatgGCCTCCTCCGAGGACGTCATCAAG

GAGTTCATGCGCTTCAAGGTGCGCATGGAGGGCTCCGTGAACGGCCACGAGTTCGA

GATCGAGGGCGAGGGCGAGGGCCGCCCCTACGAGGGCACCCAGACCGCCAAGCTG

AAGGTGACCAAGGGCGGCCCCCTGCCCTTCGCCTGGGACATCCTGTCCCCCCAGTTC

CAGTACGGCTCCAAGGTGTACGTGAAGCACCCCGCCGACATCCCCGACTACAAGAA

GCTGTCCTTCCCCGAGGGCTTCAAGTGGGAGCGCGTGATGAACTTCGAGGACGGCG

GCGTGGTGACCGTGACCCAGGACTCCTCCCTcCAGGACGGCTCCTTCATCTACAAGG

TGAAGTTCATCGGCGTGAACTTCCCCTCCGACGGCCCCGTAATGCAGAAGAAGACT

ATGGGCTGGGAGGCgTCCACCGAGCGCCTGTACCCCCGCGACGGCGTGCTGAAGGG

CGAGATCCACAAGGCCCTGAAGCTGAAGGACGGCGGCCACTACCTGGTGGAGTTCA

AGTCCATCTACATGGCCAAGAAGCCCGTGCAGCTGCCCGGCTACTACTACGTGGACT

CCAAGCTGGACATCACCTCCCACAACGAGGACTACACCATCGTGGAGCAGTACGAG

CGCGCCGAGGGCCGCCACCACCTGTTCCTGTAGgggccGCGACTCTAGATCATAATCA

GCCATACCACATTTGTAGAGGTTTTACTTGCTTTAAAAAACCTCCCACACCTCCCCCT

GAACCTGAAACATAAAATGAATGCAATTGTTGTTGTTAACTTGTTTATTGCAGCTTA

TAATGGTTACaaataaaGCAATAGCATCACAAATTTCACaaataaaGCATTTTTTTCACTGCA

TTCTAGTTGTGGTTTGTCCAAACTCATCAATGTATCTTAaccggtGGATCCCTGCAGCTG

GTTGTAGGTGCAGTTGCGCTTCTTGCACTTGGCGCACTTGAGGAGATCGGTCTTGGT

GCCCTGCACGGTGGCCAGCTGGGCATCGTTGATGGCCTCCTTGACGAACTTCTCGCG

CAGCTTCTTCATCTCGTCGCTGGCCATCTCCTCCGGCGTCATTTTGGCCAGCTGCTTG

GCAGTGACGGCGCCGCACATAAAGTTGCCGCGCAATCCAGGATTCTTGGGGTCCTTC

AGATTGGCCACGCGTGACCTAATGCGATTCTTGTACTTCATATCCGTGTTATTGAACT

CGGAGTAAATGGCATCCTCCAGTTCGGCGGCCATTTCCTCCGGCTCACCGCATCCTT

CGGGCACTTCACCAATCTTCAGTGCGGTGGCCAGCATTTCGCGGCATTTGATGCGGA

CCGCATCTGTCATGCCGCCGGAGGGAAACGAGGTCTGTGACGAGGATGTCGAGCCT

TTCTTCTCTTTATCCTTGGATGAGCTGGATGAACTGGACTTATCCTTGCCGGAGATTG

ACGACGACGACTTGGCGGCACTGGTGGACTTCGAGGCACTGCTGTTGTTGGAGGAG

CCCTCCTTAGCGGAGCTGTTGTTCGGTGTGGTTGGCGCCGGGCTGGCGAGGAATCGT

TTCCAGTTCTTGATCAGCGTCTTGGCCAGAGCGATCACCTCGTCGTCCTTGCTACTCT

TGCGCAGCTCGTTTACGGTCATGCCGATGCGCGTTTTGGTCAGAATGTCGAGATTGA

-continued

TGTTAAGCGTTTGCAGGGCCTTCAGCAGGTCCAGAGCCTGATCCTGTCCCTGTACGG

TGGATATATGTATATTTGTGACATGATGCGCGGCACGTTAGCTAATCCCGATACTTA

CTGTGCCGTCGCTGGCCATCTTGCTCATCTTCTTTTGGATTCGAAACACTTCCTCCTC

CACGCTCATTTTGGCCCACTTAATTTGATCAGAGGTTAGGTTAACTGGCGTCGGCTG

TCGGCTTTAATCGGTGCTGCGGGTCTGCGACAGTTGTTTATGCGGAAGCCGGGCTAT

TTCTTTTTTTCCCTCCAATAAATGTTGTTTACTATTTTTTTCGTTTCTGTATTCGCAGA

ACGAGTTGACAGAACACCCTAACGCGTTTTAGTGTTACCGGGCGGTGGCTTGTCAAG

AAATGCCTTCCCATGGCTAATACAATTCCCAACTGGAAGTAGTTTGGGTTTCAGAAG

TCAACAGTGTTACCGTATTTTAATGTACATCTGGCTTTTAAGCGAGTACACACACAT

AGCATTGCGATGTTTTTTAAACTTGCACTGCTTGCAAGCAGGGCTCCACTGTATTTCA

ATGAAAGAACAGCGTGTTGGGCGTTTTTGAATTATACTAATTACCTTCAATAACAAT

TCCCTATATATCACTTAGTTTTAATAAATAAATCGTTTGAGTGTGGTCTAGAGATGAT

GTATTATGATGAAGTGCGGTTGTTGGGGACAAGCGGGATACGTCTGCGGGTCAAAT

CGGCGGTGGGACATAGTGAGAGGGCAACGGCTCCAAAACCAAGCGTTGCGAACAAT

CACCAACGCGCCCTGGTACGCGAGAAATGTTGATATCGCACATGACCTCAGCATCC

ACCTTCAGTTTGAGAACAAATTAAATCAGGCACATACCAGACAACCAGGAGAACAC

TGAGGAGGCGTCATCAAAGATATCTTTGGACACGTGGCATAAACAAGCCAAACTAT

TATCTAATCAATATTTTTATACAAATTTTGTATGTTTCCATGTTATCTTCGTTGCTCCT

GTTAGTTACTACGTTTCATAGCCCTTAAATTGGTTGCTTAACGTAAAATAAAATTATA

TTGTATAAAAATAAAGAGGAATTCACCTATAACAAACGAAAAAGTAAATAAATAAG

AACTTCCCCATGTTAAAAATGCCACCACCATCTTTACATATAAGTATGTACATATGA

ATGAATCACTTAGGTTGCTTGAATATTACAATTTCATTAATAGCTAAATCACATTTGA

TGTGTTAGTGGAAAACGGCTATATATATAAATTATCGAAATTGTGAATATCGAATTG

CGATAGCACAATGGGAAATTCCACCACTAGATTTTTGGTACTTTTAACAGATCCTTTT

CGGTTTTGCGTTGCGCGAAGTGATCTGAACTTATCAAAGTTTGTAAGGTAATACATA

AAGTGAAAAAGAATTAATTTGCTCTTGAAAGGCAGGCCAAATTAAAAAAAAAAATAT

CAATCGGTACCAGATCTGGCGCGCCTAGAATGGACTATAAGGACCACGACGGAGAC

TACAAGGATCATGATATTGATTACAAAGACGATGACGATAAGATGGCCCCAAAGAA

GAAGCGGAAGGTCGGTATCCACGGAGTCCCAGCAGCCGGATCCATCAGTCTGATTG

CGGCGTTAGCGGTAGATCACGTTATCGGCATGGAAAACGCCATGCCGTGGAACCTG

CCTGCCGATCTCGCCTGGTTTAAACGCAACACCTTAAATAAACCCGTGATTATGGGC

CGCCATACCTGGGAATCAATCGGTCGTCCGTTGCCAGGACGCAAAAATATTATCCTC

TGCAGTCAACCGAGTACGGACGATCGCGTAACGTGGGTGAAGTCGGTGGGTGAAGC

CATCGCGGCGTGTGGTGACGTACCAGAAATCATGGTGATTGGCGGCGGTCGCGTTCA

TGAACAGTTCTTGCCAAAAGCGCAAAAACTGTATCTGACGCATATCGACGCAGAAG

TGGAAGGCGACACCCATTTCCCGGATTACGAGCCGGATGACTGGGAACCGGTATTC

AACGAATTCCACGATGCTGATGCGCAAAACTCTCACAGCTACCGCTTTGAGACTCTG

GGGCGACGAGGAAGCGGAAGCGGATCCGACAAGAAGTACAGCATCGGCCTGGACA

TCGGCACCAACTCTGTGGGCTGGGCCGTGATCACCGACGAGTACAAGGTGCCCAGC

AAGAAATTCAAGGTGCTGGGCAACACCGACCGGCACAGCATCAAGAAGAACCTGAT

CGGAGCCCTGCTGTTCGACAGCGGCGAAACAGCCGAGGCCACCCGGCTGAAGAGAA

-continued

CCGCCAGAAGAAGATACACCAGACGGAAGAACCGGATCTGCTATCTGCAAGAGATC

TTCAGCAACGAGATGGCCAAGGTGGACGACAGCTTCTTCCACAGACTGGAAGAGTC

CTTCCTGGTGGAAGAGGATAAGAAGCACGAGCGGCACCCCATCTTCGGCAACATCG

TGGACGAGGTGGCCTACCACGAGAAGTACCCCACCATCTACCACCTGAGAAAGAAA

CTGGTGGACAGCACCGACAAGGCCGACCTGCGGCTGATCTATCTGGCCCTGGCCCA

CATGATCAAGTTCCGGGGCCACTTCCTGATCGAGGGCGACCTGAACCCCGACAACA

GCGACGTGGACAAGCTGTTCATCCAGCTGGTGCAGACCTACAACCAGCTGTTCGAG

GAAAACCCCATCAACGCCAGCGGCGTGGACGCCAAGGCCATCCTGTCTGCCAGACT

GAGCAAGAGCAGACGGCTGGAAAATCTGATCGCCCAGCTGCCCGGCGAGAAGAAG

AATGGCCTGTTCGGCAACCTGATTGCCCTGAGCCTGGGCCTGACCCCCAACTTCAAG

AGCAACTTCGACCTGGCCGAGGATGCCAAACTGCAGCTGAGCAAGGACACCTACGA

CGACGACCTGGACAACCTGCTGGCCCAGATCGGCGACCAGTACGCCGACCTGTTTCT

GGCCGCCAAGAACCTGTCCGACGCCATCCTGCTGAGCGACATCCTGAGAGTGAACA

CCGAGATCACCAAGGCCCCCCTGAGCGCCTCTATGATCAAGAGATACGACGAGCAC

CACCAGGACCTGACCCTGCTGAAAGCTCTCGTGCGGCAGCAGCTGCCTGAGAAGTA

CAAAGAGATTTTCTTCGACCAGAGCAAGAACGGCTACGCCGGCTACATTGACGGCG

GAGCCAGCCAGGAAGAGTTCTACAAGTTCATCAAGCCCATCCTGGAAAAGATGGAC

GGCACCGAGGAACTGCTCGTGAAGCTGAACAGAGAGGACCTGCTGCGGAAGCAGC

GGACCTTCGACAACGGCAGCATCCCCCACCAGATCCACCTGGGAGAGCTGCACGCC

ATTCTGCGGCGGCAGGAAGATTTTTACCCATTCCTGAAGGACAACCGGGAAAAGAT

CGAGAAGATCCTGACCTTCCGCATCCCCTACTACGTGGGCCCTCTGGCCAGGGGAAA

CAGCAGATTCGCCTGGATGACCAGAAAGAGCGAGGAAACCATCACCCCCTGGAACT

TCGAGGAAGTGGTGGACAAGGGCGCTTCCGCCCAGAGCTTCATCGAGCGGATGACC

AACTTCGATAAGAACCTGCCCAACGAGAAGGTGCTGCCCAAGCACAGCCTGCTGTA

CGAGTACTTCACCGTGTATAACGAGCTGACCAAAGTGAAATACGTGACCGAGGGAA

TGAGAAAGCCCGCCTTCCTGAGCGGCGAGCAGAAAAAGGCCATCGTGGACCTGCTG

TTCAAGACCAACCGGAAAGTGACCGTGAAGCAGCTGAAAGAGGACTACTTCAAGAA

AATCGAGTGCTTCGACTCCGTGGAAATCTCCGGCGTGGAAGATCGGTTCAACGCCTC

CCTGGGCACATACCACGATCTGCTGAAAATTATCAAGGACAAGGACTTCCTGGACA

ATGAGGAAAACGAGGACATTCTGGAAGATATCGTGCTGACCCTGACACTGTTTGAG

GACAGAGAGATGATCGAGGAACGGCTGAAAACCTATGCCCACCTGTTCGACGACAA

AGTGATGAAGCAGCTGAAGCGGCGGAGATACACCGGCTGGGGCAGGCTGAGCCGG

AAGCTGATCAACGGCATCCGGGACAAGCAGTCCGGCAAGACAATCCTGGATTTCCT

GAAGTCCGACGGCTTCGCCAACAGAAACTTCATGCAGCTGATCCACGACGACAGCC

TGACCTTTAAAGAGGACATCCAGAAAGCCCAGGTGTCCGGCCAGGGCGATAGCCTG

CACGAGCACATTGCCAATCTGGCCGGCAGCCCCGCCATTAAGAAGGGCATCCTGCA

GACAGTGAAGGTGGTGGACGAGCTCGTGAAAGTGATGGGCCGGCACAAGCCCGAG

AACATCGTGATCGAAATGGCCAGAGAGAACCAGACCACCCAGAAGGGACAGAAGA

ACAGCCGCGAGAGAATGAAGCGGATCGAAGAGGGCATCAAAGAGCTGGGCAGCCA

GATCCTGAAAGAACACCCCGTGGAAAACACCCAGCTGCAGAACGAGAAGCTGTACC

-continued

TGTACTACCTGCAGAATGGGCGGGATATGTACGTGGACCAGGAACTGGACATCAAC

CGGCTGTCCGACTACGATGTGGACCATATCGTGCCTCAGAGCTTTCTGAAGGACGAC

TCCATCGACAACAAGGTGCTGACCAGAAGCGACAAGAACCGGGGCAAGAGCGACA

ACGTGCCCTCCGAAGAGGTCGTGAAGAAGATGAAGAACTACTGGCGGCAGCTGCTG

AACGCCAAGCTGATTACCCAGAGAAAGTTCGACAATCTGACCAAGGCCGAGAGAGG

CGGCCTGAGCGAACTGGATAAGGCCGGCTTCATCAAGAGACAGCTGGTGGAAACCC

GGCAGATCACAAAGCACGTGGCACAGATCCTGGACTCCCGGATGAACACTAAGTAC

GACGAGAATGACAAGCTGATCCGGGAAGTGAAAGTGATCACCCTGAAGTCCAAGCT

GGTGTCCGATTTCCGGAAGGATTTCCAGTTTTACAAAGTGCGCGAGATCAACAACTA

CCACCACGCCCACGACGCCTACCTGAACGCCGTCGTGGGAACCGCCCTGATCAAAA

AGTACCCTAAGCTGGAAAGCGAGTTCGTGTACGGCGACTACAAGGTGTACGACGTG

CGGAAGATGATCGCCAAGAGCGAGCAGGAAATCGGCAAGGCTACCGCCAAGTACTT

CTTCTACAGCAACATCATGAACTTTTTCAAGACCGAGATTACCCTGGCCAACGGCGA

GATCCGGAAGCGGCCTCTGATCGAGACAAACGGCGAAACCGGGGAGATCGTGTGGG

ATAAGGGCCGGGATTTTGCCACCGTGCGGAAAGTGCTGAGCATGCCCCAAGTGAAT

ATCGTGAAAAAGACCGAGGTGCAGACAGGCGGCTTCAGCAAAGAGTCTATCCTGCC

CAAGAGGAACAGCGATAAGCTGATCGCCAGAAAGAAGGACTGGGACCCTAAGAAG

TACGGCGGCTTCGACAGCCCCACCGTGGCCTATTCTGTGCTGGTGGTGGCCAAAGTG

GAAAAGGGCAAGTCCAAGAAACTGAAGAGTGTGAAAGAGCTGCTGGGGATCACCA

TCATGGAAAGAAGCAGCTTCGAGAAGAATCCCATCGACTTTCTGGAAGCCAAGGGC

TACAAAGAAGTGAAAAAGGACCTGATCATCAAGCTGCCTAAGTACTCCCTGTTCGA

GCTGGAAAACGGCCGGAAGAGAATGCTGGCCTCTGCCGGCGAACTGCAGAAGGGA

AACGAACTGGCCCTGCCCTCCAAATATGTGAACTTCCTGTACCTGGCCAGCCACTAT

GAGAAGCTGAAGGGCTCCCCCGAGGATAATGAGCAGAAACAGCTGTTTGTGGAACA

GCACAAGCACTACCTGGACGAGATCATCGAGCAGATCAGCGAGTTCTCCAAGAGAG

TGATCCTGGCCGACGCTAATCTGGACAAAGTGCTGTCCGCCTACAACAAGCACCGG

GATAAGCCCATCAGAGAGCAGGCCGAGAATATCATCCACCTGTTTACCCTGACCAA

TCTGGGAGCCCCTGCCGCCTTCAAGTACTTTGACACCACCATCGACCGGAAGAGGTA

CACCAGCACCAAAGAGGTGCTGGACGCCACCCTGATCCACCAGAGCATCACCGGCC

TGTACGAGACACGGATCGACCTGTCTCAGCTGGGAGGCGACAAAAGGCCGGCGGCC

ACGAAAAAGGCCGGCCAGGCAAAAAAGAAAAAGatcagtctgattgcggcgttagcggtagatcacgttat cggcatggaaaccgtcatgccgtggaacctgcctgccgatctcgcctggtttaaacgcaacaccttaaataaacccgtgattatgggccgcc atacctgggaatcaatcggtcgtccgttgccaggacgcaaaaatattatcctcagcagtcaaccgagtacggacgatcgcgtaacgtgggt gaagtcggtggatgaagccatcgcggcgtgtggtgacgtaccagaaatcatggttattggcggcggtcgcgtttatgaacagttcttgccaa aagcgcaaaaactgtatctgacgcatatcgacgcagaagtggaaggcgacacccatttcccggattacgagccggatgactgggaatcgg tattcagcgaattccacgatgctgatgcgcagaactctcacagctattgctttgagattctggagcggcgaTAATCTAGGCCTGA

GCTCAATGTATGGACATAGATTTCAAATAATTAAATGTAATGCAGTAATTGATGTAA

TTAGTTAAATAAGTTAGATATTAATAACATATTAATTATATGTATTATAACGCATAT

AATAATAAAATGCATATTTAGGATATGCAAGCCATTCGAATTTTCTATTTTAATTTCC

TTTTACAAAGAAATGTATAACAAAATATAATTTGAAAAAATGTTCTGGCTCTAATTC

GATTTCTTTTAAGTATTTTGTGAACTGCTTTTAATAACGAGCGGTTGCAAAACTTAAC

-continued

AGAAACGTGCACTTTGATCCCAACTAATACCGTGTACTATCACGTGTTTGGTTTTAA

GTACTCATCCTTCGTGTTTCGTTGTTTGTTGTTTGCCTTGCTGTACACTTGGCTCTTGC

GCTCTCTCGCTCTCCGTTGGAGCCGGCTTTTTGAATGCATGCCTCGCCCTGCTCGCGC

CCAGTCCTCCTCCCCCGAAAAGCATGCCGACCAGCAAATGTTGCCCTTTTGCGTTTG

CTGTCTTTGCAGAAGCAAAATCAATAACTGAGAAATCCACCACACTGCTGCTCTTCG

TGTTGCTAGCttccagtgtccaaaacccacagccgaccacactcatccactttaatgcggtaggcagtggtaatactgttggcgcaa tctccagctgtatttgagcgccaatctggatacggaattagctccggtgaacccgtcaaactgcggtccatgtttatataggtcagagtggccg gaatccctaaaaaataaaataggagaattagcagggccaaactattattgaggcactaaataaagtttgttttgaatatttaattaactggaatttc tgcctaaattccttctttggattattatactaagcaatgttgcaagttatcgctgtctgttttctggataatatgtaaatgcatacagatgtaaaggta aattagaatcgcttatgtttggcatttaattatttatatacctatttgtcattattttggacacaaggaatcataagcaatggtaactgccgtgctaat ggctctttttttctgcttgtacatctactggaagtttatgttaaaagatccccggctatatgtacttcagtcataattggcactattgcaagttgcgtgc aatttgcgatgtcattagccgtctgaagcaattgcgtctgacatcattatcaatatgtataccatatatcgctgttaaatgtatatgtggccattggc agtatttcgaccgatttccgctccagttcttttccttctttatttcttcgttaattgaatttaaagacatttattgtttctgggaacttttaatgtttttatagc aggcgagtgagactgcaacgaccagaaaatatagcttttatcgatttaccgacccatcttcttaaaaatcaaaccaggcgtttttgctttacaaa gtaaccgggggttgcgataaatatacatttgagcataatgcacctttcaatctttatttaattcataacttttaaaataacaatctaattcagtcaaat ataaagtatttgaacaaatttatattttgacatgtgctctttcagtcctaaaacctcgcaacAAGGGCGAATTCTGCAGATAT

CCATCACACTGGCGGCCGCTCGAGCATGCATCTAGAGGGCCCAATTCGCCCTATAGT

GAGTCGTATTACAATTCACTGGCCGTCGTTTTACAACGTCGTGACTGGGAAAACCCT

GGCGTTACCCAACTTAATCGCCTTGCAGCACATCCCCCTTTCGCCAGCTGGCGTAAT

AGCGAAGAGGCCCGCACCGATCGCCCTTCCCAACAGTTGCGCAGCCTGAATGGCGA

ATGGACGCGCCCTGTAGCGGCGCATTAAGCGCGGCGGGTGTGGTGGTTACGCGCAG

CGTGACCGCTACACTTGCCAGCGCCCTAGCGCCCGCTCCTTTCGCTTTCTTCCCTTCC

TTTCTCGCCACGTTCGCCGGCTTTCCCCGTCAAGCTCTAAATCGGGGGCTCCCTTTAG

GGTTCCGATTTAGTGCTTTACGGCACCTCGACCCCAAAAAACTTGATTAGGGTGATG

GTTCACGTAGTGGGCCATCGCCCTGATAGACGGTTTTTCGCCCTTTGACGTTGGAGT

CCACGTTCTTTAATAGTGGACTCTTGTTCCAAACTGGAACAACACTCAACCCTATCTC

GGTCTATTCTTTTGATTTATAAGGGATTTTGCCGATTTCGGCCTATTGGTTAAAAAAT

GAGCTGATTTAACAAAAATTTAACGCGAATTTTAACAAAATTCAGGGCGCAAGGGC

TGCTAAAGGAAGCGGAACACGTAGAAAGCCAGTCCGCAGAAACGGTGCTGACCCCG

GATGAATGTCAGCTACTGGGCTATCTGGACAAGGGAAAACGCAAGCGCAAAGAGAA

AGCAGGTAGCTTGCAGTGGGCTTACATGGCGATAGCTAGACTGGGCGGTTTTATGGA

CAGCAAGCGAACCGGAATTGCCAGCTGGGGCGCCCTCTGGTAAGGTTGGGAAGCCC

TGCAAAGTAAACTGGATGGCTTTCTTGCCGCCAAGGATCTGATGGCGCAGGGGATC

AAGATCTGATCAAGAGACAGGATGAGGATCGTTTCGCATGATTGAACAAGATGGAT

TGCACGCAGGTTCTCCGGCCGCTTGGGTGGAGAGGCTATTCGGCTATGACTGGGCAC

AACAGACAATCGGCTGCTCTGATGCCGCCGTGTTCCGGCTGTCAGCGCAGGGGCGC

CCGGTTCTTTTTGTCAAGACCGACCTGTCCGGTGCCCTGAATGAACTGCAGGACGAG

GCAGCGCGGCTATCGTGGCTGGCCACGACGGGCGTTCCTTGCGCAGCTGTGCTCGAC

GTTGTCACTGAAGCGGGAAGGGACTGGCTGCTATTGGGCGAAGTGCCGGGGCAGGA

TCTCCTGTCATCCCACCTTGCTCCTGCCGAGAAAGTATCCATCATGGCTGATGCAAT

-continued

GCGGCGGCTGCATACGCTTGATCCGGCTACCTGCCCATTCGACCACCAAGCGAAAC

ATCGCATCGAGCGAGCACGTACTCGGATGGAAGCCGGTCTTGTCGATCAGGATGAT

CTGGACGAAGAGCATCAGGGGCTCGCGCCAGCCGAACTGTTCGCCAGGCTCAAGGC

GCGCATGCCCGACGGCGAGGATCTCGTCGTGACCCATGGCGATGCCTGCTTGCCGA

ATATCATGGTGGAAAATGGCCGCTTTTCTGGATTCATCGACTGTGGCCGGCTGGGTG

TGGCGGACCGCTATCAGGACATAGCGTTGGCTACCCGTGATATTGCTGAAGAGCTTG

GCGGCGAATGGGCTGACCGCTTCCTCGTGCTTTACGGTATCGCCGCTCCCGATTCGC

AGCGCATCGCCTTCTATCGCCTTCTTGACGAGTTCTTCTGAATTGAAAAAGGAAGAG

TATGAGTATTCAACATTTCCGTGTCGCCCTTATTCCCTTTTTTGCGGCATTTTGCCTTC

CTGTTTTTGCTCACCCAGAAACGCTGGTGAAAGTAAAAGATGCTGAAGATCAGTTGG

GTGCACGAGTGGGTTACATCGAACTGGATCTCAACAGCGGTAAGATCCTTGAGAGTT

TTCGCCCCGAAGAACGTTTTCCAATGATGAGCACTTTTAAAGTTCTGCTATGTGGCG

CGGTATTATCCCGTATTGACGCCGGGCAAGAGCAACTCGGTCGCCGCATACACTATT

CTCAGAATGACTTGGTTGAGTACTCACCAGTCACAGAAAAGCATCTTACGGATGGCA

TGACAGTAAGAGAATTATGCAGTGCTGCCATAACCATGAGTGATAACACTGCGGCC

AACTTACTTCTGACAACGATCGGAGGACCGAAGGAGCTAACCGCTTTTTTGCACAAC

ATGGGGGATCATGTAACTCGCCTTGATCGTTGGGAACCGGAGCTGAATGAAGCCAT

ACCAAACGACGAGCGTGACACCACGATGCCTGTAGCAATGGCAACAACGTTGCGCA

AACTATTAACTGGCGAACTACTTACTCTAGCTTCCCGGCAACAATTAATAGACTGGA

TGGAGGCGGATAAAGTTGCAGGACCACTTCTGCGCTCGGCCCTTCCGGCTGGCTGGT

TTATTGCTGATAAATCTGGAGCCGGTGAGCGTGGGTCTCGCGGTATCATTGCAGCAC

TGGGGCCAGATGGTAAGCCCTCCCGTATCGTAGTTATCTACACGACGGGGAGTCAG

GCAACTATGGATGAACGAAATAGACAGATCGCTGAGATAGGTGCCTCACTGATTAA

GCATTGGTAACTGTCAGACCAAGTTTACTCATATATACTTTAGATTGATTTAAAACTT

CATTTTTAATTTAAAAGGATCTAGGTGAAGATCCTTTTTGATAATCTCATGACCAAA

ATCCCTTAACGTGAGTTTTCGTTCCACTGAGCGTCAGACCCCGTAGAAAAGATCAAA

GGATCTTCTTGAGATCCTTTTTTTCTGCGCGTAATCTGCTGCTTGCAAACAAAAAAAC

CACCGCTACCAGCGGTGGTTTGTTTGCCGGATCAAGAGCTACCAACTCTTTTTCCGA

AGGTAACTGGCTTCAGCAGAGCGCAGATACCAAATACTGTTCTTCTAGTGTAGCCGT

AGTTAGGCCACCACTTCAAGAACTCTGTAGCACCGCCTACATACCTCGCTCTGCTAA

TCCTGTTACCAGTGGCTGCTGCCAGTGGCGATAAGTCGTGTCTTACCGGGTTGGACT

CAAGACGATAGTTACCGGATAAGGCGCAGCGGTCGGGCTGAACGGGGGGTTCGTGC

ACACAGCCCAGCTTGGAGCGAACGACCTACACCGAACTGAGATACCTACAGCGTGA

GCTATGAGAAAGCGCCACGCTTCCCGAAGGGAGAAAGGCGGACAGGTATCCGGTAA

GCGGCAGGGTCGGAACAGGAGAGCGCACGAGGGAGCTTCCAGGGGGAAACGCCTG

GTATCTTTATAGTCCTGTCGGGTTTCGCCACCTCTGACTTGAGCGTCGATTTTTGTGA

TGCTCGTCAGGGGGGCGGAGCCTATGGAAAAACGCCAGCAACGCGGCCTTTTTACG

GTTCCTGGCCTTTTGCTGGCCTTTTGCTCACATGTTCTTTCCTGCGTTATCCCCTGATT

CTGTGGATAACCGTATTACCGCCTTTGAGTGAGCTGATACCGCTCGCCGCAGCCGAA

CGACCGAGCGCAGCGAGTCAGTGAGCGAGGAAGCGGAAGAGCGCCCAATACGCAA

ACCGCCTCTCCCCGCGCGTTGGCCGATTCATTAATGCAGCTGGCACGACAGGTTTCC

-continued

CGACTGGAAAGCGGGCAGTGAGCGCAACGCAATTAATGTGAGTTAGCTCACTCATT

AGGCACCCCAGGCTTTACACTTTATGCTTCCGGCTCGTATGTTGTGTGGAATTGTGA

GCGGATAACAATTTCACACAGGAAACAGCTATGACCATGATTACGCCAAGCTATTTA

GGTGACACTATAGAATACTCAAGCTATGCATCAAGCTTGGTACCGAGCTCGGATCCA

CTAGTAACGGCCGCCAGTGTGCTGGAATTCGCCCTTctggagactacattgcctgaattggcgggcaaat aagtgcgacttggaggaggcggcgaggaagcccagctggtctgaggtttctgtggcaagacaggacgatattgtttcgtatataacggtgg acccattggcaaaacggcttgttttggtattgaaacggtatttggcggcccataggcgttattcctcaaatcacacacagtattctcaattaaagt ggccaagggagccgtgtaaattcggaaattagtatctgaataatccaagtcagacagcaagaaaacgggcatcctatcggatagaacccaa acgtttttgttctcatcaattttcacatcggccggaaaaactaagccaacgtcatcgcgatccacaatgccatgaaattgcggtgagtacggca ttgatgagtgccagcaacccactgcattttgatctattaaattgaacagctcaattccatcatcgctcatcacacgtgaagtggtatgggagtttg gaccccgttcatctaaggcaacaaagtcatgatagctatcttccgtcctggtttcatccctcaaaatcctcgtggatacggcaaattgtcgatga cttgctaacggactaaagtacagggtacgataaccatccgatcgaatgggcgaaagggacataccaaatataccctcctcgccccattgga agttaataccagcgacattgaaatcgcccctcaatggatcggggaaaaaatacgaatgtgccgagaatctccaggacttgttcagttcccag gagtaagcaatcaagccgtatcccaattcatcggcaaaataggcatatgcatcatcgcaatttttgcctatatccacggcaatgttagctatgaa agtatttggatttgtgtccacgccaggtagctcgtatctccgaattcgcgtatccgtggtcaagtcaaagacatttaccgcataggggcacgga ttagtGGTGGTATTGCCGA (SEQ ID NO: 102)

TGCCCACGGAGACGTCAAaccggtGGATCTAATTCAATTAGAGACTAATT

CAATTAGAGCTAATTCAATTAGGATCCAAGCTTATCGATTTCGAACCCTCGACCGCC

GGAGTATAAATAGAGGCGCTTCGTCTACGGAGCGACAATTCAATTCAAACAAGCAA

AGTGAACACGTCGCTAAGCGAAAGCTAAGCAAATAAACAAGCGCAGCTGAACAAG

CTAAACAATCGGCTCGAAGCCGGTCGCCACCatgGCCTCCTCCGAGGACGTCATCAAG

GAGTTCATGCGCTTCAAGGTGCGCATGGAGGGCTCCGTGAACGGCCACGAGTTCGA

GATCGAGGGCGAGGGCGAGGGCCGCCCCTACGAGGGCACCCAGACCGCCAAGCTG

AAGGTGACCAAGGGCGGCCCCCTGCCCTTCGCCTGGGACATCCTGTCCCCCCAGTTC

CAGTACGGCTCCAAGGTGTACGTGAAGCACCCCGCCGACATCCCCGACTACAAGAA

GCTGTCCTTCCCCGAGGGCTTCAAGTGGGAGCGCGTGATGAACTTCGAGGACGGCG

GCGTGGTGACCGTGACCCAGGACTCCTCCCTcCAGGACGGCTCCTTCATCTACAAGG

TGAAGTTCATCGGCGTGAACTTCCCCTCCGACGGCCCCGTAATGCAGAAGAAGACT

ATGGGCTGGGAGGCgTCCACCGAGCGCCTGTACCCCCGCGACGGCGTGCTGAAGGG

CGAGATCCACAAGGCCCTGAAGCTGAAGGACGGCGGCCACTACCTGGTGGAGTTCA

AGTCCATCTACATGGCCAAGAAGCCCGTGCAGCTGCCCGGCTACTACTACGTGGACT

CCAAGCTGGACATCACCTCCCACAACGAGGACTACACCATCGTGGAGCAGTACGAG

CGCGCCGAGGGCCGCCACCACCTGTTCCTGTAGgggccGCGACTCTAGATCATAATCA

GCCATACCACATTTGTAGAGGTTTTACTTGCTTTAAAAAACCTCCCACACCTCCCCCT

GAACCTGAAACATAAAATGAATGCAATTGTTGTTGTTAACTTGTTTATTGCAGCTTA

TAATGGTTACaaataaaGCAATAGCATCACAAATTTCACaaataaaGCATTTTTTTCACTGCA

TTCTAGTTGTGGTTTGTCCAAACTCATCAATGTATCTTAaccggtGGATCCCTGCAGCTG

GTTGTAGGTGCAGTTGCGCTTCTTGCACTTGGCGCACTTGAGGAGATCGGTCTTGGT

-continued

GCCCTGCACGGTGGCCAGCTGGGCATCGTTGATGGCCTCCTTGACGAACTTCTCGCG

CAGCTTCTTCATCTCGTCGCTGGCCATCTCCTCCGGCGTCATTTTGGCCAGCTGCTTG

GCAGTGACGGCGCCGCACATAAAGTTGCCGCGCAATCCAGGATTCTTGGGGTCCTTC

AGATTGGCCACGCGTGACCTAATGCGATTCTTGTACTTCATATCCGTGTTATTGAACT

CGGAGTAAATGGCATCCTCCAGTTCGGCGGCCATTTCCTCCGGCTCACCGCATCCTT

CGGGCACTTCACCAATCTTCAGTGCGGTGGCCAGCATTTCGCGGCATTTGATGCGGA

CCGCATCTGTCATGCCGCCGGAGGGAAACGAGGTCTGTGACGAGGATGTCGAGCCT

TTCTTCTCTTTATCCTTGGATGAGCTGGATGAACTGGACTTATCCTTGCCGGAGATTG

ACGACGACGACTTGGCGGCACTGGTGGACTTCGAGGCACTGCTGTTGTTGGAGGAG

CCCTCCTTAGCGGAGCTGTTGTTCGGTGTGGTTGGCGCCGGGCTGGCGAGGAATCGT

TTCCAGTTCTTGATCAGCGTCTTGGCCAGAGCGATCACCTCGTCGTCCTTGCTACTCT

TGCGCAGCTCGTTTACGGTCATGCCGATGCGCGTTTTGGTCAGAATGTCGAGATTGA

TGTTAAGCGTTTGCAGGGCCTTCAGCAGGTCCAGAGCCTGATCCTGTCCCTGTACGG

TGGATATATGTATATTTGTGACATGATGCGCGGCACGTTAGCTAATCCCGATACTTA

CTGTGCCGTCGCTGGCCATCTTGCTCATCTTCTTTTGGATTCGAAACACTTCCTCCTC

CACGCTCATTTTGGCCCACTTAATTTGATCAGAGGTTAGGTTAACTGGCGTCGGCTG

TCGGCTTTAATCGGTGCTGCGGGTCTGCGACAGTTGTTTATGCGGAAGCCGGGCTAT

TTCTTTTTTTCCCTCCAATAAATGTTGTTTACTATTTTTTTCGTTTCTGTATTCGCAGA

ACGAGTTGACAGAACACCCTAACGCGTTTTAGTGTTACCGGGCGGTGGCTTGTCAAG

AAATGCCTTCCCATGGCTAATACAATTCCCAACTGGAAGTAGTTTGGGTTTCAGAAG

TCAACAGTGTTACCGTATTTTAATGTACATCTGGCTTTTAAGCGAGTACACACACAT

AGCATTGCGATGTTTTTTAAACTTGCACTGCTTGCAAGCAGGGCTCCACTGTATTTCA

ATGAAAGAACAGCGTGTTGGGCGTTTTTGAATTATACTAATTACCTTCAATAACAAT

TCCCTATATATCACTTAGTTTTAATAAATAAATCGTTTGAGTGTGGTCTAGAGATGAT

GTATTATGATGAAGTGCGGTTGTTGGGGACAAGCGGGATACGTCTGCGGGTCAAAT

CGGCGGTGGGACATAGTGAGAGGGCAACGGCTCCAAAACCAAGCGTTGCGAACAAT

CACCAACGCGCCCTGGTACGCGAGAAATGTTGATATCGCACATGACCTCAGCATCC

ACCTTCAGTTTGAGAACAAATTAAATCAGGCACATACCAGACAACCAGGAGAACAC

TGAGGAGGCGTCATCAAAGATATCTTTGGACACGTGGCATAAACAAGCCAAACTAT

TATCTAATCAATATTTTTATACAAATTTTGTATGTTTCCATGTTATCTTCGTTGCTCCT

GTTAGTTACTACGTTTCATAGCCCTTAAATTGGTTGCTTAACGTAAAATAAAATTATA

TTGTATAAAAATAAAGAGGAATTCACCTATAACAAACGAAAAAGTAAATAAATAAG

AACTTCCCCATGTTAAAAATGCCACCACCATCTTTACATATAAGTATGTACATATGA

ATGAATCACTTAGGTTGCTTGAATATTACAATTTCATTAATAGCTAAATCACATTTGA

TGTGTTAGTGGAAAACGGCTATATATATAAATTATCGAAATTGTGAATATCGAATTG

CGATAGCACAATGGGAAATTCCACCACTAGATTTTTGGTACTTTTAACAGATCCTTTT

CGGTTTTGCGTTGCGCGAAGTGATCTGAACTTATCAAAGTTTGTAAGGTAATACATA

AAGTGAAAAAGAATTAATTTGCTCTTGAAAGGCAGGCCAAATTAAAAAAAAAATAT

CAATCGGTACCAGATCTGGCGCGCCTAGAATGGACTATAAGGACCACGACGGAGAC

TACAAGGATCATGATATTGATTACAAAGACGATGACGATAAGATGGCCCCAAAGAA

GAAGCGGAAGGTCGGTATCCACGGAGTCCCAGCAGCCGGATCCATCAGTCTGATTG

-continued

CGGCGTTAGCGGTAGATCACGTTATCGGCATGGAAAACGCCATGCCGTGGAGCCTG

CCTGCCGATCTCGCCTGGTTTAAACGCAACACCTTAAATAAACCCGTGATTATGGGC

CGCCATACCTGGGAATCAATCGGTCGTCCGTTGCCAGGACGCAAAAACATTATCCTC

AGCAGTCAACCGAGTACGGACGATCGCGTAACGTGGGTGAAGTCGGCGGATGAAGC

CATCGCGGCGTGTGGTGACGTACCAGAAATCATGGTGATTGGCGGCGGTCGCGTTTA

TGAGCAGTTCTTGCCAAAAGCGCAAAAACTGTATCTGACGCATATCGACGCAGAAG

TGGGAGGCGACACCCATTTCCCGGATTACGAGCCGGATGACTGGGGATCGGTATTC

AGCGAATTCCACGATGCTGATGCGCAGAACTCTCACAGCTATTGCTTTGTGATTCTG

GGGCGGCGAGGAAGCGGAAGCGGATCCGACAAGAAGTACAGCATCGGCCTGGACA

TCGGCACCAACTCTGTGGGCTGGGCCGTGATCACCGACGAGTACAAGGTGCCCAGC

AAGAAATTCAAGGTGCTGGGCAACACCGACCGGCACAGCATCAAGAAGAACCTGAT

CGGAGCCCTGCTGTTCGACAGCGGCGAAACAGCCGAGGCCACCCGGCTGAAGAGAA

CCGCCAGAAGAAGATACACCAGACGGAAGAACCGGATCTGCTATCTGCAAGAGATC

TTCAGCAACGAGATGGCCAAGGTGGACGACAGCTTCTTCCACAGACTGGAAGAGTC

CTTCCTGGTGGAAGAGGATAAGAAGCACGAGCGGCACCCCATCTTCGGCAACATCG

TGGACGAGGTGGCCTACCACGAGAAGTACCCCACCATCTACCACCTGAGAAAGAAA

CTGGTGGACAGCACCGACAAGGCCGACCTGCGGCTGATCTATCTGGCCCTGGCCCA

CATGATCAAGTTCCGGGGCCACTTCCTGATCGAGGGCGACCTGAACCCCGACAACA

GCGACGTGGACAAGCTGTTCATCCAGCTGGTGCAGACCTACAACCAGCTGTTCGAG

GAAAACCCCATCAACGCCAGCGGCGTGGACGCCAAGGCCATCCTGTCTGCCAGACT

GAGCAAGAGCAGACGGCTGGAAAATCTGATCGCCCAGCTGCCCGGCGAGAAGAAG

AATGGCCTGTTCGGCAACCTGATTGCCCTGAGCCTGGGCCTGACCCCCAACTTCAAG

AGCAACTTCGACCTGGCCGAGGATGCCAAACTGCAGCTGAGCAAGGACACCTACGA

CGACGACCTGGACAACCTGCTGGCCCAGATCGGCGACCAGTACGCCGACCTGTTTCT

GGCCGCCAAGAACCTGTCCGACGCCATCCTGCTGAGCGACATCCTGAGAGTGAACA

CCGAGATCACCAAGGCCCCCCTGAGCGCCTCTATGATCAAGAGATACGACGAGCAC

CACCAGGACCTGACCCTGCTGAAAGCTCTCGTGCGGCAGCAGCTGCCTGAGAAGTA

CAAAGAGATTTTCTTCGACCAGAGCAAGAACGGCTACGCCGGCTACATTGACGGCG

GAGCCAGCCAGGAAGAGTTCTACAAGTTCATCAAGCCCATCCTGGAAAAGATGGAC

GGCACCGAGGAACTGCTCGTGAAGCTGAACAGAGAGGACCTGCTGCGGAAGCAGC

GGACCTTCGACAACGGCAGCATCCCCCACCAGATCCACCTGGGAGAGCTGCACGCC

ATTCTGCGGCGGCAGGAAGATTTTTACCCATTCCTGAAGGACAACCGGGAAAAGAT

CGAGAAGATCCTGACCTTCCGCATCCCCTACTACGTGGGCCCTCTGGCCAGGGGAAA

CAGCAGATTCGCCTGGATGACCAGAAAGAGCGAGGAAACCATCACCCCCTGGAACT

TCGAGGAAGTGGTGGACAAGGGCGCTTCCGCCCAGAGCTTCATCGAGCGGATGACC

AACTTCGATAAGAACCTGCCCAACGAGAAGGTGCTGCCCAAGCACAGCCTGCTGTA

CGAGTACTTCACCGTGTATAACGAGCTGACCAAAGTGAAATACGTGACCGAGGGAA

TGAGAAAGCCCGCCTTCCTGAGCGGCGAGCAGAAAAAGGCCATCGTGGACCTGCTG

TTCAAGACCAACCGGAAAGTGACCGTGAAGCAGCTGAAAGAGGACTACTTCAAGAA

AATCGAGTGCTTCGACTCCGTGGAAATCTCCGGCGTGGAAGATCGGTTCAACGCCTC

-continued

CCTGGGCACATACCACGATCTGCTGAAAATTATCAAGGACAAGGACTTCCTGGACA

ATGAGGAAAACGAGGACATTCTGGAAGATATCGTGCTGACCCTGACACTGTTTGAG

GACAGAGAGATGATCGAGGAACGGCTGAAAACCTATGCCCACCTGTTCGACGACAA

AGTGATGAAGCAGCTGAAGCGGCGGAGATACACCGGCTGGGGCAGGCTGAGCCGG

AAGCTGATCAACGGCATCCGGGACAAGCAGTCCGGCAAGACAATCCTGGATTTCCT

GAAGTCCGACGGCTTCGCCAACAGAAACTTCATGCAGCTGATCCACGACGACAGCC

TGACCTTTAAAGAGGACATCCAGAAAGCCCAGGTGTCCGGCCAGGGCGATAGCCTG

CACGAGCACATTGCCAATCTGGCCGGCAGCCCCGCCATTAAGAAGGGCATCCTGCA

GACAGTGAAGGTGGTGGACGAGCTCGTGAAAGTGATGGGCCGGCACAAGCCCGAG

AACATCGTGATCGAAATGGCCAGAGAGAACCAGACCACCCAGAAGGGACAGAAGA

ACAGCCGCGAGAGAATGAAGCGGATCGAAGAGGGCATCAAAGAGCTGGGCAGCCA

GATCCTGAAAGAACACCCCGTGGAAAACACCCAGCTGCAGAACGAGAAGCTGTACC

TGTACTACCTGCAGAATGGGCGGGATATGTACGTGGACCAGGAACTGGACATCAAC

CGGCTGTCCGACTACGATGTGGACCATATCGTGCCTCAGAGCTTTCTGAAGGACGAC

TCCATCGACAACAAGGTGCTGACCAGAAGCGACAAGAACCGGGGCAAGAGCGACA

ACGTGCCCTCCGAAGAGGTCGTGAAGAAGATGAAGAACTACTGGCGGCAGCTGCTG

AACGCCAAGCTGATTACCCAGAGAAAGTTCGACAATCTGACCAAGGCCGAGAGAGG

CGGCCTGAGCGAACTGGATAAGGCCGGCTTCATCAAGAGACAGCTGGTGGAAACCC

GGCAGATCACAAAGCACGTGGCACAGATCCTGGACTCCCGGATGAACACTAAGTAC

GACGAGAATGACAAGCTGATCCGGGAAGTGAAAGTGATCACCCTGAAGTCCAAGCT

GGTGTCCGATTTCCGGAAGGATTTCCAGTTTTACAAAGTGCGCGAGATCAACAACTA

CCACCACGCCCACGACGCCTACCTGAACGCCGTCGTGGGAACCGCCCTGATCAAAA

AGTACCCTAAGCTGGAAAGCGAGTTCGTGTACGGCGACTACAAGGTGTACGACGTG

CGGAAGATGATCGCCAAGAGCGAGCAGGAAATCGGCAAGGCTACCGCCAAGTACTT

CTTCTACAGCAACATCATGAACTTTTTCAAGACCGAGATTACCCTGGCCAACGGCGA

GATCCGGAAGCGGCCTCTGATCGAGACAAACGGCGAAACCGGGGAGATCGTGTGGG

ATAAGGGCCGGGATTTTGCCACCGTGCGGAAAGTGCTGAGCATGCCCCAAGTGAAT

ATCGTGAAAAAGACCGAGGTGCAGACAGGCGGCTTCAGCAAAGAGTCTATCCTGCC

CAAGAGGAACAGCGATAAGCTGATCGCCAGAAAGAAGGACTGGGACCCTAAGAAG

TACGGCGGCTTCGACAGCCCCACCGTGGCCTATTCTGTGCTGGTGGTGGCCAAAGTG

GAAAAGGGCAAGTCCAAGAAACTGAAGAGTGTGAAAGAGCTGCTGGGGATCACCA

TCATGGAAAGAAGCAGCTTCGAGAAGAATCCCATCGACTTTCTGGAAGCCAAGGGC

TACAAAGAAGTGAAAAAGGACCTGATCATCAAGCTGCCTAAGTACTCCCTGTTCGA

GCTGGAAAACGGCCGGAAGAGAATGCTGGCCTCTGCCGGCGAACTGCAGAAGGGA

AACGAACTGGCCCTGCCCTCCAAATATGTGAACTTCCTGTACCTGGCCAGCCACTAT

GAGAAGCTGAAGGGCTCCCCCGAGGATAATGAGCAGAAACAGCTGTTTGTGGAACA

GCACAAGCACTACCTGGACGAGATCATCGAGCAGATCAGCGAGTTCTCCAAGAGAG

TGATCCTGGCCGACGCTAATCTGGACAAAGTGCTGTCCGCCTACAACAAGCACCGG

GATAAGCCCATCAGAGAGCAGGCCGAGAATATCATCCACCTGTTTACCCTGACCAA

TCTGGGAGCCCCTGCCGCCTTCAAGTACTTTGACACCACCATCGACCGGAAGAGGTA

CACCAGCACCAAAGAGGTGCTGGACGCCACCCTGATCCACCAGAGCATCACCGGCC

-continued

TGTACGAGACACGGATCGACCTGTCTCAGCTGGGAGGCGACAAAAGGCCGGCGGCC

ACGAAAAAGGCCGGCCAGGCAAAAAAGAAAAAGatcagtctgattgcggcgttagcggtagatcacgttat cggcatggaaaccgtcatgccgtggaacctgcctgccgatctcgcctggtttaaacgcaacaccttaaataaacccgtgattatgggccgcc atacctgggaatcaatcggtcgtccgttgccaggacgcaaaaatattatcctcagcagtcaaccgagtacggacgatcgcgtaacgtgggt gaagtcggtggatgaagccatcgcggcgtgtggtgacgtaccagaaatcatggttattggcggcggtcgcgtttatgaacagttcttgccaa aagcgcaaaaactgtatctgacgcatatcgacgcagaagtggaaggcgacacccatttcccggattacgagccggatgactgggaatcgg tattcagcgaattccacgatgctgatgcgcagaactctcacagctattgctttgagattctggagcggcgaTAATCTAGGCCTGA

GCTCAATGTATGGACATAGATTTCAAATAATTAAATGTAATGCAGTAATTGATGTAA

TTAGTTAAATAAGTTAGATATTAATAACATATTAATTATATGTATTATAACGCATAT

AATAATAAAATGCATATTTAGGATATGCAAGCCATTCGAATTTTCTATTTTAATTTCC

TTTTACAAAGAAATGTATAACAAAATATAATTTGAAAAAATGTTCTGGCTCTAATTC

GATTTCTTTTAAGTATTTTGTGAACTGCTTTTAATAACGAGCGGTTGCAAAACTTAAC

AGAAACGTGCACTTTGATCCCAACTAATACCGTGTACTATCACGTGTTTGGTTTTAA

GTACTCATCCTTCGTGTTTCGTTGTTTGTTGTTTGCCTTGCTGTACACTTGGCTCTTGC

GCTCTCTCGCTCTCCGTTGGAGCCGGCTTTTTGAATGCATGCCTCGCCCTGCTCGCGC

CCAGTCCTCCTCCCCCGAAAAGCATGCCGACCAGCAAATGTTGCCCTTTTGCGTTTG

CTGTCTTTGCAGAAGCAAAATCAATAACTGAGAAATCCACCACACTGCTGCTCTTCG

TGTTGCTAGCttccagtgtccaaaacccacagccgaccacactcatccactttaatgcggtaggcagtggtaatactgttggcgcaa tctccagctgtatttgagcgccaatctggatacggaattagctccggtgaacccgtcaaactgcggtccatgtttatataggtcagagtggccg gaatccctaaaaaataaaataggagaattagcagggccaaactattattgaggcactaaataaagtttgttttgaatatttaattaactggaatttc tgcctaaattccttctttggattattatactaagcaatgttgcaagttatcgctgtctgttttctggataatatgtaaatgcatacagatgtaaaggta aattagaatcgcttatgtttggcatttaattatttatatacctatttgtcattattttggacacaaggaatcataagcaatggtaactgccgtgctaat ggctctttttttctgcttgtacatctactggaagtttatgttaaaagatccccggctatatgtacttcagtcataattggcactattgcaagttgcgtgc aatttgcgatgtcattagccgtctgaagcaattgcgtctgacatcattatcaatatgtataccatatatcgctgttaaatgtatatgtggccattggc agtatttcgaccgatttccgctccagttcttttccttctttatttcttcgttaattgaatttaaagacatttattgtttctgggaacttttaatgtttttatagc aggcgagtgagactgcaacgaccagaaaatatagcttttatcgatttaccgacccatcttcttaaaaatcaaaccaggcgttttttgctttacaaa gtaaccgggggttgcgataaatatacatttgagcataatgcacctttcaatctttatttaattcataacttttaaaataacaatctaattcagtcaaat ataaagtatttgaacaaatttatattttgacatgtgctctttcagtcctaaaacctcgcaacAAGGGCGAATTCTGCAGATAT

CCATCACACTGGCGGCCGCTCGAGCATGCATCTAGAGGGCCCAATTCGCCCTATAGT

GAGTCGTATTACAATTCACTGGCCGTCGTTTTACAACGTCGTGACTGGGAAAACCCT

GGCGTTACCCAACTTAATCGCCTTGCAGCACATCCCCCTTTCGCCAGCTGGCGTAAT

AGCGAAGAGGCCCGCACCGATCGCCCTTCCCAACAGTTGCGCAGCCTGAATGGCGA

ATGGACGCGCCCTGTAGCGGCGCATTAAGCGCGGCGGGTGTGGTGGTTACGCGCAG

CGTGACCGCTACACTTGCCAGCGCCCTAGCGCCCGCTCCTTTCGCTTTCTTCCCTTCC

TTTCTCGCCACGTTCGCCGGCTTTCCCCGTCAAGCTCTAAATCGGGGGCTCCCTTTAG

GGTTCCGATTTAGTGCTTTACGGCACCTCGACCCCAAAAAACTTGATTAGGGTGATG

GTTCACGTAGTGGGCCATCGCCCTGATAGACGGTTTTTCGCCCTTTGACGTTGGAGT

CCACGTTCTTTAATAGTGGACTCTTGTTCCAAACTGGAACAACACTCAACCCTATCTC

GGTCTATTCTTTTGATTTATAAGGGATTTTGCCGATTTCGGCCTATTGGTTAAAAAAT

GAGCTGATTTAACAAAAATTTAACGCGAATTTTAACAAAATTCAGGGCGCAAGGGC

-continued

TGCTAAAGGAAGCGGAACACGTAGAAAGCCAGTCCGCAGAAACGGTGCTGACCCCG

GATGAATGTCAGCTACTGGGCTATCTGGACAAGGGAAAACGCAAGCGCAAAGAGAA

AGCAGGTAGCTTGCAGTGGGCTTACATGGCGATAGCTAGACTGGGCGGTTTTATGGA

CAGCAAGCGAACCGGAATTGCCAGCTGGGGCGCCCTCTGGTAAGGTTGGGAAGCCC

TGCAAAGTAAACTGGATGGCTTTCTTGCCGCCAAGGATCTGATGGCGCAGGGGATC

AAGATCTGATCAAGAGACAGGATGAGGATCGTTTCGCATGATTGAACAAGATGGAT

TGCACGCAGGTTCTCCGGCCGCTTGGGTGGAGAGGCTATTCGGCTATGACTGGGCAC

AACAGACAATCGGCTGCTCTGATGCCGCCGTGTTCCGGCTGTCAGCGCAGGGGCGC

CCGGTTCTTTTTGTCAAGACCGACCTGTCCGGTGCCCTGAATGAACTGCAGGACGAG

GCAGCGCGGCTATCGTGGCTGGCCACGACGGGCGTTCCTTGCGCAGCTGTGCTCGAC

GTTGTCACTGAAGCGGGAAGGGACTGGCTGCTATTGGGCGAAGTGCCGGGGCAGGA

TCTCCTGTCATCCCACCTTGCTCCTGCCGAGAAAGTATCCATCATGGCTGATGCAAT

GCGGCGGCTGCATACGCTTGATCCGGCTACCTGCCCATTCGACCACCAAGCGAAAC

ATCGCATCGAGCGAGCACGTACTCGGATGGAAGCCGGTCTTGTCGATCAGGATGAT

CTGGACGAAGAGCATCAGGGGCTCGCGCCAGCCGAACTGTTCGCCAGGCTCAAGGC

GCGCATGCCCGACGGCGAGGATCTCGTCGTGACCCATGGCGATGCCTGCTTGCCGA

ATATCATGGTGGAAAATGGCCGCTTTTCTGGATTCATCGACTGTGGCCGGCTGGGTG

TGGCGGACCGCTATCAGGACATAGCGTTGGCTACCCGTGATATTGCTGAAGAGCTTG

GCGGCGAATGGGCTGACCGCTTCCTCGTGCTTTACGGTATCGCCGCTCCCGATTCGC

AGCGCATCGCCTTCTATCGCCTTCTTGACGAGTTCTTCTGAATTGAAAAAGGAAGAG

TATGAGTATTCAACATTTCCGTGTCGCCCTTATTCCCTTTTTTGCGGCATTTTGCCTTC

CTGTTTTTGCTCACCCAGAAACGCTGGTGAAAGTAAAAGATGCTGAAGATCAGTTGG

GTGCACGAGTGGGTTACATCGAACTGGATCTCAACAGCGGTAAGATCCTTGAGAGTT

TTCGCCCCGAAGAACGTTTTCCAATGATGAGCACTTTTAAAGTTCTGCTATGTGGCG

CGGTATTATCCCGTATTGACGCCGGGCAAGAGCAACTCGGTCGCCGCATACACTATT

CTCAGAATGACTTGGTTGAGTACTCACCAGTCACAGAAAAGCATCTTACGGATGGCA

TGACAGTAAGAGAATTATGCAGTGCTGCCATAACCATGAGTGATAACACTGCGGCC

AACTTACTTCTGACAACGATCGGAGGACCGAAGGAGCTAACCGCTTTTTTGCACAAC

ATGGGGGATCATGTAACTCGCCTTGATCGTTGGGAACCGGAGCTGAATGAAGCCAT

ACCAAACGACGAGCGTGACACCACGATGCCTGTAGCAATGGCAACAACGTTGCGCA

AACTATTAACTGGCGAACTACTTACTCTAGCTTCCCGGCAACAATTAATAGACTGGA

TGGAGGCGGATAAAGTTGCAGGACCACTTCTGCGCTCGGCCCTTCCGGCTGGCTGGT

TTATTGCTGATAAATCTGGAGCCGGTGAGCGTGGGTCTCGCGGTATCATTGCAGCAC

TGGGGCCAGATGGTAAGCCCTCCCGTATCGTAGTTATCTACACGACGGGGAGTCAG

GCAACTATGGATGAACGAAATAGACAGATCGCTGAGATAGGTGCCTCACTGATTAA

GCATTGGTAACTGTCAGACCAAGTTTACTCATATATACTTTAGATTGATTTAAAACTT

CATTTTTAATTTAAAAGGATCTAGGTGAAGATCCTTTTTGATAATCTCATGACCAAA

ATCCCTTAACGTGAGTTTTCGTTCCACTGAGCGTCAGACCCCGTAGAAAAGATCAAA

GGATCTTCTTGAGATCCTTTTTTTCTGCGCGTAATCTGCTGCTTGCAAACAAAAAAAC

CACCGCTACCAGCGGTGGTTTGTTTGCCGGATCAAGAGCTACCAACTCTTTTTCCGA

AGGTAACTGGCTTCAGCAGAGCGCAGATACCAAATACTGTTCTTCTAGTGTAGCCGT

-continued

```
AGTTAGGCCACCACTTCAAGAACTCTGTAGCACCGCCTACATACCTCGCTCTGCTAA
TCCTGTTACCAGTGGCTGCTGCCAGTGGCGATAAGTCGTGTCTTACCGGGTTGGACT
CAAGACGATAGTTACCGGATAAGGCGCAGCGGTCGGGCTGAACGGGGGGTTCGTGC
ACACAGCCCAGCTTGGAGCGAACGACCTACACCGAACTGAGATACCTACAGCGTGA
GCTATGAGAAAGCGCCACGCTTCCCGAAGGGAGAAAGGCGGACAGGTATCCGGTAA
GCGGCAGGGTCGGAACAGGAGAGCGCACGAGGGAGCTTCCAGGGGGAAACGCCTG
GTATCTTTATAGTCCTGTCGGGTTTCGCCACCTCTGACTTGAGCGTCGATTTTTGTGA
TGCTCGTCAGGGGGGCGGAGCCTATGGAAAAACGCCAGCAACGCGGCCTTTTTACG
GTTCCTGGCCTTTTGCTGGCCTTTTGCTCACATGTTCTTTCCTGCGTTATCCCCTGATT
CTGTGGATAACCGTATTACCGCCTTTGAGTGAGCTGATACCGCTCGCCGCAGCCGAA
CGACCGAGCGCAGCGAGTCAGTGAGCGAGGAAGCGGAAGAGCGCCCAATACGCAA
ACCGCCTCTCCCCGCGCGTTGGCCGATTCATTAATGCAGCTGGCACGACAGGTTTCC
CGACTGGAAAGCGGGCAGTGAGCGCAACGCAATTAATGTGAGTTAGCTCACTCATT
AGGCACCCCAGGCTTTACACTTTATGCTTCCGGCTCGTATGTTGTGTGGAATTGTGA
GCGGATAACAATTTCACACAGGAAACAGCTATGACCATGATTACGCCAAGCTATTTA
GGTGACACTATAGAATACTCAAGCTATGCATCAAGCTTGGTACCGAGCTCGGATCCA
CTAGTAACGGCCGCCAGTGTGCTGGAATTCGCCCTTctggagactacattgcctgaattggcgggcaaat
aagtgcgacttggaggaggcggcgaggaagcccagctggtctgaggtttctgtggcaagacaggacgatattgtttcgtatataacggtgg
acccattggcaaaacggcttgttttggtattgaaacggtatttggcggcccataggcgttattcctcaaatcacacacagtattctcaattaaagt
ggccaagggagccgtgtaaattcggaaattagtatctgaataatccaagtcagacagcaagaaaacgggcatcctatcggatagaacccaa
acgtttttgttctcatcaattttcacatcggccggaaaaactaagccaacgtcatcgcgatccacaatgccatgaaattgcggtgagtacggca
ttgatgagtgccagcaacccactgcattttgatctattaaattgaacagctcaattccatcatcgctcatcacacgtgaagtggtatgggagtttg
gaccccgttcatctaaggcaacaaagtcatgatagctatcttccgtcctggtttcatccctcaaaatcctcgtggatacggcaaattgtcgatga
cttgctaacggactaaagtacagggtacgataaccatccgatcgaatgggcgaaagggacataccaaatataccctcctcgccccattgga
agttaataccagcgacattgaaatcgcccctcaatggatcggggaaaaaatacgaatgtgccgagaatctccaggacttgttcagttcccag
gagtaagcaatcaagccgtatcccaattcatcggcaaaataggcatatgcatcatcgcaatttttgcctatatccacggcaatgttagctatgaa
agtatttggatttgtgtccacgccaggtagctcgtatctccgaattcgcgtatccgtggtcaagtcaaagacatttaccgcataggggcacgga
ttagtGGTGGTATTGCCGA
```

Example 2: Multidimensional Chemogenic Control of Endogenous Transcript Levels The DHFR DD was genetically fused to the N-terminus of dSpCas9.VP64 (14) to test for small molecule control of endogenous gene transcription. Addition of trimethoprim (TMP), a DIFR-stabilizing small molecule, to cells expressing both DHFR.dSpCas9.VP64 and appropriate guide RNAs yielded a small amount of induction of target genes. Similarly, in our hands a previously reported DHFR.dSpCas9.VP192 fusion (15) was capable of only minimally upregulating target genes and displayed very high basal activity upon transient transfection. This is consistent with prior work showing that dSpCas9.VP64 alone is less efficient for inducing transcription of many target genes.

We shifted our focus to a second-generation platform for dCas9-mediated transcriptional activation. In this platform, guide RNAs are modified to also display an RNA aptamer that recruits an aptamer binding-transcriptional activation domain effector protein fusion (e.g., PP7.VP64 (17) or MS2.p65.HSF1 (16)) to form a highly active ternary complex with dSpCas9.VP64. We elected to employ dSpCas9 lacking the VP64 transcription activation domain, and to confer conditional activity by fusing DDs to an appropriate effector protein for transcriptional control. Cells transiently expressing DHFR.PP7.VP64, dSpCas9, and a guide RNA targeting IL1RN show robust upregulation of IL1RN mRNA upon treatment with TMP, demonstrating chemogenic control of transcript induction through stabilization of the DD-transcription activation domain. There was (1) minimal basal transcriptional activation in vehicle-treated samples, (2) induction strength similar to that achieved with an unregulated PP7.VP64 system, and (3) a short time required to initiate transcript induction.

Although some methods for small molecule-based induction of transcription are available (7, 18), reversible control of endogenous transcript induction remains a significant challenge. Such an ability would enable biologists to "pulse"

transcript activation, mimicking typical physiological processes. We predicted that rapid turnover of DD-fusion proteins upon removal of the stabilizing small molecule would yield the requisite dynamics. We treated cells transfected with DHFR.PP7.VP64, dSpCas9 and gRNA with TMP to upregulate endogenous genes prior to a chase period with media lacking TMP. Removal of TMP rapidly depletes induced mRNA transcript levels within <8 h for multiple genes. Thus, dynamic and rapid reversibility is engendered by our DD-mediated, chemogenic control of the second-generation dCas9 platform for endogenous transcript induction.

Figure 1:
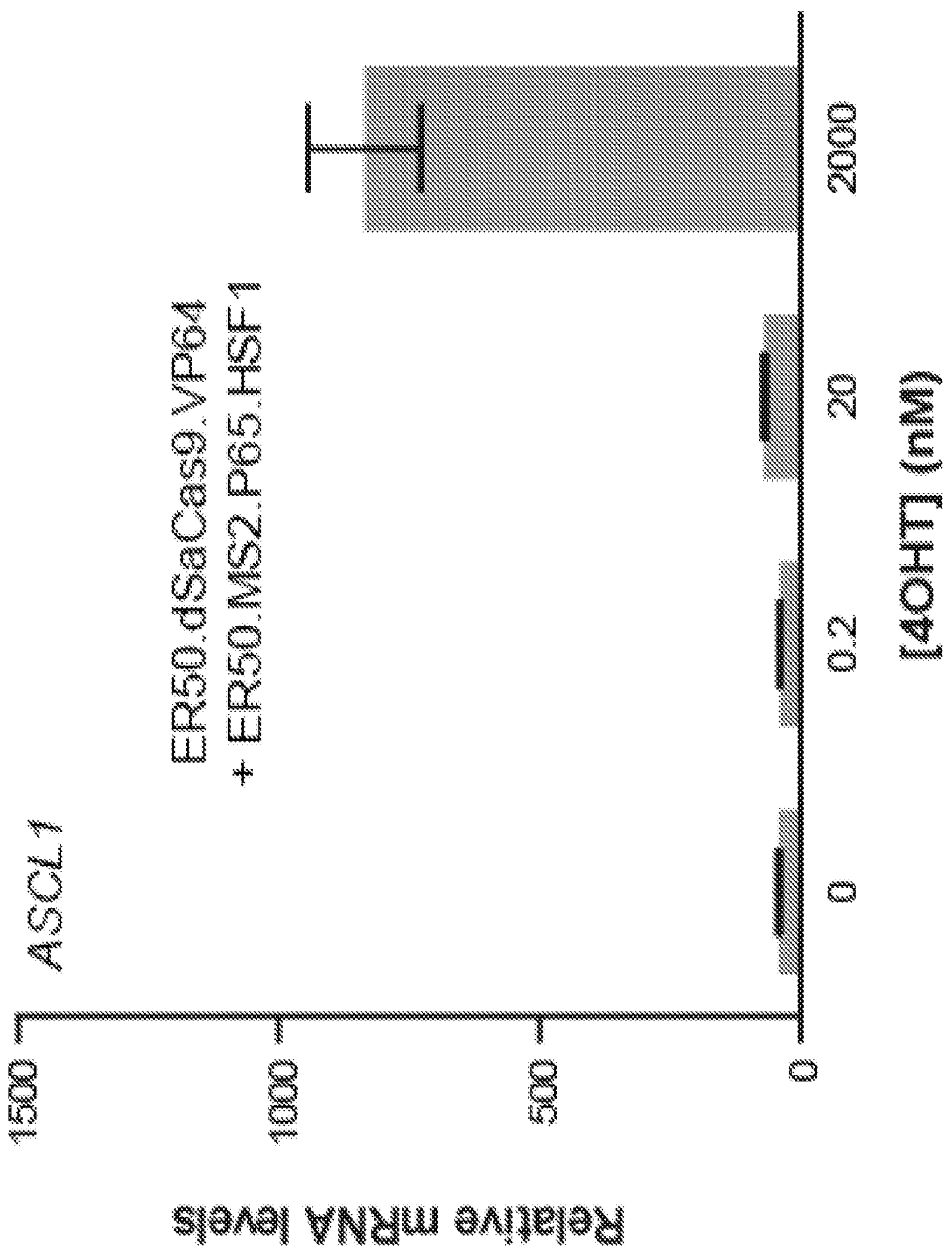
FIG. 1. Regulation of dSaCas9 transcriptional activity using the ER50 DD. qPCR analysis of HEK293T cells expressing ER50.dSaCas9, ER50.MS2.P65.HSF1 and gRNAs targeted to ASCL1 following treatment with increasing concentrations of 40HT for 18 h. Data is representative of three biological replicates, and error bars represent standard deviation.
Figure 13A:
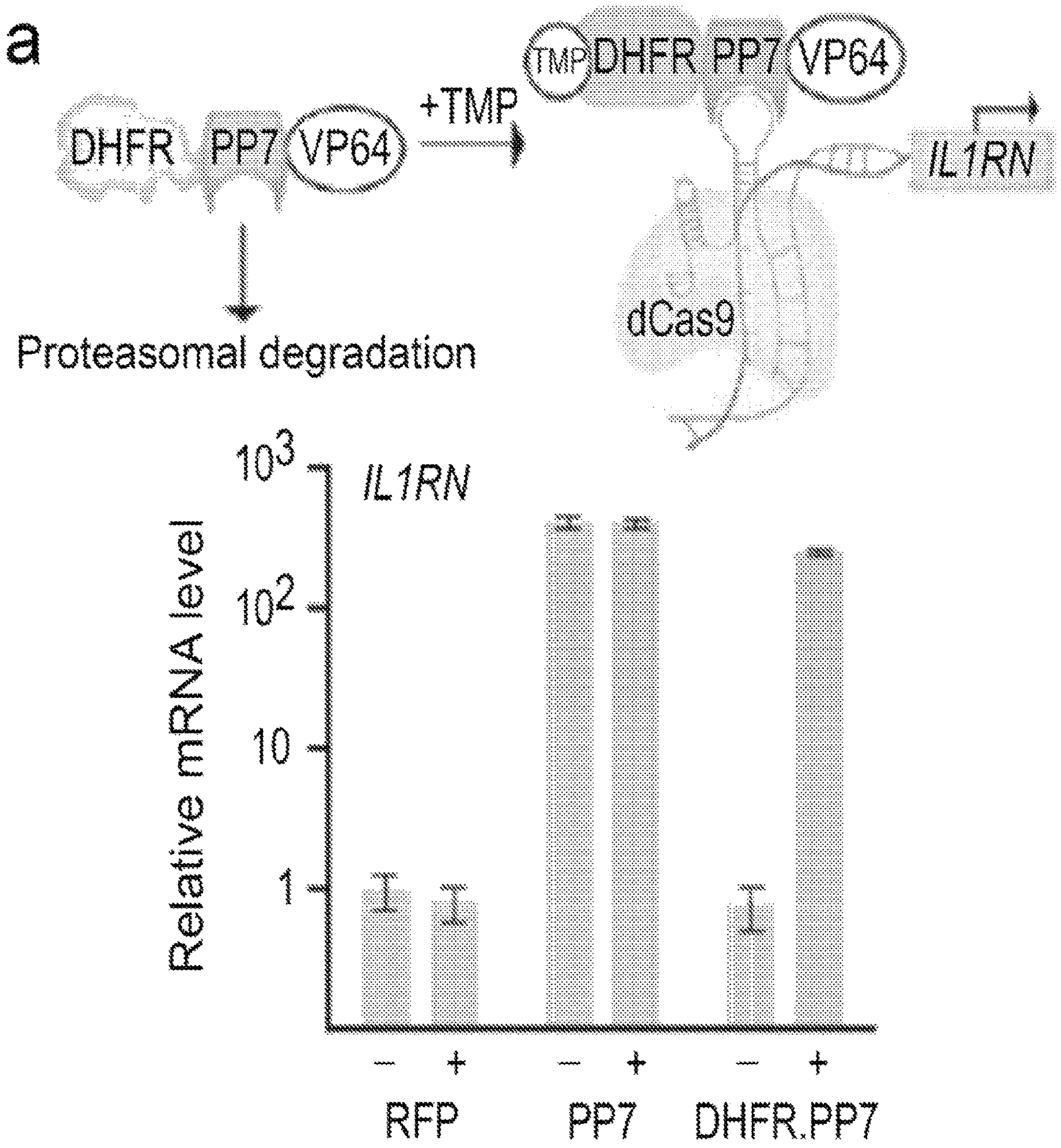
Figure 13B:
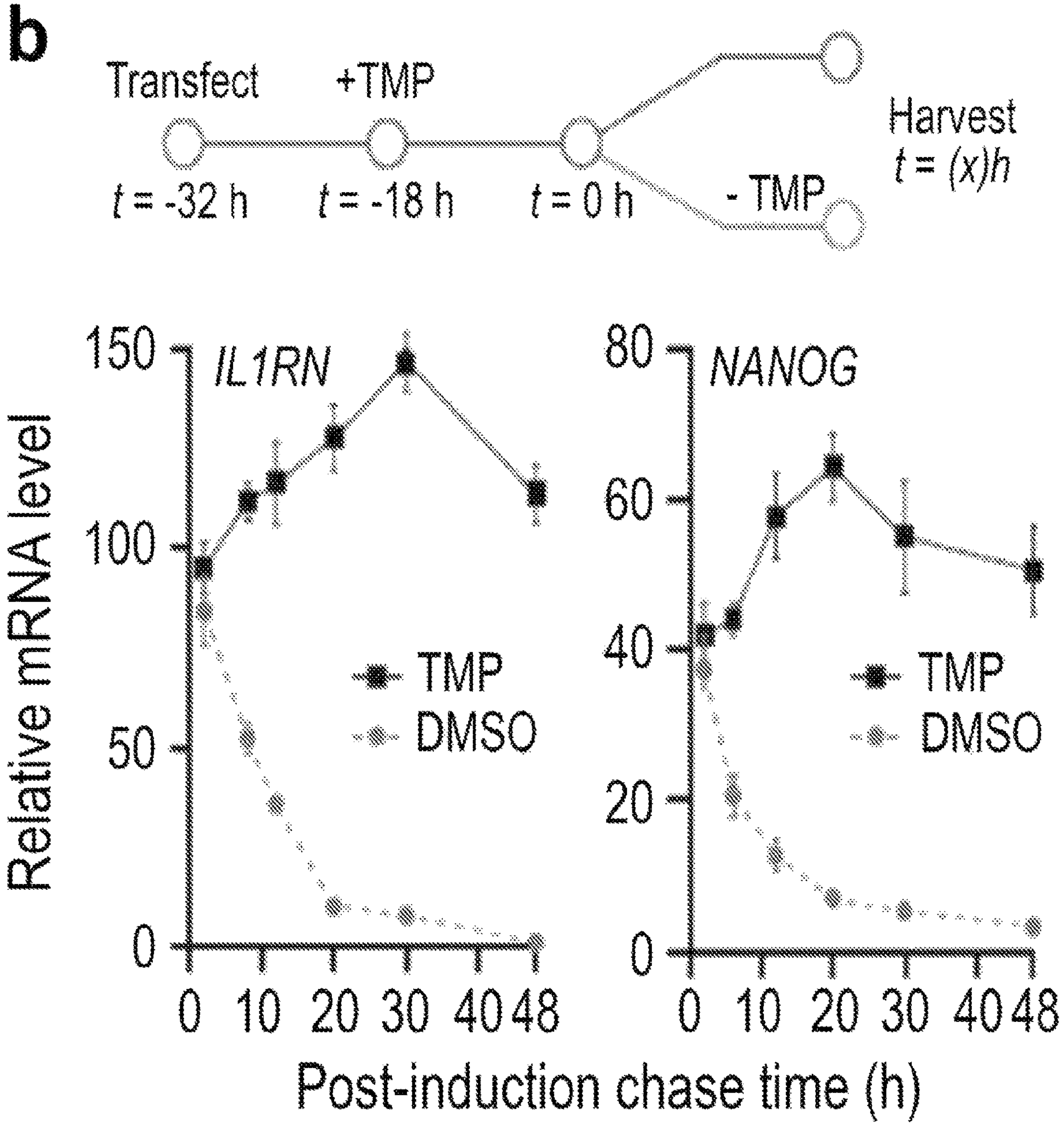
Figure 13C:
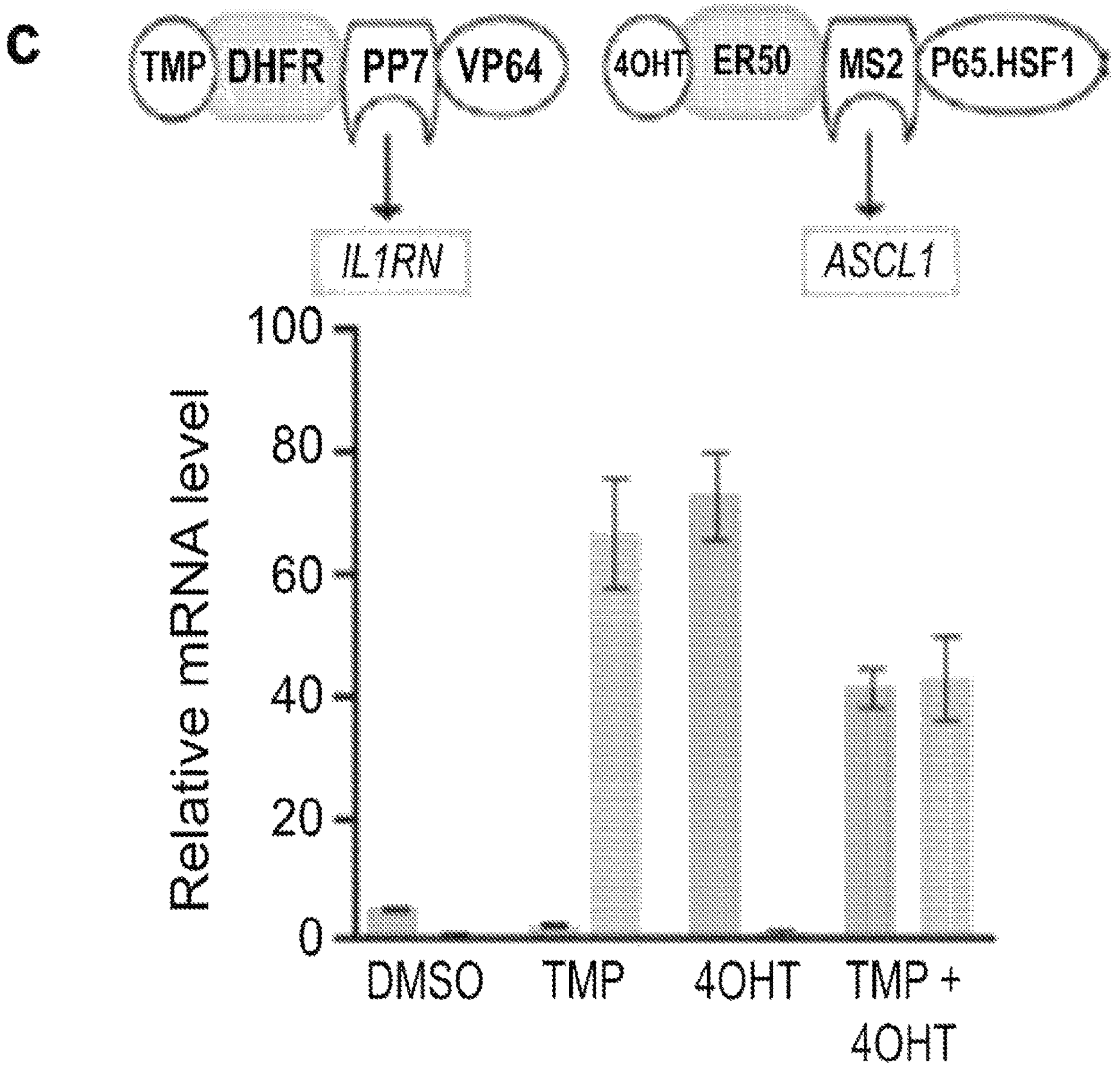
Figure 13D:
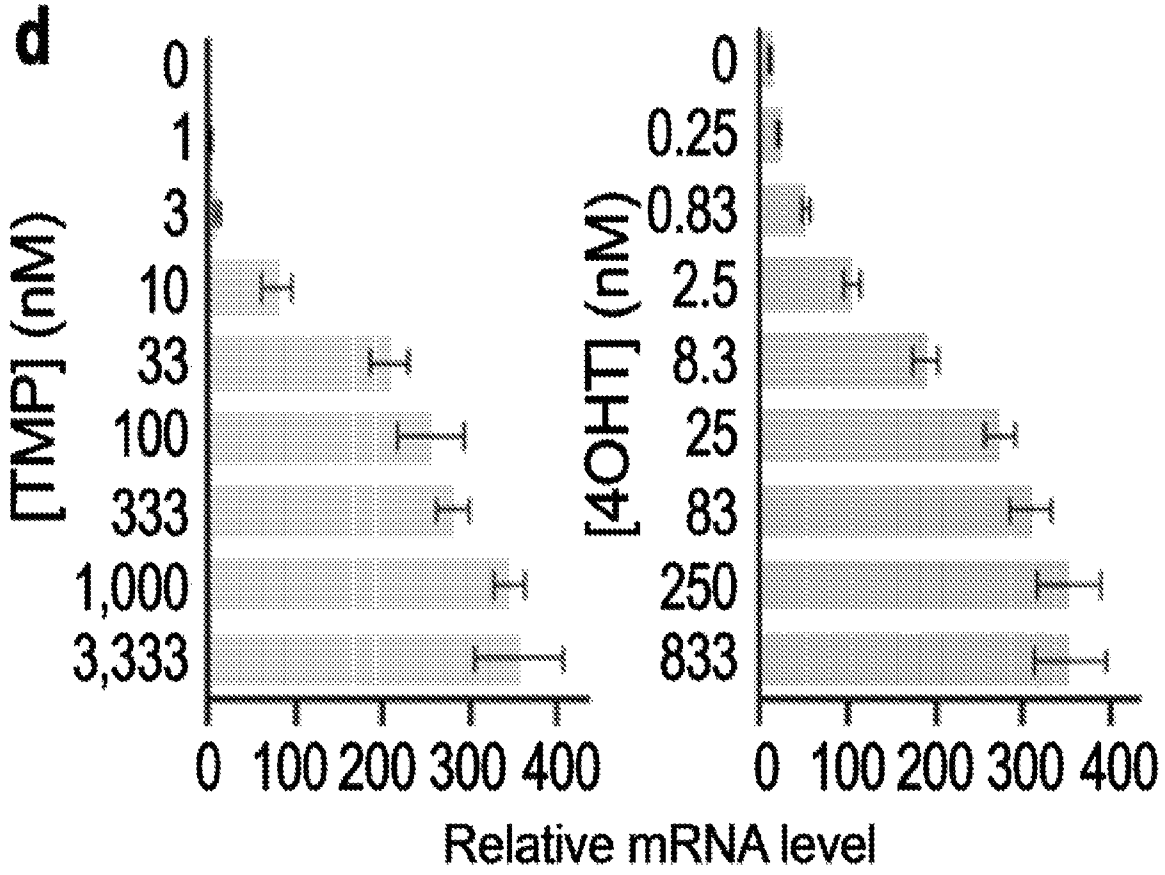

Several degrons regulated by distinctive small molecules are currently available (9, 10, 19). Because many biological pathways are differentially regulated by multiple genes, the usefulness of our method would be significantly enhanced if it were possible to orthogonally control the expression of multiple transcripts in a single cell. MS2.p65.HSF1 is a transcriptional effector fusion protein (16) that binds aptamers distinct from those bound by PP7.VP64 (17). We predicted that fusion of the ER50 DD, which is stabilized by the small molecule (Z)-4-hydroxytamoxifen (40HT) (10), to MS2.p65.HSF1 would provide a means to upregulate endogenous mRNA transcripts with an orthogonal small molecule. Similar to our previous observations using DHFR.PP7.VP64, co-expression of ER50.MS2.p65.HSF1 with dCas9 and an appropriate gRNA yields 40HT-dependent endogenous transcript induction (FIG. 14C). Most importantly, co-expression of both DHFR.PP7.VP64 and ER50.MS2.p65,HSF1, along with dCas9 and appropriate gRNAs, permits conditional and orthogonal activation of two (or more) endogenous genes when either TMP, 40HT, or both TMP and 40HT are added to cells (FIG. 13C). We note that the ER50 DD can also be deployed to regulate the activity of dSaCas9 (20), a Cas9 variant that binds distinctive gRNAs (FIG. 1), highlighting the potential of our modular strategy for direct application to next-generation RNA-guided gene targeting methods.

Meaningful interrogation of gene function by transcript-level regulation requires the ability to induce biologically relevant levels of mRNAs. The pharmacologic chaperoning-based mechanism of DD stabilization can engender a broad range of dosable regulation (12, 13). Indeed, as shown in FIG. 14D, the levels of TMP-mediated IL1RN mRNA induction can be controlled using the DHFR-regulated PP7.VP64 transcriptional effector across several orders of magnitude simply by modulating the dose of TMP. ASCL1 mRNA upregulation can be controlled across a similar range by modulating the 40HT dose in cells expressing the ER50.MS2.p65.HSF1 transcriptional effector (FIG. 14D). This high-precision tuneability of transcriptional activity demands no optimization of dCas9, gRNA, or transcriptional effector expression levels, simply requiring the addition of an appropriate concentration of TMP or 40HT.

These data demonstrate chemogenic control of endogenous transcripts across multiple dimensions, including time, dose, and transcript identity, with a single method requiring minimal optimization.

Figure 2:
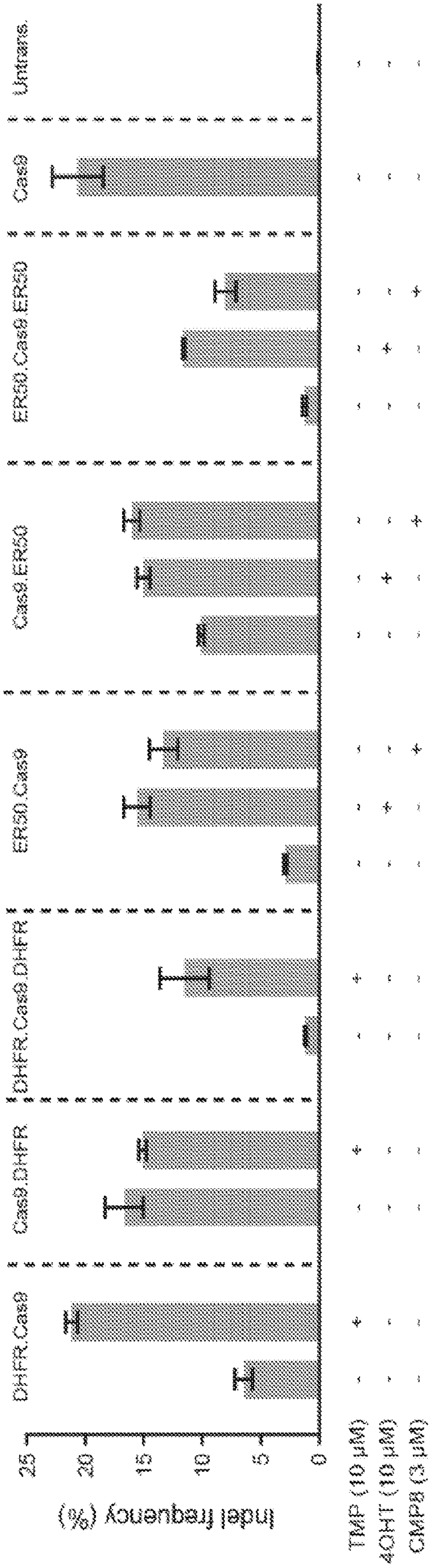
FIG. 2. Regulation of genome editing with DD.Cas9. Gene editing efficiency of different generation of DD-regulated Cas9 system in HEK293T cells either in the presence or absence of stabilizing small molecules (TMP, 40HT, and CMP8). Samples were prepared by transfecting HEK293T cells with the indicated plasmid along with EMX1(1) targeted gRNA and incubated for 72 h either in the presence or absence of small molecules. Both TMP and 40HT were used at 10 nM while CMP8 was used at 3 nM. Indel-frequencies were measured by next-generation sequencing. The studies revealed that dual DD-regulated Cas9 systems provide superior gene editing ability over the corresponding single DD-regulated analogs. Error bars for each panel represent standard deviation from biological replicates (n=4).
Figure 3A:
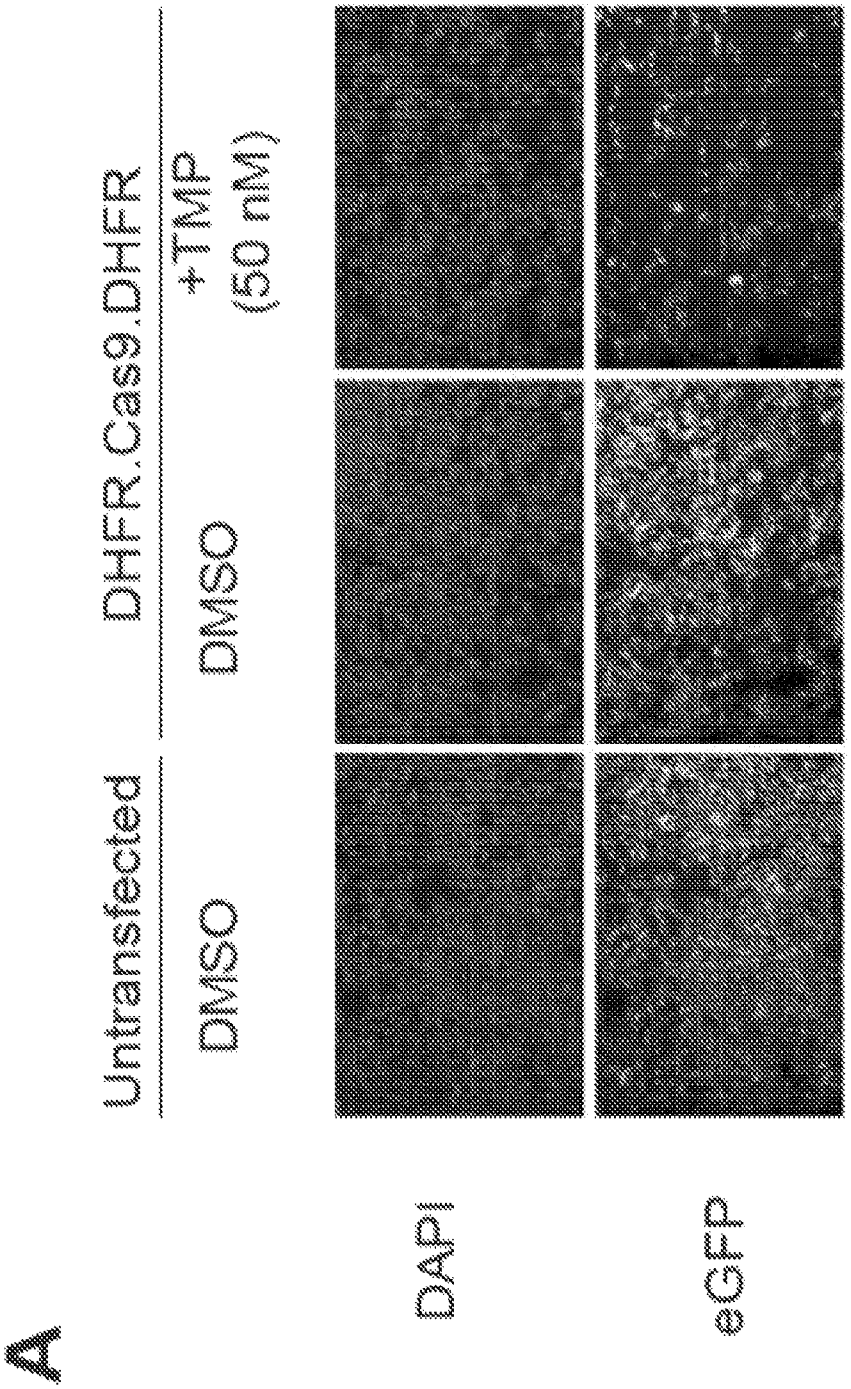
FIG. 3A-3B. Assessment of dose-responsiveness of DD-regulated Cas9 gene editing activity. (a) Representative images of conditional control of Cas9-mediated eGFP knockout in U20S.eGFP-PEST cells. Cells nucleofected with DHFR.Cas9.DHFR show a marked decrease in eGFP signal detected with a high content screening microscope after treatment with the DD-stabilizing small molecule TMP (50 nM) for 48 h. (b) High dosability of genome editing observed in U20S.eGFP-PEST cells nucleofected with DHFR.Cas9.DHFR or ER50.Cas9.ER50 following treatment with increasing concentrations of the stabilizing small molecules TMP or 40HT (0.5-1000 nM) for 48 h. Error bars represent standard deviation from biological replicates (n=6).
Figure 3B:
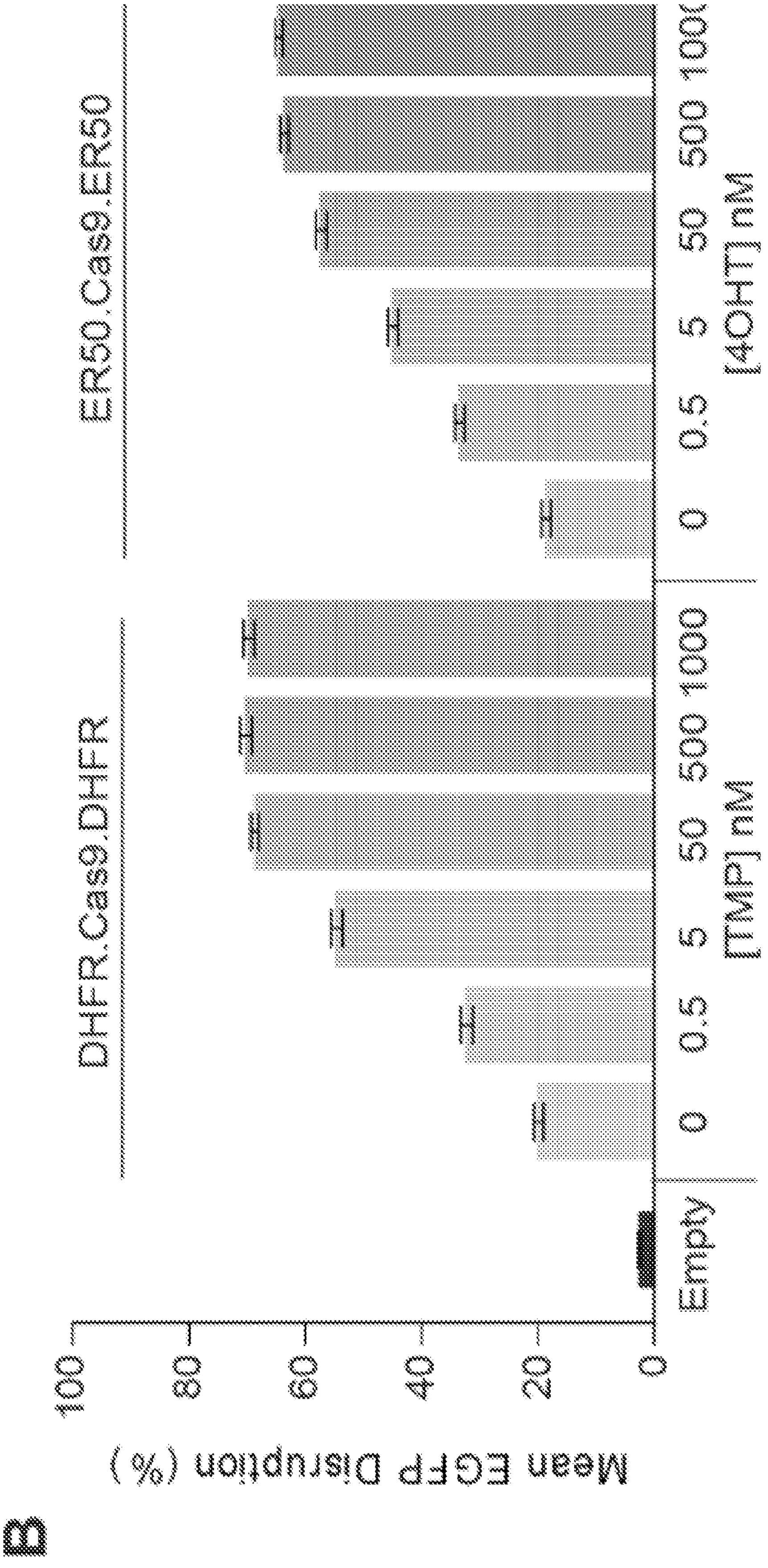
Figure 4:
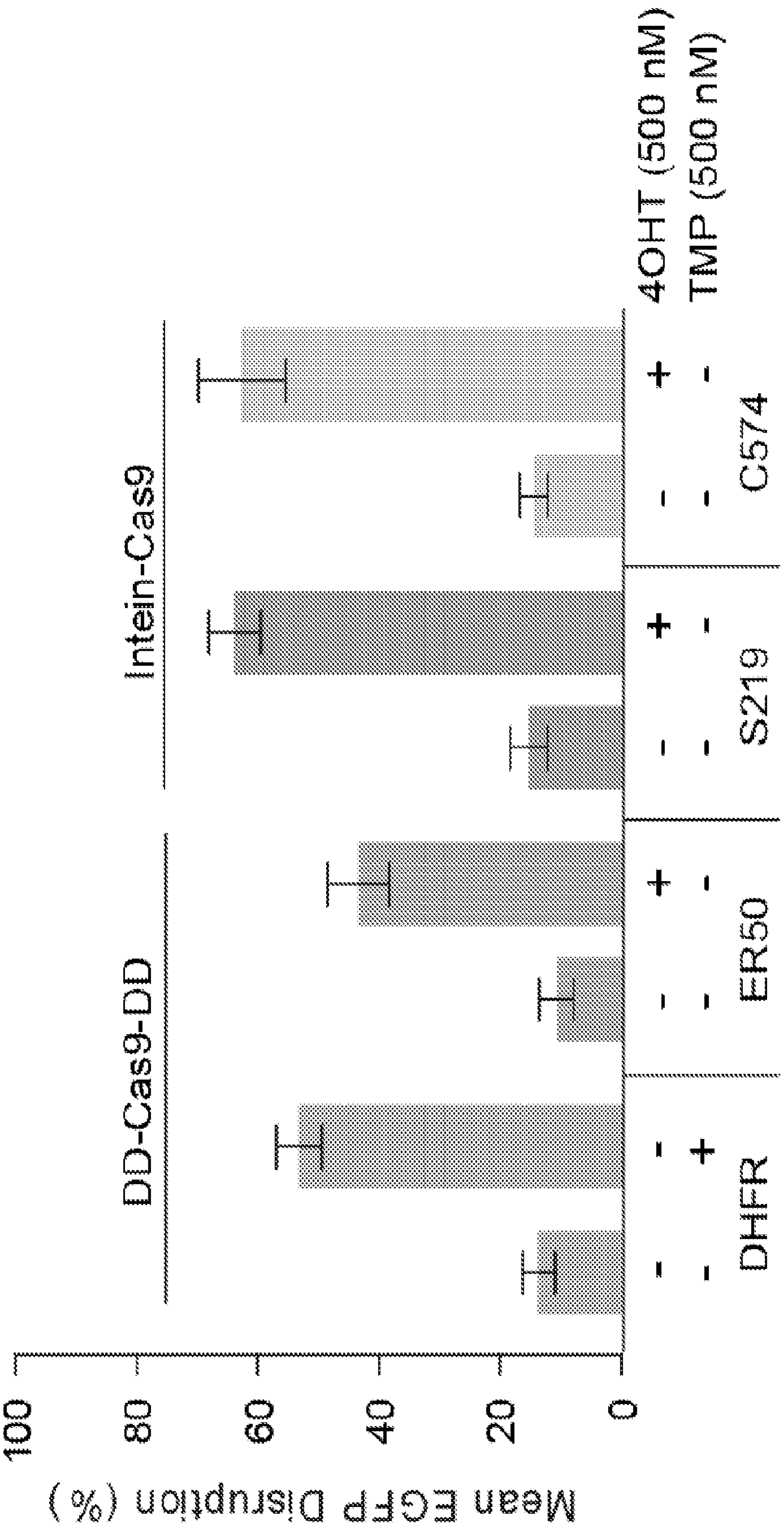
FIG. 4. Assessment of small molecule-regulated Cas9 gene editing systems. Quantitation of basal and induced genome editing activities of Cas9 systems mediated by DDs or a 40HT-sensitive self-splicing intein (S219 and C574). Measurements were performed using the eGFP disruption assay in U20S.eGFP-PEST cells after 48 h of treatment with 500 nM TMP or 40HT. Error bars represent SEM from biological replicates (n=6).
Figure 5A:
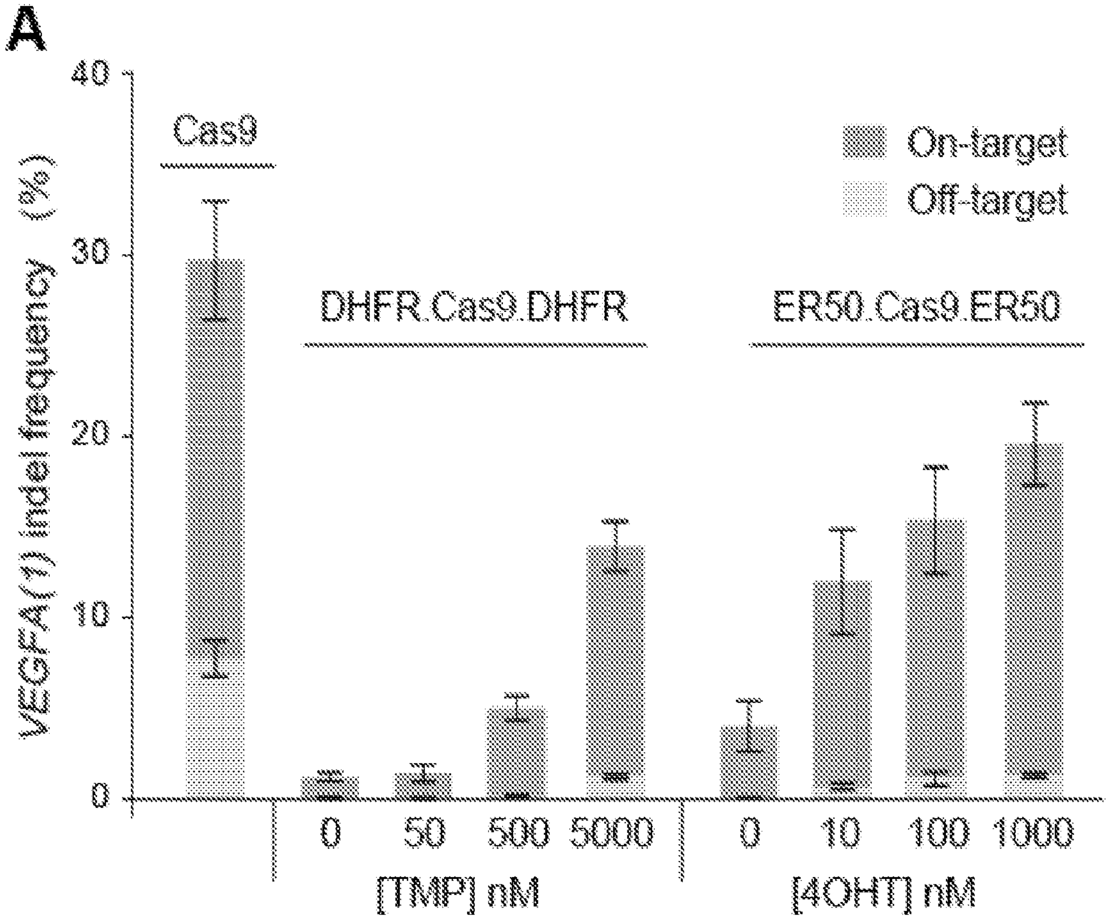
FIG. 5A-5E. Dose and temporal regulation of DD.Cas9.DD-mediated genome editing. (a-b) TMP- and 40HT dose-dependent control of on- and off-target activity of DD.Cas9.DD targeting VEGFA (a) or EMX1 (b). HEK293T cells were transfected with Cas9, DHFR.Cas9.DHFR, or ER50.Cas9.Er50 and treated with the indicated doses of vehicle, TMP, or 40HT for 48 h prior to genomic DNA extraction and analysis of on-target and off-target indel frequencies by next-generation sequencing. (c-d) Ratiometric representation of On-target:Off-target indel frequencies of DD.Cas9.DD for VEGFA (a) or EMX1 (b). (e) Temporal control of DHFR.Cas9.DHFR-mediated genome editing analyzed by an eGFP disruption assay. U20s.eGFP-PEST cells nucleofected with a plasmid expressing DHFR.SpCas9.DHFR and a gRNA targeting eGFP were incubated with the indicated concentrations of TMP for increasing periods of time (6-48 h) prior to media swap to remove TMP. eGFP positive cells were counted using automated, high-content imaging micros-copy. Error bars for all panels represent SEM from biological replicates (n=5).
Figure 5B:
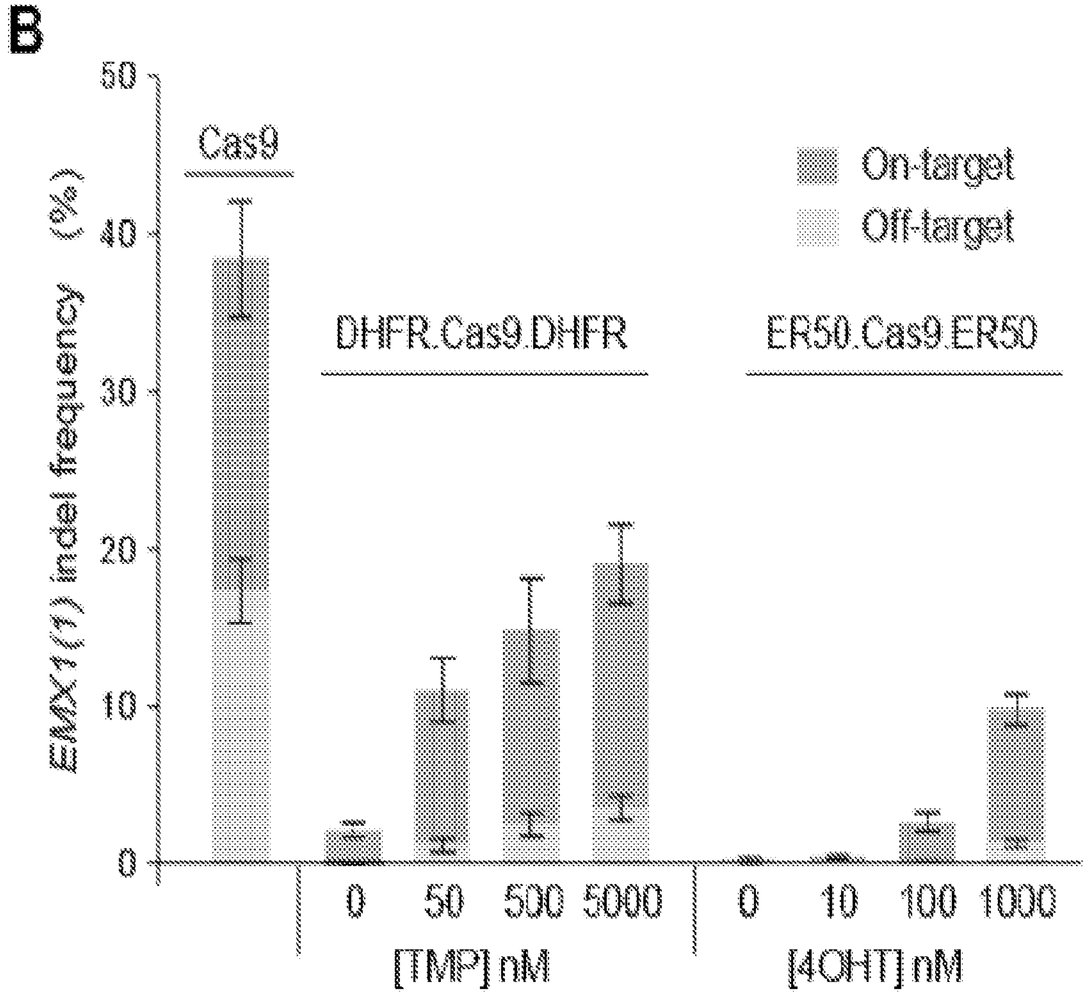
Figures 5C, 5D:
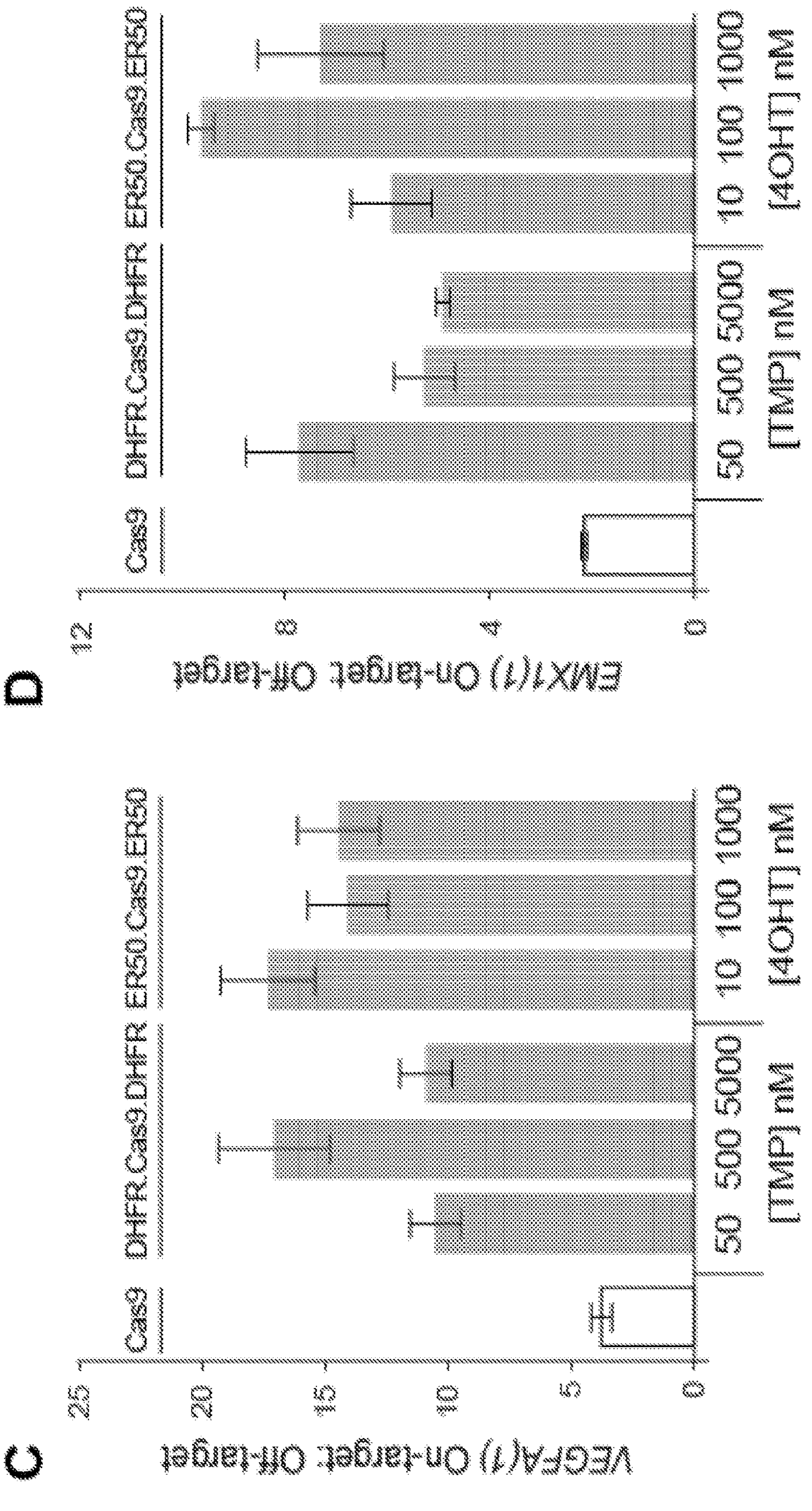
Figure 5E:
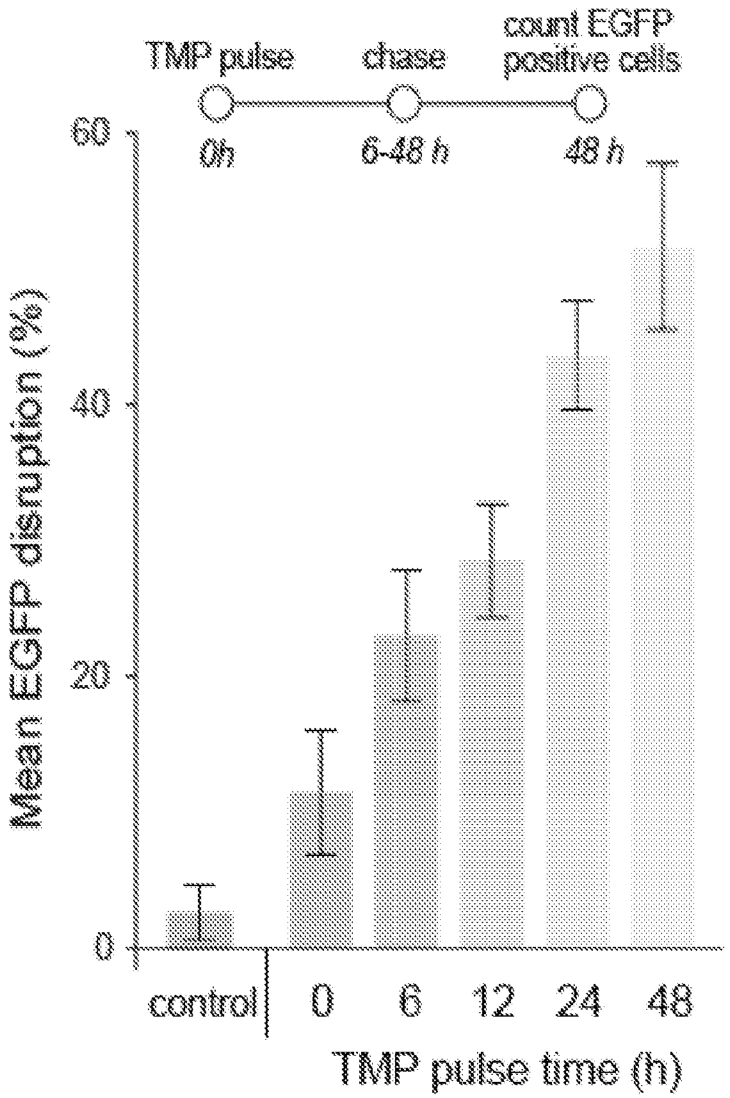
Figure 6:
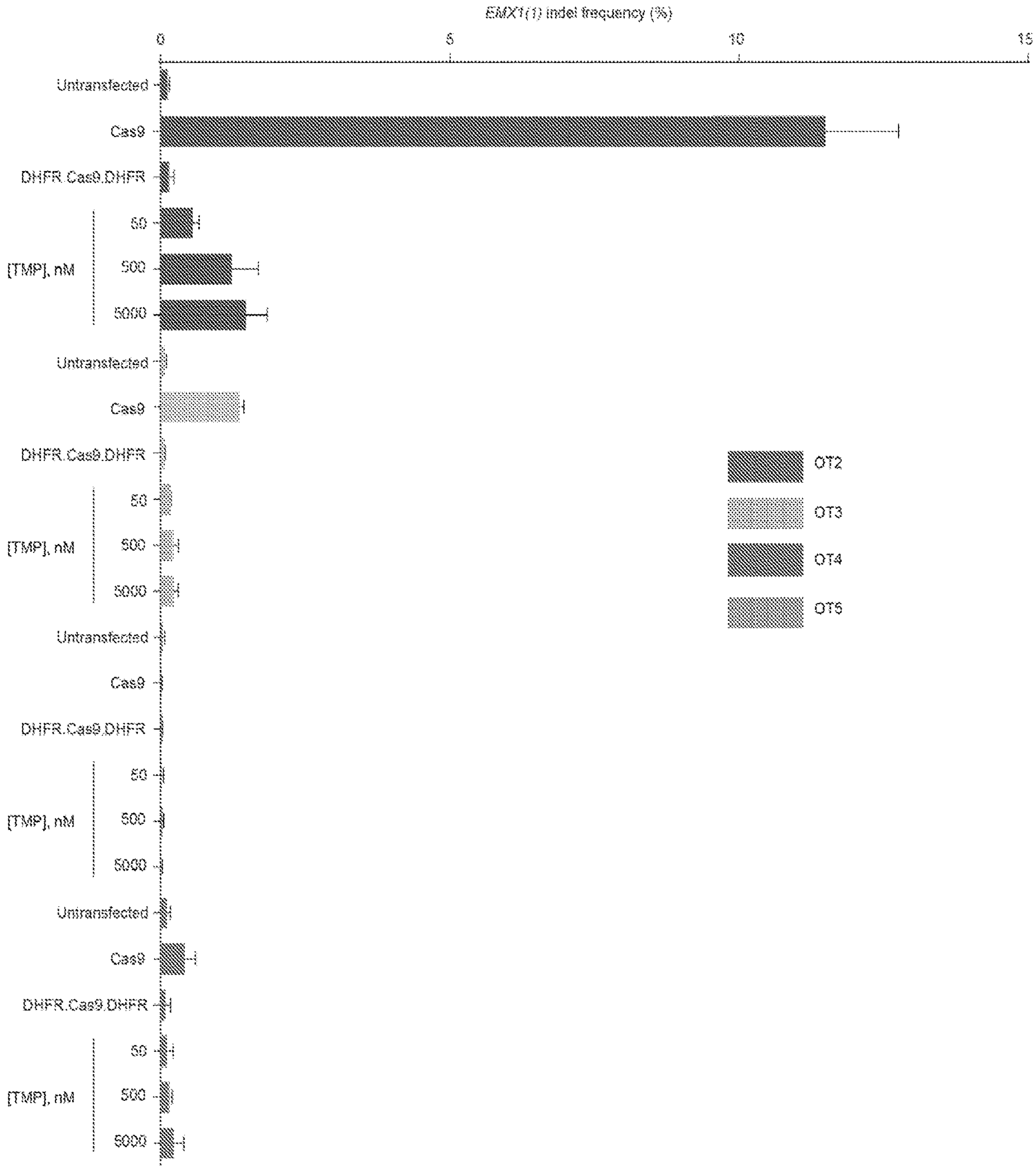
FIG. 6. Specificity of DHFR.Cas9.DHFR gene editing system. Measurement of off-target activities for DHFR.Cas9.DHFR construct targeted to the EMX1 gene. Samples were prepared by transfecting HEK293T cells with the DHFR.Cas9.DHFR plasmid along with EMX1(1) targeted gRNA and incubated for 72 h either in the presence or absence of increasing concentrations of TMP (50-5000 nM). Indel frequency plots measured by next-generation sequencing indicate significant alleviation in the off-target activities for DHFR.Cas9.DHFR in comparison with Cas9. Error bars for each panel represent standard deviation from biological replicates (n=4).
Figure 7:
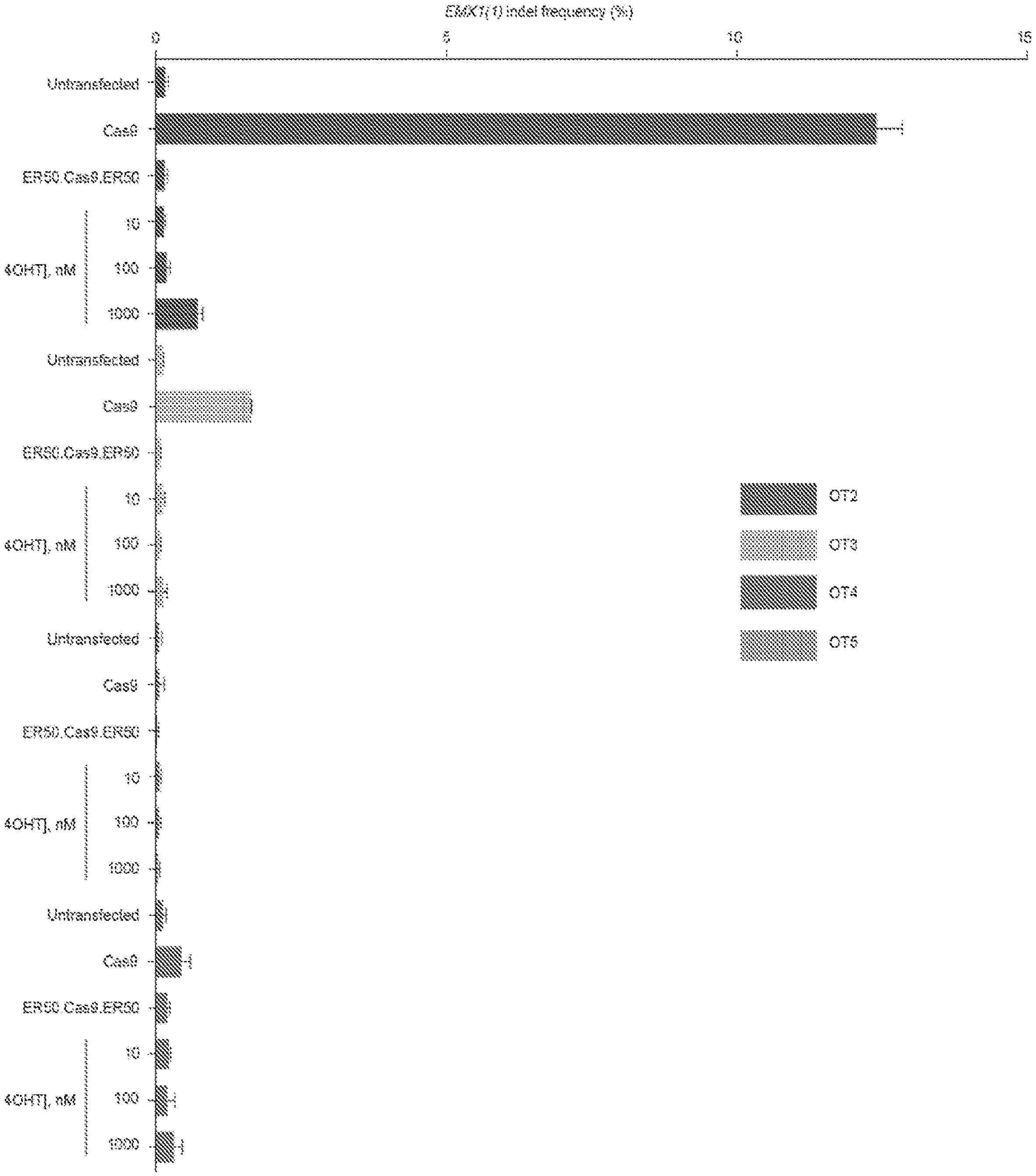
FIG. 7. Specificity of ER50.Cas9.ER50 gene editing system. Measurement of off-target activities for the ER50.Cas9.ER50 construct targeted to the EMX1 gene. Samples were prepared by transfecting HEK293T cells with the ER50.Cas9.ER50 plasmid along with EMX1(1) targeted gRNA and incubated for 72 h either in the presence or absence of increasing concentrations of 40HT (10-1000 nM). Indel frequency plots measured by next-generation sequencing indicate significant alleviation in the off-target activities for ER50.Cas9.ER50 in comparison with Cas9. Error bars for each panel represent standard deviation from biological replicates (n=4).
Figure 8:
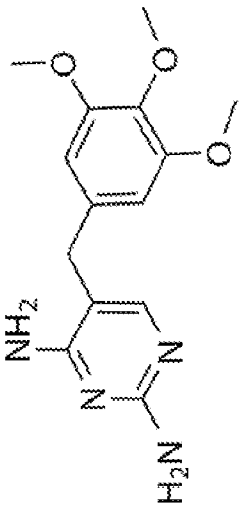
FIG. 8. Chemical structures of small molecules (i.e. stabilizing ligands) used in the studies.
Figure 8:
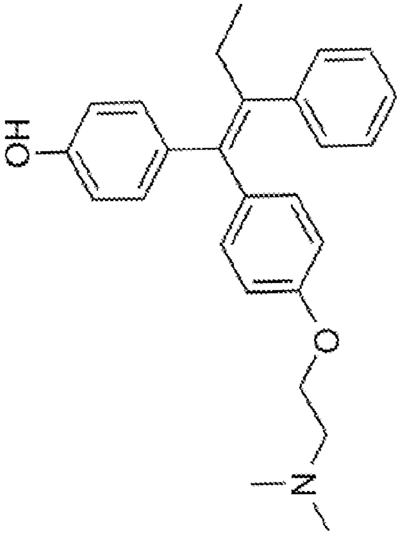
Figure 8:
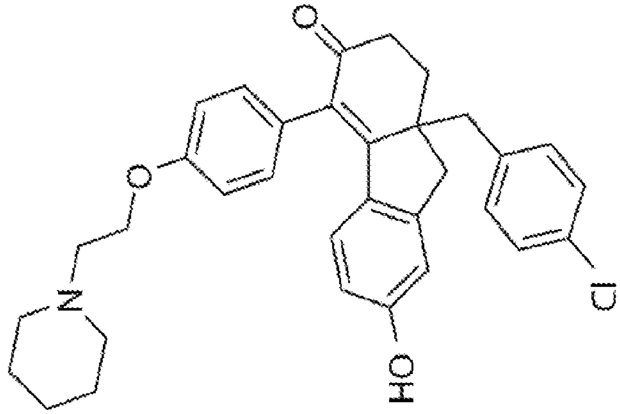
Figure 9:
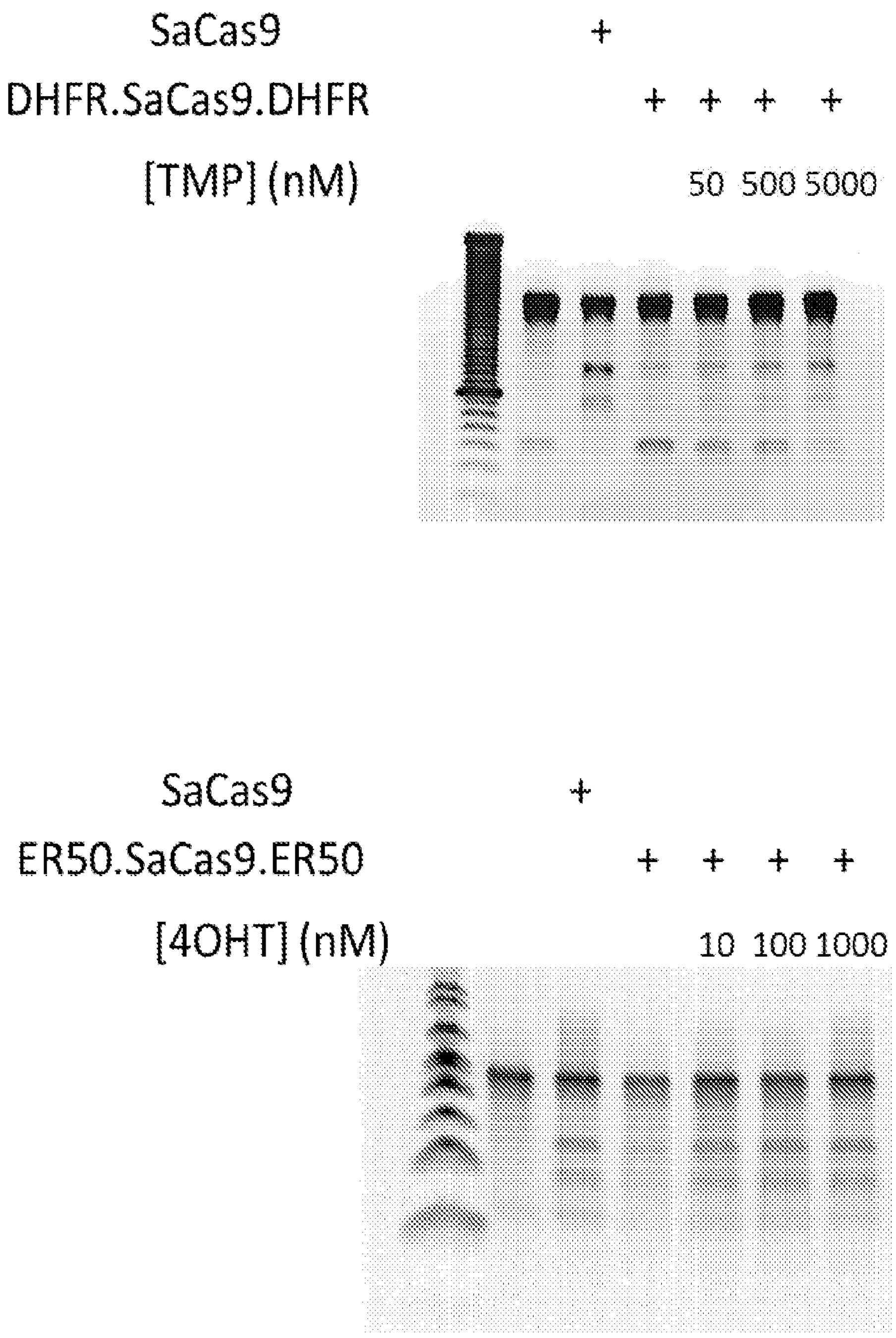
FIG. 9. Assessment of dose-responsiveness of DD-regulated SaCas9 gene editing activity. Cells expressing DHFR.SaCas9.DHFR (top) or ER50.SaCas9.ER50 (bottom) were treated with TMP or 40HT respectively in the amounts indicated. Indel activity detected Surveyor assay shows dose dependent increase in nuclease activity.
Figure 10:
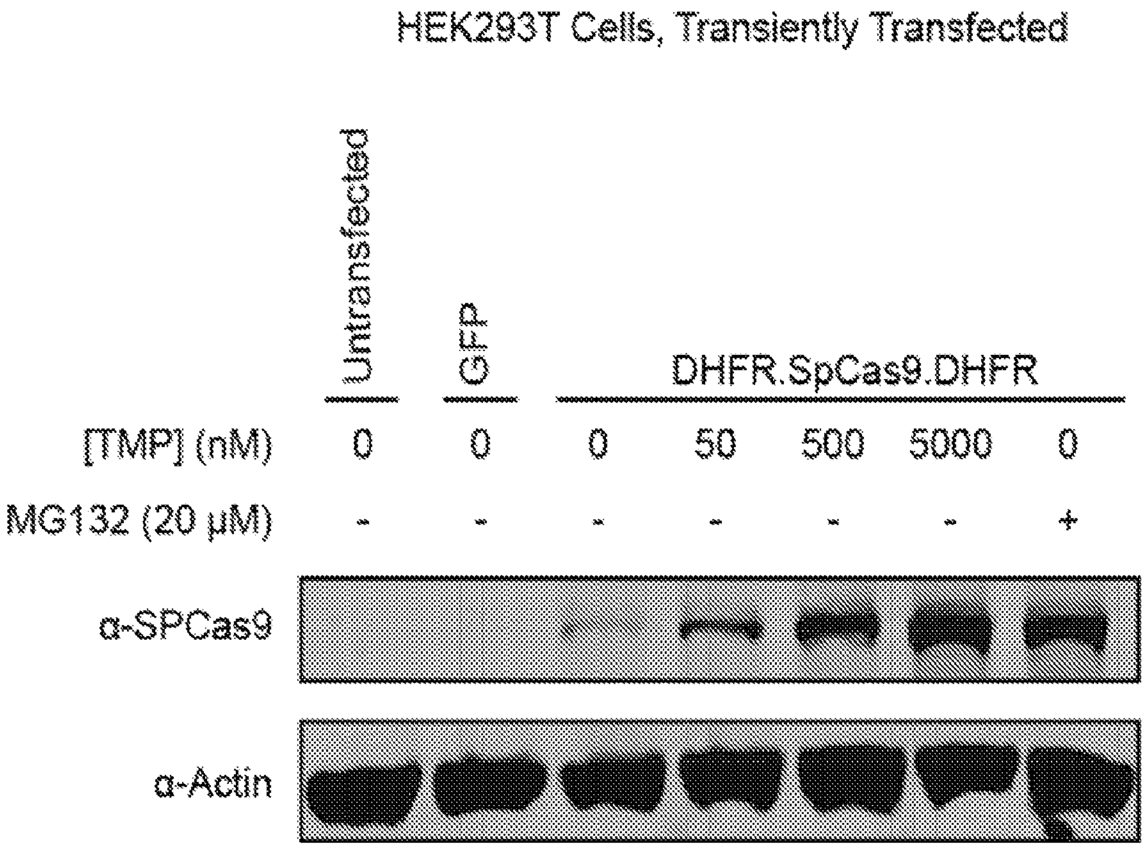
FIG. 10. Assessment of stabilization of DHFR.SpCas9.DHFR protein by TMP. HEK293T cells transiently transfected to express DHFR.SpCas9.DHFR were treated with TMP at the indicated concentrations. Transfected cell preparations display dose-dependent TMP stabilization of SpCas9.

We next focused on chemogenic regulation of Cas9-mediated genome editing. Temporal control of editing activity is critical for emerging 'Gene Drive' technologies (3, 21) and other biological applications. Therefore, we sought to engineer small molecule-regulated Cas9 variants displaying dosable, reversible, and highly specific gene editing activity. Consistent with our observations for dSpCas9.VP64, we found that the fusion of a DHFR or ER50 DD to either the N- or C-terminus of SpCas9 results in limited small molecule-dependent control of editing activity (FIG. 2). In contrast, fusing DHFR or ER50 DDs to both the N- and C-termini of SpCas9 (DHFR.SpCas9.DHFR) is more successful (FIG. 2). Furthermore, we observe strongly dose-dependent control of gene editing activity for both our DD.SpCas9.DD constructs (FIG. 3), with basal activity similar to that previously reported for a split SpCas9 regulated by intein self-splicing (22) (FIG. 4).

Example 3: Dose and Temporal Regulation of DD.Cas9.DD-Mediated Genome Editing

Undesired off-target activity of Cas9 nucleases can lead to catastrophic biological events, including chromosomal translocations.(23) Improving genome editing specificity is therefore a topic of strong scientific and therapeutic interest. Truncation of gRNAs significantly enhances Cas9 specificity, and modifications to Cas9 including the single mutant Cas9 approach, RNA-guided FokI nuclease-dCas9 nuclease, and high fidelity Cas9 variants also offer improvements. We anticipated that the precise regulation of Cas9 levels afforded by fusion to small molecule-controlled DDs would allow us to titer in optimal Cas9 concentrations to maximize on-target while minimizing off-target gene editing (22, 24). Indeed, we observe strongly enhanced specificity for on-target versus known sequence-alike off-target sites of VEGFA and EMX1 upon administering optimized doses of TMP or 40HT for the DHFR.SpCas9.DHFR or ER50.SpCas9.ER50 systems, respectively (FIGS. 5*a-d*, Table 4, and FIGS. 6 and 7).

Limiting Cas9 activity to a short temporal window is another promising avenue to enhance genome-editing specificity, and a key advantage of DD-mediated Cas9 regulation is the rapid reversibility of protein levels. In the context of gene editing, this feature is highlighted by our observation that a short pulse of TMP (6 h) in U20S.eGFP-PEST cells (25) co-expressing DHFR.SpCas9.DHFR and GFP-targeting gRNAs results in significantly less GFP knockout than a 48 h pulse over the same timecourse. Cumulatively, these results highlight the potential of DD-regulation to enhance the specificity of Cas9 gene editing tools. It should be straightforward to extend our modular method to other next-generation RNA-targeted endonucleases (see, for example, FIG. 1) with higher specificity (26, 27), additively enhancing their selectivity for on-target editing.

TABLE 4

Average indel frequency assessed by next-generation sequencing.

| Sample | ON | OT1 | OT2 | OT3 | OT4 | OT5 |
|---|---|---|---|---|---|---|
| GFP_EMX1(1) | 0.16 | 0.14 | 0.12 | 0.08 | 0.03 | 0.10 |
| Cas9 + EMX1(1) | 41.10 | 18.85 | 11.50 | 1.37 | 0.02 | 0.41 |
| DHFR.Cas9.DHFR + EMX1(1) | 2.23 | 0.18 | 0.15 | 0.07 | 0.03 | 0.08 |
| +TMP 50 nM | 11.67 | 1.55 | 0.56 | 0.18 | 0.03 | 0.11 |
| +TMP 500 nM | 16.33 | 3.15 | 1.23 | 0.22 | 0.04 | 0.15 |

TABLE 4-continued

Average indel frequency assessed by next-generation sequencing.

| Sample | ON | OT1 | OT2 | OT3 | OT4 | OT5 |
|---|---|---|---|---|---|---|
| +TMP 5000 nM | 19.76 | 4.02 | 1.47 | 0.23 | 0.02 | 0.23 |
| GFP_EMX1(1) | 0.17 | 0.20 | 0.16 | 0.12 | 0.05 | 0.13 |
| Cas9 + EMX1(1) | 43.22 | 20.80 | 12.41 | 1.64 | 0.06 | 0.44 |
| ER50.Cas9.ER50 + EMX1(1) | 0.56 | 0.31 | 0.15 | 0.08 | 0.02 | 0.20 |
| +4OHT 10 nM | 0.72 | 0.12 | 0.14 | 0.11 | 0.07 | 0.23 |
| +4OHT 100 nM | 4.02 | 0.18 | 0.18 | 0.07 | 0.06 | 0.20 |
| +4OHT 1000 nM | 14.04 | 2.10 | 0.72 | 0.12 | 0.04 | 0.32 |
| GFP_VEGFA(1) | 0.16 | 0.14 | | | | |

| Sample | ON | OT1 |
|---|---|---|
| GFP_VEGFA(1) | 0.16 | 0.14 |
| Cas9 + VEGFA(1) | 29.78 | 7.83 |
| DHFR.Cas9.DHFR + VEGFA(1) | 1.29 | 0.14 |
| +TMP 50 nM | 1.58 | 0.19 |
| +TMP 500 nM | 5.09 | 0.31 |
| +TMP 5000 nM | 14.00 | 1.28 |
| GFP_VEGFA(1) | 1.81 | 0.45 |
| Cas9 + VEGFA(1) | 29.25 | 6.38 |
| ER50.Cas9.ER50 + VEGFA(1) | 4.11 | 0.21 |
| +4OHT 10 nM | 12.04 | 0.77 |
| +4OHT 100 nM | 15.43 | 1.18 |
| +4OHT 1000 nM | 19.66 | 1.36 |

Figure 11:
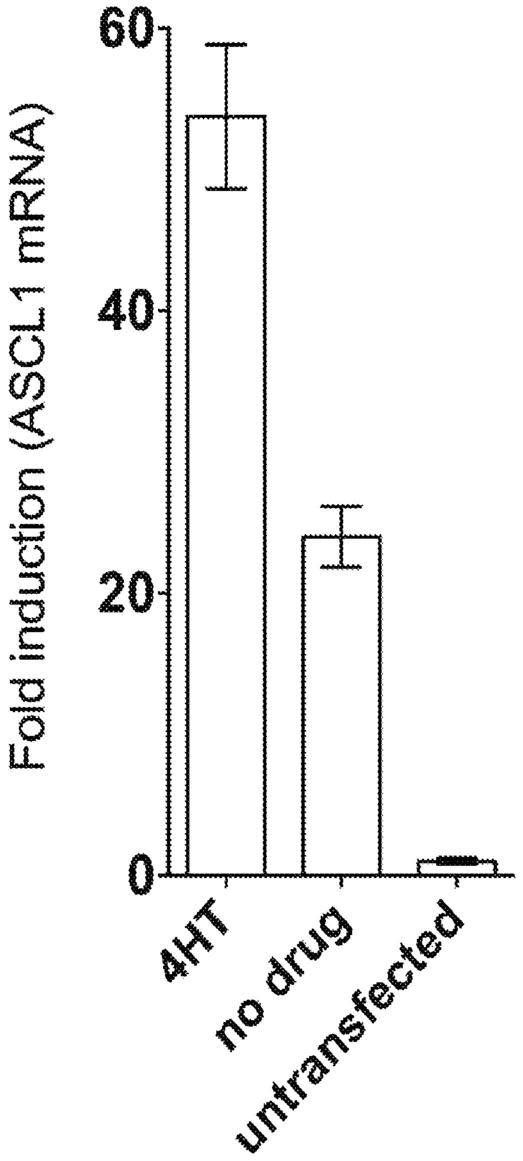
FIG. 11. Assessment of induction of ASCL1 mRNA by engineered Cas9 system comprising a functionalized guide with DHFR destabilization domain and stabilizing ligand 4HT. Cells were transiently transfected with engineered DD-Cas9 SAM and ASCL1 mRNA was measured. Compared to untransfected cells, DD-Cas9-SAM induced expression of ASCL1 mRNA is observed. Treatment with stabilizing ligand 4HT results in significant increase of ASCL1 mRNA.
Figure 12:
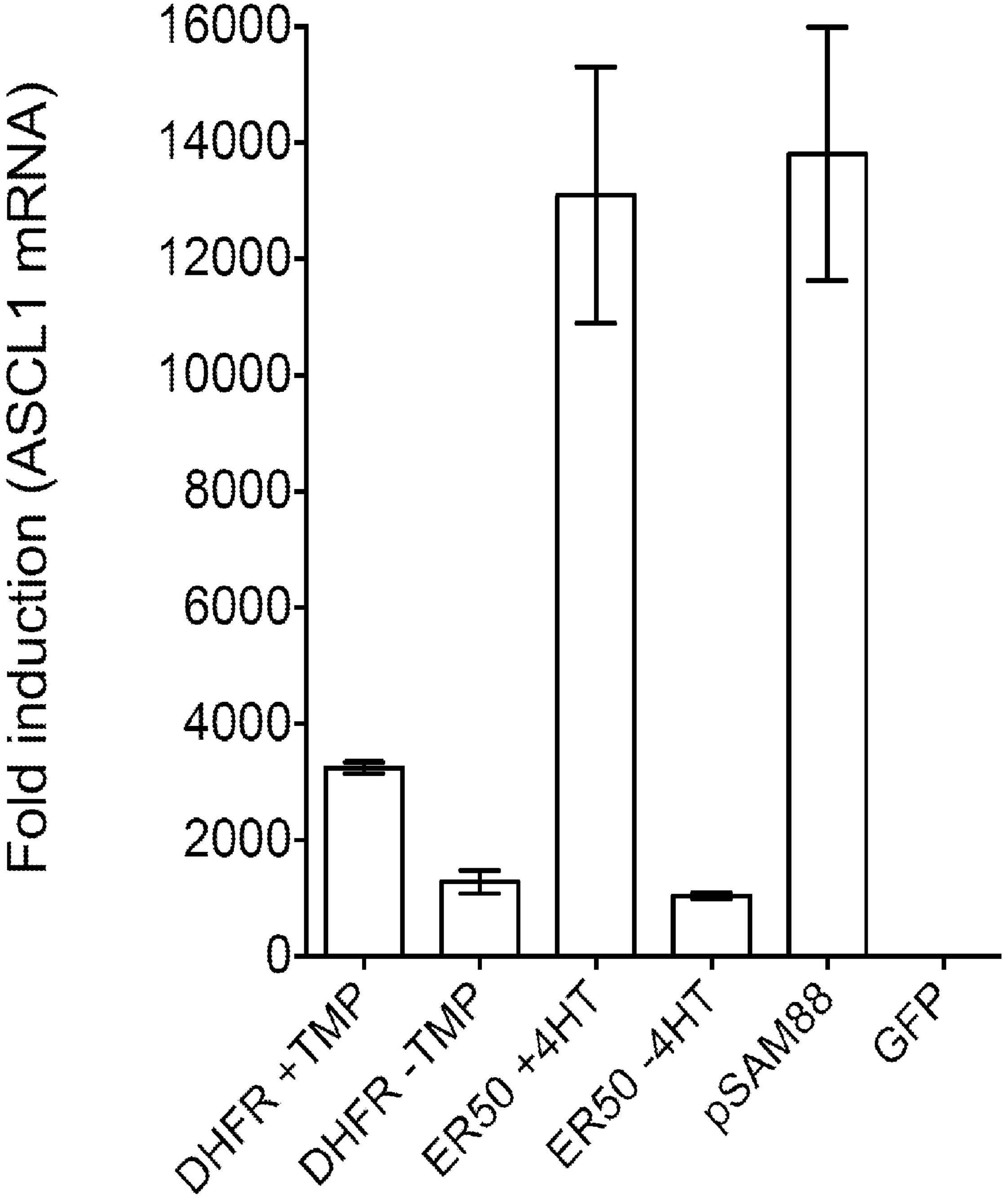
FIG. 12. Induction of ASCL1 mRNA by DD-Cas9 SAM and stabilizing ligands. Cells transfected with an engineered Cas9-SAM system comprising a DD (DHFR or ER50) were treated with stabilizing ligand (TMP or 4HT respectively)

Furthermore, mRNA express can be controlled in a similar manner. Using a DD-Cas9-SAM system to induce mRNA expression, stabilizing ligand-controlled upregulation is observed (FIGS. 11 and 12).

Example 4: Spatially-Controlled and Site-Specific Genome Editing

Systemically active SpCas9 in mice can result in several undesired offtarget effects, pointing to the need to confine SpCas9 activity to a specific site. A destabilized-domain-based SpCas9 activated by a small molecule which can be converted from prodrug to drug to effect site-specific genome editing lowers off-site genome editing in an organismal context.

A hindered ester was appended to trimethoprim with the result that the ability of trimethoprim to bind to DHFR and activate (i.e., block degradation of) destabilized-domain bearing SpCas9 was hindered. Trimethoprim's 2,4-position on the pyrimidine ring was chosen for appending the hindered esters as the pyrimidine ring is deeply buried in the DHFR binding pocket (FIG. 13B). Trimethoprim analogs bearing various hindered esters at these sites (FIG. 13A) were unable to activate destabilized-domain SpCas9 in the eGFP disruption assay. It was then confirmed using LCMS that pig liver esterase can hydrolyze-off the hindered esters from trimethoprim (FIG. 13C). In an eGFP disruption assay, a pig liver esterase plasmid was transformed in addition to destabilized-domain SpCas9 and cells treated with trimethoprim's hindered esters (FIG. 13D). eGFP disruption was observe in pig liver esterase transfected cells but not in untransfected cells.

Example 5: Light modulation ofDD-dependent CRISPR function

Figures 14A, 14B:
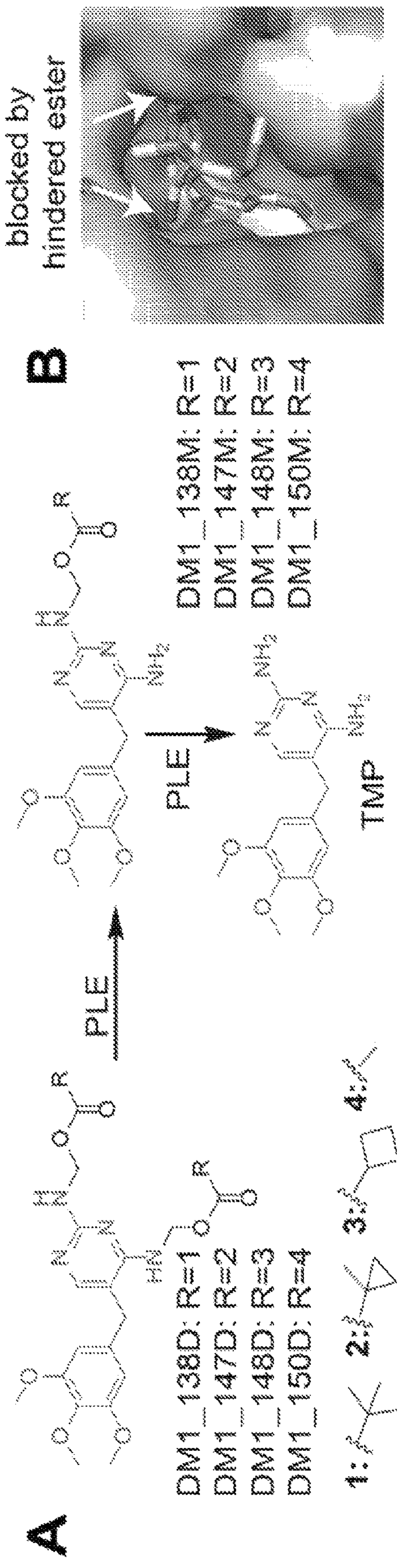
Figure 14C:
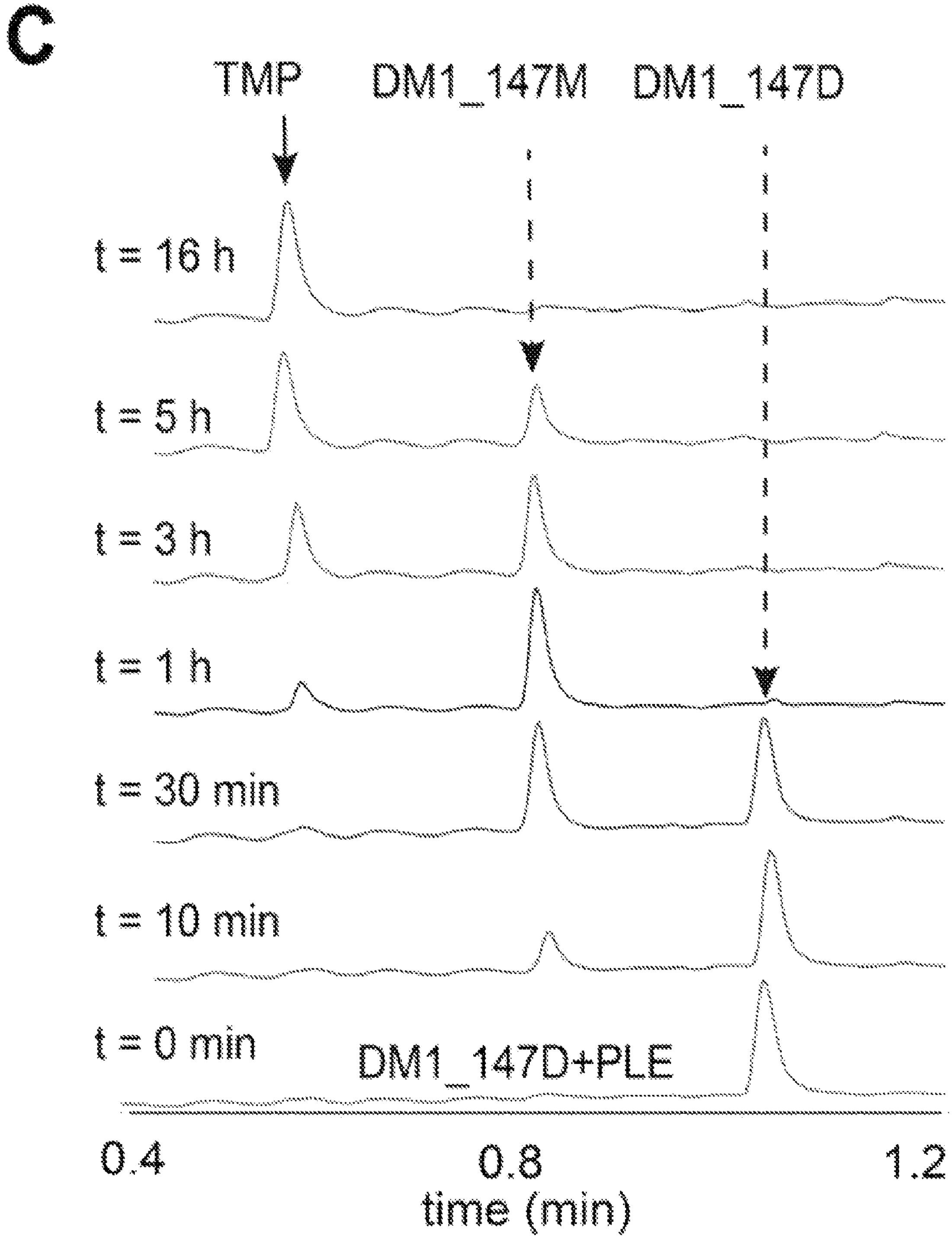
Figure 14D:
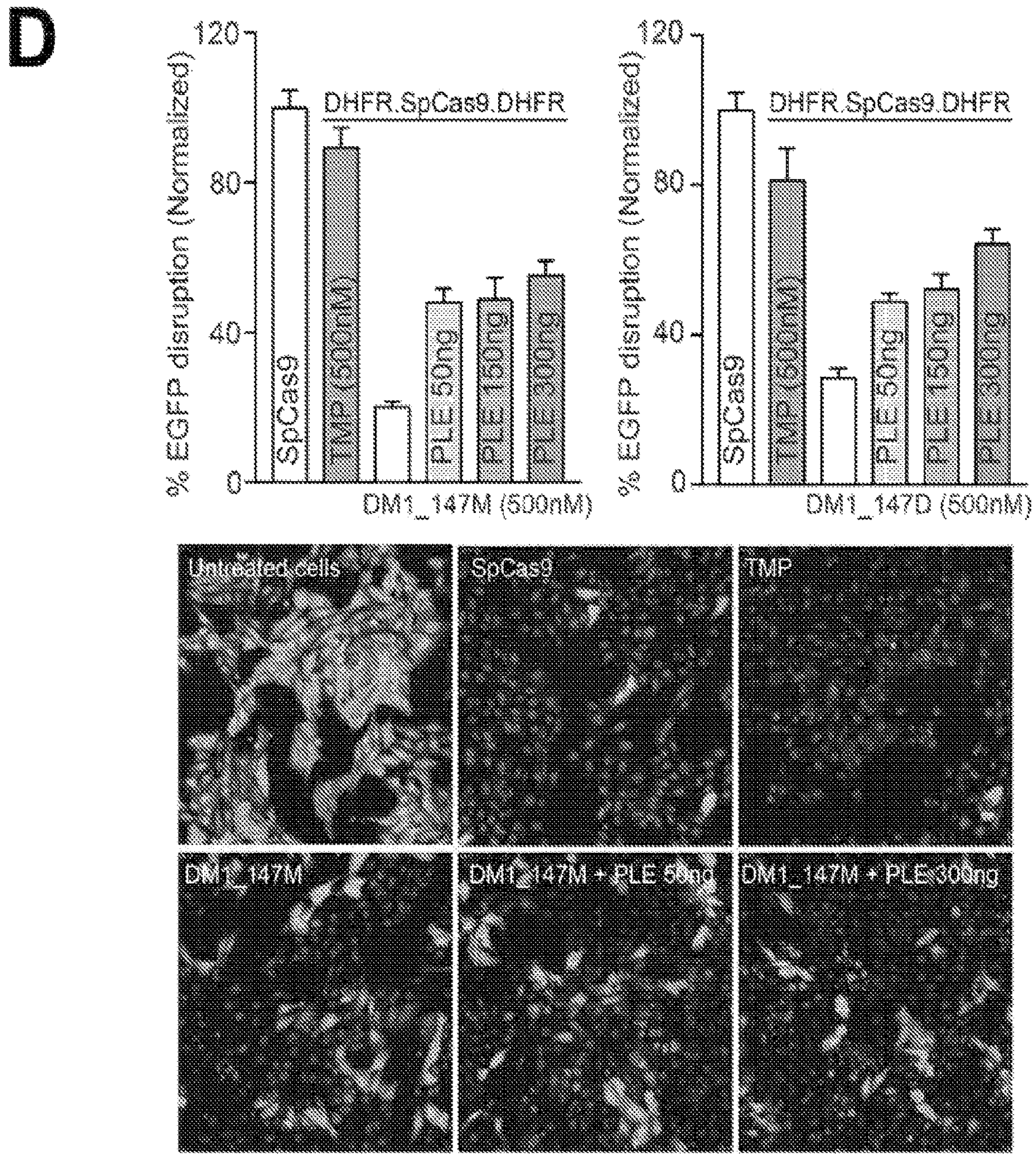

The inventors have developed a photocaged TMP derivative which is light activatable (FIG. 14A). Binding of the photocaged TMP to DHFR is blocked by the appended NVOC group. Upon exposure to light, the NVOC group is released, and TMP binds to and stabilizes DHFR-DD and the protein to which DHFF-DD is fused, for example a DD-DHFR-Cas9 protein fusion, and a dd-DHFR-aptamer-binding domain-functional domain fusion protein. HPLC analysis of the photocaged TMP-NVOC (FIG. 14B) shows the time course of conversion of photocaged TMP-NVOC to TMP upon exposure to blue light.

Example 6: Small-Molecule-Based Gene Drive Control in *Drosophila*

Dose- and temporal-control of SpCas9 activity was demonstrated in *Drosophila* (FIG. 6D). Transgenic *Drosophila* lines were generated bearing destabilized-domain SpCas9, which was optimized for the low body temperature of flies (i.e. 25° C.) and whose expression was confined to germline using the nanos promoter. The ebony gene (responsible for cuticle color) was targeted for SpCas9-mediated knockout employing ebony-specific gRNA provided genetically by an F0 male. Wildtype flies have a tan-colored cuticle, whereas ebony homozygous mutant flies have a black cuticle. The haploid gametes of the F1 females are either ebony mutant or wildtype depending on presence/absence of knockout, respectively. The ebony cuticular trait is recessive, and thus a test cross with a known ebony homozygous mutant male is needed to assess phenotypic effects in the F2 generation.

If ebony editing occurs and creates non-functional allele, the progeny at F2 generation will have a black cuticle. For dose-controlled SpCas9 activation experiments, we provided F1 virgin females with the indicated concentrations (0-80 μM range) of trimethoprim in the fly food. Dose-dependent Cas9-activation was observed with ~63% activation at full dose, which is similar to that reported for the wild type Cas9 for this gene (FIG. 6E). At 80 M, a drop in % activation of SpCas9 was observed likely due to poor palatability of trimethoprim at that high concentration. Reversibility was also demonstrated. Here, F1 virgin females were pre-fed with trimethoprim orally in 5% sucrose for three days and subsequently fed food lacking the small molecule. This withdrawal resulted in lowering of Cas9 activation within 24 hrs (FIG. 6F).

Small-molecule controlled gene-drive activation in *Drosophila* was demonstrated (FIG. 6G). Transgenic flies were created bearing destabilized-domain SpCas9 and monitored the transmission of GFP gene using trans-complementing configuration reported previously. In normal Mendelian inheritance (when gene drive is turned-off), 50% of the progeny will bear the engineered gene, which was observed for DMSO control. Upon gene-drive activation by trimethoprim, super-Mendelian inheritance with ~83% inheritance of the GFP was observed, which compares favorably to ~92% observed with the wildtype SpCas9-based gene drive.

In summary, chemogenic control of Cas9 endowed by DD fusion enables robust control of genome-interrogating activities across multiple dimensions, including dose, time, gene targets, and specificity. The small molecules employed are inexpensive, non-toxic, display favorable pharmacologic properties, and TMP is blood brain barrier-permeable. Our methodology is easily transportable to other cells and to complex organisms (6), enabling not just biomedical applications but also control of CRISPR-gene drives. Finally, our modular approach should prove readily extensible to next-generation RNA-guided endonucleases that continue to emerge.

REFERENCES

1. Doudna, J. A. & Charpentier, E. Genome editing. The new frontier of genome engineering with CRISPR-Cas9. *Science* 346, 1258096 (2014).
2. Hsu, P. D., Lander, E. S. & Zhang, F. Development and applications of CRISPR-Cas9 for genome engineering. Cell 157, 1262-1278 (2014).
3. Gantz, V. M. & Bier, E. The dawn of active genetics. Bioessays 38, 50-63 (2016).
4. Chen, B. et al. Dynamic imaging of genomic loci in living human cells by an optimized CRISPR/Cas system. *Cell* 155, 1479-1491 (2013).
5. Hilton, I. B. et al. Epigenome editing by a CRISPR-Cas9-based acetyltransferase activates genes from promoters and enhancers. *Nat. Biotechnol.* 33, 510-517 (2015).
6. Dominguez, A. A., Lim, W. A. & Qi, L. S. Beyond editing: repurposing CRISPR-Cas9 for precision genome regulation and interrogation. *Nat. Rev.* Mol. CellBiol. 17, 5-15 (2016).
7. Nunez, J. K., Harrington, L. B. & Doudna, J. A. Chemical and biophysical modulation of Cas9 for tunable genome engineering. *ACS Chem. Biol.* (2016).
8. Oakes, B. L. et al. Profiling of engineering hotspots identifies an allosteric CRISPR-Cas9 switch. *Nat. Biotechnol.* (2016), in press.
9. Iwamoto, M., Bjorklund, T., Lundberg, C., Kirik, D. & Wandless, T.J. A general chemical method to regulate protein stability in the mammalian central nervous system. *Chem. Biol.* 17, 981-988 (2010).
10. Miyazaki, Y., Imoto, H., Chen, L.C. & Wandless, T. J. Destabilizing domains derived from the human estrogen receptor. *J. Am. Chem. Soc.* 134, 3942-3945 (2012).
11. Banaszynski, L. A., Chen, L. C., Maynard-Smith, L. A., Ooi, A. G. & Wandless, T. J. A rapid, reversible, and tunable method to regulate protein function in living cells using synthetic small molecules. Cell 126, 995-1004 (2006).
12. Moore, C. L. et al. Transportable, chemical genetic methodology for the small molecule-mediated inhibition of heat shock factor 1. *ACS Chem. Biol.* 11, 200-210 (2016).
13. Shoulders, M. D., Ryno, L. M., Cooley, C. B., Kelly, J. W. & Wiseman, R. L. Broadly applicable methodology for the rapid and dosable small molecule-mediated regulation of transcription factors in human cells. *J. Am. Chem. Soc.* 135, 8129-8132 (2013).
14. Perez-Pinera, P. et al. RNA-guided gene activation by CRISPR-Cas9-based transcription factors. *Nat. Methods* 10, 973-976 (2013).
15. Balboa, D. et al. Conditionally stabilized dCas9 activator for controlling gene expression in human cell reprogramming and differentiation. *Stem CellRep.* 5, 448-459 (2015).
16. Konermann, S. et al. Genome-scale transcriptional activation by an engineered CRISPR-Cas9 complex. *Nature* 517, 583-588 (2015).
17. Zalatan, J. G. et al. Engineering complex synthetic transcriptional programs with CRISPR RNA scaffolds. *Cell* 160, 339-350 (2015).
18. Zetsche, B., Volz, S.E. & Zhang, F. A split-Cas9 architecture for inducible genome editing and transcription modulation. *Nat. Biotechnol.* 33, 139-142 (2015).
19. Buckley, D. L. & Crews, C.M. Small-molecule control of intracellular protein levels through modulation of the ubiquitin proteasome system. *Angew. Chem. Int. Ed.* 53, 2312-2330 (2014).
20. Nishimasu, H. et al. Crystal structure of *Staphylococcus aureus* Cas9. Cell 162, 1113-1126 (2015).
21. Esvelt, K. M., Smidler, A. L., Catteruccia, F. & Church, G.M. Concerning RNA-guided gene drives for the alteration of wild populations. eLife, e03401 (2014).
22. Davis, K. M., Pattanayak, V., Thompson, D. B., Zuris, J. A. & Liu, D. R. Small molecule-triggered Cas9 protein with improved genome-editing specificity. *Nat. Chem. Biol.* 11, 316-318 (2015).
23. Tsai, S. Q. & Joung, J. K. Defining and improving the genome-wide specificities of CRISPR-Cas9 nucleases. *Nat. Rev. Genet.* 17, 300-312 (2016).
24. Zuris, J. A. et al. Cationic lipid-mediated delivery of proteins enables efficient protein-based genome editing in vitro and in vivo. *Nat. Biotechnol.* 33, 73-80 (2015).
25. Fu, Y. et al. High-frequency off-target mutagenesis induced by CRISPR-Cas nucleases in human cells. *Nat. Biotechnol.* 31, 822-826 (2013).
26. Slaymaker, I. M. et al. Rationally engineered Cas9 nucleases with improved specificity. *Science* 351, 84-88 (2016).
27. Kleinstiver, B. P. et al. High-fidelity CRISPR-Cas9 nucleases with no detectable genome-wide off-target effects. *Nature* 529, 490-495 (2016).

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

SEQUENCE LISTING

```
<160> NUMBER OF SEQ ID NOS: 108

<210> SEQ ID NO 1
<211> LENGTH: 15
<212> TYPE: PRT
```

```
<213> ORGANISM: Artificial Sequence
<220> FEATURE:
<223> OTHER INFORMATION: Synthetic peptide

<400> SEQUENCE: 1

Gly Gly Gly Gly Ser Gly Gly Gly Gly Ser Gly Gly Gly Gly Ser
1               5                   10                  15


<210> SEQ ID NO 2
<211> LENGTH: 34
<212> TYPE: DNA
<213> ORGANISM: Artificial Sequence
<220> FEATURE:
<223> OTHER INFORMATION: Synthetic oligonucleotide

<400> SEQUENCE: 2

ggccaacatg aggatcaccc atgtctgcag ggcc                                  34


<210> SEQ ID NO 3
<211> LENGTH: 4
<212> TYPE: PRT
<213> ORGANISM: Artificial Sequence
<220> FEATURE:
<223> OTHER INFORMATION: Synthetic peptide

<400> SEQUENCE: 3

Gly Gly Gly Ser
1


<210> SEQ ID NO 4
<211> LENGTH: 12
<212> TYPE: PRT
<213> ORGANISM: Artificial Sequence
<220> FEATURE:
<223> OTHER INFORMATION: Synthetic peptide

<400> SEQUENCE: 4

Gly Gly Gly Ser Gly Gly Gly Ser Gly Gly Gly Ser
1               5                   10


<210> SEQ ID NO 5
<211> LENGTH: 30
<212> TYPE: PRT
<213> ORGANISM: Artificial Sequence
<220> FEATURE:
<223> OTHER INFORMATION: Synthetic peptide

<400> SEQUENCE: 5

Gly Gly Gly Gly Ser Gly Gly Gly Gly Ser Gly Gly Gly Gly Ser Gly
1               5                   10                  15

Gly Gly Gly Ser Gly Gly Gly Gly Ser Gly Gly Gly Gly Ser
            20                  25                  30


<210> SEQ ID NO 6
<211> LENGTH: 5
<212> TYPE: PRT
<213> ORGANISM: Artificial Sequence
<220> FEATURE:
<223> OTHER INFORMATION: Synthetic peptide

<400> SEQUENCE: 6

Gly Gly Gly Gly Ser
1               5


<210> SEQ ID NO 7
<211> LENGTH: 12
```

<212> TYPE: RNA
<213> ORGANISM: Artificial Sequence
<220> FEATURE:
<223> OTHER INFORMATION: Synthetic oligonucleotide

<400> SEQUENCE: 7
gcuagaauag ca 12

<210> SEQ ID NO 8
<211> LENGTH: 14
<212> TYPE: RNA
<213> ORGANISM: Artificial Sequence
<220> FEATURE:
<223> OTHER INFORMATION: Synthetic oligonucleotide

<400> SEQUENCE: 8
aacuugaaaa agug 14

<210> SEQ ID NO 9
<211> LENGTH: 12
<212> TYPE: DNA
<213> ORGANISM: Artificial Sequence
<220> FEATURE:
<223> OTHER INFORMATION: Synthetic oligonucleotide

<400> SEQUENCE: 9
acttgtttaa gt 12

<210> SEQ ID NO 10
<211> LENGTH: 12
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: MISC_FEATURE
<222> LOCATION: (1)..(4)
<223> OTHER INFORMATION: n represents any complementary set of nucleotides that together will base pair to n in positions 9-12 to create a stem
<220> FEATURE:
<221> NAME/KEY: MISC_FEATURE
<222> LOCATION: (9)..(12)
<223> OTHER INFORMATION: n represents any complementary set of nucleotides that together will base pair to n in positions 1-4 to create a stem

<400> SEQUENCE: 10
nnnngtttnn nn 12

<210> SEQ ID NO 11
<211> LENGTH: 16
<212> TYPE: DNA
<213> ORGANISM: Artificial Sequence
<220> FEATURE:
<223> OTHER INFORMATION: Synthetic oligonucleotide

<400> SEQUENCE: 11
ggcaccgagt cggtgc 16

<210> SEQ ID NO 12
<211> LENGTH: 30
<212> TYPE: RNA
<213> ORGANISM: Artificial Sequence
<220> FEATURE:
<223> OTHER INFORMATION: Synthetic oligonucleotide
<220> FEATURE:
<221> NAME/KEY: MISC_FEATURE
<222> LOCATION: (8)..(8)

<223> OTHER INFORMATION: n can be a or g or c or t/u, unknown, or other
      and represents part of the bulge in the DR:tracrRNA duplex
<220> FEATURE:
<221> NAME/KEY: MISC_FEATURE
<222> LOCATION: (9)..(12)
<223> OTHER INFORMATION: n represents any complementary set of
      nucleotides that together will base pair to n in positions 17-20
<220> FEATURE:
<221> NAME/KEY: MISC_FEATURE
<222> LOCATION: (13)..(16)
<223> OTHER INFORMATION: n can be a or g or c or t/u, unknown, or other,
      and represents a linker sequence
<220> FEATURE:
<221> NAME/KEY: MISC_FEATURE
<222> LOCATION: (17)..(20)
<223> OTHER INFORMATION: n represents any complementary set of
      nucleotides that together will base pair to n in positions 9-12
<220> FEATURE:
<221> NAME/KEY: MISC_FEATURE
<222> LOCATION: (21)..(23)
<223> OTHER INFORMATION: n can be a or g or c or t/u, unknown, or other
      and represents part of the bulge in the DR:tracrRNA duplex

<400> SEQUENCE: 12
gyyyyagnnn nnnnnnnnnn aanuurrrru 30

<210> SEQ ID NO 13
<211> LENGTH: 7
<212> TYPE: PRT
<213> ORGANISM: Simian virus 40

<400> SEQUENCE: 13

Pro Lys Lys Lys Arg Lys Val
1               5

<210> SEQ ID NO 14
<211> LENGTH: 16
<212> TYPE: PRT
<213> ORGANISM: Artificial Sequence
<220> FEATURE:
<223> OTHER INFORMATION: Synthetic nucleoplasmin bipartite NLS sequence

<400> SEQUENCE: 14

Lys Arg Pro Ala Ala Thr Lys Lys Ala Gly Gln Ala Lys Lys Lys Lys
1               5                   10                  15

<210> SEQ ID NO 15
<211> LENGTH: 9
<212> TYPE: PRT
<213> ORGANISM: Homo sapiens

<400> SEQUENCE: 15

Pro Ala Ala Lys Arg Val Lys Leu Asp
1               5

<210> SEQ ID NO 16
<211> LENGTH: 11
<212> TYPE: PRT
<213> ORGANISM: Homo sapiens

<400> SEQUENCE: 16

Arg Gln Arg Arg Asn Glu Leu Lys Arg Ser Pro
1               5                   10

<210> SEQ ID NO 17
<211> LENGTH: 38
<212> TYPE: PRT
<213> ORGANISM: Homo sapiens

<400> SEQUENCE: 17

Asn Gln Ser Ser Asn Phe Gly Pro Met Lys Gly Gly Asn Phe Gly Gly
1 5 10 15

Arg Ser Ser Gly Pro Tyr Gly Gly Gly Gly Gln Tyr Phe Ala Lys Pro
20 25 30

Arg Asn Gln Gly Gly Tyr
35

<210> SEQ ID NO 18
<211> LENGTH: 42
<212> TYPE: PRT
<213> ORGANISM: Homo sapiens

<400> SEQUENCE: 18

Arg Met Arg Ile Glx Phe Lys Asn Lys Gly Lys Asp Thr Ala Glu Leu
1 5 10 15

Arg Arg Arg Arg Val Glu Val Ser Val Glu Leu Arg Lys Ala Lys Lys
20 25 30

Asp Glu Gln Ile Leu Lys Arg Arg Asn Val
35 40

<210> SEQ ID NO 19
<211> LENGTH: 8
<212> TYPE: PRT
<213> ORGANISM: Homo sapiens

<400> SEQUENCE: 19

Val Ser Arg Lys Arg Pro Arg Pro
1 5

<210> SEQ ID NO 20
<211> LENGTH: 8
<212> TYPE: PRT
<213> ORGANISM: Homo sapiens

<400> SEQUENCE: 20

Pro Pro Lys Lys Ala Arg Glu Asp
1 5

<210> SEQ ID NO 21
<211> LENGTH: 8
<212> TYPE: PRT
<213> ORGANISM: Homo sapiens

<400> SEQUENCE: 21

Pro Gln Pro Lys Lys Lys Pro Leu
1 5

<210> SEQ ID NO 22
<211> LENGTH: 12
<212> TYPE: PRT
<213> ORGANISM: Mus sp.

<400> SEQUENCE: 22

Ser Ala Leu Ile Lys Lys Lys Lys Lys Met Ala Pro
1 5 10

<210> SEQ ID NO 23
<211> LENGTH: 5
<212> TYPE: PRT
<213> ORGANISM: Influenza virus

<400> SEQUENCE: 23

Asp Arg Leu Arg Arg
1 5

<210> SEQ ID NO 24
<211> LENGTH: 7
<212> TYPE: PRT
<213> ORGANISM: Influenza virus

<400> SEQUENCE: 24

Pro Lys Gln Lys Lys Arg Lys
1 5

<210> SEQ ID NO 25
<211> LENGTH: 10
<212> TYPE: PRT
<213> ORGANISM: Hepatitis D virus

<400> SEQUENCE: 25

Arg Lys Leu Lys Lys Lys Ile Lys Lys Leu
1 5 10

<210> SEQ ID NO 26
<211> LENGTH: 10
<212> TYPE: PRT
<213> ORGANISM: Mus sp.

<400> SEQUENCE: 26

Arg Glu Lys Lys Lys Phe Leu Lys Arg Arg
1 5 10

<210> SEQ ID NO 27
<211> LENGTH: 20
<212> TYPE: PRT
<213> ORGANISM: Homo sapiens

<400> SEQUENCE: 27

Lys Arg Lys Gly Asp Glu Val Asp Gly Val Asp Glu Val Ala Lys Lys
1 5 10 15

Lys Ser Lys Lys
20

<210> SEQ ID NO 28
<211> LENGTH: 17
<212> TYPE: PRT
<213> ORGANISM: Homo sapiens

<400> SEQUENCE: 28

Arg Lys Cys Leu Gln Ala Gly Met Asn Leu Glu Ala Arg Lys Thr Lys
1 5 10 15

Lys

<210> SEQ ID NO 29
<211> LENGTH: 23
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: MISC_FEATURE
<222> LOCATION: (1)..(20)
<223> OTHER INFORMATION: n is a or g or t or c
<220> FEATURE:
<221> NAME/KEY: MISC_FEATURE
<222> LOCATION: (21)..(21)
<223> OTHER INFORMATION: n is a or g or c or t, unknown, or orther

<400> SEQUENCE: 29
nnnnnnnnnn nnnnnnnnnn ngg 23

<210> SEQ ID NO 30
<211> LENGTH: 15
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: MISC_FEATURE
<222> LOCATION: (1)..(12)
<223> OTHER INFORMATION: n is a or c or t or g
<220> FEATURE:
<221> NAME/KEY: MISC_FEATURE
<222> LOCATION: (13)..(13)
<223> OTHER INFORMATION: n is a or c or t or g, or unknown, or other

<400> SEQUENCE: 30
nnnnnnnnnn nnngg 15

<210> SEQ ID NO 31
<211> LENGTH: 24
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: MISC_FEATURE
<222> LOCATION: (1)..(20)
<223> OTHER INFORMATION: n is a or c or t or g
<220> FEATURE:
<221> NAME/KEY: MISC_FEATURE
<222> LOCATION: (21)..(21)
<223> OTHER INFORMATION: n is a or c or t or g, or unknown, or other
<220> FEATURE:
<221> NAME/KEY: misc_feature
<222> LOCATION: (22)..(22)
<223> OTHER INFORMATION: n is a, c, g, or t

<400> SEQUENCE: 31
nnnnnnnnnn nnnnnnnnnn nngg 24

<210> SEQ ID NO 32
<211> LENGTH: 14
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: MISC_FEATURE
<222> LOCATION: (1)..(11)
<223> OTHER INFORMATION: n is a or c or t or g
<220> FEATURE:
<221> NAME/KEY: MISC_FEATURE
<222> LOCATION: (12)..(12)
<223> OTHER INFORMATION: n is a or c or t or g, or unknown, or other

<400> SEQUENCE: 32
nnnnnnnnnn nngg 14

<210> SEQ ID NO 33
<211> LENGTH: 27
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: MISC_FEATURE
<222> LOCATION: (1)..(20)

<223> OTHER INFORMATION: n is a or c or t or g
<220> FEATURE:
<221> NAME/KEY: MISC_FEATURE
<222> LOCATION: (21)..(22)
<223> OTHER INFORMATION: n is a or c or t or g, or unknown, or other
<220> FEATURE:
<221> NAME/KEY: MISC_FEATURE
<222> LOCATION: (27)..(27)
<223> OTHER INFORMATION: n is a or t

<400> SEQUENCE: 33
nnnnnnnnnn nnnnnnnnnn nnagaan 27

<210> SEQ ID NO 34
<211> LENGTH: 19
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: MISC_FEATURE
<222> LOCATION: (1)..(12)
<223> OTHER INFORMATION: n is a or c or t or g
<220> FEATURE:
<221> NAME/KEY: MISC_FEATURE
<222> LOCATION: (13)..(14)
<223> OTHER INFORMATION: n is a or c or t or g, or unknown, or other
<220> FEATURE:
<221> NAME/KEY: MISC_FEATURE
<222> LOCATION: (19)..(19)
<223> OTHER INFORMATION: n is a or t

<400> SEQUENCE: 34
nnnnnnnnnn nnnnagaan 19

<210> SEQ ID NO 35
<211> LENGTH: 27
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: MISC_FEATURE
<222> LOCATION: (1)..(20)
<223> OTHER INFORMATION: n is a or c or t or g
<220> FEATURE:
<221> NAME/KEY: MISC_FEATURE
<222> LOCATION: (21)..(22)
<223> OTHER INFORMATION: n is a or c or t or g, or unknown, or other
<220> FEATURE:
<221> NAME/KEY: MISC_FEATURE
<222> LOCATION: (27)..(27)
<223> OTHER INFORMATION: n is a or t

<400> SEQUENCE: 35
nnnnnnnnnn nnnnnnnnnn nnagaan 27

<210> SEQ ID NO 36
<211> LENGTH: 18
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: MISC_FEATURE
<222> LOCATION: (1)..(11)
<223> OTHER INFORMATION: n is a or c or t or g
<220> FEATURE:
<221> NAME/KEY: MISC_FEATURE
<222> LOCATION: (12)..(13)
<223> OTHER INFORMATION: n is a or c or t or g, or unknown, or other
<220> FEATURE:
<221> NAME/KEY: MISC_FEATURE
<222> LOCATION: (18)..(18)
<223> OTHER INFORMATION: n is a or t

<400> SEQUENCE: 36
nnnnnnnnnn nnnagaan 18

<210> SEQ ID NO 37
<211> LENGTH: 25
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: MISC_FEATURE
<222> LOCATION: (1)..(20)
<223> OTHER INFORMATION: n can be a, g, t or c
<220> FEATURE:
<221> NAME/KEY: MISC_FEATURE
<222> LOCATION: (21)..(21)
<223> OTHER INFORMATION: n is a or c or t or g, or unknown, or other
<220> FEATURE:
<221> NAME/KEY: MISC_FEATURE
<222> LOCATION: (24)..(24)
<223> OTHER INFORMATION: n is a or c or t or g, or unknown, or other

<400> SEQUENCE: 37
nnnnnnnnnn nnnnnnnnnn nggng 25

<210> SEQ ID NO 38
<211> LENGTH: 17
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: MISC_FEATURE
<222> LOCATION: (1)..(12)
<223> OTHER INFORMATION: n is a or g or t or c
<220> FEATURE:
<221> NAME/KEY: MISC_FEATURE
<222> LOCATION: (13)..(13)
<223> OTHER INFORMATION: n is a or c or t or g, or unknown, or other
<220> FEATURE:
<221> NAME/KEY: MISC_FEATURE
<222> LOCATION: (16)..(16)
<223> OTHER INFORMATION: n is a or c or t or g, or unknown, or other

<400> SEQUENCE: 38
nnnnnnnnnn nnnggng 17

<210> SEQ ID NO 39
<211> LENGTH: 25
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: MISC_FEATURE
<222> LOCATION: (1)..(20)
<223> OTHER INFORMATION: n can be a or c or t or g
<220> FEATURE:
<221> NAME/KEY: MISC_FEATURE
<222> LOCATION: (21)..(21)
<223> OTHER INFORMATION: n is a or c or t or g, or unknown, or other
<220> FEATURE:
<221> NAME/KEY: MISC_FEATURE
<222> LOCATION: (24)..(24)
<223> OTHER INFORMATION: n is a or c or t or g, or unknown, or other

<400> SEQUENCE: 39
nnnnnnnnnn nnnnnnnnnn nggng 25

<210> SEQ ID NO 40
<211> LENGTH: 16
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: MISC_FEATURE
<222> LOCATION: (1)..(11)
<223> OTHER INFORMATION: n is a or c or t or g
<220> FEATURE:
<221> NAME/KEY: MISC_FEATURE
<222> LOCATION: (12)..(12)
<223> OTHER INFORMATION: n is a or c or t or g, or unknown, or other
<220> FEATURE:
<221> NAME/KEY: MISC_FEATURE
<222> LOCATION: (15)..(15)
<223> OTHER INFORMATION: n is a or c or t or g, or unknown, or other

<400> SEQUENCE: 40
nnnnnnnnnn nnggng 16

<210> SEQ ID NO 41
<211> LENGTH: 137
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (1)..(20)
<223> OTHER INFORMATION: n is a, c, g, or t

<400> SEQUENCE: 41
nnnnnnnnnn nnnnnnnnnn gtttttgtac tctcaagatt tagaaataaa tcttgcagaa 60
gctacaaaga taaggcttca tgccgaaatc aacaccctgt cattttatgg cagggtgttt 120
tcgttattta atttttt 137

<210> SEQ ID NO 42
<211> LENGTH: 123
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (1)..(20)
<223> OTHER INFORMATION: n is a, c, g, or t

<400> SEQUENCE: 42
nnnnnnnnnn nnnnnnnnnn gtttttgtac tctcagaaat gcagaagcta caaagataag 60
gcttcatgcc gaaatcaaca ccctgtcatt ttatggcagg gtgttttcgt tatttaattt 120
ttt 123

<210> SEQ ID NO 43
<211> LENGTH: 110
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (1)..(20)
<223> OTHER INFORMATION: n is a, c, g, or t

<400> SEQUENCE: 43
nnnnnnnnnn nnnnnnnnnn gtttttgtac tctcagaaat gcagaagcta caaagataag 60
gcttcatgcc gaaatcaaca ccctgtcatt ttatggcagg gtgttttttt 110

<210> SEQ ID NO 44
<211> LENGTH: 102
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (1)..(20)
<223> OTHER INFORMATION: n is a, c, g, or t

<400> SEQUENCE: 44
nnnnnnnnnn nnnnnnnnnn gttttagagc tagaaatagc aagttaaaat aaggctagtc 60
cgttatcaac ttgaaaaagt ggcaccgagt cggtgctttt tt 102

<210> SEQ ID NO 45
<211> LENGTH: 88
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (1)..(20)
<223> OTHER INFORMATION: n is a, c, g, or t

<400> SEQUENCE: 45
nnnnnnnnnn nnnnnnnnnn gttttagagc tagaaatagc aagttaaaat aaggctagtc 60
cgttatcaac ttgaaaaagt gttttttt 88

<210> SEQ ID NO 46
<211> LENGTH: 76
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (1)..(20)
<223> OTHER INFORMATION: n is a, c, g, or t

<400> SEQUENCE: 46
nnnnnnnnnn nnnnnnnnnn gttttagagc tagaaatagc aagttaaaat aaggctagtc 60
cgttatcatt tttttt 76

<210> SEQ ID NO 47
<211> LENGTH: 20
<212> TYPE: DNA
<213> ORGANISM: Homo sapiens

<400> SEQUENCE: 47
gagtccgagc agaagaagaa 20

<210> SEQ ID NO 48
<211> LENGTH: 20
<212> TYPE: DNA
<213> ORGANISM: Homo sapiens

<400> SEQUENCE: 48
gagtcctagc aggagaagaa 20

<210> SEQ ID NO 49

<211> LENGTH: 20
<212> TYPE: DNA
<213> ORGANISM: Homo sapiens

<400> SEQUENCE: 49
gagtctaagc agaagaagaa 20

<210> SEQ ID NO 50
<211> LENGTH: 7
<212> TYPE: PRT
<213> ORGANISM: Artificial Sequence
<220> FEATURE:
<223> OTHER INFORMATION: Synthetic peptide

<400> SEQUENCE: 50

Ala Glu Ala Ala Ala Lys Ala
1 5

<210> SEQ ID NO 51
<211> LENGTH: 45
<212> TYPE: PRT
<213> ORGANISM: Artificial Sequence
<220> FEATURE:
<223> OTHER INFORMATION: Synthetic polypeptide

<400> SEQUENCE: 51

Gly Gly Gly Gly Ser Gly Gly Gly Gly Ser Gly Gly Gly Gly Ser Gly
1 5 10 15

Gly Gly Gly Ser Gly Gly Gly Gly Ser Gly Gly Gly Gly Ser Gly Gly
20 25 30

Gly Gly Ser Gly Gly Gly Gly Ser Gly Gly Gly Gly Ser
35 40 45

<210> SEQ ID NO 52
<211> LENGTH: 60
<212> TYPE: PRT
<213> ORGANISM: Artificial Sequence
<220> FEATURE:
<223> OTHER INFORMATION: Synthetic polypeptide

<400> SEQUENCE: 52

Gly Gly Gly Gly Ser Gly Gly Gly Gly Ser Gly Gly Gly Gly Ser Gly
1 5 10 15

Gly Gly Gly Ser Gly Gly Gly Gly Ser Gly Gly Gly Gly Ser Gly Gly
20 25 30

Gly Gly Ser Gly Gly Gly Gly Ser Gly Gly Gly Gly Ser Gly Gly Gly
35 40 45

Gly Ser Gly Gly Gly Gly Ser Gly Gly Gly Gly Ser
50 55 60

<210> SEQ ID NO 53
<211> LENGTH: 10
<212> TYPE: PRT
<213> ORGANISM: Artificial Sequence
<220> FEATURE:
<223> OTHER INFORMATION: Synthetic peptide

<400> SEQUENCE: 53

Gly Gly Gly Gly Ser Gly Gly Gly Gly Ser
1 5 10

<210> SEQ ID NO 54
<211> LENGTH: 20
<212> TYPE: PRT

```
<213> ORGANISM: Artificial Sequence
<220> FEATURE:
<223> OTHER INFORMATION: Synthetic peptide

<400> SEQUENCE: 54

Gly Gly Gly Gly Ser Gly Gly Gly Gly Ser Gly Gly Gly Gly Ser Gly
1               5                   10                  15

Gly Gly Gly Ser
            20


<210> SEQ ID NO 55
<211> LENGTH: 25
<212> TYPE: PRT
<213> ORGANISM: Artificial Sequence
<220> FEATURE:
<223> OTHER INFORMATION: Synthetic polypeptide

<400> SEQUENCE: 55

Gly Gly Gly Gly Ser Gly Gly Gly Gly Ser Gly Gly Gly Gly Ser Gly
1               5                   10                  15

Gly Gly Gly Ser Gly Gly Gly Gly Ser
            20                  25


<210> SEQ ID NO 56
<211> LENGTH: 35
<212> TYPE: PRT
<213> ORGANISM: Artificial Sequence
<220> FEATURE:
<223> OTHER INFORMATION: Synthetic polypeptide

<400> SEQUENCE: 56

Gly Gly Gly Gly Ser Gly Gly Gly Gly Ser Gly Gly Gly Gly Ser Gly
1               5                   10                  15

Gly Gly Gly Ser Gly Gly Gly Gly Ser Gly Gly Gly Gly Ser Gly Gly
            20                  25                  30

Gly Gly Ser
        35


<210> SEQ ID NO 57
<211> LENGTH: 40
<212> TYPE: PRT
<213> ORGANISM: Artificial Sequence
<220> FEATURE:
<223> OTHER INFORMATION: Synthetic polypeptide

<400> SEQUENCE: 57

Gly Gly Gly Gly Ser Gly Gly Gly Gly Ser Gly Gly Gly Gly Ser Gly
1               5                   10                  15

Gly Gly Gly Ser Gly Gly Gly Gly Ser Gly Gly Gly Gly Ser Gly Gly
            20                  25                  30

Gly Gly Ser Gly Gly Gly Gly Ser
        35                  40


<210> SEQ ID NO 58
<211> LENGTH: 50
<212> TYPE: PRT
<213> ORGANISM: Artificial Sequence
<220> FEATURE:
<223> OTHER INFORMATION: Synthetic polypeptide

<400> SEQUENCE: 58

Gly Gly Gly Gly Ser Gly Gly Gly Gly Ser Gly Gly Gly Gly Ser Gly
1               5                   10                  15
```

```
Gly Gly Gly Ser Gly Gly Gly Gly Ser Gly Gly Gly Gly Ser Gly Gly
            20                  25                  30

Gly Gly Ser Gly Gly Gly Gly Ser Gly Gly Gly Gly Ser Gly Gly Gly
        35                  40                  45

Gly Ser
    50


<210> SEQ ID NO 59
<211> LENGTH: 55
<212> TYPE: PRT
<213> ORGANISM: Artificial Sequence
<220> FEATURE:
<223> OTHER INFORMATION: Synthetic polypeptide

<400> SEQUENCE: 59

Gly Gly Gly Gly Ser Gly Gly Gly Gly Ser Gly Gly Gly Gly Ser Gly
1               5                   10                  15

Gly Gly Gly Ser Gly Gly Gly Gly Ser Gly Gly Gly Gly Ser Gly Gly
            20                  25                  30

Gly Gly Ser Gly Gly Gly Gly Ser Gly Gly Gly Gly Ser Gly Gly Gly
        35                  40                  45

Gly Ser Gly Gly Gly Gly Ser
    50                  55


<210> SEQ ID NO 60
<211> LENGTH: 414
<212> TYPE: DNA
<213> ORGANISM: Artificial Sequence
<220> FEATURE:
<223> OTHER INFORMATION: Synthetic polynucleotide

<400> SEQUENCE: 60

ctgaaccccg acaacagcga cgtggacaag ctgttcatcc agctggtgca gacctacaac     60

cagctgttcg aggaaaaccc catcaacgcc agcggcgtgg acgccaaggc catcctgtct    120

gccagactga gcaagagcag acggctggaa aatctgatcg cccagctgcc cggcgagaag    180

aagaatggcc tgttcggaaa cctgattgcc ctgagcctgg gcctgacccc caacttcaag    240

agcaacttcg acctggccga ggatgccaaa ctgcagctga gcaaggacac ctacgacgac    300

gacctggaca acctgctggc ccagatcggc gaccagtacg ccgacctgtt tctggccgcc    360

aagaacctgt ccgacgccat cctgctgagc gacatcctga gagtgaacac cgag          414


<210> SEQ ID NO 61
<211> LENGTH: 4
<212> TYPE: PRT
<213> ORGANISM: Artificial Sequence
<220> FEATURE:
<223> OTHER INFORMATION: Synthetic peptide

<400> SEQUENCE: 61

Gly Gly Ser Gly
1


<210> SEQ ID NO 62
<211> LENGTH: 12
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (2)..(2)
<223> OTHER INFORMATION: Aminohexanoyl
```

<220> FEATURE:
<221> NAME/KEY: MOD_RES
<222> LOCATION: (5)..(5)
<223> OTHER INFORMATION: Aminohexanoyl
<220> FEATURE:
<221> NAME/KEY: MOD_RES
<222> LOCATION: (8)..(8)
<223> OTHER INFORMATION: Aminohexanoyl
<220> FEATURE:
<221> NAME/KEY: MOD_RES
<222> LOCATION: (11)..(11)
<223> OTHER INFORMATION: Aminohexanoyl

<400> SEQUENCE: 62

Arg Xaa Arg Arg Xaa Arg Arg Xaa Arg Arg Xaa Arg
1 5 10

<210> SEQ ID NO 63
<211> LENGTH: 12
<212> TYPE: RNA
<213> ORGANISM: Artificial Sequence
<220> FEATURE:
<223> OTHER INFORMATION: Synthetic oligonucleotide

<400> SEQUENCE: 63
guuuuagagc ua 12

<210> SEQ ID NO 64
<211> LENGTH: 9
<212> TYPE: PRT
<213> ORGANISM: Artificial Sequence
<220> FEATURE:
<223> OTHER INFORMATION: LAGLIDADG family peptide motif sequence

<400> SEQUENCE: 64

Leu Ala Gly Leu Ile Asp Ala Asp Gly
1 5

<210> SEQ ID NO 65
<211> LENGTH: 18
<212> TYPE: DNA
<213> ORGANISM: Artificial Sequence
<220> FEATURE:
<223> OTHER INFORMATION: Synthetic primer

<400> SEQUENCE: 65
cgtcgcctcc tacctgct 18

<210> SEQ ID NO 66
<211> LENGTH: 20
<212> TYPE: DNA
<213> ORGANISM: Artificial Sequence
<220> FEATURE:
<223> OTHER INFORMATION: Synthetic primer

<400> SEQUENCE: 66
gatttgtggg cctgaagaaa 20

<210> SEQ ID NO 67
<211> LENGTH: 24
<212> TYPE: DNA
<213> ORGANISM: Artificial Sequence
<220> FEATURE:
<223> OTHER INFORMATION: Synthetic primer

<400> SEQUENCE: 67
ccattcagct cactgataac cttg 24

<210> SEQ ID NO 68
<211> LENGTH: 20
<212> TYPE: DNA
<213> ORGANISM: Artificial Sequence
<220> FEATURE:
<223> OTHER INFORMATION: Synthetic primer

<400> SEQUENCE: 68
cagatccatg gaggaaggaa 20

<210> SEQ ID NO 69
<211> LENGTH: 23
<212> TYPE: DNA
<213> ORGANISM: Artificial Sequence
<220> FEATURE:
<223> OTHER INFORMATION: Synthetic primer

<400> SEQUENCE: 69
gagtccgagc agaagaagaa ggg 23

<210> SEQ ID NO 70
<211> LENGTH: 23
<212> TYPE: DNA
<213> ORGANISM: Artificial Sequence
<220> FEATURE:
<223> OTHER INFORMATION: Synthetic primer

<400> SEQUENCE: 70
gagttagagc agaagaagaa agg 23

<210> SEQ ID NO 71
<211> LENGTH: 23
<212> TYPE: DNA
<213> ORGANISM: Artificial Sequence
<220> FEATURE:
<223> OTHER INFORMATION: Synthetic primer

<400> SEQUENCE: 71
gagtctaagc agaagaagaa gag 23

<210> SEQ ID NO 72
<211> LENGTH: 23
<212> TYPE: DNA
<213> ORGANISM: Artificial Sequence
<220> FEATURE:
<223> OTHER INFORMATION: Synthetic primer

<400> SEQUENCE: 72
gagtcctagc aggagaagaa gag 23

<210> SEQ ID NO 73
<211> LENGTH: 23
<212> TYPE: DNA
<213> ORGANISM: Artificial Sequence
<220> FEATURE:
<223> OTHER INFORMATION: Synthetic primer

<400> SEQUENCE: 73
aagtctgagc acaagaagaa tgg 23

<210> SEQ ID NO 74
<211> LENGTH: 23
<212> TYPE: DNA
<213> ORGANISM: Artificial Sequence
<220> FEATURE:
<223> OTHER INFORMATION: Synthetic primer

<400> SEQUENCE: 74
gaggccgagc agaagaaaga cgg 23

<210> SEQ ID NO 75
<211> LENGTH: 23
<212> TYPE: DNA
<213> ORGANISM: Artificial Sequence
<220> FEATURE:
<223> OTHER INFORMATION: Synthetic primer

<400> SEQUENCE: 75
ggtgagtgag tgtgtgcgtg tgg 23

<210> SEQ ID NO 76
<211> LENGTH: 23
<212> TYPE: DNA
<213> ORGANISM: Artificial Sequence
<220> FEATURE:
<223> OTHER INFORMATION: Synthetic primer

<400> SEQUENCE: 76
gctgagtgag tgtatgcgtg tgg 23

<210> SEQ ID NO 77
<211> LENGTH: 44
<212> TYPE: DNA
<213> ORGANISM: Artificial Sequence
<220> FEATURE:
<223> OTHER INFORMATION: Synthetic primer

<400> SEQUENCE: 77
ccatctcatc cctgcgtgtc tcccaaagta caaacggcag aagc 44

<210> SEQ ID NO 78
<211> LENGTH: 43
<212> TYPE: DNA
<213> ORGANISM: Artificial Sequence
<220> FEATURE:
<223> OTHER INFORMATION: Synthetic primer

<400> SEQUENCE: 78
ccatctcatc cctgcgtgtc tccttctgag ggctgctacc tgt 43

<210> SEQ ID NO 79
<211> LENGTH: 43
<212> TYPE: DNA
<213> ORGANISM: Artificial Sequence
<220> FEATURE:
<223> OTHER INFORMATION: Synthetic primer

<400> SEQUENCE: 79
ccatctcatc cctgcgtgtc tcccacggcc tttgcaaata gag 43

<210> SEQ ID NO 80
<211> LENGTH: 44
<212> TYPE: DNA
<213> ORGANISM: Artificial Sequence
<220> FEATURE:
<223> OTHER INFORMATION: Synthetic primer

<400> SEQUENCE: 80
ccatctcatc cctgcgtgtc tccccagact cagtaaagcc tgga 44

<210> SEQ ID NO 81

<211> LENGTH: 46
<212> TYPE: DNA
<213> ORGANISM: Artificial Sequence
<220> FEATURE:
<223> OTHER INFORMATION: Synthetic primer

<400> SEQUENCE: 81
ccatctcatc cctgcgtgtc tccgttctga cattcctcct gaggga 46

<210> SEQ ID NO 82
<211> LENGTH: 43
<212> TYPE: DNA
<213> ORGANISM: Artificial Sequence
<220> FEATURE:
<223> OTHER INFORMATION: Synthetic primer

<400> SEQUENCE: 82
ccatctcatc cctgcgtgtc tcctgggaga gagaccccctt ctt 43

<210> SEQ ID NO 83
<211> LENGTH: 43
<212> TYPE: DNA
<213> ORGANISM: Artificial Sequence
<220> FEATURE:
<223> OTHER INFORMATION: Synthetic primer

<400> SEQUENCE: 83
ccatctcatc cctgcgtgtc tccgcgtctt cgagagtgag gac 43

<210> SEQ ID NO 84
<211> LENGTH: 43
<212> TYPE: DNA
<213> ORGANISM: Artificial Sequence
<220> FEATURE:
<223> OTHER INFORMATION: Synthetic primer

<400> SEQUENCE: 84
ccatctcatc cctgcgtgtc tccgcccatt tctcctttga ggt 43

<210> SEQ ID NO 85
<211> LENGTH: 43
<212> TYPE: DNA
<213> ORGANISM: Artificial Sequence
<220> FEATURE:
<223> OTHER INFORMATION: Synthetic primer

<400> SEQUENCE: 85
ccatctcatc cctgcgtgtc tccgttgccc accctagtca ttg 43

<210> SEQ ID NO 86
<211> LENGTH: 43
<212> TYPE: DNA
<213> ORGANISM: Artificial Sequence
<220> FEATURE:
<223> OTHER INFORMATION: Synthetic primer

<400> SEQUENCE: 86
ccatctcatc cctgcgtgtc tccgcccaat cattgatgct ttt 43

<210> SEQ ID NO 87
<211> LENGTH: 43
<212> TYPE: DNA
<213> ORGANISM: Artificial Sequence
<220> FEATURE:
<223> OTHER INFORMATION: Synthetic primer

<400> SEQUENCE: 87
ccatctcatc cctgcgtgtc tccggctttc acaaggatgc agt 43

<210> SEQ ID NO 88
<211> LENGTH: 43
<212> TYPE: DNA
<213> ORGANISM: Artificial Sequence
<220> FEATURE:
<223> OTHER INFORMATION: Synthetic primer

<400> SEQUENCE: 88
ccatctcatc cctgcgtgtc tcctggcccc agtctctctt cta 43

<210> SEQ ID NO 89
<211> LENGTH: 57
<212> TYPE: DNA
<213> ORGANISM: Artificial Sequence
<220> FEATURE:
<223> OTHER INFORMATION: Synthetic primer

<400> SEQUENCE: 89
ccatctcatc cctgcgtgtc tccatggctt acatatttat tagataaaat gtattcc 57

<210> SEQ ID NO 90
<211> LENGTH: 47
<212> TYPE: DNA
<213> ORGANISM: Artificial Sequence
<220> FEATURE:
<223> OTHER INFORMATION: Synthetic primer

<400> SEQUENCE: 90
ccatctcatc cctgcgtgtc tcctcctgct ctcacttaga ctttctc 47

<210> SEQ ID NO 91
<211> LENGTH: 43
<212> TYPE: DNA
<213> ORGANISM: Artificial Sequence
<220> FEATURE:
<223> OTHER INFORMATION: Synthetic primer

<400> SEQUENCE: 91
ccatctcatc cctgcgtgtc tccggggaga gggacacaca gat 43

<210> SEQ ID NO 92
<211> LENGTH: 43
<212> TYPE: DNA
<213> ORGANISM: Artificial Sequence
<220> FEATURE:
<223> OTHER INFORMATION: Synthetic primer

<400> SEQUENCE: 92
ccatctcatc cctgcgtgtc tccagccaca gaggtggaga ctg 43

<210> SEQ ID NO 93
<211> LENGTH: 4701
<212> TYPE: DNA
<213> ORGANISM: Artificial Sequence
<220> FEATURE:
<223> OTHER INFORMATION: Synthetic polynucleotide

<400> SEQUENCE: 93
atggccccaa agaagaagcg gaaggtcggt atccacggag tcccagcagc cggatccatc 60
agtctgattg cggcgttagc ggtagattac gttatcggca tggaaaacgc catgccgtgg 120
aacctgcctg ccgatctcgc ctggtttaaa cgcaacacct taaataaacc cgtgattatg 180

-continued ggccgccata cctgggaatc aatcggtcgt ccgttgccag gacgcaaaaa tattatcctc 240
agcagtcaac cgagtacgga cgatcgcgta acgtgggtga agtcggtgga tgaagccatc 300
gcggcgtgtg gtgacgtacc agaaatcatg gtgattggcg gcggtcgcgt tattgaacag 360
ttcttgccaa aagcgcaaaa actgtatctg acgcatatcg acgcagaagt ggaaggcgac 420
acccatttcc cggattacga gccggatgac tgggaatcgg tattcagcga attccacgat 480
gctgatgcgc agaactctca cagctattgc tttgagattc tggagcggcg aggaagcgga 540
agcggatccg acaagaagta cagcatcggc ctggacatcg gcaccaactc tgtgggctgg 600
gccgtgatca ccgacgagta caaggtgccc agcaagaaat tcaaggtgct gggcaacacc 660
gaccggcaca gcatcaagaa gaacctgatc ggagccctgc tgttcgacag cggcgaaaca 720
gccgaggcca cccggctgaa gagaaccgcc agaagaagat acaccagacg gaagaaccgg 780
atctgctatc tgcaagagat cttcagcaac gagatggcca aggtggacga cagcttcttc 840
cacagactgg aagagtcctt cctggtggaa gaggataaga agcacgagcg gcaccccatc 900
ttcggcaaca tcgtggacga ggtggcctac cacgagaagt accccaccat ctaccacctg 960
agaaagaaac tggtggacag caccgacaag gccgacctgc ggctgatcta tctggccctg 1020
gcccacatga tcaagttccg gggccacttc ctgatcgagg gcgacctgaa ccccgacaac 1080
agcgacgtgg acaagctgtt catccagctg gtgcagacct acaaccagct gttcgaggaa 1140
aaccccatca acgccagcgg cgtggacgcc aaggccatcc tgtctgccag actgagcaag 1200
agcagacggc tggaaaatct gatcgcccag ctgcccggcg agaagaagaa tggcctgttc 1260
ggaaacctga ttgccctgag cctgggcctg acccccaact tcaagagcaa cttcgacctg 1320
gccgaggatg ccaaactgca gctgagcaag gacacctacg acgacgacct ggacaacctg 1380
ctggcccaga tcggcgacca gtacgccgac ctgtttctgg ccgccaagaa cctgtccgac 1440
gccatcctgc tgagcgacat cctgagagtg aacaccgaga tcaccaaggc ccccctgagc 1500
gcctctatga tcaagagata cgacgagcac caccaggacc tgaccctgct gaaagctctc 1560
gtgcggcagc agctgcctga gaagtacaaa gagattttct tcgaccagag caagaacggc 1620
tacgccggct acattgacgg cggagccagc caggaagagt tctacaagtt catcaagccc 1680
atcctggaaa agatggacgg caccgaggaa ctgctcgtga agctgaacag agaggacctg 1740
ctgcggaagc agcggacctt cgacaacggc agcatccccc accagatcca cctgggagag 1800
ctgcacgcca ttctgcggcg gcaggaagat ttttacccat tcctgaagga caaccgggaa 1860
aagatcgaga agatcctgac cttccgcatc ccctactacg tgggccctct ggccagggga 1920
aacagcagat tcgcctggat gaccagaaag agcgaggaaa ccatcacccc ctggaacttc 1980
gaggaagtgg tggacaaggg cgcttccgcc cagagcttca tcgagcggat gaccaacttc 2040
gataagaacc tgcccaacga gaaggtgctg cccaagcaca gcctgctgta cgagtacttc 2100
accgtgtata acgagctgac caaagtgaaa tacgtgaccg agggaatgag aaagcccgcc 2160
ttcctgagcg gcgagcagaa aaaggccatc gtggacctgc tgttcaagac caaccggaaa 2220
gtgaccgtga agcagctgaa agaggactac ttcaagaaaa tcgagtgctt cgactccgtg 2280
gaaatctccg gcgtggaaga tcggttcaac gcctccctgg gcacatacca cgatctgctg 2340
aaaattatca aggacaagga cttcctggac aatgaggaaa acgaggacat tctggaagat 2400
atcgtgctga ccctgacact gtttgaggac agagagatga tcgaggaacg gctgaaaacc 2460
tatgcccacc tgttcgacga caaagtgatg aagcagctga agcggcggag atacaccggc 2520
tggggcaggc tgagccggaa gctgatcaac ggcatccggg acaagcagtc cggcaagaca 2580

```
atcctggatt tcctgaagtc cgacggcttc gccaacagaa acttcatgca gctgatccac   2640
gacgacagcc tgacctttaa agaggacatc cagaaagccc aggtgtccgg ccagggcgat   2700
agcctgcacg agcacattgc caatctggcc ggcagccccg ccattaagaa gggcatcctg   2760
cagacagtga aggtggtgga cgagctcgtg aaagtgatgg gccggcacaa gcccgagaac   2820
atcgtgatcg aaatggccag agagaaccag accacccaga agggacagaa gaacagccgc   2880
gagagaatga agcggatcga agagggcatc aaagagctgg gcagccagat cctgaaagaa   2940
cacccccgtgg aaaacaccca gctgcagaac gagaagctgt acctgtacta cctgcagaat   3000
gggcgggata tgtacgtgga ccaggaactg gacatcaacc ggctgtccga ctacgatgtg   3060
gaccatatcg tgcctcagag ctttctgaag gacgactcca tcgacaacaa ggtgctgacc   3120
agaagcgaca agaaccgggg caagagcgac aacgtgccct ccgaagaggt cgtgaagaag   3180
atgaagaact actggcggca gctgctgaac gccaagctga ttacccagag aaagttcgac   3240
aatctgacca aggccgagag aggcggcctg agcgaactgg ataaggccgg cttcatcaag   3300
agacagctgg tggaaacccg gcagatcaca aagcacgtgg cacagatcct ggactcccgg   3360
atgaacacta agtacgacga gaatgacaag ctgatccggg aagtgaaagt gatcaccctg   3420
aagtccaagc tggtgtccga tttccggaag gatttccagt tttacaaagt gcgcgagatc   3480
aacaactacc accacgccca cgacgcctac ctgaacgccg tcgtgggaac cgccctgatc   3540
aaaaagtacc ctaagctgga aagcgagttc gtgtacggcg actacaaggt gtacgacgtg   3600
cggaagatga tcgccaagag cgagcaggaa atcggcaagg ctaccgccaa gtacttcttc   3660
tacagcaaca tcatgaactt tttcaagacc gagattaccc tggccaacgg cgagatccgg   3720
aagcggcctc tgatcgagac aaacggcgaa accggggaga tcgtgtggga taagggccgg   3780
gattttgcca ccgtgcggaa agtgctgagc atgccccaag tgaatatcgt gaaaaagacc   3840
gaggtgcaga caggcggctt cagcaaagag tctatcctgc ccaagaggaa cagcgataag   3900
ctgatcgcca gaaagaagga ctgggaccct aagaagtacg gcggcttcga cagccccacc   3960
gtggcctatt ctgtgctggt ggtggccaaa gtggaaaagg gcaagtccaa gaaactgaag   4020
agtgtgaaag agctgctggg gatcaccatc atggaaagaa gcagcttcga gaagaatccc   4080
atcgactttc tggaagccaa gggctacaaa gaagtgaaaa aggacctgat catcaagctg   4140
cctaagtact ccctgttcga gctggaaaac ggccggaaga gaatgctggc ctctgccggc   4200
gaactgcaga agggaaacga actggccctg ccctccaaat atgtgaactt cctgtacctg   4260
gccagccact atgagaagct gaagggctcc cccgaggata atgagcagaa acagctgttt   4320
gtggaacagc acaagcacta cctggacgag atcatcgagc agatcagcga gttctccaag   4380
agagtgatcc tggccgacgc taatctggac aaagtgctgt ccgcctacaa caagcaccgg   4440
gataagccca tcagagagca ggccgagaat atcatccacc tgtttaccct gaccaatctg   4500
ggagcccctg ccgccttcaa gtactttgac accaccatcg accggaagag gtacaccagc   4560
accaaagagg tgctggacgc caccctgatc caccagagca tcaccggcct gtacgagaca   4620
cggatcgacc tgtctcagct gggaggcgac aaaaggccgg cggccacgaa aaaggccggc   4680
caggcaaaaa agaaaaagta a                                             4701
```

<210> SEQ ID NO 94
<211> LENGTH: 4677
<212> TYPE: DNA
<213> ORGANISM: Artificial Sequence
<220> FEATURE:

<223> OTHER INFORMATION: Synthetic polynucleotide

<400> SEQUENCE: 94
atggccccaa agaagaagcg gaaggtcggt atccacggag tcccagcagc cgacaagaag 60
tacagcatcg gcctggacat cggcaccaac tctgtgggct gggccgtgat caccgacgag 120
tacaaggtgc ccagcaagaa attcaaggtg ctgggcaaca ccgaccggca cagcatcaag 180
aagaacctga tcggagccct gctgttcgac agcggcgaaa cagccgaggc cacccggctg 240
aagagaaccg ccagaagaag atacaccaga cggaagaacc ggatctgcta tctgcaagag 300
atcttcagca acgagatggc caaggtggac gacagcttct tccacagact ggaagagtcc 360
ttcctggtgg aagaggataa gaagcacgag cggcacccca tcttcggcaa catcgtggac 420
gaggtggcct accacgagaa gtaccccacc atctaccacc tgagaaagaa actggtggac 480
agcaccgaca aggccgacct gcggctgatc tatctggccc tggcccacat gatcaagttc 540
cggggccact tcctgatcga gggcgacctg aaccccgaca acagcgacgt ggacaagctg 600
ttcatccagc tggtgcagac ctacaaccag ctgttcgagg aaaaccccat caacgccagc 660
ggcgtggacg ccaaggccat cctgtctgcc agactgagca agagcagacg gctggaaaat 720
ctgatcgccc agctgcccgg cgagaagaag aatggcctgt tcggaaacct gattgccctg 780
agcctgggcc tgacccccaa cttcaagagc aacttcgacc tggccgagga tgccaaactg 840
cagctgagca aggacaccta cgacgacgac ctggacaacc tgctggccca gatcggcgac 900
cagtacgccg acctgtttct ggccgccaag aacctgtccg acgccatcct gctgagcgac 960
atcctgagag tgaacaccga gatcaccaag gcccccctga gcgcctctat gatcaagaga 1020
tacgacgagc accaccagga cctgaccctg ctgaaagctc tcgtgcggca gcagctgcct 1080
gagaagtaca aagagatttt cttcgaccag agcaagaacg gctacgccgg ctacattgac 1140
ggcggagcca gccaggaaga gttctacaag ttcatcaagc ccatcctgga aaagatggac 1200
ggcaccgagg aactgctcgt gaagctgaac agagaggacc tgctgcggaa gcagcggacc 1260
ttcgacaacg gcagcatccc ccaccagatc cacctgggag agctgcacgc cattctgcgg 1320
cggcaggaag atttttaccc attcctgaag gacaaccggg aaaagatcga gaagatcctg 1380
accttccgca tcccctacta cgtgggccct ctggccaggg gaaacagcag attcgcctgg 1440
atgaccagaa agagcgagga aaccatcacc ccctggaact tcgaggaagt ggtggacaag 1500
ggcgcttccg cccagagctt catcgagcgg atgaccaact tcgataagaa cctgcccaac 1560
gagaaggtgc tgcccaagca cagcctgctg tacgagtact tcaccgtgta taacgagctg 1620
accaaagtga aatacgtgac cgagggaatg agaaagcccg ccttcctgag cggcgagcag 1680
aaaaaggcca tcgtggacct gctgttcaag accaaccgga aagtgaccgt gaagcagctg 1740
aaagaggact acttcaagaa aatcgagtgc ttcgactccg tggaaatctc cggcgtggaa 1800
gatcggttca acgcctccct gggcacatac cacgatctgc tgaaaattat caaggacaag 1860
gacttcctgg acaatgagga aaacgaggac attctggaag atatcgtgct gaccctgaca 1920
ctgtttgagg acagagagat gatcgaggaa cggctgaaaa cctatgccca cctgttcgac 1980
gacaaagtga tgaagcagct gaagcggcgg agatacaccg gctggggcag gctgagccgg 2040
aagctgatca acggcatccg ggacaagcag tccggcaaga caatcctgga tttcctgaag 2100
tccgacggct tcgccaacag aaacttcatg cagctgatcc acgacgacag cctgaccttt 2160
aaagaggaca tccagaaagc ccaggtgtcc ggccagggcg atagcctgca cgagcacatt 2220
gccaatctgg ccggcagccc cgccattaag aagggcatcc tgcagacagt gaaggtggtg 2280
gacgagctcg tgaaagtgat gggccggcac aagcccgaga acatcgtgat cgaaatggcc 2340
agagagaacc agaccaccca gaagggacag aagaacagcc gcgagagaat gaagcggatc 2400
gaagagggca tcaaagagct gggcagccag atcctgaaag aacaccccgt ggaaaacacc 2460
cagctgcaga acgagaagct gtacctgtac tacctgcaga atgggcggga tatgtacgtg 2520
gaccaggaac tggacatcaa ccggctgtcc gactacgatg tggaccatat cgtgcctcag 2580
agctttctga aggacgactc catcgacaac aaggtgctga ccagaagcga caagaaccgg 2640
ggcaagagcg acaacgtgcc ctccgaagag gtcgtgaaga agatgaagaa ctactggcgg 2700
cagctgctga acgccaagct gattacccag agaaagttcg acaatctgac caaggccgag 2760
agaggcggcc tgagcgaact ggataaggcc ggcttcatca agagacagct ggtggaaacc 2820
cggcagatca caaagcacgt ggcacagatc ctggactccc ggatgaacac taagtacgac 2880
gagaatgaca agctgatccg ggaagtgaaa gtgatcaccc tgaagtccaa gctggtgtcc 2940
gatttccgga aggatttcca gttttacaaa gtgcgcgaga tcaacaacta ccaccacgcc 3000
cacgacgcct acctgaacgc cgtcgtggga accgccctga tcaaaaagta ccctaagctg 3060
gaaagcgagt tcgtgtacgg cgactacaag gtgtacgacg tgcggaagat gatcgccaag 3120
agcgagcagg aaatcggcaa ggctaccgcc aagtacttct tctacagcaa catcatgaac 3180
tttttcaaga ccgagattac cctggccaac ggcgagatcc ggaagcggcc tctgatcgag 3240
acaaacggcg aaaccgggga gatcgtgtgg gataagggcc gggattttgc caccgtgcgg 3300
aaagtgctga gcatgcccca agtgaatatc gtgaaaaaga ccgaggtgca gacaggcggc 3360
ttcagcaaag agtctatcct gcccaagagg aacagcgata agctgatcgc cagaaagaag 3420
gactgggacc ctaagaagta cggcggcttc gacagcccca ccgtggccta ttctgtgctg 3480
gtggtggcca aagtggaaaa gggcaagtcc aagaaactga agagtgtgaa agagctgctg 3540
gggatcacca tcatggaaag aagcagcttc gagaagaatc ccatcgactt tctggaagcc 3600
aagggctaca aagaagtgaa aaaggacctg atcatcaagc tgcctaagta ctccctgttc 3660
gagctggaaa acggccggaa gagaatgctg gcctctgccg gcgaactgca gaagggaaac 3720
gaactggccc tgccctccaa atatgtgaac ttcctgtacc tggccagcca ctatgagaag 3780
ctgaagggct cccccgagga taatgagcag aaacagctgt ttgtggaaca gcacaagcac 3840
tacctggacg agatcatcga gcagatcagc gagttctcca agagagtgat cctggccgac 3900
gctaatctgg acaaagtgct gtccgcctac aacaagcacc gggataagcc catcagagag 3960
caggccgaga atatcatcca cctgtttacc ctgaccaatc tgggagcccc tgccgccttc 4020
aagtactttg acaccaccat cgaccggaag aggtacacca gcaccaaaga ggtgctggac 4080
gccaccctga tccaccagag catcaccggc ctgtacgaga cacggatcga cctgtctcag 4140
ctgggaggcg acaaaaggcc ggcggccacg aaaaaggccg gccaggcaaa aaagaaaaag 4200
atcagtctga ttgcggcgtt agcggtagat cacgttatcg gcatggaaac cgtcatgccg 4260
tggaacctgc ctgccgatct cgcctggttt aaacgcaaca ccttaaataa acccgtgatt 4320
atgggccgcc atacctggga atcaatcggt cgtccgttgc caggacgcaa aaatattatc 4380
ctcagcagtc aaccgagtac ggacgatcgc gtaacgtggg tgaagtcggt ggatgaagcc 4440
atcgcggcgt gtggtgacgt accagaaatc atggttattg gcggcggtcg cgtttatgaa 4500
cagttcttgc caaaagcgca aaaactgtat ctgacgcata tcgacgcaga agtggaaggc 4560
gacacccatt tcccggatta cgagccggat gactgggaat cggtattcag cgaattccac 4620
gatgctgatg cgcagaactc tcacagctat tgctttgaga ttctggagcg gcgataa 4677

<210> SEQ ID NO 95
<211> LENGTH: 5175
<212> TYPE: DNA
<213> ORGANISM: Artificial Sequence
<220> FEATURE:
<223> OTHER INFORMATION: Synthetic polynucleotide

<400> SEQUENCE: 95
atggccccaa agaagaagcg gaaggtcggt atccacggag tcccagcagc cggatccatc 60
agtctgattg cggcgttagc ggtagattac gttatcggca tggaaaacgc catgccgtgg 120
aacctgcctg ccgatctcgc ctggtttaaa cgcaacacct taaataaacc cgtgattatg 180
ggccgccata cctgggaatc aatcggtcgt ccgttgccag gacgcaaaaa tattatcctc 240
agcagtcaac cgagtacgga cgatcgcgta acgtgggtga agtcggtgga tgaagccatc 300
gcggcgtgtg gtgacgtacc agaaatcatg gtgattggcg gcggtcgcgt tattgaacag 360
ttcttgccaa aagcgcaaaa actgtatctg acgcatatcg acgcagaagt ggaaggcgac 420
acccatttcc cggattacga gccggatgac tgggaatcgg tattcagcga attccacgat 480
gctgatgcgc agaactctca cagctattgc tttgagattc tggagcggcg aggaagcgga 540
agcggatccg acaagaagta cagcatcggc ctggacatcg gcaccaactc tgtgggctgg 600
gccgtgatca ccgacgagta caaggtgccc agcaagaaat tcaaggtgct gggcaacacc 660
gaccggcaca gcatcaagaa gaacctgatc ggagccctgc tgttcgacag cggcgaaaca 720
gccgaggcca cccggctgaa gagaaccgcc agaagaagat acaccagacg gaagaaccgg 780
atctgctatc tgcaagagat cttcagcaac gagatggcca aggtggacga cagcttcttc 840
cacagactgg aagagtcctt cctggtggaa gaggataaga agcacgagcg gcaccccatc 900
ttcggcaaca tcgtggacga ggtggcctac cacgagaagt accccaccat ctaccacctg 960
agaaagaaac tggtggacag caccgacaag gccgacctgc ggctgatcta tctggccctg 1020
gcccacatga tcaagttccg gggccacttc ctgatcgagg gcgacctgaa ccccgacaac 1080
agcgacgtgg acaagctgtt catccagctg gtgcagacct acaaccagct gttcgaggaa 1140
aaccccatca acgccagcgg cgtggacgcc aaggccatcc tgtctgccag actgagcaag 1200
agcagacggc tggaaaatct gatcgcccag ctgcccggcg agaagaagaa tggcctgttc 1260
ggaaacctga ttgccctgag cctgggcctg acccccaact tcaagagcaa cttcgacctg 1320
gccgaggatg ccaaactgca gctgagcaag gacacctacg acgacgacct ggacaacctg 1380
ctggcccaga tcggcgacca gtacgccgac ctgtttctgg ccgccaagaa cctgtccgac 1440
gccatcctgc tgagcgacat cctgagagtg aacaccgaga tcaccaaggc cccccctgagc 1500 gcctctatga tcaagagata cgacgagcac caccaggacc tgaccctgct gaaagctctc 1560
gtgcggcagc agctgcctga gaagtacaaa gagattttct tcgaccagag caagaacggc 1620
tacgccggct acattgacgg cggagccagc caggaagagt tctacaagtt catcaagccc 1680
atcctggaaa agatggacgg caccgaggaa ctgctcgtga agctgaacag agaggacctg 1740
ctgcggaagc agcggacctt cgacaacggc agcatccccc accagatcca cctgggagag 1800
ctgcacgcca ttctgcggcg gcaggaagat ttttacccat tcctgaagga caaccgggaa 1860
aagatcgaga agatcctgac cttccgcatc ccctactacg tgggccctct ggccagggga 1920
aacagcagat tcgcctggat gaccagaaag agcgaggaaa ccatcacccc ctggaacttc 1980
gaggaagtgg tggacaaggg cgcttccgcc cagagcttca tcgagcggat gaccaacttc 2040
gataagaacc tgcccaacga gaaggtgctg cccaagcaca gcctgctgta cgagtacttc 2100
accgtgtata acgagctgac caaagtgaaa tacgtgaccg agggaatgag aaagcccgcc 2160
ttcctgagcg gcgagcagaa aaaggccatc gtggacctgc tgttcaagac caaccggaaa 2220
gtgaccgtga agcagctgaa agaggactac ttcaagaaaa tcgagtgctt cgactccgtg 2280
gaaatctccg gcgtggaaga tcggttcaac gcctccctgg gcacatacca cgatctgctg 2340
aaaattatca aggacaagga cttcctggac aatgaggaaa acgaggacat tctggaagat 2400
atcgtgctga ccctgacact gtttgaggac agagagatga tcgaggaacg gctgaaaacc 2460
tatgcccacc tgttcgacga caaagtgatg aagcagctga agcggcggag atacaccggc 2520
tggggcaggc tgagccggaa gctgatcaac ggcatccggg acaagcagtc cggcaagaca 2580
atcctggatt tcctgaagtc cgacggcttc gccaacagaa acttcatgca gctgatccac 2640
gacgacagcc tgacctttaa agaggacatc cagaaagccc aggtgtccgg ccagggcgat 2700
agcctgcacg agcacattgc caatctggcc ggcagccccg ccattaagaa gggcatcctg 2760
cagacagtga aggtggtgga cgagctcgtg aaagtgatgg gccggcacaa gcccgagaac 2820
atcgtgatcg aaatggccag agagaaccag accacccaga agggacagaa gaacagccgc 2880
gagagaatga agcggatcga agagggcatc aaagagctgg gcagccagat cctgaaagaa 2940
caccccgtgg aaaacaccca gctgcagaac gagaagctgt acctgtacta cctgcagaat 3000
gggcgggata tgtacgtgga ccaggaactg gacatcaacc ggctgtccga ctacgatgtg 3060
gaccatatcg tgcctcagag ctttctgaag gacgactcca tcgacaacaa ggtgctgacc 3120
agaagcgaca agaaccgggg caagagcgac aacgtgccct ccgaagaggt cgtgaagaag 3180
atgaagaact actggcggca gctgctgaac gccaagctga ttacccagag aaagttcgac 3240
aatctgacca aggccgagag aggcggcctg agcgaactgg ataaggccgg cttcatcaag 3300
agacagctgg tggaaacccg gcagatcaca aagcacgtgg cacagatcct ggactcccgg 3360
atgaacacta agtacgacga gaatgacaag ctgatccggg aagtgaaagt gatcaccctg 3420
aagtccaagc tggtgtccga tttccggaag gatttccagt tttacaaagt gcgcgagatc 3480
aacaactacc accacgccca cgacgcctac ctgaacgccg tcgtgggaac cgccctgatc 3540
aaaaagtacc ctaagctgga aagcgagttc gtgtacggcg actacaaggt gtacgacgtg 3600
cggaagatga tcgccaagag cgagcaggaa atcggcaagg ctaccgccaa gtacttcttc 3660
tacagcaaca tcatgaactt tttcaagacc gagattaccc tggccaacgg cgagatccgg 3720
aagcggcctc tgatcgagac aaacggcgaa accggggaga tcgtgtggga taagggccgg 3780
gattttgcca ccgtgcggaa agtgctgagc atgccccaag tgaatatcgt gaaaaagacc 3840
gaggtgcaga caggcggctt cagcaaagag tctatcctgc ccaagaggaa cagcgataag 3900
ctgatcgcca gaaagaagga ctgggaccct aagaagtacg gcggcttcga cagccccacc 3960
gtggcctatt ctgtgctggt ggtggccaaa gtggaaaagg gcaagtccaa gaaactgaag 4020
agtgtgaaag agctgctggg gatcaccatc atggaaagaa gcagcttcga gaagaatccc 4080
atcgactttc tggaagccaa gggctacaaa gaagtgaaaa aggacctgat catcaagctg 4140
cctaagtact ccctgttcga gctggaaaac ggccggaaga gaatgctggc ctctgccggc 4200
gaactgcaga agggaaacga actggccctg ccctccaaat atgtgaactt cctgtacctg 4260
gccagccact atgagaagct gaagggctcc cccgaggata atgagcagaa acagctgttt 4320
gtggaacagc acaagcacta cctggacgag atcatcgagc agatcagcga gttctccaag 4380
agagtgatcc tggccgacgc taatctggac aaagtgctgt ccgcctacaa caagcaccgg 4440
gataagccca tcagagagca ggccgagaat atcatccacc tgtttaccct gaccaatctg 4500
ggagcccctg ccgccttcaa gtactttgac accaccatcg accggaagag gtacaccagc 4560
accaaagagg tgctggacgc caccctgatc caccagagca tcaccggcct gtacgagaca 4620
cggatcgacc tgtctcagct gggaggcgac aaaaggccgg cggccacgaa aaaggccggc 4680
caggcaaaaa agaaaaagat cagtctgatt gcggcgttag cggtagatca cgttatcggc 4740
atggaaaccg tcatgccgtg gaacctgcct gccgatctcg cctggtttaa acgcaacacc 4800
ttaaataaac ccgtgattat gggccgccat acctgggaat caatcggtcg tccgttgcca 4860
ggacgcaaaa atattatcct cagcagtcaa ccgagtacgg acgatcgcgt aacgtgggtg 4920
aagtcggtgg atgaagccat cgcggcgtgt ggtgacgtac cagaaatcat ggttattggc 4980
ggcggtcgcg tttatgaaca gttcttgcca aaagcgcaaa aactgtatct gacgcatatc 5040
gacgcagaag tggaaggcga cacccatttc ccggattacg agccggatga ctgggaatcg 5100
gtattcagcg aattccacga tgctgatgcg cagaactctc acagctattg ctttgagatt 5160
ctggagcggc gataa 5175

<210> SEQ ID NO 96
<211> LENGTH: 4962
<212> TYPE: DNA
<213> ORGANISM: Artificial Sequence
<220> FEATURE:
<223> OTHER INFORMATION: Synthetic polynucleotide

<400> SEQUENCE: 96
atggccccaa agaagaagcg gaaggtcggt atccacggag tcccagcagc cggatccagc 60
cttgccctgt cacttacagc cgaccagatg gtttccgcgc ttctcgacgc tgaacctcca 120
attctctatt ccgaatacga cccaaccagg ccgttctccg aggcatctat gatgggtctg 180
ctgacaaatc tggcagacag ggaactggtg cacatgatca attgggcgaa gcgcgtaccc 240
ggattcgtcg atcttgcact ccatgatcag gtgcacttgc tggagtgcgc ttggatggag 300
atcctcatga tcgggctggt gtggcggagt atggaacacc ccggcaagtt gctgtttgcg 360
cctaacctcc tgttggacag gaaccagggg aaatgtgtgg agggcggtgt ggaaatcttt 420
gacatgctcc tcgctacctc aagccggttt aggatgatga atctgcaggg cgaagagttc 480
gtgtgtctca aatctatcat actgttgaac agcggagtct acaccttcct ctccagtact 540
ctgaaatctc tggaggagaa agatcatatc catcgcgtgc tggacaagat aaccgacacg 600
ttgattcact tgatggccaa agctgggctc actctgcaac aacaacatca gcgactggca 660
cagctgttgc tgattttgag ccacattcgg cacatgtcca gcaagagaat ggagcacctc 720
tatagtatga agtgcaagaa cgtcgtaccc ctgtcagatc tgcttcttga aatgcttgat 780
gcccaccggc tgggaagcgg aagcggatcc gacaagaagt acagcatcgg cctggacatc 840
ggcaccaact ctgtgggctg ggccgtgatc accgacgagt acaaggtgcc cagcaagaaa 900
ttcaaggtgc tgggcaacac cgaccggcac agcatcaaga agaacctgat cggagccctg 960
ctgttcgaca gcggcgaaac agccgaggcc acccggctga agagaaccgc cagaagaaga 1020
tacaccagac ggaagaaccg gatctgctat ctgcaagaga tcttcagcaa cgagatggcc 1080
aaggtggacg acagcttctt ccacagactg gaagagtcct tcctggtgga agaggataag 1140
aagcacgagc ggcaccccat cttcggcaac atcgtggacg aggtggccta ccacgagaag 1200
taccccacca tctaccacct gagaaagaaa ctggtggaca gcaccgacaa ggccgacctg 1260

```
cggctgatct atctggccct ggcccacatg atcaagttcc ggggccactt cctgatcgag   1320
ggcgacctga accccgacaa cagcgacgtg gacaagctgt tcatccagct ggtgcagacc   1380
tacaaccagc tgttcgagga aaaccccatc aacgccagcg gcgtggacgc caaggccatc   1440
ctgtctgcca gactgagcaa gagcagacgg ctggaaaatc tgatcgccca gctgcccggc   1500
gagaagaaga atggcctgtt cggaaacctg attgccctga gcctgggcct gacccccaac   1560
ttcaagagca acttcgacct ggccgaggat gccaaactgc agctgagcaa ggacacctac   1620
gacgacgacc tggacaacct gctggcccag atcggcgacc agtacgccga cctgtttctg   1680
gccgccaaga acctgtccga cgccatcctg ctgagcgaca tcctgagagt gaacaccgag   1740
atcaccaagg cccccctgag cgcctctatg atcaagagat acgacgagca ccaccaggac   1800
ctgaccctgc tgaaagctct cgtgcggcag cagctgcctg agaagtacaa agagattttc   1860
ttcgaccaga gcaagaacgg ctacgccggc tacattgacg gcggagccag ccaggaagag   1920
ttctacaagt tcatcaagcc catcctggaa aagatggacg gcaccgagga actgctcgtg   1980
aagctgaaca gagaggacct gctgcggaag cagcggacct tcgacaacgg cagcatcccc   2040
caccagatcc acctgggaga gctgcacgcc attctgcggc ggcaggaaga tttttaccca   2100
ttcctgaagg acaaccggga aaagatcgag aagatcctga ccttccgcat cccctactac   2160
gtgggccctc tggccagggg aaacagcaga ttcgcctgga tgaccagaaa gagcgaggaa   2220
accatcaccc cctggaactt cgaggaagtg gtggacaagg gcgcttccgc ccagagcttc   2280
atcgagcgga tgaccaactt cgataagaac ctgcccaacg agaaggtgct gcccaagcac   2340
agcctgctgt acgagtactt caccgtgtat aacgagctga ccaaagtgaa atacgtgacc   2400
gagggaatga gaaagcccgc cttcctgagc ggcgagcaga aaaaggccat cgtggacctg   2460
ctgttcaaga ccaaccggaa agtgaccgtg aagcagctga aagaggacta cttcaagaaa   2520
atcgagtgct tcgactccgt ggaaatctcc ggcgtggaag atcggttcaa cgcctccctg   2580
ggcacatacc acgatctgct gaaaattatc aaggacaagg acttcctgga caatgaggaa   2640
aacgaggaca ttctggaaga tatcgtgctg accctgacac tgtttgagga cagagagatg   2700
atcgaggaac ggctgaaaac ctatgcccac ctgttcgacg acaaagtgat gaagcagctg   2760
aagcggcgga gatacaccgg ctggggcagg ctgagccgga agctgatcaa cggcatccgg   2820
gacaagcagt ccggcaagac aatcctggat ttcctgaagt ccgacggctt cgccaacaga   2880
aacttcatgc agctgatcca cgacgacagc ctgaccttta aagaggacat ccagaaagcc   2940
caggtgtccg gccagggcga tagcctgcac gagcacattg ccaatctggc cggcagcccc   3000
gccattaaga agggcatcct gcagacagtg aaggtggtgg acgagctcgt gaaagtgatg   3060
ggccggcaca agcccgagaa catcgtgatc gaaatggcca gagagaacca gaccacccag   3120
aagggacaga agaacagccg cgagagaatg aagcggatcg aagagggcat caaagagctg   3180
ggcagccaga tcctgaaaga acaccccgtg gaaaacaccc agctgcagaa cgagaagctg   3240
tacctgtact acctgcagaa tgggcgggat atgtacgtgg accaggaact ggacatcaac   3300
cggctgtccg actacgatgt ggaccatatc gtgcctcaga gctttctgaa ggacgactcc   3360
atcgacaaca aggtgctgac cagaagcgac aagaaccggg gcaagagcga caacgtgccc   3420
tccgaagagg tcgtgaagaa gatgaagaac tactggcggc agctgctgaa cgccaagctg   3480
attacccaga gaaagttcga caatctgacc aaggccgaga gaggcggcct gagcgaactg   3540
gataaggccg gcttcatcaa gagacagctg gtggaaaccc ggcagatcac aaagcacgtg   3600
```

gcacagatcc tggactcccg gatgaacact aagtacgacg agaatgacaa gctgatccgg 3660
gaagtgaaag tgatcaccct gaagtccaag ctggtgtccg atttccggaa ggatttccag 3720
ttttacaaag tgcgcgagat caacaactac caccacgccc acgacgccta cctgaacgcc 3780
gtcgtgggaa ccgccctgat caaaaagtac cctaagctgg aaagcgagtt cgtgtacggc 3840
gactacaagg tgtacgacgt gcggaagatg atcgccaaga gcgagcagga aatcggcaag 3900
gctaccgcca agtacttctt ctacagcaac atcatgaact tttcaagac cgagattacc 3960 ctggccaacg gcgagatccg gaagcggcct ctgatcgaga caaacggcga aaccggggag 4020
atcgtgtggg ataagggccg ggattttgcc accgtgcgga aagtgctgag catgccccaa 4080
gtgaatatcg tgaaaaagac cgaggtgcag acaggcggct tcagcaaaga gtctatcctg 4140
cccaagagga acagcgataa gctgatcgcc agaaagaagg actgggaccc taagaagtac 4200
ggcggcttcg acagccccac cgtggcctat tctgtgctgg tggtggccaa agtggaaaag 4260
ggcaagtcca agaaactgaa gagtgtgaaa gagctgctgg ggatcaccat catggaaaga 4320
agcagcttcg agaagaatcc catcgacttt ctggaagcca agggctacaa agaagtgaaa 4380
aaggacctga tcatcaagct gcctaagtac tccctgttcg agctggaaaa cggccggaag 4440
agaatgctgg cctctgccgg cgaactgcag aagggaaacg aactggccct gccctccaaa 4500
tatgtgaact tcctgtacct ggccagccac tatgagaagc tgaagggctc cccgaggat 4560 aatgagcaga aacagctgtt tgtggaacag cacaagcact acctggacga gatcatcgag 4620
cagatcagcg agttctccaa gagagtgatc ctggccgacg ctaatctgga caaagtgctg 4680
tccgcctaca acaagcaccg ggataagccc atcagagagc aggccgagaa tatcatccac 4740
ctgtttaccc tgaccaatct gggagcccct gccgccttca agtactttga caccaccatc 4800
gaccggaaga ggtacaccag caccaaagag gtgctggacg ccaccctgat ccaccagagc 4860
atcaccggcc tgtacgagac acggatcgac ctgtctcagc tgggaggcga caaaaggccg 4920
gcggccacga aaaaggccgg ccaggcaaaa aagaaaaagt aa 4962

<210> SEQ ID NO 97
<211> LENGTH: 4938
<212> TYPE: DNA
<213> ORGANISM: Artificial Sequence
<220> FEATURE:
<223> OTHER INFORMATION: Synthetic polynucleotide

<400> SEQUENCE: 97
atggccccaa agaagaagcg gaaggtcggt atccacggag tcccagcagc cgacaagaag 60
tacagcatcg gcctggacat cggcaccaac tctgtgggct gggccgtgat caccgacgag 120
tacaaggtgc ccagcaagaa attcaaggtg ctgggcaaca ccgaccggca cagcatcaag 180
aagaacctga tcggagccct gctgttcgac agcggcgaaa cagccgaggc cacccggctg 240
aagagaaccg ccagaagaag atacaccaga cggaagaacc ggatctgcta tctgcaagag 300
atcttcagca acgagatggc caaggtggac gacagcttct tccacagact ggaagagtcc 360
ttcctggtgg aagaggataa gaagcacgag cggcacccca tcttcggcaa catcgtggac 420
gaggtggcct accacgagaa gtaccccacc atctaccacc tgagaaagaa actggtggac 480
agcaccgaca aggccgacct gcggctgatc tatctggccc tggcccacat gatcaagttc 540
cggggccact tcctgatcga gggcgacctg aaccccgaca acagcgacgt ggacaagctg 600
ttcatccagc tggtgcagac ctacaaccag ctgttcgagg aaaaccccat caacgccagc 660
ggcgtggacg ccaaggccat cctgtctgcc agactgagca agagcagacg gctggaaaat 720

-continued

```
ctgatcgccc agctgcccgg cgagaagaag aatggcctgt tcggaaacct gattgccctg    780
agcctgggcc tgacccccaa cttcaagagc aacttcgacc tggccgagga tgccaaactg    840
cagctgagca aggacaccta cgacgacgac ctggacaacc tgctggccca gatcggcgac    900
cagtacgccg acctgtttct ggccgccaag aacctgtccg acgccatcct gctgagcgac    960
atcctgagag tgaacaccga gatcaccaag gcccccctga gcgcctctat gatcaagaga   1020
tacgacgagc accaccagga cctgaccctg ctgaaagctc tcgtgcggca gcagctgcct   1080
gagaagtaca aagagatttt cttcgaccag agcaagaacg gctacgccgg ctacattgac   1140
ggcggagcca gccaggaaga gttctacaag ttcatcaagc ccatcctgga aaagatggac   1200
ggcaccgagg aactgctcgt gaagctgaac agagaggacc tgctgcggaa gcagcggacc   1260
ttcgacaacg gcagcatccc ccaccagatc cacctgggag agctgcacgc cattctgcgg   1320
cggcaggaag atttttaccc attcctgaag gacaaccggg aaaagatcga gaagatcctg   1380
accttccgca tcccctacta cgtgggccct ctggccaggg gaaacagcag attcgcctgg   1440
atgaccagaa agagcgagga aaccatcacc ccctggaact tcgaggaagt ggtggacaag   1500
ggcgcttccg cccagagctt catcgagcgg atgaccaact tcgataagaa cctgcccaac   1560
gagaaggtgc tgcccaagca cagcctgctg tacgagtact tcaccgtgta taacgagctg   1620
accaaagtga aatacgtgac cgagggaatg agaaagcccg ccttcctgag cggcgagcag   1680
aaaaaggcca tcgtggacct gctgttcaag accaaccgga aagtgaccgt gaagcagctg   1740
aaagaggact acttcaagaa aatcgagtgc ttcgactccg tggaaatctc cggcgtggaa   1800
gatcggttca acgcctccct gggcacatac cacgatctgc tgaaaattat caaggacaag   1860
gacttcctgg acaatgagga aaacgaggac attctggaag atatcgtgct gaccctgaca   1920
ctgtttgagg acagagagat gatcgaggaa cggctgaaaa cctatgccca cctgttcgac   1980
gacaaagtga tgaagcagct gaagcggcgg agatacaccg gctggggcag gctgagccgg   2040
aagctgatca acggcatccg ggacaagcag tccggcaaga caatcctgga tttcctgaag   2100
tccgacggct tcgccaacag aaacttcatg cagctgatcc acgacgacag cctgaccttt   2160
aaagaggaca tccagaaagc ccaggtgtcc ggccagggcg atagcctgca cgagcacatt   2220
gccaatctgg ccggcagccc cgccattaag aagggcatcc tgcagacagt gaaggtggtg   2280
gacgagctcg tgaaagtgat gggccggcac aagcccgaga acatcgtgat cgaaatggcc   2340
agagagaacc agaccaccca gaagggacag aagaacagcc gcgagagaat gaagcggatc   2400
gaagagggca tcaaagagct gggcagccag atcctgaaag aacaccccgt ggaaaacacc   2460
cagctgcaga acgagaagct gtacctgtac tacctgcaga atgggcggga tatgtacgtg   2520
gaccaggaac tggacatcaa ccggctgtcc gactacgatg tggaccatat cgtgcctcag   2580
agctttctga aggacgactc catcgacaac aaggtgctga ccagaagcga caagaaccgg   2640
ggcaagagcg acaacgtgcc ctccgaagag gtcgtgaaga agatgaagaa ctactggcgg   2700
cagctgctga acgccaagct gattacccag agaaagttcg acaatctgac caaggccgag   2760
agaggcggcc tgagcgaact ggataaggcc ggcttcatca agagacagct ggtggaaacc   2820
cggcagatca caaagcacgt ggcacagatc ctggactccc ggatgaacac taagtacgac   2880
gagaatgaca agctgatccg ggaagtgaaa gtgatcaccc tgaagtccaa gctggtgtcc   2940
gatttccgga aggatttcca gttttacaaa gtgcgcgaga tcaacaacta ccaccacgcc   3000
cacgacgcct acctgaacgc cgtcgtggga accgccctga tcaaaaagta ccctaagctg   3060
```

gaaagcgagt tcgtgtacgg cgactacaag gtgtacgacg tgcggaagat gatcgccaag 3120
agcgagcagg aaatcggcaa ggctaccgcc aagtacttct tctacagcaa catcatgaac 3180
tttttcaaga ccgagattac cctggccaac ggcgagatcc ggaagcggcc tctgatcgag 3240
acaaacggcg aaaccgggga gatcgtgtgg gataagggcc gggattttgc caccgtgcgg 3300
aaagtgctga gcatgcccca agtgaatatc gtgaaaaaga ccgaggtgca gacaggcggc 3360
ttcagcaaag agtctatcct gcccaagagg aacagcgata agctgatcgc cagaaagaag 3420
gactgggacc ctaagaagta cggcggcttc gacagcccca ccgtggccta ttctgtgctg 3480
gtggtggcca aagtggaaaa gggcaagtcc aagaaactga agagtgtgaa agagctgctg 3540
gggatcacca tcatggaaag aagcagcttc gagaagaatc ccatcgactt tctggaagcc 3600
aagggctaca aagaagtgaa aaaggacctg atcatcaagc tgcctaagta ctccctgttc 3660
gagctggaaa acggccggaa gagaatgctg gcctctgccg gcgaactgca gaagggaaac 3720
gaactggccc tgccctccaa atatgtgaac ttcctgtacc tggccagcca ctatgagaag 3780
ctgaagggct cccccgagga taatgagcag aaacagctgt ttgtggaaca gcacaagcac 3840
tacctggacg agatcatcga gcagatcagc gagttctcca agagagtgat cctggccgac 3900
gctaatctgg acaaagtgct gtccgcctac aacaagcacc gggataagcc catcagagag 3960
caggccgaga atatcatcca cctgtttacc ctgaccaatc tgggagcccc tgccgccttc 4020
aagtactttg acaccaccat cgaccggaag aggtacacca gcaccaaaga ggtgctggac 4080
gccaccctga tccaccagag catcaccggc ctgtacgaga cacggatcga cctgtctcag 4140
ctgggaggcg acaaaaggcc ggcggccacg aaaaaggccg gccaggcaaa aaagaaaaag 4200
agccttgccc tgtcacttac agccgaccag atggtttccg cgcttctcga cgctgaacct 4260
ccaattctct attccgaata cgacccaacc aggccgttct ccgaggcatc tatgatgggt 4320
ctgctgacaa atctggcaga cagggaactg gtgcacatga tcaattgggc gaagcgcgta 4380
cccggattcg tcgatcttgc actccatgat caggtgcact tgctggagtg cgcttggatg 4440
gagatcctca tgatcgggct ggtgtggcgg agtatggaac accccggcaa gttgctgttt 4500
gcgcctaacc tcctgttgga caggaaccag gggaaatgtg tggagggcgg tgtggaaatc 4560
tttgacatgc tcctcgctac ctcaagccgg tttaggatga tgaatctgca gggcgaagag 4620
ttcgtgtgtc tcaaatctat catactgttg aacagcggag tctacacctt cctctccagt 4680
actctgaaat ctctggagga gaaagatcat atccatcgcg tgctggacaa gataaccgac 4740
acgttgattc acttgatggc caaagctggg ctcactctgc aacaacaaca tcagcgactg 4800
gcacagctgt tgctgatttt gagccacatt cggcacatgt ccagcaagag aatggagcac 4860
ctctatagta tgaagtgcaa gaacgtcgta cccctgtcag atctgcttct tgaaatgctt 4920
gatgcccacc ggctgtaa 4938

<210> SEQ ID NO 98
<211> LENGTH: 5697
<212> TYPE: DNA
<213> ORGANISM: Artificial Sequence
<220> FEATURE:
<223> OTHER INFORMATION: Synthetic polynucleotide

<400> SEQUENCE: 98
atggccccaa agaagaagcg gaaggtcggt atccacggag tcccagcagc cggatccagc 60
cttgccctgt cacttacagc cgaccagatg gtttccgcgc ttctcgacgc tgaacctcca 120
attctctatt ccgaatacga cccaaccagg ccgttctccg aggcatctat gatgggtctg 180

```
ctgacaaatc tggcagacag ggaactggtg cacatgatca attgggcgaa gcgcgtaccc    240
ggattcgtcg atcttgcact ccatgatcag gtgcacttgc tggagtgcgc ttggatggag    300
atcctcatga tcgggctggt gtggcggagt atggaacacc ccggcaagtt gctgtttgcg    360
cctaacctcc tgttggacag gaaccagggg aaatgtgtgg agggcggtgt ggaaatcttt    420
gacatgctcc tcgctacctc aagccggttt aggatgatga atctgcaggg cgaagagttc    480
gtgtgtctca aatctatcat actgttgaac agcggagtct acaccttcct ctccagtact    540
ctgaaatctc tggaggagaa agatcatatc catcgcgtgc tggacaagat aaccgacacg    600
ttgattcact tgatggccaa agctgggctc actctgcaac aacaacatca gcgactggca    660
cagctgttgc tgattttgag ccacattcgg cacatgtcca gcaagagaat ggagcacctc    720
tatagtatga agtgcaagaa cgtcgtaccc ctgtcagatc tgcttcttga aatgcttgat    780
gcccaccggc tgggaagcgg aagcggatcc gacaagaagt acagcatcgg cctggacatc    840
ggcaccaact ctgtgggctg ggccgtgatc accgacgagt acaaggtgcc cagcaagaaa    900
ttcaaggtgc tgggcaacac cgaccggcac agcatcaaga agaacctgat cggagccctg    960
ctgttcgaca gcggcgaaac agccgaggcc acccggctga agagaaccgc cagaagaaga   1020
tacaccagac ggaagaaccg gatctgctat ctgcaagaga tcttcagcaa cgagatggcc   1080
aaggtggacg acagcttctt ccacagactg gaagagtcct tcctggtgga agaggataag   1140
aagcacgagc ggcaccccat cttcggcaac atcgtggacg aggtggccta ccacgagaag   1200
taccccacca tctaccacct gagaaagaaa ctggtggaca gcaccgacaa ggccgacctg   1260
cggctgatct atctggccct ggcccacatg atcaagttcc ggggccactt cctgatcgag   1320
ggcgacctga accccgacaa cagcgacgtg gacaagctgt tcatccagct ggtgcagacc   1380
tacaaccagc tgttcgagga aaaccccatc aacgccagcg gcgtggacgc caaggccatc   1440
ctgtctgcca gactgagcaa gagcagacgg ctggaaaatc tgatcgccca gctgcccggc   1500
gagaagaaga atggcctgtt cggaaacctg attgccctga gcctgggcct gacccccaac   1560
ttcaagagca acttcgacct ggccgaggat gccaaactgc agctgagcaa ggacacctac   1620
gacgacgacc tggacaacct gctggcccag atcggcgacc agtacgccga cctgtttctg   1680
gccgccaaga acctgtccga cgccatcctg ctgagcgaca tcctgagagt gaacaccgag   1740
atcaccaagg ccccccctgag cgcctctatg atcaagagat acgacgagca ccaccaggac   1800
ctgaccctgc tgaaagctct cgtgcggcag cagctgcctg agaagtacaa agagattttc   1860
ttcgaccaga gcaagaacgg ctacgccggc tacattgacg gcggagccag ccaggaagag   1920
ttctacaagt tcatcaagcc catcctggaa aagatggacg gcaccgagga actgctcgtg   1980
aagctgaaca gagaggacct gctgcggaag cagcggacct tcgacaacgg cagcatcccc   2040
caccagatcc acctgggaga gctgcacgcc attctgcggc ggcaggaaga tttttaccca   2100
ttcctgaagg acaaccggga aaagatcgag aagatcctga ccttccgcat ccccctactac   2160
gtgggccctc tggccagggg aaacagcaga ttcgcctgga tgaccagaaa gagcgaggaa   2220
accatcaccc cctggaactt cgaggaagtg gtggacaagg gcgcttccgc ccagagcttc   2280
atcgagcgga tgaccaactt cgataagaac ctgcccaacg agaaggtgct gcccaagcac   2340
agcctgctgt acgagtactt caccgtgtat aacgagctga ccaaagtgaa atacgtgacc   2400
gagggaatga gaaagcccgc cttcctgagc ggcgagcaga aaaaggccat cgtggacctg   2460
ctgttcaaga ccaaccggaa agtgaccgtg aagcagctga aagaggacta cttcaagaaa   2520
```

-continued

```
atcgagtgct tcgactccgt ggaaatctcc ggcgtggaag atcggttcaa cgcctccctg   2580
ggcacatacc acgatctgct gaaaattatc aaggacaagg acttcctgga caatgaggaa   2640
aacgaggaca ttctggaaga tatcgtgctg accctgacac tgtttgagga cagagagatg   2700
atcgaggaac ggctgaaaac ctatgcccac ctgttcgacg acaaagtgat gaagcagctg   2760
aagcggcgga gatacaccgg ctggggcagg ctgagccgga agctgatcaa cggcatccgg   2820
gacaagcagt ccggcaagac aatcctggat ttcctgaagt ccgacggctt cgccaacaga   2880
aacttcatgc agctgatcca cgacgacagc ctgaccttta aagaggacat ccagaaagcc   2940
caggtgtccg gccagggcga tagcctgcac gagcacattg ccaatctggc cggcagcccc   3000
gccattaaga agggcatcct gcagacagtg aaggtggtgg acgagctcgt gaaagtgatg   3060
ggccggcaca agcccgagaa catcgtgatc gaaatggcca gagagaacca gaccacccag   3120
aagggacaga agaacagccg cgagagaatg aagcggatcg aagagggcat caaagagctg   3180
ggcagccaga tcctgaaaga acaccccgtg gaaaacaccc agctgcagaa cgagaagctg   3240
tacctgtact acctgcagaa tgggcgggat atgtacgtgg accaggaact ggacatcaac   3300
cggctgtccg actacgatgt ggaccatatc gtgcctcaga gctttctgaa ggacgactcc   3360
atcgacaaca aggtgctgac cagaagcgac aagaaccggg gcaagagcga caacgtgccc   3420
tccgaagagg tcgtgaagaa gatgaagaac tactggcggc agctgctgaa cgccaagctg   3480
attacccaga gaaagttcga caatctgacc aaggccgaga gaggcggcct gagcgaactg   3540
gataaggccg gcttcatcaa gagacagctg gtggaaaccc ggcagatcac aaagcacgtg   3600
gcacagatcc tggactcccg gatgaacact aagtacgacg agaatgacaa gctgatccgg   3660
gaagtgaaag tgatcaccct gaagtccaag ctggtgtccg atttccggaa ggatttccag   3720
ttttacaaag tgcgcgagat caacaactac caccacgccc acgacgccta cctgaacgcc   3780
gtcgtgggaa ccgccctgat caaaaagtac cctaagctgg aaagcgagtt cgtgtacggc   3840
gactacaagg tgtacgacgt gcggaagatg atcgccaaga gcgagcagga aatcggcaag   3900
gctaccgcca agtacttctt ctacagcaac atcatgaact ttttcaagac cgagattacc   3960
ctggccaacg gcgagatccg gaagcggcct ctgatcgaga caaacggcga aaccggggag   4020
atcgtgtggg ataagggccg ggattttgcc accgtgcgga aagtgctgag catgccccaa   4080
gtgaatatcg tgaaaaagac cgaggtgcag acaggcggct tcagcaaaga gtctatcctg   4140
cccaagagga acagcgataa gctgatcgcc agaaagaagg actgggaccc taagaagtac   4200
ggcggcttcg acagccccac cgtggcctat tctgtgctgg tggtggccaa agtggaaaag   4260
ggcaagtcca agaaactgaa gagtgtgaaa gagctgctgg ggatcaccat catggaaaga   4320
agcagcttcg agaagaatcc catcgacttt ctggaagcca agggctacaa agaagtgaaa   4380
aaggacctga tcatcaagct gcctaagtac tccctgttcg agctggaaaa cggccggaag   4440
agaatgctgg cctctgccgg cgaactgcag aagggaaacg aactggccct gccctccaaa   4500
tatgtgaact tcctgtacct ggccagccac tatgagaagc tgaagggctc ccccgaggat   4560
aatgagcaga aacagctgtt tgtggaacag cacaagcact acctggacga gatcatcgag   4620
cagatcagcg agttctccaa gagagtgatc ctggccgacg ctaatctgga caaagtgctg   4680
tccgcctaca acaagcaccg ggataagccc atcagagagc aggccgagaa tatcatccac   4740
ctgtttaccc tgaccaatct gggagcccct gccgccttca agtactttga caccaccatc   4800
gaccggaaga ggtacaccag caccaaagag gtgctggacg ccaccctgat ccaccagagc   4860
atcaccggcc tgtacgagac acggatcgac ctgtctcagc tgggaggcga caaaaggccg   4920
```

```
gcggccacga aaaaggccgg ccaggcaaaa aagaaaaaga gccttgccct gtcacttaca   4980

gccgaccaga tggtttccgc gcttctcgac gctgaacctc caattctcta ttccgaatac   5040

gacccaacca ggccgttctc cgaggcatct atgatgggtc tgctgacaaa tctggcagac   5100

agggaactgg tgcacatgat caattgggcg aagcgcgtac ccggattcgt cgatcttgca   5160

ctccatgatc aggtgcactt gctggagtgc gcttggatgg agatcctcat gatcgggctg   5220

gtgtggcgga gtatggaaca ccccggcaag ttgctgtttg cgcctaacct cctgttggac   5280

aggaaccagg ggaaatgtgt ggagggcggt gtggaaatct ttgacatgct cctcgctacc   5340

tcaagccggt ttaggatgat gaatctgcag ggcgaagagt tcgtgtgtct caaatctatc   5400

atactgttga acagcggagt ctacaccttc ctctccagta ctctgaaatc tctggaggag   5460

aaagatcata tccatcgcgt gctggacaag ataaccgaca cgttgattca cttgatggcc   5520

aaagctgggc tcactctgca acaacaacat cagcgactgg cacagctgtt gctgattttg   5580

agccacattc ggcacatgtc cagcaagaga atggagcacc tctatagtat gaagtgcaag   5640

aacgtcgtac ccctgtcaga tctgcttctt gaaatgcttg atgcccaccg gctgtaa      5697
```

<210> SEQ ID NO 99
<211> LENGTH: 1137
<212> TYPE: DNA
<213> ORGANISM: Artificial Sequence
<220> FEATURE:
<223> OTHER INFORMATION: Synthetic polynucleotide

<400> SEQUENCE: 99

```
atgatcagtc tgattgcggc gttagcggta gattacgtta tcggcatgga aaacgccatg     60

ccgtggaacc tgcctgccga tctcgcctgg tttaaacgca acaccttaaa taaacccgtg    120

attatgggcc gccatacctg ggaatcaatc ggtcgtccgt tgccaggacg caaaaatatt    180

atcctcagca gtcaaccgag tacggacgat cgcgtaacgt gggtgaagtc ggtggatgaa    240

gccatcgcgg cgtgtggtga cgtaccagaa atcatggtga ttggcggcgg tcgcgttatt    300

gaacagttct tgccaaaagc gcaaaaactg tatctgacgc atatcgacgc agaagtggaa    360

ggcgacaccc atttcccgga ttacgagccg gatgactggg aatcggtatt cagcgaattc    420

cacgatgctg atgcgcagaa ctctcacagc tattgctttg agattctgga gcggcgaggt    480

ggaggaggtt caggaggtgg aggctctgga ggtggaggca gctccaaaac catcgttctt    540

tcggtcggcg aggctactcg cactctgact gagatccagt ccaccgcaga ccgtcagatc    600

ttcgaagaga aggtcgggcc tctggtgggt cggctgcgcc tcacggcttc gctccgtcaa    660

aacggagcca agaccgcgta tcgcgtcaac ctaaaactgg atcaggcgga cgtcgttgat    720

tccggacttc cgaaagtgcg ctacactcag gtatggtcgc acgacgtgac aatcgttgcg    780

aatagcaccg aggcctcgcg caaatcgttg tacgatttga ccaagtccct cgtcgcgacc    840

tcgcaggtcg aagatcttgt cgtcaacctt gtgccgctgg gccgtagcgc tggaggaggt    900

ggaagcggag gaggaggaag cggaggagga ggtagcggac ctaagaaaaa gaggaaggtg    960

gcggccgctg gatccggacg ggctgacgca ttggacgatt ttgatctgga tatgctggga   1020

agtgacgccc tcgatgattt tgaccttgac atgcttggtt cggatgccct tgatgacttt   1080

gacctcgaca tgctcggcag tgacgccctt gatgatttcg acctggacat gctgtaa      1137
```

<210> SEQ ID NO 100
<211> LENGTH: 2202
<212> TYPE: DNA

<213> ORGANISM: Artificial Sequence
<220> FEATURE:
<223> OTHER INFORMATION: Synthetic polynucleotide

<400> SEQUENCE: 100
atgagccttg ccctgtcact tacagccgac cagatggttt ccgcgcttct cgacgctgaa 60
cctccaattc tctattccga atacgaccca accaggccgt tctccgaggc atctatgatg 120
ggtctgctga caaatctggc agacagggaa ctggtgcaca tgatcaattg ggcgaagcgc 180
gtacccggat tcgtcgatct tgcactccat gatcaggtgc acttgctgga gtgcgcttgg 240
atggagatcc tcatgatcgg gctggtgtgg cggagtatgg aacaccccgg caagttgctg 300
tttgcgccta acctcctgtt ggacaggaac caggggaaat gtgtggaggg cggtgtggaa 360
atctttgaca tgctcctcgc tacctcaagc cggtttagga tgatgaatct gcagggcgaa 420
gagttcgtgt gtctcaaatc tatcatactg ttgaacagcg gagtctacac cttcctctcc 480
agtactctga aatctctgga ggagaaagat catatccatc gcgtgctgga caagataacc 540
gacacgttga ttcacttgat ggccaaagct gggctcactc tgcaacaaca acatcagcga 600
ctggcacagc tgttgctgat tttgagccac attcggcaca tgtccagcaa gagaatggag 660
cacctctata gtatgaagtg caagaacgtc gtacccctgt cagatctgct tcttgaaatg 720
cttgatgccc accggctggg tggaggaggt tcaggaggtg gaggctctgg aggtggaggc 780
agcgcttcaa actttactca gttcgtgctc gtggacaatg gtgggacagg ggatgtgaca 840
gtggctcctt ctaatttcgc taatggggtg gcagagtgga tcagctccaa ctcacggagc 900
caggcctaca aggtgacatg cagcgtcagg cagtctagtg cccagaagag aaagtatacc 960
atcaaggtgg aggtccccaa agtggctacc cagacagtgg gcggagtcga actgcctgtc 1020
gccgcttgga ggtcctacct gaacatggag ctcactatcc caattttcgc taccaattct 1080
gactgtgaac tcatcgtgaa ggcaatgcag gggctcctca aagacggtaa tcctatccct 1140
tccgccatcg ccgctaactc aggtatctac agcgctggag gaggtggaag cggaggagga 1200
ggaagcggag gaggaggtag cggacctaag aaaaagagga aggtggcggc cgctggatcc 1260
ccttcagggc agatcagcaa ccaggccctg gctctggccc ctagctccgc tccagtgctg 1320
gcccagacta tggtgccctc tagtgctatg gtgcctctgg cccagccacc tgctccagcc 1380
cctgtgctga ccccaggacc accccagtca ctgagcgctc cagtgcccaa gtctacacag 1440
gccggcgagg ggactctgag tgaagctctg ctgcacctgc agttcgacgc tgatgaggac 1500
ctgggagctc tgctggggaa cagcaccgat cccggagtgt tcacagatct ggcctccgtg 1560
gacaactctg agtttcagca gctgctgaat cagggcgtgt ccatgtctca tagtacagcc 1620
gaaccaatgc tgatggagta ccccgaagcc attacccggc tggtgaccgg cagccagcgg 1680
ccccccgacc ccgctccaac tcccctggga accagcggcc tgcctaatgg gctgtccgga 1740
gatgaagact tctcaagcat cgctgatatg gactttagtg ccctgctgtc acagatttcc 1800
tctagtgggc agggaggagg tggaagcggc ttcagcgtgg acaccagtgc cctgctggac 1860
ctgttcagcc cctcggtgac cgtgcccgac atgagcctgc ctgaccttga cagcagcctg 1920
gccagtatcc aagagctcct gtctccccag gagcccccca ggcctcccga ggcagagaac 1980
agcagcccgg attcagggaa gcagctggtg cactacacag cgcagccgct gttcctgctg 2040
gaccccggct ccgtggacac cgggagcaac gacctgccgg tgctgtttga gctgggagag 2100
ggctcctact tctccgaagg ggacggcttc gccgaggacc ccaccatctc cctgctgaca 2160
ggctcggagc ctcccaaagc caaggacccc actgtctcct aa 2202

<210> SEQ ID NO 101
<211> LENGTH: 15272
<212> TYPE: DNA
<213> ORGANISM: Artificial Sequence
<220> FEATURE:
<223> OTHER INFORMATION: Synthetic polynucleotide

<400> SEQUENCE: 101

```
tgcccacgga gacgtcaaac cggtggatct aattcaatta gagactaatt caattagagc     60
taattcaatt aggatccaag cttatcgatt tcgaaccctc gaccgccgga gtataaatag    120
aggcgcttcg tctacggagc gacaattcaa ttcaaacaag caaagtgaac acgtcgctaa    180
gcgaaagcta agcaaataaa caagcgcagc tgaacaagct aaacaatcgg ctcgaagccg    240
gtcgccacca tggcctcctc cgaggacgtc atcaaggagt tcatgcgctt caaggtgcgc    300
atggagggct ccgtgaacgg ccacgagttc gagatcgagg gcgagggcga gggccgcccc    360
tacgagggca cccagaccgc caagctgaag gtgaccaagg gcggccccct gcccttcgcc    420
tgggacatcc tgtcccccca gttccagtac ggctccaagg tgtacgtgaa gcaccccgcc    480
gacatccccg actacaagaa gctgtccttc cccgagggct tcaagtggga gcgcgtgatg    540
aacttcgagg acggcggcgt ggtgaccgtg acccaggact cctccctcca ggacggctcc    600
ttcatctaca aggtgaagtt catcggcgtg aacttcccct ccgacggccc cgtaatgcag    660
aagaagacta tgggctggga ggcgtccacc gagcgcctgt acccccgcga cggcgtgctg    720
aagggcgaga tccacaaggc cctgaagctg aaggacggcg gccactacct ggtggagttc    780
aagtccatct acatggccaa gaagcccgtg cagctgcccg gctactacta cgtggactcc    840
aagctggaca tcacctccca caacgaggac tacaccatcg tggagcagta cgagcgcgcc    900
gagggccgcc accacctgtt cctgtagggg ccgcgactct agatcataat cagccatacc    960
acatttgtag aggttttact tgctttaaaa aacctcccac acctccccct gaacctgaaa   1020
cataaaatga atgcaattgt tgttgttaac ttgtttattg cagcttataa tggttacaaa   1080
taaagcaata gcatcacaaa tttcacaaat aaagcatttt tttcactgca ttctagttgt   1140
ggtttgtcca aactcatcaa tgtatcttaa ccggtggatc cctgcagctg gttgtaggtg   1200
cagttgcgct tcttgcactt ggcgcacttg aggagatcgg tcttggtgcc ctgcacggtg   1260
gccagctggg catcgttgat ggcctccttg acgaacttct cgcgcagctt cttcatctcg   1320
tcgctggcca tctcctccgg cgtcattttg gccagctgct tggcagtgac ggcgccgcac   1380
ataaagttgc cgcgcaatcc aggattcttg ggtccttca gattggccac gcgtgaccta    1440
atgcgattct tgtacttcat atccgtgtta ttgaactcgg agtaaatggc atcctccagt   1500
tcggcggcca tttcctccgg ctcaccgcat ccttcgggca cttcaccaat cttcagtgcg   1560
gtggccagca tttcgcggca tttgatgcgg accgcatctg tcatgccgcc ggagggaaac   1620
gaggtctgtg acgaggatgt cgagcctttc ttctctttat ccttggatga gctggatgaa   1680
ctggacttat ccttgccgga gattgacgac gacgacttgg cggcactggt ggacttcgag   1740
gcactgctgt tgttggagga gccctcctta gcggagctgt tgttcggtgt ggttggcgcc   1800
gggctggcga ggaatcgttt ccagttcttg atcagcgtct tggccagagc gatcacctcg   1860
tcgtccttgc tactcttgcg cagctcgttt acggtcatgc cgatgcgcgt tttggtcaga   1920
atgtcgagat tgatgttaag cgtttgcagg gccttcagca ggtccagagc ctgatcctgt   1980
ccctgtacgg tggatatatg tatatttgtg acatgatgcg cggcacgtta gctaatcccg   2040
```

atacttactg tgccgtcgct ggccatcttg ctcatcttct tttggattcg aaacacttcc 2100
tcctccacgc tcattttggc ccacttaatt tgatcagagg ttaggttaac tggcgtcggc 2160
tgtcggcttt aatcggtgct gcgggtctgc gacagttgtt tatgcggaag ccgggctatt 2220
tctttttttc cctccaataa atgttgttta ctattttttt cgtttctgta ttcgcagaac 2280
gagttgacag aacaccctaa cgcgttttag tgttaccggg cggtggcttg tcaagaaatg 2340
ccttcccatg gctaatacaa ttcccaactg gaagtagttt gggtttcaga agtcaacagt 2400
gttaccgtat tttaatgtac atctggcttt taagcgagta cacacacata gcattgcgat 2460 gtttttttaaa cttgcactgc ttgcaagcag ggctccactg tatttcaatg aaagaacagc 2520
gtgttgggcg tttttgaatt atactaatta ccttcaataa caattcccta tatatcactt 2580
agttttaata aataaatcgt ttgagtgtgg tctagagatg atgtattatg atgaagtgcg 2640
gttgttgggg acaagcggga tacgtctgcg ggtcaaatcg gcggtgggac atagtgagag 2700
ggcaacggct ccaaaaccaa gcgttgcgaa caatcaccaa cgcgccctgg tacgcgagaa 2760
atgttgatat cgcacatgac ctcagcatcc accttcagtt tgagaacaaa ttaaatcagg 2820
cacataccag acaaccagga gaacactgag gaggcgtcat caaagatatc tttggacacg 2880
tggcataaac aagccaaact attatctaat caatattttt atacaaattt tgtatgtttc 2940
catgttatct tcgttgctcc tgttagttac tacgtttcat agcccttaaa ttggttgctt 3000
aacgtaaaat aaaattatat tgtataaaaa taaagaggaa ttcacctata acaaacgaaa 3060
aagtaaataa ataagaactt ccccatgtta aaaatgccac caccatcttt acatataagt 3120
atgtacatat gaatgaatca cttaggttgc ttgaatatta caatttcatt aatagctaaa 3180
tcacatttga tgtgttagtg gaaaacggct atatatataa attatcgaaa ttgtgaatat 3240
cgaattgcga tagcacaatg ggaaattcca ccactagatt tttggtactt ttaacagatc 3300
cttttcggtt ttgcgttgcg cgaagtgatc tgaacttatc aaagtttgta aggtaataca 3360
taaagtgaaa aagaattaat ttgctcttga aaggcaggcc aaattaaaaa aaaaatatca 3420
atcggtacca gatctggcgc gcctagaatg gactataagg accacgacgg agactacaag 3480
gatcatgata ttgattacaa agacgatgac gataagatgg ccccaaagaa gaagcggaag 3540
gtcggtatcc acggagtccc agcagccgga tccatcagtc tgattgcggc gttagcggta 3600
gatcacgtta tcggcatgga aaacgccatg ccgtggaacc tgcctgccga tctcgcctgg 3660
tttaaacgca acaccttaaa taaacccgtg attatgggcc gccatacctg ggaatcaatc 3720
ggtcgtccgt tgccaggacg caaaaatatt atcctctgca gtcaaccgag tacggacgat 3780
cgcgtaacgt gggtgaagtc ggtgggtgaa gccatcgcgg cgtgtggtga cgtaccagaa 3840
atcatggtga ttggcggcgg tcgcgttcat gaacagttct tgccaaaagc gcaaaaactg 3900
tatctgacgc atatcgacgc agaagtggaa ggcgacaccc atttcccgga ttacgagccg 3960
gatgactggg aaccggtatt caacgaattc cacgatgctg atgcgcaaaa ctctcacagc 4020
taccgctttg agactctggg gcgacgagga agcggaagcg gatccgacaa gaagtacagc 4080
atcggcctgg acatcggcac caactctgtg ggctgggccg tgatcaccga cgagtacaag 4140
gtgcccagca agaaattcaa ggtgctgggc aacaccgacc ggcacagcat caagaagaac 4200
ctgatcggag ccctgctgtt cgacagcggc gaaacagccg aggccacccg gctgaagaga 4260
accgccagaa gaagatacac cagacggaag aaccggatct gctatctgca agagatcttc 4320
agcaacgaga tggccaaggt ggacgacagc ttcttccaca gactggaaga gtccttcctg 4380
gtggaagagg ataagaagca cgagcggcac cccatcttcg gcaacatcgt ggacgaggtg 4440
gcctaccacg agaagtaccc caccatctac cacctgagaa agaaactggt ggacagcacc 4500
gacaaggccg acctgcggct gatctatctg gccctggccc acatgatcaa gttccggggc 4560
cacttcctga tcgagggcga cctgaacccc gacaacagcg acgtggacaa gctgttcatc 4620
cagctggtgc agacctacaa ccagctgttc gaggaaaacc ccatcaacgc cagcggcgtg 4680
gacgccaagg ccatcctgtc tgccagactg agcaagagca gacggctgga aaatctgatc 4740
gcccagctgc ccggcgagaa gaagaatggc ctgttcggca acctgattgc cctgagcctg 4800
ggcctgaccc ccaacttcaa gagcaacttc gacctggccg aggatgccaa actgcagctg 4860
agcaaggaca cctacgacga cgacctggac aacctgctgg cccagatcgg cgaccagtac 4920
gccgacctgt ttctggccgc caagaacctg tccgacgcca tcctgctgag cgacatcctg 4980
agagtgaaca ccgagatcac caaggccccc ctgagcgcct ctatgatcaa gagatacgac 5040
gagcaccacc aggacctgac cctgctgaaa gctctcgtgc ggcagcagct gcctgagaag 5100
tacaaagaga ttttcttcga ccagagcaag aacggctacg ccggctacat tgacggcgga 5160
gccagccagg aagagttcta caagttcatc aagcccatcc tggaaaagat ggacggcacc 5220
gaggaactgc tcgtgaagct gaacagagag gacctgctgc ggaagcagcg gaccttcgac 5280
aacggcagca tcccccacca gatccacctg ggagagctgc acgccattct gcggcggcag 5340
gaagattttt acccattcct gaaggacaac cgggaaaaga tcgagaagat cctgaccttc 5400
cgcatcccct actacgtggg ccctctggcc aggggaaaca gcagattcgc ctggatgacc 5460
agaaagagcg aggaaaccat caccccctgg aacttcgagg aagtggtgga caagggcgct 5520
tccgcccaga gcttcatcga gcggatgacc aacttcgata agaacctgcc caacgagaag 5580
gtgctgccca agcacagcct gctgtacgag tacttcaccg tgtataacga gctgaccaaa 5640
gtgaaatacg tgaccgaggg aatgagaaag cccgccttcc tgagcggcga gcagaaaaag 5700
gccatcgtgg acctgctgtt caagaccaac cggaaagtga ccgtgaagca gctgaaagag 5760
gactacttca agaaaatcga gtgcttcgac tccgtggaaa tctccggcgt ggaagatcgg 5820
ttcaacgcct ccctgggcac ataccacgat ctgctgaaaa ttatcaagga caaggacttc 5880
ctggacaatg aggaaaacga ggacattctg gaagatatcg tgctgaccct gacactgttt 5940
gaggacagag agatgatcga ggaacggctg aaaacctatg cccacctgtt cgacgacaaa 6000
gtgatgaagc agctgaagcg gcggagatac accggctggg gcaggctgag ccggaagctg 6060
atcaacggca tccgggacaa gcagtccggc aagacaatcc tggatttcct gaagtccgac 6120
ggcttcgcca acagaaactt catgcagctg atccacgacg acagcctgac ctttaaagag 6180
gacatccaga aagcccaggt gtccggccag ggcgatagcc tgcacgagca cattgccaat 6240
ctggccggca gccccgccat taagaagggc atcctgcaga cagtgaaggt ggtggacgag 6300
ctcgtgaaag tgatgggccg gcacaagccc gagaacatcg tgatcgaaat ggccagagag 6360
aaccagacca cccagaaggg acagaagaac agccgcgaga gaatgaagcg gatcgaagag 6420
ggcatcaaag agctgggcag ccagatcctg aaagaacacc ccgtggaaaa cacccagctg 6480
cagaacgaga agctgtacct gtactacctg cagaatgggc gggatatgta cgtggaccag 6540
gaactggaca tcaaccggct gtccgactac gatgtggacc atatcgtgcc tcagagcttt 6600
ctgaaggacg actccatcga caacaaggtg ctgaccagaa gcgacaagaa ccggggcaag 6660
agcgacaacg tgccctccga agaggtcgtg aagaagatga agaactactg gcggcagctg 6720
ctgaacgcca agctgattac ccagagaaag ttcgacaatc tgaccaaggc cgagagaggc 6780

```
ggcctgagcg aactggataa ggccggcttc atcaagagac agctggtgga aacccggcag   6840
atcacaaagc acgtggcaca gatcctggac tcccggatga acactaagta cgacgagaat   6900
gacaagctga tccgggaagt gaaagtgatc accctgaagt ccaagctggt gtccgatttc   6960
cggaaggatt tccagtttta caaagtgcgc gagatcaaca actaccacca cgcccacgac   7020
gcctacctga acgccgtcgt gggaaccgcc ctgatcaaaa agtaccctaa gctggaaagc   7080
gagttcgtgt acggcgacta caaggtgtac gacgtgcgga agatgatcgc caagagcgag   7140
caggaaatcg gcaaggctac cgccaagtac ttcttctaca gcaacatcat gaactttttc   7200
aagaccgaga ttaccctggc caacggcgag atccggaagc ggcctctgat cgagacaaac   7260
ggcgaaaccg gggagatcgt gtgggataag ggccgggatt ttgccaccgt gcggaaagtg   7320
ctgagcatgc cccaagtgaa tatcgtgaaa aagaccgagg tgcagacagg cggcttcagc   7380
aaagagtcta tcctgcccaa gaggaacagc gataagctga tcgccagaaa gaaggactgg   7440
gaccctaaga agtacggcgg cttcgacagc cccaccgtgg cctattctgt gctggtggtg   7500
gccaaagtgg aaaagggcaa gtccaagaaa ctgaagagtg tgaaagagct gctggggatc   7560
accatcatgg aaagaagcag cttcgagaag aatcccatcg actttctgga agccaagggc   7620
tacaaagaag tgaaaaagga cctgatcatc aagctgccta agtactccct gttcgagctg   7680
gaaaacggcc ggaagagaat gctggcctct gccggcgaac tgcagaaggg aaacgaactg   7740
gccctgccct ccaaatatgt gaacttcctg tacctggcca gccactatga gaagctgaag   7800
ggctcccccg aggataatga gcagaaacag ctgtttgtgg aacagcacaa gcactacctg   7860
gacgagatca tcgagcagat cagcgagttc tccaagagag tgatcctggc cgacgctaat   7920
ctggacaaag tgctgtccgc ctacaacaag caccgggata agcccatcag agagcaggcc   7980
gagaatatca tccacctgtt taccctgacc aatctgggag cccctgccgc cttcaagtac   8040
tttgacacca ccatcgaccg gaagaggtac accagcacca aagaggtgct ggacgccacc   8100
ctgatccacc agagcatcac cggcctgtac gagacacgga tcgacctgtc tcagctggga   8160
ggcgacaaaa ggccggcggc cacgaaaaag gccggccagg caaaaaagaa aaagatcagt   8220
ctgattgcgg cgttagcggt agatcacgtt atcggcatgg aaaccgtcat gccgtggaac   8280
ctgcctgccg atctcgcctg gtttaaacgc aacaccttaa ataaacccgt gattatgggc   8340
cgccatacct gggaatcaat cggtcgtccg ttgccaggac gcaaaaatat tatcctcagc   8400
agtcaaccga gtacggacga tcgcgtaacg tgggtgaagt cggtggatga agccatcgcg   8460
gcgtgtggtg acgtaccaga aatcatggtt attggcggcg gtcgcgttta tgaacagttc   8520
ttgccaaaag cgcaaaaact gtatctgacg catatcgacg cagaagtgga aggcgacacc   8580
catttcccgg attacgagcc ggatgactgg gaatcggtat tcagcgaatt ccacgatgct   8640
gatgcgcaga actctcacag ctattgcttt gagattctgg agcggcgata atctaggcct   8700
gagctcaatg tatggacata gatttcaaat aattaaatgt aatgcagtaa ttgatgtaat   8760
tagttaaata agttagatat taataacata ttaattatat gtattataac gcatataata   8820
ataaaatgca tatttaggat atgcaagcca ttcgaatttt ctattttaat ttccttttac   8880
aaagaaatgt ataacaaaat ataatttgaa aaaatgttct ggctctaatt cgatttcttt   8940
taagtatttt gtgaactgct tttaataacg agcggttgca aaacttaaca gaaacgtgca   9000
ctttgatccc aactaatacc gtgtactatc acgtgtttgg ttttaagtac tcatccttcg   9060
tgtttcgttg tttgttgttt gccttgctgt acacttggct cttgcgctct ctcgctctcc   9120
gttggagccg gctttttgaa tgcatgcctc gccctgctcg cgcccagtcc tcctccccg    9180
```

```
aaaagcatgc cgaccagcaa atgttgccct tttgcgtttg ctgtctttgc agaagcaaaa   9240
tcaataactg agaaatccac cacactgctg ctcttcgtgt tgctagcttc cagtgtccaa   9300
aacccacagc cgaccacact catccacttt aatgcggtag gcagtggtaa tactgttggc   9360
gcaatctcca gctgtatttg agcgccaatc tggatacgga attagctccg gtgaacccgt   9420
caaactgcgg tccatgttta tataggtcag agtggccgga atccctaaaa aataaaatag   9480
gagaattagc agggccaaac tattattgag gcactaaata aagtttgttt tgaatattta   9540
attaactgga atttctgcct aaattccttc tttggattat tatactaagc aatgttgcaa   9600
gttatcgctg tctgttttct ggataaatatg taaatgcata cagatgtaaa ggtaaattag   9660
aatcgcttat gtttggcatt taattattta tatacctatt tgtcattatt ttggacacaa   9720
ggaatcataa gcaatggtaa ctgccgtgct aatggctctt ttttctgctt gtacatctac   9780
tggaagttta tgttaaaaga tccccggcta tatgtacttc agtcataatt ggcactattg   9840
caagttgcgt gcaatttgcg atgtcattag ccgtctgaag caattgcgtc tgacatcatt   9900
atcaatatgt ataccatata tcgctgttaa atgtatatgt ggccattggc agtatttcga   9960
ccgatttccg ctccagttct tttccttctt tatttcttcg ttaattgaat ttaaagacat  10020
ttattgtttc tgggaacttt taatgttttt atagcaggcg agtgagactg caacgaccag  10080
aaaatatagc ttttatcgat ttaccgaccc atcttcttaa aaatcaaacc aggcgttttt  10140
gctttacaaa gtaaccgggg gttgcgataa atatacattt gagcataatg cacctttcaa  10200
tctttattta attcataact tttaaaataa caatctaatt cagtcaaata taaagtattt  10260
gaacaaattt atattttgac atgtgctctt tcagtcctaa aacctcgcaa caagggcgaa  10320
ttctgcagat atccatcaca ctggcggccg ctcgagcatg catctagagg gcccaattcg  10380
ccctatagtg agtcgtatta caattcactg gccgtcgttt tacaacgtcg tgactgggaa  10440
aaccctggcg ttacccaact taatcgcctt gcagcacatc ccccttttcgc cagctggcgt  10500
aatagcgaag aggcccgcac cgatcgccct tcccaacagt tgcgcagcct gaatggcgaa  10560
tggacgcgcc ctgtagcggc gcattaagcg cggcgggtgt ggtggttacg cgcagcgtga  10620
ccgctacact tgccagcgcc ctagcgcccg ctcctttcgc tttcttccct tcctttctcg  10680
ccacgttcgc cggctttccc cgtcaagctc taaatcgggg gctcccttta gggttccgat  10740
ttagtgcttt acggcacctc gaccccaaaa aacttgatta gggtgatggt tcacgtagtg  10800
ggccatcgcc ctgatagacg gtttttcgcc ctttgacgtt ggagtccacg ttctttaata  10860
gtggactctt gttccaaact ggaacaacac tcaaccctat ctcggtctat tcttttgatt  10920
tataagggat tttgccgatt tcggcctatt ggttaaaaaa tgagctgatt taacaaaaat  10980
ttaacgcgaa ttttaacaaa attcagggcg caagggctgc taaaggaagc ggaacacgta  11040
gaaagccagt ccgcagaaac ggtgctgacc ccggatgaat gtcagctact gggctatctg  11100
gacaagggaa aacgcaagcg caaagagaaa gcaggtagct tgcagtgggc ttacatggcg  11160
atagctagac tgggcggttt tatggacagc aagcgaaccg gaattgccag ctggggcgcc  11220
ctctggtaag gttgggaagc cctgcaaagt aaactggatg gctttcttgc cgccaaggat  11280
ctgatggcgc aggggatcaa gatctgatca agagacagga tgaggatcgt ttcgcatgat  11340
tgaacaagat ggattgcacg caggttctcc ggccgcttgg gtggagaggc tattcggcta  11400
tgactgggca caacagacaa tcggctgctc tgatgccgcc gtgttccggc tgtcagcgca  11460
ggggcgcccg gttctttttg tcaagaccga cctgtccggt gccctgaatg aactgcagga  11520
```

cgaggcagcg cggctatcgt ggctggccac gacgggcgtt ccttgcgcag ctgtgctcga 11580
cgttgtcact gaagcgggaa gggactggct gctattgggc gaagtgccgg ggcaggatct 11640
cctgtcatcc caccttgctc ctgccgagaa agtatccatc atggctgatg caatgcggcg 11700
gctgcatacg cttgatccgg ctacctgccc attcgaccac caagcgaaac atcgcatcga 11760
gcgagcacgt actcggatgg aagccggtct tgtcgatcag gatgatctgg acgaagagca 11820
tcaggggctc gcgccagccg aactgttcgc caggctcaag gcgcgcatgc ccgacggcga 11880
ggatctcgtc gtgacccatg gcgatgcctg cttgccgaat atcatggtgg aaaatggccg 11940
cttttctgga ttcatcgact gtggccggct gggtgtggcg gaccgctatc aggacatagc 12000
gttggctacc cgtgatattg ctgaagagct tggcggcgaa tgggctgacc gcttcctcgt 12060
gctttacggt atcgccgctc ccgattcgca gcgcatcgcc ttctatcgcc ttcttgacga 12120
gttcttctga attgaaaaag gaagagtatg agtattcaac atttccgtgt cgcccttatt 12180
cccttttttg cggcattttg ccttcctgtt tttgctcacc cagaaacgct ggtgaaagta 12240
aaagatgctg aagatcagtt gggtgcacga gtgggttaca tcgaactgga tctcaacagc 12300
ggtaagatcc ttgagagttt tcgccccgaa gaacgttttc caatgatgag cacttttaaa 12360
gttctgctat gtggcgcggt attatcccgt attgacgccg ggcaagagca actcggtcgc 12420
cgcatacact attctcagaa tgacttggtt gagtactcac cagtcacaga aaagcatctt 12480
acggatggca tgacagtaag agaattatgc agtgctgcca taaccatgag tgataacact 12540
gcggccaact tacttctgac aacgatcgga ggaccgaagg agctaaccgc ttttttgcac 12600
aacatggggg atcatgtaac tcgccttgat cgttgggaac cggagctgaa tgaagccata 12660
ccaaacgacg agcgtgacac cacgatgcct gtagcaatgg caacaacgtt gcgcaaacta 12720
ttaactggcg aactacttac tctagcttcc cggcaacaat taatagactg gatggaggcg 12780
gataaagttg caggaccact tctgcgctcg gcccttccgg ctggctggtt tattgctgat 12840
aaatctggag ccggtgagcg tgggtctcgc ggtatcattg cagcactggg gccagatggt 12900
aagccctccc gtatcgtagt tatctacacg acggggagtc aggcaactat ggatgaacga 12960
aatagacaga tcgctgagat aggtgcctca ctgattaagc attggtaact gtcagaccaa 13020
gtttactcat atatacttta gattgattta aaacttcatt tttaatttaa aaggatctag 13080
gtgaagatcc tttttgataa tctcatgacc aaaatccctt aacgtgagtt ttcgttccac 13140
tgagcgtcag accccgtaga aaagatcaaa ggatcttctt gagatccttt ttttctgcgc 13200
gtaatctgct gcttgcaaac aaaaaaacca ccgctaccag cggtggtttg tttgccggat 13260
caagagctac caactctttt tccgaaggta actggcttca gcagagcgca gataccaaat 13320
actgttcttc tagtgtagcc gtagttaggc caccacttca agaactctgt agcaccgcct 13380
acatacctcg ctctgctaat cctgttacca gtggctgctg ccagtggcga taagtcgtgt 13440
cttaccgggt tggactcaag acgatagtta ccggataagg cgcagcggtc gggctgaacg 13500
gggggttcgt gcacacagcc cagcttggag cgaacgacct acaccgaact gagataccta 13560
cagcgtgagc tatgagaaag cgccacgctt cccgaaggga gaaaggcgga caggtatccg 13620
gtaagcggca gggtcggaac aggagagcgc acgagggagc ttccaggggg aaacgcctgg 13680
tatctttata gtcctgtcgg gtttcgccac ctctgacttg agcgtcgatt tttgtgatgc 13740
tcgtcagggg ggcggagcct atggaaaaac gccagcaacg cggccttttt acggttcctg 13800
gccttttgct ggccttttgc tcacatgttc tttcctgcgt tatcccctga ttctgtggat 13860
aaccgtatta ccgcctttga gtgagctgat accgctcgcc gcagccgaac gaccgagcgc 13920
agcgagtcag tgagcgagga agcggaagag cgcccaatac gcaaaccgcc tctccccgcg 13980
cgttggccga ttcattaatg cagctggcac gacaggtttc ccgactggaa agcgggcagt 14040
gagcgcaacg caattaatgt gagttagctc actcattagg caccccaggc tttacacttt 14100
atgcttccgg ctcgtatgtt gtgtggaatt gtgagcggat aacaatttca cacaggaaac 14160
agctatgacc atgattacgc caagctattt aggtgacact atagaatact caagctatgc 14220
atcaagcttg gtaccgagct cggatccact agtaacggcc gccagtgtgc tggaattcgc 14280
ccttctggag actacattgc ctgaattggc gggcaaataa gtgcgacttg gaggaggcgg 14340
cgaggaagcc cagctggtct gaggtttctg tggcaagaca ggacgatatt gtttcgtata 14400
taacggtgga cccattggca aaacggcttg ttttggtatt gaaacggtat ttggcggccc 14460
ataggcgtta ttcctcaaat cacacacagt attctcaatt aaagtggcca agggagccgt 14520
gtaaattcgg aaattagtat ctgaataatc caagtcagac agcaagaaaa cgggcatcct 14580
atcggataga acccaaacgt ttttgttctc atcaattttc acatcggccg gaaaaactaa 14640
gccaacgtca tcgcgatcca caatgccatg aaattgcggt gagtacggca ttgatgagtg 14700
ccagcaaccc actgcatttt gatctattaa attgaacagc tcaattccat catcgctcat 14760
cacacgtgaa gtggtatggg agtttggacc ccgttcatct aaggcaacaa agtcatgata 14820
gctatcttcc gtcctggttt catccctcaa aatcctcgtg gatacggcaa attgtcgatg 14880
acttgctaac ggactaaagt acagggtacg ataaccatcc gatcgaatgg gcgaaaggga 14940
cataccaaat ataccctcct cgccccattg gaagttaata ccagcgacat tgaaatcgcc 15000
cctcaatgga tcggggaaaa aatacgaatg tgccgagaat ctccaggact tgttcagttc 15060
ccaggagtaa gcaatcaagc cgtatcccaa ttcatcggca aaataggcat atgcatcatc 15120
gcaatttttg cctatatcca cggcaatgtt agctatgaaa gtatttggat ttgtgtccac 15180
gccaggtagc tcgtatctcc gaattcgcgt atccgtggtc aagtcaaaga catttaccgc 15240
ataggggcac ggattagtgg tggtattgcc ga 15272

<210> SEQ ID NO 102
<211> LENGTH: 15272
<212> TYPE: DNA
<213> ORGANISM: Artificial Sequence
<220> FEATURE:
<223> OTHER INFORMATION: Synthetic polynucleotide

<400> SEQUENCE: 102
tgcccacgga gacgtcaaac cggtggatct aattcaatta gagactaatt caattagagc 60
taattcaatt aggatccaag cttatcgatt tcgaaccctc gaccgccgga gtataaatag 120
aggcgcttcg tctacggagc gacaattcaa ttcaaacaag caaagtgaac acgtcgctaa 180
gcgaaagcta agcaaataaa caagcgcagc tgaacaagct aaacaatcgg ctcgaagccg 240
gtcgccacca tggcctcctc cgaggacgtc atcaaggagt tcatgcgctt caaggtgcgc 300
atggagggct ccgtgaacgg ccacgagttc gagatcgagg gcgagggcga gggccgcccc 360
tacgagggca cccagaccgc caagctgaag gtgaccaagg gcggccccct gcccttcgcc 420
tgggacatcc tgtcccccca gttccagtac ggctccaagg tgtacgtgaa gcaccccgcc 480
gacatccccg actacaagaa gctgtccttc cccgagggct tcaagtggga gcgcgtgatg 540
aacttcgagg acggcggcgt ggtgaccgtg acccaggact cctccctcca ggacggctcc 600
ttcatctaca aggtgaagtt catcggcgtg aacttcccct ccgacggccc cgtaatgcag 660

-continued

```
aagaagacta tgggctggga ggcgtccacc gagcgcctgt acccccgcga cggcgtgctg    720
aagggcgaga tccacaaggc cctgaagctg aaggacggcg gccactacct ggtggagttc    780
aagtccatct acatggccaa gaagcccgtg cagctgcccg gctactacta cgtggactcc    840
aagctggaca tcacctccca caacgaggac tacaccatcg tggagcagta cgagcgcgcc    900
gagggccgcc accacctgtt cctgtagggg ccgcgactct agatcataat cagccatacc    960
acatttgtag aggttttact tgctttaaaa aacctcccac acctccccct gaacctgaaa   1020
cataaaatga atgcaattgt tgttgttaac ttgtttattg cagcttataa tggttacaaa   1080
taaagcaata gcatcacaaa tttcacaaat aaagcatttt tttcactgca ttctagttgt   1140
ggtttgtcca aactcatcaa tgtatcttaa ccggtggatc cctgcagctg gttgtaggtg   1200
cagttgcgct tcttgcactt ggcgcacttg aggagatcgg tcttggtgcc ctgcacggtg   1260
gccagctggg catcgttgat ggcctccttg acgaacttct cgcgcagctt cttcatctcg   1320
tcgctggcca tctcctccgg cgtcattttg gccagctgct tggcagtgac ggcgccgcac   1380
ataaagttgc cgcgcaatcc aggattcttg ggtccttca gattggccac gcgtgaccta    1440
atgcgattct tgtacttcat atccgtgtta ttgaactcgg agtaaatggc atcctccagt   1500
tcggcggcca tttcctccgg ctcaccgcat ccttcgggca cttcaccaat cttcagtgcg   1560
gtggccagca tttcgcggca tttgatgcgg accgcatctg tcatgccgcc ggagggaaac   1620
gaggtctgtg acgaggatgt cgagcctttc ttctctttat ccttggatga gctggatgaa   1680
ctggacttat ccttgccgga gattgacgac gacgacttgg cggcactggt ggacttcgag   1740
gcactgctgt tgttggagga gccctcctta gcggagctgt tgttcggtgt ggttggcgcc   1800
gggctggcga ggaatcgttt ccagttcttg atcagcgtct tggccagagc gatcacctcg   1860
tcgtccttgc tactcttgcg cagctcgttt acggtcatgc cgatgcgcgt tttggtcaga   1920
atgtcgagat tgatgttaag cgtttgcagg gccttcagca ggtccagagc ctgatcctgt   1980
ccctgtacgg tggatatatg tatatttgtg acatgatgcg cggcacgtta gctaatcccg   2040
atacttactg tgccgtcgct ggccatcttg ctcatcttct tttggattcg aaacacttcc   2100
tcctccacgc tcattttggc ccacttaatt tgatcagagg ttaggttaac tggcgtcggc   2160
tgtcggcttt aatcggtgct gcgggtctgc gacagttgtt tatgcggaag ccgggctatt   2220
tctttttttc cctccaataa atgttgttta ctattttttt cgtttctgta ttcgcagaac   2280
gagttgacag aacaccctaa cgcgttttag tgttaccggg cggtggcttg tcaagaaatg   2340
ccttcccatg gctaatacaa ttcccaactg gaagtagttt gggtttcaga agtcaacagt   2400
gttaccgtat tttaatgtac atctggcttt taagcgagta cacacacata gcattgcgat   2460
gtttttaaa cttgcactgc ttgcaagcag ggctccactg tatttcaatg aaagaacagc    2520
gtgttgggcg tttttgaatt atactaatta ccttcaataa caattcccta tatatcactt   2580
agttttaata aataaatcgt ttgagtgtgg tctagagatg atgtattatg atgaagtgcg   2640
gttgttgggg acaagcggga tacgtctgcg ggtcaaatcg gcggtgggac atagtgagag   2700
ggcaacggct ccaaaaccaa gcgttgcgaa caatcaccaa cgcgccctgg tacgcgagaa   2760
atgttgatat cgcacatgac ctcagcatcc accttcagtt tgagaacaaa ttaaatcagg   2820
cacataccag acaaccagga gaacactgag gaggcgtcat caaagatatc tttggacacg   2880
tggcataaac aagccaaact attatctaat caatattttt atacaaattt tgtatgtttc   2940
catgttatct tcgttgctcc tgttagttac tacgtttcat agcccttaaa ttggttgctt   3000
aacgtaaaat aaaattatat tgtataaaaa taaagaggaa ttcacctata acaaacgaaa   3060
```

-continued

```
aagtaaataa ataagaactt ccccatgtta aaaatgccac caccatcttt acatataagt   3120
atgtacatat gaatgaatca cttaggttgc ttgaatatta caatttcatt aatagctaaa   3180
tcacatttga tgtgttagtg gaaaacggct atatatataa attatcgaaa ttgtgaatat   3240
cgaattgcga tagcacaatg ggaaattcca ccactagatt tttggtactt ttaacagatc   3300
cttttcggtt ttgcgttgcg cgaagtgatc tgaacttatc aaagtttgta aggtaataca   3360
taaagtgaaa aagaattaat ttgctcttga aaggcaggcc aaattaaaaa aaaaatatca   3420
atcggtacca gatctggcgc gcctagaatg gactataagg accacgacgg agactacaag   3480
gatcatgata ttgattacaa agacgatgac gataagatgg ccccaaagaa gaagcggaag   3540
gtcggtatcc acggagtccc agcagccgga tccatcagtc tgattgcggc gttagcggta   3600
gatcacgtta tcggcatgga aaacgccatg ccgtggagcc tgcctgccga tctcgcctgg   3660
tttaaacgca acaccttaaa taaacccgtg attatgggcc gccatacctg ggaatcaatc   3720
ggtcgtccgt tgccaggacg caaaaacatt atcctcagca gtcaaccgag tacggacgat   3780
cgcgtaacgt gggtgaagtc ggcggatgaa gccatcgcgg cgtgtggtga cgtaccagaa   3840
atcatggtga ttggcggcgg tcgcgtttat gagcagttct tgccaaaagc gcaaaaactg   3900
tatctgacgc atatcgacgc agaagtggga ggcgacaccc atttcccgga ttacgagccg   3960
gatgactggg gatcggtatt cagcgaattc cacgatgctg atgcgcagaa ctctcacagc   4020
tattgctttg tgattctggg gcggcgagga agcggaagcg gatccgacaa gaagtacagc   4080
atcggcctgg acatcggcac caactctgtg ggctgggccg tgatcaccga cgagtacaag   4140
gtgcccagca agaaattcaa ggtgctgggc aacaccgacc ggcacagcat caagaagaac   4200
ctgatcggag ccctgctgtt cgacagcggc gaaacagccg aggccacccg gctgaagaga   4260
accgccagaa gaagatacac cagacggaag aaccggatct gctatctgca agagatcttc   4320
agcaacgaga tggccaaggt ggacgacagc ttcttccaca gactggaaga gtccttcctg   4380
gtggaagagg ataagaagca cgagcggcac cccatcttcg gcaacatcgt ggacgaggtg   4440
gcctaccacg agaagtaccc caccatctac cacctgagaa agaaactggt ggacagcacc   4500
gacaaggccg acctgcggct gatctatctg gccctggccc acatgatcaa gttccggggc   4560
cacttcctga tcgagggcga cctgaacccc gacaacagcg acgtggacaa gctgttcatc   4620
cagctggtgc agacctacaa ccagctgttc gaggaaaacc ccatcaacgc cagcggcgtg   4680
gacgccaagg ccatcctgtc tgccagactg agcaagagca gacggctgga aaatctgatc   4740
gcccagctgc ccggcgagaa gaagaatggc ctgttcggca acctgattgc cctgagcctg   4800
ggcctgaccc ccaacttcaa gagcaacttc gacctggccg aggatgccaa actgcagctg   4860
agcaaggaca cctacgacga cgacctggac aacctgctgg cccagatcgg cgaccagtac   4920
gccgacctgt ttctggccgc caagaacctg tccgacgcca tcctgctgag cgacatcctg   4980
agagtgaaca ccgagatcac caaggccccc ctgagcgcct ctatgatcaa gagatacgac   5040
gagcaccacc aggacctgac cctgctgaaa gctctcgtgc ggcagcagct gcctgagaag   5100
tacaaagaga ttttcttcga ccagagcaag aacggctacg ccggctacat tgacggcgga   5160
gccagccagg aagagttcta caagttcatc aagcccatcc tggaaaagat ggacggcacc   5220
gaggaactgc tcgtgaagct gaacagagag gacctgctgc ggaagcagcg gaccttcgac   5280
aacggcagca tcccccacca gatccacctg ggagagctgc acgccattct gcggcggcag   5340
gaagattttt acccattcct gaaggacaac cgggaaaaga tcgagaagat cctgaccttc   5400
```

-continued

```
cgcatcccct actacgtggg ccctctggcc aggggaaaca gcagattcgc ctggatgacc   5460
agaaagagcg aggaaaccat cacccccctgg aacttcgagg aagtggtgga caagggcgct   5520
tccgcccaga gcttcatcga gcggatgacc aacttcgata agaacctgcc caacgagaag   5580
gtgctgccca agcacagcct gctgtacgag tacttcaccg tgtataacga gctgaccaaa   5640
gtgaaatacg tgaccgaggg aatgagaaag cccgccttcc tgagcggcga gcagaaaaag   5700
gccatcgtgg acctgctgtt caagaccaac cggaaagtga ccgtgaagca gctgaaagag   5760
gactacttca agaaaatcga gtgcttcgac tccgtggaaa tctccggcgt ggaagatcgg   5820
ttcaacgcct ccctgggcac ataccacgat ctgctgaaaa ttatcaagga caaggacttc   5880
ctggacaatg aggaaaacga ggacattctg gaagatatcg tgctgaccct gacactgttt   5940
gaggacagag agatgatcga ggaacggctg aaaacctatg cccacctgtt cgacgacaaa   6000
gtgatgaagc agctgaagcg gcggagatac accggctggg gcaggctgag ccggaagctg   6060
atcaacggca tccgggacaa gcagtccggc aagacaatcc tggatttcct gaagtccgac   6120
ggcttcgcca acagaaactt catgcagctg atccacgacg acagcctgac ctttaaagag   6180
gacatccaga aagcccaggt gtccggccag ggcgatagcc tgcacgagca cattgccaat   6240
ctggccggca gccccgccat taagaagggc atcctgcaga cagtgaaggt ggtggacgag   6300
ctcgtgaaag tgatgggccg gcacaagccc gagaacatcg tgatcgaaat ggccagagag   6360
aaccagacca cccagaaggg acagaagaac agccgcgaga gaatgaagcg gatcgaagag   6420
ggcatcaaag agctgggcag ccagatcctg aaagaacacc ccgtggaaaa cacccagctg   6480
cagaacgaga agctgtacct gtactacctg cagaatgggc gggatatgta cgtggaccag   6540
gaactggaca tcaaccggct gtccgactac gatgtggacc atatcgtgcc tcagagcttt   6600
ctgaaggacg actccatcga caacaaggtg ctgaccagaa gcgacaagaa ccggggcaag   6660
agcgacaacg tgccctccga agaggtcgtg aagaagatga agaactactg gcggcagctg   6720
ctgaacgcca agctgattac ccagagaaag ttcgacaatc tgaccaaggc cgagagaggc   6780
ggcctgagcg aactggataa ggccggcttc atcaagagac agctggtgga aacccggcag   6840
atcacaaagc acgtggcaca gatcctggac tcccggatga acactaagta cgacgagaat   6900
gacaagctga tccgggaagt gaaagtgatc accctgaagt ccaagctggt gtccgatttc   6960
cggaaggatt tccagtttta caaagtgcgc gagatcaaca actaccacca cgcccacgac   7020
gcctacctga acgccgtcgt gggaaccgcc ctgatcaaaa agtaccctaa gctggaaagc   7080
gagttcgtgt acggcgacta caaggtgtac gacgtgcgga agatgatcgc caagagcgag   7140
caggaaatcg gcaaggctac cgccaagtac ttcttctaca gcaacatcat gaactttttc   7200
aagaccgaga ttaccctggc caacggcgag atccggaagc ggcctctgat cgagacaaac   7260
ggcgaaaccg gggagatcgt gtgggataag ggccgggatt ttgccaccgt gcggaaagtg   7320
ctgagcatgc cccaagtgaa tatcgtgaaa aagaccgagg tgcagacagg cggcttcagc   7380
aaagagtcta tcctgcccaa gaggaacagc gataagctga tcgccagaaa gaaggactgg   7440
gaccctaaga agtacggcgg cttcgacagc cccaccgtgg cctattctgt gctggtggtg   7500
gccaaagtgg aaaagggcaa gtccaagaaa ctgaagagtg tgaaagagct gctggggatc   7560
accatcatgg aaagaagcag cttcgagaag aatcccatcg actttctgga agccaagggc   7620
tacaaagaag tgaaaaagga cctgatcatc aagctgccta agtactccct gttcgagctg   7680
gaaaacggcc ggaagagaat gctggcctct gccggcgaac tgcagaaggg aaacgaactg   7740
gccctgccct ccaaatatgt gaacttcctg tacctggcca gccactatga gaagctgaag   7800
```

ggctcccccg aggataatga gcagaaacag ctgtttgtgg aacagcacaa gcactacctg 7860
gacgagatca tcgagcagat cagcgagttc tccaagagag tgatcctggc cgacgctaat 7920
ctggacaaag tgctgtccgc ctacaacaag caccgggata agcccatcag agagcaggcc 7980
gagaatatca tccacctgtt taccctgacc aatctgggag cccctgccgc cttcaagtac 8040
tttgacacca ccatcgaccg gaagaggtac accagcacca aagaggtgct ggacgccacc 8100
ctgatccacc agagcatcac cggcctgtac gagacacgga tcgacctgtc tcagctggga 8160
ggcgacaaaa ggccggcggc cacgaaaaag gccggccagg caaaaaagaa aaagatcagt 8220
ctgattgcgg cgttagcggt agatcacgtt atcggcatgg aaaccgtcat gccgtggaac 8280
ctgcctgccg atctcgcctg gtttaaacgc aacaccttaa ataaacccgt gattatgggc 8340
cgccatacct gggaatcaat cggtcgtccg ttgccaggac gcaaaaatat tatcctcagc 8400
agtcaaccga gtacggacga tcgcgtaacg tgggtgaagt cggtggatga agccatcgcg 8460
gcgtgtggtg acgtaccaga aatcatggtt attggcggcg gtcgcgttta tgaacagttc 8520
ttgccaaaag cgcaaaaact gtatctgacg catatcgacg cagaagtgga aggcgacacc 8580
catttcccgg attacgagcc ggatgactgg gaatcggtat tcagcgaatt ccacgatgct 8640
gatgcgcaga actctcacag ctattgcttt gagattctgg agcggcgata atctaggcct 8700
gagctcaatg tatggacata gatttcaaat aattaaatgt aatgcagtaa ttgatgtaat 8760
tagttaaata agttagatat taataacata ttaattatat gtattataac gcatataata 8820
ataaaatgca tatttaggat atgcaagcca ttcgaatttt ctattttaat ttccttttac 8880
aaagaaatgt ataacaaaat ataatttgaa aaaatgttct ggctctaatt cgatttcttt 8940
taagtatttt gtgaactgct tttaataacg agcggttgca aaacttaaca gaaacgtgca 9000
ctttgatccc aactaatacc gtgtactatc acgtgtttgg ttttaagtac tcatccttcg 9060
tgtttcgttg tttgttgttt gccttgctgt acacttggct cttgcgctct ctcgctctcc 9120
gttggagccg gctttttgaa tgcatgcctc gccctgctcg cgcccagtcc tcctcccccg 9180
aaaagcatgc cgaccagcaa atgttgccct tttgcgtttg ctgtctttgc agaagcaaaa 9240
tcaataactg agaaatccac cacactgctg ctcttcgtgt tgctagcttc cagtgtccaa 9300
aacccacagc cgaccacact catccacttt aatgcggtag gcagtggtaa tactgttggc 9360
gcaatctcca gctgtatttg agcgccaatc tggatacgga attagctccg gtgaacccgt 9420
caaactgcgg tccatgttta tataggtcag agtggccgga atccctaaaa aataaaatag 9480
gagaattagc agggccaaac tattattgag gcactaaata aagtttgttt tgaatattta 9540
attaactgga atttctgcct aaattccttc tttggattat tatactaagc aatgttgcaa 9600
gttatcgctg tctgttttct ggataaatatg taaatgcata cagatgtaaa ggtaaattag 9660
aatcgcttat gtttggcatt taattattta tatacctatt tgtcattatt ttggacacaa 9720
ggaatcataa gcaatggtaa ctgccgtgct aatggctctt ttttctgctt gtacatctac 9780
tggaagttta tgttaaaaga tccccggcta tatgtacttc agtcataatt ggcactattg 9840
caagttgcgt gcaatttgcg atgtcattag ccgtctgaag caattgcgtc tgacatcatt 9900
atcaatatgt ataccatata tcgctgttaa atgtatatgt ggccattggc agtatttcga 9960
ccgatttccg ctccagttct tttccttctt tatttcttcg ttaattgaat ttaaagacat 10020
ttattgtttc tgggaacttt taatgttttt atagcaggcg agtgagactg caacgaccag 10080
aaaatatagc ttttatcgat ttaccgaccc atcttcttaa aaatcaaacc aggcgttttt 10140

-continued

```
gctttacaaa gtaaccgggg gttgcgataa atatacattt gagcataatg cacctttcaa  10200
tctttattta attcataact tttaaaataa caatctaatt cagtcaaata taaagtattt  10260
gaacaaattt atattttgac atgtgctctt tcagtcctaa aacctcgcaa caagggcgaa  10320
ttctgcagat atccatcaca ctggcggccg ctcgagcatg catctagagg gcccaattcg  10380
ccctatagtg agtcgtatta caattcactg gccgtcgttt tacaacgtcg tgactgggaa  10440
aaccctggcg ttacccaact taatcgcctt gcagcacatc ccccttttcgc cagctggcgt  10500
aatagcgaag aggcccgcac cgatcgccct tcccaacagt tgcgcagcct gaatggcgaa  10560
tggacgcgcc ctgtagcggc gcattaagcg cggcgggtgt ggtggttacg cgcagcgtga  10620
ccgctacact tgccagcgcc ctagcgcccg ctcctttcgc tttcttccct tcctttctcg  10680
ccacgttcgc cggctttccc cgtcaagctc taaatcgggg gctcccttta gggttccgat  10740
ttagtgcttt acggcacctc gaccccaaaa aacttgatta gggtgatggt tcacgtagtg  10800
ggccatcgcc ctgatagacg gtttttcgcc ctttgacgtt ggagtccacg ttctttaata  10860
gtggactctt gttccaaact ggaacaacac tcaaccctat ctcggtctat tcttttgatt  10920
tataagggat tttgccgatt tcggcctatt ggttaaaaaa tgagctgatt taacaaaaat  10980
ttaacgcgaa ttttaacaaa attcagggcg caagggctgc taaaggaagc ggaacacgta  11040
gaaagccagt ccgcagaaac ggtgctgacc ccggatgaat gtcagctact gggctatctg  11100
gacaagggaa aacgcaagcg caaagagaaa gcaggtagct tgcagtgggc ttacatggcg  11160
atagctagac tgggcggttt tatggacagc aagcgaaccg gaattgccag ctggggcgcc  11220
ctctggtaag gttgggaagc cctgcaaagt aaactggatg gctttcttgc cgccaaggat  11280
ctgatggcgc aggggatcaa gatctgatca agagacagga tgaggatcgt ttcgcatgat  11340
tgaacaagat ggattgcacg caggttctcc ggccgcttgg gtggagaggc tattcggcta  11400
tgactgggca caacagacaa tcggctgctc tgatgccgcc gtgttccggc tgtcagcgca  11460
ggggcgcccg gttctttttg tcaagaccga cctgtccggt gccctgaatg aactgcagga  11520
cgaggcagcg cggctatcgt ggctggccac gacgggcgtt ccttgcgcag ctgtgctcga  11580
cgttgtcact gaagcgggaa gggactggct gctattgggc gaagtgccgg ggcaggatct  11640
cctgtcatcc caccttgctc ctgccgagaa agtatccatc atggctgatg caatgcggcg  11700
gctgcatacg cttgatccgg ctacctgccc attcgaccac caagcgaaac atcgcatcga  11760
gcgagcacgt actcggatgg aagccggtct tgtcgatcag gatgatctgg acgaagagca  11820
tcaggggctc gcgccagccg aactgttcgc caggctcaag gcgcgcatgc ccgacggcga  11880
ggatctcgtc gtgacccatg gcgatgcctg cttgccgaat atcatggtgg aaaatggccg  11940
cttttctgga ttcatcgact gtggccggct gggtgtggcg gaccgctatc aggacatagc  12000
gttggctacc cgtgatattg ctgaagagct tggcggcgaa tgggctgacc gcttcctcgt  12060
gctttacggt atcgccgctc ccgattcgca gcgcatcgcc ttctatcgcc ttcttgacga  12120
gttcttctga attgaaaaag gaagagtatg agtattcaac atttccgtgt cgcccttatt  12180
ccctttttttg cggcattttg ccttcctgtt tttgctcacc cagaaacgct ggtgaaagta  12240
aaagatgctg aagatcagtt gggtgcacga gtgggttaca tcgaactgga tctcaacagc  12300
ggtaagatcc ttgagagttt tcgccccgaa gaacgttttc caatgatgag cacttttaaa  12360
gttctgctat gtggcgcggt attatcccgt attgacgccg ggcaagagca actcggtcgc  12420
cgcatacact attctcagaa tgacttggtt gagtactcac cagtcacaga aaagcatctt  12480
acggatggca tgacagtaag agaattatgc agtgctgcca taaccatgag tgataacact  12540
```

gcggccaact tacttctgac aacgatcgga ggaccgaagg agctaaccgc ttttttgcac 12600
aacatggggg atcatgtaac tcgccttgat cgttgggaac cggagctgaa tgaagccata 12660
ccaaacgacg agcgtgacac cacgatgcct gtagcaatgg caacaacgtt gcgcaaacta 12720
ttaactggcg aactacttac tctagcttcc cggcaacaat taatagactg gatggaggcg 12780
gataaagttg caggaccact tctgcgctcg gcccttccgg ctggctggtt tattgctgat 12840
aaatctggag ccggtgagcg tgggtctcgc ggtatcattg cagcactggg gccagatggt 12900
aagccctccc gtatcgtagt tatctacacg acggggagtc aggcaactat ggatgaacga 12960
aatagacaga tcgctgagat aggtgcctca ctgattaagc attggtaact gtcagaccaa 13020
gtttactcat atatacttta gattgattta aaacttcatt tttaatttaa aaggatctag 13080
gtgaagatcc tttttgataa tctcatgacc aaaatccctt aacgtgagtt ttcgttccac 13140
tgagcgtcag accccgtaga aaagatcaaa ggatcttctt gagatccttt ttttctgcgc 13200
gtaatctgct gcttgcaaac aaaaaaacca ccgctaccag cggtggtttg tttgccggat 13260
caagagctac caactctttt tccgaaggta actggcttca gcagagcgca gataccaaat 13320
actgttcttc tagtgtagcc gtagttaggc caccacttca agaactctgt agcaccgcct 13380
acatacctcg ctctgctaat cctgttacca gtggctgctg ccagtggcga taagtcgtgt 13440
cttaccgggt tggactcaag acgatagtta ccggataagg cgcagcggtc gggctgaacg 13500
gggggttcgt gcacacagcc cagcttggag cgaacgacct acaccgaact gagataccta 13560
cagcgtgagc tatgagaaag cgccacgctt cccgaaggga gaaaggcgga caggtatccg 13620
gtaagcggca gggtcggaac aggagagcgc acgagggagc ttccaggggg aaacgcctgg 13680
tatctttata gtcctgtcgg gtttcgccac ctctgacttg agcgtcgatt tttgtgatgc 13740
tcgtcagggg ggcggagcct atggaaaaac gccagcaacg cggccttttt acggttcctg 13800
gccttttgct ggccttttgc tcacatgttc tttcctgcgt tatcccctga ttctgtggat 13860
aaccgtatta ccgcctttga gtgagctgat accgctcgcc gcagccgaac gaccgagcgc 13920
agcgagtcag tgagcgagga agcggaagag cgcccaatac gcaaaccgcc tctccccgcg 13980
cgttggccga ttcattaatg cagctggcac gacaggtttc ccgactggaa agcgggcagt 14040
gagcgcaacg caattaatgt gagttagctc actcattagg caccccaggc tttacacttt 14100
atgcttccgg ctcgtatgtt gtgtggaatt gtgagcggat aacaatttca cacaggaaac 14160
agctatgacc atgattacgc caagctattt aggtgacact atagaatact caagctatgc 14220
atcaagcttg gtaccgagct cggatccact agtaacggcc gccagtgtgc tggaattcgc 14280
ccttctggag actacattgc ctgaattggc gggcaaataa gtgcgacttg gaggaggcgg 14340
cgaggaagcc cagctggtct gaggtttctg tggcaagaca ggacgatatt gtttcgtata 14400
taacggtgga cccattggca aaacggcttg ttttggtatt gaaacggtat ttggcggccc 14460
ataggcgtta ttcctcaaat cacacacagt attctcaatt aaagtggcca agggagccgt 14520
gtaaattcgg aaattagtat ctgaataatc caagtcagac agcaagaaaa cgggcatcct 14580
atcggataga acccaaacgt tttgttctc atcaattttc acatcggccg gaaaaactaa 14640
gccaacgtca tcgcgatcca caatgccatg aaattgcggt gagtacggca ttgatgagtg 14700
ccagcaaccc actgcatttt gatctattaa attgaacagc tcaattccat catcgctcat 14760
cacacgtgaa gtggtatggg agtttggacc ccgttcatct aaggcaacaa agtcatgata 14820
gctatcttcc gtcctggttt catccctcaa aatcctcgtg gatacggcaa attgtcgatg 14880

```
acttgctaac ggactaaagt acagggtacg ataaccatcc gatcgaatgg gcgaaaggga  14940

cataccaaat ataccctcct cgccccattg gaagttaata ccagcgacat tgaaatcgcc  15000

cctcaatgga tcggggaaaa aatacgaatg tgccgagaat ctccaggact tgttcagttc  15060

ccaggagtaa gcaatcaagc cgtatcccaa ttcatcggca aaataggcat atgcatcatc  15120

gcaatttttg cctatatcca cggcaatgtt agctatgaaa gtatttggat ttgtgtccac  15180

gccaggtagc tcgtatctcc gaattcgcgt atccgtggtc aagtcaaaga catttaccgc  15240

ataggggcac ggattagtgg tggtattgcc ga                                15272


<210> SEQ ID NO 103
<211> LENGTH: 17
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: MISC_FEATURE
<222> LOCATION: (1)..(7)
<223> OTHER INFORMATION: n represents any complementary set of
      nucleotides that together will base pair to n in positions 11-17
      to create a stem
<220> FEATURE:
<221> NAME/KEY: MISC_FEATURE
<222> LOCATION: (11)..(17)
<223> OTHER INFORMATION: n represents any complementary set of
      nucleotides that together will base pair to n in positions 1-7 to
      create a stem

<400> SEQUENCE: 103

nnnnnnnagt nnnnnnn                                                    17


<210> SEQ ID NO 104
<211> LENGTH: 12
<212> TYPE: PRT
<213> ORGANISM: Artificial Sequence
<220> FEATURE:
<223> OTHER INFORMATION: Synthetic oligopeptide

<400> SEQUENCE: 104

Phe Trp Tyr His Lys Met Ile Leu Val Ala Gly Cys
1               5                   10


<210> SEQ ID NO 105
<211> LENGTH: 4
<212> TYPE: PRT
<213> ORGANISM: Artificial Sequence
<220> FEATURE:
<223> OTHER INFORMATION: Synthetic oligopeptide

<400> SEQUENCE: 105

Phe Trp Tyr His
1


<210> SEQ ID NO 106
<211> LENGTH: 12
<212> TYPE: PRT
<213> ORGANISM: Artificial Sequence
<220> FEATURE:
<223> OTHER INFORMATION: Synthetic oligopeptide

<400> SEQUENCE: 106

Trp Tyr His Lys Arg Glu Asp Cys Ser Thr Asn Gln
1               5                   10


<210> SEQ ID NO 107
```

-continued

<211> LENGTH: 5
<212> TYPE: PRT
<213> ORGANISM: Artificial Sequence
<220> FEATURE:
<223> OTHER INFORMATION: Synthetic oligopeptide

<400> SEQUENCE: 107

His Lys Arg Glu Asp
1 5

<210> SEQ ID NO 108
<211> LENGTH: 9
<212> TYPE: PRT
<213> ORGANISM: Artificial Sequence
<220> FEATURE:
<223> OTHER INFORMATION: Synthetic oligopeptide

<400> SEQUENCE: 108

Val Cys Ala Gly Ser Pro Thr Asn Asp
1 5

What is claimed:

1. A light activatable stabilizing ligand of the formula:

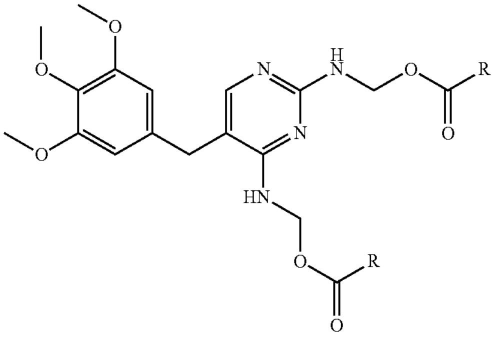

or

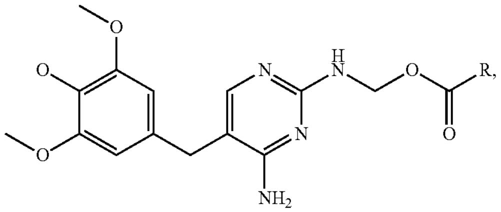

wherein R is selected from:

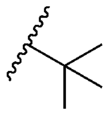

;

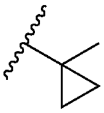

;

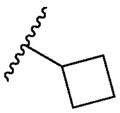

; and

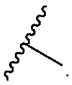

.

2. The ligand of claim 1, wherein the formula is,

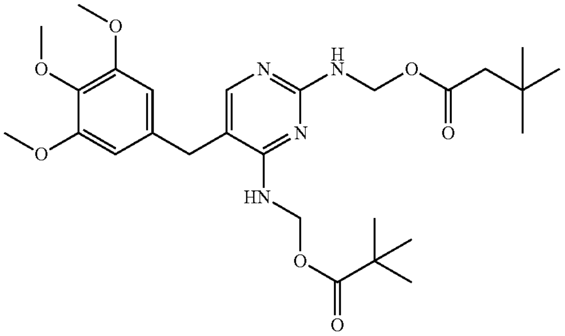

,

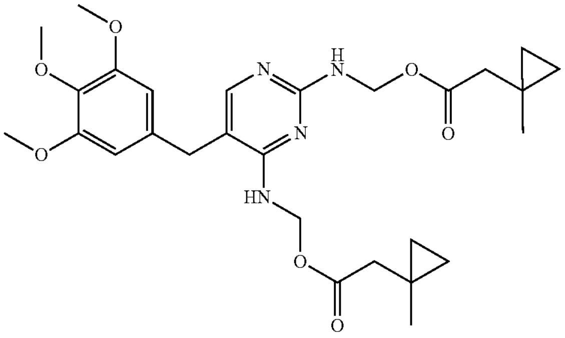

,

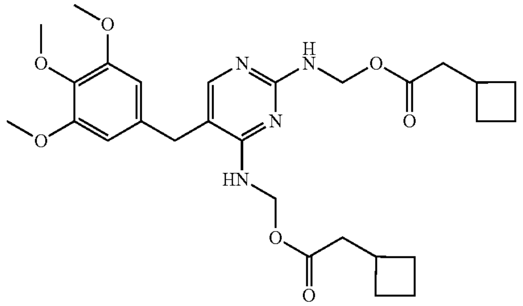

and

-continued

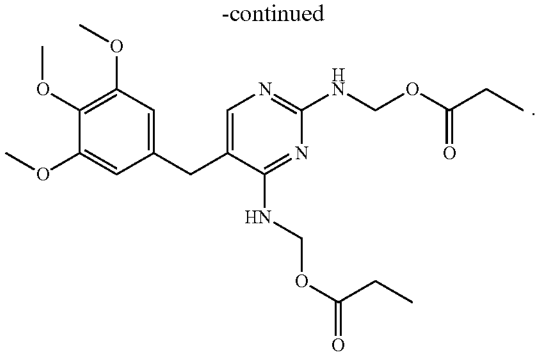

3. The ligand of claim 1, wherein the formula is,

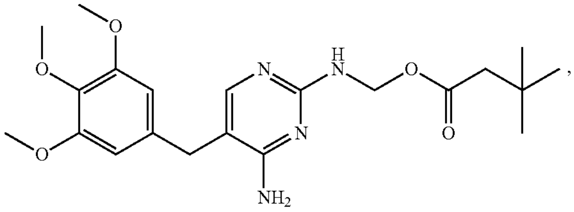

,

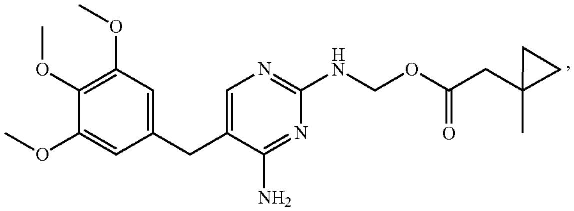

,

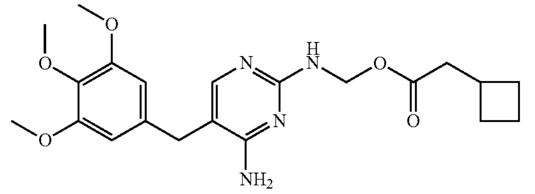

and

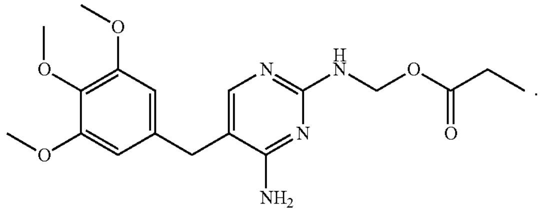

.

4. A transcriptional control system comprising;

a fusion protein comprising:

(i) one or more DHFR50 destabilization domains;

(ii) a CRISPR-Cas system comprising a catalytically inactive Cas protein and a guide molecule, the guide molecule comprising a binding recognition site;

(iii) an adaptor protein configured to bind to a binding recognition site of the guide molecule of the CRISPR-Cas system, and (iv) a transcriptional activation domain or a transcriptional repressor domain; and a light activatable stabilizing ligand of the formula:

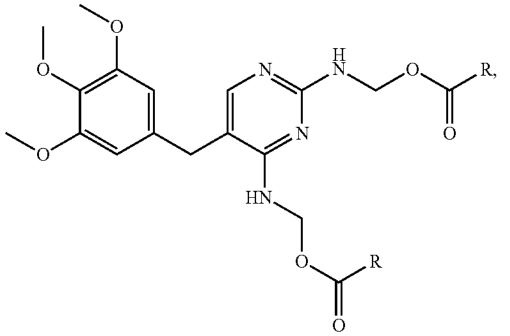

or

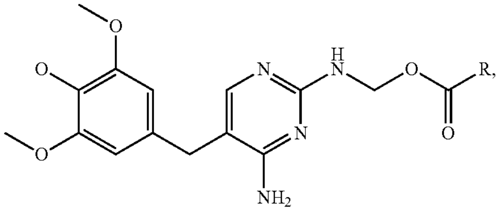

wherein R is selected from:

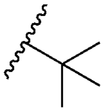

;

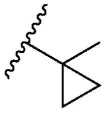

;

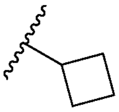

;

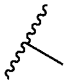

.

5. The transcriptional control system according to claim 4, wherein, the catalytically inactive Cas protein is or comprises *Streptococcus pyogenes* Cas9 (SpCas9), *Staphylococcus aureus* Cas9 (SaCas9), or a Cas protein variant thereof;

wherein, the catalytically inactive Cas protein comprises one or more functional domains;

wherein, the catalytically inactive Cas protein comprises one or more nuclear localization signals or one or more nuclear export signals;

wherein, the catalytically inactive Cas protein comprises one or more mutations, or wherein the one or more mutations are in a catalytic domain;

wherein, the catalytically inactive Cas protein is a nickase, the nickase comprising or corresponding to N863A in SpCas9;

wherein, the catalytically inactive Cas protein is codon optimized, optionally codon optimized for expression in a eukaryotic cell;

wherein, the catalytically inactive Cas protein is a chimeric Cas protein; or wherein, the catalytically inactive Cas protein is a split Cas protein.

6. The transcriptional control system of claim 4, wherein said guide molecule is a functionalized guide.

7. The transcriptional control system of claim 4, wherein at least one loop of the guide molecule is modified by an insertion of one or more aptamers that bind to said adaptor protein or said adaptor protein is an aptamer ligand;

wherein, the aptamer is an RNA or DNA sequence;

wherein, the guide molecule comprises two or more aptamer sequences, two or more different aptamer sequences, or two or more different aptamer sequences binding to different adaptor proteins; or any combination thereof.

8. The transcriptional control system of claim 7, wherein said at least one loop of the guide molecule is a tetraloop and/or stem loop 2;

wherein the guide molecule is modified by insertion of one or more distinct RNA or DNA sequences capable of binding said adaptor protein;

wherein the guide molecule is modified to have at least one non-coding functional loop;

wherein the guide molecule comprises a guide sequence capable of hybridizing to a target sequence in a polynucleic acid locus of interest in a cell;

wherein the guide molecule is an escorted guide, a protected guide, or a dead guide;

wherein the guide molecule comprises a direct repeat sequence capable of being bound by a CRISPR/Cas system effector protein;

wherein the guide comprises a tracr RNA sequence fused to a guide sequence; or wherein the guide molecule is a single guide RNA (sgRNA).

9. The transcriptional control system of claim 4, wherein a CRISPR/Cas effector protein forms a complex with the guide and upon binding of the said complex to a locus of interest the effector protein induces a modification of a sequences associated with or at the locus of interest.

10. The transcriptional control system of claim 4, wherein said transcriptional activation domain or a transcriptional repressor domain is a heterologous transcriptional activation domain or a transcriptional repressor domain.

11. The transcriptional control system of claim 4, wherein said transcriptional repressor domain comprises a KRAB domain, a NuE domain, NcoR domain, SID domain or a SID4X domain.

12. The transcriptional control system of claim 4, wherein said adaptor protein comprises MS2, PP7, Qβ, F2, GA, fr, JP501, M12, R17, BZ13, JP34, JP500, KU1, M11, MX1, TW18, VK, SP, FI, ID2, NL95, TW19, AP205, ϕCb5, ϕCb8r, ϕCb12r, ϕCb23r, 7s, or PRR1.

13. The transcriptional control system of claim 4, wherein the destabilization domain and/or the transcriptional activation domain or a transcriptional repressor domain is attached so that upon binding to the guide and target the respective domain is in a spatial orientation allowing for the respective domain to function in its attributed function; or wherein the one or more domains are attached via a GlySer linker.

14. The transcriptional control system of claim 4, wherein said destabilization domain is N-terminally and/or C-terminally present in said fusion protein.

15. The transcriptional control system of claim 4, comprising two destabilizing domains.

16. The transcriptional control system of claim 4, comprising two different destabilizing domains.

17. The transcriptional control system of claim 4, wherein the stabilizing ligand is activated by photolytic cleavage of a precursor;

or wherein, the fusion protein comprising one or more destabilization domains, one or more adaptor proteins capable of binding to a CRISPR/Cas guide is codon optimized for expression in a eukaryotic cell.

18. An isolated host cell or progeny thereof comprising the transcriptional control system of claim 4, the transcriptional control system components (i)-(iv) encoded in one or more polynucleic acids and the light activatable stabilizing ligand, or a vector comprising the one or more polynucleic acids encoding the transcriptional control system components i)-(iv) and the light activatable stabilizing ligand.

19. The isolated host cell according to claim 18, wherein the cell is a eukaryotic cell;

wherein the eukaryotic cell is a mammalian cell and the mammalian cell is a mouse cell
or a human cell; or
the eukaryotic cell is a plant cell; and
wherein the cell is a cell line.

20. A non-human eukaryote comprising the transcriptional control system of claim 4, the transcriptional control system components (i)-(iv) encoded in one or more polynucleic acids and the light activatable stabilizing ligand, or a vector comprising the one or more polynucleic acids encoding the transcriptional control system components (i)-(iv) and the light activatable stabilizing ligand.

21. A kit comprising the transcriptional control system of claim 4, the transcriptional control system components (i)-(iv) encoded in one or more polynucleic acids and the light activatable stabilizing ligand, or a vector comprising the one or more polynucleic acids encoding the transcriptional control system components (i)-(iv) and the light activatable stabilizing ligand.

22. A composition comprising one or more transcriptional control systems of claim 4, further comprising one or more guides, and/or one or more CRISPR/Cas effector proteins;

wherein, the composition further comprising a polynucleotide template for homologous recombination; and wherein, the template comprises at least 250 nucleotides, at least 500 nucleotides, at least 1000 nucleotides, at least 2000 nucleotides, at least 3000 nucleotides, at least 4000 nucleotides, at least 5000 nucleotides, at least 6000 nucleotides, at least 7000 nucleotides, at least 8000 nucleotides, at least 9000 nucleotides, or at least 10000 nucleotides.

23. The composition of claim 22, operable in plants or a host cell that is a plant cell.

24. A plant transformed by the composition of claim 22 or progeny thereof.

25. A vector comprising the transcriptional control system of claim 4 wherein components (i)-(iv) are encoded in one or more polynucleic acids wherein, expression is conditional and/or inducible; and wherein, the vector comprises one or more polynucleic acids encoding the fusion protein and regulatory element(s) operable in a host cell operably linked to the one or more polynucleic acids.

26. An ex vivo method of modifying a polynucleic acid target locus or introducing a polynucleic acid locus event in a subject, comprising administering to the cells of the subject the transcriptional control system of claim 4 or a vector comprising the transcriptional control system; and activating the light activatable stabilizing ligand by exposing it to light, wherein the transcriptional control system is administered ex vivo.

27. The method according to claim 26, wherein the method is a method of treating or inhibiting a condition caused by a defect in a target sequence in the polynucleic acid target locus in the subject, wherein the transcriptional control system modifies the defect in the target sequence in the polynucleic acid locus or introduces a polynucleic event at the target locus in the polynucleic acid locus.

28. The method of claim 27, wherein the condition caused by a defect in a target sequence in the polynucleic acid target locus in the subject is a blood disease or disorder.

29. The method of claim 26, wherein delivering the transcriptional control system to eye cells of the subject in need thereof to treat an eye disease or disorder.

30. An ex vivo method of treating a pathogenic disease, optional a viral disease, in a subject in need thereof, the method comprising administering to the subject the transcriptional control system of claim 4 or a vector comprising the transcriptional control system, wherein the transcriptional control system modifies a polynucleic acid locus or introduces a polynucleic acid locus event at a target locus of the pathogenic organism; and activating the light activatable stabilizing ligand by exposing it to light, wherein the transcriptional control system is administered ex vivo.

31. The method according to claim 30, wherein said viral disease is HBV.

* * * * *